US012472496B2

(12) United States Patent
Wagner et al.

(10) Patent No.: US 12,472,496 B2
(45) Date of Patent: Nov. 18, 2025

(54) PLATFORMS AND SYSTEMS FOR AUTOMATED CELL CULTURE

(71) Applicant: Cellino Biotech, Inc., Cambridge, MA (US)

(72) Inventors: Matthias Wagner, Cambridge, MA (US); Suvi Aivio, Arlington, MA (US); Mariangela Amenduni, Arlington, MA (US); Catherine Pilsmaker, Arlington, MA (US); Arnaldo Pereira, Cambridge, MA (US); Ananya Zutshi, Boston, MA (US); Ozge Whiting, Pawtucket, RI (US); George Harb, Providence, RI (US); Steven Nagle, Wayland, MA (US); Anthia Toure, Boston, MA (US); Matthew Sullivan, Westwood, MA (US); Maya Berlin-Udi, Acton, MA (US); Lukas Vasadi, Cambridge, MA (US); Alexander Stange, Somerville, MA (US); Sangkyun Lee, Newton, MA (US); Stefanie Morgan, Hanover, MA (US); Nick Seay, Charlottesville, VA (US); Scott Luro, Somerville, MA (US)

(73) Assignee: Cellino Biotech, Inc., Cambridge, MA (US)

( * ) Notice: Subject to any disclaimer, the term of this patent is extended or adjusted under 35 U.S.C. 154(b) by 0 days.

(21) Appl. No.: 18/391,002

(22) Filed: Dec. 20, 2023

(65) Prior Publication Data

US 2024/0253032 A1 Aug. 1, 2024

Related U.S. Application Data

(63) Continuation of application No. 17/930,413, filed on Sep. 7, 2022, now Pat. No. 11,931,737.

(Continued)

(51) Int. Cl.
*C12M 1/00* (2006.01)
*B01L 3/00* (2006.01)
(Continued)

(52) U.S. Cl.
CPC ....... *B01L 3/502715* (2013.01); *C12M 23/14* (2013.01); *C12M 23/22* (2013.01);
(Continued)

(58) Field of Classification Search
CPC ... B01L 3/502715; C12M 47/04; C12M 41/48
See application file for complete search history.

(56) References Cited

U.S. PATENT DOCUMENTS

| | | |
|---|---|---|
| 5,900,374 A | 5/1999 | Otto-Nagels |
| 6,096,532 A | 8/2000 | Armstrong et al. |

(Continued)

FOREIGN PATENT DOCUMENTS

| | | |
|---|---|---|
| CN | 105492888 B | 8/2018 |
| CN | 113421221 A | 9/2021 |

(Continued)

OTHER PUBLICATIONS

Aasen et al.: Isolation and cultivation of human keratinocytes from skin or plucked hair for the generation of induced pluripotent stem cells. Nat Protoc. 2010 5(2):371-382 doi:10.1038/nprot.2009.241 (2010).

(Continued)

*Primary Examiner* — Nathan A Bowers
(74) *Attorney, Agent, or Firm* — WILSON SONSINI GOODRICH & ROSATI

(57) ABSTRACT

Disclosed herein are platforms, systems, and methods including a cell culture system that includes a cell culture container comprising a cell culture, the cell culture receiving input cells, a cell imaging subsystem configured to acquire images of the cell culture, a computing subsystem config- (Continued)

ured to perform a cell culture process on the cell culture according to the images acquired by the cell imaging subsystem, and a cell editing subsystem configured to edit the cell culture to produce output cell products according to the cell culture process.

26 Claims, 138 Drawing Sheets

Related U.S. Application Data

(60) Provisional application No. 63/370,994, filed on Aug. 10, 2022, provisional application No. 63/370,912, filed on Aug. 9, 2022, provisional application No. 63/370,486, filed on Aug. 4, 2022, provisional application No. 63/370,209, filed on Aug. 2, 2022, provisional application No. 63/369,900, filed on Jul. 29, 2022, provisional application No. 63/369,589, filed on Jul. 27, 2022, provisional application No. 63/391,453, filed on Jul. 22, 2022, provisional application No. 63/347,506, filed on May 31, 2022, provisional application No. 63/311,673, filed on Feb. 18, 2022, provisional application No. 63/298,241, filed on Jan. 11, 2022, provisional application No. 63/297,290, filed on Jan. 7, 2022, provisional application No. 63/295,968, filed on Jan. 3, 2022, provisional application No. 63/288,859, filed on Dec. 13, 2021, provisional application No. 63/284,839, filed on Dec. 1, 2021, provisional application No. 63/282,351, filed on Nov. 23, 2021, provisional application No. 63/249,698, filed on Sep. 29, 2021.

(51) Int. Cl.

| | |
|---|---|
| ***C12M 1/06*** | (2006.01) |
| ***C12M 1/12*** | (2006.01) |
| ***C12M 1/34*** | (2006.01) |
| ***C12M 1/36*** | (2006.01) |
| ***C12M 3/00*** | (2006.01) |
| ***C12N 5/00*** | (2006.01) |
| ***G01N 15/10*** | (2006.01) |
| ***G06T 7/00*** | (2017.01) |

(52) U.S. Cl.

CPC ............ *C12M 23/26* (2013.01); *C12M 23/42* (2013.01); *C12M 23/44* (2013.01); *C12M 23/48* (2013.01); *C12M 25/06* (2013.01); *C12M 27/02* (2013.01); *C12M 29/02* (2013.01); *C12M 41/12* (2013.01); *C12M 41/26* (2013.01); *C12M 41/48* (2013.01); *C12M 47/04* (2013.01); *C12N 5/0081* (2013.01); *G01N 15/1023* (2024.01); *G06T 7/0016* (2013.01); *B01L 2300/0663* (2013.01); *G01N 2015/1006* (2013.01); *G06T 2207/10056* (2013.01); *G06T 2207/10064* (2013.01); *G06T 2207/20081* (2013.01); *G06T 2207/30024* (2013.01); *G06T 2207/30072* (2013.01)

(56) References Cited

U.S. PATENT DOCUMENTS

| | | | |
|---|---|---|---|
| 6,153,400 | A | 11/2000 | Matsumura et al. |
| 6,673,008 | B1 | 1/2004 | Thompson et al. |
| 7,754,148 | B2 | 7/2010 | Yu et al. |
| 8,492,140 | B2 | 7/2013 | Smith et al. |
| 8,546,142 | B2 | 10/2013 | Martin et al. |
| 9,181,529 | B2 | 11/2015 | Kattman et al. |
| 9,499,780 | B2 | 11/2016 | Smith et al. |
| 9,783,768 | B2 | 10/2017 | Larcher et al. |
| 10,078,075 | B2 | 9/2018 | Wikswo et al. |
| 10,829,729 | B2 | 11/2020 | Mazur et al. |
| 10,876,086 | B2 | 12/2020 | Suzuki et al. |
| 11,028,358 | B2 | 6/2021 | Kelso et al. |
| 11,643,667 | B2 | 5/2023 | Wagner et al. |
| 11,680,247 | B2 | 6/2023 | Wagner et al. |
| 11,708,563 | B2 | 7/2023 | Wagner et al. |
| 11,866,735 | B2 | 1/2024 | Wagner et al. |
| 11,913,029 | B2 | 2/2024 | Wagner et al. |
| 11,931,737 | B2 | 3/2024 | Wagner et al. |
| 2002/0055166 | A1 | 5/2002 | Cannon et al. |
| 2003/0039384 | A1 | 2/2003 | Bacus |
| 2003/0040104 | A1 | 2/2003 | Barbera-Guillem |
| 2003/0054335 | A1 | 3/2003 | Taya et al. |
| 2003/0068814 | A1 | 4/2003 | Malinge |
| 2005/0026221 | A1 | 2/2005 | Richmond et al. |
| 2007/0163963 | A1 | 7/2007 | Faustman et al. |
| 2007/0212747 | A1 | 9/2007 | Browne et al. |
| 2007/0292312 | A1 | 12/2007 | Bachman et al. |
| 2009/0258417 | A1 | 10/2009 | Tanaka et al. |
| 2009/0286317 | A1 | 11/2009 | Demmler et al. |
| 2012/0130287 | A1 | 5/2012 | Gruber |
| 2012/0208273 | A1 | 8/2012 | Tarunina et al. |
| 2012/0294836 | A1 | 11/2012 | Rowley et al. |
| 2012/0315620 | A1 | 12/2012 | Watakabe et al. |
| 2012/0329123 | A1 | 12/2012 | Nakashima et al. |
| 2013/0102772 | A1 | 4/2013 | Eshima et al. |
| 2013/0169969 | A1 | 7/2013 | Popescu et al. |
| 2013/0337492 | A1 | 12/2013 | Axelrod et al. |
| 2014/0004507 | A1 | 1/2014 | Malic et al. |
| 2014/0030805 | A1 | 1/2014 | Kasuto et al. |
| 2015/0107995 | A1 | 4/2015 | Sista et al. |
| 2016/0177244 | A1 | 6/2016 | Conway et al. |
| 2016/0195523 | A1 | 7/2016 | Chatterjee et al. |
| 2016/0237392 | A1 | 8/2016 | Lee |
| 2017/0009252 | A1 | 1/2017 | Baylink et al. |
| 2017/0014824 | A1 | 1/2017 | Boyd et al. |
| 2017/0029864 | A1 | 2/2017 | Straus |
| 2017/0037351 | A1* | 2/2017 | Shimase ................ C12M 23/50 |
| 2018/0072975 | A1 | 3/2018 | Aviles et al. |
| 2018/0087021 | A1 | 3/2018 | Blanchard |
| 2018/0120294 | A1* | 5/2018 | Collins .............. G01N 33/5058 |
| 2018/0282682 | A1* | 10/2018 | Pebay .................... C12M 41/48 |
| 2018/0321128 | A1 | 11/2018 | Harriman et al. |
| 2019/0009274 | A1 | 1/2019 | Novak et al. |
| 2019/0169572 | A1 | 6/2019 | Shi et al. |
| 2019/0352589 | A1 | 11/2019 | Jing et al. |
| 2019/0359924 | A1* | 11/2019 | Kerns ................. C12N 5/0622 |
| 2020/0087607 | A1 | 3/2020 | Magnant |
| 2020/0131465 | A1 | 4/2020 | Floto et al. |
| 2020/0141961 | A1 | 5/2020 | Ahlfors |
| 2020/0200781 | A1 | 6/2020 | Smith et al. |
| 2020/0208095 | A1 | 7/2020 | Oram et al. |
| 2020/0318053 | A1 | 10/2020 | Kojima et al. |
| 2021/0123008 | A1 | 4/2021 | Trainor et al. |
| 2021/0130774 | A1* | 5/2021 | Sances ................... C12M 41/46 |
| 2021/0253991 | A1 | 8/2021 | Kelso et al. |
| 2021/0261899 | A1 | 8/2021 | Blanchard |
| 2021/0283606 | A1 | 9/2021 | Thakkar et al. |
| 2021/0317399 | A1 | 10/2021 | Nazareth et al. |
| 2021/0403942 | A1 | 12/2021 | Wang et al. |
| 2022/0106549 | A1 | 4/2022 | Magnant |
| 2022/0107488 | A1 | 4/2022 | Berns et al. |
| 2022/0226814 | A1 | 7/2022 | Iida et al. |
| 2022/0276463 | A1 | 9/2022 | Hunt et al. |
| 2022/0282201 | A1 | 9/2022 | Wagner et al. |
| 2022/0282203 | A1 | 9/2022 | Wagner et al. |
| 2023/0235295 | A1 | 7/2023 | Wagner et al. |
| 2023/0265394 | A1 | 8/2023 | Wagner et al. |
| 2023/0332111 | A1 | 10/2023 | Wagner et al. |
| 2024/0191204 | A1 | 6/2024 | Wagner et al. |

FOREIGN PATENT DOCUMENTS

| | | | |
|---|---|---|---|
| EP | 3556841 A1 | 10/2019 | |
| JP | 2013179916 A | 9/2013 | |
| KR | 20070012514 A | 1/2007 | |
| WO | WO-2007052716 A1 | 5/2007 | |

(56) References Cited

FOREIGN PATENT DOCUMENTS

| | | | |
|---|---|---|---|
| WO | WO-2011132584 | A1 | 10/2011 |
| WO | WO-2016114438 | A1 | 7/2016 |
| WO | WO-2017079682 | A1 | 5/2017 |
| WO | WO-2018101004 | A1 | 6/2018 |
| WO | WO-2019178561 | A2 | 9/2019 |
| WO | WO-2019241885 | A1 | 12/2019 |
| WO | WO-2020033871 | A1 | 2/2020 |
| WO | WO-2020097083 | A1 | 5/2020 |
| WO | WO-2021150631 | A1 | 7/2021 |
| WO | WO-2022096315 | A1 | 5/2022 |
| WO | WO-2022192157 | A1 | 9/2022 |
| WO | WO-2023055543 | A1 | 4/2023 |

OTHER PUBLICATIONS

Ahmed et al.: In situ self-assembly of gold nanoparticles on hydrophilic and hydrophobic substrates for influenza virus-sensing platform. Sci Rep. 7:44495: 1-11 doi:10.1038/srep44495 (2017).
Ban et al.: Efficient generation of transgene-free human induced pluripotent stem cells (iPSCs) by temperature-sensitive Sendai virus vectors. Proc Natl Acad Sci USA 108(34):14234-14239 doi:10.1073/pnas.1103509108 (2011).
Bar-Nur et al. Epigenetic memory and preferential lineage-specific differentiation in induced pluripotent stem cells derived from human pancreatic islet Beta cells. Cell Stem Cell 9:17-23 (2011).
Chen et al.: Nanofabrication by electron beam lithography and its applications: A review. Microelectronic Engineering 135:57-72 https://doi.org/10.1016/j.mee.2015.02.042 (2015).
Co-pending U.S. Appl. No. 18/391,053, inventors Wagner; Matthias et al., filed Dec. 20, 2023.
Drews et al.: The cytotoxic and immunogenic hurdles associated with non-viral mRNA-mediated reprogramming of human fibroblasts. Biomaterials 33(16):4059-4068 doi:10.1016/j.biomaterials.2012.02.025 (2012).
Drozd et al., Generation of Human iPSCs From Cells of Fibroblastic and Epithelial Origin by Means of the oriP/EBNA-1 Episomal Reprogramming System. Stem Cell Res Ther 6 (1): 122 (2015).
Gill et al.: Progress and prospects: the design and production of plasmid vectors. Gene Ther. 16(2):165-171 doi:10.1038/gt.2008.183 (2009).
He et al.: Single-shot aperture-scanning Fourier ptychography. Opt Express 26(22):28187-28196 doi:10.1364/OE.26.028187 (2018).
Hu et al.: Fluorescence in situ hybridization (FISH): an increasingly demanded tool for biomarker research and personalized medicine. Biomark Res. 2:3:1-13 doi:10.1186/2050-7771-2-3 (2014).
Hudin et al.: Localized Tactile Stimulation by Time-Reversal of Flexural Waves: Case Study With a Thin Sheet of Glass. IEEE World Haptics Conference, pp. 1-6 DOI:10.1109/WHC.2013.6548386 (2013).
Jingshan et al.: Transport of Intensity phase imaging by intensity spectrum fitting of exponentially spaced defocus planes. Opt Express. 22(9):10661-10674 doi:10.1364/OE.22.010661 (2014).
Jo et al.: Quantitative Phase Imaging and Artificial Intelligence: A Review. IEEE Journal of Selected Topics in Quantum Electronics 25(1):1-14 (2019).
Kashyap et al.: Selective local lysis and sampling of live cells for nucleic acid analysis using a microfluidic probe. Sci Rep. 6:29579:1-10 doi:10.1038/srep29579 (2016).
Kim et al.: Generation of human induced pluripotent stem cells by direct delivery of reprogramming proteins. Cell Stem Cell 5;4(6):472-476 doi:10.1016/j.stem.2009.05.005 (2009).
Kim et al.: Generation of human induced pluripotent stem cells from osteoarthritis patient-derived synovial cells. Arthritis Rheum 63(10):3010-3021 doi:10.1002/art.30488 (2011).
Kogler et al.: Comparison of time-gated surface-enhanced raman spectroscopy (TG-SERS) and classical SERS based monitoring of *Escherichia coli* cultivation samples. Biotechnol Prog. 34(6):1533-1542 doi:10.1002/btpr.2665 (2018).
Kulik et al.: Parallelization in automated stem cell culture. 3rd CIRP Conference on BioManufacturing, Procedia CIRP 65:242-247 (2017).
Lee et al.:Single-shot phase retrieval via Fourier ptychographic microscopy. Optica 5(8):976-983 https://doi.org/10.1364/OPTICA.5.000976 (2018).
Li et al.: Excitable networks controlling cell migration during development and disease. Semin Cell Dev Biol. 100:133-142 doi:10.1016/j.semcdb.2019.11.001 (2020).
Loh, et al. Reprogramming of T Cells from Human Peripheral Blood. Cell Stem Cell. Jul. 2, 2010; 7(1): 15-19.
Lopatynskyi et al.: Au nanostructure arrays for plasmonic applications: annealed island films versus nanoimprint lithography. Nanoscale Res Lett. 10:99: 1-9 doi:10.1186/s11671-015-0819-1 (2015).
Mann: Rapid isolation of antigen-specific clones from hybridoma fusions. Nat Methods 4, i-ii URL:https://doi.org/10.1038/nmeth1028 (2007).
Meier et al.: Fast electrically assisted regeneration of on chip SERS substrates. Lab on a Chip 15:2923-2927 DOI:10.1039/C5LC00397K (2015).
Okita et al.: A more efficient method to generate integration-free human iPS cells. Nat Methods 8(5):409-412 (2011).
Okita et al.: Generation of mouse-induced pluripotent stem cells with plasmid vectors. Nature Protocols 5(3):418-428 (2010).
PCT/US2022/019196 International Search Report and Written Opinion dated Jun. 1, 2022.
PCT/US2022/042811 International Search Report and Written Opinion dated Nov. 22, 2022.
Rim et al.: Chondrogenic Differentiation from Induced Pluripotent Stem Cells Using Non-Viral Minicircle Vectors. Cells 9(3):582:1-21 doi:10.3390/cells9030582 (2020).
Sanchez-Esquivel et al.: Spectral dependence of nonlinear absorption in ordered silver metallic nanoprism arrays. Sci Rep. 7(1):5307:1-9 doi:10.1038/s41598-017-04814-2 (2017).
Segalman: Patterning with block copolymer thin films. Materials Science and Engineering R Reports 48(6):191-226 DOI:10.1016/j.mser.2004.12.003 (2005).
Skorik et al.: Xeno-Free Reprogramming of Peripheral Blood Mononuclear Erythroblasts on Laminin-521. Curr Protoc Stem Cell Biol. 52(1):e103:1-41 doi:10.1002/cpsc. 103 (2020).
Stewart et al.: Intracellular Delivery by Membrane Disruption: Mechanisms, Strategies, and Concepts. Chem Rev. 118(16):7409-7531 doi:10.1021/acs.chemrev.7b00678 (2018).
Takahashi et al. Induction of Pluripotent Stem Cells from Adult Human Fibroblasts by Defined Factors. Cell 131:861-872 (2007).
Thiers: Dermatology and Dermatologic Surgery. Chapter 15—Miscellaneous Topics in Clinical Dermatology, Elsevier—Health Sciences Division, pp. 302-303 (2008).
Tvarozek et al.: Plasmonic behaviour of sputtered Au nanoisland arrays. Applied Surface Science 395:241-247 DOI:10.1016/j.apsusc.2016.04.183 (2017).
U.S. Appl. No. 17/688,837 Final Office Action dated Oct. 5, 2022.
U.S. Appl. No. 17/688,837 Non-Final Office Action dated Apr. 6, 2023.
U.S. Appl. No. 17/688,837 Non-Final Office Action dated May 26, 2022.
U.S. Appl. No. 17/688,854 Final Office Action dated Aug. 1, 2023.
U.S. Appl. No. 17/688,854 Non-Final Office Action dated Apr. 21, 2023.
U.S. Appl. No. 17/688,854 Non-Final Office Action dated May 11, 2022.
U.S. Appl. No. 17/688,857 Final Office Action dated Oct. 14, 2022.
U.S. Appl. No. 17/688,857 Non-Final Office Action dated Jun. 9, 2022.
U.S. Appl. No. 17/688,859 Final Office Action dated Sep. 27, 2022.
U.S. Appl. No. 17/688,859 Non-Final Office Action dated Jun. 10, 2022.
U.S. Appl. No. 17/688,861 Final Office Action dated Nov. 7, 2022.
U.S. Appl. No. 17/688,861 Final Office Action dated Oct. 12, 2023.
U.S. Appl. No. 17/688,861 Non-Final Office Action dated Jun. 24, 2022.
U.S. Appl. No. 17/688,861 Non-Final Office Action dated May 11, 2023.
U.S. Appl. No. 17/930,413 Final Office Action dated May 26, 2023.

(56) References Cited

OTHER PUBLICATIONS

U.S. Appl. No. 17/930,413 Non-Final Office Action dated Jan. 26, 2023.
U.S. Appl. No. 17/930,413 Non-Final Office Action dated Nov. 30, 2022.
U.S. Appl. No. 17/930,413 Office Action dated Aug. 25, 2023.
U.S. Appl. No. 18/061,811 Final Office Action dated Apr. 21, 2023.
U.S. Appl. No. 18/061,811 Non-Final Office Action dated Jan. 12, 2023.
U.S. Appl. No. 18/190,775 Final Office Action dated Jan. 12, 2024.
U.S. Appl. No. 18/190,775 Office Action dated Oct. 5, 2023.
U.S. Appl. No. 18/339,779 Office Action dated Mar. 13, 2024.
U.S. Appl. No. 18/061,811 Office Action dated Aug. 15, 2023.
Warren et al., Highly efficient reprogramming to pluripotency and directed differentiation of human cells with synthetic modified mRNA. Cell Stem Cell 7(5):618-630 (2010).
Watt et al.: Ion beam lithography and nanofabrication: A review. International Journal of Nanoscience 4(3):269-286 DOI:10.1142/S0219581X05003139 (2005).
Yoshioka et al.: Efficient generation of human iPSCs by a synthetic self-replicative RNA. Cell Stem Cell 13(2):246-254 doi:10.1016/j.stem.2013.06.001 (2013).
Zheng et al.: Concept, implementations and applications of Fourier ptychography. Nature Physics Reviews 3(3):207-223 DOI:10.1038/s42254-021-00280-y (2021).
Zhou et al.: Generation of induced pluripotent stem cells from urine. J Am Soc Nephrol. 22(7):1221-1228 doi:10.1681/ASN.2011010106 (2011).
Zhou et al.: Integration-free Methods for Generating Induced Pluripotent Stem Cells. Genomics, Proteomics & Bioinformatics 11(5):284-287 (2013).
Zhou et al.: Si surface passivation by SiOx : H films deposited by a low-frequency ICP for solar cell applications. Journal of Physics D Applied Physics 45(39):395401, pp. 1-8 DOI:10.1088/0022-3727/45/39/395401 (2012).
Zou et al.: High-resolution transport-of-intensity quantitative phase microscopy with annular illumination. arXiv:1704.04091v3 [physics.optics], pp. 1-25 doi:10.48550/ARXIV.1704.04091 (2017).
Zou et al.: High-resolution transport-of-intensity quantitative phase microscopy with annular illumination. Sci Rep. 7(1):7654, pp. 1-22 doi:10.1038/s41598-017-06837-1 (2017).
Zuo et al.: Transport of intensity equation: a tutorial. Optics and Lasers in Engineering 135(106187):1-98 URL:https://doi.org/10.1016/j.optlaseng.2020.106187 (2020).
U.S. Appl. No. 18/190,775 Office Action dated Apr. 24, 2024.

* cited by examiner

9100

9400

PLATFORMS AND SYSTEMS FOR AUTOMATED CELL CULTURE

CROSS-REFERENCE

This application is a continuation of U.S. application Ser. No. 17/930,413, filed Sep. 7, 2022, which claims the benefit of U.S. Provisional Application No. 63/249,698, filed Sep. 29, 2021, U.S. Provisional Application No. 63/282,351, filed Nov. 23, 2021, U.S. Provisional Application No. 63/284,839, filed Dec. 1, 2021, U.S. Provisional Application No. 63/288,859, filed Dec. 13, 2021, U.S. Provisional Application No. 63/295,968, filed Jan. 3, 2022, U.S. Provisional Application No. 63/297,290, filed Jan. 7, 2022, U.S. Provisional Application No. 63/298,241, filed Jan. 11, 2022, U.S. Provisional Application No. 63/311,673, filed Feb. 18, 2022, U.S. Provisional Application No. 63/347,506, filed May 31, 2022, U.S. Provisional Application No. 63/391,453, filed Jul. 22, 2022, U.S. Provisional Application No. 63/369,589, filed Jul. 27, 2022, U.S. Provisional Application No. 63/369,900, filed Jul. 29, 2022, U.S. Provisional Application No. 63/370,209, filed Aug. 2, 2022, U.S. Provisional Application No. 63/370,486, filed Aug. 4, 2022, U.S. Provisional Application No. 63/370,912, filed Aug. 9, 2022, and U.S. Provisional Application No. 63/370,994, filed Aug. 10, 2022, each of which is incorporated by reference herein in its entirety.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND

The stochastic nature of cell processes has long plagued biological manufacturing efforts. This has been particularly true of processes in mammalian cells that involve phenotype transitions, for example induced pluripotent stem cell (iPSC) reprogramming or stem cell differentiation into targets cells or trans-differentiation. Additionally, processes including gene editing, which may be combined with the above processes, add yet more process variability. Finally, patient-specific processes, such as those for autologous cell therapies or patient-specific drug discovery, are notoriously unpredictable. As a result, many cell processes are so variable, low-yielding, and/or labor intensive that they do not reach the clinic. Even if they do, the low yields, labor requirements, required purification and sorting steps, and multiple transfers between cell culture containers make the process extremely expensive and unscalable to a large patient population.

One current approach for large scale biological manufacturing involves the use of large bioreactors, such as stirred bioreactors, in which cells are cultured in suspension, often in clumps/aggregates or on microcarriers. However, yields from such bulk processes are typically inefficient, manually managed 2-dimensional cell culture vessels. The advantage of the bioreactor approach is sheer volume of cells, but the process has virtually no feedback control to account for lot-to-lot, patient-to-patient or clone-to-clone variability. Filtration steps may be added to refine the cell product, but these often reduce the viability or functionality of the cell product and can have enormous yield impacts. A deviation in cell behavior early in the process may cause catastrophically low yield or performance on quality control (QC) assays and is almost never detectable until the end of the process.

The manual approach in 2D cell culture vessels seeks to address this variability by adding a highly-trained operator or scientist to make observations and "edits" to the cell culture. Most often these edits take the form of selective transfer from one culture container/vessel to another, repeated on a regular basis as the cell culture grows to maximum density, often due to the growth of undesirable cells alongside the target cells. While this manual process can eliminate gross deviations in the cell culture process, the subjective decision making (often based on single timepoint views through a dissection microscope), manual mechanical manipulation of cells and colonies, and frequent transfer between cell culture containers make this process expensive, unscalable, and prone to a high degree of variability and subject to contamination unless performed in dedicated, expensive, high-grade cleanroom facilities. Automation would solve some of these issues, but objective evaluation of the quality of cell cultures during the cell culture process is lacking. Thus, a fast, accurate, automated, and scalable system for biological manufacturing is needed.

SUMMARY

Disclosed herein are platforms, systems, and methods for biological manufacturing. Various implementations of the present disclosure provide distinct advantages over the conventional cell culture process such as automated cell culture for more efficient manufacturing, enhanced cell/colony imaging techniques for detection of cell quality features without invasive labeling, machine learning image analysis for objective determination of cell product quality, closed-environment cell culture systems allowing end-to-end sterile manufacturing, improved cell culture editing for selection of high quality cell products, and scalable/modular cell culture systems for more efficient manufacturing. Components and subsystems of the overall platform or system can be implemented individually or in any combination to achieve one or more of these advantages.

Disclosed herein are platforms, systems, and methods including a cell culture system that includes a cell culture container comprising a cell culture, the cell culture receiving input cells, a cell imaging subsystem configured to acquire images of the cell culture, a computing subsystem configured to perform a cell culture process on the cell culture according to the images acquired by the cell imaging subsystem, and a cell editing subsystem configured to edit the cell culture to produce output cell products according to the cell culture process. The subsystems disclosed herein can function as independent systems that provide technical improvements over the conventional cell culture process without requiring the other subsystems. Alternatively, one or more combinations of the subsystems can be integrated within an overall platform or cell culture system to achieve greater synergy in providing a fast, accurate, automated, and scalable system for biological manufacturing.

Disclosed herein are platforms, systems, and methods for automated cell culture. The automated cell culture can be carried out by a cell culture system comprising a cell culture container comprising a cell culture (e.g., a cell culture chamber comprising one or more adherent or semi-adherent cells), the cell culture configured to receive input cells. The cell culture system can include a cell imaging subsystem configured to acquire images of the cell culture. The cell culture system can include a computing subsystem configured to perform a cell culture process on the cell culture. The cell culture process can be computed based on analysis of images acquired by the cell imaging subsystem and/or based on user input (e.g., user selection of a cell colony for destruction or removal based on image analysis indicating the colony as being low quality or undesirable). The image analysis may be performed using one or more machine learning models or algorithms trained to evaluate quality of a cell and/or colony based on features determined to be predictive. The computing subsystem can control a cell editing subsystem to perform the cell culture process. The cell culture process may include addition of fresh media, removal of old media, mixing of media within the cell culture container, poration of target cell membranes (e.g., to enable cellular internalization of reprogramming vector(s)), lysis of target cells or cell colonies, removal of lysed cells or cellular debris, detachment of one or more target cells, collection of detached cells for further non-imaging analysis (e.g., qPCR for gene expression analysis). The cell culture process can be carried out by the cell editing subsystem using one or more mechanisms such as laser, ultrasound, physical/mechanical (e.g., magnetic tool), or any combination thereof. The cell culture container or chamber can be configured within a modular cell culture cassette capable of maintaining a cell culture for extended periods of time within a closed sterile environment without breaching that closed environment. The cell culture system can be a modular cell culture system comprising multiple cell culture cassettes that are stored and maintained within a supporting structure, wherein each cassette can be used to generate a desired cell product. When the cell culture cassettes are configured as closed cell culture environments, their modular nature enables multiple different cell products to be produced without requiring a clean room or only requiring one clean room to store the supporting structure comprising the plurality of modular cell culture cassettes. Each subsystem described herein can be used independently to achieve an improvement of the conventional cell culture process.

Additional implementations disclosed herein include an imaging system. The imaging system can be a standalone system for imaging cell culture or an integrated subsystem of an overall platform or cell culture system. In some implementations, the imaging system includes a cell culture moving relative to the imaging system along a direction of movement, a light source that illuminates the cell culture, one or more sensors configured to detect a plurality of light signals, and a mechanism disposed between the cell culture surface and the sensor configured to generate the plurality of light signals from light transmitted or reflected by the cell culture, wherein the plurality of light signals are representative of cell location and refractive index structure data.

Another aspect provided herein is an imaging and scanning system, comprising: at least one light source illuminating a cell culture sample having cells grown on a growth plane of the cell culture sample; an objective capturing light from the at least one light source passing through the cell culture sample, wherein the objective it tilted at an angle with respect to a perpendicular axis of the growth plane; and one or more sensors to measure the light from the objective; wherein the cell culture sample is moved relative to the imaging and scanning system such that the imaging system generates images at multiple heights along the perpendicular axis of the growth plane. In some implementations, the system further comprises: a laser pulse generated by a laser source and incident on the cell culture sample; and an acousto-optic deflector/modular to adjust an incident angle of the laser pulse relative to the perpendicular axis of the growth plane; wherein the cell culture sample is moved relative to the imaging and scanning system such that the laser pulse is capable of focusing on any part of the growth plane. The imaging and scanning system can be a standalone system for imaging and scanning cell culture or an integrated subsystem of an overall platform or cell culture system.

Another aspect provided herein is a cell culture chamber, comprising: fluid media between a first wall and a second wall, wherein the second wall is flexible; a cell culture adherent or semi-adherent on the inside of the first wall; and a first actuator configured to push against the second wall to create a constricted region in the cell culture chamber; and a mechanism to create a high velocity flow through the constricted region, causing dislodging of cells or cell debris from the first wall. In some implementations, the mechanism comprises a pump that pumps the fluid media through the constricted region. In some implementations, the cell culture chamber is sealed and the mechanism comprises a second actuator that pushes against the second wall to force the fluid media through the constricted region. The cell culture chamber can be a standalone chamber used for cell culturing or an integrated component of an overall platform or cell culture system.

Another aspect provided herein is a cell culture chamber, comprising: fluid media between a first wall and a second wall, wherein the second wall is flexible; a cell culture adherent or semi-adherent on the inside of the first wall; and at least one acoustic transducer configured to apply acoustic waves to the cell culture chamber, causing dislodging of cells or cell debris from the first wall. In some implementations, the at least one acoustic transducer is located on the outside of the cell culture chamber proximate to the first wall and applies the acoustic towards the first wall in a direction perpendicular to a plane of the first wall. In some implementations, the at least one acoustic transducer comprises two acoustic transducers coupled to the outside of the first wall and configured to create local distortions perpendicular to the plane of the first wall using the acoustic waves.

Further implementations include a method of controlling a cell culture system, including receiving, at a plurality of points of time, a plurality of images of a cell culture, identifying a plurality of cells from the plurality of images, identifying one or more cell colonies from the plurality of cells, tracking the one or more cell colonies through the plurality of points of time, predicting an outcome of the one or more cell colonies, and editing the cell culture based on the predicted outcomes of the one or more cell colonies.

Another aspect provided herein is a method of classifying image data in a cell culture system, comprising: growing one or more cell cultures of a first cell type; obtaining image data of the one or more cell cultures; generating, by an unsupervised learning engine, a plurality of visual categories for the first cell type from the image data; associating, by the unsupervised learning engine, the plurality of visual categories with a plurality of attribute categories; and labeling, by an unsupervised inference engine, the image data with the plurality of attribute categories. In some implementations, the image data is label-free. In some implementations, the method further comprises: acquiring assay data from the one or more cell cultures; and utilizing the assay data to associate the plurality of visual categories with a plurality of attribute categories. In some implementations, the method further comprises: obtaining labeled image data of the one or more cell cultures; and utilizing the labeled image data to associate the plurality of visual categories with a plurality of attribute categories.

Another aspect provided herein is a method producing cells in a cell culture system, comprising: growing one or more cell cultures of a first cell type; obtaining image data of the one or more cell cultures; generating, by an unsupervised inference engine, one or more attribute maps from the image data, wherein each attribute map comprises an image of a cell culture annotated with cell attributes; determining one or more actions based on the one or more attribute maps. In some implementations, the cell attributes are associated with visual categories identifiable in the image data. In some implementations, the one or more actions comprise lysing select cells in the one or more cell cultures, collecting assays on select cells in the one or more cell cultures, or changing parameters of cell growth of the one or more cell cultures.

Provided herein is a cell culture system, comprising: a cell culture chamber having a first surface; one or more cells in an interior of the cell culture chamber and adhered to the first surface; an imaging subsystem configured to collect images of the one or more cells; a computing subsystem configured to select a subset of cells for analysis based on the images; a cell editing subsystem for dislodging the subset of cells from the first surface; a mechanism to remove the subset of cells from the cell culture chamber for analysis.

Another aspect provided herein is a method of cell extraction and analysis in a cell culture system, comprising: growing a cell culture in a cell culture container; obtaining one or more images of the cell culture; identifying one or more cells to extract from the cell culture based on the one or more images; extracting the identified cells from the cell culture chamber; and analyzing the extracted cells. In some implementations, the method further comprises adjusting a cell culture process for the cell culture based on the analysis. In some implementations, the steps of growing, obtaining, extracting, and analyzing is performed by an automated cell culture system. In some implementations, the step of identifying is performed by a person.

Another aspect provided herein is a cell culture chamber, comprising: a cell bearing surface; a plurality of cells grown on the cell bearing surface; and a resonant optical film located on the cell bearing surface. In some implementations, the resonant optical film absorbs more than 5% of incident light at a cell editing optical wavelength. In some implementations, the resonant optical film absorbs less than 20% of incident light at a cell imaging optical wavelength. In some implementations, the resonant optical film has physical features smaller than 50% of the cell imaging optical wavelength. In some implementations, there is a foil with a resonant optical film on the cell bearing surface, the foil inserted into the cell culture chamber. In some implementations, the foil is a membrane with pores. In some implementations, the resonant optical film has a resonant absorption peak at 532 nanometers (nm) and/or 1064 nm. In some implementations, the resonant optical film comprises gold nano-islands attached to an optically transparent material selected from the following: glass, cyclic olefin copolymer, polystyrene, polycarbonate, polyethylene terephthalate. In some implementations, the gold nano-islands have a mean diameter less than 50 nm along at least one axis.

Another aspect disclosed herein is a cassette system for cell culture processing, comprising: a) one or more cell culture chambers, each cell culture chamber configured to: i) provide a growth environment for adherent cell cultures; and ii) allow imaging of the adherent cell cultures grown in the cell culture chamber; and b) a liquid system coupled to the one or more cell culture chambers, wherein the liquid system is configured to: i) provide input fluid media to the one or more cell culture chambers; and ii) receive output fluid media from the one or more cell culture chambers; wherein the liquid system is configured to provide a closed, sterile liquid environment for the adherent cell cultures in each cell culture chamber. In some implementations, at least one of the input fluid media and the output fluid media comprises at least one of growth media, reagents, buffers, fluid waste, and cell collection media. In some implementations, the liquid system comprises one or more reservoirs for holding different types of fluid media. In some implementations, the cassette system further comprises at least one pump for directing the input fluid media, the output fluid media, or both through the liquid system. In some implementations, the at least one pump is bidirectional. In some implementations, each cell culture chamber comprises a first semi-transparent surface to allow for imaging of the adherent cell cultures. In some implementations, each cell culture chamber is further configured to allow removal of cells from the cell culture chamber using a cell editing mechanism. In some implementations, the cell editing mechanism is configured to direct laser energy, ultrasound, or mechanical forces upon the cell culture chamber to effectuate removal of cells. In some implementations, the laser energy comprises pulsed laser light. In some implementations, the first semi-transparent surface comprises a coating configured to absorb the laser energy at one or more wavelengths and convert the laser energy into thermal or mechanical energy to remove cells. In some implementations, at least one of the one or more cell culture chambers has a cell growth area of at least 50 $cm^2$. In some implementations, at least one of the one or more cell culture chambers is completely filled with fluid media. In some implementations, an internal height of at least one of the one or more cell culture chambers is less than 1 millimeter. In some implementations, the system further comprises: a) one or more sensors; and b) a processor configured to communicate with the one or more sensors and a process module hosting the cassette system via a pluggable connector. In some implementations, the cassette system is removably coupled to the process module. In some implementations, the cassette system is configured for insertion into the process module in a first orientation, a second, inverted orientation, or both. In some implementations, the one or more sensors comprise a temperature sensor, a humidity sensor, a gas-phase oxygen concentration sensor, a gas-phase carbon dioxide concentration sensor, a dissolved oxygen concentration sensor, a dissolved carbon dioxide concentration sensor, a gas flow rate sensor, a liquid flow rate sensor, a pH sensor, an optical absorption sensor, an optical scattering sensor, a mass spectroscopic sensor, a viscosity sensor, or any combination thereof. In some implementations, each cell culture chamber comprises a gas-permeable surface. In some implementations, the liquid system provides the input fluid media, receives the output fluid media, or both, via a one-time aseptic connector, a one-time aseptic disconnector, a reusable non-aseptic connector, or any combination thereof. In some implementations, the system further comprises a mixing and exchange section configured to: a) mix a circulated fluid comprising the input fluid, the output fluid, or both; b) control a concentration of a dissolved gas in the circulated fluid; or c) control a temperature of the one or more cell culture chambers. In some implementations, the mixing and exchange section comprises a liquid feedback mechanism, a gas exchange mechanism, or both. In some implementations, the system further comprises a sensing section configured to monitor a condition of the input fluid media, the output fluid media, or both. In some implementations, the liquid system is configured to provide the input media to each cell culture chamber at a velocity flow that applies a continuous or directional shear stress of less than about 10 dyne/$cm^2$ to the adherent cell culture. In some implementations, each adherent cell culture chamber comprises a registration mark, and wherein the imaging of the adherent cell cultures captures an image of the registration mark. In some implementations, the cassette system comprises a single-use portion and a permanent portion comprising a reusable housing enclosing the single-use portion, wherein the single-use portion comprises the one or more cell culture chambers and the liquid system. In some implementations, the single-use portion comprises one or more bags or chambers for holding media reagents, waste products, or cellular products. In some implementations: a) the input fluid media is provided to the one or more cell culture chambers via a first valve; b) the output fluid media is received from the one or more cell culture chambers via a second valve; or c) both. In some implementations, imaging the cell cultures comprises transmission imaging, reflection imaging, brightfield imaging, darkfield imaging, phase imaging, differential interference contrast (DIC) imaging, quantitative phase imaging (QPI), transmission Fourier ptychographic imaging, reflection transmission Fourier ptychographic imaging, holographic imaging, or any combination thereof.

Another aspect disclosed herein is a cell culture system, comprising: a) a cell culture chamber having a first surface, a second surface, and an interior between the first surface and the second surface; b) a plurality of cells in the interior of the cell culture chamber and adhered to the first surface; c) a magnetic tool in the interior of the cell culture chamber; d) a magnetic component located exterior to the cell culture chamber, the magnetic component magnetically coupled to the magnetic tool; and e) an actuator removably coupled to the magnetic component and configured to move the magnetic component in one or more directions, wherein moving the magnetic component also moves the magnetic tool in the same manner. In some implementations, the actuator is configured to translate and/or rotate the magnetic component, thereby translating and/or rotating the magnetic tool. In some implementations, the translation and/or rotation of the magnetic tool inside the cell culture chamber agitates fluid media inside the cell culture chamber. In some implementations, the agitation dislodges cells, cell components, or cell products from the first surface and/or moves cells, cell components, or cell products floating in the fluid media around the cell culture chamber. In some implementations, the magnetic tool makes physical contact with one or more cells in the plurality of cells to dislodge them from the first surface. In some implementations, the system further comprises an imaging subsystem configured to capture images of the plurality of cells. In some implementations, the system further comprises a computing subsystem configured to: a) identify one or more cells in the plurality of cells for removal based on the images; and b) control the actuator to move the magnetic tool to remove the one or more cells. In some implementations, the imaging system is further configured to capture images of the magnetic tool. In some implementations, the computing subsystem identifies the one or more cells using a machine learning algorithm. In some implementations, the computing subsystem is further configured to control a velocity, an orientation, a path, or any combination thereof of the actuator. In some implementations, the computing subsystem is further configured to control a magnetic pole alignment of the actuator. In some implementations, the computing subsystem is further configured to: a) engage the actuator with the first surface of the cell culture chamber; b) engage the actuator with the second surface of the cell culture chamber; c) disengage the actuator with the first surface of the cell culture chamber; d) disengage the actuator with the second surface of the cell culture chamber; or e) any combination thereof. In some implementations, the system further comprises a cell culture container enclosing the cell culture chamber, wherein the cell culture container controls fluid media into and out of the cell culture chamber in a closed loop, sterile environment. In some implementations, the cell culture container encloses a plurality of cell culture chambers. In some implementations, the magnetic tool contacts the first surface and the magnetic component rests on the exterior of the first surface. In some implementations, the magnetic tool contacts the second surface and the magnetic component rests on the exterior of the second surface. In some implementations, at least a portion of the magnetic tool and/or magnetic component is coated with a polymer. In some implementations, the polymer is configured to make a surface of the magnetic tool and/or magnetic component that contacts the cell culture chamber inert, biocompatible, non-stick, non-scratching, or any combination thereof. In some implementations, the cell culture chamber has a growth area of at least about 50 $cm^2$. In some implementations, the cell culture chamber has a chamber height of less than about 3 mm. In some implementations, the magnetic tool further comprises a blade configured to lift one or more of the plurality of cells from the first surface, the second surface, or both. In some implementations, the blade comprises a low angle edge configured for non-destructive incremental lifting of one or more of the plurality of cells. In some implementations, the blade comprises a high angle edge configured to lyse and/or destroy one or more of the plurality of cells. In some implementations, at least a portion of the magnetic tool is flexible.

Another aspect disclosed herein is a modular bioprocessing system, comprising: a) one or more process modules, each process module configured to manage and monitor a cell culture process; b) a server rack, wherein the one or more process modules are removably located on the server rack; and c) one or more shared subsystems on the server rack and supporting the one or more process systems. In some implementations, each process module is configured to removably couple to a cell culture cassette hosting the cell cultures via one or more pluggable connectors. In some implementations, the cell culture process is carried out within a cell culture container comprising a closed cassette system, a micro plate, a flask, a cell culture vessel, a microfluidic chamber, or any combination thereof. In some implementations, the system further comprises a transport mechanism configured to transport the cell culture container between locations within the server rack. In some implementations, the transport mechanism comprises a rail, a linear actuator, a motor, a bearing, a wheel, or any combination thereof. In some implementations, the transport mechanism is configured to provide horizontal and/or vertical transportation of the cell culture container. In some implementations, the closed cassette system comprises at least one transparent or semi-transparent surface that allows for light or laser-based imaging and editing. In some implementations, the system further comprises a front-facing instrument panel configured to receive and/or eject the closed cassette system, the micro plate, the flask, the cell culture vessel, the microfluidic chamber, or any combination thereof. In some implementations, the one or more shared subsystems comprise at least one of a computing subsystem, a data storage subsystem, an environmental control subsystem, a laser source subsystem, and a gas distribution subsystem. In some implementations, the one or more process modules comprises at least one of a cell imaging subsystem, a cell editing subsystem, and a temperature control subsystem. In some implementations, the cell imaging subsystem comprises a brightfield imaging system, a phase imaging system, a quantitative phase imaging system, a transmissive darkfield imaging system, a reflective darkfield, imaging system, a fluorescent imaging system, or any combination thereof. In some implementations, the cell imaging subsystem is configured to capture images of the cell culture process. In some implementations, the one or more shared subsystems comprises a computing subsystem configured to perform a machine learning function to monitor the cell culture process based on the images. In some implementations, the cell editing subsystem is configured to selectively remove one or more cells from the cell culture process. In some implementations, the server rack has one or more standardized computer server rack sizes. In some implementations, the system further comprises a backup power module for providing uninterrupted power to the one or more process modules and the one or more shared subsystems. In some implementations, the system further comprises a temperature control subsystem configured to manage a temperature of at least one of the cell culture process and a reagent. In some implementations, the system further comprises a pH control subsystem configured to manage a pH of the cell culture process. In some implementations, the system further comprises a gas content control subsystem configured to manage a dissolved oxygen and/or carbon dioxide content of at least one of the cell culture process and a reagent. In some implementations, the system further comprises a media control subsystem configured to provide and/or extract a media from at least one of the one or more process modules. In some implementations, the cell culture process comprises cell reprogramming, cell differentiation, cell gene editing, cell incubation, cell expansion, cell sorting or purification, cell-based bioproduction, or any combination thereof. In some implementations, the modular bioprocessing system has a multi-rack configuration comprising a plurality of the server rack.

Another aspect disclosed herein is an imaging system, comprising: a) at least one light source illuminating a sample; b) an objective capturing light from the at least one light source passing through the sample; and c) one or more sensors to measure the light captured by the objective, wherein the sample moves continuously relative to the at least one light source and the objective during the measurement; and d) a computing subsystem configured to generate quantitative phase images of the sample based on the measurements from the one or more sensors. In some implementations, the movement of the sample relative to the at least one light source and the objective during the measurement generates image data at multiple focal planes along an axis perpendicular to a horizontal plane of the sample and the quantitative phase images are generated from the image data at multiple focal planes. In some implementations, the objective is tilted at an angle with respect to the axis. In some implementations, the movement of the sample relative to the at least one light source and the objective during the measurement generates image data at multiple illumination angles relative to the sample and the quantitative phase images are generated from the image data at multiple illumination angles. In some implementations, the at least one light source emits light at multiple wavelengths and different wavelengths illuminate the sample at different angles. In some implementations, the system further comprises a laser source configured to manipulate the sample based on the quantitative phase images. In some implementations, the sample is moved continuously relative to the laser source. In some implementations, the laser source and the one or more light sources share the objective. In some implementations, the sample is a cell culture sample and the laser source is configured to edit the cell culture sample. In some implementations, the cell culture sample is enclosed in a cell culture chamber, the cell culture chamber comprising at least one transparent or semi-transparent surface. In some implementations, the cell culture chamber comprises a transparent upper window and a transparent lower window. In some implementations, the cell culture chamber comprises at least one semi-transparent coating on the at least one transparent surface configured to absorb laser radiation and direct absorbed energy to one or more cells in the cell culture chamber. In some implementations, the system further comprises a film within the cell culture chamber, wherein the film comprises a fiducial marker and wherein the fiducial marker is patterned in the laser absorbing film. In some implementations, the laser source is configured to generate a laser having a wavelength of about 500 nm to about 600 nm or about 1000 nm to about 1100. In some implementations, the laser source is configured to generate a laser having a pulse rate of at least about 100 kHz. In some implementations, the system further comprises a laser autofocus system configured to: a) project a laser from the laser source onto the cell culture; b) move the sample relative to the laser source; c) repeat steps a) and b); d) measure a sharpness of the laser based on the light captured by the objective lens during steps a)-c); and e) focus the laser based on the measured sharpness. In some implementations, the sensor comprises a CMOS sensor, a CCD sensor, or both. In some implementations, the sensor comprises an array of sensors in one or more directions. In some implementations, the computing subsystem is configured to compute structural information on individual cells, groups of cells, or regions or colonies using the quantitative phase images of the sample. In some implementations, the computing subsystem is configured to apply machine learning to analyze the measurements from the one or more samples. In some implementations, the computing subsystem is configured to use a convolutional neural network to reconstruct sample amplitude and phase. In some implementations, the computing subsystem is configured to use a convolutional neural network to reconstruct sample amplitude and phase or determine one or more cell quality features. In some implementations, wherein the system comprises a first light source and a second light source, wherein the first light source and the second light source emit light at different wavelengths.

Another aspect disclosed herein is a method for generating quantitative phase images of a sample, comprising: a) illuminating a sample using at least one light source; b) capturing, with an objective, light from the at least one light source passing through the sample; and c) measuring, with one or more sensors, the light captured by the objective, wherein the sample moves continuously relative to the at least one light source and the objective during the measurement; and d) generating, with a computing subsystem, quantitative phase images of the sample based on the measurements from the one or more sensors.

Another aspect disclosed herein is a monoclonal induced pluripotent stem cell (iPSC) product made by the process comprising: a) placing input cells in a cell culture chamber of a closed cell culture container; b) reprogramming at least a portion of the input cells into a plurality of clonal iPSC candidate cells; c) collecting imaging data on a plurality of clonal iPSC candidate cell colonies emerging from the plurality of clonal iPSC candidate cells; d) selecting one of the plurality of clonal iPSC candidates cell colonies for expansion based on the imaging data; e) removing non-selected clonal iPSC candidate cell colonies using a cell editing mechanism; and f) expanding the selected clonal iPSC candidate cell colony into the monoclonal iPSC product. In some implementations, the imaging data comprises a time-series images of the plurality of clonal iPSC candidate cell colonies. In some implementations, selecting one of the plurality of clonal iPSC candidates cell colonies for expansion comprises: a) applying a predictive model to the image data to predict clonal quality and functionality of each of the plurality of clonal iPSC candidate cell colonies; and b) selecting one of the plurality of clonal iPSC candidates cell colonies based on the predicted clonal quality and functionality of each of the plurality of clonal iPSC candidate cell colonies. In some implementations, the predictive model is trained on prior clonal cell colony data and clonal iPSC product quality and functionality assays. In some implementations, the clonal quality and functionality are determined by based on one or more phenotypic features. In some implementations, the one or more phenotypic features comprise a cell morphology, a cell proliferation rate, a chromatin condensation, a nucleus to cytosol ratio, a cell migration pattern, or any combination thereof. In some implementations, the process further comprises removing contaminant cells in proximity to the plurality of clonal iPSC candidate cell colonies using the cell editing mechanism. In some implementations, the closed cell culture container further comprises a sterile-sealed liquid system for providing fluid media to the cell culture chamber and receiving fluid media from the cell culture chamber. In some implementations, the cell editing mechanism comprises laser radiation. In some implementations, a surface of the cell culture chamber is laser-absorbent. In some implementations, the cell editing mechanism comprises a magnetic tool in the cell culture chamber and actuated from outside the cell culture chamber. In some implementations, the magnetic tool comprises a rare-earth magnet. In some implementations, the cell editing mechanism comprises focused ultrasound waves. In some implementations, the cell editing mechanism comprises directed energy projected from outside the cell culture chamber. In some implementations, the closed cell culture container comprises a single closed cell culture container. In some implementations, the one or more of the input cells comprise a B lymphocytes cell, a blood-derived epithelial cell, a C lymphocytes cell, a cardiac muscle cell, a chondrocyte cell, an endothelial cell, an epidermal cell, an epithelial cell, an erythrocyte cell, a fibroblast cell, a granulosa epithelial cell, a hair follicle cell, a hematopoietic cell, a hepatocyte cell, a keratinocyte cell, a macrophage cell, a melanocyte cell, a monocyte cell, a mononuclear cell, a neuron cell, a pancreatic islet cell, a sertoli cell, a somatic cells, a urine-derived epithelial cell, or any combination thereof. In some implementations, the reprogramming is performed using genome integration, non-genome integration, minicircle vectors, the Sendai protocol, mRNA, self-replicating RNA, CRISPR activators, recombinant proteins, or any combination thereof. In some implementations, the monoclonal iPSC product is transgene-free. In some implementations, the monoclonal iPSC product is suitable for differentiation into a target cell type. In some implementations, the non-selected clonal iPSC candidate cell colonies are determined based on at least a cell division time, a cell high reprogramming cargo load, a cell migration characteristic, a cell speed, a cell trackability, or any combination thereof. In some implementations, the process is performed within a cassette system providing a closed, sterile environment for cell culture processing. In some implementations, the process is performed within a modular bioprocessing system configured to produce a plurality of monoclonal iPSC products corresponding to different subjects.

Another aspect disclosed herein is a method for producing a monoclonal induced pluripotent stem cell (iPSC) product, comprising: a) placing input cells in a cell culture chamber of a closed cell culture container; b) reprogramming at least a portion of the input cells into a plurality of clonal iPSC candidate cells; c) collecting imaging data on a plurality of clonal iPSC candidate cell colonies emerging from the plurality of clonal iPSC candidate cells; d) selecting one of the plurality of clonal iPSC candidates cell colonies for expansion based on the imaging data; e) removing non-selected clonal iPSC candidate cell colonies using a cell editing mechanism; and f) expanding the selected clonal iPSC candidate cell colony into the monoclonal iPSC product.

Another aspect disclosed herein is a cell culture container, comprising: a cell culture chamber enclosing fluid media, wherein the cell culture chamber comprises a first surface interior to the cell culture chamber, wherein the first surface is at least partially transparent; a film attached to the first surface, wherein the film is configured to at least partially absorb a first incident light within a first wavelength range and at least partially transmit a second incident light within a second wavelength range; and a cell culture comprising cells adhered to the film. In some implementations, the second incident light within the second wavelength range is used for performing optical imaging of the cell culture. In some implementations, the film absorbs less than 20% of the second incident light within the second wavelength range. In some implementations, the first incident light within the first wavelength range is used for performing laser editing operations on the cell culture. In some implementations, the laser editing operations further comprise at least one of removal of one or more cells in the cell culture and poration of one or more cells in the cell culture. In some implementations, responsive to providing a pulsed laser having a wavelength within the first wavelength range incident on the first surface, the film absorbs energy from the pulsed laser and forms microbubbles proximal to one or more cells in the cell culture. In some implementations, the microbubbles dislodge the one or more cells from the film. In some implementations, the microbubbles porate the one or more cells, thereby allowing transport of cargo into and out of the one or more cells. In some implementations, the first incident light within the first wavelength range and the second incident light within the second wavelength range are generated by a pulsed laser that is incident on the first surface. In some implementations, the film has a resonant absorption peak between 500 and 600 nanometers. In some implementations, the film further comprises gold nano-islands attached to the first surface. In some implementations, the first surface comprises a material selected from: glass, cyclic olefin copolymer, polystyrene, polycarbonate, and polyethylene terephthalate. In some implementations, the film further comprises one or more fiducial markings thereon. In some implementations, the one or more fiducial markers are used to determine a position of the first surface relative to at least one of an imaging subsystem and a cell editing subsystem. In some implementations: the first surface is configured to be illuminated with the second incident light within the second wavelength range to allow images of the cell culture to be captured without capturing images of the fiducial markings; and the first surface is configured to be illuminated with the first incident light within the first wavelength range to allow images of the fiducial markings to be captured. In some implementations: the film further comprises a plasmonic film having a resonant peak responsive to being irradiated with the first incident light within the first wavelength range. In some implementations, responsive to the plasmonic film being irradiated at the resonant peak at a first location, a spectral response of the plasmonic film contains information indicative of one or more of: cells in the cell culture proximal to the first location, the fluid media proximal to the first location, and adsorbed protein molecules proximal to the first location. In some implementations, the resonant peak does not overlap with the first wavelength range and the second wavelength range. In some implementations, the plasmonic film comprises gold nanoislands. In some implementations, the first surface is transparent.

Another aspect disclosed herein is a cell culture system, comprising: a cell culture container, the cell culture container comprising a cell culture chamber containing a cell culture of a first cell type adhered to a first interior surface of the cell culture chamber, wherein the first interior surface is at least partially transparent; a cell imaging subsystem configured to capture images of the cell culture; a cell editing subsystem configured to perform cell editing operations on the cell culture; and a computer processor programmed to: analyze the images to determine a location and one or more characteristics of a set of cell colonies in the cell culture; identify at least one of the set of cell colonies to be destroyed based at least in part on the location and the one or more characteristics of the set of cell colonies; and control the cell editing subsystem to destroy the identified at least one of the set of cell colonies; and repeat a) to d) as the cell culture undergoes a cell culture process to transform from the first cell type to a second cell type. In some implementations, the cell culture process is a reprogramming process, wherein the first cell type is a somatic cell, and wherein the second cell type is an induced pluripotent stem cell (iPSC). In some implementations, the cell culture process is a differentiation process, wherein the first cell type is an induced pluripotent stem cell (iPSC). In some implementations, the second cell type is a dopaminergic neuron cell or a retinal pigment epithelium cell. In some implementations, the cell culture comprises cells that are adhered to the first interior surface throughout the cell culture process. In some implementations, the cell editing subsystem further comprises a laser processing subsystem configured to generate laser illumination incident on the cell culture chamber. In some implementations, the cell culture comprises cells that are adhered to a film attached to the first interior surface, wherein the film is configured to at least partially absorb a first incident light within a first wavelength range and at least partially transmit a second incident light within a second wavelength range. In some implementations, the cell imaging subsystem is further configured to generate imaging illumination within the second wavelength range. In some implementations, the laser processing subsystem is further configured to generate laser processing illumination within the first wavelength range. In some implementations, responsive to providing a pulsed laser having a wavelength within the first wavelength range incident on the first surface, the film absorbs energy from the pulsed laser and forms microbubbles proximal to one or more cells in the cell culture. In some implementations, the microbubbles dislodge the one or more cells from the film. In some implementations, the microbubbles porate the one or more cells, thereby allowing transport of cargo into and out of the one or more cells. In some implementations, the cell imaging subsystem is further configured to generate quantitative phase images of the cell culture. In some implementations, the cell imaging subsystem is further configured to perform label-free capture of the images of the cell culture. In some implementations, the computer processor is further programmed to use one a machine learning algorithm to determine the one or more characteristics of the set of cell colonies. In some implementations, the computer processor is further programmed to use a machine learning algorithm to identify the at least one of the set of cell colonies to be destroyed. In some implementations, the cell culture chamber is a sterile, sealed fluidic chamber. In some implementations, the cell culture container is a closed cassette. In some implementations, the cell culture system further comprises a plurality of cell culture containers. In some implementations, each individual cell culture container of the plurality of cell culture containers comprising an individual cell culture chamber containing an individual cell culture of a cell type adhered to an individual interior surface of the individual cell culture chamber, wherein the individual interior surface is at least partially transparent. In some implementations, at least one of the cell imaging subsystem, the cell editing subsystem, and the computer processor are shared among the plurality of cell culture containers.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative implementations, in which the principles of the disclosure are utilized, and the accompanying drawings of which:

Figure 99A:
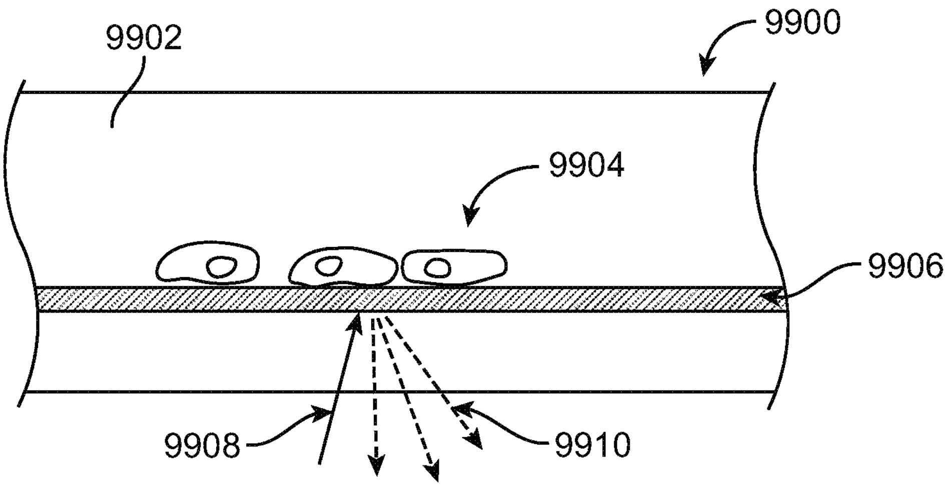
Figure 99B:
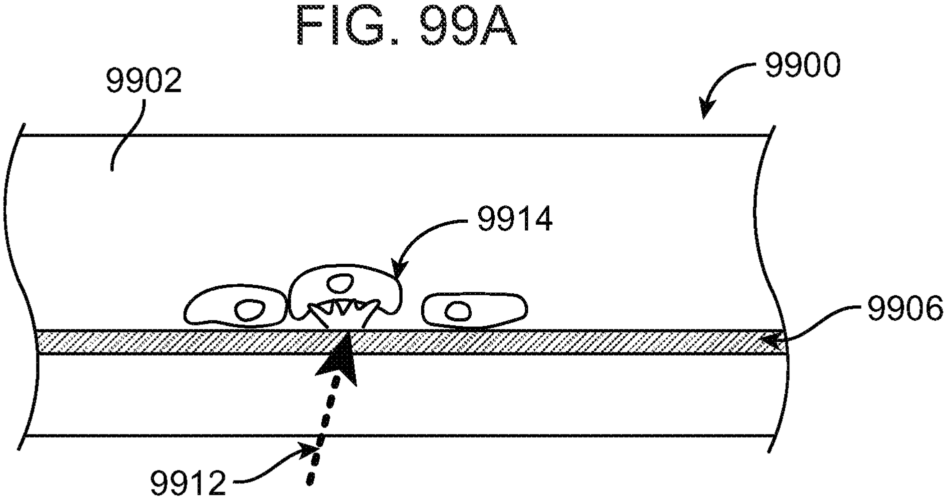
Figure 99C:
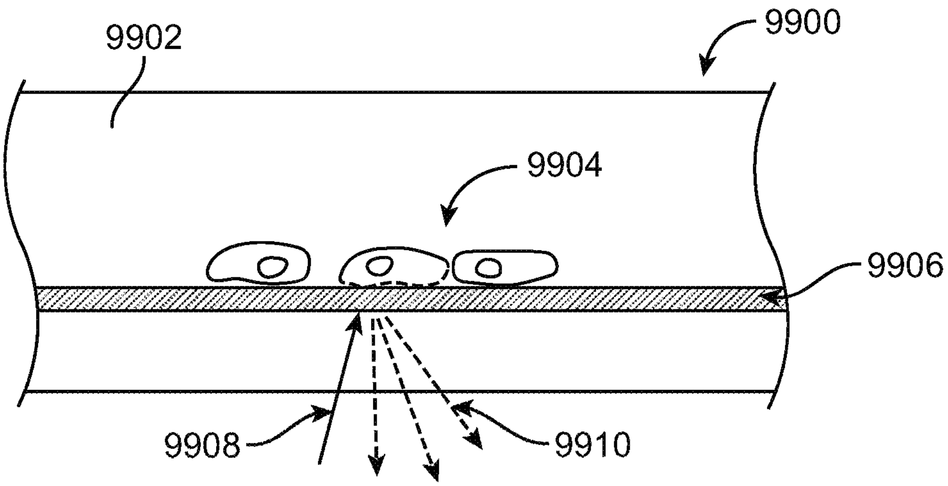
Figure 100:
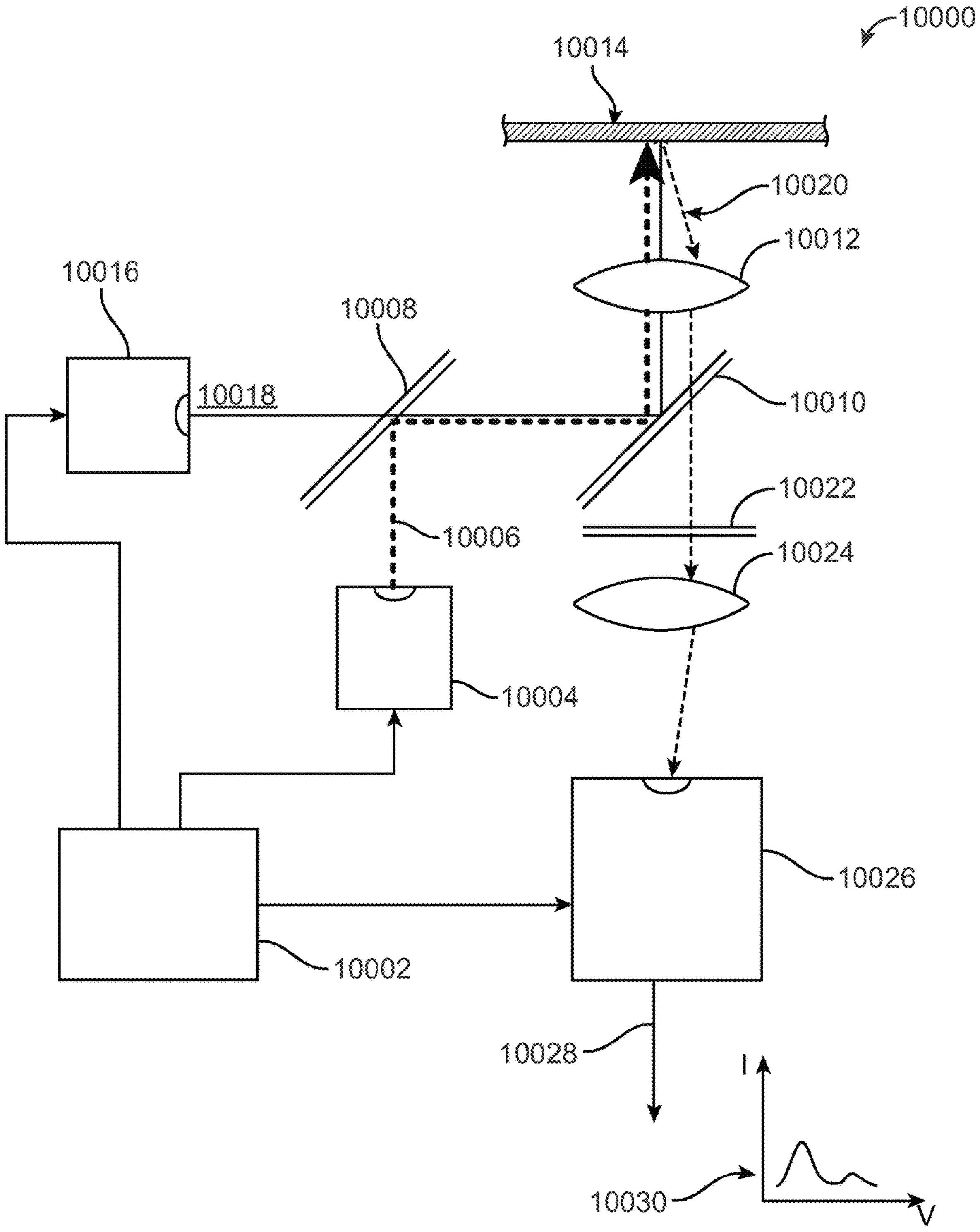
Figure 101:
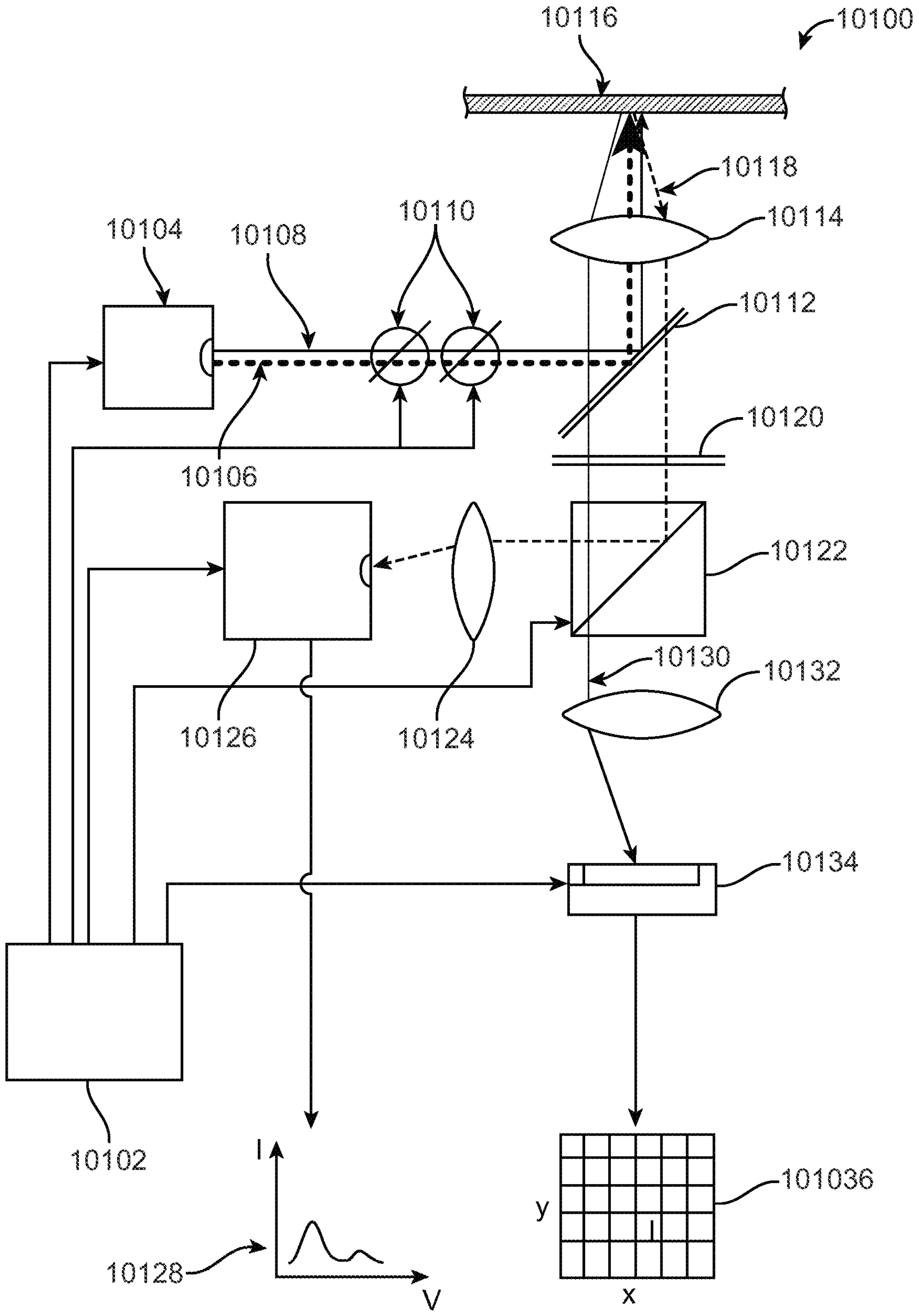
Figure 102:
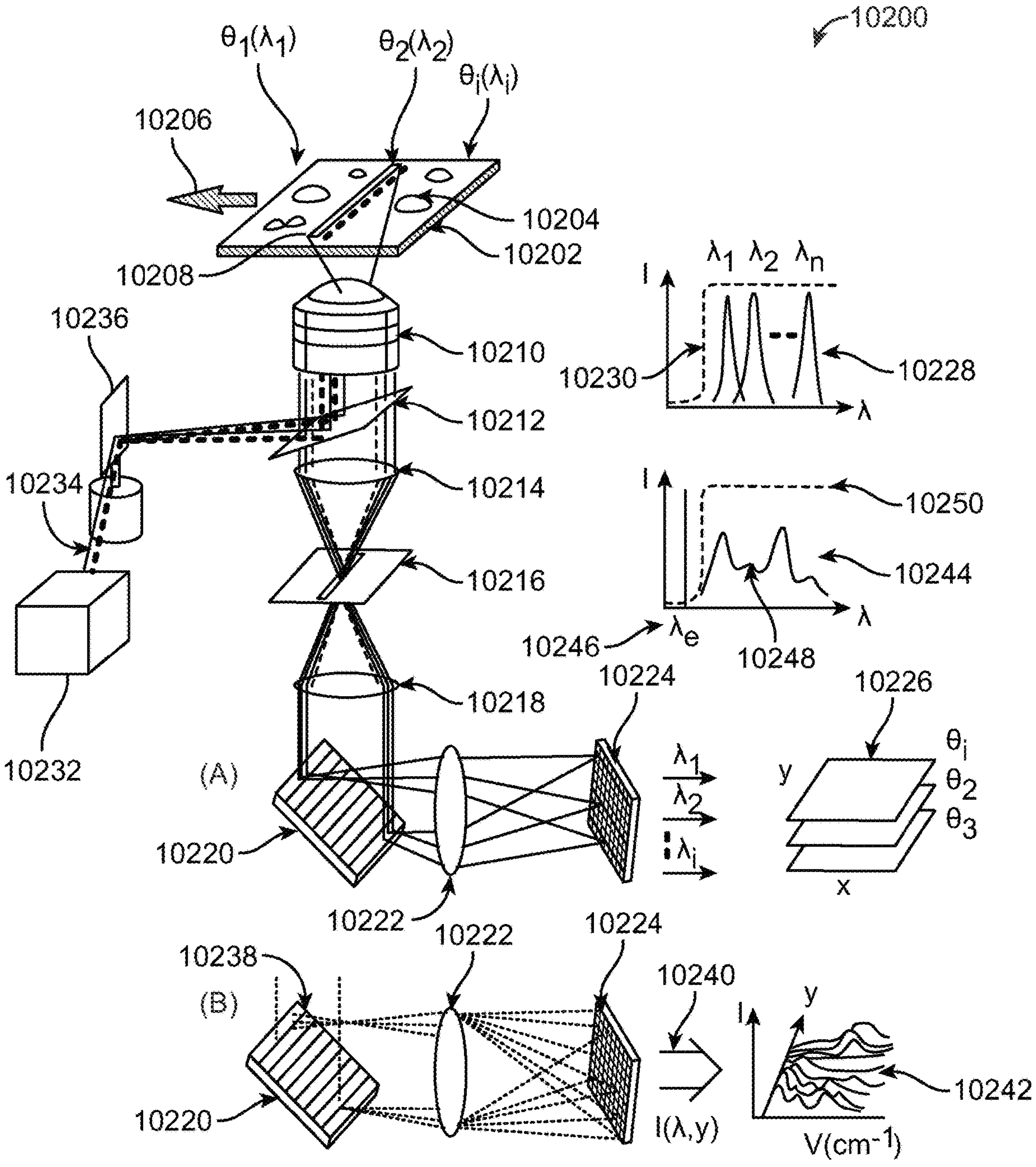
Figure 103:
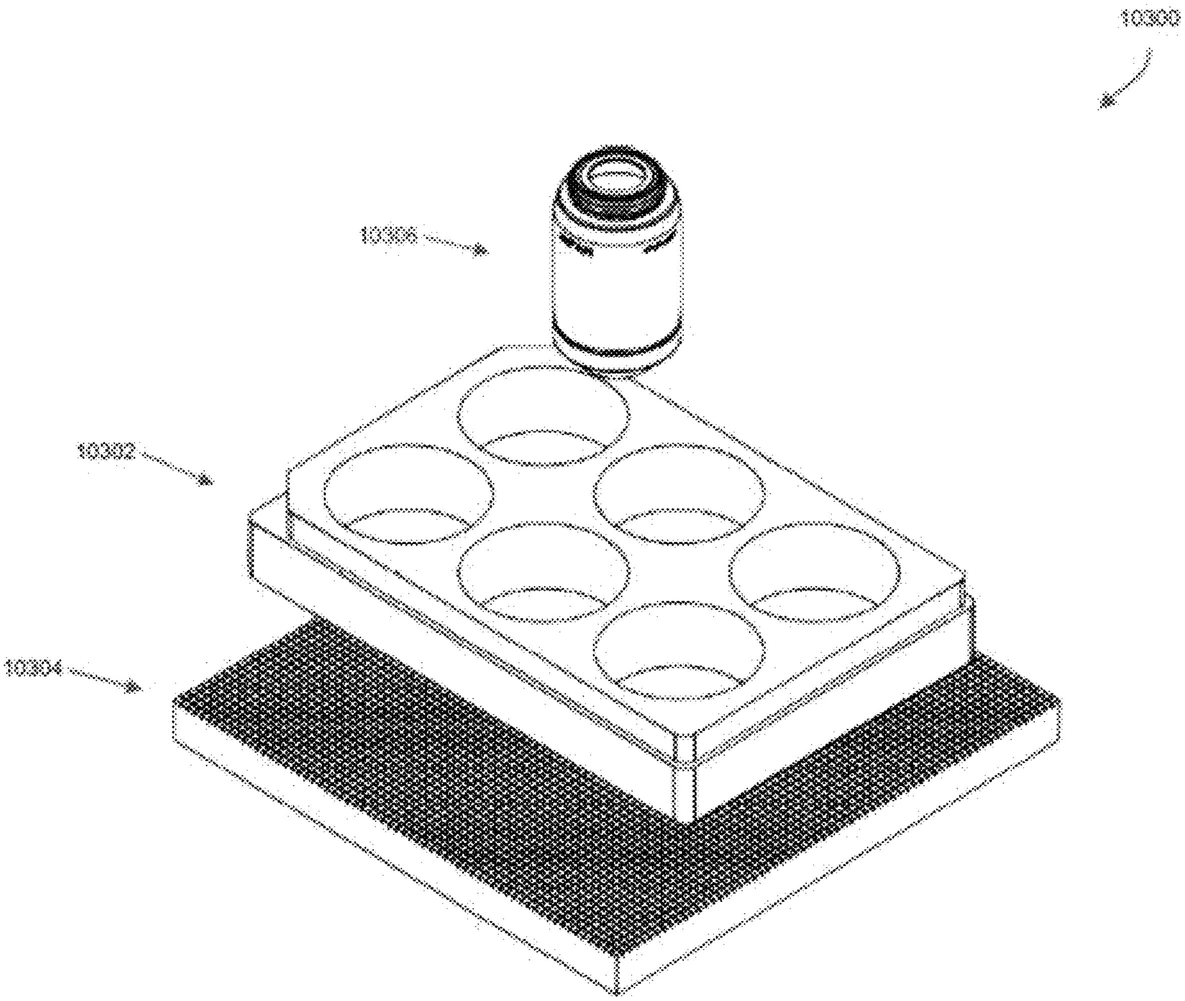

FIGS. 97A-D are diagrams depicting use of SERS to measure contents in a cell culture container in accordance with various implementations;

FIGS. 98A-F are diagrams depicting laser clearing of a cell culture container film during SERS measurement in accordance with various implementations;

FIGS. 99A-C are diagrams depicting poration of cells in a cell culture container during SERS measurement in accordance with various implementations;

FIG. 100 is a block diagram of an example SERS subsystem for use in a cell culture system in accordance with various implementations;

FIG. 101 is a block diagram of another example SERS subsystem for use in a cell culture system in accordance with various implementations;

FIG. 102 is a block diagram of another example SERS subsystem for use in a cell culture system in accordance with various implementations;

FIG. 103 is a diagram of an imaging subsystem in accordance with various implementations.

Figure 104:
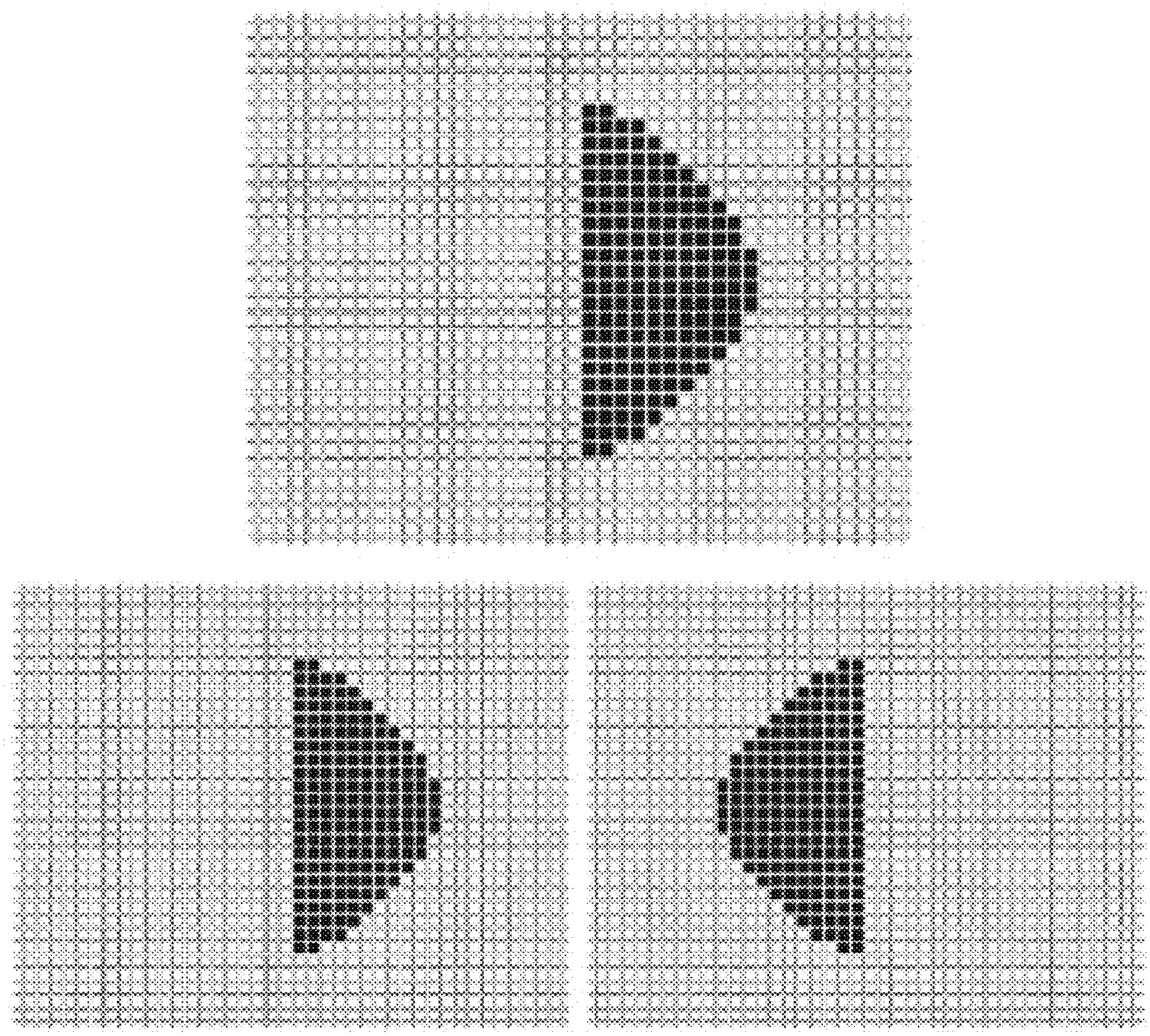
Figure 105:
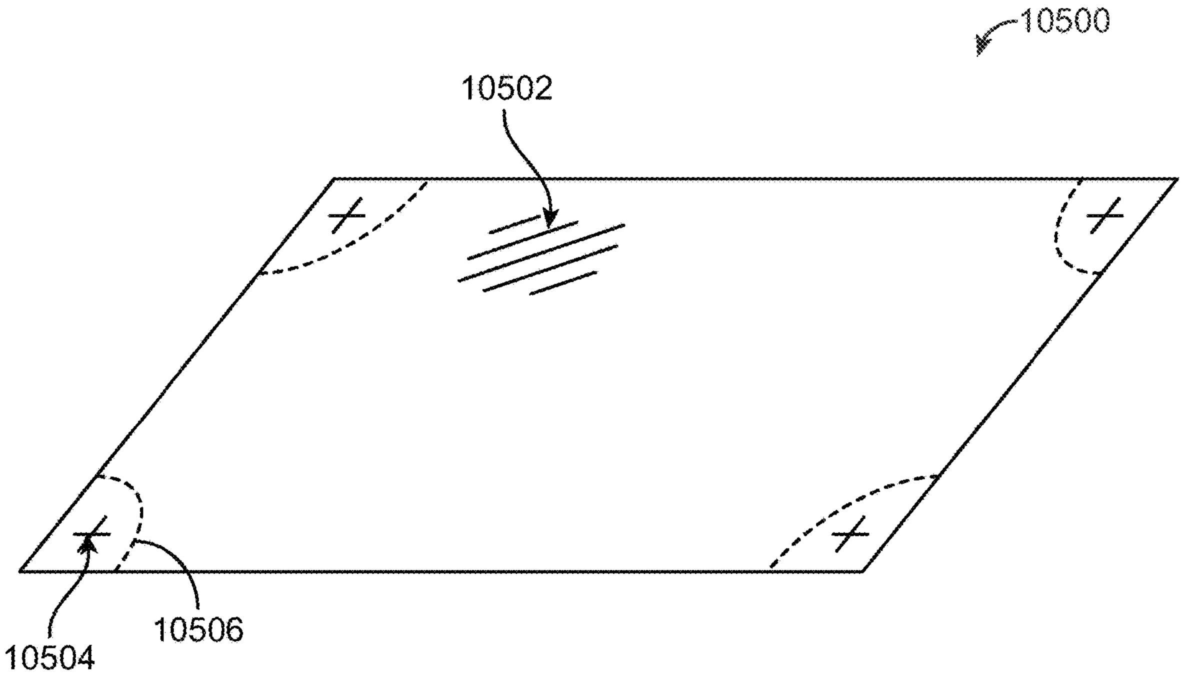
Figure 106A:
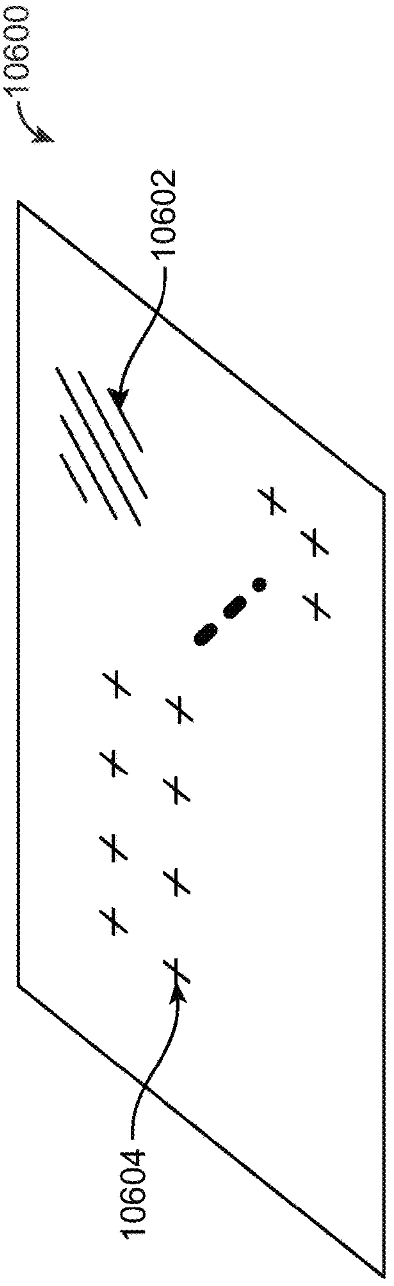
Figure 106B:
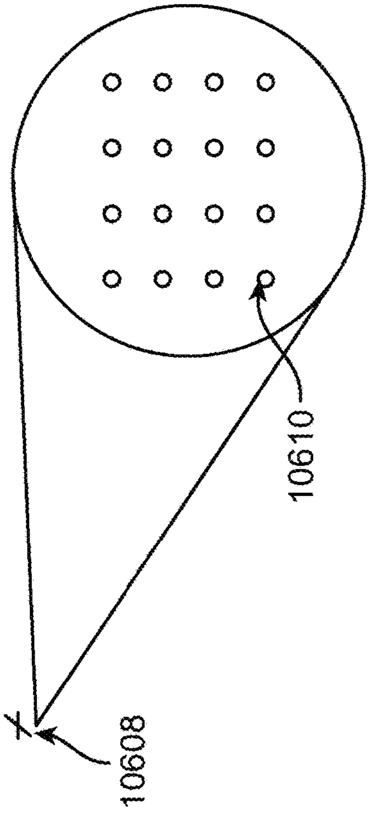
Figure 106C:
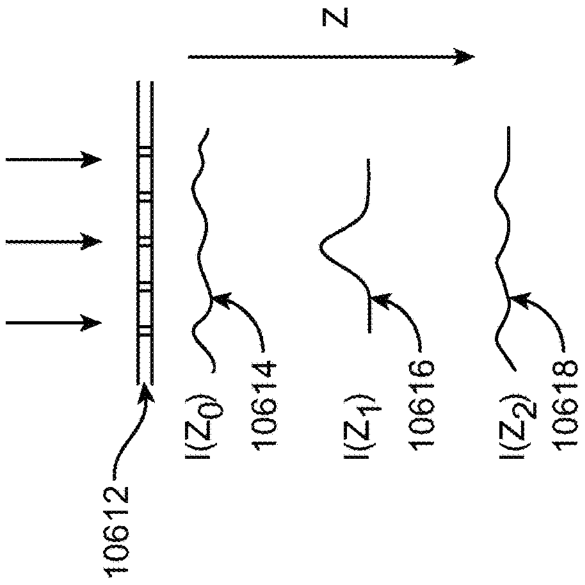
Figure 107:
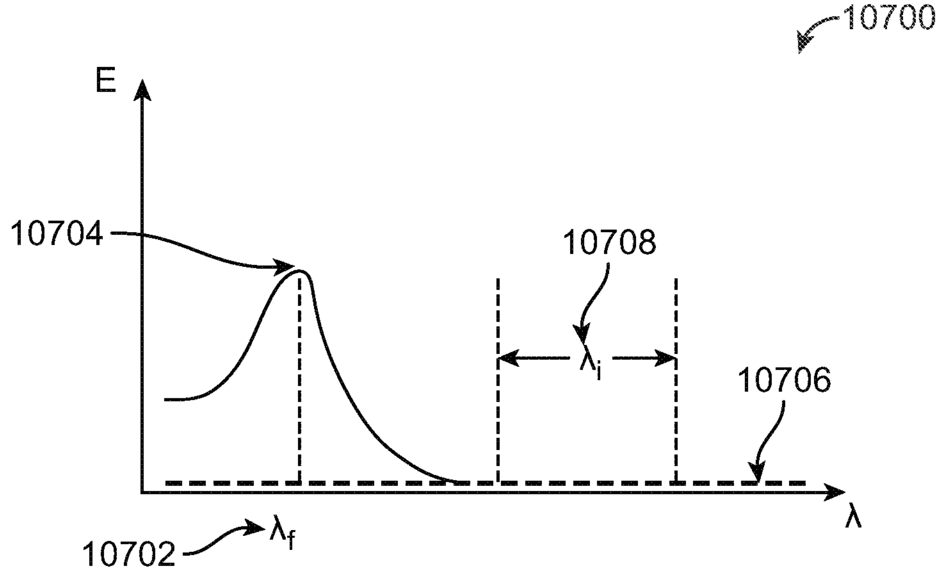
Figure 108:
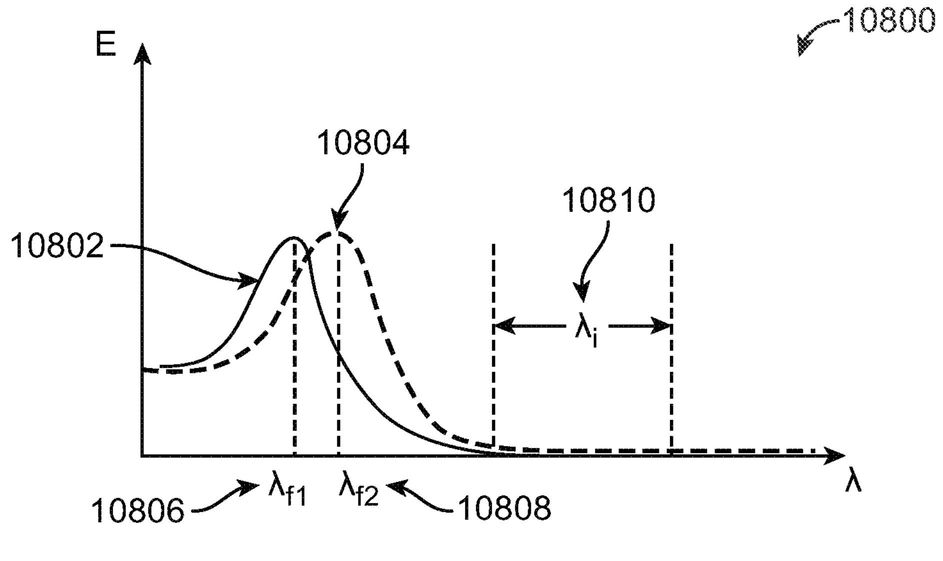
Figure 109:
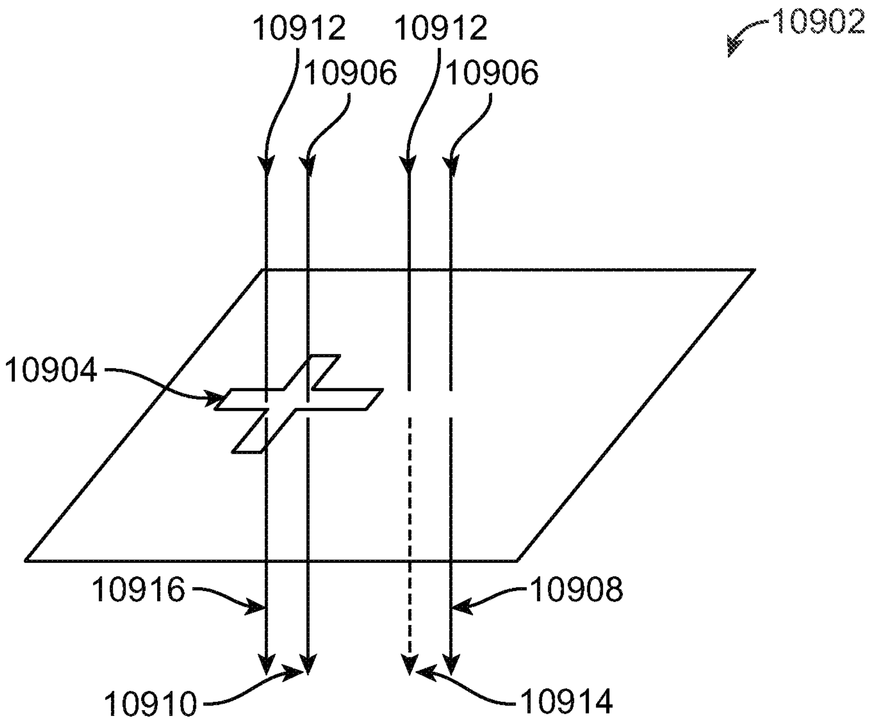
Figure 110:
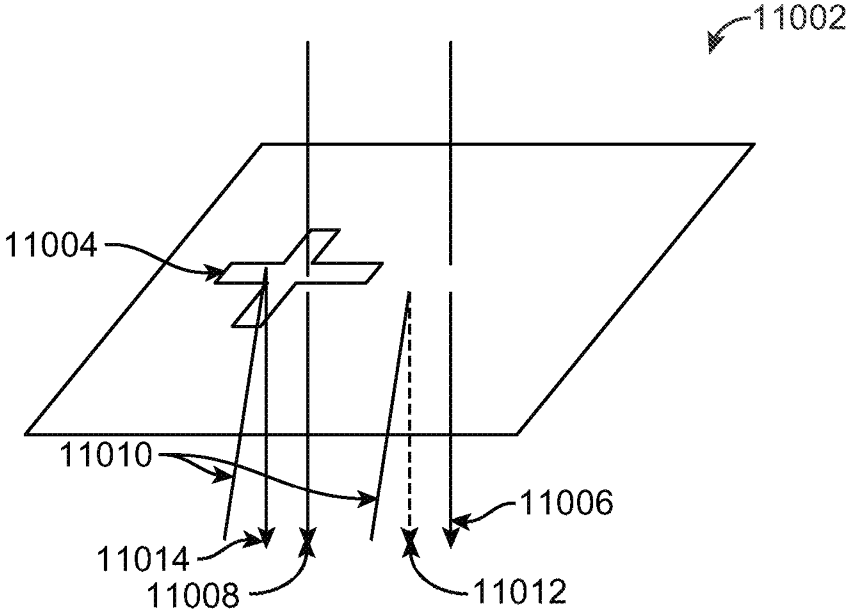
Figure 111:
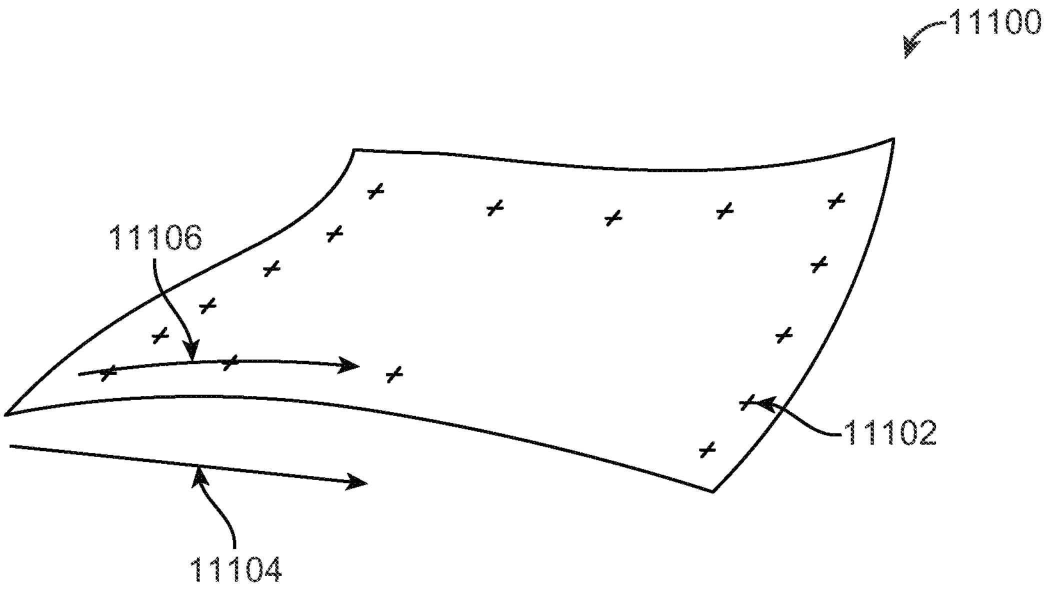
Figure 112:
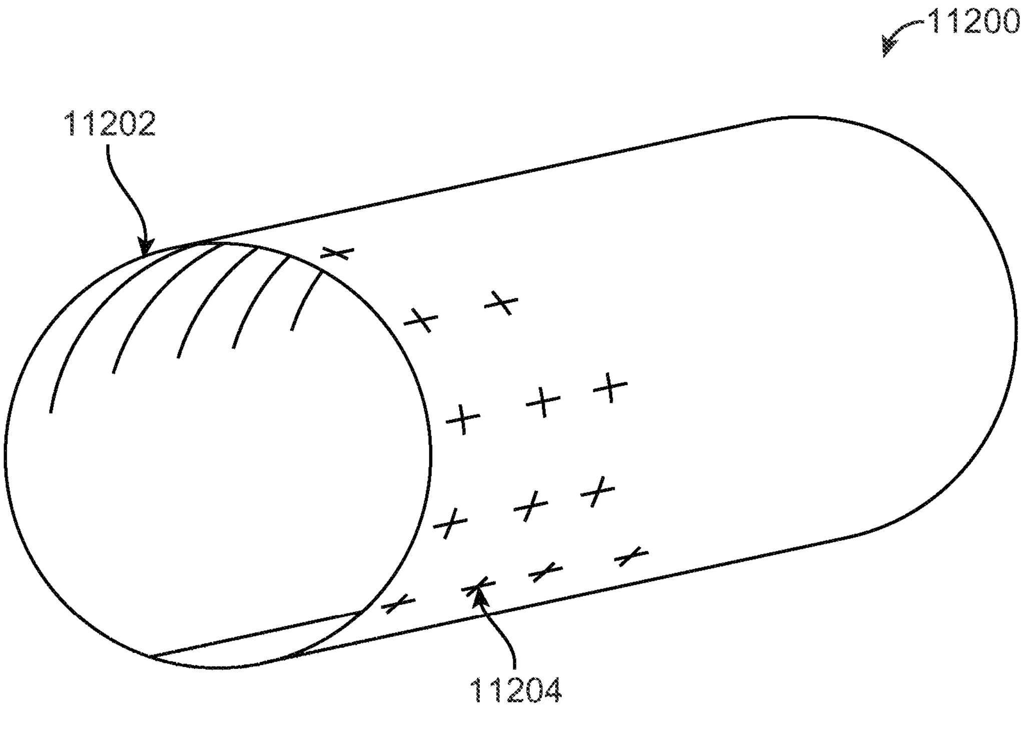
Figure 113:
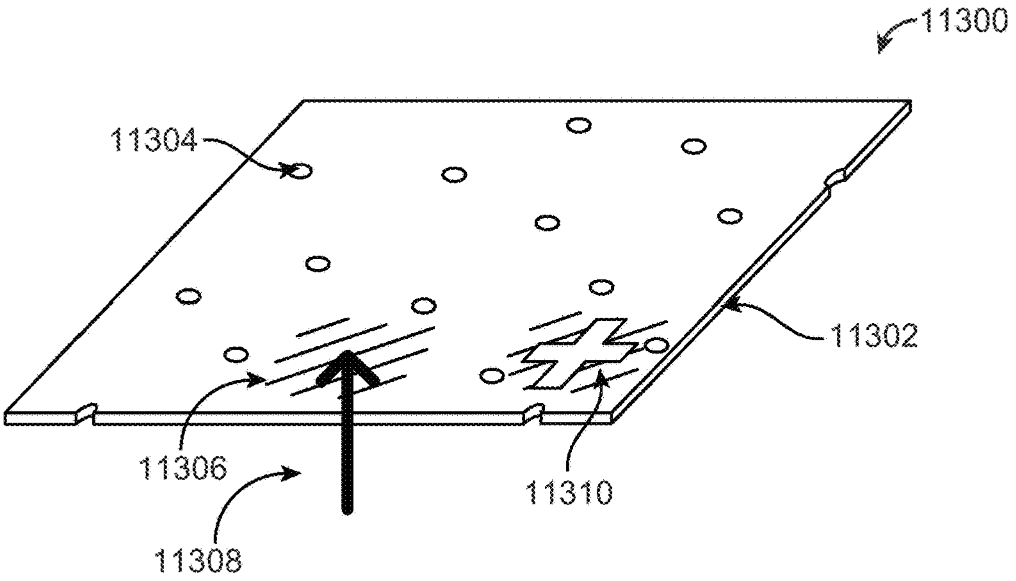
Figure 114:
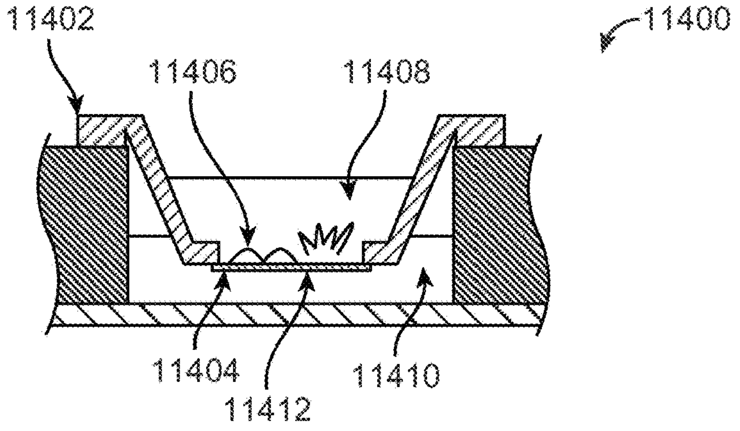
Figure 115:
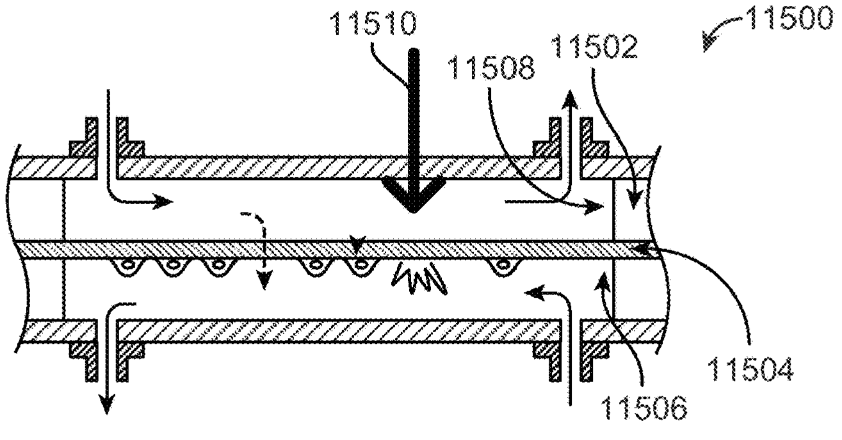
Figure 116:
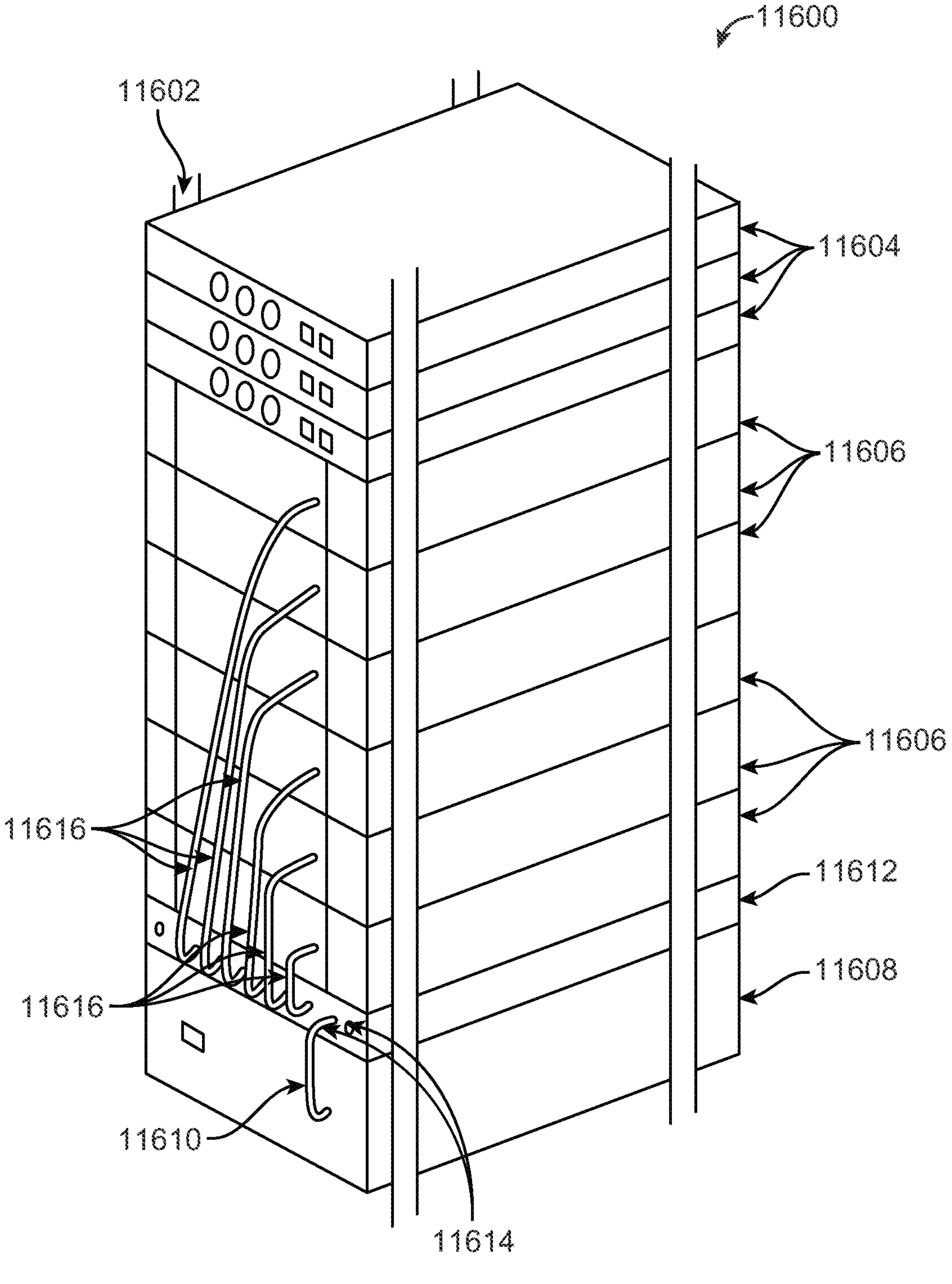
Figure 117:
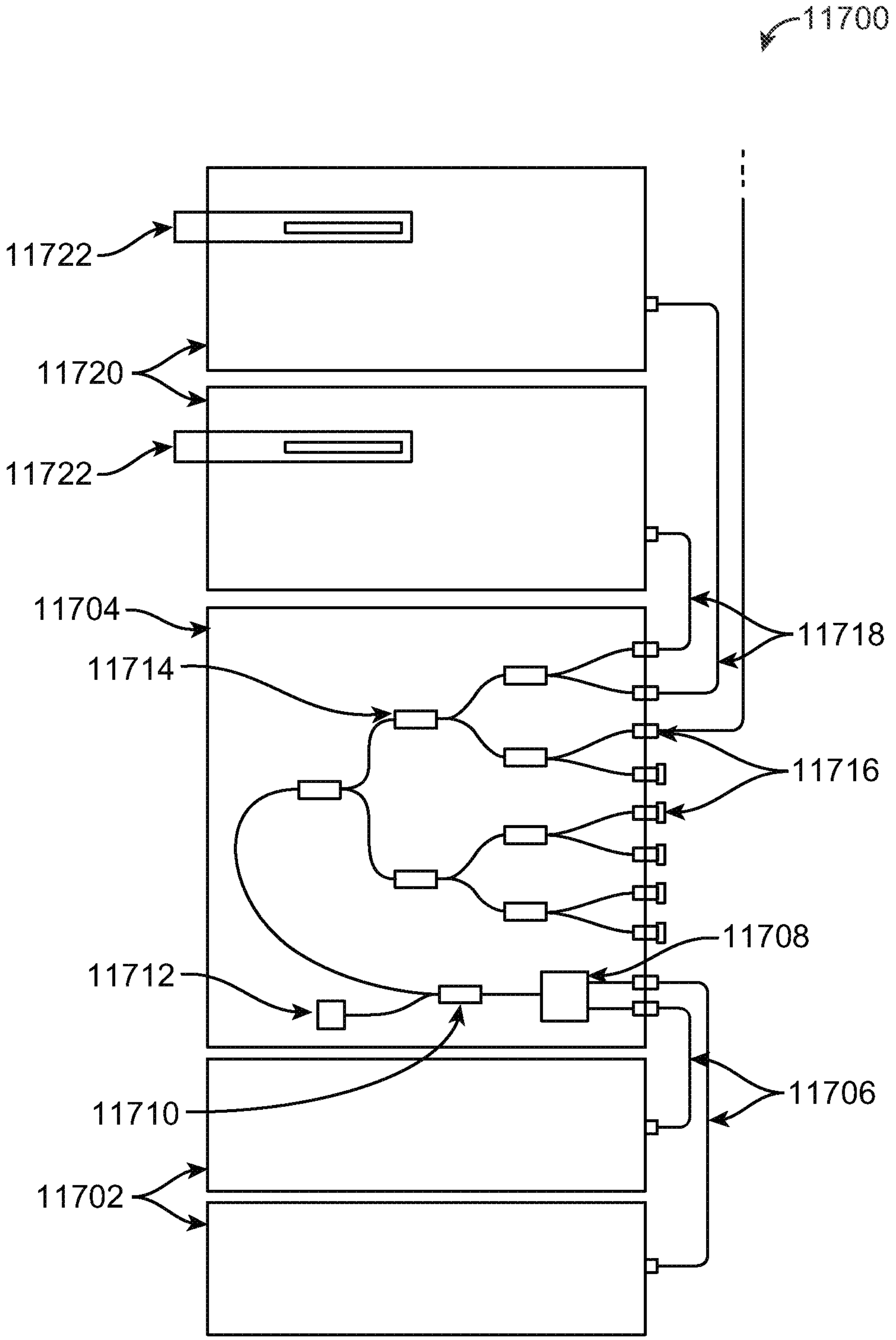
Figure 118:
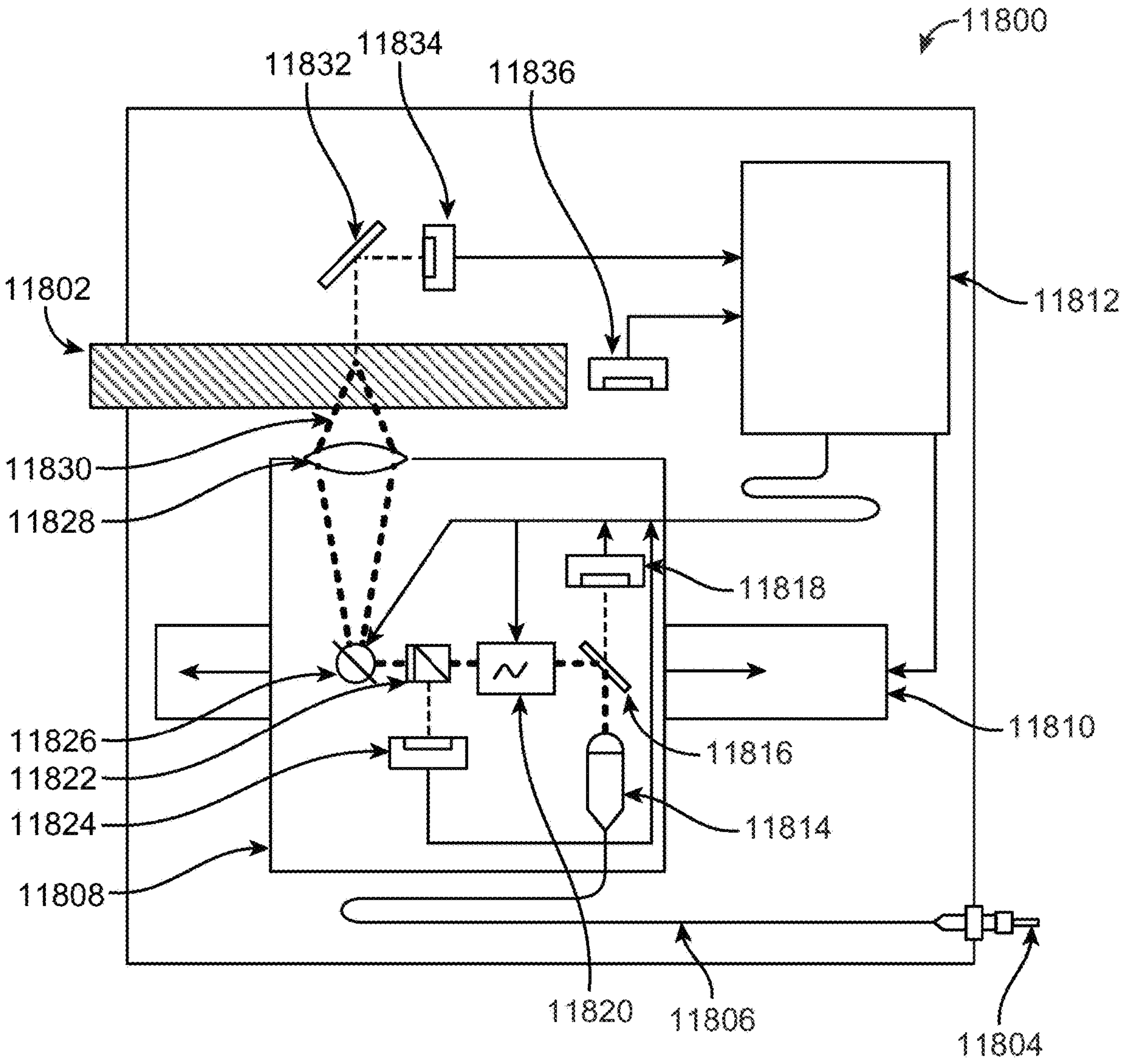
Figure 119:
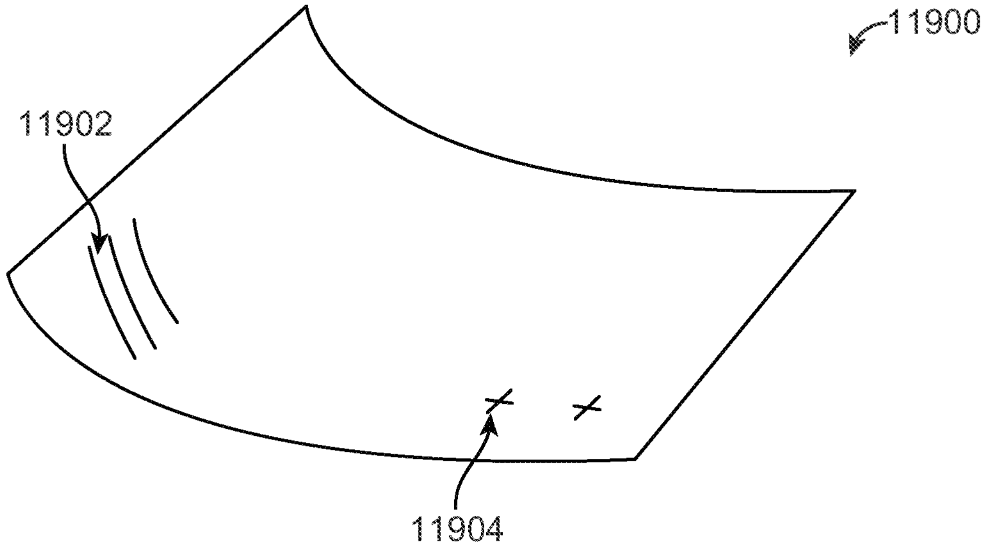
Figure 120:
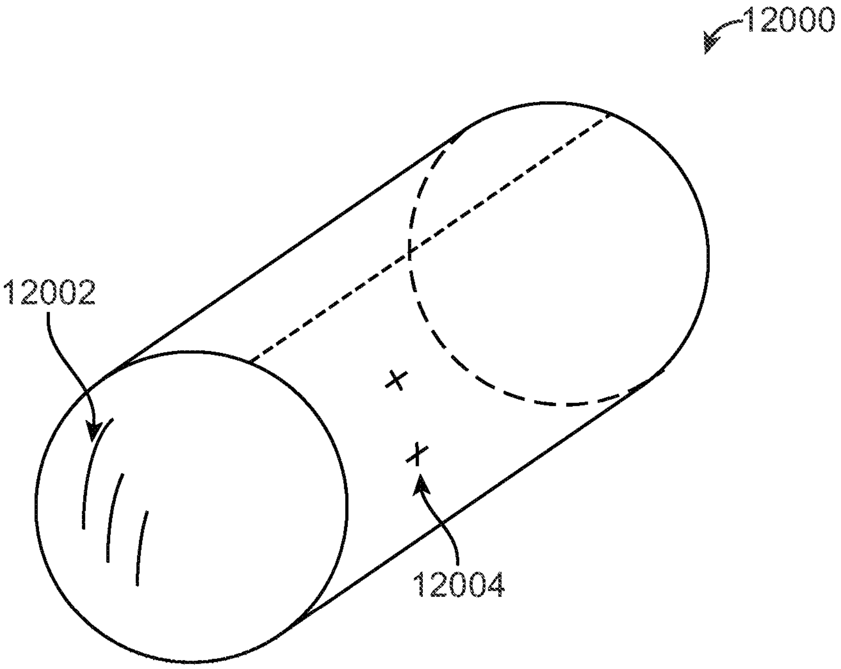
Figure 121:
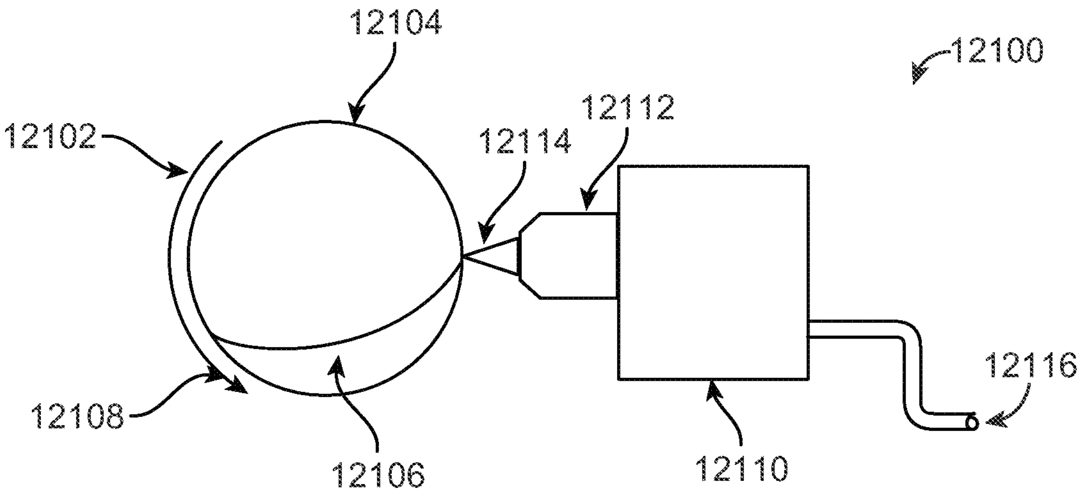
Figure 122:
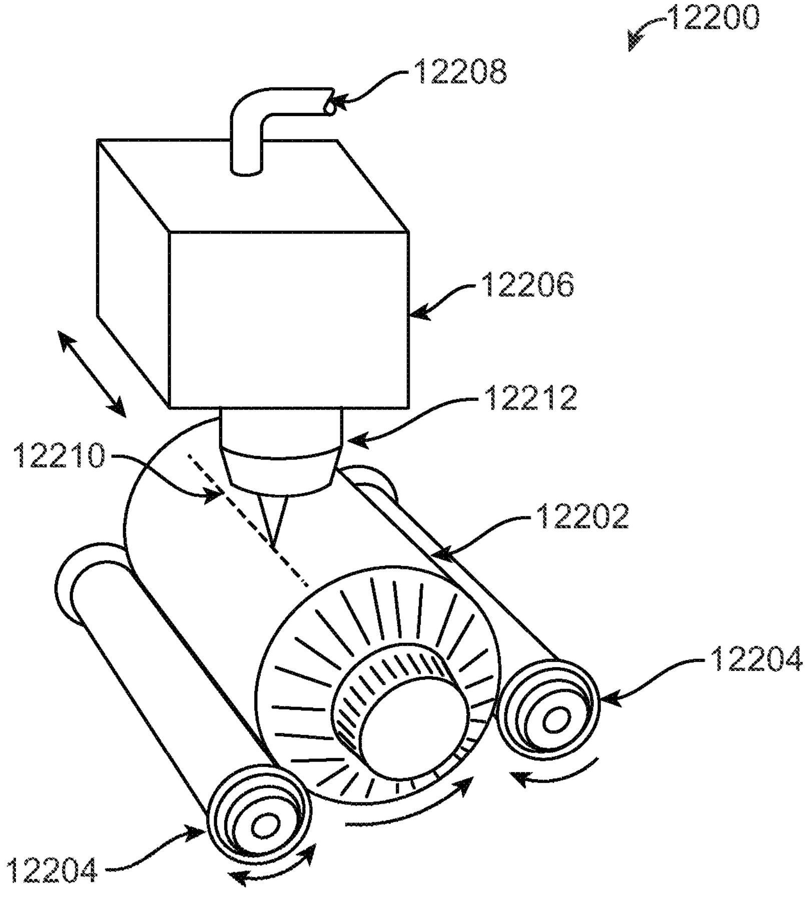
Figure 123:
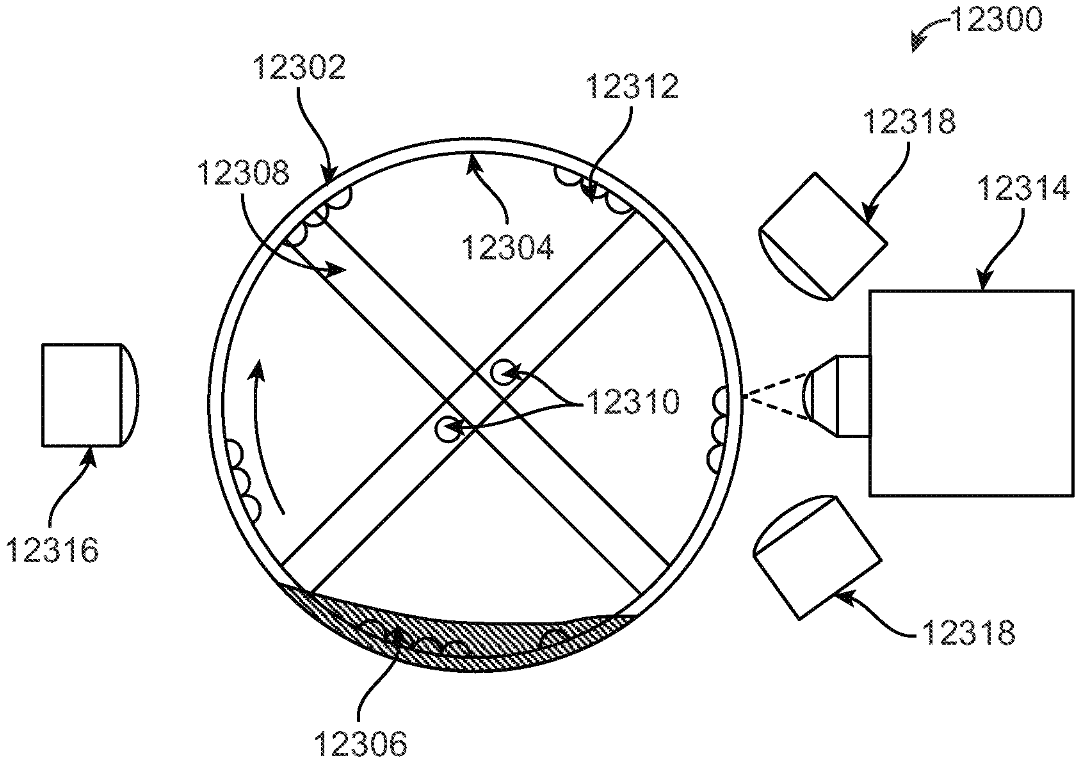
Figure 124:
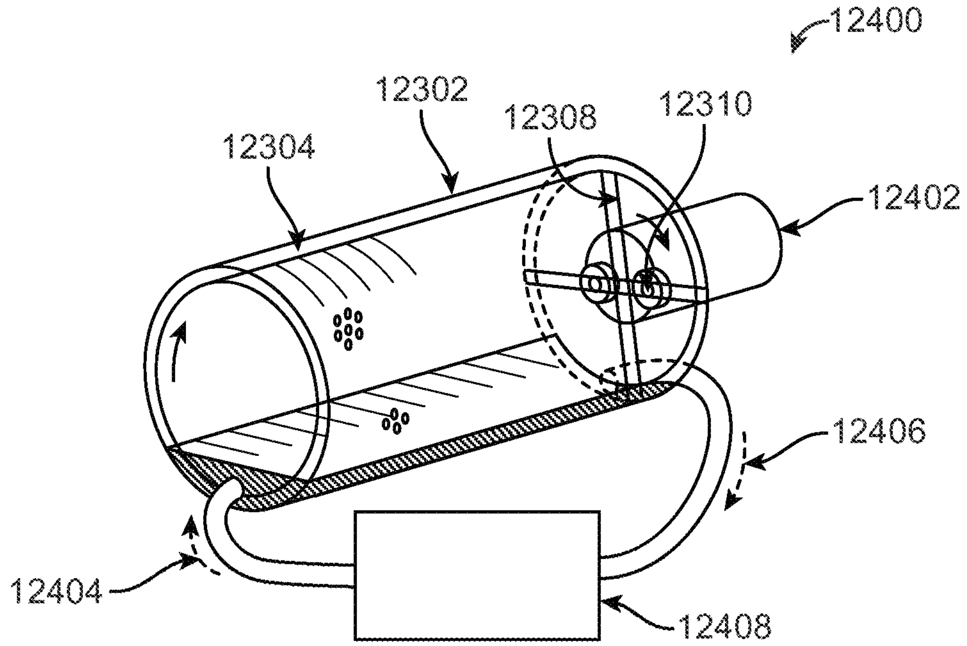
Figure 125:
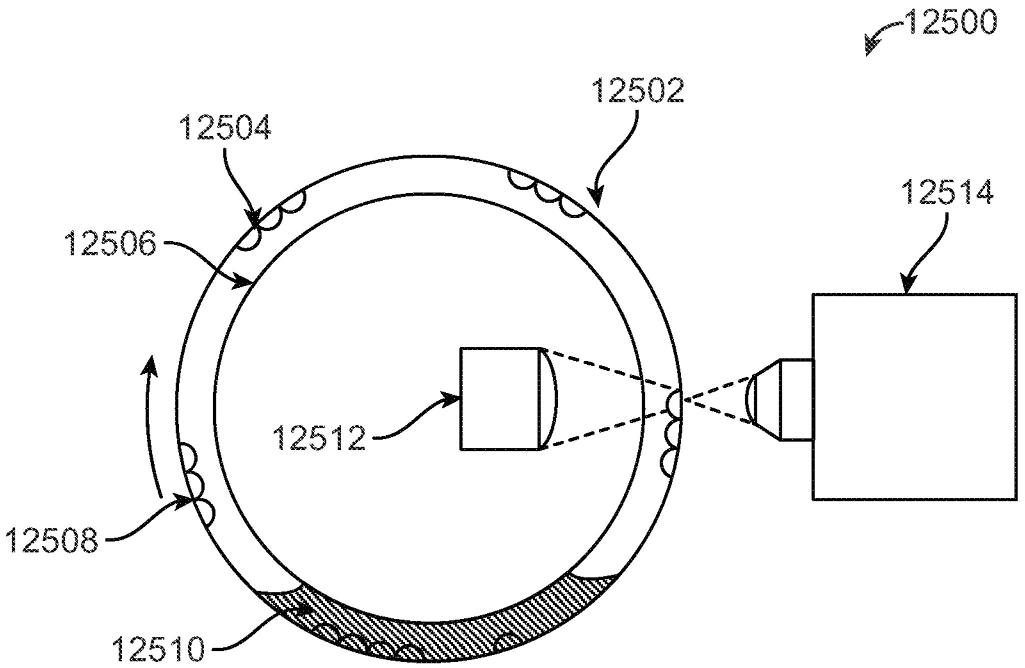
Figure 126:
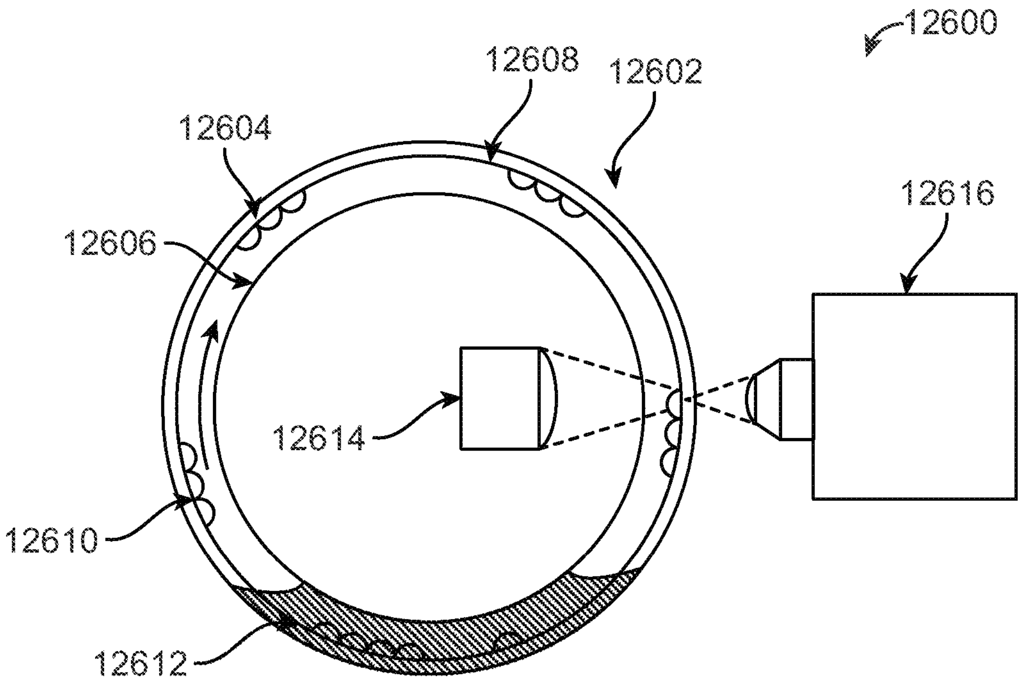
Figure 127:
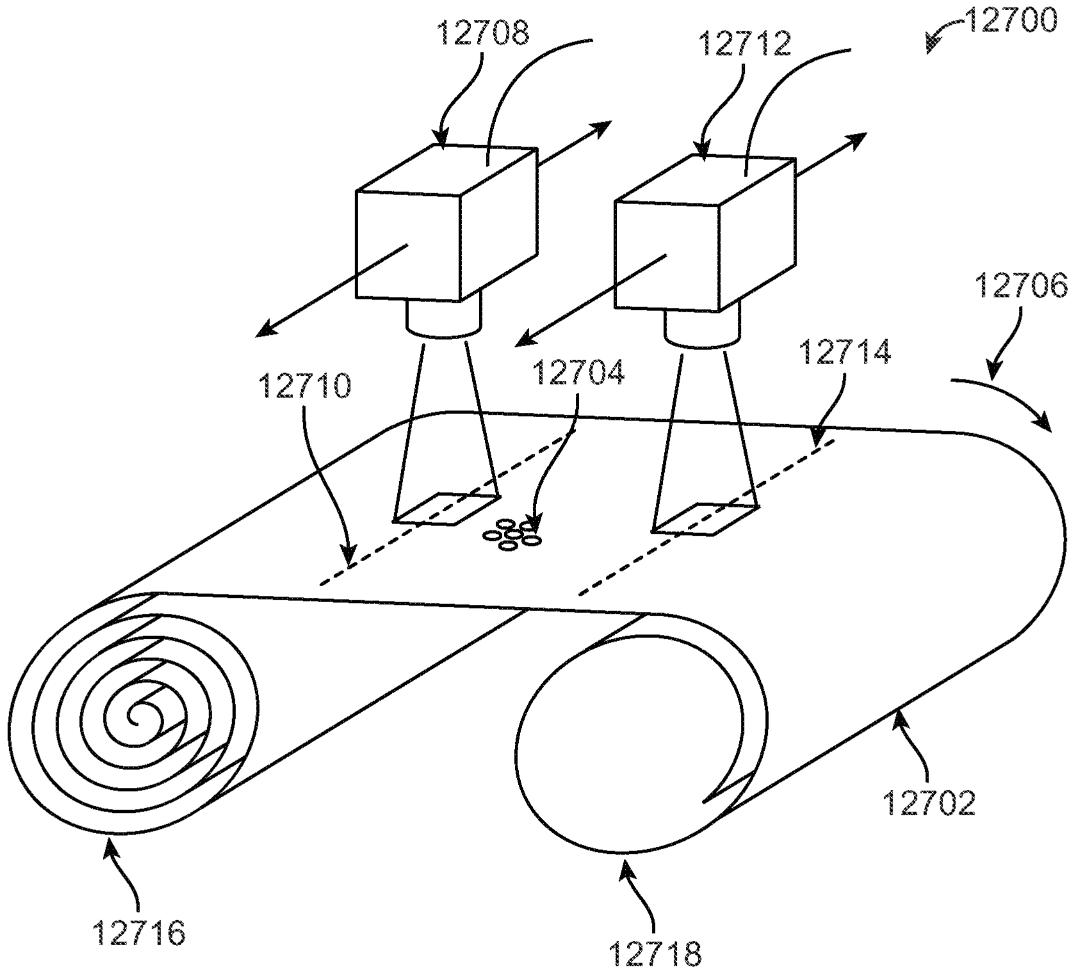
Figure 128:
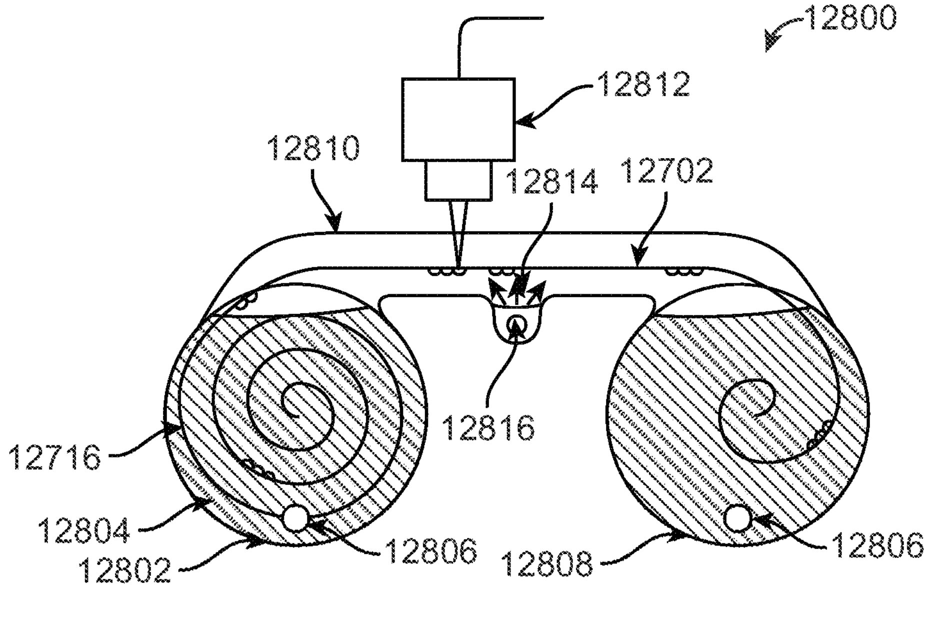
Figure 129:
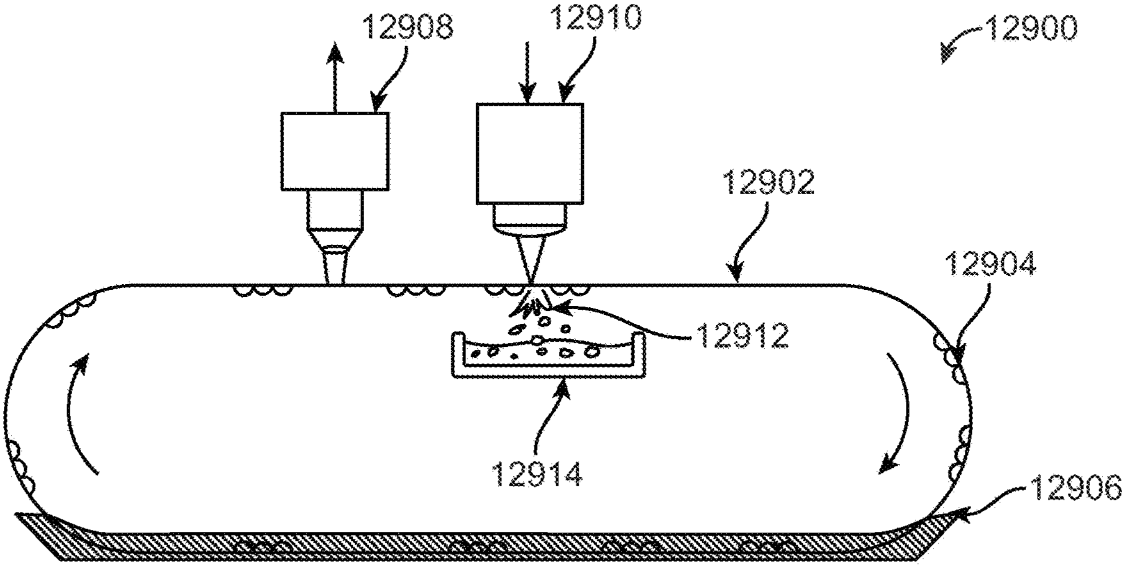
Figure 130:
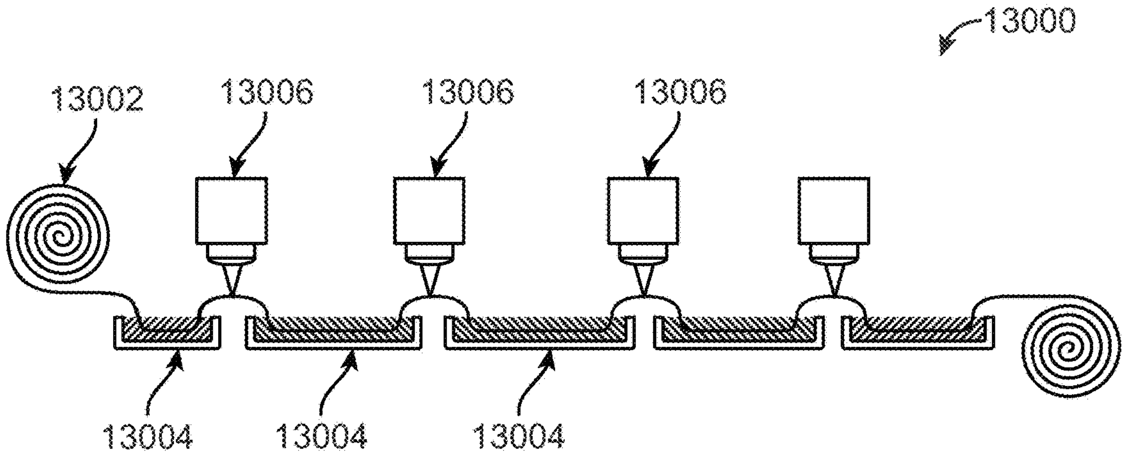
Figure 131:
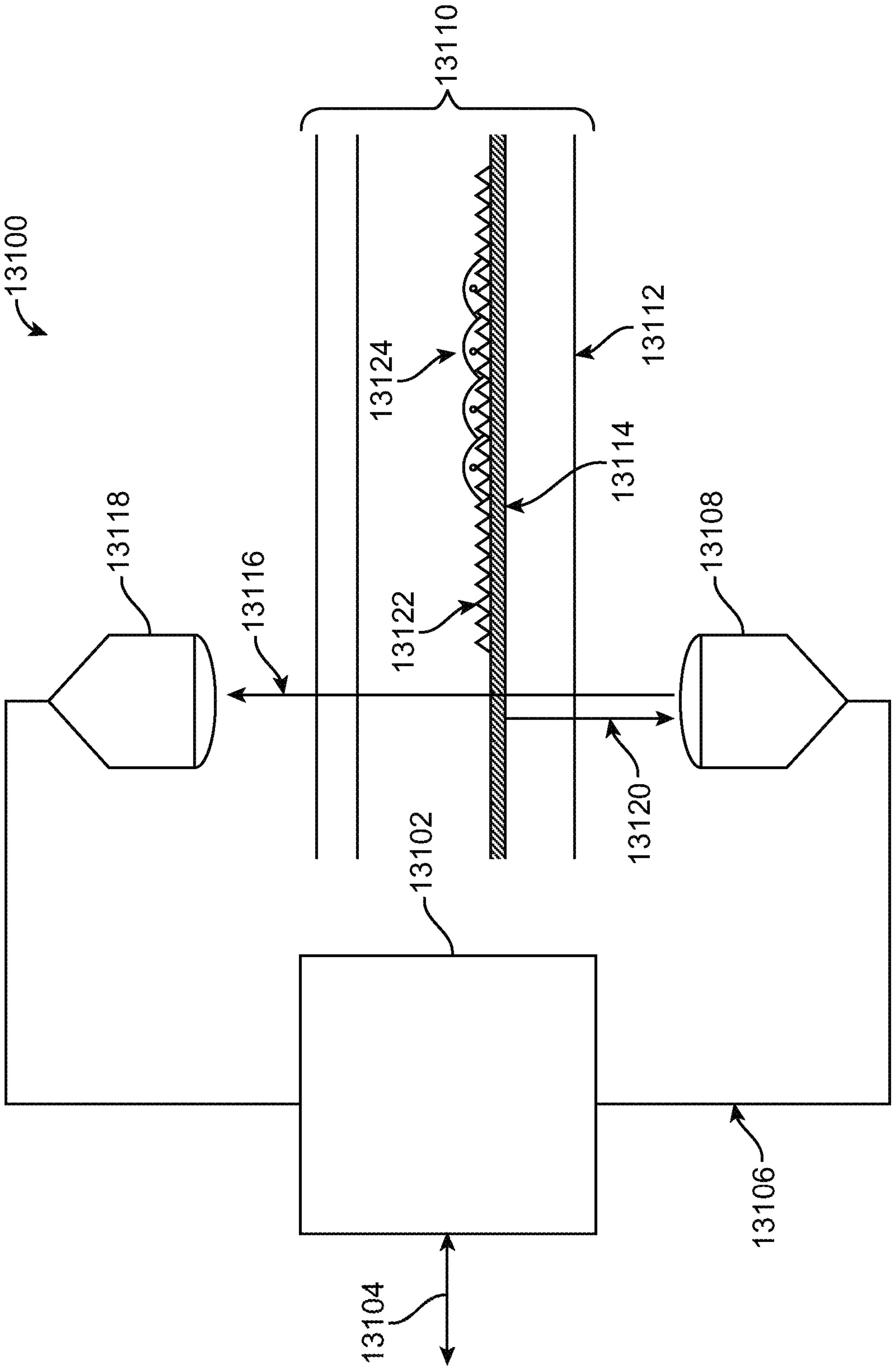
Figure 133:
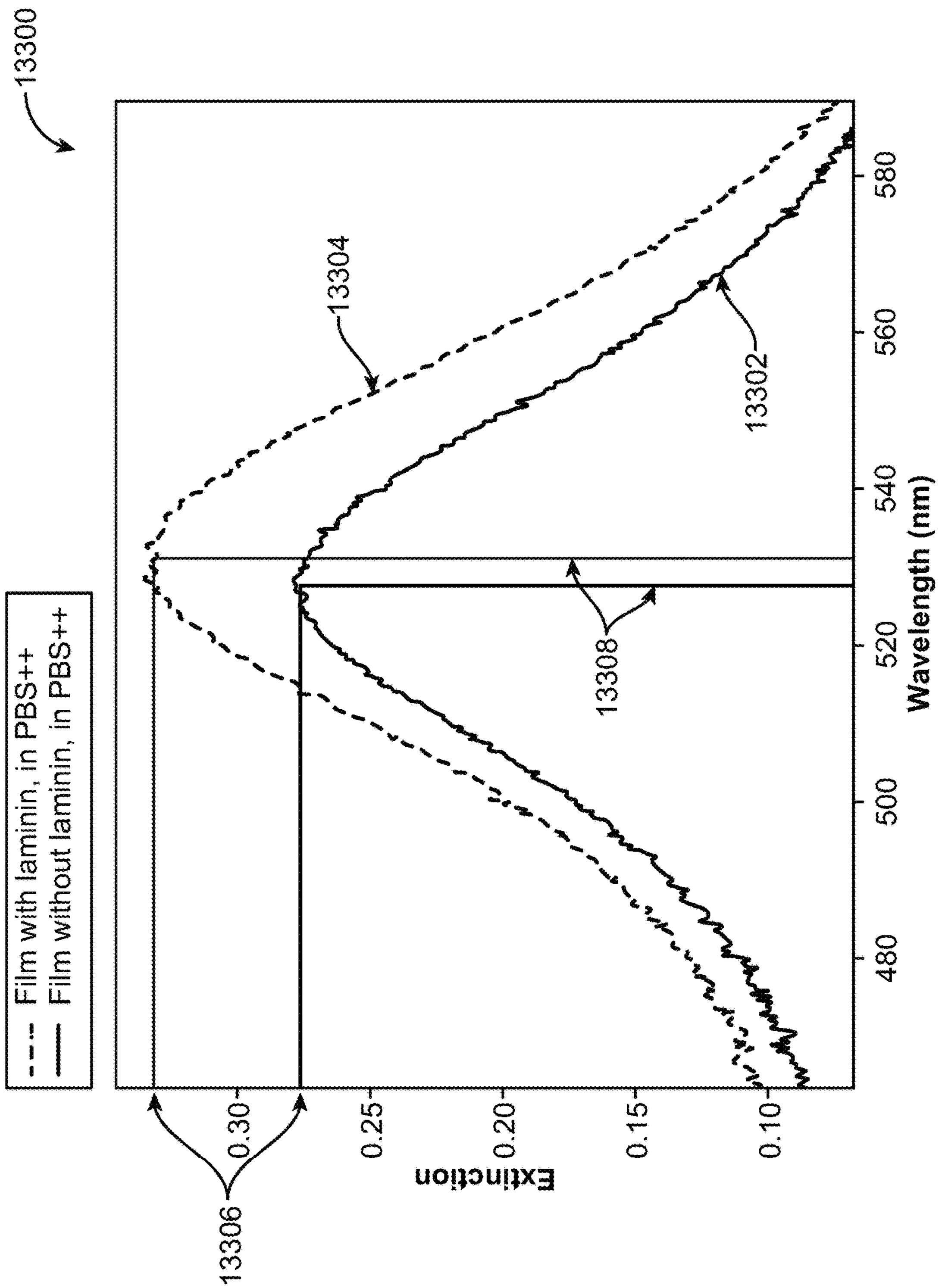
Figure 134:
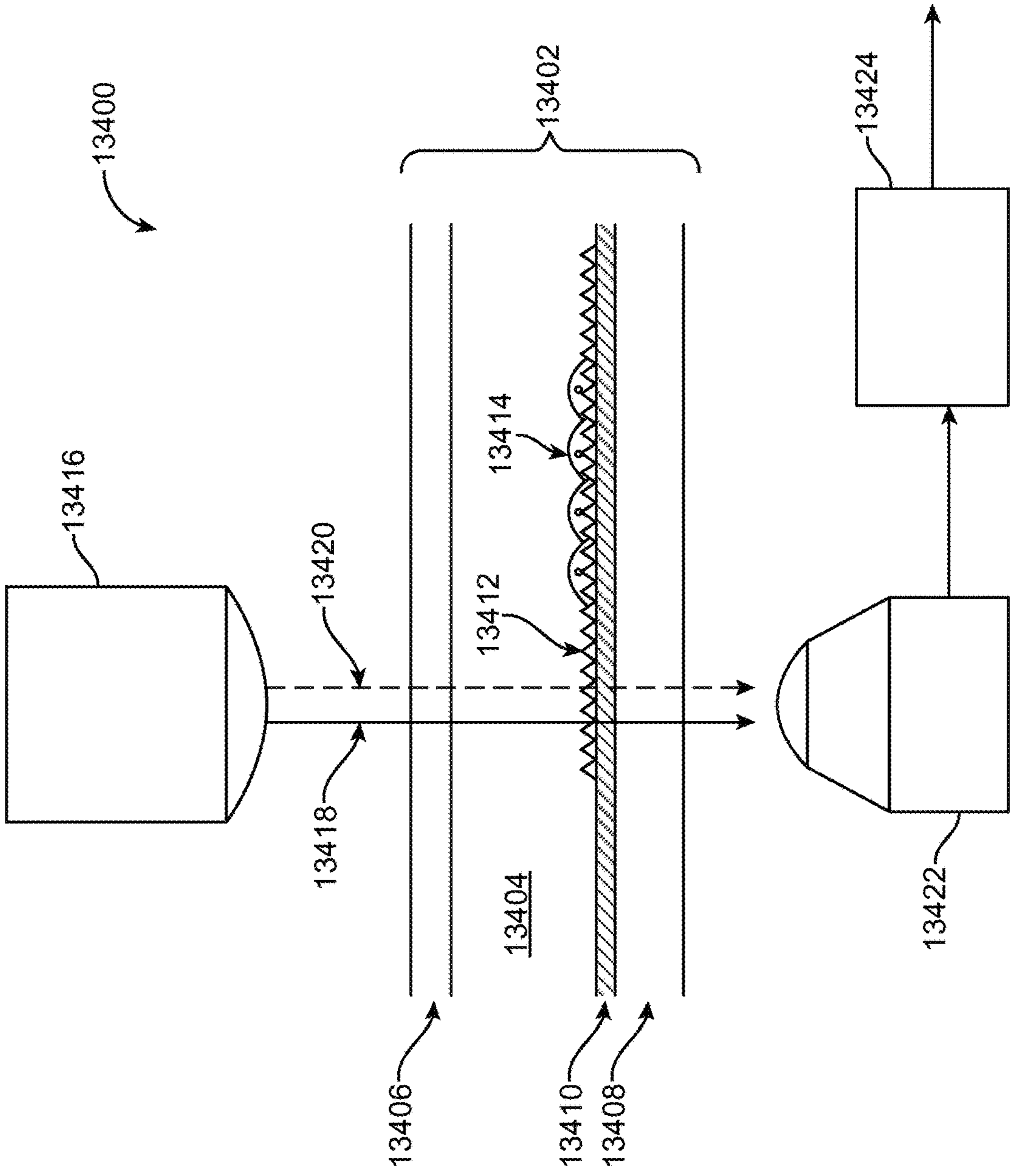
Figure 135:
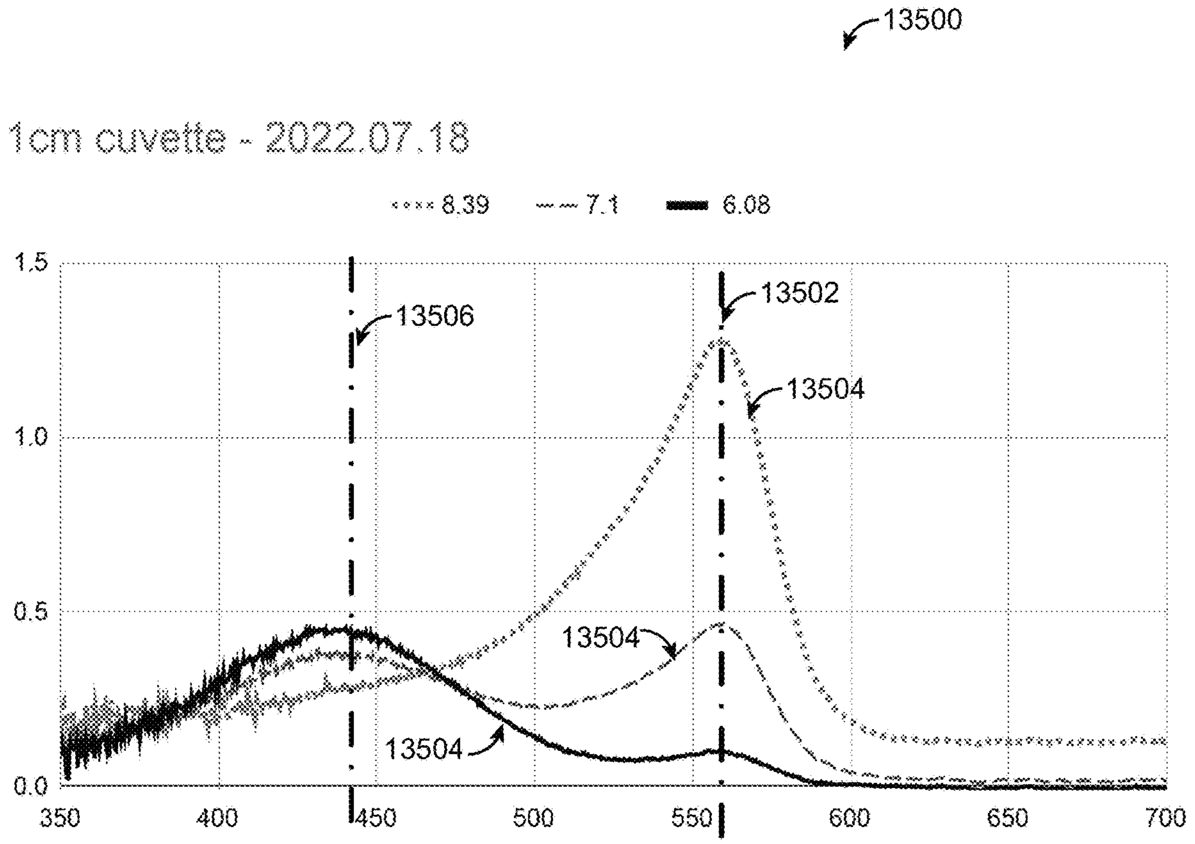
Figure 136:
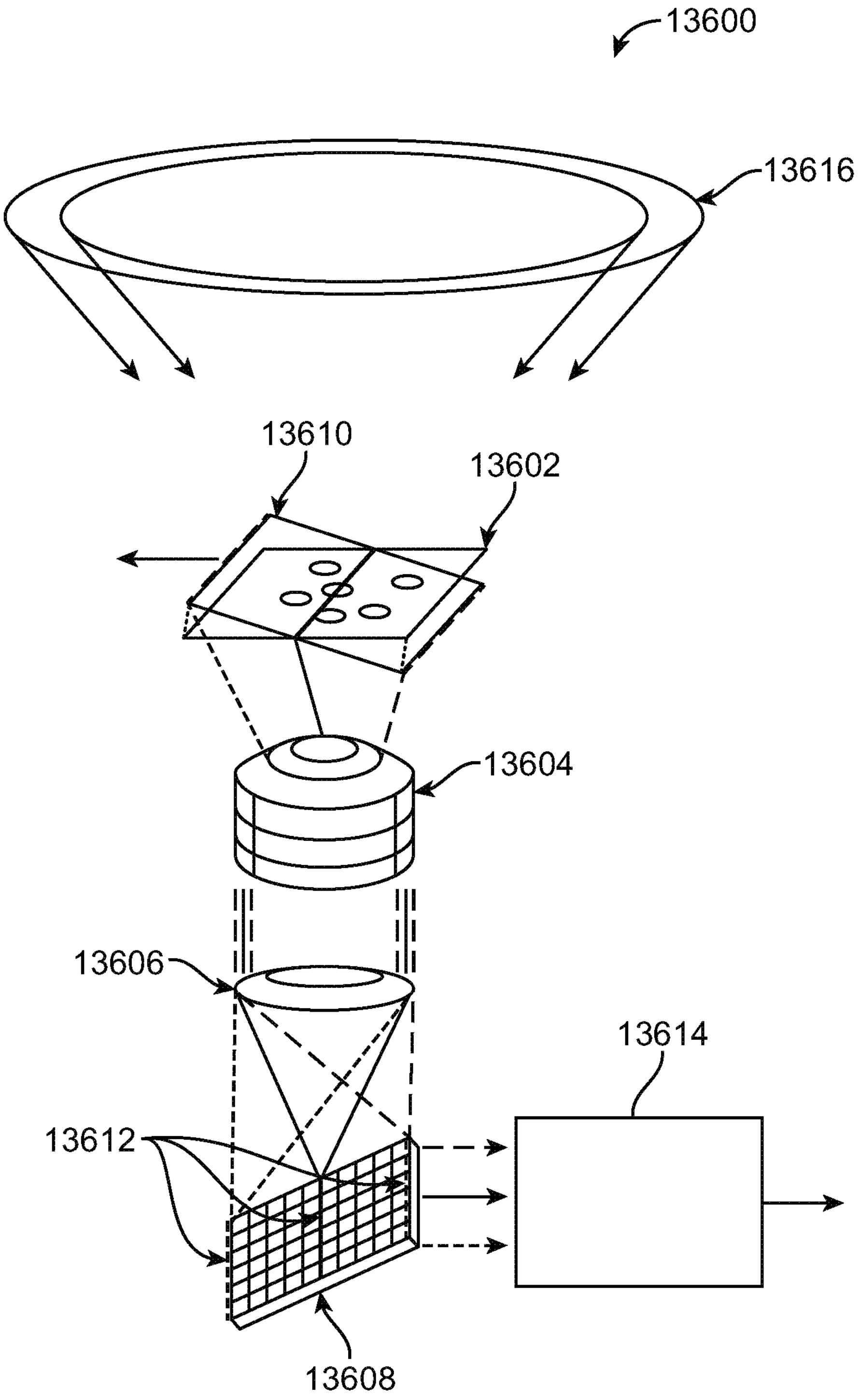
Figure 137:
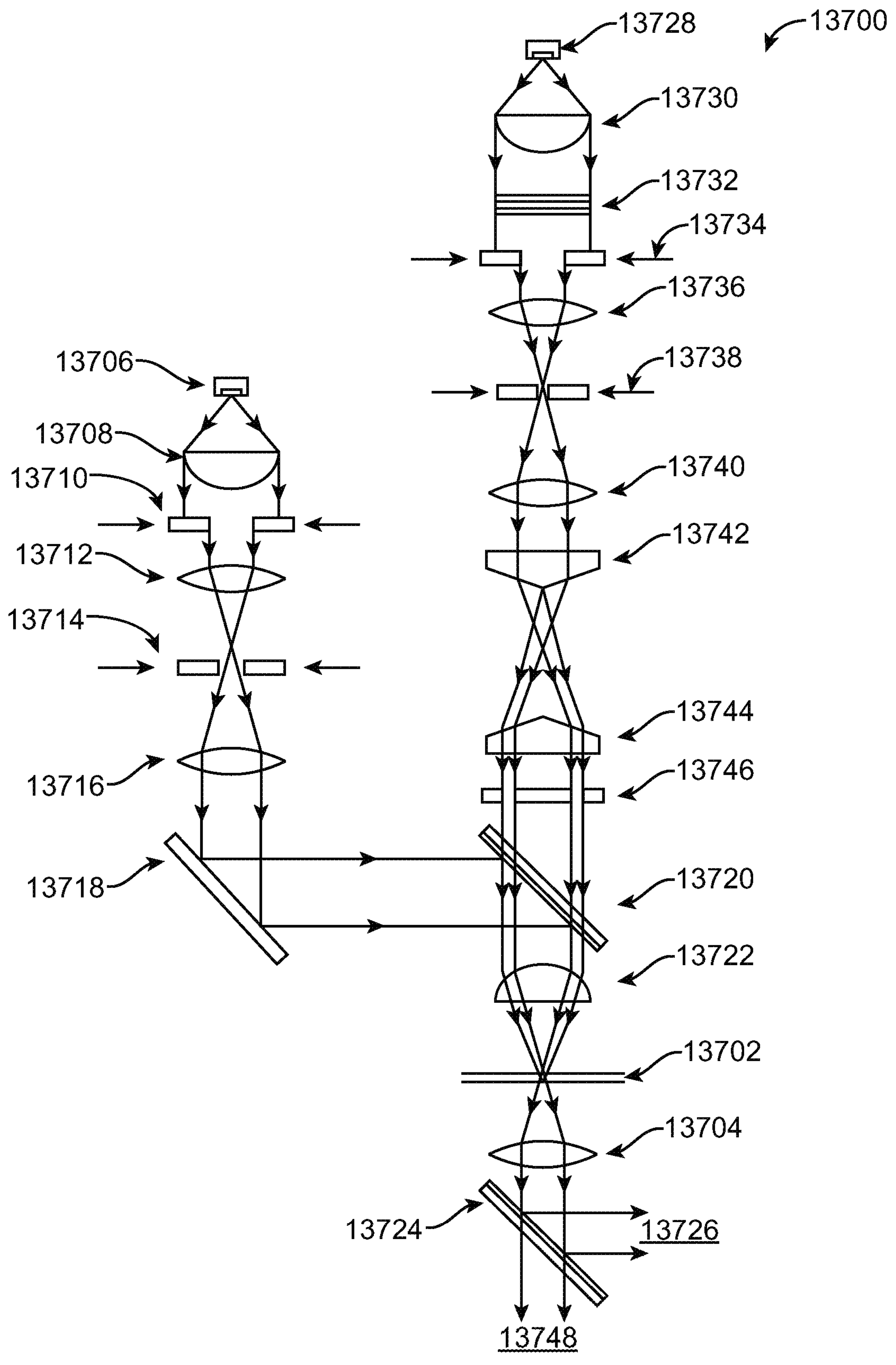
Figure 138:
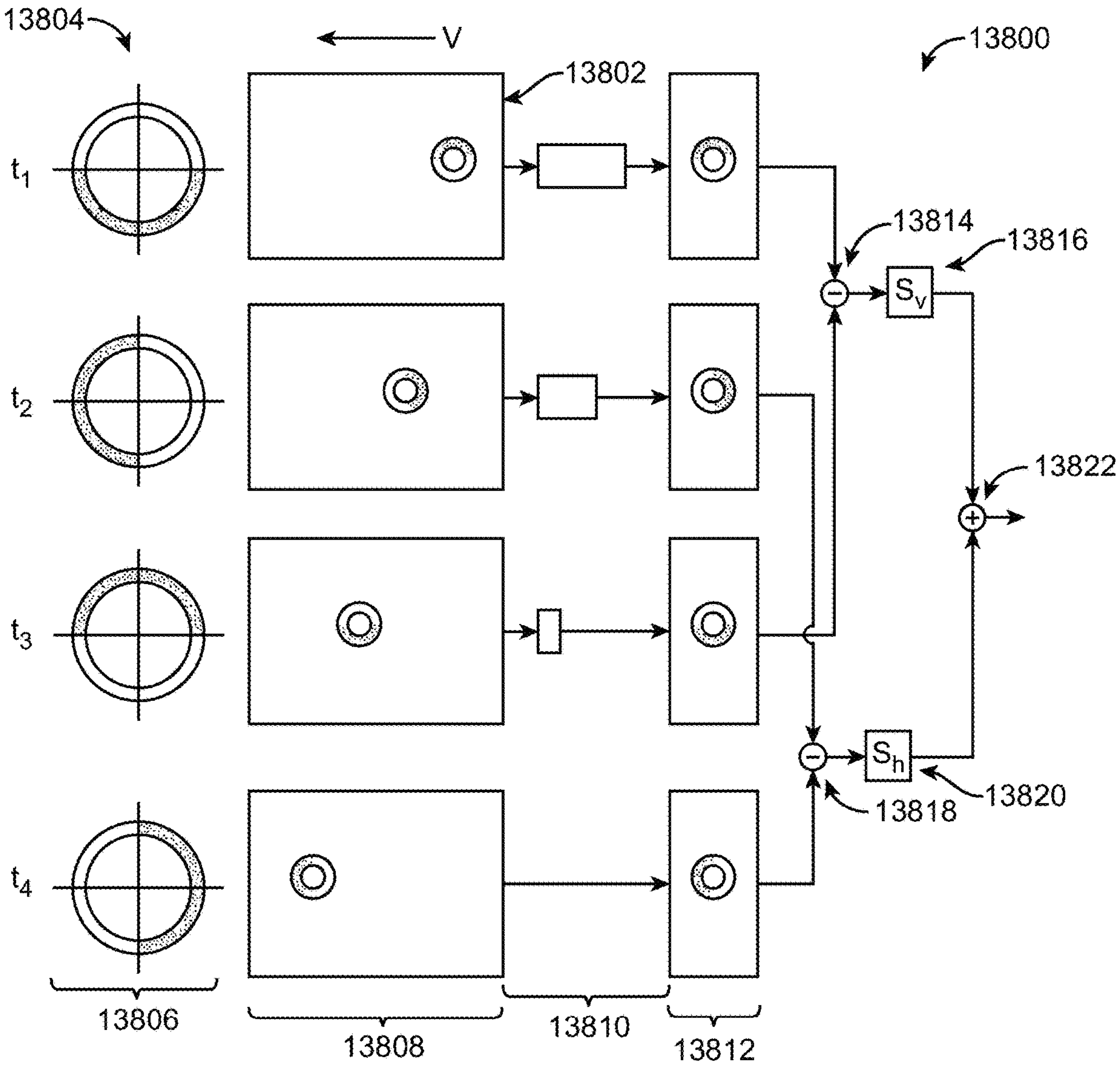
Figure 139:
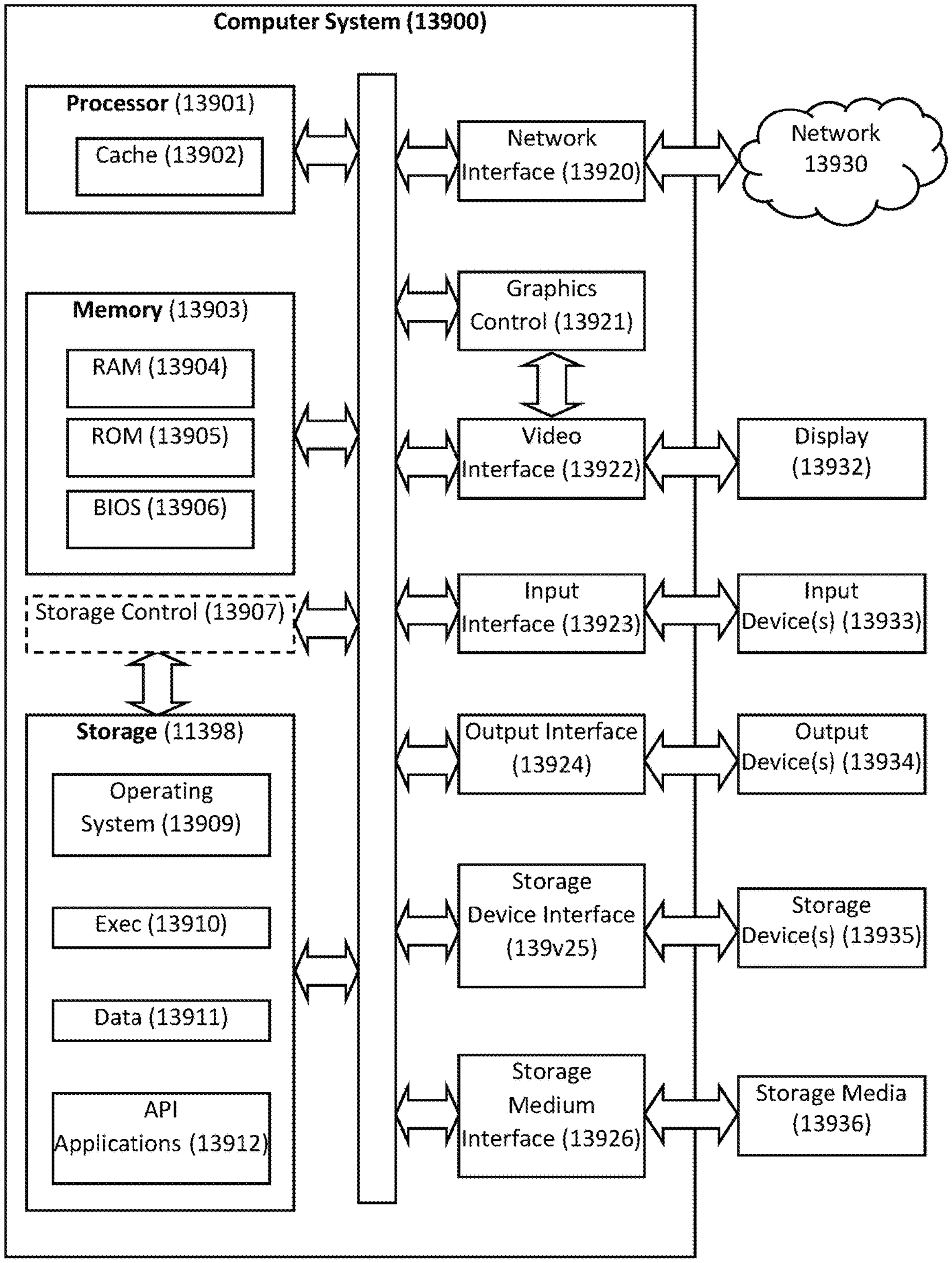

FIG. 104 illustrates example patterns created by an LED array in an imaging subsystem in accordance with various implementations;

FIG. 105 illustrates fiducial markers for use in a cell culture system in accordance with various implementations;

FIGS. 106A-C are diagrams further illustrating fiducial markers for use in a cell culture system in accordance with various implementations;

FIGS. 107-108 are graphs illustrating example optical extinction spectrums for a film used in a cell culture container in accordance with various implementations;

FIGS. 109-110 are diagrams illustrating the use of fiducial markers during imaging of a cell culture system in accordance with various implementations;

FIGS. 111-112 are diagrams illustrating different shapes for cell culture containers and accompanying films in accordance with various implementations;

FIG. 113 is a diagram of a porous membrane for use in a cell culture container in accordance with various implementations;

FIG. 114 is a diagram illustrating use of a porous membrane in a multi-well plate in accordance with various implementations;

FIG. 115 is a diagram illustrating use of a porous membrane in a cell culture container in accordance with various implementations;

FIG. 116 is a diagram illustrating a cell culture system with shared laser resources in accordance with various implementations;

FIG. 117 is a diagram illustrating another cell culture system with shared laser resources in accordance with various implementations;

FIG. 118 is a diagram illustrating a cell process module utilizing shared laser resources in accordance with various implementations;

FIG. 118 is a diagram illustrating a cell process module utilizing shared laser resources in accordance with various implementations;

FIG. 119 is a diagram illustrating a flexible foil used in a cell culture container in accordance with various implementations;

FIG. 120 is a diagram illustrating a cylindrical flexible foil used in a cell culture container in accordance with various implementations;

FIG. 121 is a diagram illustrating a cell culture system including a roller bottle cell culture container in accordance with various implementations;

FIG. 122 is a diagram illustrating another view of a cell culture system including a roller bottle cell culture container in accordance with various implementations;

FIG. 123 is a diagram illustrating a cross-sectional view of a cell culture system including a roller bottle cell culture container in accordance with various implementations;

FIG. 124 is a diagram illustrating another view of the cell culture system of FIG. 123 in accordance with various implementations;

FIG. 125 is a diagram illustrating a roller bottle implementation in a cell culture system in accordance with various implementations;

FIG. 126 is a diagram illustrating another roller bottle implementation in a cell culture system in accordance with various implementations;

FIG. 127 is a diagram illustrating a cell culture system including a multi-roll cell culture container in accordance with various implementations;

FIG. 128 is a diagram illustrating another view of a cell culture system including a multi-roll cell culture container in accordance with various implementations;

FIG. 129 is a diagram illustrating a cell culture system using flexible foil in accordance with various implementations;

FIG. 130 is a diagram illustrating a cell culture system with sequential stations in accordance with various implementations;

FIG. 131 is a diagram illustrating a cell culture system with a plasmonic film in accordance with various implementations;

FIGS. 132A-D are diagrams illustrating extinction spectra of plasmonic films in a cell culture system in accordance with various implementations;

FIG. 133 is a diagram illustrating extinction spectra of plasmonic films in a cell culture system in accordance with various implementations;

FIG. 134 is a diagram illustrating a cell culture system with a plasmonic film in accordance with various implementations;

FIG. 135 is a graph of absorbance of cell culture media measured within a cell culture container having a plasmonic film in accordance with various implementations;

FIG. 136 is a diagram illustrating a high-speed imaging subsystem for use in a cell culture system in accordance with various implementations;

FIG. 137 is a diagram illustrating another high-speed imaging subsystem for use in a cell culture system in accordance with various implementations;

FIG. 138 is a diagram illustrating another high-speed imaging subsystem for use in a cell culture system in accordance with various implementations;

FIG. 139 shows an exemplary computer system in accordance with various implementations.

These and other features of the present implementations will be understood better by reading the following detailed description, taken together with the figures herein described. The accompanying drawings are not intended to be drawn to scale. For purposes of clarity, not every component may be labeled in every drawing.

DETAILED DESCRIPTION

Disclosed herein are systems and methods including an automated cell culture system that may quickly and accurately produce output cell products and that is easily scalable to enable large scale biological manufacturing. The system may include cell imaging subsystems to acquire images of a cell culture, a cell editing subsystem to edit (e.g., remove) one or more cells during the cell culture process, a computing subsystem that controls the cell editing subsystem based on the acquired images, or any combination thereof. The computing subsystem may apply machine learning to data collected by the system (e.g., imaging data, sensor data, input, and output assay data) to determine how to effectively edit the cell culture to reach the desired output. This allows for dynamic monitoring and control of how the cell culture develops from input cells to output cell products. The automated nature of the system removes the need for manual human intervention at many stages of cell culture development, thus reducing the time and cost of making output cell products. It also allows for easy scalability, as the computing subsystem may monitor and control multiple cell culture processes at the same time.

Figure 1:
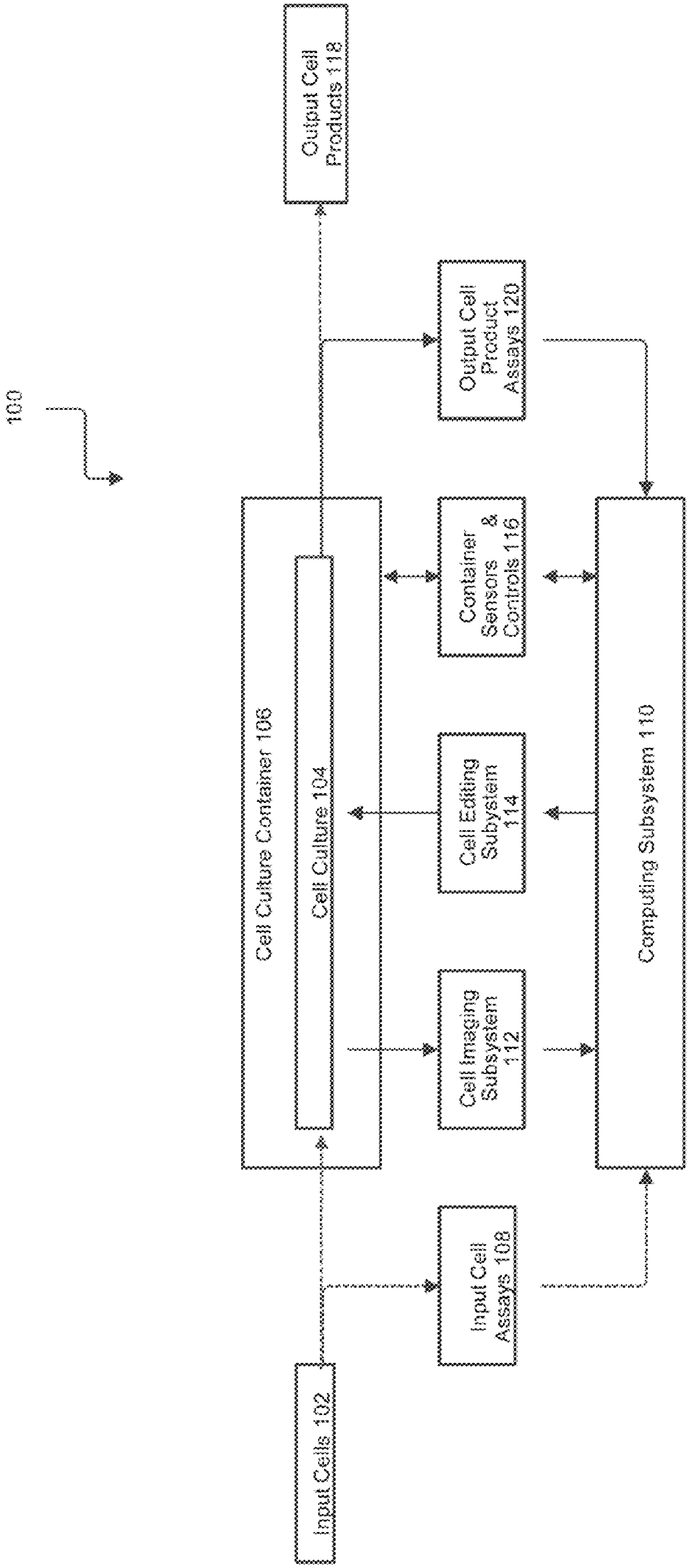
FIG. 1 is a block diagram of a cell culture system in accordance with various implementations.

FIG. 1 is a block diagram of a cell culture system 100 in accordance with various implementations. The cell culture system 100 receives input cells 102 as "source" cells upon which the cell culture system 100 performs various cell culture processes. The input cells 102 may be sorted, expanded, or otherwise modified prior to the cell culture performed by the cell culture system 100. Input cell types may include, but are not limited to, somatic cells (including but not limited to fibroblasts, mature blood and progenitor cells, such as CD34+ cells and erythroblasts, keratinocytes, epithelial cells, including blood and urine-derived epithelial cells, Sertoli cells, endothelial cells, granulosa epithelial, neurons, pancreatic islet cells, epidermal cells, epithelial cells, hepatocytes, hair follicle cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, other muscle cells, and generally any live somatic cells. The term "somatic cells," as used herein, also includes adult stem cells and pluripotent stem cells (including but not limited to induced pluripotent stem cells and embryonic stem cells).

The input cells 102 may be analyzed with one or more input cell assays 108 which serve to quantify the state of the input cells 102. The input cell assays 108 may be nondestructive (such as cell counting) or a sample may be extracted for tests including, but not limited to, genomic profiling, gene expression assays such as PCR, qPCR, microarray, single-cell RNA sequencing, whole exome sequencing (WES), whole genome sequencing (WGS), karyotyping, short tandem repeat (STR) analysis, sterility testing (testing for bacteria and viruses), or other phenotype analysis including but not limited to cell surface antigen or intracellular staining-based immunofluorescence or flow analysis, and cell viability, morphology and migration assays, or any other implementations known to persons of ordinary skill in the art. The sample extraction can be performed using automated or semi-automated processes within a closed cell culture environment to enable continued propagation of the cell culture within a sterile environment. The results of these assays are transmitted to a computing subsystem 110, which may use the results in various software applications to monitor, predict, and control the cell culture process performed by the cell culture system 100.

The input cells 102 are placed into a cell culture 104, where they will remain for the duration of the processes performed by the cell culture system 100. The cell culture 104 may reside in a cell culture container 106. The cell culture container 106 may include one or more chambers to hold the cell cultures, and may take the form of microwell plates, flasks, stackable cell culture containers, closed cassette systems, microfluidic chambers, purpose-built bioreactor vessels, or any other implementations known to persons of ordinary skill in the art. The cell culture container 106 may be a closed/sealed sterile environment for the cell culture 104 and fluid media used in cell culture processes.

The cell culture 104 may be used for a number of cell processes performed and monitored by the cell culture system 100, including but not limited to: cell reprogramming (into pluripotent or multipotent forms), cell differentiation, cell trans-differentiation, cell expansion, cell sorting, clonal isolation, cell gene editing, cell-based protein production, cell-based viral production, combinations thereof, or any other implementations known to persons of ordinary skill in the art.

The cell culture container 106 may be in a format that allows for observation of the cell culture 104 at regular intervals using an imaging subsystem 112. For example, the cell culture container 106 may include a closed cassette system having at least one transparent or semi-transparent surface that allows for light or laser-based imaging and editing. The imaging subsystem 112 may be configured to provide label-free imaging suitable for long-term cell culture observation, although some implementations may include fluorescent imaging capability for immunofluorescent or other labeled images. Label-free modalities employed by the imaging subsystem 112 may include, but are not limited to, brightfield imaging, phase imaging, darkfield imaging, transmission imaging, reflection imaging, quantitative phase imaging, holographic imaging, two-photon imaging, autofluorescence imaging, Fourier ptychographic imaging, defocus imaging or any other implementations known to persons of ordinary skill in the art.

The cell culture system 100 further includes a cell editing subsystem 114 for editing the cell culture 104. The cell editing subsystem 114 may edit the cell culture 104 at a regional, colony-specific, and/or cell-specific level. Editing, in this context, may include selective destruction and/or removal of cells or cell regions, and non-destructive operations on cells (including intracellular delivery of compounds into cells or extraction of compounds from cells). The cell editing subsystem 114 may edit the cell culture 104 through a variety of directed energy mechanisms. In other words, the cell editing subsystem 114 may generate energy that is directly used to edits cells and/or converts energy of one form (e.g., light, mechanical) into energy of another form to achieve cell editing. The mechanism by which the cell editing subsystem 114 acts upon cells in the cell culture may include, but not be limited to, robotic systems that mechanically actuate a tip or tool across the cell culture, magnetic actuators in conjunction with magnetic tools that interact with the cell culture, systems that are configured to selectively apply an electric field across portions of the cell culture, ultrasound systems that are configured to apply ultrasonic energy to portions of the cell culture, droplet or particle ejection/acceleration systems that are designed to impact droplets or particles on portions of the cell culture, optical systems that are designed to deliver optical energy to portions of the cell culture, combinations thereof, or any other implementations known to persons of ordinary skill in the art.

Optical mechanisms for cell editing may include, but are not limited to, optical systems that direct energy directly into cells or surrounding media in the cell culture, optical systems that direct energy into particles or dyes that are added to the cell culture media (including but not limited to particles functionalized in a manner to attach to specific cells, or that are taken up by cells), or optical systems that direct energy into particles or films that are on surfaces proximate to portions of the cell culture, or any other implementations known to persons of ordinary skill in the art. Optical mechanisms may operate on the cell culture by a number of approaches including, but not limited to, elevating the local temperature to a point where cells are destroyed due to heat damage, elevating local temperature to cause boiling and/or bubble formation to cause portions of the cell culture to detach from a surface, or elevating local temperature rapidly in order to cause rapid bubble formation and then subsequent collapse to affect mechanical forces on the local cell membranes, or combinations thereof.

The cell culture system 100 may also include a number of sensors and controls 116 which may measure or act upon the cell culture 104. For example, the sensors and controls 116 may carry out functions such as measuring media conditions within the cell culture 104, causing fresh media to be supplied, or adding reagents or gases in order to adjust media conditions for optimal cell culture growth. Sensors that sense the state of the cell culture 104, cell culture media, and/or surrounding cell culture container 106 may include, but are not limited to, temperature sensors, humidity sensors, gas composition sensors including but not limited to $O_2$ and $CO_2$ concentration sensors, gas flow rate sensors, dissolved gas sensors including but not limited to dissolved $O_2$ sensors, liquid flow rate sensors, and sensors to measure cell culture media constituents (such as nutrients, waste products, vitamins, metabolites, proteins, extracellular vesicles, cell mass, or cell debris) including but not limited to optical absorption sensors, optical scattering sensors, mass spectroscopic sensor systems, optical or electrical pH sensors, and viscosity sensors.

Controls that may interact with the cell culture 104 or the cell culture container 106 may include, but are not limited to, liquid handling systems that inject or extract various liquids to/from the cell culture 104 or the cell culture container 106, environmental control systems that control the temperature or other environmental parameters of the cell culture 104 or the cell culture container 106, power systems that provide electrical power to the cell culture container 106, and mechanical or robotic systems that may move or manipulate the cell culture container 106 or portions thereof.

The computing subsystem 110 may be configured to control the other components of the cell culture system 100 to perform the specified cell culture process on the cell culture 104 to produce output cell products 118. The output cell products 118 may include both cells and cell-derived products, and may be harvested from the cell culture 104. Output cell products 118 that may be produced by the computing subsystem 110 may include, but are not limited to, induced pluripotent stem cells, proteins (e.g., cytokines, antibodies, hormones), lipid particles (e.g., exosomes), viral particles, somatic cells (including but not limited to fibroblasts, mature blood and progenitor cells, such as CD34+ cells and erythroblasts, keratinocytes, epithelial cells, including blood and urine-derived epithelial cells, Sertoli cells, endothelial cells, granulosa epithelial, neurons, pancreatic islet cells, epidermal cells, epithelial cells, hepatocytes, hair follicle cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, other muscle cells, generally any live somatic cells, and the combination of any of the above. The term "somatic cells," as used herein, also includes adult stem cells.

The output cell products 118 may be measured by output cell product assays 120 in order to determine critical product parameters such as phenotype distribution, protein production, gene activation, genomic makeup (including but not limited to genomic profiling assays such as PCR, qPCR, microarray, single-cell RNA sequencing, whole exome sequencing (WES), whole genome sequencing (WGS), karyotyping, short tandem repeat (STR) analysis, sterility testing (testing for bacteria and viruses)), or other phenotype analysis including but not limited to cell surface antigen or intracellular staining and immunofluorescence or flow analysis and cell viability, morphology and migration assays, or potency assays such as self-renewal and teratoma formation assays, and germ-layer differentiation assays. The output assay data may be conveyed to the computing subsystem 110 in order to refine predictive models (based on image data, sensor data, information from prior cell culture processes, and other information sources) for cell culture monitoring and control. Output cell product assays 120 may include, but not be limited to, viability assays, cell counting, flow cytometry, immunostained imaging assays, PCR assays (including but not limited qPCR, ddPCR), RNA sequencing assays including single-cell RNA assays, cell differentiation assays, embryoid body formation assays, trilineage differentiation assays, karyotyping assays, DNA sequencing, or any other implementations known to persons of ordinary skill in the art.

The computing subsystem 110 is configured to gather data from a range of sources, organizes the data in a manner that allows it to make predictions of success/quality/functionality of the cell culture 104, and in many cases do so on a cell-by-cell, colony-by-colony, or region-by-region basis. For example, using local cell density and proliferation rate data obtained through analysis of the time series of label-free images provided by the imaging subsystem 112, in conjunction with data regarding the input cells (in order to control for patient-specific factors, for instance), and based on a large number of observed histories and corresponding cell quality data measured by the output cell product assays 120, the computing subsystem 110 may predict which regions of cells are most likely to yield superior cell products, and which regions are less likely to yield good product. In situations where cell media is limited or there is competition between cells for space in the cell culture container 106, the computing subsystem 110 may instruct the cell editing subsystem 114 to remove the regions or even individual cells predicted to underperform.

Another function of the computing subsystem 110 is to use cell data derived from imaging in conjunction with sensor data from the sensors and controls 116 and assay data from the input cells 102 and/or the output cell products 118 in order to pre-emptively adjust cell culture conditions according to cell count, proliferation rate, differentiation status, phenotype, or other factors in addition to real-time cell media readings. Using a model trained on previous iterations, the computing subsystem 110 may adjust media conditions such as fresh media feed, media type, temperature, pH, dissolved Oxygen levels, reagent or vitamin levels or other global cell culture properties using the controls 116. Similarly, the computing subsystem 110 may use cell data obtained from imaging, potentially in conjunction with cell media sensor data, to determine when the cell culture 104 is ready for harvest. Actuators utilized by the controls 116 may include, but are not limited to: liquid handling robots, liquid circulation systems including valves and pumps, temperature control elements, pH controllers, gas exchange mechanisms to control dissolved gases or any other implementations known to persons of ordinary skill in the art.

The computing subsystem 110 may control the cell editing subsystem 114 to make edits to the cell culture 104 according to cell management algorithms (for example, to maintain a certain cell density, to maintain certain exclusion areas within the cell culture container), in a timed manner (for example, delivering gene-activating or gene-editing compounds to cells at a specific interval), and/or as a result of predictions made by the computing subsystem 110 (for example, removal of cells predicted not to yield the desired phenotype or optimal level of function). "Editing" includes both destruction of cells and/or colonies (including inducing apoptosis, lysing, physically removing) as well as selective delivery of compounds into cells and/or regions of cells via intracellular delivery mechanisms, or selective extraction of compounds from the cells via intracellular delivery mechanisms.

The computing system 110 may include elements that perform conventional image processing (including but not limited to filtering, normalization, contrast enhancement, z-stack processing, thresholding, histogram transformations, edge detection, correlations, convolutions, frequency space operations, blob detection, morphological operations, registration, warping, object detection, object tracking or combinations thereof), deep learning based image processing (including but not limited to convolutional neural networks, fully-connected neural networks, semantic and instance-level segmentation, encoder-decoder networks, multi-scale algorithms, recurrent networks, visual attention models, vision transformers, generative adversarial models, U-Nets, ResU-Net, SegNet, X-Net, ENet, BoxENet, long short-term memory neural networks, and combinations thereof), statistical models, pattern recognition, statistical learning (including but not limited to linear regression, non-linear regression, hierarchical regression, generalized linear models, logistic regression, log-linear models, non-parametric models), machine learning (including but not limited to decision trees, random forest, support vector machines, neural nets, deep learning, association models, sequence modeling, genetic modeling), clustering techniques including hierarchical and non-hierarchical clustering, supervised machine learning models, unsupervised machine learning models, databases (including but not limited to SQL databases and NoSQL databases), visualization tools for image, cell, colony, clone and other data, combinations of these elements, or any other implementations known to persons of ordinary skill in the art.

The computing subsystem 110 may also include data storage for storing image data, sensor data, the results of data analysis, and program code that the computing subsystem 110 executes. The computing subsystem 110 may also include input/output devices to allow users to view data and monitor and control the cell culture system 100, or to transfer data in and out of the cell culture system 100. For example, the computing subsystem 110 may include display screens, monitors, communications/interface ports, keyboards, audio systems, and the like. The computing subsystem 110 may be proximate to the other components in the cell culture system 100 (e.g., a local computer) or may be remote from the other components in the cell culture system 100 (e.g., a cloud server). In some implementations, the computing subsystem 110 may have one or more components proximate the other components in the cell culture system 100 and some components remote from the other components in the cell culture system 100. The computing subsystem 110 may be configured to communicate with the other components in the cell culture system 100 utilizing a wired and/or wireless connection (e.g., Ethernet cables, optical fiber, Wi-Fi, Bluetooth), and may be configured to communicate with external components utilizing a wired and/or wireless connection. The computing subsystem 110 may have additional functionality and components not disclosed herein, but would be apparent to a person of ordinary skill in the art.

The cell culture system 100 may be configured to allow extended cell culture processes to be performed within a single cell culture container 106 using the cell editing subsystem 114. Because the cell editing subsystem 114, as directed by the computing subsystem 110, can selectively remove cells from cell culture, the cell culture does not overgrow the cell culture container, and therefore does not require frequent transfers ("passaging") which are stressful on cell populations, disrupt cell processes, introduce potential sterility and contamination issues, and make time series tracking of cell-, region-, colony- or clone-specific behavior impossible. Thus, the combination of continuous monitoring via image and sensor data—enabled by the single-container process—may allow the computing subsystem 110 to predict the optimal regions or cells to remove in order to maintain low enough cell density to remain in the single cell culture container 106. In the process the cell culture system 100 may also perform in-place "sorting" of cells in order to enrich the population according to real-time measurements.

Figure 2:
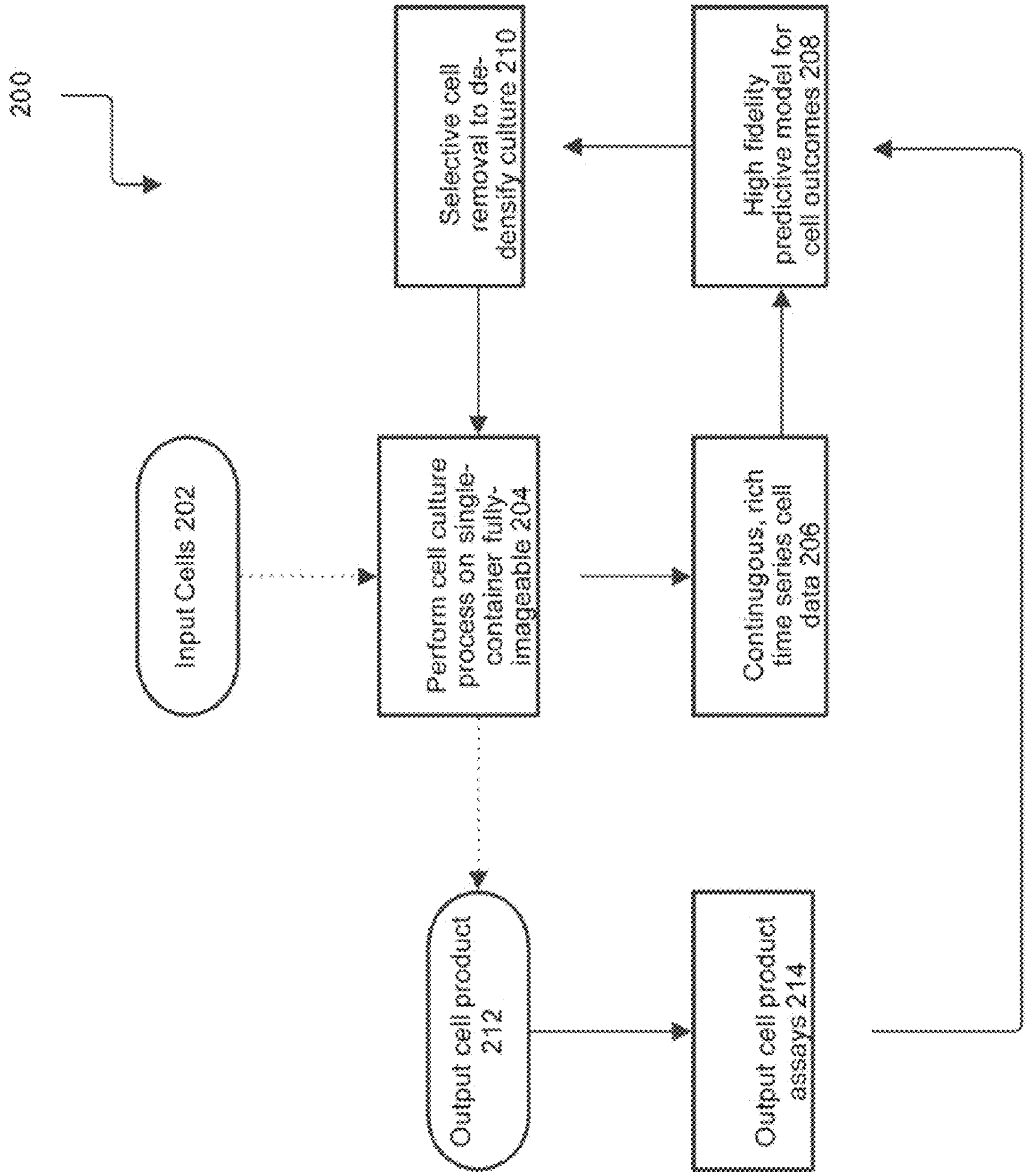
FIG. 2 is a flow chart of a method of operating a cell culture system in accordance with various implementations.

FIG. 2 is a flow chart of an example method 200 of operating a cell culture system in accordance with various implementations. The method 200 may be performed by a cell culture system, such as cell culture system 100. In block 202, input cells are seeded into a cell culture container that is fully imageable and able to support a cell culture for the duration of the cell process. This results in a single-container, fully-imageable cell culture. The cell culture container may provide a closed, sterile environment for cell culture processes. In block 204, a cell culture process may be performed on the single-container, fully-imageable cell culture. The cell culture process may be sustained within a single container for the duration of the process (as opposed to transferring, sometimes selectively, cells from container to container to maintain property density). The cell culture process may be monitored and controlled by a computing subsystem in the cell culture system.

In block 206, the cells may be observed with an imaging subsystem to acquire unbroken, contiguous, rich time series of cell data. In block 208, the computing subsystem may analyze the cell data to develop a high fidelity predictive model for cell outcomes. The computing subsystem may utilize the predictive model to adjust the cell culture process dynamically. For example, in block 210, the computing subsystem may control a cell editing subsystem to selectively remove cells from the cell culture in order to de-densify the cell culture. The selective removal, in turn, is optimally configured to improve the predicted yield, functionality, phenotype, or other properties of the output cell product. The method 200 may iterate through the steps of collecting imaging data, refining the predictive model, and editing the cell culture until the output cell product is produced in block 212.

In block 214, output cell product assay 214 may be performed on the output cell product at the end of a cell culture operation. The results of the assays may be used in conjunction with the time series cell data to adjust the predictive model in block 208. In some cases, the output cell product may be harvested dynamically from the process (for example, a subset of cells may be selected and removed from the cell culture, or cell products within the media are removed from the cell culture) and the corresponding assay results immediately fed back into the predictive model. In this manner, the method 200 allows for a completely automated method for dynamically processing and editing cell cultures, from input cells to output cell products. This allows for faster, more accurate cell culture processes without the time and expense of manual human intervention, which in turn reduces the time and cost for producing output cell products. This approach is also easily scalable to enable large scale biological manufacturing.

In some implementations, preliminary process optimization and/or training of models is carried out using cells from non-human species, for example mouse cells, which have a segmentation clock of 2 hours vs 5 hours for humans, and proliferate at a rate of 2-3× faster than humans. For example, non-human cells may be used for the development of fluidic chamber processes for reprogramming and/or differentiation more rapidly than would otherwise be possible with slower-growing human cells. In addition, training of machine learning models for cell localization, pluripotency or differentiation prediction, cell colony tracking, cell colony outcome, and combinations thereof may be performed using non-human cells. As another example, optimization of directed energy cell culture editing strategies, patterns, algorithms, conditions, in microwell plate formats and/or in closed liquid chamber formats, may be carried out using non-human cells.

Multi-Focus Imaging Subsystems

In many cell culture systems, it is challenging to obtain high-throughput, high-content label-free cell culture images. Label-free imaging means methods of imaging cells without labeling or altering the cells. An example of labelled imaging is fluorescent microscopy, in which cells are stained with fluorescent compounds that interact with certain laser wavelengths to allow for high contrast imaging. However, labeling cells may alter and damage cells, which may lead to defects in the output cell product. Conventional label-free imaging methods have their own drawbacks. For example, brightfield imaging gives little contrast and little information about cellular or intracellular structures. Phase contrast imaging gives only very local, relative phase information which is not consistent across cell types and densities.

In addition, maintaining focus is often an issue. To achieve steady focus, most cell culture imaging systems either use a step-and-image system (where the XY motion, settling, and autofocus take significant time) and/or use a low magnification/numerical aperture (NA) to achieve a large focus depth, which again reduces cell data. The problem is compounded if used in conjunction with a laser cell editing system, in which the laser must accurately hit cells/regions and be in focus to achieve its intended effect (e.g., destroying/removing individual cells or regions, or temporarily permeabilizing cell membranes to allow intracellular transport of compounds).

The systems and methods disclosed herein solves multiple issues in conducting high-speed, label-free cell culture imaging by using linear defocused (or "multi-focused") images. Multi-focus imaging allows for continuous focus adjustment for imaging as well as optional laser scanning, and multi-focus imaging of cells which serves to provide data that provides enhanced structural information regarding cells or regions of cells. The various implementations disclosed herein allow this functionality to be integrated into a continuous-motion imaging subsystem for high-throughput imaging and/or laser editing.

Various implementations disclosed herein include an imaging subsystem that makes multiple passes over a cell culture container to obtain image stripes. The image stripes may be assembled into a complete picture of the cell culture. For example, the image may include information along the X, Y, and Z axes using the multi-focus capability described herein. This image may be processed and analyzed by a computing subsystem to develop a cell editing strategy. In cases in which the cell editing subsystem is a laser editing mechanism, another pass over the cell culture is made and the laser is used to edit cells, with the multi-focus imaging subsystem used to ensure that the edits are made at the intended locations.

Figure 3:
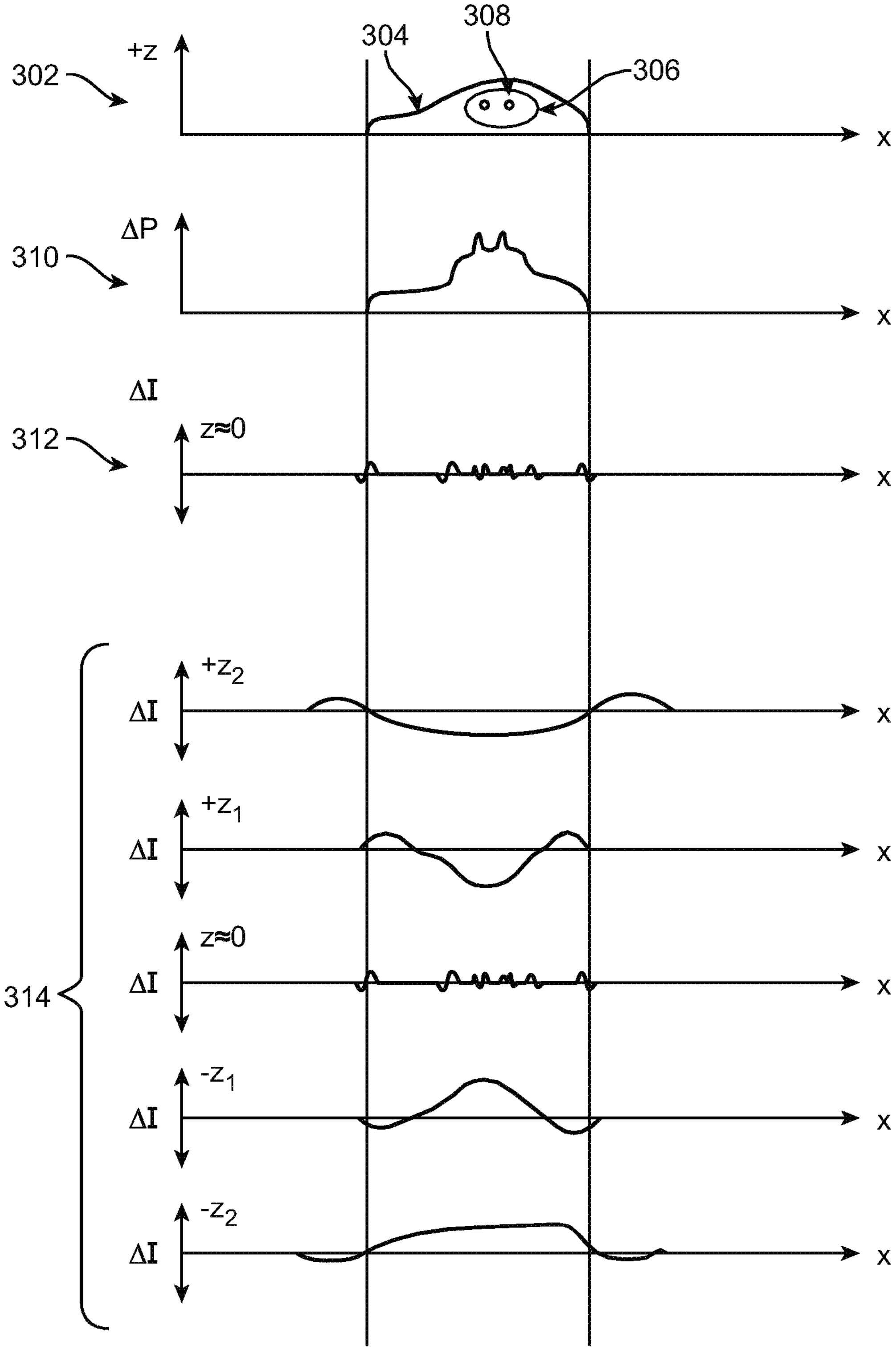
FIG. 3 are graphs illustrating how cell features may be observed at different focus planes in a brightfield illuminated cell culture in accordance with various implementations.

FIG. 3 include graphs illustrating how cell features may be observed at different focus planes in a brightfield illuminated cell culture in accordance with various implementations. For example, graph 302 depicts a cross-section of a single cell along the X axis, with the Z axis in the vertical direction and representing height. Graph 302 shows a cell body 304 containing cytoplasm and various other components, a nucleus 306, and nucleoli 604. In many applications the nuclear location is used to locate cells, but the cell body extent and shape, as well as the intracellular or nuclear components, may also give information about the cell state, phenotype, health, cell cycle, etc. For example, it is known that human iPSCs typically have two or more prominent nucleoli.

The shading in FIG. 3 is meant to depict the relative refractive index of the components, with the cell body 304 being at a higher refractive index than the surrounding cell media, and the nucleus 306 typically being at a higher refractive index than the cell body 304. It is these differences in refractive index that make cells or colonies visible in light microscopy, based on how the cellular components cause a phase delay in light passing through them, with resulting diffraction of light. There may also be some absorption (imaginary component of complex refractive index) by cellular components (for example if melanin is present), but typically the real component of the complex refractive index dominates in 2D adherent cell culture imaging.

Graph 310 shows the phase delay (vertical axis) created by light passing through the cell structure, with illumination parallel to the Z axis. The resulting wavefront propagates and through constructive and destructive interference creates a range of images at different Z focuses.

Graph 312 shows an example of image intensity (vertical axis) of the cell culture at approximately the plane of the cell (i.e., Z~0). At this focus level, the resulting signals are typically extremely small, and correspond to the smallest features in the cell and their diffraction patterns. Typical image-based microscopy autofocus systems select this plane because they seek a Z focus where the smallest resolvable features have maximum intensity (i.e., where single-pixel features are most prominent). However, as can be seen from graph 312, the images obtained at this plane typically contain only edge information, and can be difficult to interpret, particularly in dense cell cultures.

Graphs 314 shows an example of the image intensities (vertical axes) obtained at a range of Z focuses (e.g., $+Z_2$, $+Z_1$, 0, $-Z_1$, $-Z_2$). As is seen in the graphs 314, as Z moves away from the "zero" or "in-focus" plane, larger structures can be resolved in the intensity images, because the phase effects of these structures cause constructive or destructive interference as they propagate a sufficient distance. Images may be sampled at both positive and negative Z levels. Even though pairs of images at the same positive and negative Z displacements may be rough inverses of one another, they may be combined in subsequent computations to remove baseline or background effects, and also to compute both real (refractive index/phase delay) and imaginary (extinction) effects of the cell culture. Thus, collecting imaging information from three dimensions of a cell culture provides additional information that is valuable for data analysis and cell editing decisions.

Figure 4:
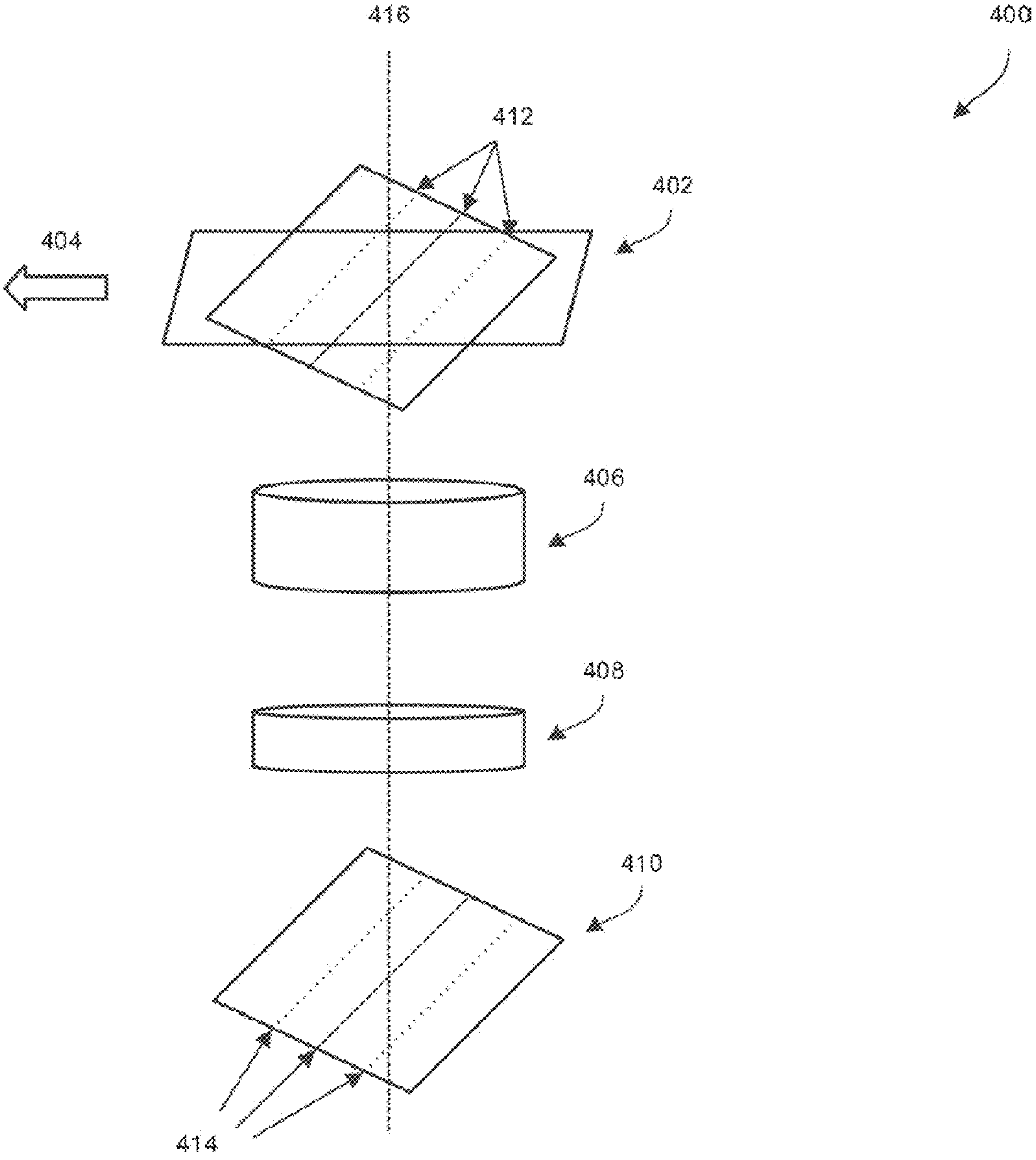
FIG. 4 is a block diagram of an example imaging subsystem of a cell culture system in accordance with various implementations.

FIG. 4 is a block diagram of an example imaging subsystem 400 of a cell culture system (e.g., cell culture system 100) in accordance with various implementations. A cell culture surface 402 is moved relative to the imaging subsystem 400 in a direction of motion 404. For example, this direction of motion 404 may be orthogonal to a vertical axis 416 of the imaging subsystem 400. The cell culture container containing the cell culture surface 402 may be translated and the imaging subsystem 400 may be held still, or vice versa. Optical elements, such as objective lens 406 and tube lens 408, may project an image of the cell culture surface 402 onto an image sensor 410. The image sensor 410 may be an area sensor (CMOS, CCD), or a series of linear detector arrays arranged perpendicular to the direction of motion 404. The image sensor 410 may be tilted along the direction of motion 404 such that the imaged plane in the sample is tilted, as indicated by parallel lines 412 on a projected tilt of the cell culture surface 402 and lines 414 on the image sensor 410. Using this arrangement and the linear motion of the imaging subsystem 400 relative to the cell culture surface 402, each portion of the sample is imaged at multiple Z planes as it is translated, which is illustrated in further detail with respect to FIG. 5. With a known relative velocity, the individual (linear) Z focus images are then realigned to form a composite multi-focus image of each point in the cell culture surface 402.

With respect to the various imaging systems and/or imaging subsystems disclosed herein, a cell culture (e.g., a closed cell culture chamber of a cell culture cassette) may undergo movement relative to the imaging system while imaging data is collected for the sample disposed within the cell culture chamber. When there is relative movement between a cell culture and an imaging system, the cell culture movement can include movement of the cell culture alone, movement of the imaging system, or both. For example, (i) a cell culture chamber may undergo continuous movement relative to the light source and the objective of an imaging system or (ii) the light source and the objective of the imaging system may undergo continuous movement relative to the cell culture chamber, or both, while the image data is acquired. The simultaneous collection of imaging data combined with the continuous relative movement may enable the efficient evaluation of cells within the cell culture, for example, with respect to cell quality metrics, cellular characteristics, or phenotypic features relevant to adherent cells such as iPSCs. This increased imaging efficiency can provide tremendous advantages over conventional imaging approaches such as non-continuous imaging of free floating cells in which each cell may require a z-axis focusing step to properly focus the imaging system before a single image is captured for each cell at a discrete time point. For example, when a cell culturing platform utilizes a cell culture rack with one or more imaging systems/subsystems that are shared amongst a plurality of cell culture process modules and the corresponding cell culture containers (e.g., cell culture cassettes), non-continuous imaging may be insufficient for a shared imaging system to efficiently gather the requisite imaging data to generate images having sufficient resolution to effectively evaluate the cells. Therefore, the continuous movement and cell imaging provides a technical solution that solves a technological problem that arises within cell culturing, and particularly when evaluating iPSCs during automated or semi-automated cell culturing processes.

Figure 5:
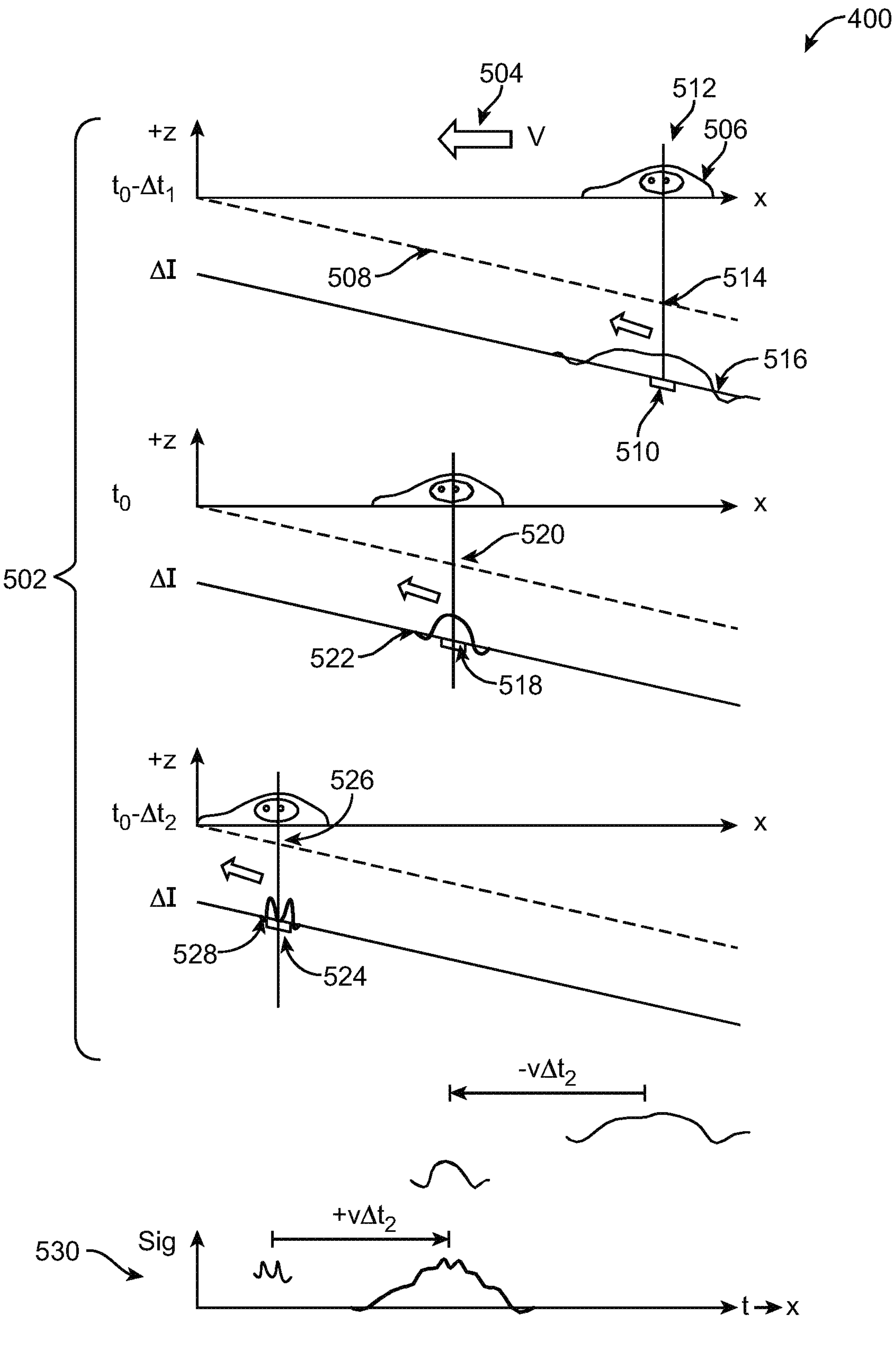
FIG. 5 are graphs illustrating the imaging of a single cell using a multi-focus imaging subsystem in accordance with various implementations.

FIG. 5 include graphs illustrating the imaging of a single cell using a multi-focus imaging subsystem (e.g., imaging sub-system 400) in accordance with various implementations. The imaging subsystem may sample at three different points along the Z axis using three detectors. The graphs illustrate the imaging process along a single dimension (e.g., the X axis), but it should be understood that each detector may be a linear detector array (e.g., linear along the Y axis orthogonal to the figure). The detector arrays may be a single linear array, or arrays with a number of lines, for example a 2048×16 array, with the longer axis perpendicular to the relative motion between the cell culture and imaging subsystem. The linear detector arrays may be portions of an area sensor, as shown in FIG. 4. However, in the simplified example shown in FIG. 5, three discrete detectors and the corresponding signals as a cell passes through the imaging volume are shown.

Graphs 502 show three timepoints as the cell passes the imaging subsystem at a velocity vin a direction of motion 504. A single cell 506 is shown moving across the imaging subsystem along the direction of motion 504, and a series of images along a tilted focus plane 508 (tilted along the Z axis) are sampled to obtain signals that can be used to compute cellular structural information. At a first time point $t_0-\Delta t_1$, a first detector array 510 samples a first position 512 as the cell passes through it, with the focus adjusted to a first Z position 514 (e.g., a first −Z offset). The resulting intensity signal 516 is shown as a complete trace (observed over a short time period), but is sampled at high speed as the cell passes the first position 512, indicated by the vertical line. Since the first detector array 510 is imaging a plane at a significant Z offset, the signals observed by it correspond to diffraction from larger structures in the cell culture.

At a second time point to, a second detector array 518 is used to image a second Z position 520 and produces a time-dependent signal 522 as the cell passes the second Z position 520. The signal produced at this Z position may correspond to medium-sized structures such as the cell nucleus. At a third time point $t_0+\Delta t_1$, a third detector array 524 is used to image a third Z position 526 and produces a time-dependent signal 528 as the cell passes the third Z position 526. The signal produced at this Z position may correspond to small-sized structures such as the cell nucleoli.

Graph 530 shows how the signals generated by the detector arrays in graphs 502 may be combined using appropriate time delays (corresponding to spatial distance along the X axis in this imaging configuration) to produce a composite image of the cell that contains multi-scale structural information in a single image. A relatively simple addition operation is shown here, but more sophisticated operations such as iterative transport of intensity solutions may be employed to obtain a good prediction of phase delay through the cell and its components.

The multi-focus image generated by the imaging subsystem 400 may then be used to compute structural information on individual cells, groups of cells, regions, or colonies. This structural information includes but is not limited to location, density, nuclear location, intracellular structures, 3D profile, and refractive index. Data processing and analysis may be performed in order to obtain additional information, such as estimating internal structure, phase shift, refractive index and/or Z profile. More generally, these techniques may be used to build a quantitative phase image (QPI) of the cell culture, without the use of laser or other interferometric hardware implementations and techniques with their added complexity, instability, and phase-unwrapping calculation requirements. These computational methods include but are not limited to solving the Transport of Intensity (TIE) equation from the multiple focus images, which is described in Zhong, Jinshan, et al., "Transport of Intensity phase imaging by intensity spectrum fitting of exponentially space defocus planes," Optics Express Vol. 22, Issue 9, pp. 10661-10674 (2014), which is incorporated by reference in its entirety, and as described in conjunction with a range of illumination arrangements in Zou, Chao et al., "High-resolution transport-of-intensity quantitative phase microscopy with annular illumination," Nature Scientific Reports Vol. 7:7654 (2017), which is incorporated by reference in its entirety. In other implementations, deep learning models such as convolutional neural networks (CNNs) may be used to directly process the captured image data and output higher-level predictions about the cells, cell regions, colonies, or cell culture as a whole. For example, a CNN may be used to create a virtual fluorescence image from the multi-focus component images generated by the multi-focus imaging subsystems disclosed herein. This may be more efficient than first computing a phase image and then using this phase image as an input to downstream models or processing.

Figure 6:
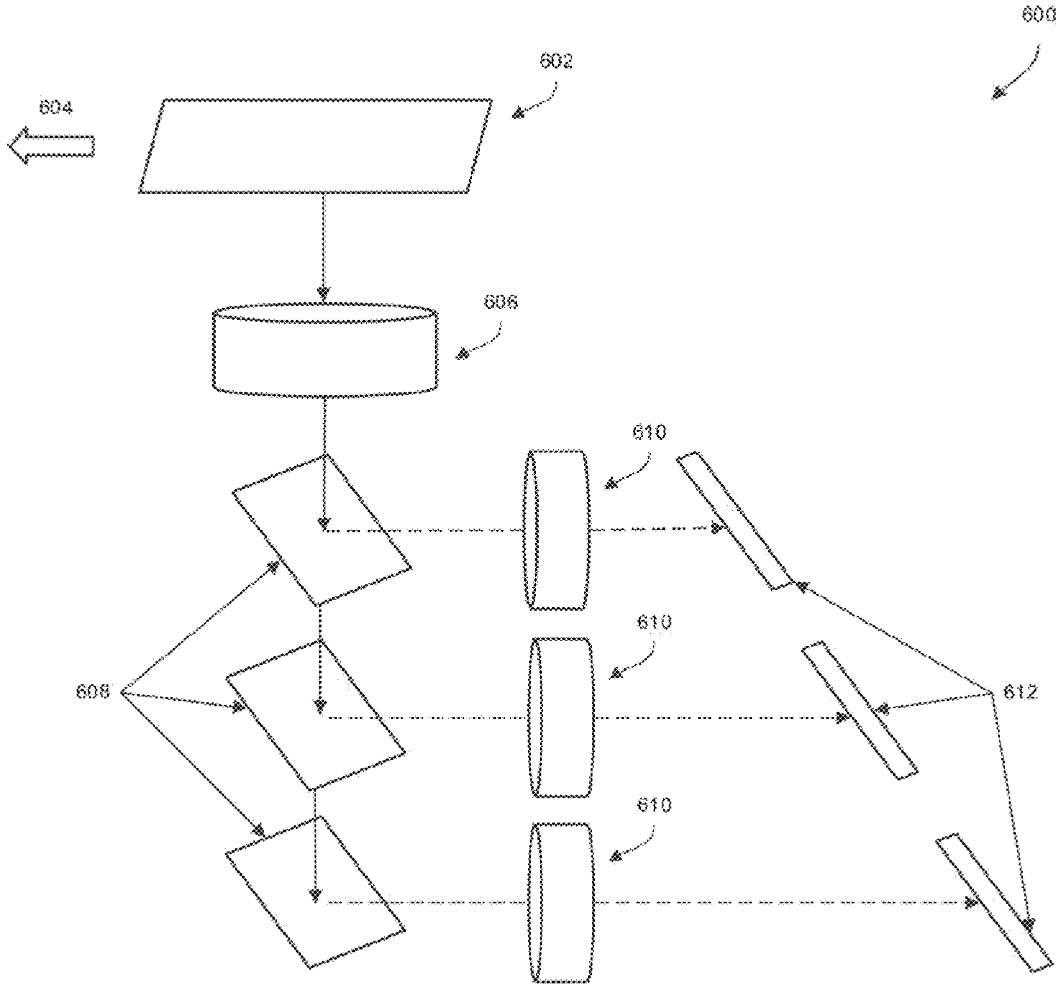
FIG. 6 is a block diagram of another example imaging subsystem of a cell culture system in accordance with various implementations.

FIG. 6 is a block diagram of another example imaging subsystem 600 in a cell culture system in accordance with various implementations. A cell culture surface 602 is moved relative to the imaging subsystem 600 in a direction of motion 604. For example, this direction of motion 604 may be orthogonal to a vertical axis of the imaging subsystem 600. The cell culture container containing the cell culture surface 602 may be translated and the imaging subsystem 600 may be held still, or vice versa. Optical elements, such as objective lens 606, may project an image of the cell culture surface 602 onto a plurality of beam splitters 608.

The beam splitters 608 may split the light from the objective lens 606 into a plurality of paths, each path passing through a tube lens 610 that focuses the light onto a sensor 612. The sensors 612 may be placed at varying distances from the tube lenses 610 in order to sample multiple Z planes within the image signal. The sensors 612 may be oriented flatly along the focus plane of the tube lenses 610. The sensors 612 may be linear detector arrays, linear detector arrays with a few elements along the short axis (for example, 2048×4), or an area sensor. Area sensors may be used in a number of modes, such as (1) full-frame mode, (2) utilizing one or more regions of interest to correspond with linear sections projected onto them (for higher speed operation), or (3) in subsampling mode in which a small number of lines are sampled (for higher speed operation).

Figure 7:
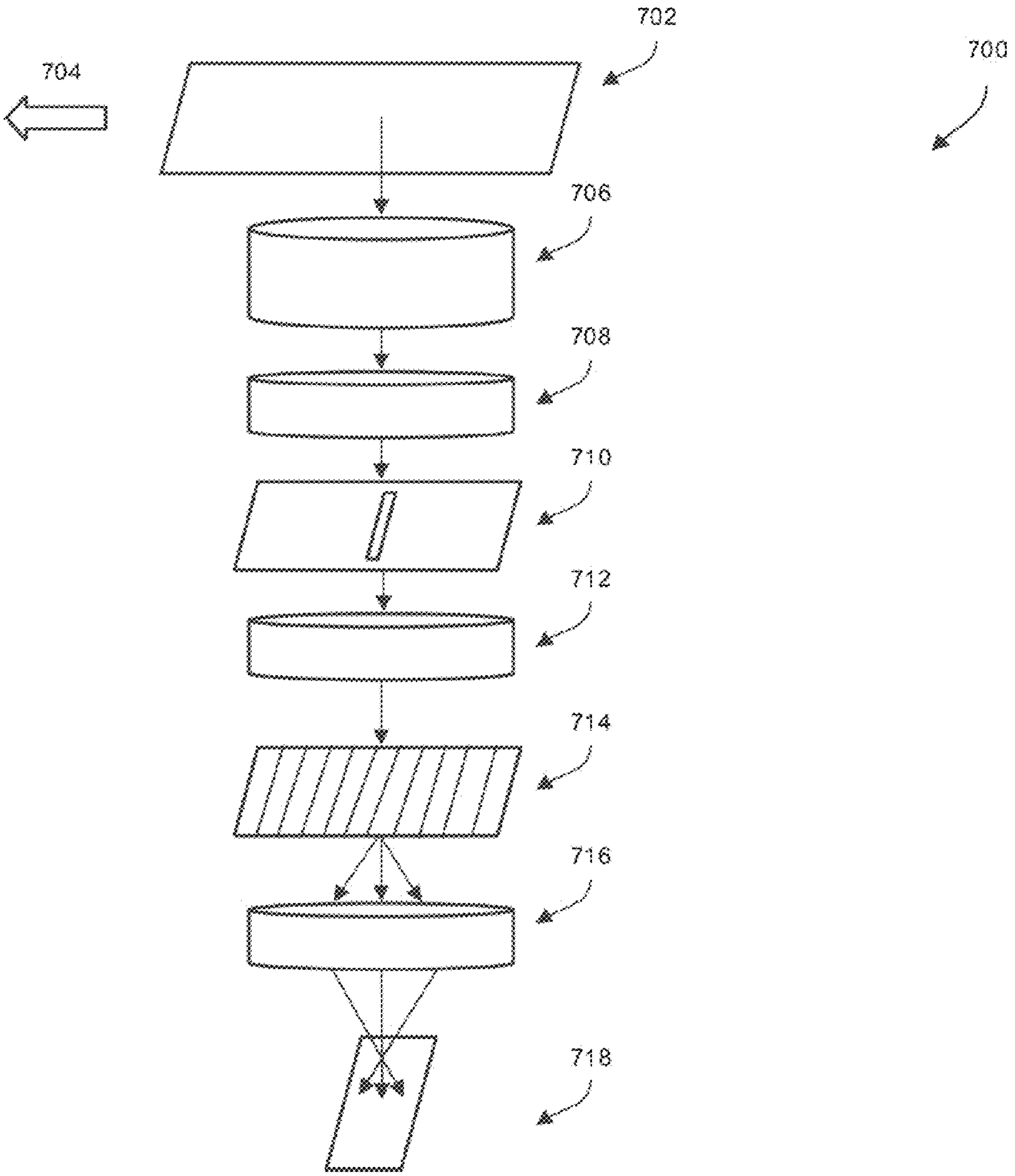
FIG. 7 is a block diagram of another example imaging subsystem of a cell culture system in accordance with various implementations.

FIG. 7 is a block diagram of another example imaging subsystem 700 in a cell culture system in accordance with various implementations. A cell culture surface 702 is moved relative to the imaging subsystem 700 in a direction of motion 704. For example, this direction of motion 704 may be orthogonal to a vertical axis of the imaging subsystem 700. The cell culture container containing the cell culture surface 702 may be translated and the imaging subsystem 700 may be held still, or vice versa. Optical elements, such as objective lens 706, may project an image of the cell culture surface 702 onto a focusing lens 708. The focusing lens 708 may focus light onto a slit aperture 710 which serves to isolate and filter the signal from the imaged line. A collimator lens 712 captures and collimates the filtered light and projects it onto a multi-focus diffractive element 714. The multi-focus diffractive element 714 may be configured to diffract the light into multiple discrete image paths, each with a different effective Z focus. A lens

716 images these image paths onto a sensor 718, which may be an area sensor or multiple linear detector arrays. Example implementations of the multi-focus diffractive element 714 and sensor 718 setup is described with more detail in reference to FIGS. 8-9. Using this configuration, multiple images of the light signal from the cell culture are captured simultaneously as the imaging subsystem moves relative to the cell culture. A computing subsystem may be configured to re-compose the images into multiple 2D images, each representing a different Z focus image of the cell culture.

Figure 8:
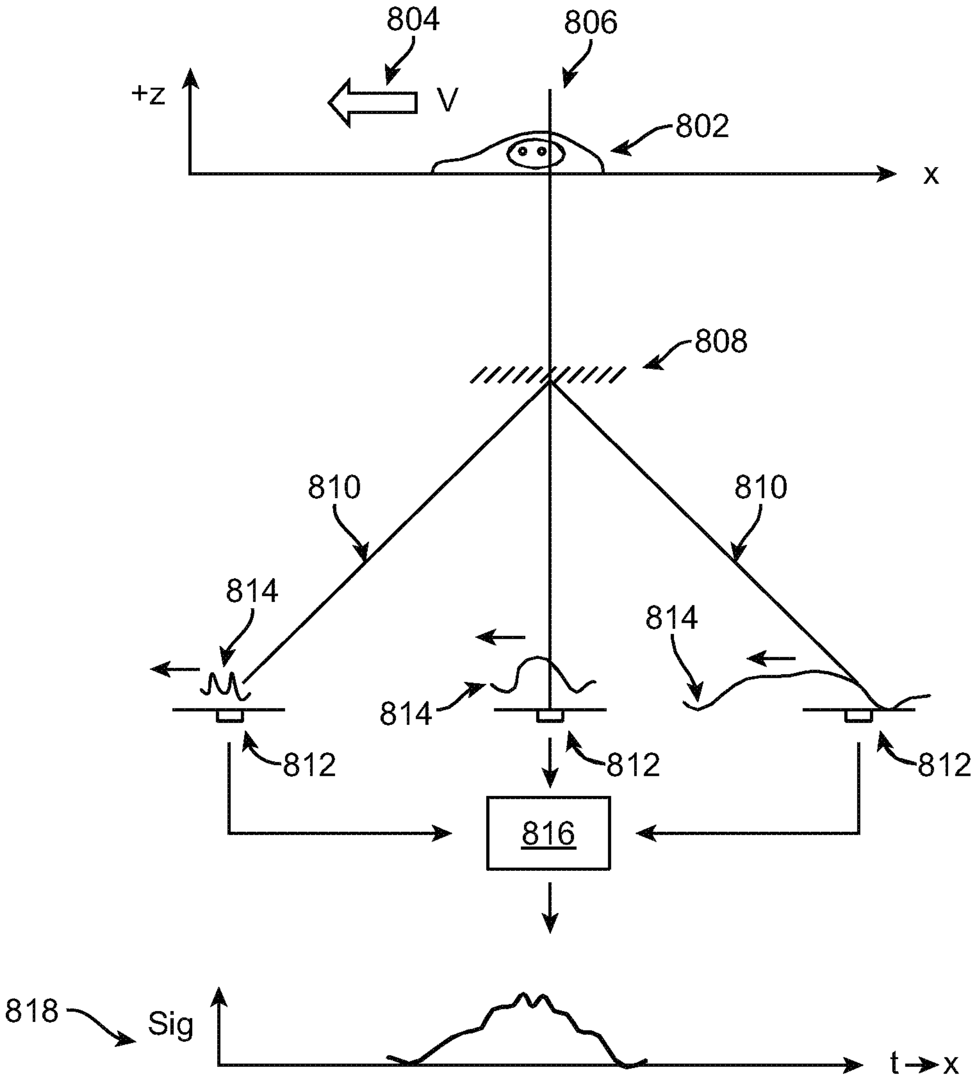
FIG. 8 is a diagram of an example implementation of a multi-focus diffractive element and a detector in accordance with various implementations.

FIG. 8 is a diagram of a multi-focus diffractive element projecting multiple Z focus plane images onto multiple detectors in accordance with various implementations. FIG. 8 illustrates one example implementation of the multi-focus diffractive element and sensor setup shown in FIG. 7. A cell 802 moves relative to the imaging subsystem along a direction of motion 804 with a velocity v, which may be a constant velocity in some implementations. At a certain point in time during the imaging, a line 806 along the Y axis (shown here as a single vertical slice in one dimension) is imaged. A multi-focus element 808 splits the optical signal along the line 806 into a plurality of beams 810, each corresponding to different Z focuses (i.e., different values along the Z axis). A number of optical elements (e.g., objective, lenses, and apertures) may be disposed between the multi-focus element 808 and detectors 812, the optical elements not shown in FIG. 8 for simplicity. A series of detectors 812, for example linear detector arrays or portions of an area sensor array, convert the optical signals corresponding to different Z focus images into electrical signals 814. These electrical signals are combined by a computing subsystem 816 (which may be similar to computing subsystem 110 in FIG. 1) to form a representation of the cell as a function of X (derived from time and velocity), as shown in graph 818. In other implementations, the individual images from the multiple detectors 812 may be built up separately. Then the multiple focus images may be used as an input to CNNs or other models directly in order to predict cell, cell region, cell colony or cell culture properties such as cell locations, nuclear locations, cell cycle, cell density, cell layer thickness, cell phenotype, cell colony information, or a variety of other properties.

Figure 9:
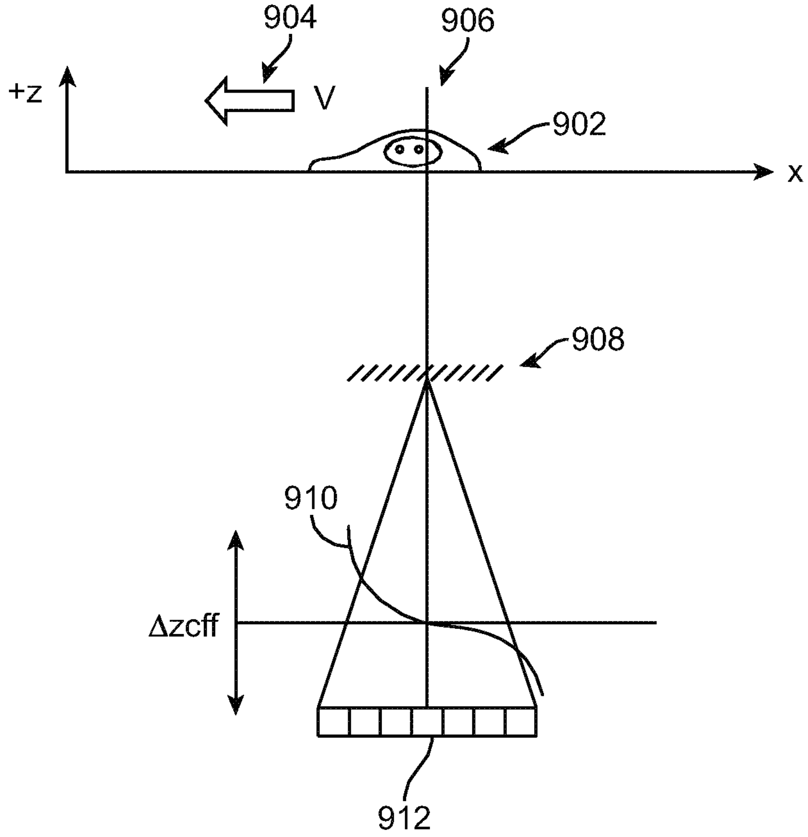
FIG. 9 is a diagram of another example implementation of a multi-focus diffractive element and a detector in accordance with various implementations.

FIG. 9 is a diagram of another example implementation of a multi-focus diffractive element and a detector in accordance with various implementations. FIG. 9 illustrates another example implementation of the multi-focus diffractive element and sensor setup shown in FIG. 7. A cell 902 moves relative to the imaging subsystem along a direction of motion 904 with a velocity v, which may be a constant velocity in some implementations. At a certain point in time during the imaging, a line 906 along the Y axis (shown here as a single vertical slice in one dimension) is imaged. The light signal is received by an optical element 908, which is configured to produce a continuous range of Z focuses along the imaging line 906. The effective Z focus is depicted by the curve 910, shown here with a non-uniform focus spacing such that finer increments of focus are captured near Z=0, and broader steps are captured at large +/−Z. This continuously-variable focus image is projected onto a detector array 912.

The detector array 912 may have a large number of elements along the Y axis (orthogonal to the figure) to sample the image line 906 as the cell culture is translated by the imaging system. The detector array 912 may also have a series of elements along the X axis configured to sample the different Z planes as projected by the optical element 908. For example, a linear array such as the Hamamatsu S10202-16-01 CCD array (4096×128 elements) may be used to image a Y-axis stripe as the sample is translated along the X axis. The optical element 908 projects different Z focus images across the 128-wide direction, so that as cells move across the image line 906 a multi-focus image of each cell is captured and then a representation is reconstructed from this data. In some implementations, the detector array 912 may operate in "frame mode," in which the entire 4096×128 image is exposed and read out simultaneously at a high rate. In other implementations, the detector array 912 may be used in time-delay integration (TDI) mode, which integrates signals along the 128-element axis as objects translate across the X axis. In a tilted-focus configuration such as the one shown in FIGS. 4-5, the imaging subsystem may be configured to sample a range of −Z planes where objects diffract light to form bright areas, with the Z depth of this brightness dependent on the size of the phase objects. By synchronizing the TDI transfer and integration with the motion of the cell culture relative to the imaging subsystem, a "summed" signal across multiple focus depths may be produced in the integrated output of the detector array 912. Using the example of a Hamamatsu sensor, this scheme could produce a phase representation of a cell culture at 100,000 lines/second x 4096 pixels=over 400M pixels/second.

Figure 10A:
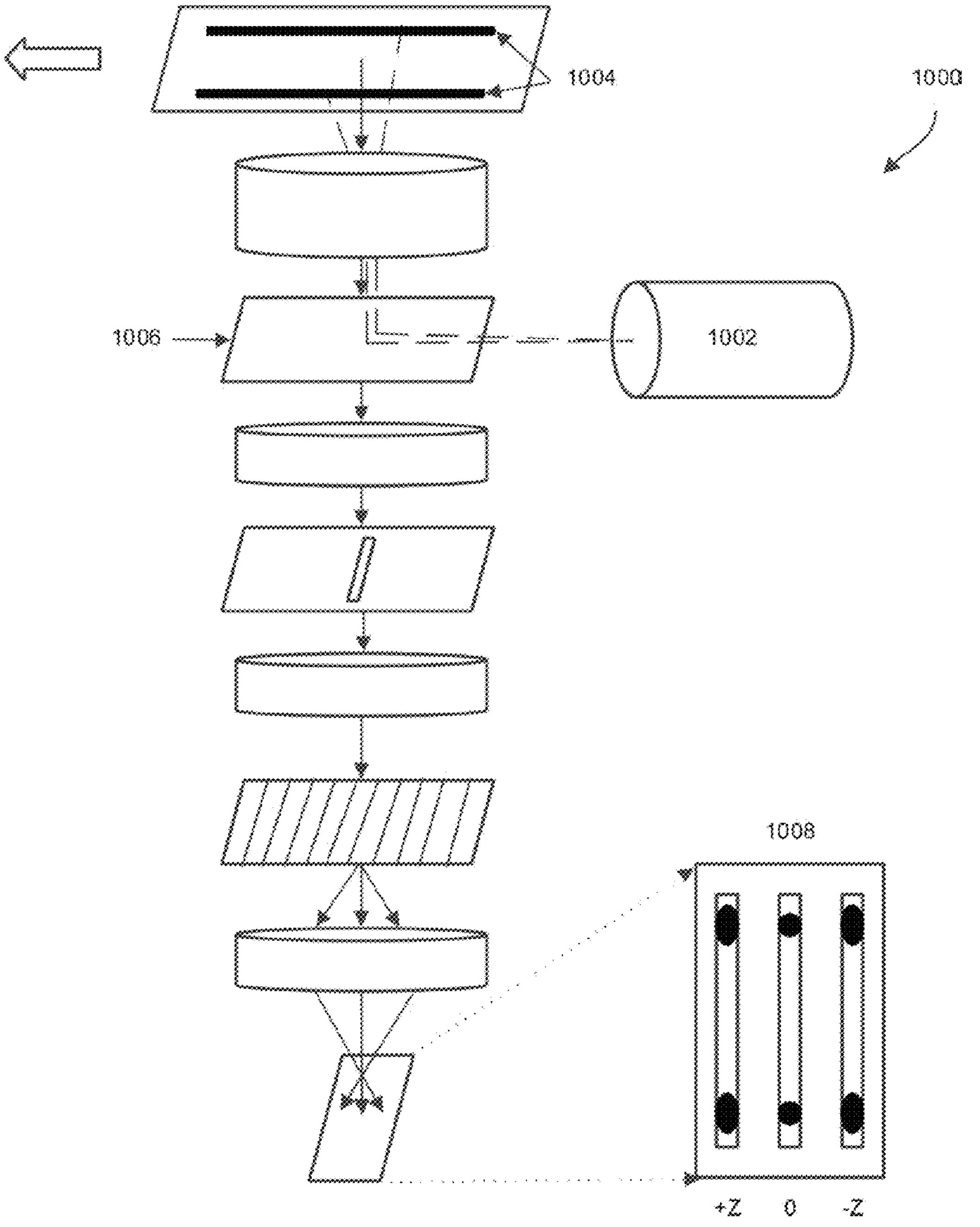
FIG. 10A is a block diagram of an extension of the imaging subsystem shown in FIG. 7 in accordance with various implementations.

FIG. 10A is a block diagram of an extension of the imaging subsystem shown in FIG. 7 in accordance with various implementations. In implementations without an auxiliary optical focus guide (e.g., the imaging subsystem 700), focus may be measured from the captured images. For example, a gradient measurement method that produces a peak signal when the image of the cell culture is in focus may be used. The overall system focus may be adjusted such that this "focus" signal is at a maximum for the central linear image capture (and then the adjacent linear detectors capture the +Z and −Z focus images).

Imaging subsystem 1000 in FIG. 10A includes an illumination subsystem configured to enhance autofocus capability. In this implementation, a laser module 1002 having optics (e.g., diffractive and lenses) projects two lines 1004 onto the cell culture surface via a beam splitter/combiner 1006. This light is reflected from the surface bearing the cell culture and into the multi-focus imaging subsystem 1000. The sensor detects the light reflected from the lines 1004, as shown in inset 1008. The lines are positioned at one or both edges of the imaged region, and parallel to the relative motion of the imaging subsystem to the cell culture. Inset 1008 shows an example of the laser focus guides projected onto a 3-linear element imaging system, each element representing focus planes at +Z, Z~0, and −Z. The projected lines are defocused and produce larger spots in the +/−Z plane detectors, while the spots at the Z~0 detector is smaller. The imaging subsystem and/or computing subsystem may then use a number of control strategies by which to adjust focus. For example, it can minimize the spot size in the central linear sensor (Z~0), or also use the relative spot sizes in the +/−Z linear sensors to adjust overall focus (mechanically) in order to equalize or maintain a certain proportion between spot sizes in +/−Z.

Figure 10B:
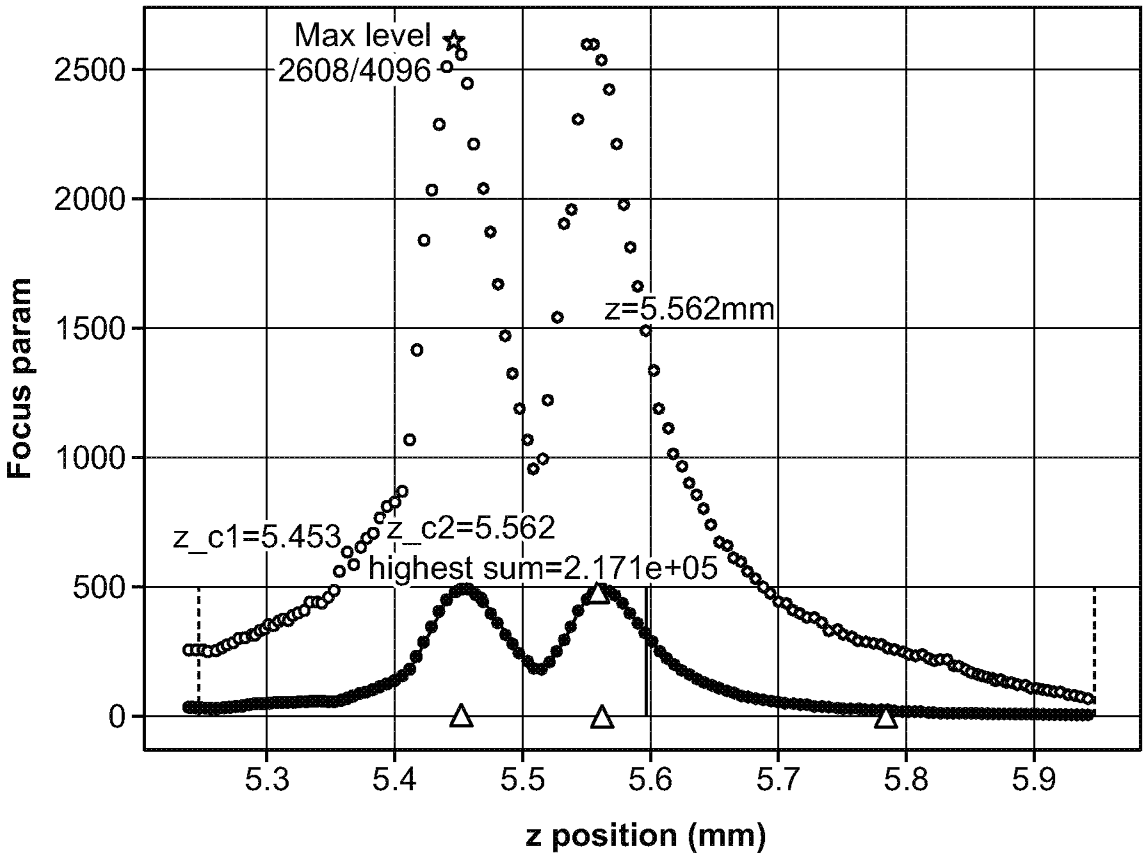
FIG. 10B shows an exemplary autofocus output from a system utilizing a 532 nm pulsed laser in accordance with various implementations.

FIG. 10B shows autofocus system output from a system utilizing a 532 nm pulsed laser for cell culture editing as well as autofocus functions. A laser steering system projects a repeated pattern of points into the field of view of the imaging system, and a z translator translates the objective relative to the cell culture container. The "focus parameter" (y axis) indicates the sharpness of the projected points in the imaging system. Two peaks are shown, one at the external face of the wall of the cell culture vessel, another at the internal face where cells adhere. Accordingly, FIG. 10B illustrates the use of existing system components within an imaging and laser cell editing system/subsystem to achieve accurate autofocus.

Figure 11:
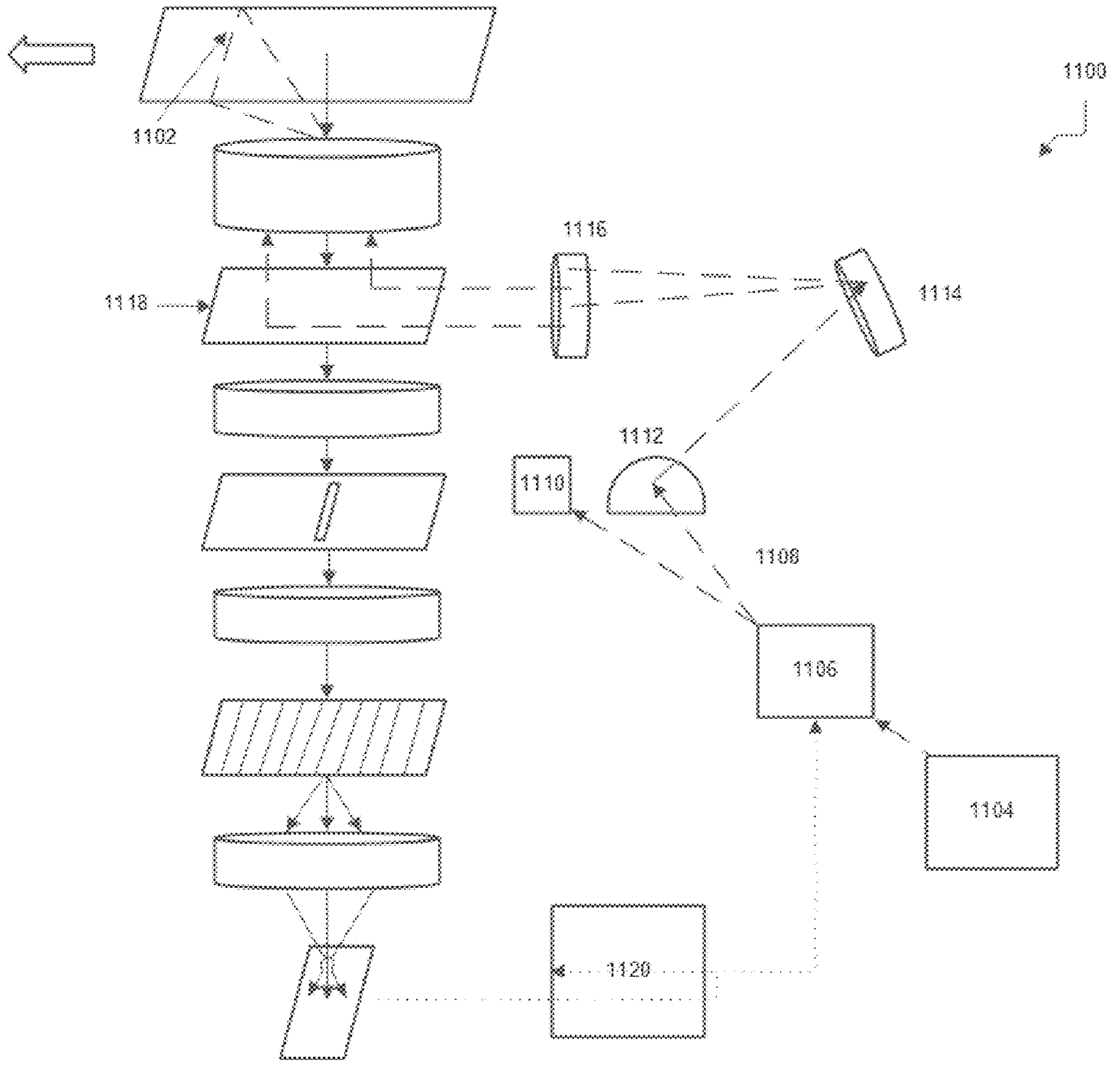
FIG. 11 is a block diagram of an imaging subsystem combined with a cell editing subsystem in accordance with various implementations.

FIG. 11 is a block diagram of a system 1100 that includes an imaging subsystem combined with a cell editing subsystem in accordance with various implementations. The imaging subsystem may be similar to the imaging subsystem 700 shown in FIG. 7. The cell editing subsystem may be used to edit the cell culture and may be similar to cell editing subsystem 114 in FIG. 1. The cell editing subsystem shown in FIG. 11 may be a laser scanning system. In this implementation, the laser scanning system raster-scans perpendicular to the direction of relative motion as indicated by dashed line 1102, and the energy is modulated according to cell editing instructions generated by a computing subsystem.

The cell editing subsystem may include a pulsed laser 1104 that generates laser pulses that are projected into an acousto-optic deflector and modulator (AODM) 1106. The AODM 1106 modulates the pulse energy on a per-pulse basis by deflecting some energy into a first order beam 1108, while allowing the zero-order beam to pass through to a beam dump 1110. By varying both the RF frequency and RF power to the AODM 1106, it is possible to adjust the angle of the first order beam 1108 on a pulse-by-pulse basis. This angle may correspond to the axis of travel of the imaging subsystem relative to the cell culture. The angle adjustment by the AODM 1106 allows for a number of features, including (a) compensation of position for motion when using a resonant mirror (without this, the scan forms a "zig-zag" pattern; with this compensation, parallel lines are possible); (b) trimming of position to hit cells at specific points; and (c) adjusting the "lag" of the laser scanning line behind the imaging line (in some cases the scan line may be switched to the opposite side of the imaging line, if direction of relative motion is reversed).

The first order beam 1108 is separated from the zero-order beam using a pick-off mirror 1112, which directs it towards a rotatable mirror 1114. The rotatable mirror 1114 may be a resonant galvo mirror, a spinning polygon mirror scanner, or any or type of rotatable mirror apparatus. The rotatable mirror 1114 allows for laser scanning perpendicular to the axis of relative motion. The laser light is directed to the objective via scan optics 1116, which may include a scan lens, tube lens, and/or other optical elements. A dichroic beam combiner/splitter 1118 redirects the laser light into the objective and towards the cell culture. The dichroic beam combiner/splitter 1118 is wavelength-specific and has low loss for both the laser and imaging wavelengths, and prevents laser light from entering the imaging path.

A computing subsystem 1120 in the system 1100, which may be similar to the computing subsystem 110 in FIG. 1, may be configured to control the cell editing subsystem and the imaging subsystem. The computing subsystem 1120 may be configured to perform a number of functions including but not limited to: composing a composite 3D image from the multi-focus line images acquired during travel; adjusting overall system focus based on the collected images; processing the composite 3D images to produce information about cell location, size, shape, refractive index, intracellular structure, density, phenotype, etc.; deciding a cell editing strategy for the cell culture; during laser editing, imaging the cell culture and registering features of the cell culture or cell culture container to the previously-acquired images; and driving the AODM 1116 in order to deliver the desired effect to the cell culture on a pulse-by-pulse basis, after adjusting for registration with previously-acquired features.

Single-Shot Fourier Ptychographic Imaging Subsystems

There are several challenges when imaging live cell cultures, particularly in the context of an automated cell culture system as described herein. First, living cell cultures are generally imaged label-free because labelling could damage the cells, hinder cell growth, introduce contaminants, or other negative effects. Second, automated or analytical processes built for live cell cultures usually require a high degree of detailed information about the cells. This information includes, but are not limited to, nuclear locations, cell membrane and cytoplasm morphology, and intracellular and/or intranuclear structures and configuration.

Third, there should be high throughput for imaging of live cell cultures for several reasons, such as sensitivity to changes in environmental conditions outside an incubator. The ability to detect small changes is important for large-area, high-frequency imaging for R&D, but is especially important for clinical applications where doses are large and there should be short time gaps between imaging, image processing, decision making, and subsequent editing or other operations on the cell culture. Lastly, the system should have the ability to spatially align cell editing operations (e.g., cell removal, cell harvest, intracellular delivery, or other spatial operations) accurately with the selected cells in the live cell culture so that editing operations performed right after imaging are spatially accurate.

While certain imaging methods may be implemented in an automated cell culture system, they generally have one or more drawbacks. For example, quantitative phase imaging (QPI) has been demonstrated to provide high information content on cells and intracellular structures. However, the conventional way of acquiring QPI images using holography (interference of light passing through the sample with a reference beam) requires complex and expensive optical paths and are very sensitive to operating conditions such as small changes in path length, including nonuniformities in the coverslip, cell media, etc.

An alternative approach is Fourier ptychography (FP)—the use of multiple illumination angles on the sample, together with a conventional objective that gathers multiple low-resolution images corresponding to these illumination conditions, to reconstruct high-resolution phase and amplitude images of the sample. Fourier ptychography can use low-cost components such as off-the-shelf LED arrays, conventional, low-NA objectives, and CMOS imagers. A wide range of architectures have been developed to implement FP imaging. However, none of the FP configurations described to date are suitable for very high throughput imaging of live cell cultures, which involves translating the imager relative to large cell culture vessel surfaces to capture and process large-area, contiguous imagery for subsequent visualization and automated image processing. A description of the class of techniques and algorithms may be found in Zhen et al., "Concept, implementations and applications of Fourier ptychography", Nature Physics Reviews, 3, pp. 207-223 (2021), which is hereby incorporated by reference in its entirety.

To capture multiplex images that may be used to calculate phase data for the cell sample, while in motion relative to the sample, a "one-shot" multi-image capture architecture is required. Few "one-shot" FT configurations have been developed that capture multi-angle images simultaneously. However, these configurations are all based on illumination that is substantially normal to the sample surface, and capture the light diffracted by the sample rather than illuminating the sample at a range of angles and observing the light that is captured by the objective. In this configuration, the frequency response of the system is limited by the numerical aperture (NA) of the objective. The requirement for a very high NA objective increases cost, reduces field of view (FoV) and therefore throughput, decreases working distance which can limit system design, and reduces the depth of focus which can make the system sensitive to small variations in sample or container geometry.

Thus, there is a need in the art for a high-throughput imaging system that uses a lower-NA objective to give a large field of view, long working distance, and large depth of focus for robust, high-speed imaging. The system should also be capable of wide-angle illumination. Multiple illumination conditions from a wide range of angles, with transmission through or reflection from the sample, measured independently and then combined computationally, can be used to generate a high-resolution representation of the sample even with a relatively low-NA, wide field of view objective.

The systems and method disclosed herein include an imaging subsystem for a cell culture system that has relative low NA and wide-angle illumination. The imaging subsystem may be capable of adapting the Fourier ptychography approach to high-throughput cell culturing applications. The imaging subsystem may include a multi-angle illumination source capable of emitting multiple wavelengths, in which the wavelengths have distinct angular distributions. The imaging subsystem may also include a sample illuminated by the illumination source, an objective collecting light from the sample, one or more wavelength-dispersive or wavelength-separating elements, one or more detectors/sensors that detect the separated wavelengths/wavelength bands simultaneously, and a computing subsystem to form a representation of the sample from the individual detector signals (corresponding to different illumination angles). The representation may be quantitative phase images of the sample.

The imaging subsystem may also include several other features. For example, in some implementations the imaging subsystem may image the sample in successive linear regions. In some implementations, the imaging subsystem may utilize linear detector arrays, or linear segments of an area detector, to detect each wavelength. In some implementations, the imaging subsystem may utilize linear masks at an intermediate focal plane after the objective to select light corresponding solely to a linear region. In some implementations, the sample may be moved relative to the imaging subsystem during imaging.

Figure 12:
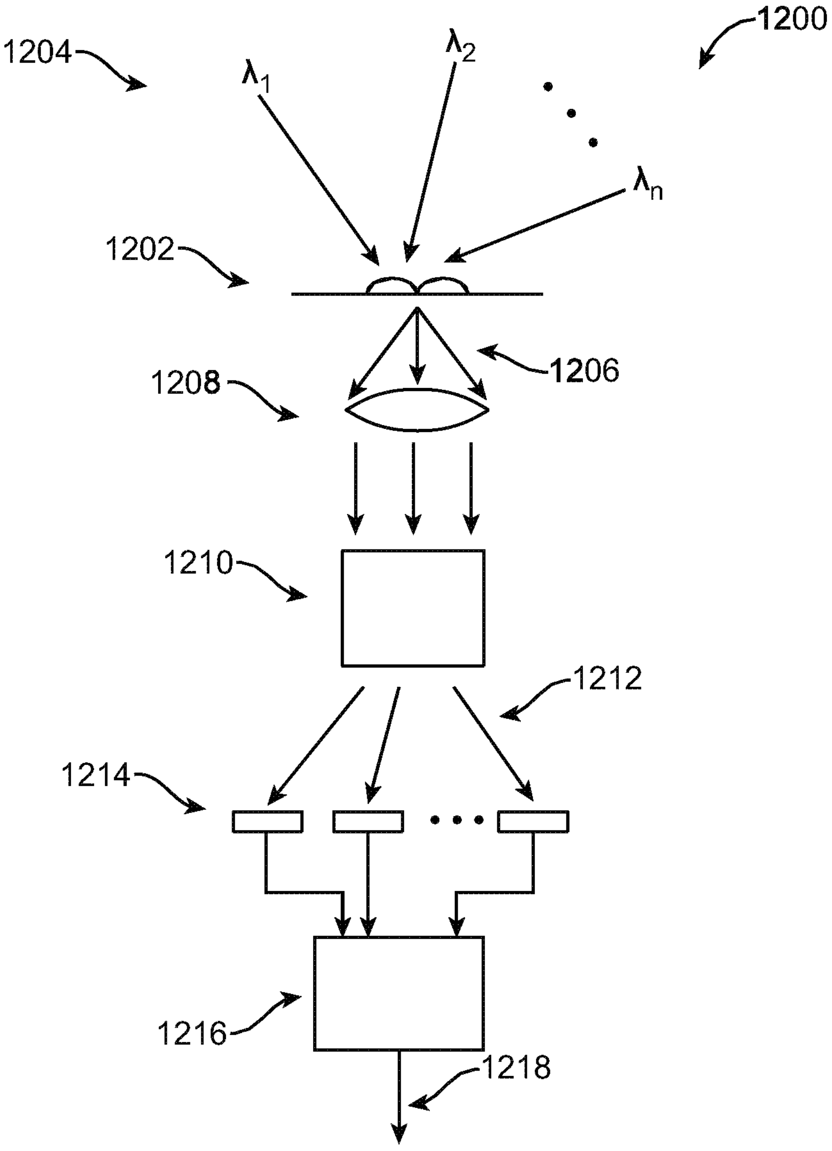
FIG. 12 is a block diagram of an imaging subsystem in accordance with various implementations.

FIG. 12 is a block diagram of an imaging subsystem 1200 in accordance with various implementations. The imaging subsystem 1200 may be part of a cell culture system, similar to imaging subsystem 112 in FIG. 1. The imaging subsystem 1200 may include a sample 1202. For example, the sample 1202 may be a cell culture inside a cell culture container (e.g., cell culture container 106) in the automated cell culture system. The sample 1202 is illuminated with a multi-wavelength light source 1204, the multiple wavelengths denoted by $\Delta_{1\text{-}n}$ in FIG. 12. Each wavelength has a distinct distribution of incident angles associated with it. In FIG. 12, the angular distribution is shown in one dimension, but in general there is a 2-dimensional angular distribution. The wavelengths may be discrete or continuous values. In the configuration shown in FIG. 12, the multi-wavelength light source 1204 illuminates the sample 1202 from the opposite side of objective lens 1208. However, in some implementations the multi-wavelength light source 1204 may be located on the same side as the objective lens 1208 (termed an epi-illumination configuration). Various examples of multi-wavelength light sources are described with respect to FIGS. 15-17.

The diffracted or reflected light 1206 exiting the sample 1202 is captured by the objective lens 1208. The light 1206 exiting the sample 1202 has a range of angles that are a result of the illumination angles and diffraction from the sample, and any light 1206 within the NA of the objective lens 1208 are captured. Light exiting the objective lens 1208 enters a wavelength separation subsystem 1210 that disperses or separates the light from the sample 1202 according to wavelength. The light may be separated into discrete bands of wavelengths (for example, with low-pass, high-pass, bandpass filters), or there may be continuous separation (for example, with transmissive or reflective diffraction gratings, prisms, or other high chromatic dispersion elements). Various examples of wavelength separation subsystems are described with respect to FIGS. 13-14.

The spatially separated light 1212 exiting the wavelength separation subsystem 1210 is incident on a plurality of detectors 1214 that detect the individual wavelength bands. For light separated into discrete bands, there may be a 1-to-1 correspondence between the number of detectors 1214 and the number of discrete bands. For light separated into a continuous wavelength spectrum, the resolution of the detectors 1214 may determine the number of measurable wavelength bands. The detectors 1214 may be implemented as single-element detectors, linear detector arrays, or 2D detector arrays.

The signals from the detectors 1214 are passed to a processing unit 1216, which may include analog and/or digital computing components that reconstructs a representation of the sample 1202 based on the light 1206 from the sample 1202, as illuminated from different angles simultaneously. The representation may be quantitative phase images of the sample 1202. The processing unit 1216 may combine the data captured by the detectors 1214 simultaneously by means of an inverse phase-retrieval calculation. There are several ways that the processing unit 1216 can achieve the reconstruction. In some implementations, the processing unit 1216 may use algorithms that reconstruct phase and amplitude iteratively by solving for a complex field (the sample 1202) that is consistent with the multiple amplitude observations by the different detectors 1214 (which correspond to different illumination angles). Alternatively, deep learning models such as convolutional neural networks (CNNs) may be applied to reconstruct sample amplitude and phase. These CNNs may be pre-trained on a large volume of examples measured by the imaging subsystem 1200 as well as a system that produces ground truth phase and amplitude (which may simply be the above iterative-type algorithms). The deep learning approach may significantly reduce computational intensity and/or improve processing throughput. Finally, a deep learning approach may be used to directly output features of interest, rather than sample amplitude and phase information. For example, a deep learning model may be trained to reproduce a fluorescently-labeled image of cells directly from the independent detector observations.

The relative intensities of the wavelengths in the multi-wavelength light source 1204 may be adjusted according to the typical amount of light in each wavelength band that is captured by the objective lens 1208, and subsequently detected by the corresponding detectors 1214. For example, if high-angle illumination results in relatively low light, the illumination at the wavelength(s) corresponding to high-angle illumination may be increased, and/or low-angle illumination decreased, in order to achieve uniform intensity across the detectors 1214, which in turn allows uniform signal-to-noise ratio and/or the same exposure time to be used across detectors. This is of particular importance in implementations in which a single 2D detector array with a single exposure clock is used to image all wavelengths, and/or where the system is continuously translating, so all detectors view the sample for the same amount of time and therefore need to acquire signals in the same amount of time.

The processing unit 1216 may output a signal 1218 that represents the sample 1202, the output signal 1218 including absorption and/or phase information, and/or 3D structural information. For example, the sample 1202 may be biological cells in a cell culture, and the output signal 1218 may be a 2D representation of absorption and phase delay through these cells. Thus, the imaging subsystem 1200 may achieve Fourier Ptychographic imaging of a sample in order to measure phase and amplitude components, while doing so in a "single shot" rather than multiple sequential illuminations and exposures, and do so with a wide frequency bandwidth but in a format that can still utilize relatively low-NA, inexpensive objectives.

Figure 13:
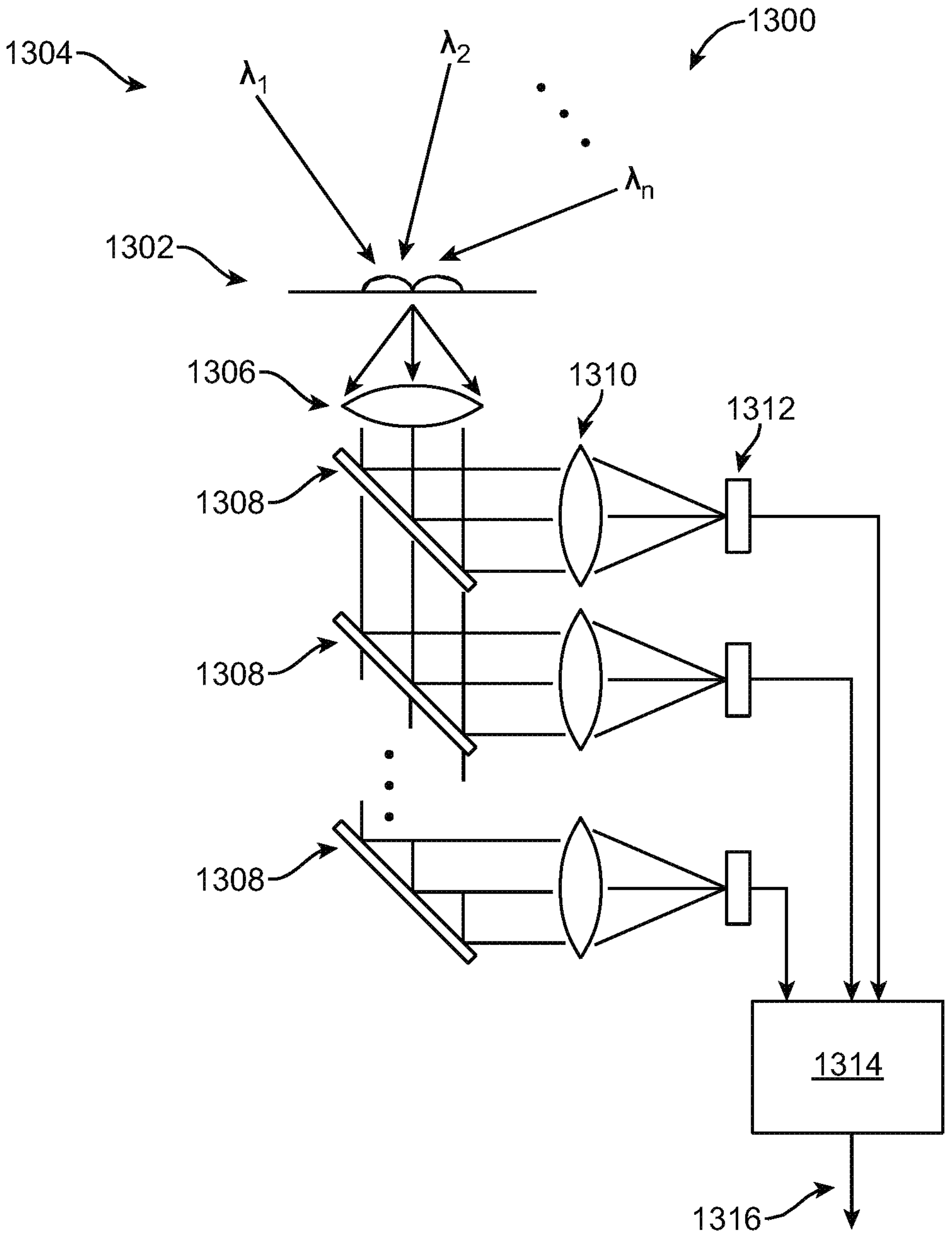
FIG. 13 is a block diagram of a wavelength separation subsystem in an imaging subsystem in accordance with various implementations.

FIG. 13 is a block diagram of a wavelength separation subsystem 1300 in an imaging subsystem in accordance with various implementations. The wavelength separation subsystem 1300 may be similar to the wavelength separation subsystem 1210 in FIG. 12. Similar to FIG. 12, sample 1302 (e.g., a cell culture) is illuminated by a multi-wavelength light source 1304, in which different wavelengths of light are incident on the sample 1302 at different angular distributions. Light diffracted by the sample 1302 (or reflected in an epi-illumination configuration) may pass through an objective lens 1306 before entering the wavelength separation subsystem 1300.

The wavelength separation subsystem 1300 may include a series of filters 1308 that act as low-pass, high-pass, or band-pass filters that reflect one wavelength band while allowing other bands to pass through. The filters 1308 split the incoming light into separate streams, each corresponding to a different wavelength band. The light then passes through lenses 1310, which focus the light onto a series of detectors 1312. For example, these could be 2D CMOS or CCD imaging detectors that simultaneously capture 2D images of the sample 1302 in each wavelength band, which in turn each correspond to a distribution of illumination angles. A processing unit 1314 collects the signals from the detectors 1312 and combines the signals, resulting in a combined signal 1316 that is a spatial representation of the sample 1302.

Figure 14:
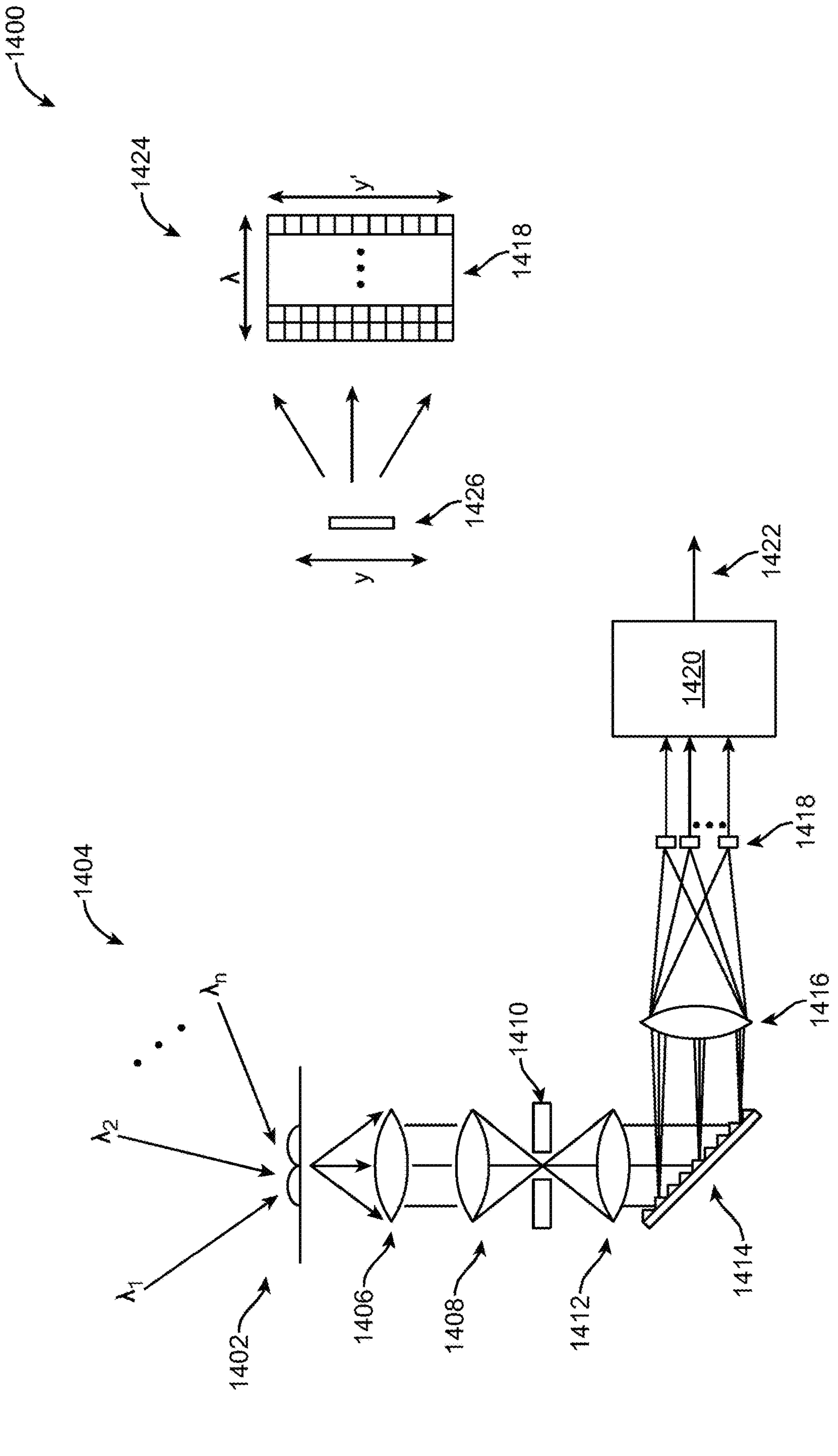
FIG. 14 is a block diagram of another multi-wavelength light source in an imaging subsystem in accordance with various implementations.

FIG. 14 is a block diagram of another wavelength separation subsystem 1400 in an imaging subsystem in accordance with various implementations. The wavelength separation subsystem 1400 may be similar to the wavelength separation subsystem 1210 in FIG. 12. Similar to FIG. 12, sample 1402 (e.g., a cell culture) is illuminated by a multi-wavelength light source 1404, in which different wavelengths of light are incident on the sample 1402 at different angular distributions. Light diffracted by the sample 1402 (or reflected in an epi-illumination configuration) may pass through an objective lens 1406 before entering the wavelength separation subsystem 1400.

The wavelength separation subsystem 1400 may include a focusing lens 1408 that focuses the light from the sample 1402 onto an intermediate focal plane. A slit aperture 1410 placed in the intermediate focus plane effectively restricts the field of view on the sample plane to a linear region (e.g., along the X or Y axis on the sample plane). In some implementations, a slit aperture may also be inserted between the multi-wavelength light source 1404 and the sample 1402 at an intermediate focal plane. This slit aperture may be used to restrict illumination of the sample 1402 to only an area including the field of view to reduce any scattered light from non-imaged areas, and to minimize any illumination-related damage or biological effects.

After the light passes through the slit aperture 1410, a collimating lens 1412 re-collimates the spatially filtered light before it reaches dispersive element 1414. The dispersive element 1414 may be a reflective diffraction grating, transmissive diffraction grating, prism, or other component that disperses the wavelength components of the optical signal in a continuous manner. The wavelength-separated (and thus angle-separated) light is then incident on focusing lens 1416 that focuses the light onto detector array 1418. The detector array 1418 may be configured to detect individual wavelength and components, may be composed of individual detectors or elements within a larger detector array (for example a 2D detector array). A processor 1420 receives electrical signals from the detector array 1418 and produces a signal 1422 representative of the sample.

In some implementations, the wavelength separation subsystem 1400 may be used in a continuous-scanning imaging architecture in which the sample and imaging/illumination system are translated relative to one another along an axis of the sample plane (e.g., along the X or Y horizontal axis of the sample plane), with one ID linear region of the sample imaged per readout of the detector arrays. Inset 1424 illustrates how a linear region 1426 of the sample 1402 is mapped to the detector array 1418. For example, the linear region 1426 may be along the Y axis of the sample 1402. The light from the linear region 1426 is incident on the 2-dimensional detector array 1418. The horizontal axis of the detector array 1418 is the wavelength-separated axis (marked with 2), which is the axis along which light from the field of view is dispersed according to wavelength. The wavelength is in turn related to a distribution of angles, so the signal along the horizontal axis corresponds to a measure of light scattering at different angles from the linear region 1426 of the sample 1402.

The vertical axis of the detector array 1418 is the spatial axis, which corresponds to the length of the linear region 1426 along the Y axis. The vertical axis on the detector array 1418 may be a magnification of the length of the linear region 1426. For example, a 0.25 mm long field of view of the linear region 1426 may be expanded to a length of 1.0 mm on the vertical axis of the detector array 1418 by a 4× objective magnification. Thus FIGS. 13-14 show several examples of wavelength separation of a light signal in an imaging subsystem. However, persons of ordinary skill in the art will understand that there are other configurations that may achieve the same result, and those implementations may be used in the imaging subsystem described herein.

Figure 15:
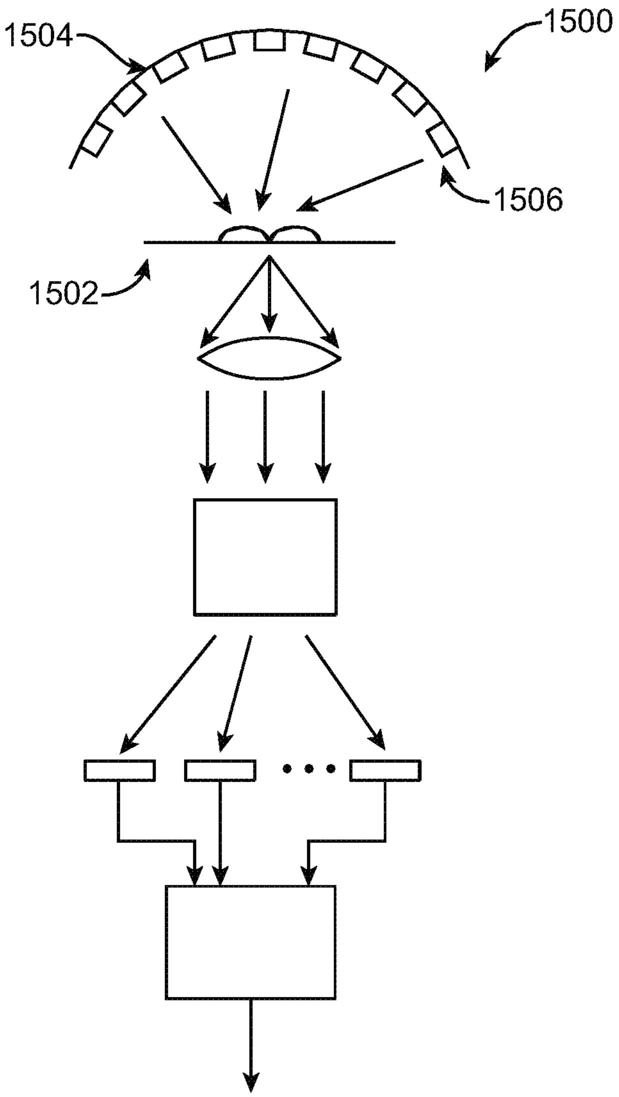
FIG. 15 is a block diagram of a multi-wavelength light source in an imaging subsystem in accordance with various implementations.

FIG. 15 is a block diagram of a multi-wavelength light source 1500 in an imaging subsystem in accordance with various implementations. The multi-wavelength light source 1500 may be similar to the multi-wavelength light source 1204 in FIG. 12. Similar to FIG. 12, sample 1502 (e.g., a cell culture) is illuminated by the multi-wavelength light source 1500, in which different wavelengths of light are incident on the sample 1502 at different angular distributions.

The multi-wavelength light source 1500 includes an assembly 1504 upon which the light sources 1506 are mounted. The assembly 1504 may be a hemispherical dome or a printed circuit board with multiple facets such that each light source 1506 illuminates the sample 1502 from a different angle. The light sources 1506 are discrete light sources, such as light emitting diodes (LEDs), arranged by emission wavelength across the assembly 1504 to provide illumination having a distinct relationship between illumination angle and wavelength. The example shown in FIG. 15 is transmissive light configuration in which light illuminates the sample 1502 from the opposite side as the objective, but it should be understood that similar discrete light sources can be used in reflective mode, either side-by-side with the imaging objective, or in an epi-illumination system where these sources are transmitted through the objective.

Figure 16:
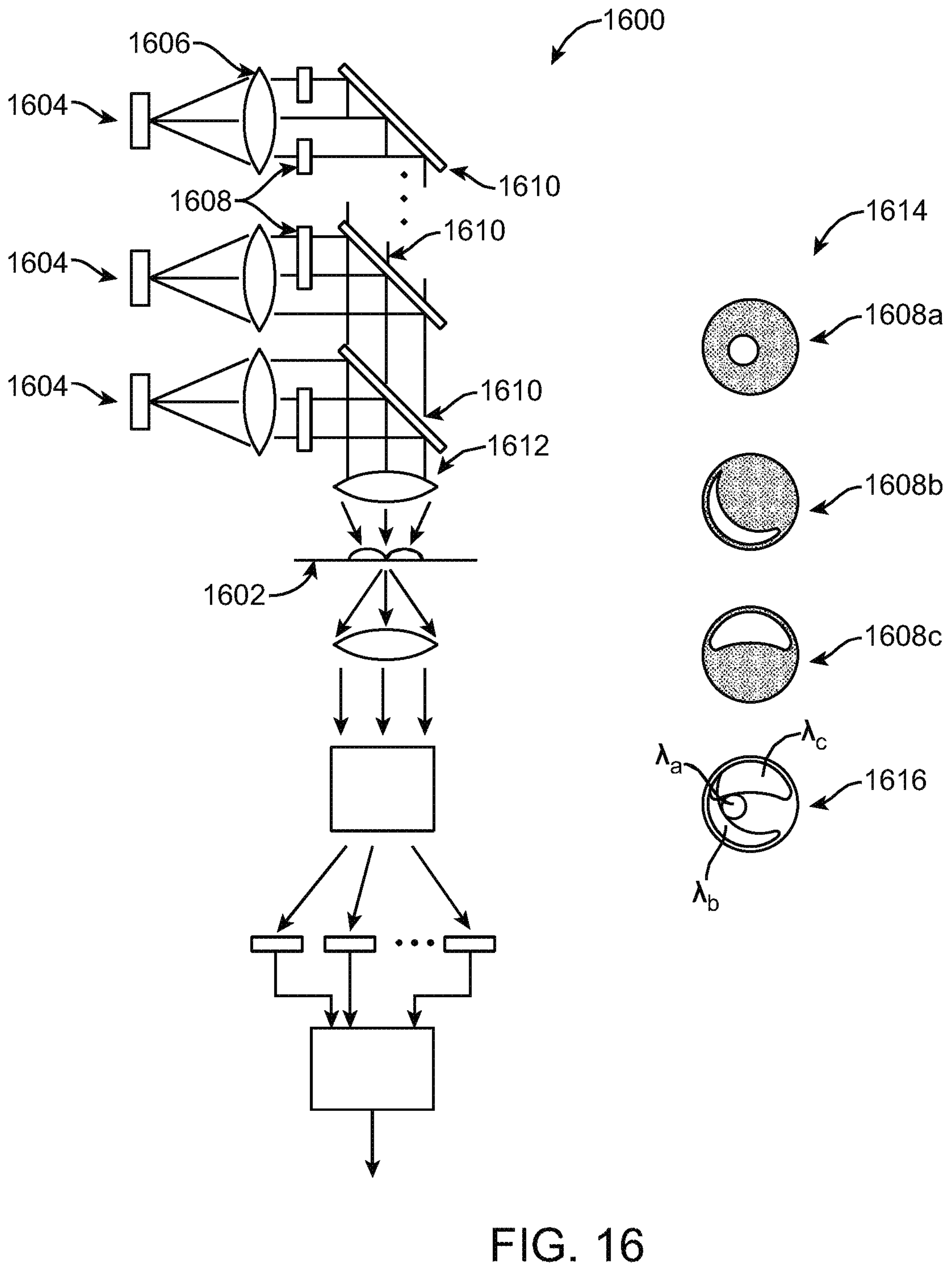
FIG. 16 is a block diagram of another multi-wavelength light source in an imaging subsystem in accordance with various implementations.

FIG. 16 is a block diagram of a multi-wavelength light source 1600 in an imaging subsystem in accordance with various implementations. The multi-wavelength light source 1600 may be similar to the multi-wavelength light source 1204 in FIG. 12. Similar to FIG. 12, sample 1602 (e.g., a cell culture) is illuminated by the multi-wavelength light source 1600, in which different wavelengths of light are incident on the sample 1602 at different angular distributions. The multi-wavelength light source 1600 includes discrete light sources 1604, which have different wavelengths/wavelength distributions. Light from each light source 1604 passes through collimating lenses 1606 and enters spatial elements 1608.

The spatial elements 1608 may be configured to alter the distribution of light coming from each light source 1604. Each light source 1604 may have a different spatial element 1608 associated with it so that it's spatial shape or distribution is unique from other light sources. The spatial elements 1608 may be simple occlusion masks, or other elements that shape light from a particular source with lower loss may also be used. Inset 1614 shows an example of how the spatial elements 1608 may generate wavelength-encoded angled illumination. In this example, collimated light from three separate light sources, each with a different wavelength ($\lambda_a$, $\lambda_b$, $\lambda_c$), pass through spatial elements **1608*a*, 1608*b*, 1608*c*. Each spatial element 1608*a*, 1608*b*, 1608*c* is a mask with an opening that allow light to pass through, the openings different and non-overlapping on each spatial element. When the light is combined after passing through the spatial elements 1608*a*, 1608*b*, 1608*c* as shown in projection 1616, each wavelength contribution occupies a different spatial region. The position distributions translate to angle distributions when focused on the sample 1602**, thereby achieving wavelength encoding of illumination angle.

After passing through the spatial elements 1608, the light strikes a series of mirrors and/or filters 1610 that combine the separate light streams by means of thin film interference filters or other elements into a single collimated optical path. This single light stream then passes through a condenser lens 1612 that focuses the illumination light onto the sample 1602 with wavelength-encoded angles.

Figure 17:
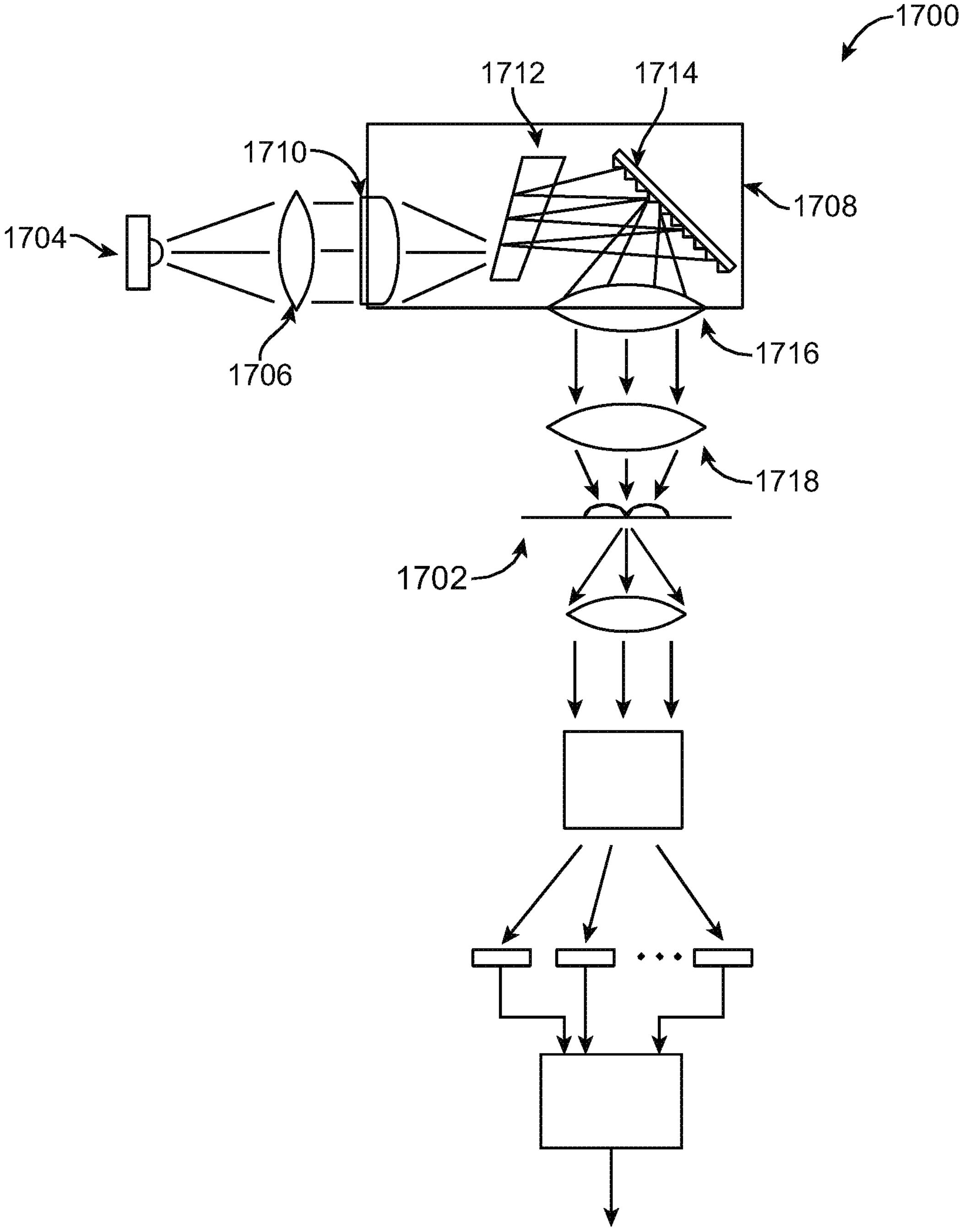
FIG. 17 is a block diagram of another multi-wavelength light source in an imaging subsystem in accordance with various implementations.

FIG. 17 is a block diagram of another multi-wavelength light source 1700 in an imaging subsystem in accordance with various implementations. The multi-wavelength light source 1700 may be similar to the multi-wavelength light source 1204 in FIG. 12. Similar to FIG. 12, sample 1702 (e.g., a cell culture) is illuminated by the multi-wavelength light source 1700, in which different wavelengths of light are incident on the sample 1702 at different angular distributions.

The multi-wavelength light source 1700 includes a broadband light source 1704, such as an LED or SLED, or incandescent light, that emits multi-spectrum light. A collimating lens 1706 captures the emitted light before it enters a 2D spatial disperser unit 1708. The 2D spatial disperser unit 1708 may include a number of components. These components may include a cylindrical lens 1710 that focuses the entering collimated light into a line that enters a virtual image phase array (VIPA) 1712. The VIPA 1712 may be configured to disperse light along one axis (e.g., Y axis respective to the sample 1702) in discrete increments. The light then hits diffraction grating 1714 that disperses light along the other axis (e.g., X axis respective to the sample 1702) depending on wavelength, thus spatially distributing the broadband light signal according to wavelength. The diffraction grating 1714 may be reflective, as shown in FIG. 17, or transmissive. After being spread out in space and wavelength, the light may pass through collimating lens 1716, resulting in light that is collimated and spatially encoded by wavelength in two dimensions. A condenser lens 1718 focuses the wavelength-encoded light on the sample 1702. Thus FIGS. 15-17 show several examples of achieving multi-wavelength illumination for an imaging subsystem in which the wavelength bands are angularly spread. However, persons of ordinary skill in the art will understand that there are other configurations that may achieve the same result, and those implementations may be used in the imaging subsystem described herein.

There may be additional features and variations of the imaging subsystem that may be incorporated into the automated cell culture system. In some implementations, there may be periodic, scheduled, and/or continuous translation and imaging of the sample. For example, an automated cell culture system may be configured to translate the imaging subsystem relative to a cell culture in a continuous manner, or periodically, or according to a user-specified schedule, to collect time-series images of the cell culture.

In some implementations, the imaging subsystem may also include an autofocus (Z-tracking) system that continuously tracks the distance between the sample and the objective, and is able to move the sample and objective relative to each other to maintain an optimum output signal distance. For example, the sample and/or objective may be coupled to an actuator that is capable of moving them relative to each other, and a computing subsystem may utilize the autofocus to determine the current distance between the sample and the objective, and control the actuators to adjust the distance. The autofocus signal that detects distance may be produced by reflecting a light from a surface proximate to the sample (e.g., a container or microscope slide/coverslip) and the resulting light is measured using the imaging subsystem detectors.

In some implementations, the imaging subsystem may include a registration (e.g., XY tracking) system that measures and tracks fiducial marks or other features in the sample or sample carrier to track location during imaging. A computing subsystem may be configured to identify fiducials in the images and determine the location of the sample relative to other components in the cell culture system. The registration system may utilize the imaging subsystem detectors to capture images of the fiducials.

In some implementations, the sample may be placed between two substantially flat pieces of material to minimize variations in the imaging caused by uneven surfaces not related to the sample properties of interest. For example, in a cell culture system the sample may be a cell culture in liquid (e.g., cell media) between two surfaces of a cell growth or observation chamber, generally without air bubbles in the media. In one implementation, this could be a closed cassette with flat, transparent cell culture chamber walls to enable imaging. In general implementations, the sample may be fixed in material between two slides, such as a histopathology sample that has been placed between two slides.

Tilt-Defocused Cell Culture Imaging and Editing Systems

Further implementations disclosed herein are directed to obtaining quantitative imaging data, label-free, with very high throughput for cell cultures. In addition, in such situations the absorption is generally very low, and small refractive index variations in cellular or subcellular objects are generally the only perturbation to the illuminating wavefronts. Several approaches to obtaining quantitative phase images, or equivalents, of cell cultures have been demonstrated in the prior art. However, almost all of these require a sequence of images to be obtained at a particular spatial location (for example, under a series of lighting conditions) or with a series of z focus positions. This dramatically lowers the throughput of these imaging systems.

The implementations disclosed herein utilize an optical and imaging subsystem that is tilted relative to the cell culture chamber and moves continuously relative to the chamber. In combination with a novel imaging sensor configuration, the present implementations enable a broad z-stack to be obtained at very high throughput. It also combines partially coherent illumination to make the resulting z-stack image suitable for transport-of-intensity equation (TIE) solutions to output quantitative phase image (QPI) data. Further, a secondary imaging system for maintaining focus in real-time is described. Lastly, a laser scanning system for cell culture editing in the same optical system is also described.

Certain implementations disclosed herein include an imaging and scanning system, the system including at least one light source illuminating a sample (e.g., a cell culture sample) having cells grown on a growth plane of the cell culture sample, an objective capturing light from the at least one light source passing through the cell culture sample, in which the objective it tilted at an angle with respect to a perpendicular axis of the growth plane, and one or more sensors to measure the light from the objective, in which the cell culture sample is moved relative to the imaging and scanning system such that the imaging system generates images at multiple heights along the perpendicular axis of the growth plane. This results in quantitative phase images of the sample. In some implementations, the imaging and scanning system further includes a laser pulse generated by a laser source and incident on the cell culture sample and an acousto-optic deflector/modular to adjust an incident angle of the laser pulse relative to the perpendicular axis of the growth plane, in which the cell culture sample is moved relative to the imaging and scanning system such that the laser pulse is capable of focusing on any part of the growth plane.

With the z-stack image data that is provided by the present implementations and using formal solution and optimization using TIE, it is possible to reconstruct a quantitative phase image of the cell culture. In many applications, however, the z-stack image output may be used directly in a deep learning based model that transforms the image data into a predicted labeled image, based on prior training data matching labelled images with z-stack image data.

The implementations disclosed herein have the potential to speed up the acquisition of quantitative phase and absorption imagery of cell cultures by many times. In addition, it has provisions for real-time autofocus based on a coating placed on the cell culture vessel wall. Finally, it integrates a high-speed laser scanning system that can edit cell cultures, usually based on the images obtained using the same imaging system. Thus, it provides a novel, highly-compact, integrated, high-capacity system for monitoring and controlling cell cultures and processes.

Figure 18:
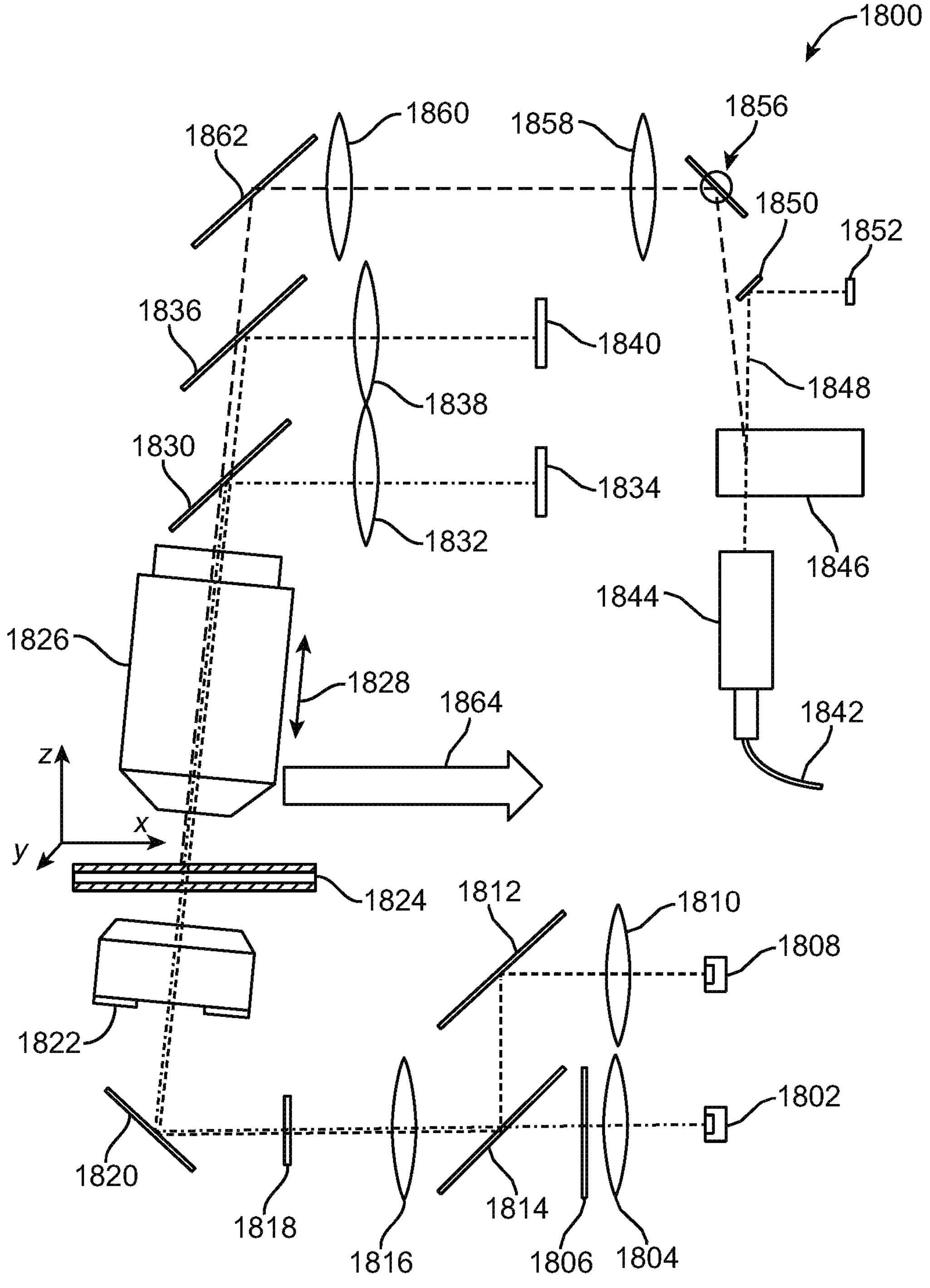
FIG. 18 is a diagram of a tilt-defocused cell culture imaging and editing system in accordance with various implementations.

FIG. 18 is a diagram of a tilt-defocused cell culture imaging and editing system 1800 in accordance with various implementations. The system 1800 may be part of a cell culture system (e.g., cell culture system 100) and may include an imaging subsystem (e.g., cell imaging subsystem 112) and an editing subsystem (e.g., cell editing subsystem 114). The imaging subsystem of the system 1800 may include a primary light source 1802. For example, the primary light source 1802 may be a light-emitting diode (LED) that emits light collimated by a collimating lens 1804. In some implementations, the primary light source 1802 may have a narrow wavelength bandwidth. In other implementations, it is desirable to further narrow the wavelength band to achieve partially-coherent illumination on the sample. In such cases, a thin film interference filter (e.g., bandpass filter) 1806 may be used to further narrow the primary illumination wavelength band. For example, the primary light source 1802 may be an LED emitting at 625 nm, with a full-width half-max (FWHM) bandwidth of 17 nm, and the thin film interference filter 1806 may be a bandpass filter with a FWHM of 10 nm that further reduces the wavelength range.

Continuing the example, a secondary light source 1808 may also be used, collimated by lens 1810 and partially reflected by a polarization beam splitter (PBS) 1812. The function of the PBS 1812 is to relay (by reflection, in this case) primarily light in one linear polarization direction. In this example, the secondary light source 1808 is polarized to better separate it from laser illumination at a downstream image sensor. The secondary light source 1808 is at a different wavelength than the primary light source 1802, and in some implementations at roughly the same wavelength as the laser source. For example, when the laser source is a 532 nm pulsed laser, the secondary illumination from the secondary light source 1808 may be provided by an LED with a peak emission in the 525-535 nm range. The light reflected by the PBS 1812 is then reflected by a dichroic filter 1814 which allows the primary light to pass through, and reflects the secondary wavelength from the secondary light source 1808 and combine them into a single optical path. In some implementations, the laser source has a wavelength of at least about 400 nm, 450 nm, or 500 nm up to about 525 nm, 550 nm, 575 nm, 600 nm, or 650 nm. In some implementations, the laser source has a wavelength of about 400 nm to about 650 nm, about 450 nm to about 600 nm, or about 500 nm to about 550 nm. In some implementations, the laser source has a wavelength of about 532 nm. In some implementations, the laser source has a wavelength of at least about 900 nm, 950 nm, 1000 nm, or 1050 nm up to about 1100 nm, 1150 nm, or about 1200 nm. In some implementations, the laser source has a wavelength of about 1064 nm.

A focusing lens 1816 then focuses all illuminating light to an image plane where it is spatially filtered by an aperture 1818. The aperture 1818 increases the spatial coherence of the illumination source(s) for the purpose of illuminating a sample with partially coherent light. A fold mirror 1820 relays the light to a condenser assembly 1822, which includes optics to illuminate a sample plane with substantially a plane wave of partially-coherent light. The condenser assembly 1822 may also include a condenser aperture (shown in black) to limit the illumination field on the sample.

The sample 1824, which in this example may be a cell culture adherent to the upper wall of a liquid-filled cell culture chamber, is shown in FIG. 18 in cross-section with two chamber walls above and below a liquid-filled cavity. The walls are both made of transparent material, for example glass or optical-grade polymer. The upper wall may be coated with a laser-absorptive coating and biocompatible coatings or matrices suitable for supporting adherent or semi-adherent cell culture. The illumination light passes through the chamber and the cell culture of the sample 1824 and is collected with a microscope objective 1826. The objective 1826 may be, for example, a 10× magnification, 0.3 numerical aperture (NA) objective. In this example, the distance between the objective 1826 and the sample 1824 is controlled via a high-speed actuator (such as a piezo-electric actuator) 1828 to control focus as the optical system moves relative to the sample 1824, or to account for sample-to-sample mechanical variations.

After being collected by the objective 1826, light from the primary light source 1802 is separated using a dichroic filter 1830 and focused via a tube lens 1832 onto a primary image sensor 1834. The primary image sensor 1834 captures an image of the tilt-focused image plane that z-samples the cell culture in the sample 1824 across the field of view. Secondary illumination wavelength light passes through the dichroic filter 1830 and is separated from the laser path using a PBS 1836, in which the PBS 1836 is oriented to reflect light matching the secondary source 1808 and the secondary source PBS 1812. This light is focused by a tube lens 1838 onto secondary image sensor 1840. The secondary image sensor 1840 is used to sense Z focus position and XY spatial position. It may do so by directly imaging the laser illumination on the laser-absorbing film within the cell culture chamber or, as in this example, by imaging the laser-absorbing film as it is trans-illuminated by the secondary light source 1808. The laser-absorbing film absorbs at this secondary wavelength, and by pre-encoding the laser-absorbing film with small, ablated markers, focus point as well as XY position may be tracked efficiently as the sample moves through the field of view of the optical subsystem.

The cell editing subsystem of the system 1800 may include laser pulses, which are supplied to the system 1800 from a pulsed laser source via an optical fiber connection 1842. The light is collimated using a fiber collimator 1844 and enters an acousto-optic deflector/modulator (AODM) 1846. The AODM 1846 passes a zero-order beam 1848 directly through, where it is picked off by a pick mirror 1850 and relayed to a photodetector 1852. The photodetector 1852 serves to measure baseline laser pulse energy being delivered to the optical subsystem (for example, to calibrate for changes over time or upon re-connection of a fiber). Additionally, in cases in which the central pulsed laser is run at a consistent pulse rate, the photodetector 1852 may be used to acquire the laser pulse signal timing and synchronize the optical scanning subsystem to the laser pulse timing. This obviates the need for a separate electronic synchronization system and wiring.

Based on this timing, for each laser pulse, a driver of the AODM 1846 sets an RF power to deflect a certain percentage of the incoming pulse into a first-order beam 1854, based on scanning instructions from a computing subsystem. Additionally, the AODM driver may vary the RF frequency slightly to change the angle of the first-order beam 1854. This allows the AODM 1846 to make adjustments to the beam angle in the "x" direction on the sample plane, for example to achieve an evenly-spaced grid of hits on the sample plane during resonant scanning and x-axis motion, or to shift the scan line (generally along the y-axis) slightly along the x-axis in order to ensure best focus on the laser absorbing film. The AODM 1846, in summary, controls pulse energy as well as pulse placement on the sample 1824 along the x-axis, on a pulse-by-pulse basis. The pulse rate of the laser source in the system may be ≥100 kHz, preferably ≥500 kHz or even ≥1 MHz. In some implementations, the pulse rate of the laser source in the system is at least about 100 kHz, 200 kHz, 300 kHz, 400 kHz, 500 kHz, 600 kHz, 700 kHz, 800 kHz, 900 kHz, or 1 MHZ.

A scanning mirror 1856 is used to scan the laser across the sample 1824 along substantially the "y" axis, in other words perpendicular to the relative motion between the optical system and sample 1824 (the scanning mirror 1856 is depicted schematically only with an axis perpendicular to the plane of the figure). The scanning system may include a resonant galvanometric or electrostatically-driven mirror, or alternatively may include a polygonal rotating mirror. In other cases, the scanning in the y direction may be achieved by use of another acousto-optic deflector. A scan lens 1858 and a tube lens 1860 are used to relay the laser beam to the objective 1826 through a fold mirror 1862. The laser pulses are focused onto the laser absorbing film of the sample 1824 by the objective 1826, and the beam is scanned in the "y" direction with the resonant scanning/polygon scanner, and relative "x" position is controlled at a short timescale using the AODM 1846 RF frequency.

The system 1800 may be translated relative to the sample 1824 as indicated by arrow 1864. This may be achieved by physically moving the sample 1824, or by an optical subsystem assembly that moves around a stationary sample holder. As the relative motion occurs, a primary imager samples multiple focus planes of the sample 1824. A secondary imager images the laser absorbing film and uses encoding markings on the film to calculate XY position in real time, as well as to calculate where the tilted focal plane intersects the laser absorbing film ("z=0"). This allows a control system to make adjustments to the objective height to keep this location at a particular point relative to the field of view. Likewise, for laser scanning and editing, the system 1800 traverses the sample 1824 and keeps it at a constant focus. The laser system scans the laser-absorbing film with a raster-scan pattern of points, in which the individual laser pulse powers (and to a small extent, relative x position) are controlled via the AODM 1846, as instructed by a computing subsystem (e.g., computing subsystem 110) that is acting to edit the cell culture by lysing cells or initiating intracellular delivery of compounds into the cells.

Figure 19:
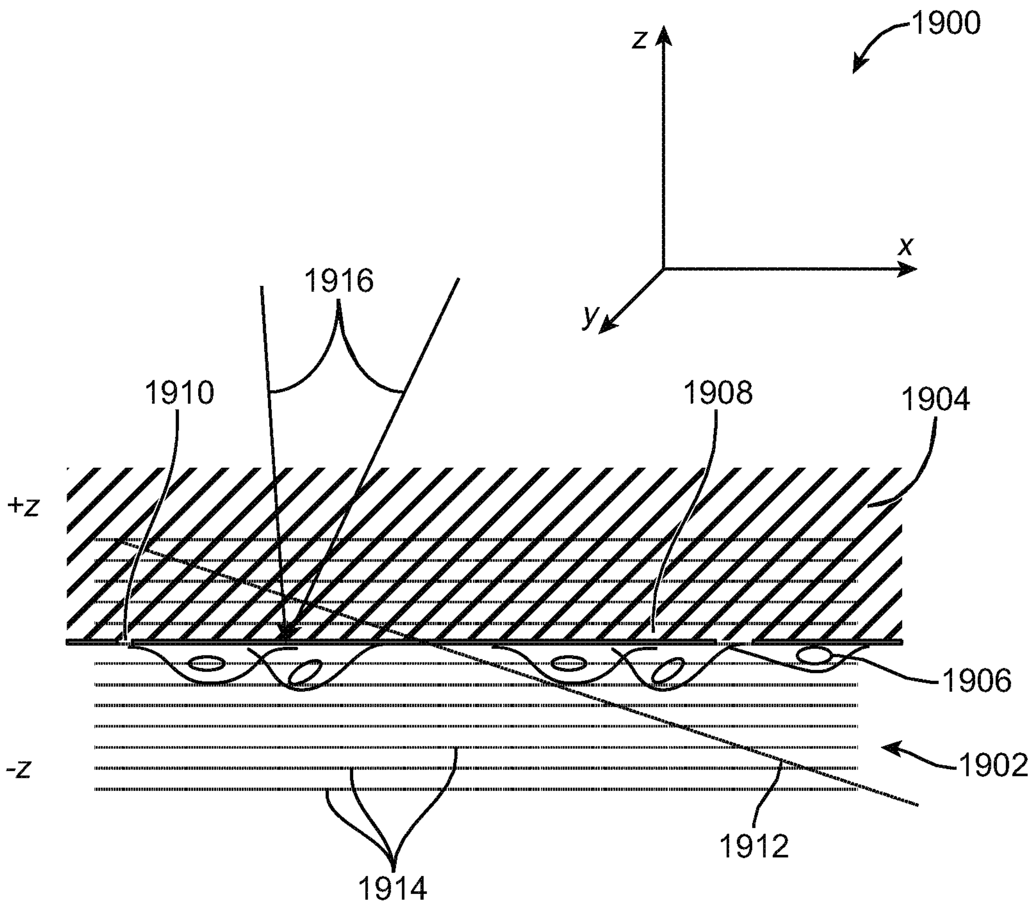
FIG. 19 is a cross-section of a cell culture chamber during tilt-defocused imaging and/or laser scanning in accordance with various implementations.

FIG. 19 is a cross-section of a cell culture chamber 1900 during tilt-defocused imaging and/or laser scanning in accordance with various implementations. A liquid cell media-filled cavity 1902 is bounded by walls, including the upper wall 1904 of the cell culture chamber 1900. In this example configuration, the cell culture chamber 1900 supports an inverted adherent cell culture 1906 on the surface of the upper wall 1904. The cell-supporting surface of the upper wall 1904 is coated with a thin laser-absorbing layer 1908 which serves to absorb laser pulses and convert a portion of the absorbed energy into mechanical energy in the form of explosive microbubbles, for the purpose of lysing cells, removing cell debris, or enabling intracellular delivery of compounds into cells.

In this implementation, the laser absorbing layer 1908 is patterned (by ablation of layer material) with very small fiducial markings 1910. Ideally these fiducial markings 1910 are smaller than the pulsed laser spot size so they do not interfere with the formation of microbubbles by the laser, but large enough to be imaged by an imager. In some implementations, the laser absorbing layer 1908 absorbs preferentially in the wavelength band of the pulsed laser, and absorbs less in the wavelength band of a primary light source of the imaging subsystem. It can therefore be illuminated with the secondary light source, which is in the laser wavelength band, and imaged with a secondary imager to clearly resolve these fiducial markings 1910. The fiducial markings 1910 do not appear, or appear only very faintly, in the primary imager data.

The focal plane 1912 of a tilted objective is tilted relative to the cell-bearing surface and cell culture 1906. As a result, as the optical assembly moves relative to the sample, a series of Z-height specific images of each location (denoted by z-heights 1914) may be captured in sequence by the primary imager and secondary imager. Additionally, the objective focuses a pulsed laser light 1916 onto the laser absorbing layer 1908. As shown here, the Z focus of the laser may be adjusted to be slightly different from the image focal plane, such that the laser scan line does not interfere with the secondary transmission imaging at the Z=0 point. The laser is scanned along the Y axis (perpendicular to the plane of the figure), and may have its "x" position tuned by an AODM in response to rapid Z focus changes (since "y" position corresponds to "z" focus).

Figure 20A:
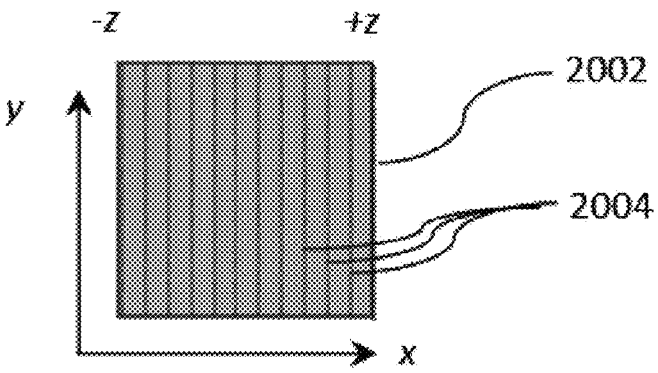
FIGS. 20A-C are imaging field views of a tilt-defocused cell culture imaging and editing system in accordance with various implementations.
Figure 20B:
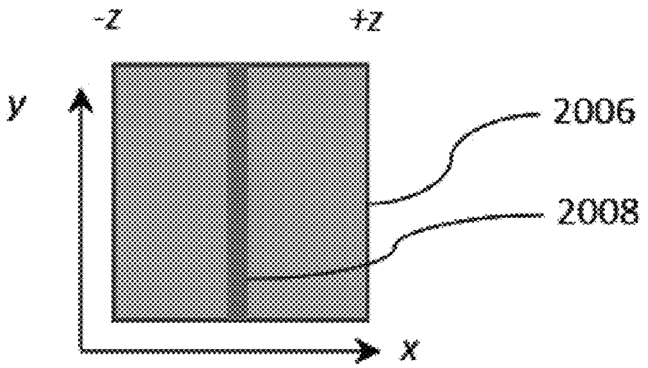
Figure 20C:
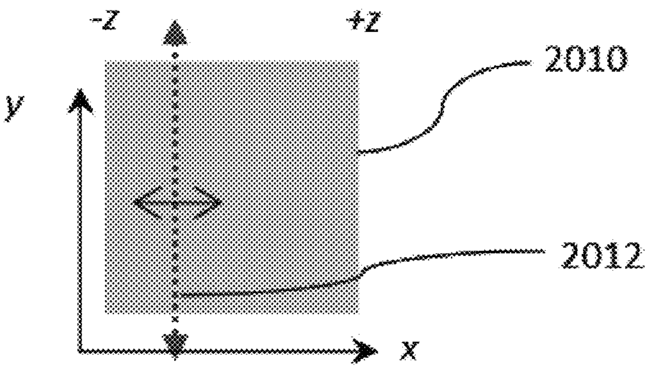

FIGS. 20A-C are imaging field views of a tilt-defocused cell culture imaging and editing system in accordance with various implementations. FIG. 20A illustrates an effective field of view of a primary imager 2002 of the tilt-defocused cell culture imaging and editing system, as well as lines that are imaged as the imaging system moves relative to the sample. The primary imager 2002 may be a CMOS image sensor, and is oriented such that its "lines" are oriented along the sample field of view y-axis. An example of a CMOS image sensor that may be used in the present implementations is the AMS/CMOSIS CMV4000 4.2-megapixel CMOS imager with global shutter. The primary imager 2002 may run at 180 frames per second at full resolution, but can run at significantly higher frame rate if fewer rows are read out. For example, if the objective is tilted such that the z height differential across the field of view 2002 along the x-axis (corresponding to "−z" to "+z") is 50 microns, and the minimum z-slice spacing in the resulting output volume is 2.5 microns, a total of 21 rows in the imager may be used, and an imaging rate of ~8650 frames per second may be achieved, meaning that over 4 complete fields of view (2048×2048 pixels) can be captured per second, with 21 z slices each. An example (schematic) arrangement of this sparse row reading is indicated by lines 2004.

FIG. 20B illustrates a field of view of a secondary imager 2006 of the tilt-defocused cell culture imaging and editing system. The secondary imager 2006 may be of the same type as the primary imager 2002. As with the primary imager 2002, it may utilize only a subset of rows, but in a different configuration, namely more densely-spaced rows 2008 around the target location within the field of view of Z=0, at which the focal plane intersects the laser absorption film. By observing small features (e.g., fiducial markings) in the laser film as they pass through this narrow X/Z range, and the focus or sharpness level of the features, a computing subsystem (e.g., computing subsystem 110) receiving the image data may compute where the optimal focus is along the x direction. A control system may shift the objective according to this output to keep the optimal focus within a small X range such that the primary imager 2002 is always obtaining the same x stack relative to the laser absorption film. In addition, high-frequency adjustments may be made during laser scanning by the use of a AODF to offset the laser scan along the x (and therefore z) direction. The computing subsystem can include one or more processors for processing or analyzing the image data.

A built-in cell processing laser, in conjunction with the imaging system/subsystem, can achieve autofocus on the sample by imaging lines/points projected using the laser and laser steering system onto the cell culture container, and measuring the sharpness of these lines or points. In this manner a very compact imaging and laser editing system can be built, without the need for additional autofocus subsystems.

FIG. 20C illustrates a field of view 2010 of the secondary imager with the laser scan line superimposed. The laser scan line is along the y-axis, perpendicular to the motion of the optical assembly relative to the sample. The laser scan line 2012 may be bi-directional (in the case of a resonant scanner) or unidirectional (in the case of a polygon mirror scanner), or random-access (in the case of an acousto-optic deflector being used for y-axis control). As described herein, the AODM may be used to adjust the x-position of the scan line 2012 on a point-by-point basis. In some implementations, the scan points may be adjusted to coincide with the secondary imaging zone (where the imaging is focused on the laser absorption film) to directly observe the laser hits on the laser absorption surface. This may be used as another method to gauge z focus in real time.

The systems and methods for imaging subsystems described with respect to FIGS. 3-20C have several common features or common permutations, and elements of each implementation may be combined with each other, and may be each be combined with a cell editing subsystem (e.g., a laser editing system) in a number of ways. For example, each of the imaging approaches described above (multi-focus, tilt-defocused, and single-shot Fourier ptychographic) are methods of retrieving quantitative phase imaging (QPI) without lasers or other interferometric setups, which add noise and complexity. In another example, the multi-focus and tilt-defocused approaches may be combined with the one-shot multi-angle illumination approach as described in the single-shot Fourier ptychographic implementations. In another example, each of the imaging approaches described above (multi-focus, tilt-defocused, and single-shot Fourier ptychographic) may be combined with a laser scanning system as described with respect to FIG. 18, and in some implementations the imaging subsystem and the laser scanning system may share a common objective. The systems and methods disclosed herein also include other permutations of the imaging approaches disclosed herein, as understood by a person of ordinary skill in the art.

Clonally Reprogrammed iPSCs

Induced pluripotent stem cells (iPSCs) have the potential to revolutionize regenerative medicine. Their capacity for self-renewal, ability to differentiate into any cell type in the body, and ability to be manufactured from small volumes of patient tissue samples make them the ideal starting material for personalized cell and tissue therapies. The same genetic plasticity that allows for these cells to be used to make biologics also makes the cell vulnerable to selective pressure and can potentially put the product and process at risk when changes are made.

However, there are several hurdles to creating cost-effective, safe, and efficient hiPSC-derived cell therapies. Creation of a master cell bank (MCB) of hiPSCs with current protocols is extremely labor- and time-intensive (up to 4 months), with estimates for the cost of generating a clinical-grade iPSC line going as high as US $1.2M. A majority of these costs include labor and quality control (QC) measures required for ensuring the safety and efficacy of the end product. Any methods aimed to reduce the cost involved in these would significantly help enable cost-effective manufacturing of hiPSC-derived cell therapy products.

One factor to the low numbers of hiPSC-lines passing the QC assays is the heterogeneous nature of the iPSC culture. There is variability both within and across iPSC lines, in terms of differentiation potential, tumorigenicity, epigenetic profile, and other parameters. The exact reason behind this remains unclear, and could be related to differences in source material, protocols, or operator technique. Nevertheless, this indicates a need for more standardization and automation across iPSC manufacturing and characterization techniques, which can help minimize the heterogeneity within the MCB and allow for well-controlled processes capable of consistent manufacturing of a product. When cell banks are nonclonal, every potential change made to the upstream process (raw materials, process parameters, manufacturing site, etc.) may put selective pressure on the cultures, which may result in changes to the manufacturing process or the final product. Clonality is a crucial step in stable cell line development (CLD) for biotherapeutic workflows and it is closely monitored by government regulators. If clonality is not sufficiently evidenced, regulatory bodies such as the US Food and Drug Administration (FDA) and the European Medicines Agency (EMA) will require additional manufacturing controls, increasing the cost of clinical trials and delaying drugs from reaching patients.

There are a number of iPSC reprogramming methods, including genome integration, non-genome integration, minicircle vectors, the Sendai protocol, mRNA, self-replicating RNA, CRISPR activators, and recombinant proteins. Each of these are summarized herein.

Genome integrating methods: one of the most commonly used methods for reprogramming is the integration of the reprogramming factors into the genome by lentiviral or retroviral transduction. This method is highly efficient but poses the threat of generating permanent random integrations of exogenous genes into the genome that can potentially have oncogenic potential and are therefore less suitable for use in therapeutic approaches.

Non-genome integrating methods: non-genome integrating methods (footprint-free) include a number of methods to exogenously express reprogramming factors and RNA components, from either episomal DNA vectors, RNA viruses, or messenger RNAs (mRNAs). Among integration-free methods, the episomal method is a technically simple, fast, convenient, and reproducible approach for generating iPSCs. However, episomal vectors have low reprogramming efficiency in comparison with viral vectors. Furthermore, in many studies that used the episomal system, the transcription factors were delivered individually by nucleofection. However, due to differences in vector uptake by nucleofection, gene expression levels between cells are highly variable.

Minicircle vectors: minicircles are DNA vectors with eliminated bacterial backbones and transcription units commonly used in episomal plasmids. Therefore, they have a relatively small size compared to other commercial vectors. The small size and the ability to avoid immune reactions leads to the high expression of the foreign gene, both in vitro and in vivo. Minicircles also show potential in pre-clinical gene therapy research and proof-of-concept studies combining minicircle vectors and stem cells suggest a potential regenerative tool for clinical applications.

Sendai: the Sendai virus is a single chain RNA virus that does not integrate into the host genome or alter the genetic information of the host cells. The virus remains in the cytoplasm and is therefore diluted out of the host cells after approximately ten passages after virus infection. Sendai virus can infect a wide range of cell types in proliferative and quiescent states with high transduction efficiency. Expression of transgenes delivered by Sendai virus is detectable as early as 6-10 hours after transduction, with maximum expression detected more than 24 hours after transduction. Sendai-based reprogramming vectors have been used to successfully reprogram neonatal and adult fibroblasts as well as blood cells with high efficiency.

CRISPR activation (CRISPRa): CRISPRa uses a catalytically inactivated CRISPR-Cas9 system (dCas9) fused to a transactivator domain for transcriptional activation of endogenous genes without editing DNA. High efficiency, multiplexed, fibroblast CRISPRa reprogramming has recently been reported with improved fidelity. Activation of reprogramming gene endogenous promoters with CRISPRa improves the quality of human pluripotent reprogramming.

mRNA: expression of reprogramming factors using mRNA provides another method to make transgene-free iPSCs. It was shown that in vitro transcribed mRNAs were able to efficiently express reprogramming factors when transfected into human fibroblasts. Although reprogramming factor mRNAs are commercially available, this method suffers from the limitations that it is labor-intensive, requires daily transfection of mRNA for 7 successive days, and there are no successful reports regarding the reprogramming of blood cells. However, despite the great advances in the development of synthetic mRNA-based reprogramming approaches, one of the main obstacles of this method is still the induction of an innate immune response following multiple daily mRNA transfections, resulting in increased cellular stress and severe cytotoxicity.

Self-replicating mRNA (srRNA): an alternative to mRNA-based reprogramming is the use of srRNA. Structurally, srRNA mimics its synthetic mRNA counterpart, and contains the coding sequences of the "Yamanaka" transcription factors Oct4, Klf4, Sox2, and cMyc, and four nonstructural proteins enabling its replication. The application of srRNA enables an extended duration of protein expression without the need of multiple daily transfections to maintain the protein expression required to reprogram cells.

Recombinant proteins: protein-based hiPS technology offers a new and potentially safe method for generating patient-specific stem cells that does not require the destruction of ex utero embryos. This system completely eliminates genome manipulation and DNA transfection, resulting in human iPS cells suitable for drug discovery, disease modeling, and future clinical translation. However, the generation of p-hiPS cells is very slow and inefficient, and requires further optimization. In particular, the whole protein extracts that are used limits the concentrations of factors delivered into the target cells, thus suggesting that p-hiPS cells may be more efficiently generated using purified reprogramming proteins.

Due to the plastic nature of somatic cells upon reprogramming, hiPSCs can be created from several cell sources that may be classified into two groups: adherent and suspension. Each comes with different sets of challenges and benefits, which are discussed herein.

Fibroblasts and other adherent cells: Fibroblasts are the most commonly used primary somatic cell type for the generation of iPSCs. Various characteristics of fibroblasts supported their utilization for the groundbreaking experiments of iPSC generation. One major advantage is the high availability of fibroblasts which can be easily isolated from skin biopsies. Furthermore, their cultivation, propagation, and cryoconservation properties are uncomplicated with respect to nutritional requirements and viability in culture. However, the required skin biopsy remains an invasive approach, representing a major drawback for using fibroblasts as the starting material. Additionally, it has been shown that especially skin fibroblasts accumulate mutations during the person's lifetime that might negatively affect the outcome of the reprogramming process. Other adherent cell types used for reprogramming include keratinocytes from hair follicles and skin biopsies, epithelial cells derived from urine and blood, synovial cells, and beta islet cells. The compatibility of all the potential somatic cell types with the existing and emerging reprogramming methods will need to be evaluated by persons of skill in the art.

Suspension cells: CD34+ blood stem cells and erythroblasts purified from peripheral blood mononucleated cells (PBMCs) are one of the most studied cell types as a starting material for reprogramming. This is mainly due to their easy harvest via blood withdrawal, and the low number of mutations these cells accumulate over the lifetime that might negatively affect the outcome. All reprogramming methods minus mRNA electroporation have been successfully used to reprogram these cell types.

Assurance of clonality is part of the overall control strategy for cell-based products. It improves the consistency of the process and directly affects the quality and safety of the products. However, for cell-based biologics entering clinical phase, there exists no single regulatory document that explicitly states that the cell banks should be monoclonal, mainly reflecting the inability of the current technologies to ensure monoclonality. However, starting with a monoclonal population would maximize the potential to optimize the manufacturing process by reducing variables associated with heterogeneous cell behavior within the culture.

The sole method currently able to distinguish a monoclonal population from a polyclonal one in an already established cell line is Fluorescent In Situ Hybridization (FISH). It relies on random monoallelic expression of genes (so-called allelic exclusion), in which a subset of human genes are normally expressed at a single allele in a fixed fraction of cells within a tissue, independent of the parental origin of the allele. It is hypothesized that application of FISH to assess the allelic expression patterns among one or more of these genes should be able to distinguish a monoclonal population of cells from a polyclonal on. However, although fairly successful in determining the clonality of B and T-cell lines due to the specific recombination events occurring in them, applying FISH to other cell types (such as hiPSCs) that do not naturally undergo genetic recombination has proven to be technically challenging and incompatible with reliable high-throughput analysis of samples. Therefore, due to lack of biological assays, the current methods to assess clonality of hiPSCs rely on image-based assurance of single-cell origin of the culture and/or statistical methods to reduce the probability of cells originating from multiple cells within the culture. Several clonality strategies are described herein.

Single-cell plating (limiting dilution): in order to create a more uniform, homogeneous population of hiPSCs, many laboratories opt for clonal derivation of the cell lines. By plating a single hiPSC per growth area for expansion, the resulting product is a clonal population of cells where each cell is genetically and phenotypically more similar to the other cells in the same culture than in hiPSC-cultures with non-clonal origin. Single-cell plating can be done with several methods from limiting dilution to cell sorting. Single-cell origin of the culture is specifically critical for gene-edited hiPSCs where each cell in the culture must carry the edited version of the gene. Unfortunately, the process of creating clonal cultures from single cells poses a significant challenge to the cells that require contact with neighboring cells to survive. Due to this, the survival rate of hiPSCs after single-cell plating is very low, and the cells that do manage to proliferate and expand often have acquired mutations beneficial for single-cell survival, but that result in failure during the end QC.

Low-density plating (repeated colony picking): to avoid having to plate hiPSCs at single cells, many laboratories and publications rely on statistical probability modeling and derive "clonal" populations by plating hiPSCs at low density and picking and replating pieces from a single colony several times either manually or with technologies such as ClonePix. This has been shown to result in highly homogenous hiPSC cultures, yet does not provide an absolute proof of clonality. This is mainly due to the probability of plated cells to reside within 150 μm distance from each other, which has been shown to cause cells to migrate and form a polyclonal colony.

Clonality assays: currently, there are no assays to address the clonality of an existing hiPSC-culture. To ensure absolute clonal origin, imaging-based techniques are suggested by the FDA to track the single cell during the expansion and MCB creation.

One of the quality aspects required from hiPSC-derived cell therapy products is the assurance of complete elimination of the reprogramming material. For integrating methods this requires the use of excisable gene cassettes (e.g., Cre-lox system) engineered into the viral vectors encoding reprogramming factors. Upon activation, an exogenous enzyme (e.g., Cre-recombinase) cuts the DNA around the insertion site and removes the cassette containing the reprogramming factor. After this the cells' own DNA repair systems repair the remaining cut in the genome and the cell is considered "safe" and ready for downstream applications, including cell therapies. To ensure the complete excision of the cassette, sequencing of the cell population is required.

For non-integrating reprogramming methods, it suffices to prove that the DNA, mRNA, or viral vector (e.g., Sendai) is no longer detected by qPCR. The mechanism of DNA elimination in the episomal and microcircle methods rely on cell-proliferation-based dilution of reprogramming plasmid in the progeny of cells. Additionally, the elimination is dependent on the type of origin of replication used to drive the replication of these plasmids and directly affects how quickly they will be diluted below the threshold of detection.

The time for complete elimination of DNA-based non-integrating reprogramming materials varies significantly between methods and clones and can take anywhere between 40-120 days, significantly slowing down the manufacturing process. Any methods allowing for a faster and more consistent elimination of the reprogramming methods would allow for more cost-effective and safe manufacturing cell therapies. Using mRNA-based reprogramming has the major advantage of producing footprint-free hiPSCs much faster than other methods. Synthetic mRNA is commonly degraded within 48 hours after its entry into the cell. However, due to its rapid degradation, up to 14 rounds of consecutive transfections is necessary to retain sufficient level of protein expression to reprogram cells. Therefore, synthetic mRNA-based reprogramming is better suitable for reprogramming hardy cell types, such as fibroblasts and epithelial cells, instead of, for example, blood stem cells sensitive to multiple rounds of transfection. To overcome the challenge of multi-round transfections and yet produce a foot-print free hiPSC line in under 40 days, a novel approach of srRNAs may be used. These synthetic mRNAs have an additional genetic element in their structure that allows them to replicate once inside mammalian cells. Depending on the type of this replicative element, srRNAs can remain in the cells up to 30 days after which they are rapidly removed by the cells' type I interferon activity after the withdrawal of interferon suppressing factor B18R.

All the above mentioned non-integrating methods have been shown to successfully reprogram somatic cells into hiPSCs. However, the high variability between clones derived using these methods is hindering their translation into commercial production. One of the greatest contributors to this variability is the initial reprogramming cargo load being introduced into the cell. There is currently no way to control the load of DNA, RNA, or protein that is delivered into each cell in the culture upon transfection. This depends on several factors such as cell cycle stage, metabolic activity, and cell surface area of the cells being transfected. However, the amount of cargo entering the cells can directly affect several aspects of the reprogramming process, including reprogramming efficiency and elimination speed of exogenous material and thus the manufacturing time. Indeed, partially due to these factors significant variation between clones is often observed, resulting in highly heterogeneous non-clonal culture of hiPSCs. The ability to use image-guided algorithms to track and analyze single cells and ensure clonality during the reprogramming and expansion process can provide a powerful tool to distinguish between fully vs partially reprogrammed clones. Especially when combined with qPCR-based quantification of the remaining reprogramming material in each clone during the early days of reprogramming, a cell culture system for growing hiPSCs may provide great insights into selecting the best clones for accelerated manufacturing of safe hiPSCs.

In summary, the problems facing quick and relatively inexpensive mass reprogramming of iPSCs include low yields and low consistency of high-quality iPSC clones. This is exacerbated by an inability to observe behavior during reprogramming vs outcomes, inconsistent handling of the cells, and frequent passaging that causes variable effects on cells. In addition, it is difficult to ensure clonality on an iPSC cell culture such that monoclonal iPSC output cell products can be reliably manufactured. Low fidelity of QC results and/or high QC volumes/costs, in addition to inconsistent behavior during reprogramming observation, further make consistent monoclonality a challenge.

The systems and methods disclosed herein provide a reliable, automated process for monoclonal reprogramming of iPSCs, and hiPSCs in particular. The cell culture system disclosed herein (e.g., cell culture system 100) may be used to produce iPSCs that are the result of a true clonal reprogramming process, in which a single iPS candidate cell or cell colony is isolated using a cell removal mechanism (e.g., cell editing subsystem 114) that acts on the other cells, and confirmed by imaging. The colony/colonies resulting from proliferation of this single cell are isolated from colonies proliferating from other cells, by use of a cell removal mechanism that acts on potentially clone cross-contaminating cells, the removal coordinated and confirmed by imaging and image analysis. The colony/colonies of a single starting cell are then isolated to form the final clonal output cell product. The entire cell culture process may be conducted in a closed system, such as a closed cassette system. The cell culture container does not need to be opened or otherwise exposed to the external environment for media exchange, imaging, cell editing, and other cell culture process operations. Thus, the cell culture system herein may be configured to grow monoclonal cell colonies (e.g., iPSC colonies) in a closed system.

In some implementations, the isolation of a single clone from multiple clonal colonies is achieved by a cell removal mechanism that acts on the other colonies, the removal coordinated and confirmed by imaging and image analysis. In some implementations, the cell removal mechanism includes at least a pulsed laser system. In some implementations, the entire process up to the output cell product is performed within a single cell culture container. In some implementations, the cells are reprogrammed in a sealed microfluidic environment, such as a closed cassette system.

The cell culture system disclosed herein provides a number of advantages over the prior art for monoclonal reprogramming of iPSCs. For example, the cell culture system may be used to track reprogrammed cells at a single-cell level, and a precision laser system may be used to remove any unwanted cells in the cell culture. Unwanted cells can be any cells analyzed and predicted by the image-based algorithms during any stage of the reprogramming and expansion stages that, according to the predictions, would not pass the QC or manufacturing requirements at the end of the manufacturing process. QC requirements focus on ensuring the safety and potency of the output cell product and are determined by the regulatory bodies. Manufacturing requirements are specific for the cell culture system and aim to reduce the cost and manufacturing time of the product, and may include but are not limited to eliminating cells that divide too slowly, cells that have high reprogramming cargo load, and migrating, hard to track cells.

The cell culture system is also agnostic to the starting material. The cell culture system may be configured to reprogram fibroblasts or other adherent cells such as keratinocytes, epithelial cells, or synovial cells, independent of the reprogramming method. The system's image-based algorithms can be used to distinguish fibroblasts from newly reprogrammed cells based on an array of phenotypic features specific to pluripotent stem cells, including but not limited to, cell morphology, cell proliferation rate, chromatin condensation, nucleus to cytosol ratio and cell migration patterns. The cell editing subsystem of the cell culture system may then be used to remove unwanted adherent cells.

When the cell culture system disclosed herein is used to reprogram suspension cells, such as CD34+ stem cells or erythroblasts, the number of cells adhering to the cell culture surface is significantly lower after reprogramming. Only at around day 5 after transfection(s) the cells that received sufficient load of reprogramming material will adhere and start to form colonies of fully or partially reprogrammed cells. Similar to the above-mentioned methods with adherent cells, the cell culture system is trained to distinguish the most promising single-cell derived colonies at an early stage and keep them isolated by removing any unwanted cells surrounding the emerging colonies and eventually all other cells in the growth area.

In addition, the cell culture system disclosed herein does not require single-cell plating, limiting dilution or repeated colony picking to create clonal populations of cells. The process of deriving clonal hiPSC-populations from single cells has been shown to be highly ineffective due to increased cell death upon 48 h after plating. The biological mechanism behind this phenomenon is poorly understood. To increase cloning efficiency, low-density plating is commonly used to ensure cell survival, but often at the cost of clonality. Despite the better survival, this method requires frequent imaging to ensure that the cells do not migrate and form a polyclonal colony. Once detected, these wells with polyclonal colonies need to be excluded from the experiment, leading to loss of money. Indeed, it has been shown that when plated closer than 150 μm apart hiPSCs tend to move together to form a colony. To date, there are no technologies able to control the distance of the cells when plated in low density fashion.

However, the cell culture system may be configured to fully reprogram hiPSCs plated at the density most likely to yield in cell separation of at least 150 μm. Due to the random plating location of each cell, the cell editing subsystem may be configured to remove any cell that resides closer than 150 μm from its neighbor, reducing the chances of polyclonal colony formation. To improve the number of monoclonal lines, low-density plating is followed by repeated rounds of hiPSC colony picking, which is not necessary when using the cell culture system. These directly translate into reduced manufacturing costs per clonal hiPSC-line when compared to methods based on single-cell plating or low-density plating followed by repeated clonal picking. An additional advantage of this approach is that the total number of cell divisions is kept to a minimum when compared to post-reprogramming clonality enforcement. It is known that hiPSCs are particularly prone to genetic or karyotypical variations, and that the load of these variations grows with the number of cell divisions (or related, "passages"). By enforcing clonality from the start of reprogramming, the full resulting population of hiPSCs at the end of the reprogramming process may be used for quality control and for the application at hand, rather than as the input to a process that restarts from a single cell.

Figure 21A:
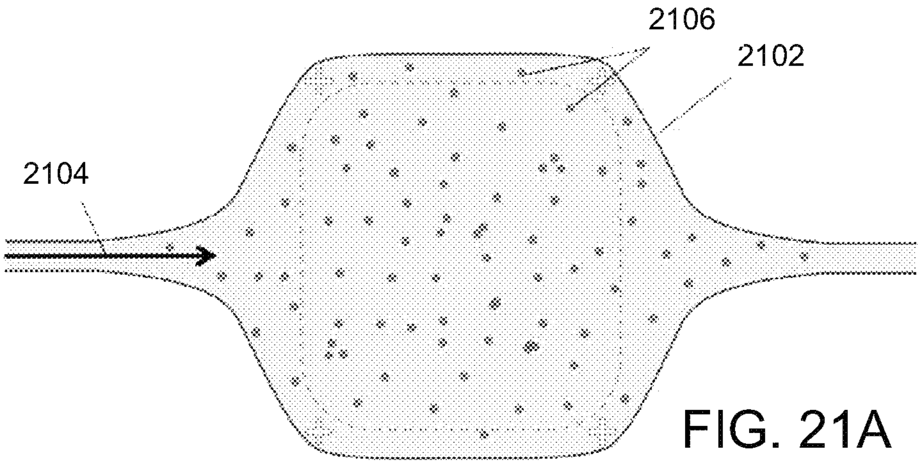
FIGS. 21A-C are diagrams illustrating a portion of a process for iPSC reprogramming in accordance with various implementations.
Figure 21B:
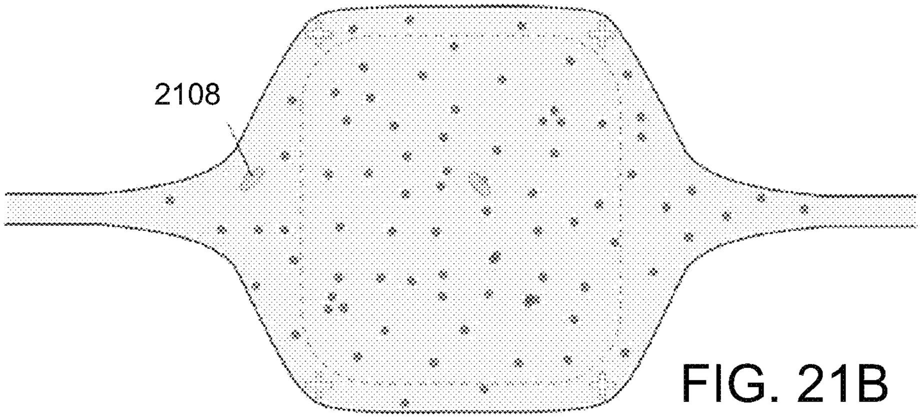
Figure 21C:
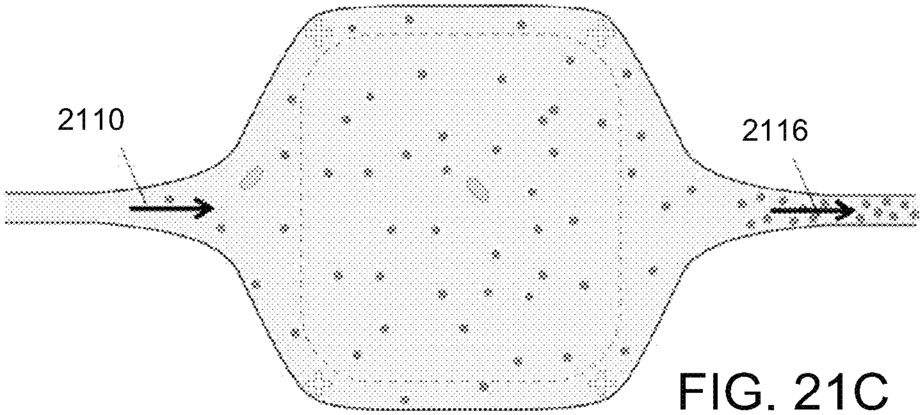

FIGS. 21A-C are diagrams illustrating a portion of a process for iPSC reprogramming in accordance with various implementations. Specifically, FIGS. 21A-C depict the cell seeding and early reprogramming phases in which somatic cells are seeded into a cell culture container, having either had reprogramming factors delivered prior to seeding, or factors delivered in the chamber itself. FIG. 21A shows an example cell culture chamber 2102, shown here as a fluidic chamber with two ports for filling/removal, and media circulation. The cell culture chamber 2102 is inoculated (shown by arrow 2104) and non-reprogrammed input cells 2106 then settle in the cell culture chamber 2102. For example, the reprogramming process may utilize CD34+ cells that have had episomal vectors delivered prior to inoculation via electroporation. FIG. 21B shows the emergence of pre-IPS cells 2108 from a subset of the non-reprogrammed input cells 2106 after some period of time. Generally, cells that have some degree of reprogramming will become adherent to a surface that has a supporting matrix. FIG. 21C shows an initial media exchange in the cell culture chamber 2102, where fresh media 2110 displaces the initial media, and in the process cells that have not become adherent (which exclude the pre-IPS cells 2108) are washed out as indicated by arrow 2116.

Figure 22A:
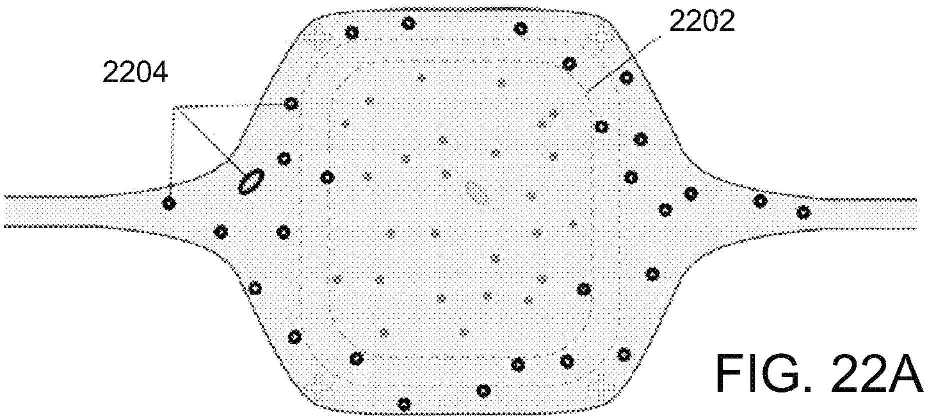
FIGS. 22A-B are diagrams illustrating cell removal during an iPSC reprogramming process in accordance with various implementations.
Figure 22B:
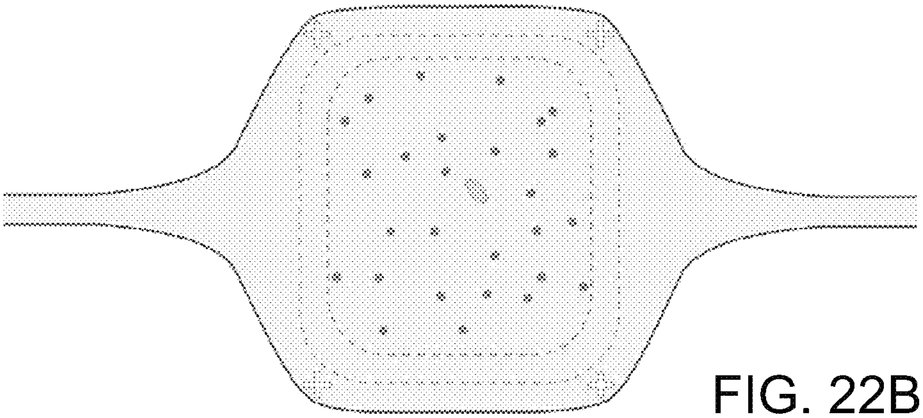

FIGS. 22A-B are diagrams illustrating cell removal during an iPSC reprogramming process in accordance with various implementations. Cell removal may be conducted to limit initial cell attachment and growth to an area where it is not perturbed by cell culture container edges or edge liquid/thermal/chemical gradient effects. FIG. 22A shows a designed area 2202 in a cell culture chamber that is designated for initial cell emergence. The designed area 2202 may be designed such that colonies that emerge within the designed area 2202 have room to grow before hitting the designated boundary away from the cell culture chamber edge (indicated by the outer dashed line). Cells that are outside of this initial boundary, denoted as cells 5304, are identified and removed using a cell removal mechanism (e.g., cell editing subsystem 114 in FIG. 1). This cell removal mechanism may be optical (laser), acoustic (focused ultrasound), mechanical, etc. but should be able to lyse, destroy, and/or lift cells off the growth surface. In any case this removal mechanism should be steered by a computing system (e.g., computing subsystem 110 in FIG. 1). Preferably, the cell removal mechanism performs this action without any need to open the cell culture container (i.e., it is compatible with closed containers/media systems). The cell removal mechanism may either target individual cells as identified through imaging, or sweep the entire area outside of the designated boundary. FIG. 22B shows the resulting cell population after removal of out-of-bounds cells, and appropriate washing to remove cell debris.

Figure 23A:
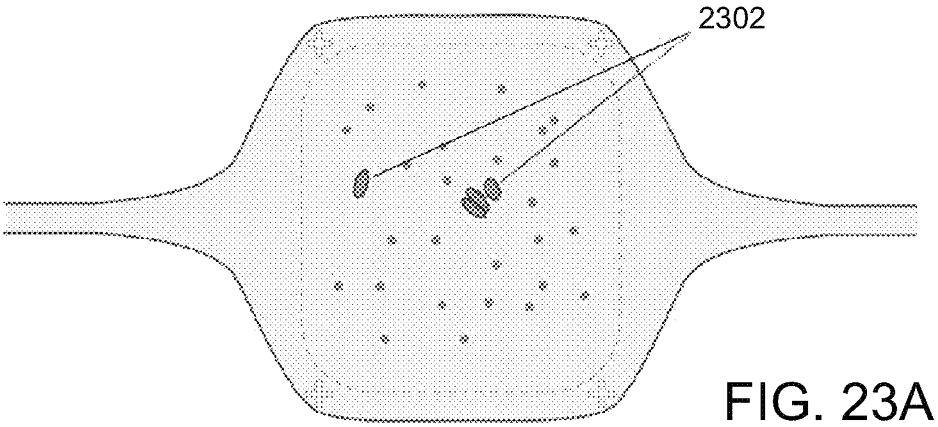
FIGS. 23A-C are diagrams illustrating cell isolation during an iPSC reprogramming process in accordance with various implementations.
Figure 23B:
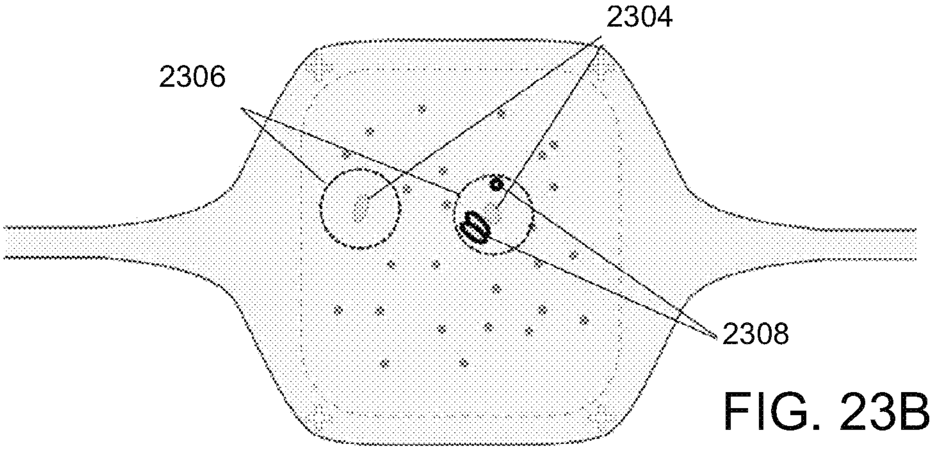
Figure 23C:
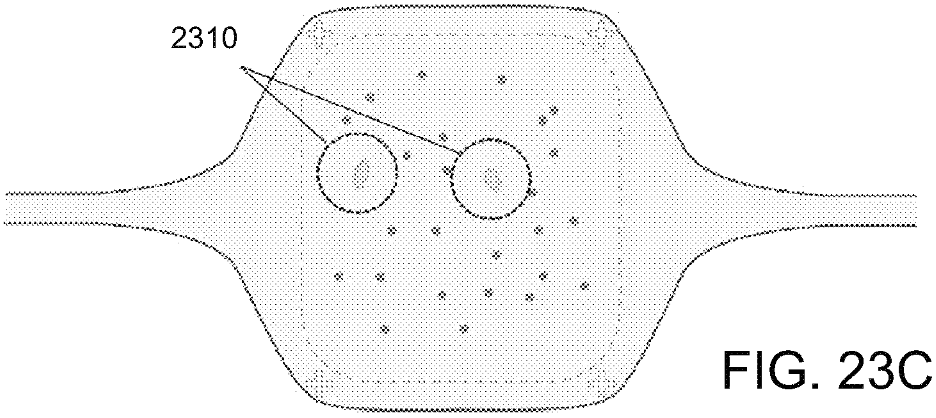

FIGS. 23A-C are diagrams illustrating cell isolation during an iPSC reprogramming process in accordance with various implementations. A cell removal mechanism (e.g., cell editing subsystem 114) may be used to isolate single cells in clusters of emerging iPSC candidates. FIG. 23A shows a cell culture chamber that includes a mix of source somatic (un-reprogrammed) cells and emerging iPS cells in small colonies 2302. Each of these colonies 2302 often corresponds to a single source cell. For example, in a case where CD34+ cells are being reprogrammed using episomal vectors delivered via electroporation, reprogramming efficiency is approximately 0.05% per cell. Thus, in a container with 10,000 CD34+ cells it would be expected that, on average, 5 cells will emerge as iPSCs. Statistically these cells are unlikely to emerge immediately adjacent to one another, but in some cases, they may be close enough to each other that they may merge into a single colony and lose monoclonality.

The cell culture system disclosed herein may ensure monoclonality using a combination of imaging, image processing from label-free images to determine precise cell location coordinates, a method for computing an optimal set of cell removals, and a mechanism for individually removing or terminally damaging the selected cells. This results in a single viable cell isolated within a sufficiently large area such that there will be no "cross-contamination" between already-emerging iPS clones, nor with yet-to-emerge iPS cells from proximate somatic cells. This selection and deletion process is shown in FIG. 23B. Selected iPS candidate cells 2304 are identified and have virtual perimeters 2306 drawn around them. Any cells lying within these perimeters that are not the selected iPS candidates are marked for removal/destruction, and the cell removal mechanism lyses/irreparably damages/removes them from the culture as indicated by outlined cell colonies 2308. After removal, the selected emerging iPS cells are left as single cells within the perimeters as illustrated in FIG. 23C with "clonal perimeters" 2310.

Figure 24A:
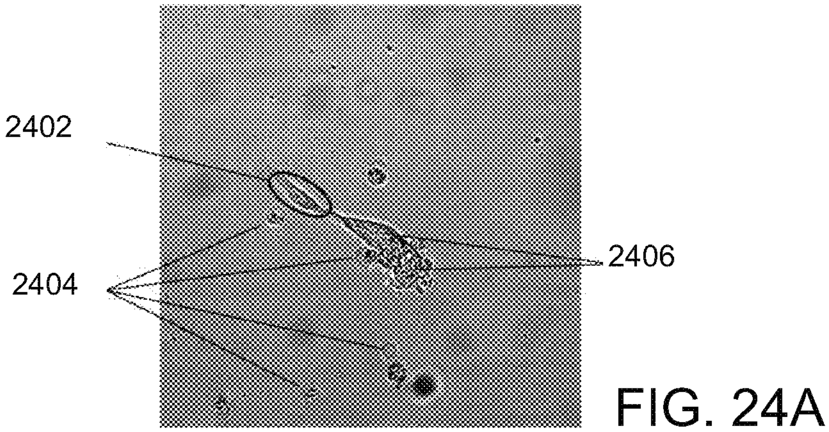
FIGS. 24A-C are images illustrating cell isolation during an iPSC reprogramming process in accordance with various implementations.
Figure 24B:
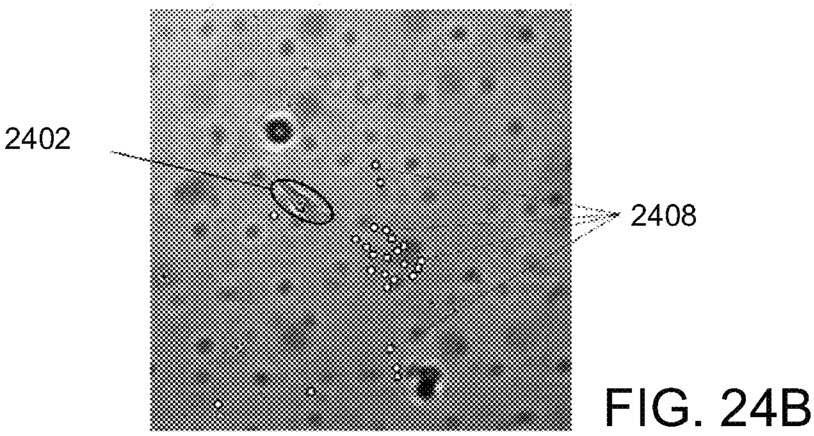
Figure 24C:
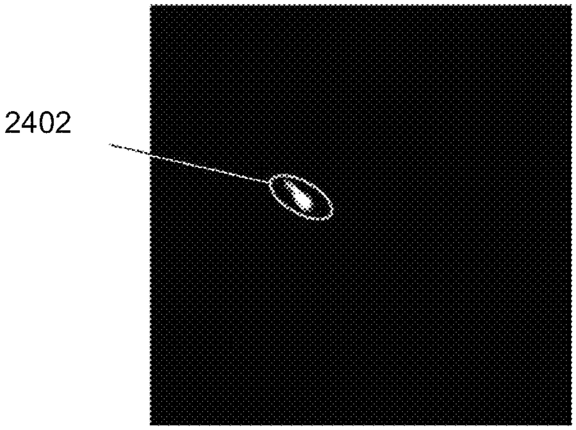

FIGS. 24A-C are images illustrating cell isolation during an iPSC reprogramming process in accordance with various implementations. FIGS. 24A-C show real images taken from a cell culture chamber undergoing the process described with respect to FIGS. 23A-C. The cells in FIGS. 24A-C are iPS cells emerging from CD34+ cells during reprogramming. In FIG. 24A a number of CD34+ cells 2404 (approximate cell diameter 10 microns, for reference) showing no signs of reprogramming are located in the neighborhood of a cluster of cells that show signs of successful reprogramming including a "selected" cell 2402 and several connected "unselected" cells 2406. As described above, the goal is to isolate the selected cell as the only viable cell in the local region. FIG. 24B shows a pattern of points 2408 that were targeted by a cell removal mechanism (e.g., cell editing subsystem 114), which in this case is a nanosecond pulsed laser (<10 ns pulse width, 532 nm) that is focused on a 20 nm Titanium semi-absorbing film on the cell growth surface. The resulting explosive microbubbles lyse and detach the target cells, while inducing little collateral damage in surrounding cells, specifically the selected iPS candidate cell 2402. In FIG. 24C a cell viability stain is used to demonstrate the viability of the selected cell 2402, and also to demonstrate that no other viable cells remain within the field of view.

Figure 25A:
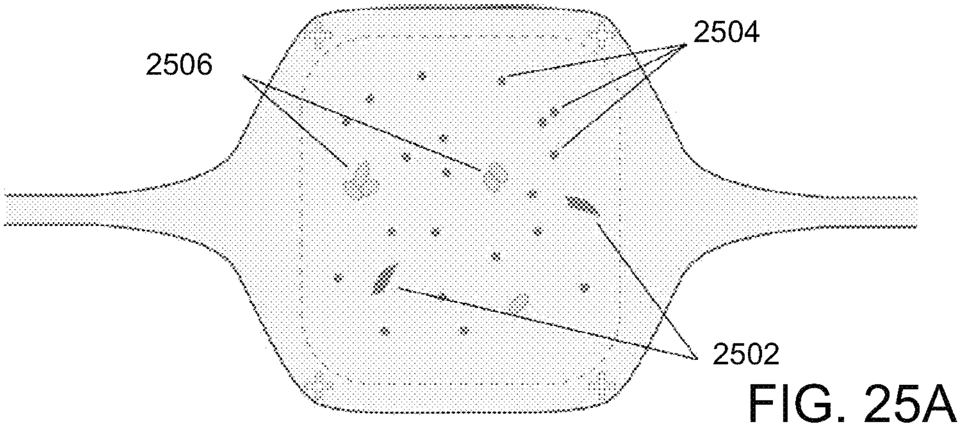
FIGS. 25A-C are diagrams illustrating non-iPS cell removal during an iPSC reprogramming process in accordance with various implementations.
Figure 25B:
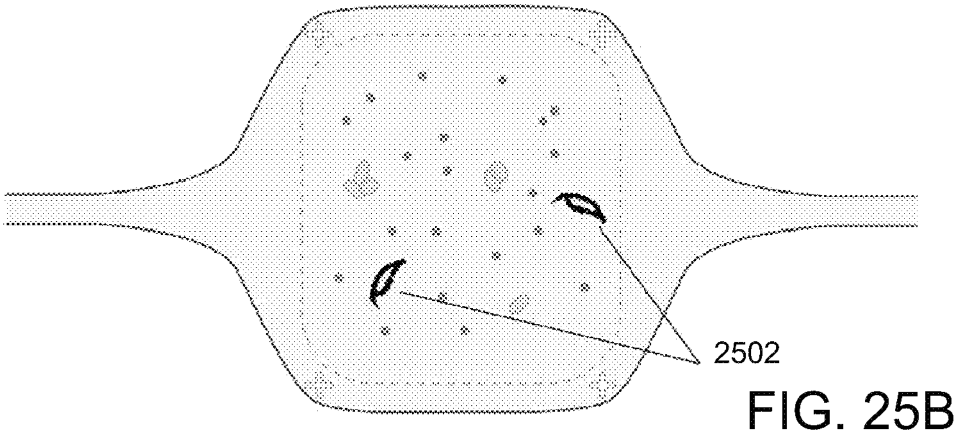
Figure 25C:
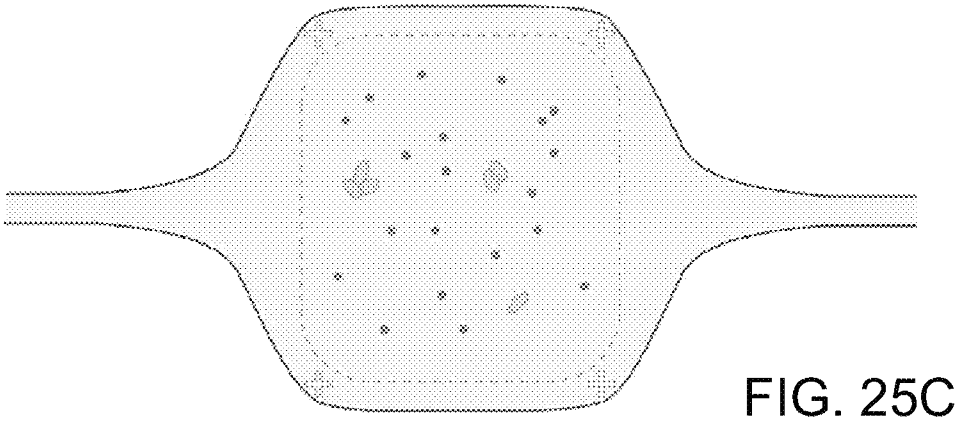

FIGS. 25A-C are diagrams illustrating non-iPS cell removal during an iPSC reprogramming process in accordance with various implementations. For example, certain cells may start differentiating into non-iPS cell types during cell culture and thus should be removed. In some cases, there may be failed partial reprogramming that causes the source somatic cells to differentiate into non-iPS cells 2502, which may potentially contaminate the emerging iPSC candidate cells or colonies 2506. These cells are located and classified by a computing subsystem as non-source and non-iPS candidates by their distinct morphological characteristics using image analysis. The non-iPS cells may be distinguished from as-yet un-reprogrammed source cells 2504 or emerging iPSC candidate cells or colonies 2506, which should remain. To prevent non-iPS cells from proliferating and contaminating the iPS cell culture, these errant cells are identified and then removed using a cell removal mechanism (e.g., cell editing subsystem 114), as shown in FIG. 25B. The non-iPS cells may be identified, located, and targeted by the cell removal mechanism. Subsequently, the cell culture chamber contains only source somatic cells and iPS candidate cells as shown in FIG. 25C.

Figure 26A:
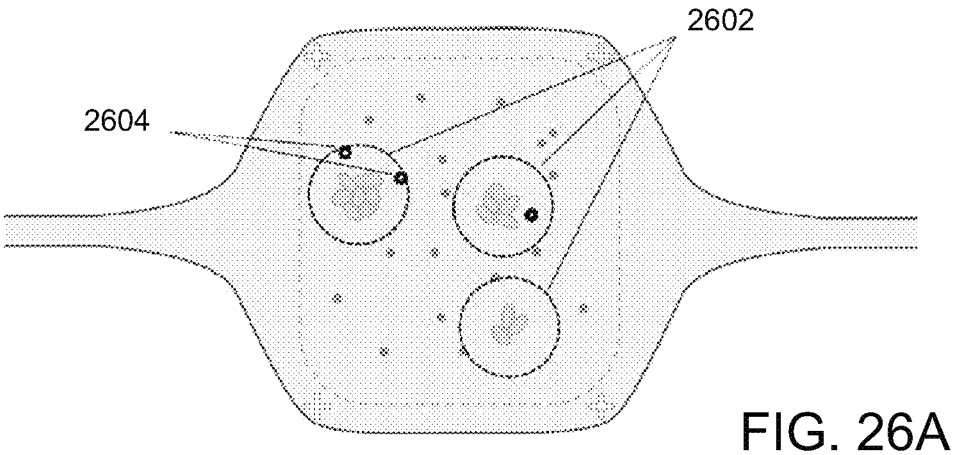
FIGS. 26A-B are diagrams illustrating neighboring cell removal around iPSC colonies during an iPSC reprogramming process in accordance with various implementations.
Figure 26B:
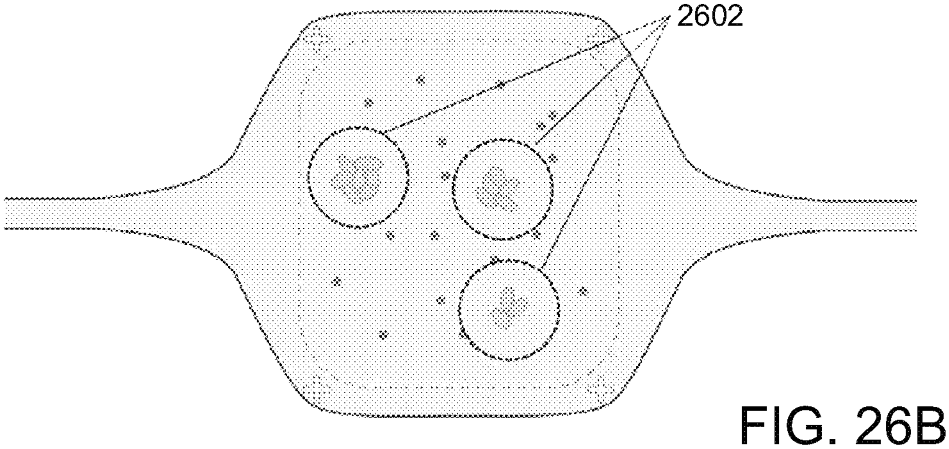

FIGS. 26A-B are diagrams illustrating neighboring cell removal around iPSC colonies during an iPSC reprogramming process in accordance with various implementations. This may be done to ensure continued clonality of the iPSC colonies. FIG. 26A shows an example where there are three clonal iPS-like colonies with corresponding exclusion zones 2602 designed to maintain clonality by removing any cells not clearly belonging to the original clonal colony. The size of these zones may be determined by the interval between imaging/selective cell removal, the expected area growth rates of the colonies, and the expected rate of emergence of other iPS candidates from somatic cells. Any neighboring cells 2604 not clearly belonging to the clonal colonies that are detected inside these clonal zones may be considered contaminant cells, are marked for deletion, and deleted. After deletion (which may include direct removal, or destruction and subsequent removal through washing), the exclusion zones 2602 are again demonstrably clonal in origin. In all the selective removal operations depicted in the current disclosure, re-imaging after removal and washing may be used to confirm removal of target cells. Any cells that remain may be retargeted with a cell removal mechanism (e.g., cell editing subsystem 114) until removal is complete.

Figure 27A:
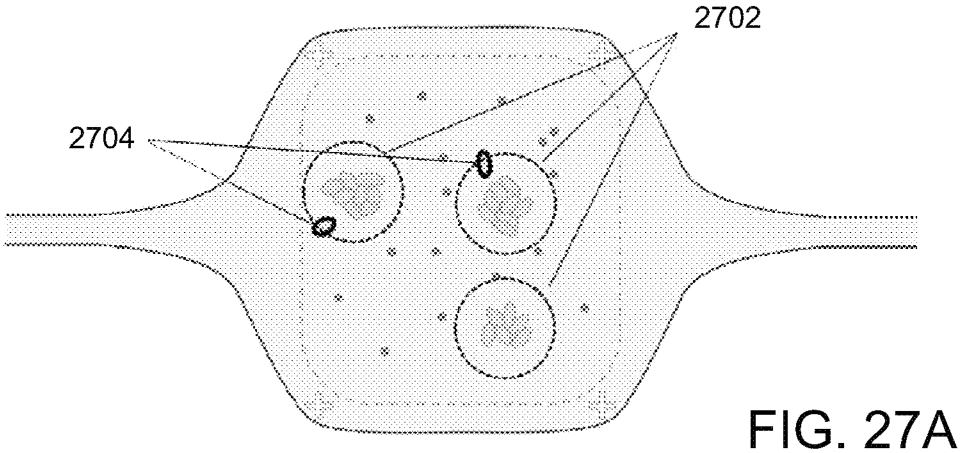
FIGS. 27A-B are diagrams illustrating removal of cells that break off from iPSC colonies during an iPSC reprogramming process in accordance with various implementations.
Figure 27B:
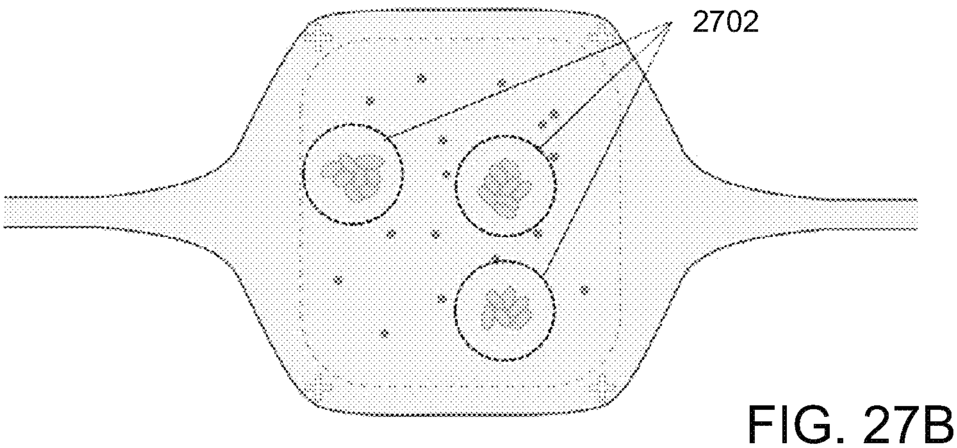

FIGS. 27A-B are diagrams illustrating removal of cells that break off from iPSC colonies during an iPSC reprogramming process in accordance with various implementations. Cells that break off from clonal iPSC candidate colonies and move beyond a defined perimeter around those colonies may endanger clonality of the verified-clonal colonies. This operation is analogous to the process described with respect to FIGS. 26A-B, except applied to cells whose origin cannot be traced to the clone owning the exclusion zones 2702. These potentially-escaped cells 2704 are considered contaminant cells and should be removed because if they cannot be traced back to an originating colony, it may be a clone of the colony. If the iPS-like cells can be traced to the local clone, then the exclusion zone 2702 may be widened to contain the cells instead. Note the circular zones drawn in FIGS. 27A-B are here are only for illustration. In most cases the exclusion zones will be a distanced-based metric from the nearest known cells belonging to the specific clone, to define a polygonal exclusion zone. After a cell removal mechanism (e.g., cell editing subsystem 114) removes the potentially-escaped cells 2704, the pure clonal zones are shown in FIG. 27B with no extraneous cells in their exclusive zones 2702.

Figure 28A:
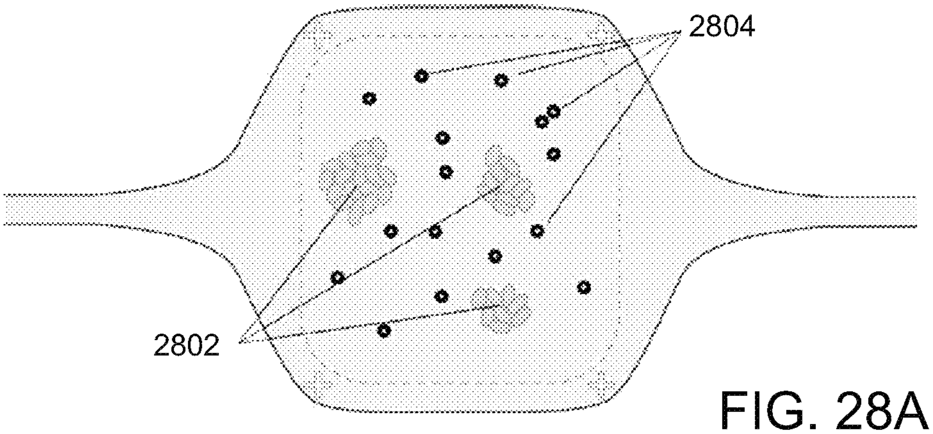
FIGS. 28A-B are diagrams illustrating removal of non-iPS cell candidates during an iPSC reprogramming process in accordance with various implementations.
Figure 28B:
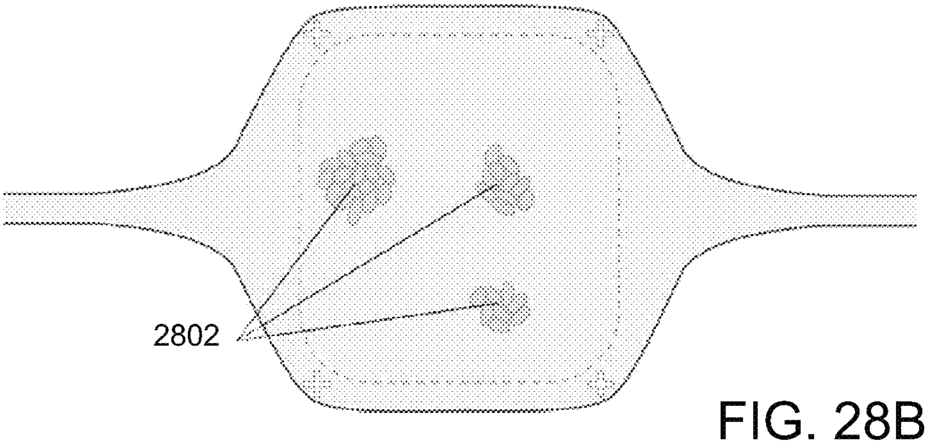

FIGS. 28A-B are diagrams illustrating removal of non-iPS cell candidates during an iPSC reprogramming process in accordance with various implementations. At a timepoint at which new iPS colonies are unlikely to emerge from somatic cells, the remaining somatic cells (for example CD34+ cells that have had episomal vector delivered) are considered contaminant cells and are actively removed from the cell culture chamber, as shown in FIG. 28A in which non-reprogrammed cells 2804 are targeted and removed while leaving iPSC colonies 2802 alone. After clearing of remaining un-reprogrammed cells, only iPS colonies 2802 remain as shown in FIG. 28B.

Figure 29A:
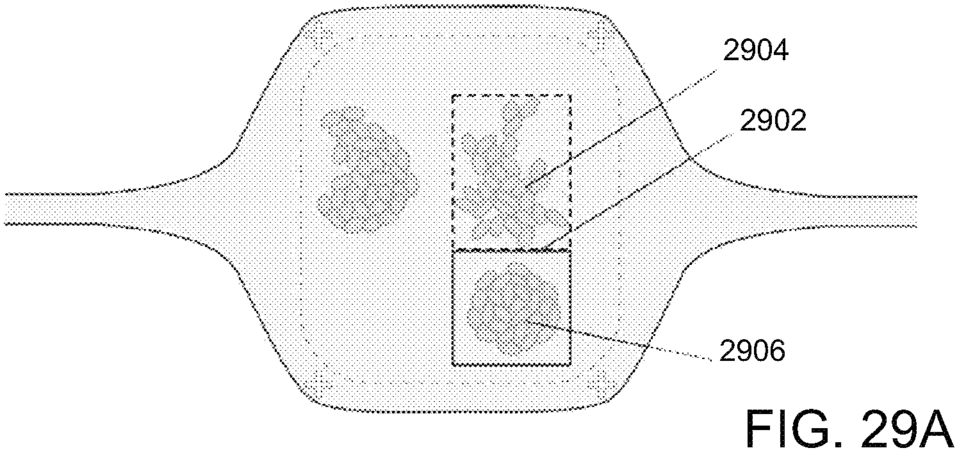
FIGS. 29A-C are diagrams illustrating removal of a cell colony during an iPSC reprogramming process in accordance with various implementations.
Figure 29B:
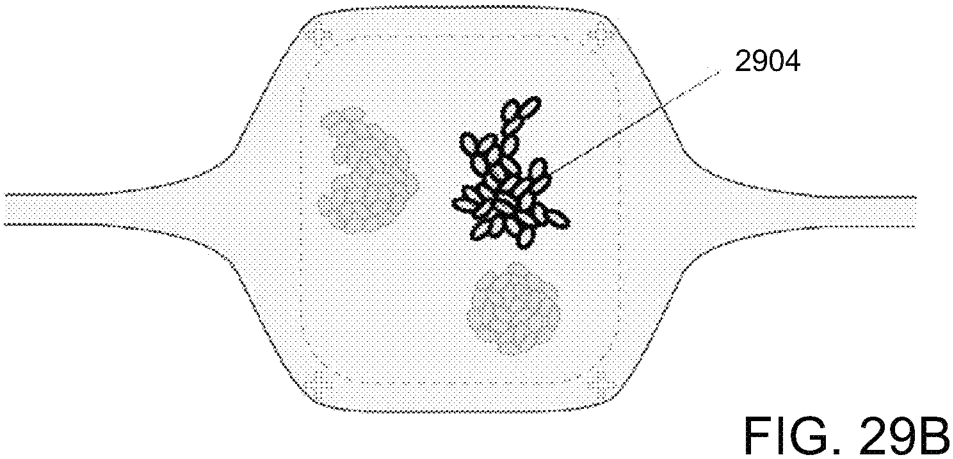
Figure 29C:
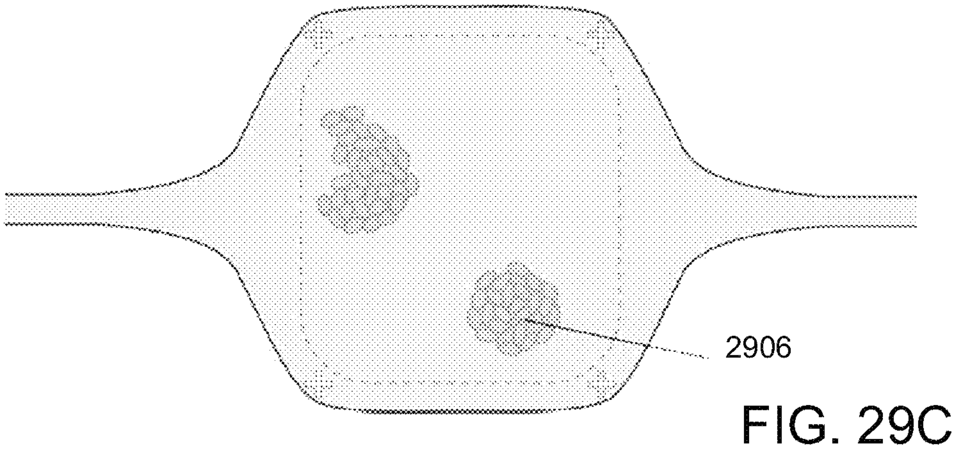

FIGS. 29A-C are diagrams illustrating removal of a cell colony during an iPSC reprogramming process in accordance with various implementations. Cell colonies may be removed when, for example, two clonal colonies of different clonal origin are in danger of colliding and cross-contaminating. The cell culture system disclosed herein has the advantage that through continuous imaging, tracking, and isolation of clonal colonies, it can allow multiple clonal colonies to co-exist in a cell culture container without the possibility of cross-contamination of clones (i.e., creation of non-clonal colonies). As a result, the behavior of each colony is more uniform due to its clonal origin, and ultimately no post-reprogramming clone process is required to ensure valid quality control results. Clone behavior can be tracked over time, and when a clone is determined to be poor, or when two clones are in danger of colliding in the container, one clone may be selected for removal.

FIG. 29A shows two clonal colonies 2904 and 2906 that have been determined to be in danger of colliding within the next imaging/editing period, as indicated by the border 2902. In this example, the clone 2906 has been determined to have a higher probability of yielding a good iPSC clone. These determinations may be made by a computing subsystem (e.g., computing subsystem 110) in coordination with a cell imaging subsystem (e.g., imaging subsystem 112), or may be determined by manual observation and selection, or a combination of automation and manual observation/selection. As a result, as shown in FIG. 29B, the colliding but (by prediction) inferior clone 2904 is selected for removal. After removal, as shown in FIG. 29C, the selected clone 2906 is now in no danger of collision or cross-clone contamination.

Figure 30A:
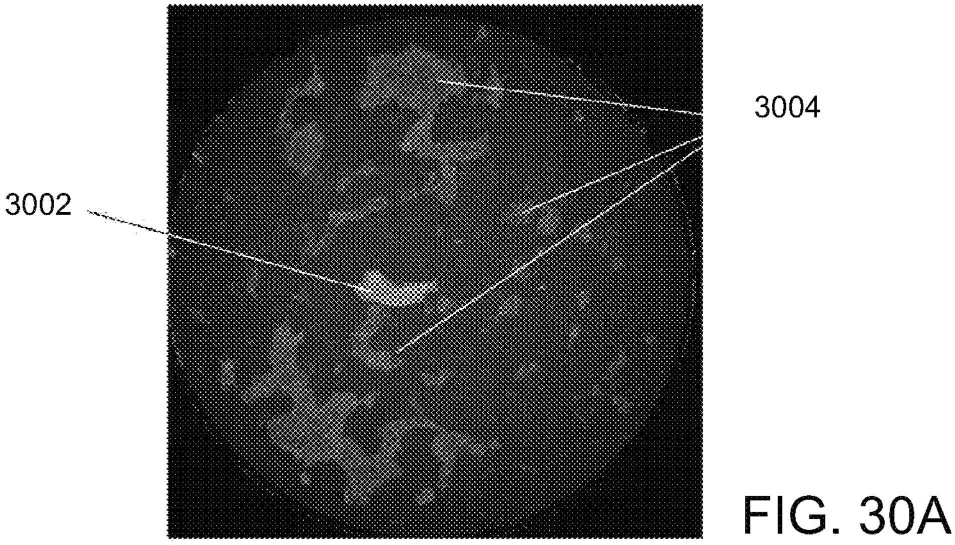
FIGS. 30A-B are images illustrating removal of a cell colony during an iPSC reprogramming process in accordance with various implementations.
Figure 30B:
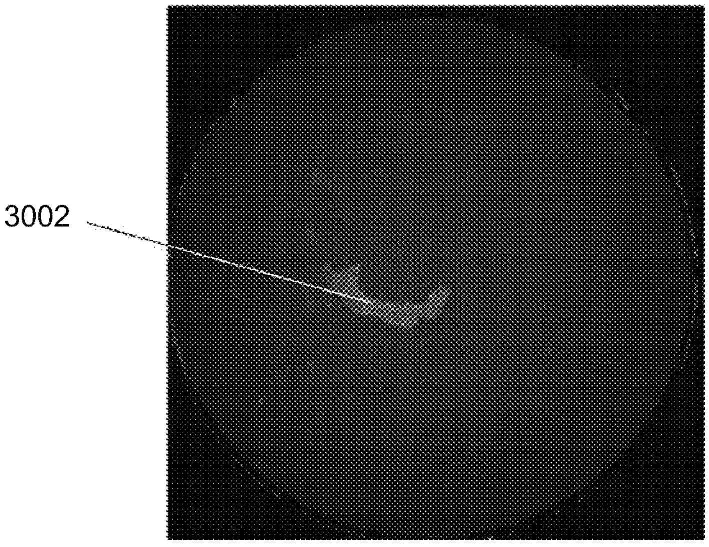

FIGS. 30A-B are images illustrating removal of a cell colony during an iPSC reprogramming process in accordance with various implementations. In the example shown in FIGS. 30A-B, a terminal decision may be made in which a single clone/colony is selected to make a single clonal sample in the cell culture container. In FIG. 30A, a desired colony 3002 is selected by manual or automatic means (e.g., by a computing subsystem). A number of other (nonselected) colonies 3004 are present in the cell culture container. In this example, the images shown are brightfield microscopy images of a single well on a 96-well microplate. The brighter (colony) regions are in fact an array of points plotted over the image that represent the extract (x, y) coordinates of each cell, as predicted by a deep learning algorithm that effectively converts brightfield images into cell nuclear coordinates. A polygon image of the desired colony 3002 represents a selection of those cells that is selected to remain in the container. The inverse of this cell selection is used to guide removal). FIG. 30B shows an image acquired 24 hours after cell removal by pulsed laser, in which the selected colony 3002 is the sole remaining colony (and has proliferated). The other colonies have been removed so that the microplate well is open for the selected colony 3002 alone to proliferate and expand.

Figure 31A:
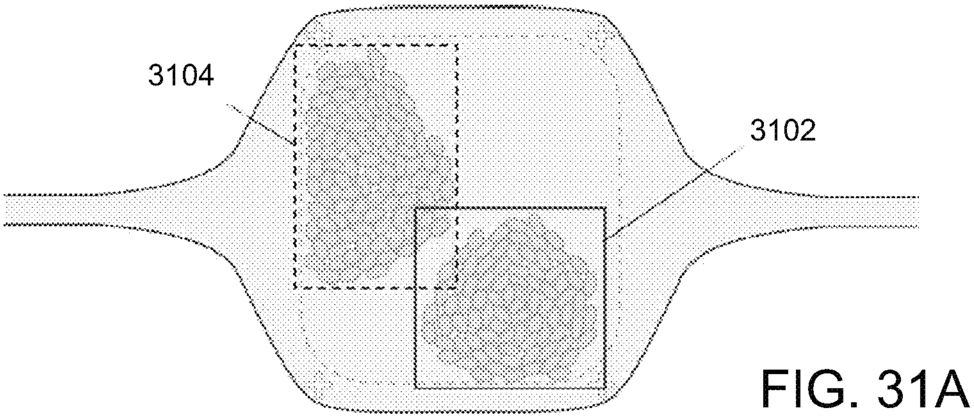
FIGS. 31A-C are diagrams illustrating selection of a cell colony during an iPSC reprogramming process in accordance with various implementations.
Figure 31B:
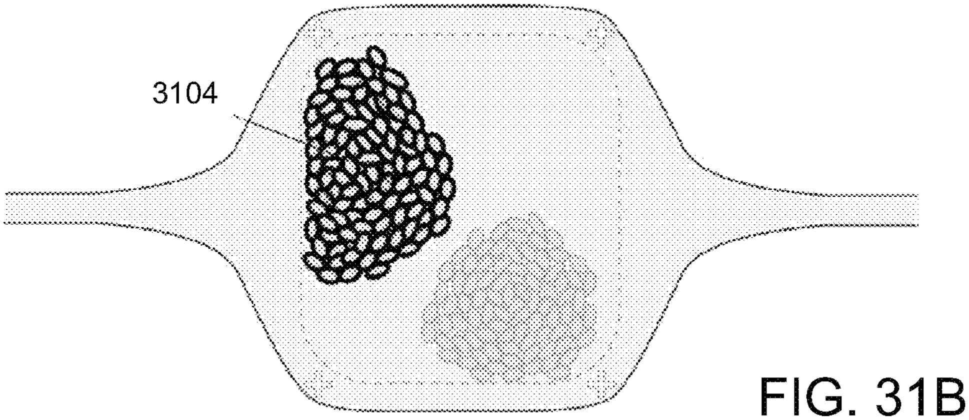
Figure 31C:
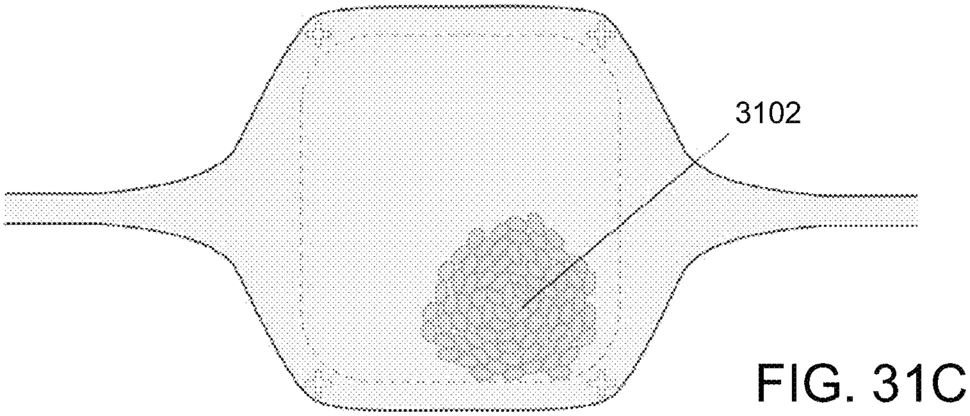

FIGS. 31A-C are diagrams illustrating selection of a cell colony during an iPSC reprogramming process in accordance with various implementations. This illustrates the ultimate selection of a single clonal colony to create the output iPS cell product. A cell removal mechanism (e.g., cell editing subsystem 114) is used to remove any other cells or colonies not stemming from the selected clone. In FIG. 31A, a selected colony 3102 is retained while any other colonies 3104 are marked for removal and removed by the cell removal mechanism as shown in FIG. 31B. Ultimately only the selected colony 3102 remains in the container, as shown in FIG. 31C. The non-presence of any other cells in the well may be checked by one or more subsequent imaging runs, and any remaining cells removed using the cell removal mechanism (and appropriate washing) until it is verified that only the desired clonal colony 3102 is present.

Figure 32A:
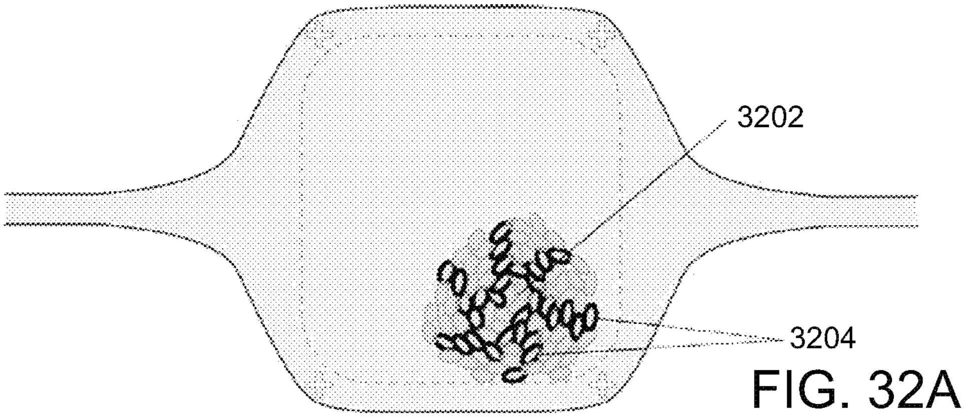
FIGS. 32A-C are diagrams illustrating spreading of a cell colony in a cell culture chamber during an iPSC reprogramming process in accordance with various implementations.
Figure 32B:
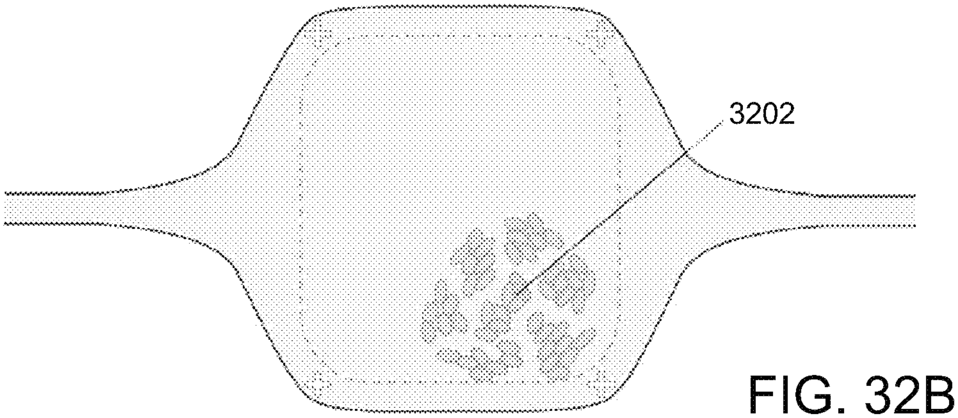
Figure 32C:
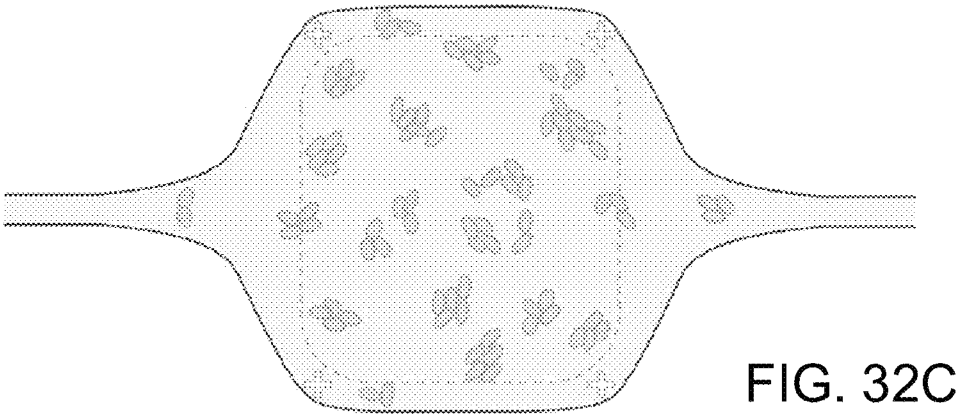
Figure 32D:
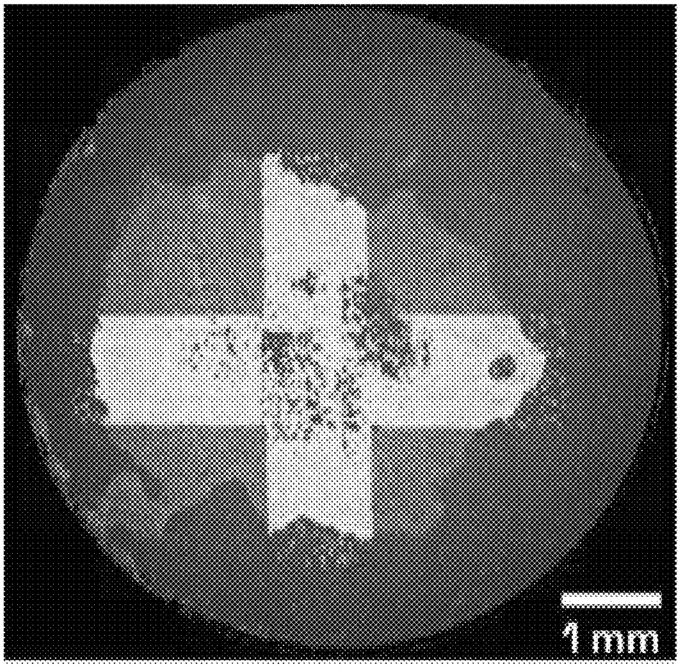
FIGS. 32D-32E show an initial colony controlled for density that spread over a growth chamber in accordance with various implementations.
Figure 32E:
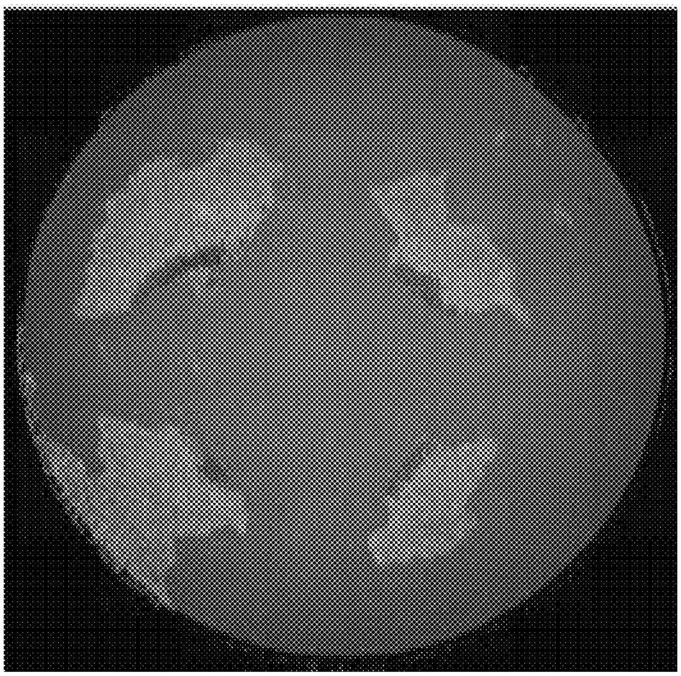

FIGS. 32A-C are diagrams illustrating spreading of a cell colony in a cell culture chamber during an iPSC reprogramming process in accordance with various implementations. Specifically, a cell removal mechanism (e.g., cell editing subsystem 114) may be used to break apart one or more cell colonies derived from a common cell (i.e., a monoclonal colony), followed by detachment of the fragments of the colony/colonies, and distribution over the cell culture container so as to provide maximum space for expansion of the clone. In the example shown in FIGS. 32A-C, a clonal colony is sectioned into pieces, then gently lifted off the cell culture surface, and then distributed across the cell culture chamber in order to seed a uniform expansion of the clone. In FIG. 32A, a clonal colony 3202 is treated with a selective cell removal mechanism acting on a subset of cells 3204, which are then removed from the cell culture container. After removal of the subset of cells 3204 as shown in FIG. 32B, the clonal colony 3202 has been fragmented. The individual colony fragments are easier to lift off the cell growth surface using trypsinization or any similar process. The pieces, once in suspension, may then be redistributed around the container as shown in FIG. 32C. FIGS. 32D-32E show an initial colony controlled for density that spread over a growth chamber. As shown in FIG. 32D, a single colony is divided into four pieces with laser processing. Next, as shown in FIG. 32E, the divided pieces of the colony continue to grow, with some preference to outward direction, after washing and continued cell culture.

Figure 33A:
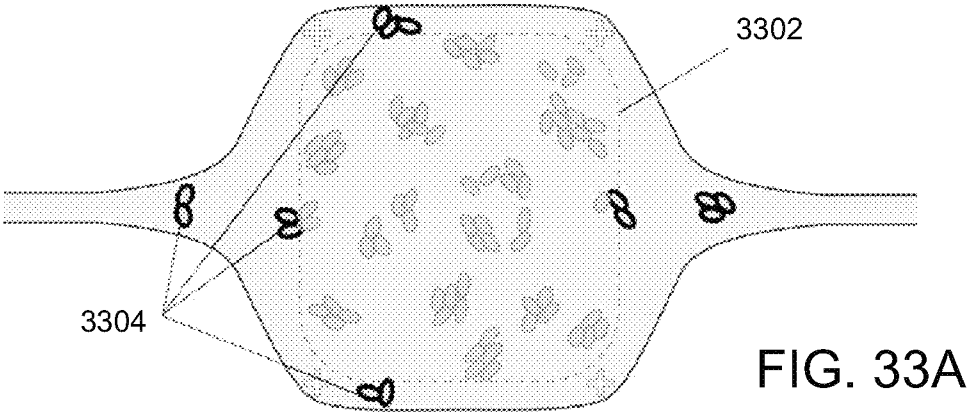
FIGS. 33A-B are diagrams illustrating removal of cells outside of designated regions during an iPSC reprogramming process in accordance with various implementations.
Figure 33B:
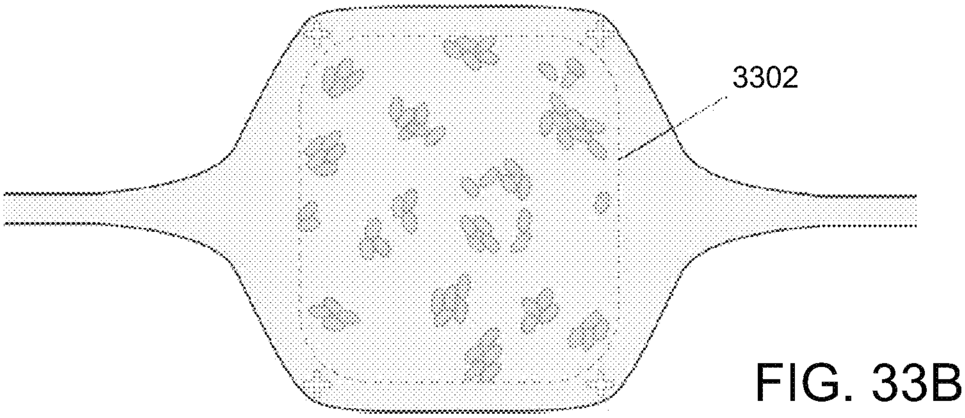

FIGS. 33A-B are diagrams illustrating removal of cells outside of designated regions during an iPSC reprogramming process in accordance with various implementations. Cells growing outside of designated regions of the cell culture chamber may be removed to prevent cell growth in border regions of the cell culture container where media conditions, chemical gradients, temperature, flow rate/shear, convection may be less uniform or consistent. FIG. 33A depicts a number of cells 3304 that are outside of a designated region 3302 of the cell culture chamber. The cells 3304 may be identified and removed using a cell removal mechanism (e.g., cell editing subsystem 114), such that afterwards all cells in the cell culture chamber are growing within the designated region 3302.

Figure 34A:
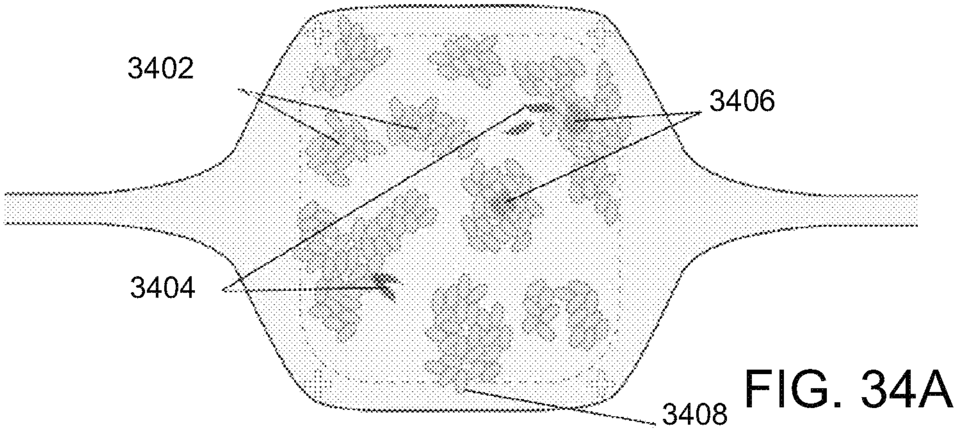
FIGS. 34A-C are images illustrating removal of various cells during an iPSC reprogramming process in accordance with various implementations.
Figure 34B:
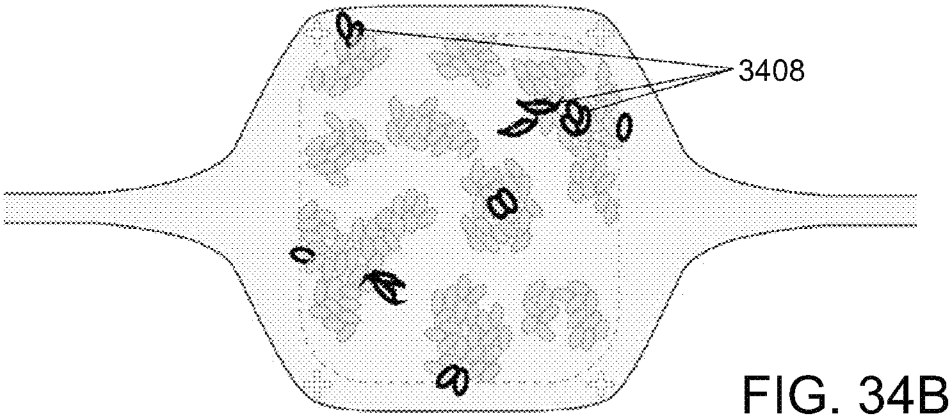
Figure 34C:
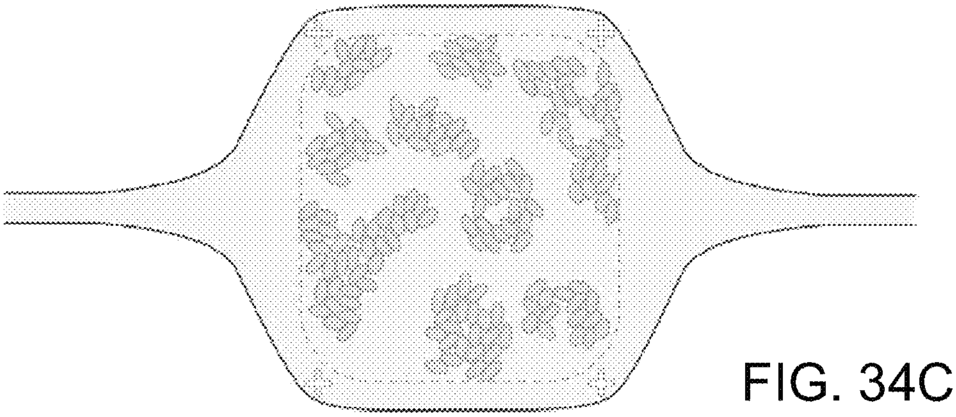

FIGS. 34A-C are images illustrating removal of various cells during an iPSC reprogramming process in accordance with various implementations. Cells may be removed during the cell culture process for a number of reasons, including cells that (a) proliferate outside the designated growth area, (b) grow to excessive density within colonies, or (c) spontaneously differentiate. FIG. 34A depicts a cell culture chamber containing a variety of cells, including iPSCs 3402 that are at desirable density and without spontaneously differentiating cells, spontaneously differentiated cells 3404, regions of iPSC colonies 3406 that are too high a density due to internal colony proliferation, and cells 3408 pushing over the established boundary for cell growth. It is desirable to control the internal density of iPSC colonies such that all cells remain observable in label-free imaging, all cells remain removable by a cell removal mechanism (e.g., cell editing subsystem 114), and cells do not grow to a density at which they spontaneously differentiate or form 3D structures that tend to differentiate. As depicted in FIG. 34B, the spontaneously differentiated cells 3404, high density colonies 3406, and boundary cells 3408 are all designated as contaminant cells targeted for removal 3410 via imaging (e.g., imaging subsystem 112) and downstream computation (e.g., computing subsystem 110). The cell culture system may determine the coordinates of the targeted cells 3410 and then remove them using the cell removal mechanism. The resulting cell culture is free of these potential impairments to a high-quality clonal iPSC culture, as shown in FIG. 34C.

Figure 35A:
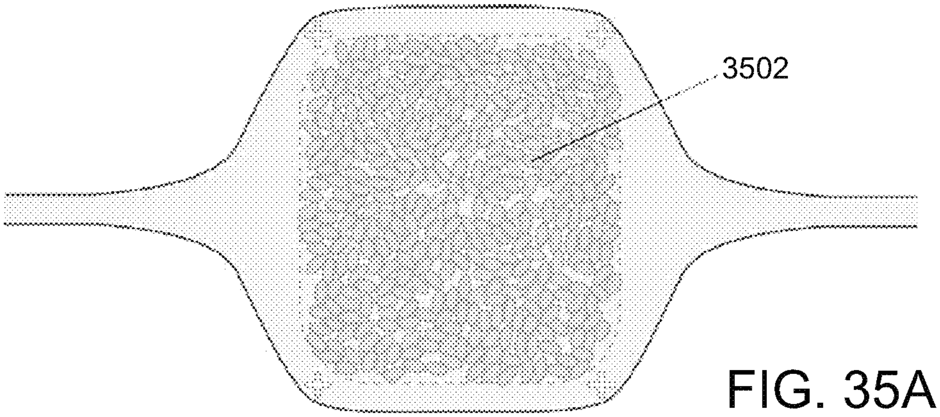
FIGS. 35A-C are diagrams illustrating fragmenting of a cell colony in a cell culture chamber during an iPSC reprogramming process in accordance with various implementations.
Figure 35B:
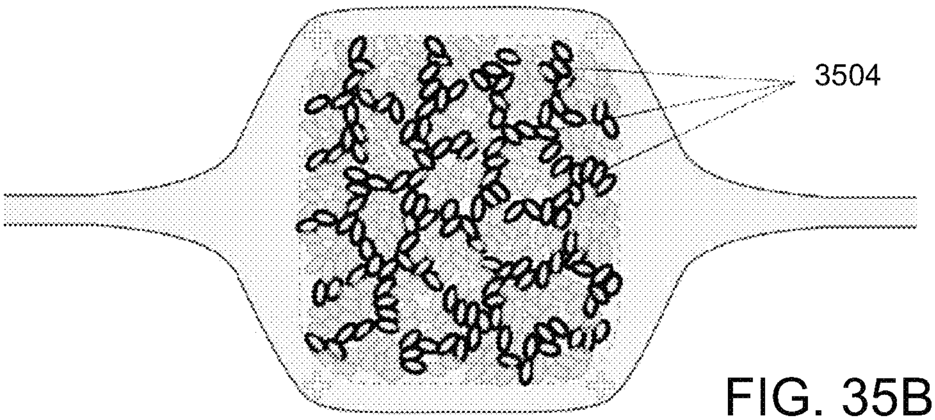
Figure 35C:
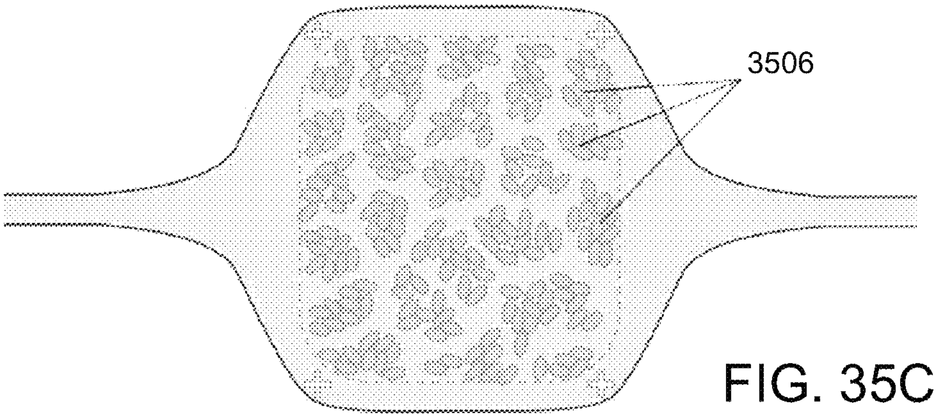

FIGS. 35A-C are diagrams illustrating fragmenting of a cell colony in a cell culture chamber during an iPSC reprogramming process in accordance with various implementations. Once a clonal cell colony reaches a maximum confluency (e.g., it grows to fill the entirety of the designated growth region of a cell culture chamber), a cell removal mechanism (e.g., cell editing subsystem 114) may repeatedly remove some of the cells to allow for multiple divisions of iPS cells (conventionally known as "passages," but as implemented herein does not require removal of the clonal iPS cells from the cell growth surface or cell culture container). This may, for example, enable clearance of a reprogramming vector including, but not limited to, episomal vectors, Sendai virus, or self-replicating mRNA. In this example, the cell count is reduced and growth areas are opened using the cell removal mechanism, but cells are removed in a biologically-relevant manner that leaves iPS cells in contact with clusters neighboring cells.

A clonal iPSC cell culture 3502 approaching high or full confluency is depicted in FIG. 35A. FIG. 35B shows a method of reducing cell count to allow cell division without overcrowding, and therefore vector clearing. Namely, a cell removal pattern 3504 is calculated based on cell imaging that leaves iPSC structures with sufficient iPSC numbers and neighbor contacts that maintain iPSC health. This is akin to clumped passaging of iPS cells in conventional container-to-container passaging, but allows the process to be conducted in a single container, which significantly simplifies the process, reduces consumable usage, lowers stress on the remaining cells, and allows the process to be performed inside of a closed, sterile container, isolated from other patient samples and potential contaminants. A computing subsystem (e.g., computing subsystem 110) may determine the cell removal pattern 3504 from images obtained from a cell imaging subsystem (e.g., imaging subsystem 112). FIG. 35C shows the remaining cell colony 3506 after the cell removal mechanism has removed the cell removal pattern 3504. The cell colony 3506 may now undergo further cell division into the resulting gaps, while keeping sufficient connection between cells to maintain cell health and chemical and mechanical signaling, which is often lost during conventional passaging. It should be noted that a number of patterns that meet these criteria are possible, for example an "island positive" pattern such as the one shown here (where on average convex islands of cell remain, surrounded by a network of cleared areas), or "island negative" where cells form a network around cleared convex areas.

Figure 36A:
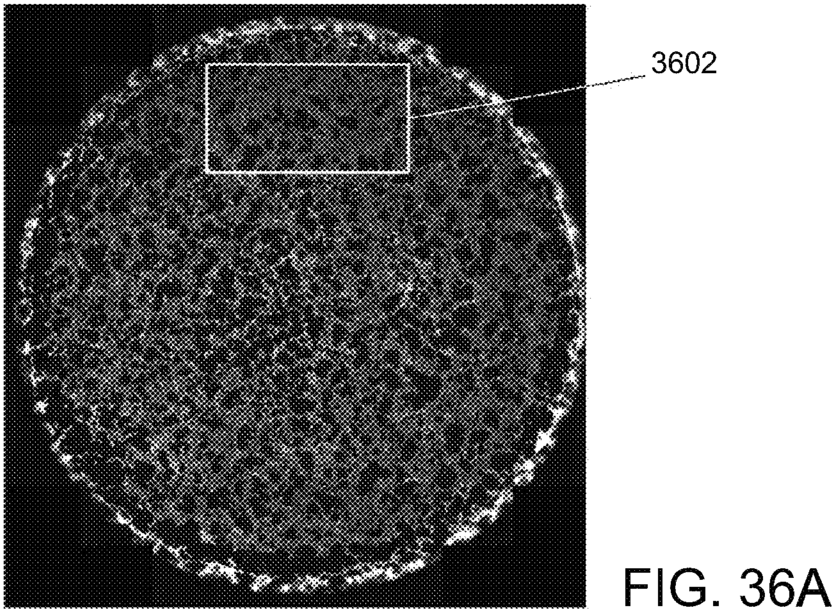
FIGS. 36A-B are images illustrating fragmenting of a cell colony in a cell culture chamber during an iPSC reprogramming process in accordance with various implementations.
Figure 36B:
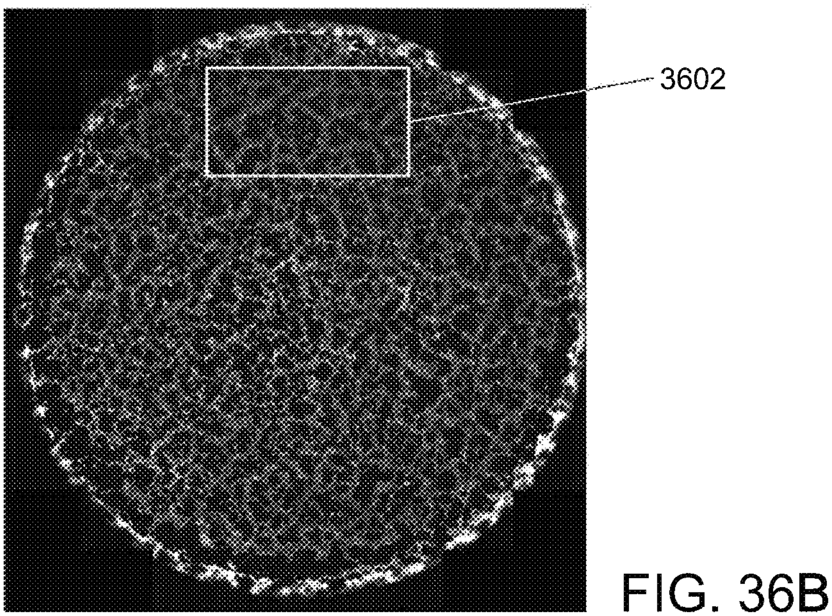
Figure 36C:
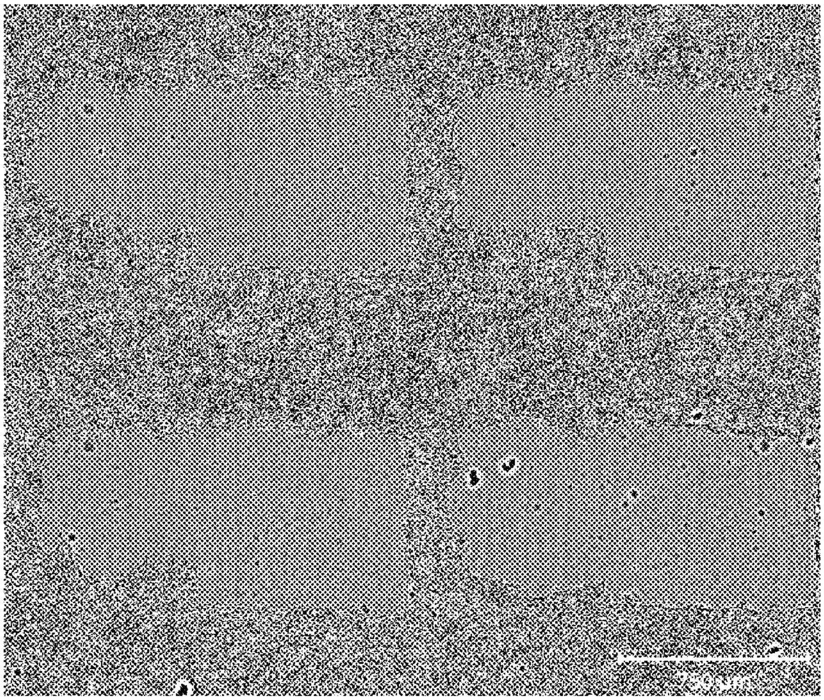
FIG. 36C shows a dense hiPSC cell culture removed using laser microbubble lysing and washing in accordance with various implementations.
Figure 36D:
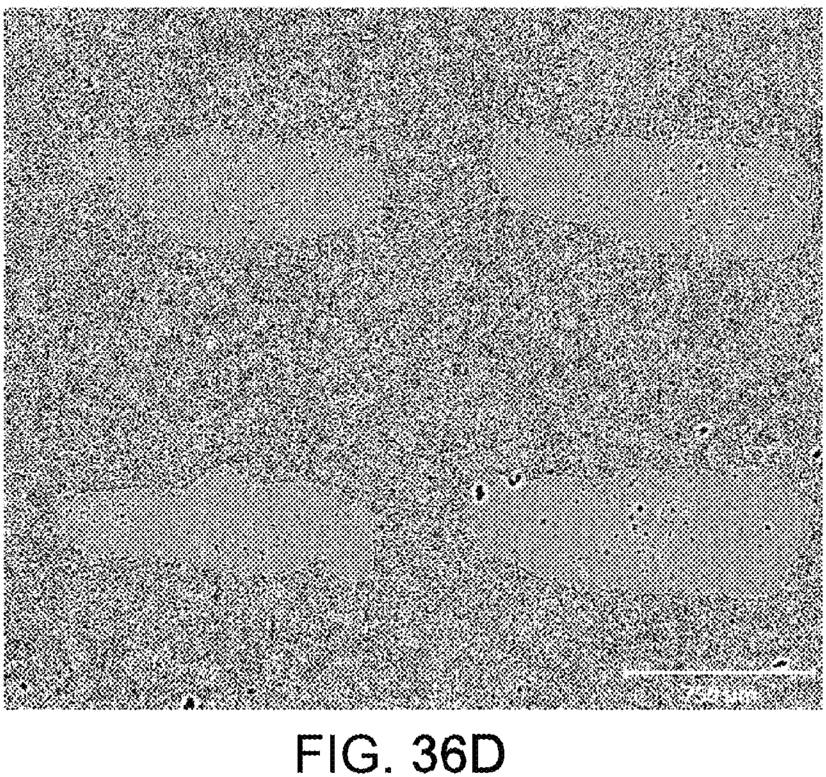
FIG. 36D shows regrowth of the hiPSC cell culture after 24 hours in accordance with various implementations.

FIGS. 36A-B are images illustrating fragmenting of a cell colony in a cell culture chamber during an iPSC reprogramming process in accordance with various implementations. FIGS. 36A-B are images illustrating the operation described with reference to FIGS. 35A-C on actual cells. FIG. 36A shows a cell culture container (e.g., a single well within a 96-well plate) with iPS cells that have been Calcein AM (live cell stain) labelled. Near the top of the well, the iPS cells have reached high density in region 3602. The cells were imaged in label-free brightfield (not shown) imaging, and a deep learning network was used to extract (x, y) coordinate positions of all cells. The cell positions were used to calculate local density. Where density was higher than desirable as in the region 3602, a pattern of cell removals that left intact contiguous networks of iPSCs was calculated. As can be observed from the difference between images in FIG. 36A (prior to selection and removal) and FIG. 36B (after selective removal of cells), the region 3602 has had density decreased significantly, while leaving a viable network of iPSCs (as indicated by the Calcein AM cell viability stain) for further proliferation. This process may be repeated to clear reprogramming vectors from the iPSCs. Another example of cell removal and subsequent regrowth is illustrated in FIGS. 36C-D. FIG. 36C shows a dense hiPSC cell culture removed using laser microbubble lysing and washing. FIG. 36D shows regrowth of the hiPSC cell culture after 24 hours.

Figure 37A:
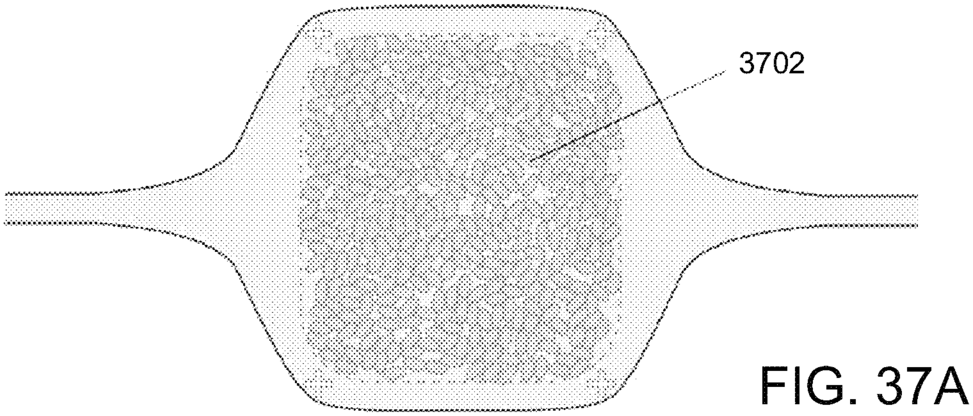
FIGS. 37A-C are diagrams illustrating harvesting of cells in a cell culture chamber during an iPSC reprogramming process in accordance with various implementations.
Figure 37B:
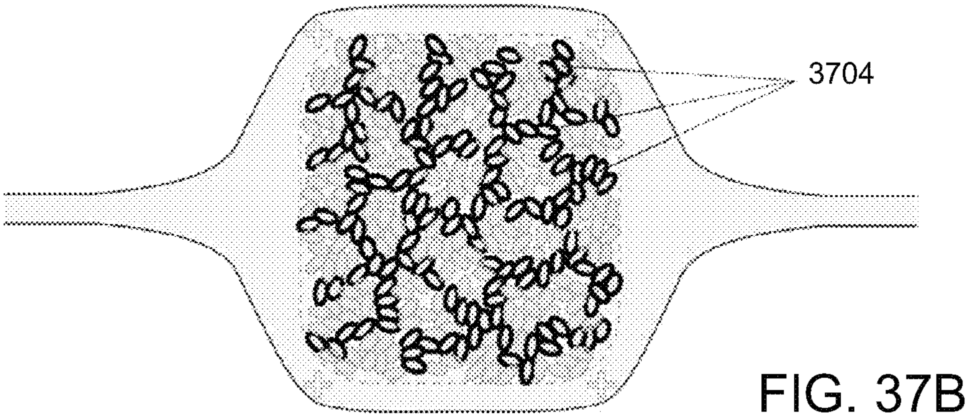
Figure 37C:
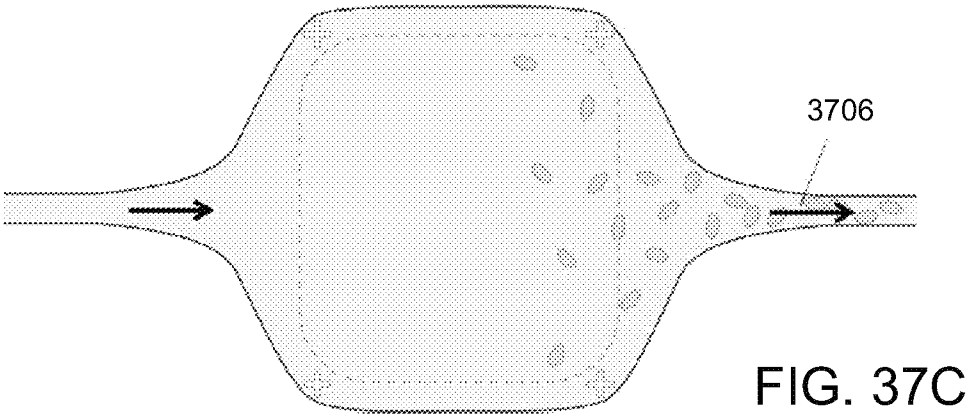

FIGS. 37A-C are diagrams illustrating harvesting of cells in a cell culture chamber during an iPSC reprogramming process in accordance with various implementations. In this example, a cell removal mechanism (e.g., cell editing subsystem 114) is used to prime the cell culture by opening up gaps between small islands of cells, making the subsequent removal with an agent such as Trypsin gentler (e.g., requiring less exposure time), before removal of the clonal iPS cells in suspension. FIG. 37A depicts a clonal cell colony 3702 produced with the systems and methods disclosed herein, approaching full confluency. The cell population may be directly treated with trypsin for liftoff and harvest. However, in this example, a selective cell removal mechanism may be used as shown in FIG. 37B to selectively remove a sparse set of cells 3704 that cuts the clonal cell colony 3702 into smaller islands prior to lift-off into suspension. Finally, as shown in FIG. 37C, clonal cells 3706 from the clonal cell colony 3702 may be harvested in suspension from the cell culture container.

The operations described with respect to FIGS. 21A-37C may be conducted by a cell culture system as disclosed herein (e.g., cell culture system 100). The cell culture system may provide a closed system for cell culture growth (e.g., a closed cassette system), as well as provide automated imaging, cell editing, cell harvesting, cell monitoring and prediction, and other cell culture functions. In some implementations, the cell culture system may operate in a fully automated fashion with user oversight of cell culture processes through user interfaces. In some implementations, the cell culture system may also operate in a semi-automated fashion, in which users may manually conduct one or more of the cell culture steps. For example, a user may manually observe the cell culture and identify cells and cell colonies that should be kept or removed, and the cell culture system may use automated cell editing functions to remove the unwanted cells and cell colonies. Thus, the cell culture system disclosed herein may be configured to produce monoclonal cell output products, such as monoclonal iPSCs, in a closed system using the operations described with respect to FIGS. 21A-37C. The use of automated cell imaging and editing may help keep cell cultures clonal during cell growth and proliferation. Because the output cell products are to be used in various cell therapies and other medical applications, ensuring monoclonality is important for a variety of reasons such as patient safety, differentiation/treatment efficacy, and adhering to applicable statutes, regulations, and standards concerning cell therapies utilizing the output cell products.

Remote Actuator Systems

Closed or sealed cell culture systems are important for producing clinical-grade cells or biologics at scale. Closed systems are preferable to open systems, in which contamination or cross-contamination are an ever-present danger and expensive, high-grade cleanrooms and regular sterilization regimes are required. Most small-scale adherent cell culturing is done in 2D vessels such as well plates or flasks. An advantage of these containers is that the cell cultures may be inspected by microscopy. However, such containers are open systems. For example, they are opened for regular cell media changes or operations on the cell culture itself, for example passaging or colony selection.

Stirred bioreactors offer a closed cell culture environment and may be used for adherent cells with appropriate use of cell aggregates or microcarriers that provide a niche for adherent cell growth. In addition, they provide good continuous mixing of cell media, meaning nutrients and dissolved gases are efficiently mixed and transported to cells, and waste products carried away. However, there is no ability to observe cell behavior via imaging, much less editing the cell culture in these systems.

Formats for 2D adherent cell cultures scale up in a semi-closed or closed environment, enable large area 2D adherent growth, and to a limited extent can enable observability by microscopy. However, they often provide uneven distribution of nutrients and dissolved gases, and the only solution is to flow media faster through the cell culture chamber, which can lead to systematic stress on cell cultures and change in gene expression, health, and/or phenotype. Thus, what is needed in the art are methods of enabling 2D adherent cell culture in a closed cell culture chamber. The closed cell culture chamber should enable a number of functions, such as observation by microscopy, cell editing, and liquid handling (such as media mixing, cell layer washing, debris removal), all without breaking the seal on the closed cell culture chamber or the liquid loop within it.

The systems and methods disclosed herein enable a cell culture system to monitor and dynamically manipulate the contents of a closed cell culture chamber of a cell culture container (e.g., cell culture container 106 in FIG. 1). These system and methods include one or more magnetic tools that function inside of a closed cell culture chamber in which adherent cells are cultured in two dimensions. The magnetic tools may reside on the surface opposite of the adherent cell culture and are magnetically coupled to external actuators that control rotation, translation, and orientation of the magnetic tools in order to provide a variety of functions, including but not limited to: mixing of media to ensure uniform distribution of nutrients, dissolved gasses, cell factors, other reagents, waste products, etc.; agitation to dislodge and wash debris away from the cell culture surface; detaching non-adherent cells from an adherent cell culture; moving debris to a collection region; ensuring uniform distribution of cells during seeding; and dislodging and washing away cells during cell harvesting.

Figure 38A:
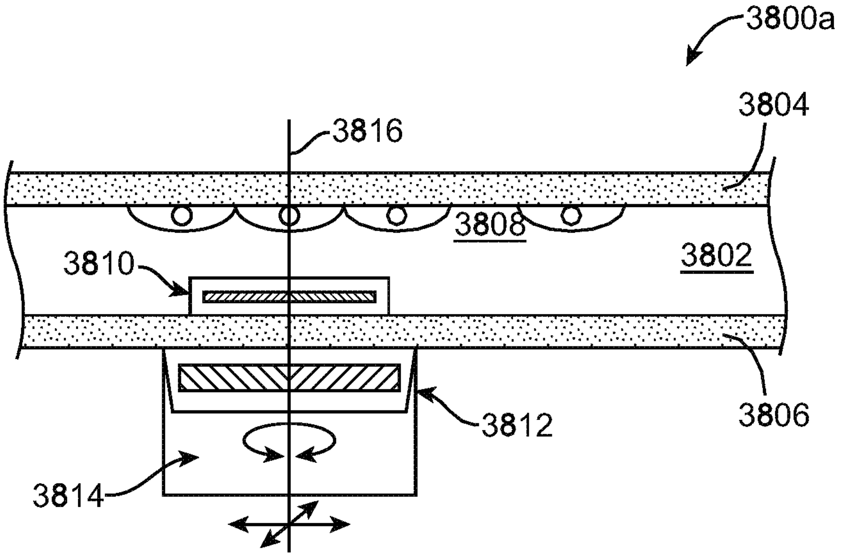
FIGS. 38A-38B are block diagrams of a closed cell culture container with a magnetic tool in accordance with various implementations.
Figure 38B:
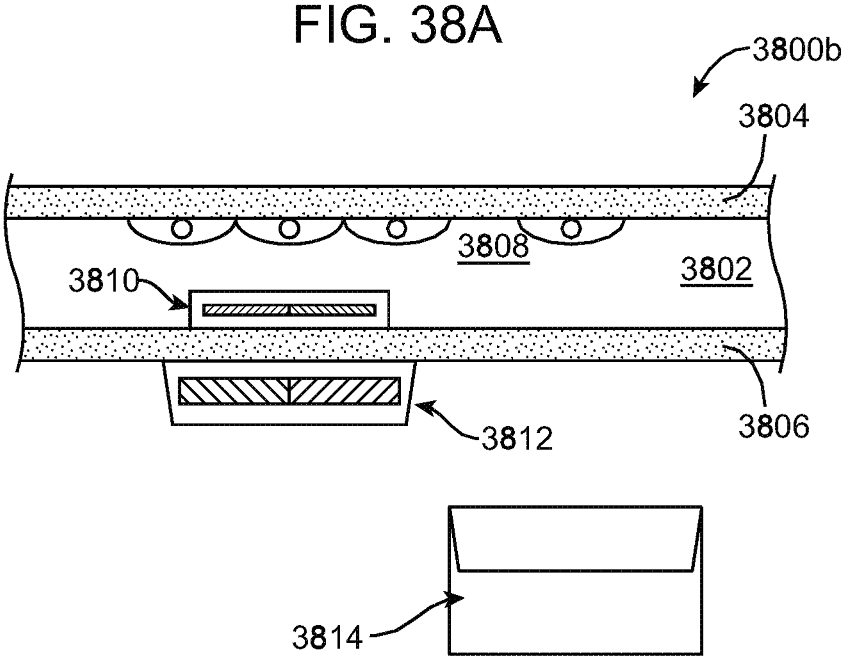

FIGS. 38A-B are block diagrams of a closed cell culture container with a magnetic tool in accordance with various implementations. FIG. 38A shows a cross-section view of a cell culture container 3800*a* with an engaged magnetic tool. The cell culture container 3800*a* may be similar to cell culture container 106 in FIG. 1, and may be part of a cell culture system. A liquid-filled cell culture chamber 3802 is enclosed by a cell-bearing surface 3804 and an opposite surface 3806. These surfaces are typically glass or polymer sheets. In many cases both are transparent to facilitate imaging of the cell culture 3808 on the cell-bearing surface 3804. In this example, an inverted cell culture is shown, where after inoculation of the cell culture chamber 3802, the vertical orientation of the chamber is opposite of what is shown in FIG. 38A, causing cells to settle and then adhere to the cell-bearing surface 3804 due to the forces of gravity. After the cells adhere, the cell culture chamber 3802 is inverted or turned around, and the majority of the cell culture process is performed in an inverted orientation such that debris or non-adherent cells settle on the opposite surface 3806, where they may be removed using the systems and methods disclosed herein.

An internal magnetic tool 3810 resides inside of the closed cell culture chamber 3802, opposite of an external magnetic component 3812. The internal magnetic tool 3810 may be pushed against the inside of the opposite surface 3806 because of magnetic attraction to the external magnetic component 3812. The internal magnetic tool 3810 may include one or more magnets that are coated appropriately for a biological environment. For example, a rectangular Neodymium rare Earth magnet may be coated with a polymer or fluoropolymer to make it inert, biocompatible, non-stick, and non-scratching as it translates or rotates on the inner surface of the cell culture chamber 3802. The external magnetic component 3812 may also be coated to prevent scratching of the outer surface of the cell culture chamber 3802.

The external magnetic component 3812 may be removably coupled to an actuator 3814 that may be configured to rotate the external magnetic component 3812, and by extension the internal magnetic tool 3810, around rotation axis 3816. The actuator 3814 may in turn be translated around the same plane as the opposite surface 3806 to allow the internal magnetic tool 3810 to traverse the entire surface of the cell culture chamber 3802. This, along with the rotation action of the actuator 3814, gives the internal magnetic tool 3810 three degrees of freedom (i.e., motion in the XY plane of the opposite surface 3806, and motion around the rotation axis 3816). The translation mechanism for the actuator 3814 is not shown in FIG. 38A. In one example, the actuator 3814 may be connected to one or more arms that move the actuator 3814 around the XY plane and may move the actuator 3814 towards or away from the opposite surface 3806. The one or more arms may be controlled by a computing subsystem in a cell culture system (e.g., system 110 in FIG. 1). In general, the actuator 3814 may be translated relative to a stationary cell culture chamber 3802, or vice versa.

FIG. 38B shows a cross-section view of a cell culture container 3800*b* having the same components as cell culture container 3800*a*, except that the external magnetic component 3812, and by extension the internal magnetic tool 3810, are disengaged from the actuator 3814. In FIG. 38B, the actuator 3814 has been retracted from the cell culture chamber 3802. The actuator 3814 may have one or more mechanisms that allow the actuator 3814 to capture or connect to the external magnetic component 3812 and disconnect from it. The internal magnetic tool 3810 and the external magnet component 3812 remain in place but are stationary due to the magnetic forces between them, and the resulting friction forces against the surface 3806, preventing the internal magnetic tool 3810 from freely moving around the cell culture chamber 3802. Thus, the cell culture container 3800*b* may be moved locations while the internal and external magnetic components 3810, 3812 stay fixed in place so that they do not damage the cell culture 3808. In some implementations, multiple internal magnetic tools 3810 and associated external magnetic components 3812 may reside on internal side and external sides, respectively, of the lower surface 3806. The actuator 3814 may engage with different external magnetic components 3812 in order to move each internal magnetic tool 3810 as needed to perform operations inside of the cell culture chamber 3802.

Figure 38C:
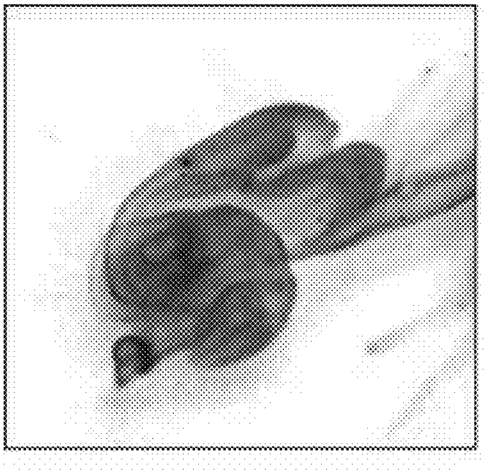
FIG. 38C shows dye in a liquid chamber of an exemplary micro-magnetic tool in accordance with various implementations.
Figure 38D:
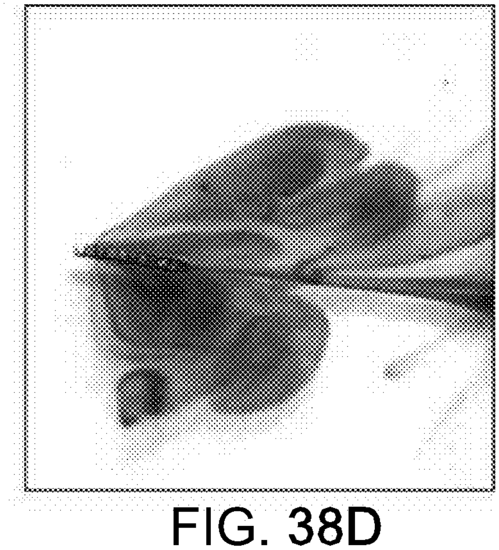
FIG. 38D shows an exemplary micro-magnetic tool being translated through liquid from right to left by an actuator external to liquid chamber in accordance with various implementations.
Figure 38E:
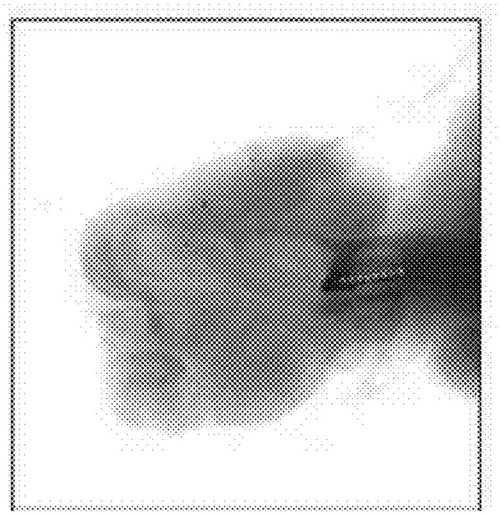
FIG. 38E shows an exemplary micro-magnetic tool being translated through liquid from right to left and counter-clockwise by an actuator external to liquid chamber in accordance with various implementations.

FIG. 38C shows dye in a liquid chamber of an exemplary micro-magnetic tool. FIG. 38D shows an exemplary micro-magnetic tool being translated through liquid from right to left by an actuator external to liquid chamber. As shown, the exemplary micro-magnetic tool is oriented to match direction of travel for minimum disturbance of the liquid. FIG. 38E shows an exemplary micro-magnetic tool being translated through liquid from right to left and counter-clockwise by an actuator external to liquid chamber. As shown, the fluid is locally mixed in the treated area.

The exemplary tool shown in FIGS. 38A-C comprises rare earth magnets (dimensions: 5.0 mm×0.5 mm×0.5 mm) inside a liquid chamber. Externally (under the cell culture container wall and a sheet of white paper, for photographic clarity), a motorized actuator with one axis of translation and one axis of rotation is placed under the magnetic tool and orients the tool in the cell culture vessel. In one example the cell culture vessel has a growth area of about 636 $cm^2$ and a chamber height of about 17 mm.

In some implementations, the cell culture vessel has a growth area of about 400 $cm^2$ to about 5000 $cm^2$. In some implementations, the cell culture vessel has a growth area of at least about 400 $cm^2$, about 450 $cm^2$, about 500 $cm^2$, about 550 $cm^2$, about 600 $cm^2$, about 650 $cm^2$, about 700 $cm^2$, about 750 $cm^2$, about 800 $cm^2$, about 850 $cm^2$, about 900 $cm^2$, about 950 $cm^2$, about 1000 $cm^2$, about 1100 $cm^2$, about 1200 $cm^2$, about 1300 $cm^2$, about 1400 $cm^2$, about 1500 $cm^2$, about 1600 $cm^2$, about 1700 $cm^2$, about 1800 $cm^2$, about 1900 $cm^2$, about 2000 $cm^2$, about 2500 $cm^2$, about 3000 $cm^2$, about 3500 $cm^2$, about 4000 $cm^2$, about 4500 $cm^2$, or about 5000 $cm^2$. In some implementations, the cell culture vessel has a growth area of at most about 400 $cm^2$, about 450 $cm^2$, about 500 $cm^2$, about 550 $cm^2$, about 600 $cm^2$, about 650 $cm^2$, about 700 $cm^2$, about 750 $cm^2$, about 800 $cm^2$, about 850 $cm^2$, about 900 $cm^2$, about 950 $cm^2$, about 1000 $cm^2$, about 1100 $cm^2$, about 1200 $cm^2$, about 1300 $cm^2$, about 1400 $cm^2$, about 1500 $cm^2$, about 1600 $cm^2$, about 1700 $cm^2$, about 1800 $cm^2$, about 1900 $cm^2$, about 2000 $cm^2$, about 2500 $cm^2$, about 3000 $cm^2$, about 3500 $cm^2$, about 4000 $cm^2$, about 4500 $cm^2$, or about 5000 $cm^2$.

According to some implementations, the cell culture vessel is scaled down to have a smaller growth area that is nonetheless sufficient for the cell culture processes disclosed herein, thereby providing greater efficiency in the use of space and resources (e.g., culture media, gases, power, rack space, etc.). In some implementations, the cell culture vessel has a growth area of about 5 $cm^2$ to about 500 $cm^2$. In some implementations, the cell culture vessel has a growth area of about 5 $cm^2$ to about 10 $cm^2$, about 5 $cm^2$ to about 50 $cm^2$, about 5 $cm^2$ to about 100 $cm^2$, about 5 $cm^2$ to about 200 $cm^2$, about 5 $cm^2$ to about 300 $cm^2$, about 5 $cm^2$ to about 400 $cm^2$, about 5 $cm^2$ to about 500 $cm^2$, about 10 $cm^2$ to about 50 $cm^2$, about 10 $cm^2$ to about 100 $cm^2$, about 10 $cm^2$ to about 200 $cm^2$, about 10 $cm^2$ to about 300 $cm^2$, about 10 $cm^2$ to about 400 $cm^2$, about 10 $cm^2$ to about 500 $cm^2$, about 50 $cm^2$ to about 100 $cm^2$, about 50 $cm^2$ to about 200 $cm^2$, about 50 $cm^2$ to about 300 $cm^2$, about 50 $cm^2$ to about 400 $cm^2$, about 50 $cm^2$ to about 500 $cm^2$, about 100 $cm^2$ to about 200 $cm^2$, about 100 $cm^2$ to about 300 $cm^2$, about 100 $cm^2$ to about 400 $cm^2$, about 100 $cm^2$ to about 500 $cm^2$, about 200 $cm^2$ to about 300 $cm^2$, about 200 $cm^2$ to about 400 $cm^2$, about 200 $cm^2$ to about 500 $cm^2$, about 300 $cm^2$ to about 400 $cm^2$, about 300 $cm^2$ to about 500 $cm^2$, or about 400 $cm^2$ to about 500 $cm^2$, including increments therein. In some implementations, the cell culture vessel has a growth area of about 5 $cm^2$, about 10 $cm^2$, about 50 $cm^2$, about 100 $cm^2$, about 200 $cm^2$, about 300 $cm^2$, about 400 $cm^2$, or about 500 $cm^2$. In some implementations, the cell culture vessel has a growth area of at least about 5 $cm^2$, about 10 $cm^2$, about 50 $cm^2$, about 100 $cm^2$, about 200 $cm^2$, about 300 $cm^2$, or about 400 $cm^2$. In some implementations, the cell culture vessel has a growth area of at most about 10 $cm^2$, about 50 $cm^2$, about 100 $cm^2$, about 200 $cm^2$, about 300 $cm^2$, about 400 $cm^2$, or about 500 $cm^2$.

In some implementations, the cell culture vessel has a chamber height of about 12 mm to about 50 mm. In some implementations, the cell culture vessel has a chamber height of at least about 12 mm, about 13 mm, about 14 mm, about 15 mm, about 16 mm, about 17 mm, about 18 mm, about 19 mm, about 20 mm, about 30 mm, or about 40 mm. In some implementations, the cell culture vessel has a chamber height of at most about 13 mm, about 14 mm, about 15 mm, about 16 mm, about 17 mm, about 18 mm, about 19 mm, about 20 mm, about 30 mm, about 40 mm, or about 50 mm.

In some implementations, the cell culture vessel has a chamber height of about 0.05 mm to about 10 mm. In some implementations, the cell culture vessel has a chamber height of about 0.05 mm to about 0.1 mm, about 0.05 mm to about 0.5 mm, about 0.05 mm to about 1 mm, about 0.05 mm to about 2 mm, about 0.05 mm to about 3 mm, about 0.05 mm to about 4 mm, about 0.05 mm to about 5 mm, about 0.05 mm to about 6 mm, about 0.05 mm to about 8 mm, about 0.05 mm to about 10 mm, about 0.1 mm to about 0.5 mm, about 0.1 mm to about 1 mm, about 0.1 mm to about 2 mm, about 0.1 mm to about 3 mm, about 0.1 mm to about 4 mm, about 0.1 mm to about 5 mm, about 0.1 mm to about 6 mm, about 0.1 mm to about 8 mm, about 0.1 mm to about 10 mm, about 0.5 mm to about 1 mm, about 0.5 mm to about 2 mm, about 0.5 mm to about 3 mm, about 0.5 mm to about 4 mm, about 0.5 mm to about 5 mm, about 0.5 mm to about 6 mm, about 0.5 mm to about 8 mm, about 0.5 mm to about 10 mm, about 1 mm to about 2 mm, about 1 mm to about 3 mm, about 1 mm to about 4 mm, about 1 mm to about 5 mm, about 1 mm to about 6 mm, about 1 mm to about 8 mm, about 1 mm to about 10 mm, about 2 mm to about 3 mm, about 2 mm to about 4 mm, about 2 mm to about 5 mm, about 2 mm to about 6 mm, about 2 mm to about 8 mm, about 2 mm to about 10 mm, about 3 mm to about 4 mm, about 3 mm to about 5 mm, about 3 mm to about 6 mm, about 3 mm to about 8 mm, about 3 mm to about 10 mm, about 4 mm to about 5 mm, about 4 mm to about 6 mm, about 4 mm to about 8 mm, about 4 mm to about 10 mm, about 5 mm to about 6 mm, about 5 mm to about 8 mm, about 5 mm to about 10 mm, about 6 mm to about 8 mm, about 6 mm to about 10 mm, or about 8 mm to about 10 mm, including increments therein. In some implementations, the cell culture vessel has a chamber height of about 0.05 mm, about 0.1 mm, about 0.5 mm, about 1 mm, about 2 mm, about 3 mm, about 4 mm, about 5 mm, about 6 mm, about 8 mm, or about 10 mm. In some implementations, the cell culture vessel has a chamber height of at least about 0.05 mm, about 0.1 mm, about 0.5 mm, about 1 mm, about 2 mm, about 3 mm, about 4 mm, about 5 mm, about 6 mm, or about 8 mm. In some implementations, the cell culture vessel has a chamber height of at most about 0.1 mm, about 0.5 mm, about 1 mm, about 2 mm, about 3 mm, about 4 mm, about 5 mm, about 6 mm, about 8 mm, or about 10 mm.

In some implementations, the cell culture vessel has a scaled-down growth area and/or chamber height that is sufficient for the cell culture processes disclosed herein.

Figure 39:
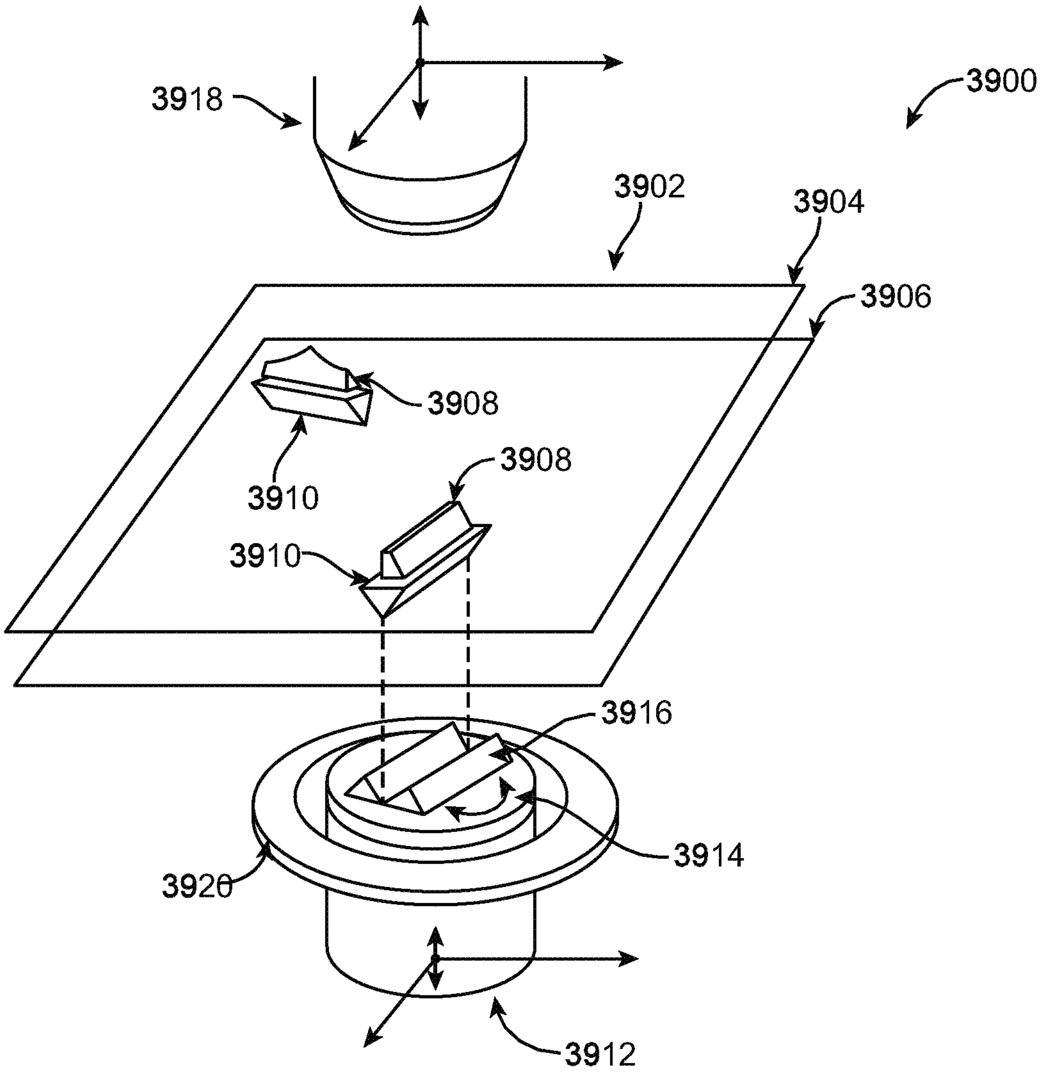
FIG. 39 is a three-dimensional view of a closed cell culture container with a magnetic tool in accordance with various implementations.

FIG. 39 is a three-dimensional view of a closed cell culture container 3900 with a magnetic tool in accordance with various implementations. The cell culture container 3900 may be similar to cell culture containers 106, 3800, 3800*b* in FIGS. 1, 38A, and 38B respectively. A liquid-filled cell culture chamber 3902 includes two surfaces, an upper surface 3904 and a lower surface 3906. Both surfaces 3904, 3906 may be transparent for imaging purposes. There is an internal magnetic tool 3908 inside the cell culture chamber 3902, held onto the lower surface 3906 by an external magnetic component 3910. In some implementations, the cell culture container 3900 may have more than one internal magnetic tool 3910 and corresponding external magnetic component 3912, as shown in FIG. 39. An actuator 3912 may move relative along the XY plane of the lower surface 3906, and may also move perpendicular to the XY plane (e.g., Z axis) in order to engage and disengage with external magnetic component(s) 3910. A rotation actuator 3914 may be used to rotate a capture mechanism 3916 to the correct angle to capture the external magnetic component 3910 when the actuator 3912 is raised. After capturing the external magnetic component 3910, the actuator 3912 may be moved around the XY plane to reposition the internal magnetic tool 3908. The rotation actuator 3914 may be used to rotate the internal magnetic tool 3908 via the external magnetic component 3910. Rotation and translation of the external magnetic component 3910, and by extension the internal magnetic tool 3908, may occur simultaneously.

An imaging objective 3918 may be positioned on the opposite side of the cell culture chamber 3902 as the actuator 3912 (e.g., above the upper surface 3904). The imaging objective 3918 may be part of an imaging subsystem (e.g., imaging subsystem 112) of a cell culture system. The imaging objective 3918 may also be translated relative to the XY plane of the cell culture chamber 3902. In some implementations, the imaging objective 3918 and the actuator 3912 are fixed relative to one another in the XY plane but may have independent Z translators. In other implementations, they may be completely independent in the X, Y, and Z planes. In yet other implementations, the imaging objective 3918 and the actuator 3912 may have one axis of common motion (e.g., the X axis), while they may move independently in the other two axes (e.g., the Y and Z axes).

The imaging objective 3918 may be configured to image the cell culture, for example a cell culture adherent to the inside of the upper surface 3904. The imaging objective 3918 may be further configured determine location and rotation information of the internal magnetic tool(s) 3910 within the cell culture chamber 3902. The location information may be used by a computing subsystem (e.g., computing subsystem 110 in FIG. 1) to control the actuator 3912 to capture and move the internal magnetic tool(s) 3910. The computing subsystem, along with an imaging subsystem that locates the contents (e.g., cells, debris) of the cell culture chamber 3902 (e.g., imaging subsystem 112 in FIG. 1), may further guide the actuator 3912 to perform tasks based on cell culture imaging or imaging of debris within the cell culture chamber 3902. In this implementation, an illuminating ring 3920 may be situated opposite the imaging objective 3918. The illuminating ring 3920 may provide fixed illumination for the imaging objective 3918, or may have multiple addressable elements (such as LEDs) to allow for selective lighting.

Examples of image-guided functions of the internal magnetic tool(s) 3910 include, but are not limited to: (a) imaging cells that have been placed into the cell culture chamber 3902 prior to adherence, and using the internal magnetic tool(s) 3910 to ensure uniformity of cell distribution prior to adhesion of the cells to the growth surface (e.g., the upper surface 3904); (b) imaging cells placed into the cell culture chamber 3902 and removing/pushing cells away from regions deemed not suitable for cell culture growth; (c) imaging the cell culture, identifying regions with attached debris or non-adherent cells that have some weak attachment, and using the internal magnetic tool(s) 3910 to wash/agitate them off the cell culture surface (e.g., the upper surface 3904); (d) imaging the surface opposite the cell culture (e.g., the lower surface 3906), identifying any areas where cells are growing, and clearing cells off the lower surface with the internal magnetic tool(s) 3910; (e) locating regions of the cell culture that have been damaged or destroyed by a cell editing mechanism (e.g., cell editing subsystem 114 in FIG. 1) and agitating the local medium to remove the cell debris from the cell culture surface (e.g., the upper surface 3904); (f) during cell harvest, locating regions that have not detached from the cell culture surface (by trypsinization or similar techniques) and agitating the local medium to hasten the detachment of cells from the cell culture surface (e.g., the upper surface 3904); (g) during cell culture, locating regions of higher or lower cell density, or specific phenotypic or other characteristics, and guiding local media mixing in order to enhance nutrient, waste product, or cell-generated factor distribution accordingly (for example, ensuring adequate supply of nutrients and/or dissolved gases to dense cell colonies within a generally sparse cell culture); (h) imaging cell debris that has fallen to the surface opposite the cell culture surface (e.g., the lower surface 3906), and guiding the internal magnetic tool(s) 3910 to remove this debris from the cell culture chamber 3902; and (i) imaging may be used to dynamically orient the internal magnetic tool(s) 3910 as they are translated along features within the cell culture chamber 3902 (e.g., boundaries, entry/exit channels, or support posts/fluidic features) in order to ensure full coverage of the chamber by the tools.

Figure 40A:
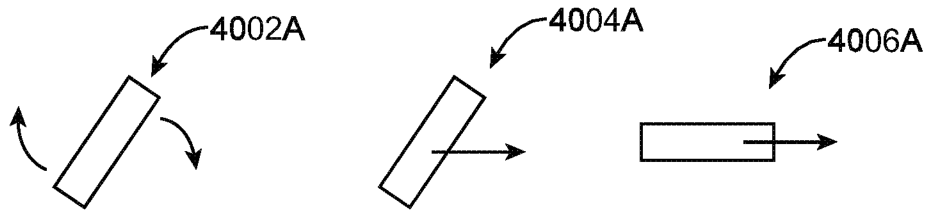
FIG. 40A is a block diagram of various modes of use for a magnetic tool in a closed cell culture container in accordance with various implementations.

FIG. 40A is a block diagram of various modes of use for an internal magnetic tool in a closed cell culture container in accordance with various implementations. In rotation mode 4002A, rotation of the magnetic tool is used to agitate local media and/or apply forces on local cells or debris. In translation mode 4004A, the magnetic tool may be translated over the surface at an angle relative to the direction of motion in order to push cells or debris. Rotation and translation modes 4002A, 4004A may be combined in multiple ways, including dynamically orienting the magnetic tool to follow chamber features or outlines. In movement mode 4006A, the magnetic tool may also be translated in an orientation that causes the least disruption to the local fluidic environment, for example if the magnetic tool should be moved to another location without disturbing the inside of the cell culture chamber. The speed of the magnetic tool may be varied depending on the function. For example, during rotation mode 4002A, the magnetic tool may be spun at a high speed to generate the necessary force to act on cells or debris. During movement mode 4006A, the magnetic tool may travel at a slow speed to avoid disturbing the fluid medium and the cells.

Figure 40B:
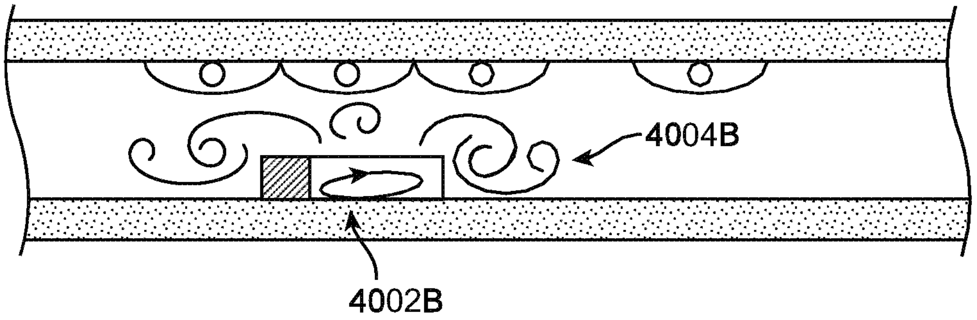
FIG. 40B illustrates rotation of an internal magnetic tool in a closed cell culture chamber in accordance with various implementations.

FIG. 40B illustrates rotation of an internal magnetic tool 4002B in a closed cell culture chamber in accordance with various implementations. As the internal magnetic tool 4002B is rotated in a cell culture chamber, it creates turbulent flows 4004B. The turbulent flows 4004B may be used for a variety of functions, such as mixing the fluid media in the cell culture chamber and other functions disclosed herein. Rotation may also be combined with translation of the internal magnetic tool to enable coverage over different regions of the cell culture container.

Figure 41A:
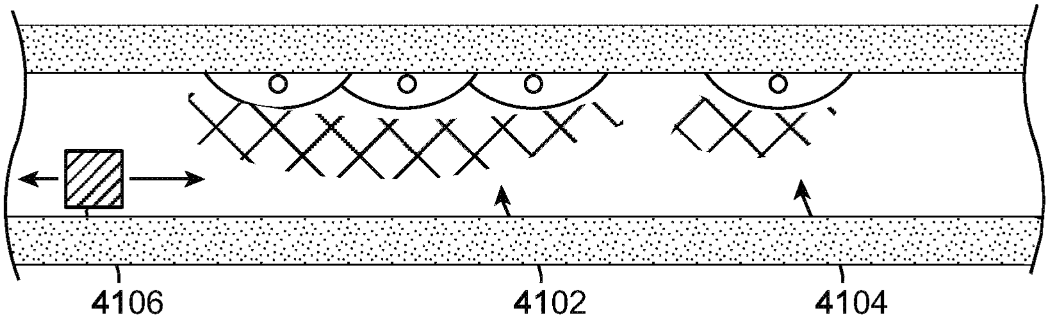
FIGS. 41A-41B illustrate use of an internal magnetic tool in a cell culture chamber for mixing media in accordance with various implementations.
Figure 41B:
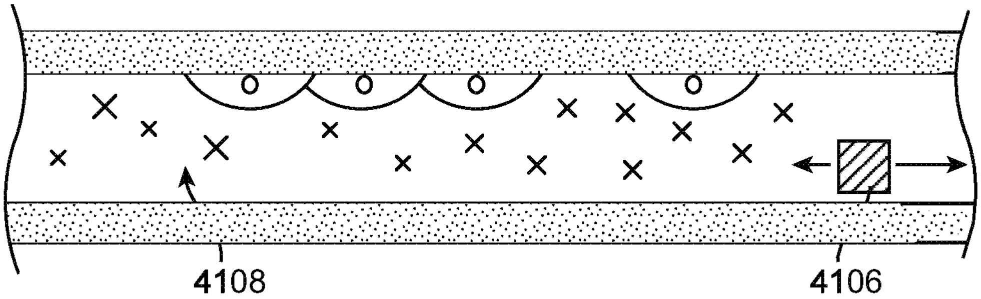

FIGS. 41A-B illustrate use of an internal magnetic tool in a cell culture chamber for mixing media in accordance with various implementations. In 2D cell cultures, a common issue is that static media causes local depletion of nutrients or oxygen where cells are dense and/or active. Likewise, waste products may build up in these regions. The typical solution is to circulate media through the chamber and mix it in the process. However, the constant, directional shear stress imparted by this media circulation may disrupt cell culture behavior. For example, such motion may trigger differentiation of stem cells into epithelial cells. Moreover, continuous media circulation has other overhead in terms of equipment, environmental handling, etc. Therefore, the ability to mix media locally within the cell culture chamber while keeping the cell culture steady is highly desirable. This would enable the desirable aspects of stirred bioreactors while keeping cells in a fully observable (by imaging) and editable (by lasers or other suitable approaches) format.

In FIG. 41A, media near high-density cell culture regions 4102 has been depleted of nutrients and is high in waste products as well as cell-derived factors that are valuable for cell-to-cell signaling. In less dense cell culture regions 4104, the media still contains a high concentration of nutrients. An internal magnetic tool 4106 is translated through the cell culture chamber, and either the translation alone, or translation and rotation, may be used to mix the liquid contents of the chamber. The translational and rotational speed of the internal magnetic tool 4106 may be regulated to allow for fluid mixing without detaching adherent cells from the cell bearing surface.

FIG. 41B shows the cell culture chamber after processing by the internal magnetic tool 4106. The internal magnetic tool 4106 has distributed the contents of the liquid media 4108 in the chamber, resulting in a more uniform distribution of the media. This mixing process may be guided by imaging from an imaging subsystem and computing of cell density and colony locations by a computing subsystem, potentially with the aid of a media and or fluidic model, to optimize the mixing function for a particular cell culture configuration and state.

Figure 42A:
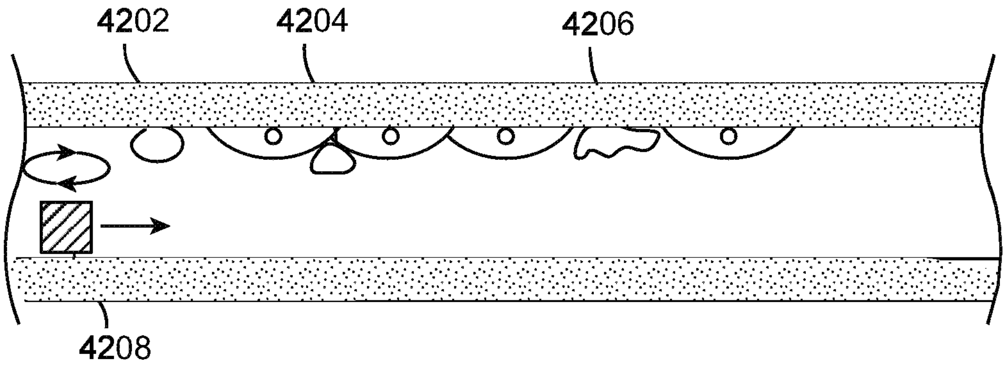
FIGS. 42A-42C illustrate use of an internal magnetic tool in a cell culture chamber for removing debris in accordance with various implementations.
Figure 42B:
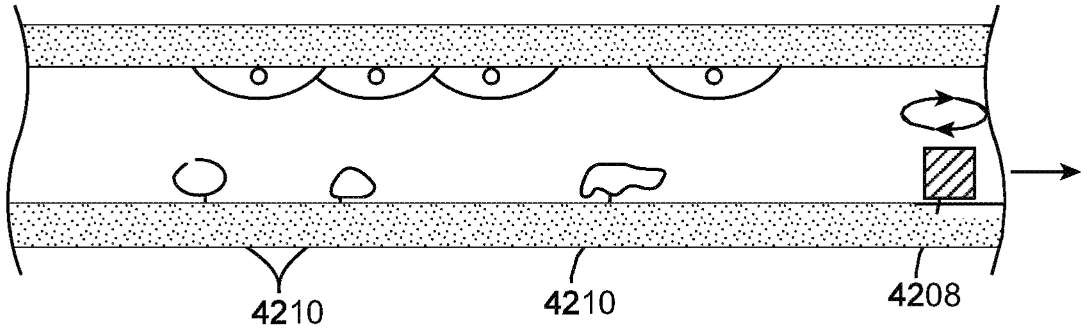
Figure 42C:
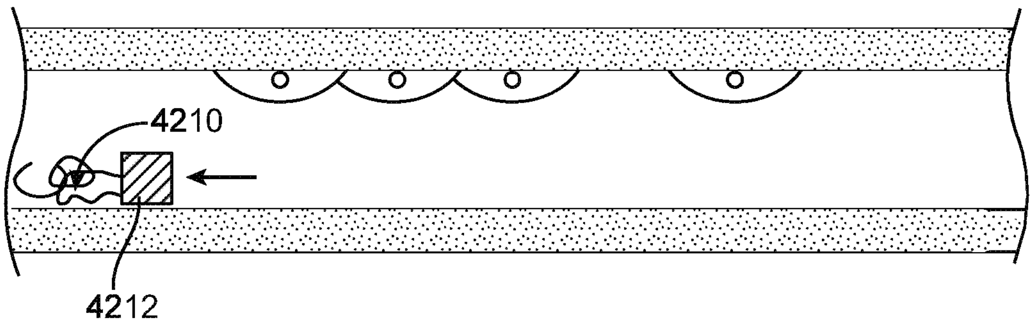

FIGS. 42A-42C illustrate use of an internal magnetic tool in a cell culture chamber for removing debris in accordance with various implementations. The removal of debris may include "washing" of non-adherent or weakly adherent cells, cell remains, and various debris (which may include but are not limited to cell debris, dead cells, matrix, biochemical agglomerates, particulates, etc.).

FIG. 42A shows an example of a cell culture in a cell culture chamber, the cell culture including weakly adherent cells 4202, particulates attached to the cell layer 4204, and dead cells 4206 on the cell culture-bearing surface of the cell culture chamber. An internal magnetic tool 4208 traverses the cell culture. Specifically, the internal magnetic tool 4208 may traverse areas with cells growing, particularly areas with dead cells/debris/weakly adherent cells as identified by an imaging subsystem. The internal magnetic tool 4208 may additionally rotate to cause local turbulence and transient shear stresses on the cell layer. This will preferentially detach weakly adherent cells 4202 from the remainder of the cell culture. FIG. 42B shows the same cell culture after the internal magnetic tool 4208 has traversed. Detached debris 4210, which may include one or more of the weakly adherent cells 4202, particulates 4204, and dead cells 4206, have settled on the opposite surface of the cell culture chamber. The detached debris 4210 may sink to the bottom surface (assuming the direction of gravity is pointing downwards in FIG. 42B) because their density is higher than the cell medium. FIG. 42C shows another function of a magnetic tool 4212, which may be the same tool as internal magnetic tool 4208 in FIG. 42A-B, or another specialized tool. The magnetic tool 4212 may be configured to push away the detached debris 4210 to an exit port in the cell culture chamber.

In some implementations, the same process as shown in FIGS. 42A-42C may be performed on the cell product itself, during the cell harvesting phase. For example, Trypsin or another disassociation agent may be added to the cell culture chamber for a period of time in order to loosen cell-cell and cell-surface bonds. The magnetic tool(s) 4208, 4212 may be used to ensure complete intrusion of the agent into the cell layers and gaps between cells. The magnetic tool(s) 4208, 4212 may then be used to provide shear forces to hasten and/or improve the loosening of the cells from each another and from the surface. Finally, after the cells fall to the opposite surface due to their higher density, the magnetic tool(s) 4208, 4212 may be used to harvest of the now detached cells from the cell culture chamber.

FIGS. 43A-43D illustrate another implementation of using an internal magnetic tool in a cell culture chamber for removing debris in accordance with various implementations. FIG. 43A-43D illustrate a top-down perspective of a cell culture chamber having sidewall sections 4302. The sidewalls 4302 may be tapered in order to create a funnel 4304 at one end of the cell culture chamber. The funnel 4304 may lead toward an outflow channel or tube. An internal magnetic tool 4306 may be located on a first surface of the cell culture chamber. The first surface may also include debris 4308 that has settled from the upper cell-bearing surface (not shown in FIGS. 43A-43D).

Figure 43A:
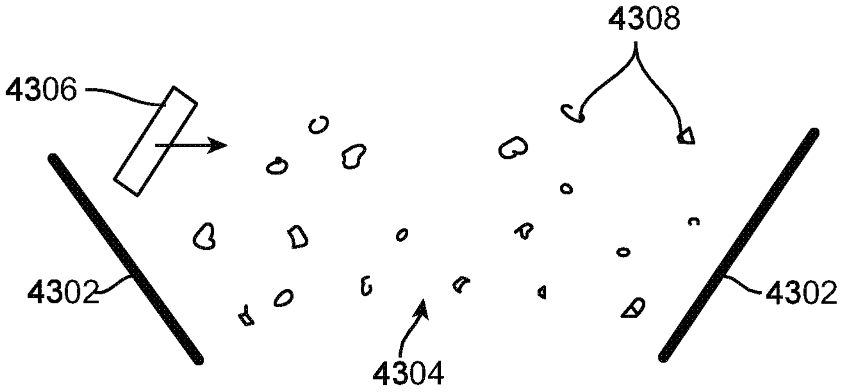
FIGS. 43A-43D also illustrates use of an internal magnetic tool in a cell culture chamber for removing debris in accordance with various implementations.
Figure 43B:
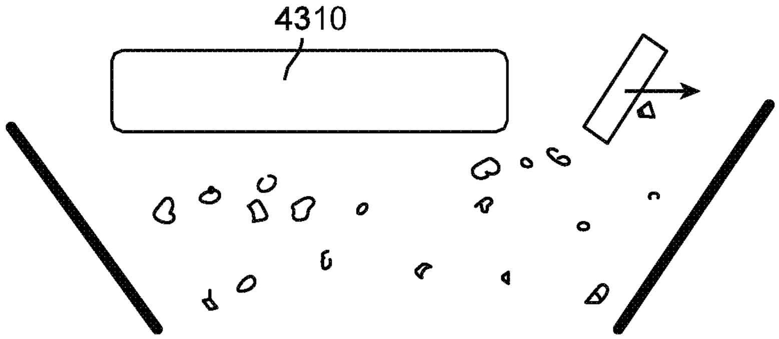
Figure 43C:
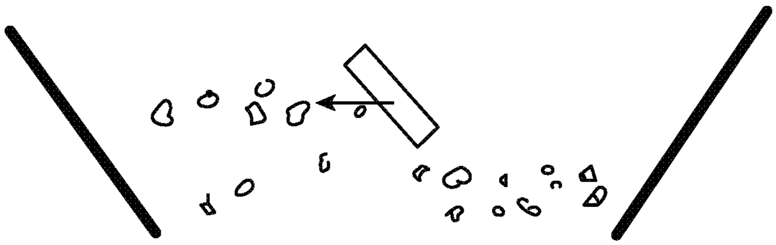

FIG. 43A illustrates the internal magnetic tool 4306 angled and ready to be translated across the cell culture chamber to provide a "plowing" function, in which debris in the path of the internal magnetic tool 4306 are pushed towards the outflow channel at the funnel 4304 as it traverses parallel to the funnel opening. FIG. 43B shows the result of the plowing motion after one traversal of the cell culture chamber. Debris 4308 that was in the path of the internal magnetic tool 4306 are pushed along with the tool, creating a cleared space 4310. The debris 4308 is pushed downwards, in the direction of the funnel 4304 that leads to an outflow channel. FIG. 43C shows the results of further passes of the internal magnetic tool 4306 across the cell culture chamber. As can be seen, all the debris 4308 in the cell culture chamber is pushed closer to the funnel 4304 as the internal magnetic tool repeatedly sweeps the surface of the cell culture chamber.

Figure 43D:
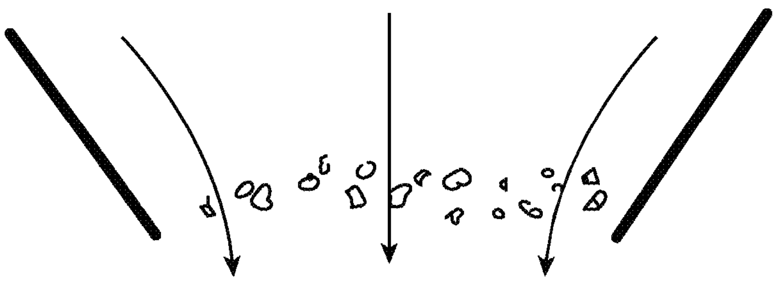

FIG. 43D shows an example of a flushing process to remove the debris 4308 from the cell culture chamber. Bulk media flow may be used to push the debris 4308 from the cell culture chamber into the outflow channel. The flow may be continuous during the process described with respect to FIGS. 43A-43D to create an overall fluid flow in the direction of the funnel 4304. Additionally, the cell culture chamber may be tilted in the vertical direction such that the funnel 4304 and the outflow channel are vertically lower than the opposite side of the cell culture chamber. This tilt further encourages the debris 4308 to move towards the funnel 4304 via gravity during the removal process.

Cell Editing Using Remote Actuator Systems

In the implementations described with respect to FIGS. 38A-43D, the internal magnetic tool in the cell culture chamber was located on the opposite surface as the cell culture. However, in other implementations, the internal magnetic tool may also be located on the same surface as the cell culture. In these implementations, the configuration and operation of the internal magnetic tool may be different to implement a variety of functions, such as cell removal or harvesting.

Figure 44:
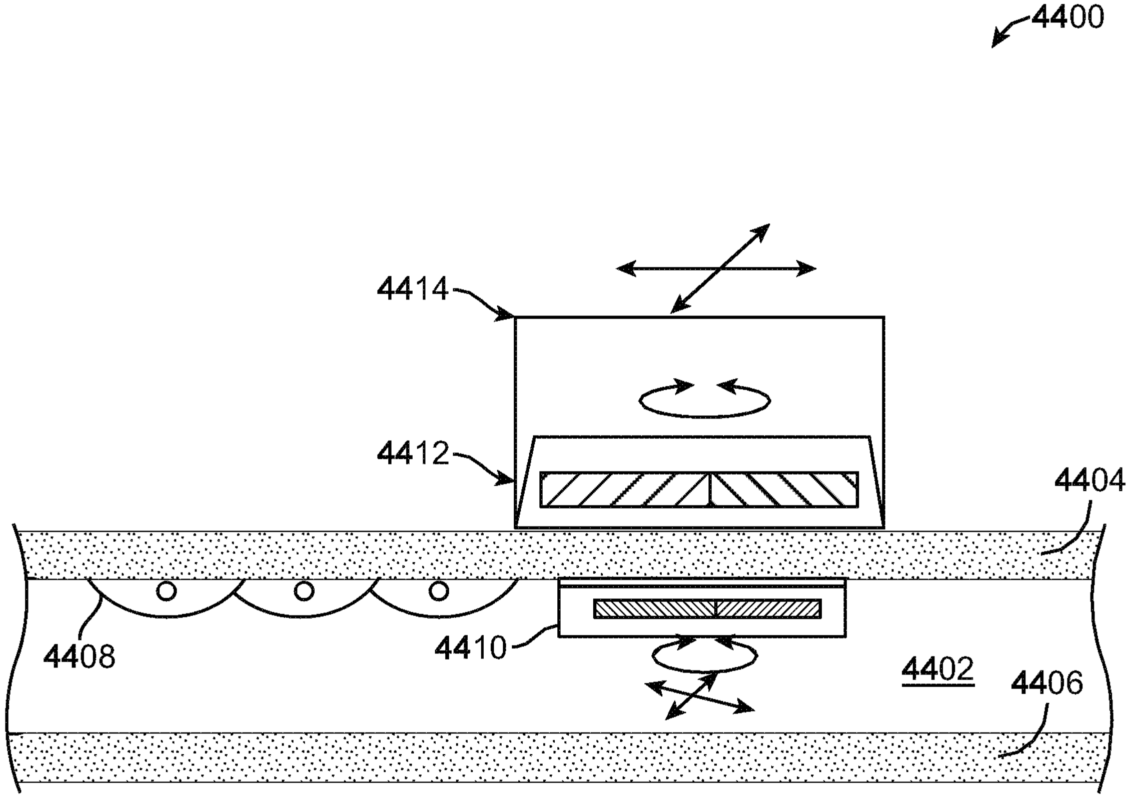
FIG. 44 is a block diagram of a closed cell culture container with a magnetic tool in accordance with various implementations.

FIG. 44 is a block diagram of a closed cell culture container 4400 with a magnetic tool in accordance with various implementations. The cell culture container 4400 may be similar to cell culture container 106 in FIG. 1, and may be part of a cell culture system. A liquid-filled cell culture chamber 4402 is enclosed by a cell-bearing surface 4404 and an opposite surface 4406. These surfaces are typically glass or polymer sheets. In many cases both are transparent to facilitate imaging of the cell culture 4408 on the cell-bearing surface 4404. In this example, an inverted cell culture is shown, where after inoculation of the cell culture chamber 4402, the vertical orientation of the chamber is opposite of what is shown in FIG. 44, causing cells to settle and then adhere to the cell-bearing surface 4404 due to the forces of gravity. After the cells adhere, the cell culture chamber 4402 is inverted or turned around, and the majority of the cell culture process is performed in an inverted orientation such that debris or non-adherent cells settle on the opposite surface 4406.

An internal magnetic tool 4410 resides inside of the closed cell culture chamber 4402, opposite of an external magnetic component 4412. The internal magnetic tool 4410 may be pushed against the inside of the cell-bearing surface 4404 because of magnetic attraction to the external magnetic component 4412. The internal magnetic tool 4410 may include one or more magnets that are coated appropriately for a biological environment. For example, a rectangular Neodymium rare Earth magnet may be coated with a polymer or fluoropolymer to make it inert, biocompatible, non-stick, and non-scratching as it translates or rotates on the inner surface of the cell culture chamber 4402. The external magnetic component 4412 may also be coated to prevent scratching of the outer surface of the cell culture chamber 4402.

The external magnetic component 4412 may be removably coupled to an actuator 4414 that may be configured to rotate the external magnetic component 4412, and by extension the internal magnetic tool 4410, around a rotation axis. The actuator 4414 may in turn be translated around the same plane as the cell-bearing surface 4404 to allow the internal magnetic tool 4410 to traverse the entire surface of the cell culture chamber 4402. This, along with the rotation action of the actuator 4414, gives the internal magnetic tool 4410 three degrees of freedom (i.e., motion in the XY plane of the cell-bearing surface 4404, and motion around the rotation axis). The translation mechanism for the actuator 4414 is not shown in FIG. 44. In one example, the actuator 4414 may be connected to one or more arms that move the actuator 4414 around the XY plane and may move the actuator 4414 towards or away from the cell-bearing surface 4404. The one or more arms may be controlled by a computing subsystem in a cell culture system (e.g., system 110 in FIG. 1). In general, the actuator 4414 may be translated relative to a stationary cell culture chamber 4402, or vice versa.

Figure 45A:
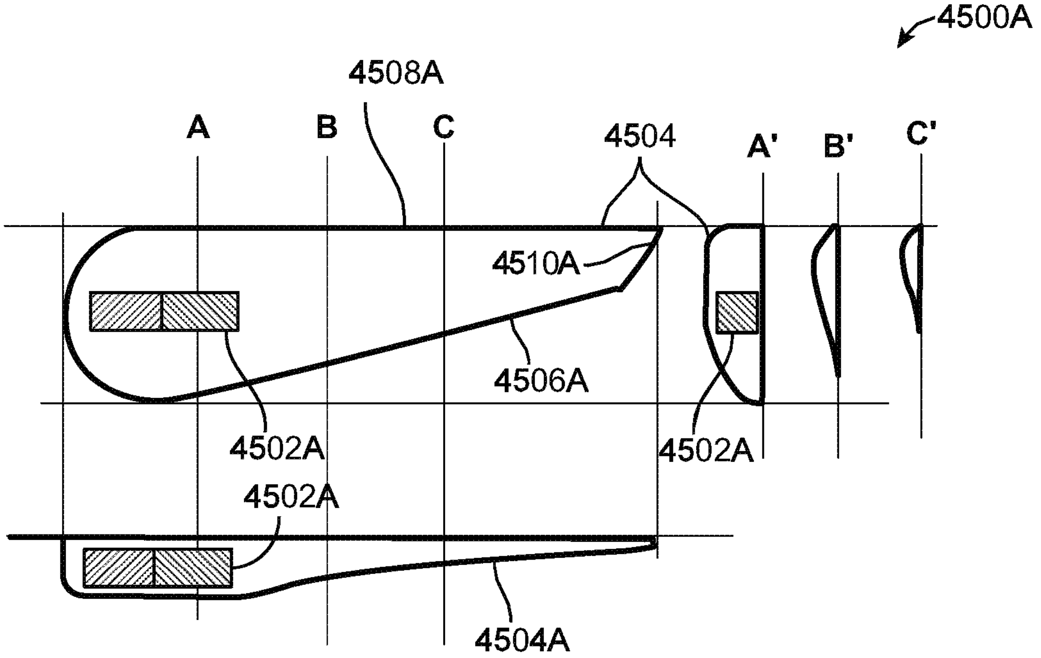
FIG. 45A illustrates various views of an internal magnetic tool for use on a cell-bearing surface in accordance with various implementations.

FIG. 45A shows various views of an internal magnetic tool 4500A for use on a cell-bearing surface in accordance with various implementations. FIG. 45A shows a top view (top left), a side view (bottom), and three cross-sectional views (top right) for the internal magnetic tool 4500A. Each cross-sectional view A', B', and C' correspond to the marked A, B, C points of the top view. The internal magnetic tool 4500A may have an asymmetric shape. The internal magnetic tool 4500A includes a permanent magnet 4502A embedded in the internal magnetic tool 4500A, which is used to control the motion of the internal magnetic tool 4500A. The permanent magnet 4502A may be made from a rare Earth material. The internal magnetic tool 4500A may also include a blade 4504A that is shaped to perform a variety of cell manipulation functions. For example, the blade 4504A may have a low-angle edge 4506A that is used to lift cells or cell sheets from the cell-bearing surface of the cell culture container without damaging the cells. The blade 4504A may also have a high-angle edge 4508A that is used to lyse or detach cells. The blade 4504A may also have a tip 4510A that is used for precision lysing, detaching, or lifting of cells. In illustrative but non-limiting examples, a low-angle blade may form an angle at its cutting edge (i.e., the intersection of the two planar surfaces of the blade) that is no more than 1 degree, 2 degrees, 3 degrees, 4 degrees, 5 degrees, 6 degrees, 7 degrees, 8 degrees, 9 degrees, 10 degrees, 11 degrees, 12 degrees, 13 degrees, 14 degrees, 15 degrees, 20 degrees, or 25 degrees. In illustrative but non-limiting examples, a high-angle blade may form an angle at its cutting edge that is at least 25 degrees, 30 degrees, 35 degrees, 40 degrees, 45 degrees, 50 degrees, 60 degrees, 70 degrees, 80 degrees, or 90 degrees or more.

Figure 45B:
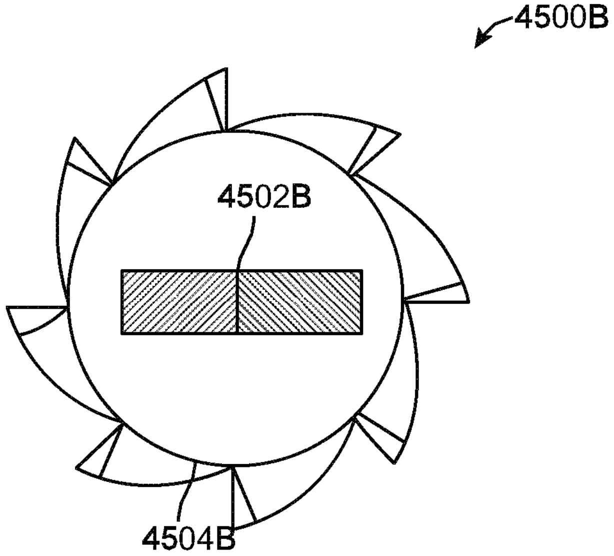
FIG. 45B illustrates another internal magnetic tool for use on a cell-bearing surface in accordance with various implementations.

FIG. 45B illustrates another internal magnetic tool 4500B for use on a cell-bearing surface in accordance with various implementations. The internal magnetic tool 4500B may be used for destructive removal of cells in a cell culture and may have a compact footprint. The internal magnetic tool 4500B may include a permanent magnet 4502B, embedded in the internal magnetic tool 4500B, which is used to control the motion of the internal magnetic tool 4500B. The permanent magnet 4502B may be made from a rare Earth material. The internal magnetic tool 4500B may also include a circular blade 4504B. The internal magnetic tool 4500B may rotate and translate along the plane of the cell-bearing surface to cut through portions of a cell culture.

The dimensions of the internal magnetic tools 4500A, 4500B may vary depending on the application. For example, in a liquid cell culture chamber there may be a relatively thin layer of liquid to achieve high cell media efficiency. The internal height of the chamber 4402 may be, for example, less than 2 mm, or less than 1 mm. In such a liquid chamber, the vertical height of the internal magnetic tools 4500A, 4500A may be less than 1 mm, or less than 0.5 mm, or even less than 0.25 mm. Similarly, the maximum horizontal dimensions may vary, but will often be less than 2 mm, or even less than 1 mm, in order to allow editing on cell cultures where desirable cell features (such as colonies) are spaced a few mm apart or less. Internal magnetic tools contemplated in this disclosure are not limited to those shown in FIGS. 45A-45B, but may encompass any variation of shapes that achieve similar functionality.

Figure 46A:
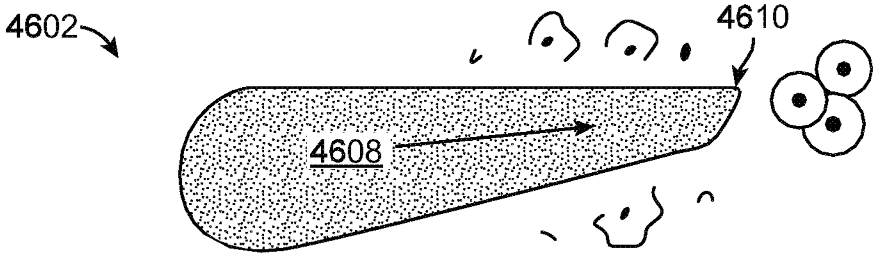
FIGS. 46A-C illustrate examples of cell editing functions provided by an internal magnetic tool in accordance with various implementations.
Figure 46B:
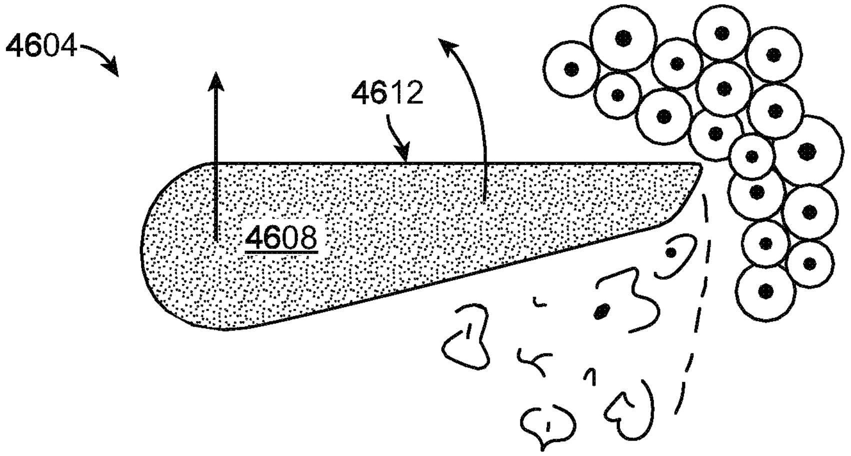
Figure 46C:
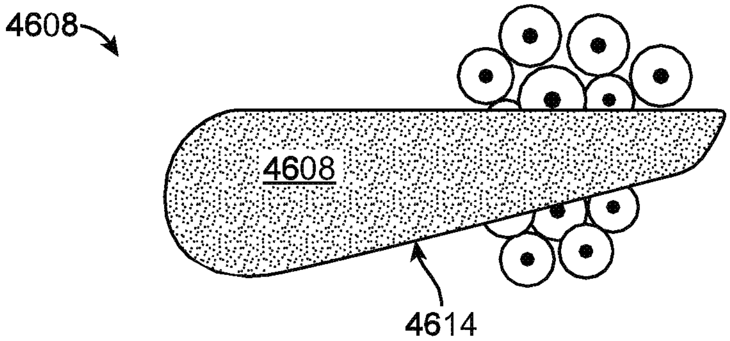

FIG. 46A-C illustrate examples of cell editing functions provided by an internal magnetic tool 4608 in accordance with various implementations. The internal magnetic tool 4608 may be similar to the internal magnetic tool 4500A described with respect to FIG. 45A. The internal magnetic tool 4608 may include a sharp tip 4610, a high-angle edge 4612, and a low-angle edge 4614.

In operation 4602, the internal magnetic tool 4608 may be translated along the plane of the cell-bearing surface with its sharp tip 4610 forward to destroy or dislodge individual cells or small groups of cells. The internal magnetic tool 4608 may also be rotated as it is translated when destroying or dislodging cells.

In operation 4604, the internal magnetic tool 4608 may be rotated and/or translated along the plane of the cell-bearing surface such that its high-angle or blunt edge 4612 disrupts cells by detaching them from the cell-bearing surface and possibly rupturing their membranes. Generally, translating the high-angle edge 4612 of the tool into cells will have the effect of destructively removing them from the cell-bearing surface. The detached cells may subsequently be removed from the chamber as debris. This action may often be performed at higher velocities to maximize the lysing effect and minimize editing time. The velocity of movement of the associated internal magnetic tool 4608 may be varied by varying the magnetic force applied to it by the external magnetic component. If variable magnetic force is used in the system, the level of force the internal magnetic tool 4608 applies towards the cell-bearing surface may be reduced in order to (i) reduce dynamic friction force and allow faster tool motion; (ii) allow a slight gap between the internal magnetic tool 4608 and the cell-bearing surface which may trap a portion of the cell and further ensure complete membrane destruction; and (iii) allow cells to be destroyed and removed without damaging the underlying cell growth matrix (such as Laminin or Matrigel), such that desirable cells may re-grow into the area.

In operation 4606, the internal magnetic tool 4608 may be translated and/or rotated along the plane of the cell-bearing surface with the low-angle or sharp edge 4614 leading to lift cells, groups of cells, colonies, or cell sheets intact from the cell-bearing surface. This may be done at low velocity to minimize stress on cells. This operation may also be done with the highest magnetic down-force applied to the internal magnetic tool 4608 by the external magnetic component in order to have the closest contact between the internal magnetic tool 4608 and the cell-bearing surface under the cells at the separation point. In some implementations, the operation 4606 may be applied iteratively, in which a small section of the cells is lifted with each pass of the low-angle edge 4614.

Figure 47A:
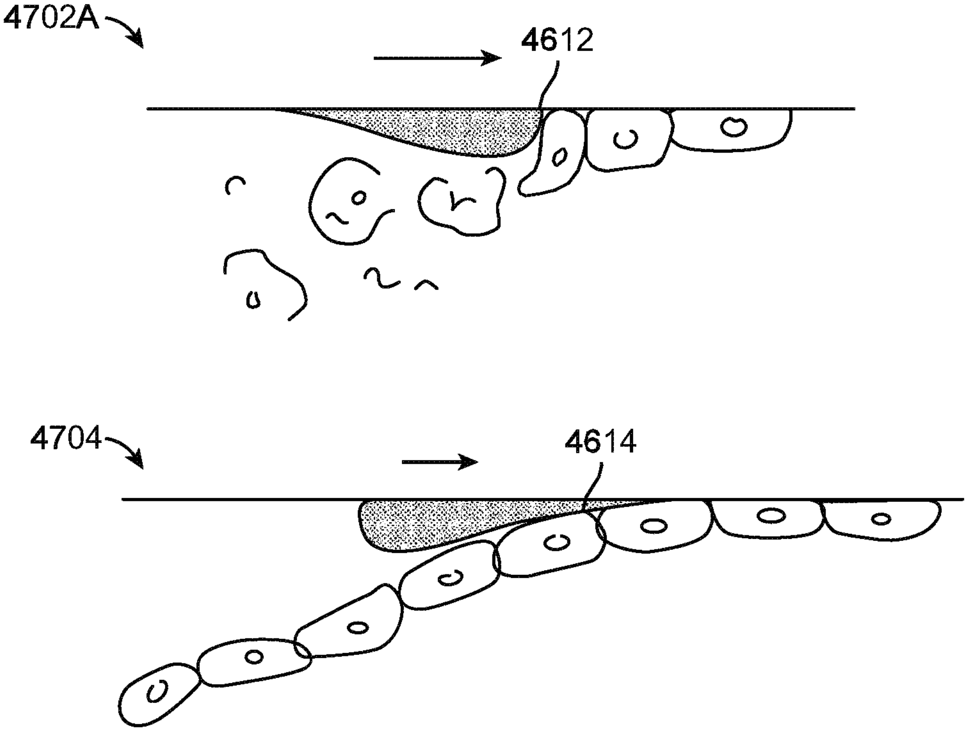
FIG. 47A illustrates cross-sectional views of examples of cell editing functions provided by an internal magnetic tool in accordance with various implementations.

FIG. 47A illustrates cross-sectional views of examples of cell editing functions provided by an internal magnetic tool in accordance with various implementations. The cross-sectional views correspond to some of the cell editing functions illustrated in FIG. 46. Specifically, cross-sectional view 4702A corresponds to operation 4604 and illustrates the use of the high-angle edge 4612 of the internal magnetic tool 4608 to remove cells from a cell-bearing surface. The internal magnetic tool 4608 may be moved with relatively high velocity to destructively remove cells. Cross-sectional view 4704 corresponds to operation 4606 and illustrates the use of the low-angle edge 4614 of the internal magnetic tool 4608 to non-destructively remove cells from a cell-bearing surface. The internal magnetic tool 4608 may be moved with relatively low velocity to remove cells without destroying them.

Figure 47B:
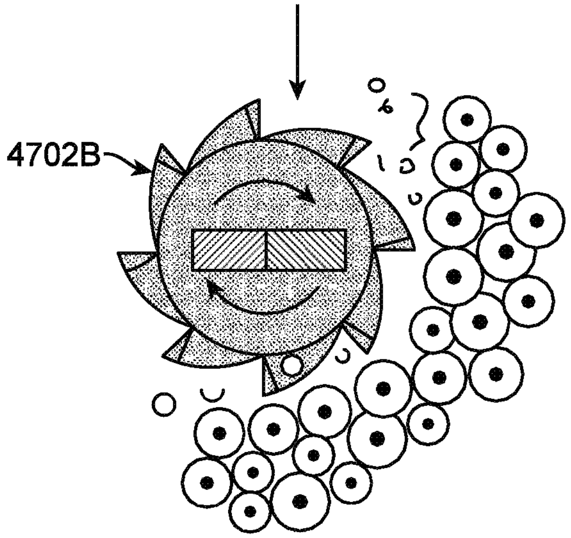
FIG. 47B illustrates an example of cell editing functions provided by an alternate internal magnetic tool in accordance with various implementations.

FIG. 47B illustrates an example of cell editing functions provided by an alternate internal magnetic tool 4702B in accordance with various implementations. The internal magnetic tool 4702B may be similar to the internal magnetic tool 4500B illustrated in FIG. 45B. The internal magnetic tool 4702 may be simultaneously translated and rotated along the cell-bearing surface to remove cells. For example, the internal magnetic tool 4702B may include a number of blades that lyse and/or lift cells from the cell-bearing surface as the internal magnetic tool 4702B is translated and rotated.

FIG. 48A-K illustrates cell editing operations conducted by an internal magnetic tool 4802 during culturing of cell colony 4804 in accordance with various implementations. The cell culturing process may be conducted by a cell culture system (e.g., system 110 in FIG. 1). The internal magnetic tool 4802 illustrated in FIG. 48 may be similar to the internal magnetic tool 4500A in FIG. 45A. The cell colony 4804 may be growing on a cell-bearing surface of a cell culture chamber and may have been selected for retrieval from the cell culture but may have some undesirable cells along its periphery. This may occur, for example, in an iPSC culturing process, in which cells along the edge of an iPSC colony may begin to differentiate. It is important to remove these cells before harvesting or transferring the cell colony.

Figure 48A:
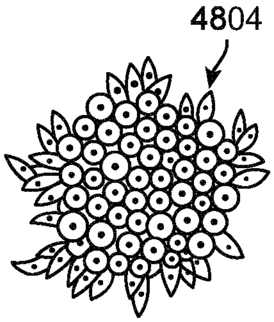
FIGS. 48A-K illustrate cell editing operations conducted by an internal magnetic tool during cell culturing in accordance with various implementations.
Figure 48B:
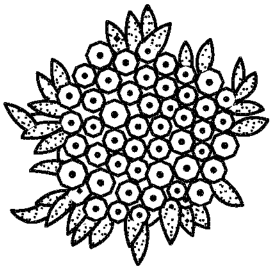

In step (a) illustrated in FIG. 48A, the cell colony 4804 may be imaged by an imaging subsystem of the cell culture system (e.g., cell imaging subsystem 112 in FIG. 1). In step (b) illustrated in FIG. 48B, a computing subsystem of the cell culture system (e.g., computing subsystem 110) may identify one or more undesirable cells in the cell colony 4804, which are shown in gray. For example, the undesirable cells may be iPSC cells that have begun to differentiate in an iPSC cell colony. A computing subsystem (e.g., computing subsystem 110) may use various machine learning and image analysis techniques on the image of the cell colony 4804 to identify the undesirable cells.

Figure 48C:
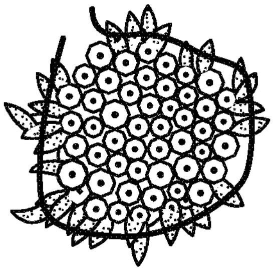

In step (c) illustrated in FIG. 48C, the computing subsystem may determine a path for the internal magnetic tool 4802 to follow to prune the undesirable cells, the path shown by the solid line. The computing subsystem may also determine various parameters for operating the internal magnetic tool 4802, such as tool orientation, direction, and velocity.

Figure 48D:
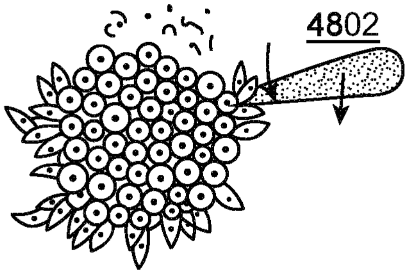

In step (d) illustrated in FIG. 48D, the computing subsystem may activate and control the internal magnetic tool 4802 to follow the path according to the determined parameters to cut out and destroy the undesirable cells. For example, the computing subsystem may control an actuator connected to an external magnetic component that is magnetically coupled to the internal magnetic tool 4802, and thus control the path and parameters of the internal magnetic tool 4802. The internal magnetic tool 4802 may have a blade with a high-angle edge that is used for lysing or destroying cells. The computing subsystem may also image the internal magnetic tool 4802 and the cell colony 4804 in real time and make dynamic changes to the path and parameters of the internal magnetic tool 4802. For example, adjustments may need to be done to remove cells that weren't removed in a first pass, or to compensate for changes or offsets to positioning.

Figure 48E:
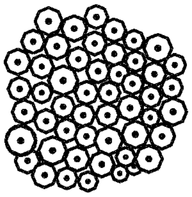
Figure 48F:
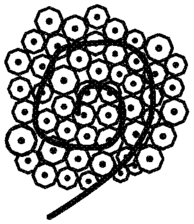

Step (e) illustrated in FIG. 48E shows the cell colony 4804 after pruning and ready for harvest. There may be several rounds of pruning (e.g., repeats of steps (a)-(d)) before the cell colony 4804 is ready for harvest. In step (f) illustrated in FIG. 48F the computing subsystem may determine a path for the internal magnetic tool 4802 to follow to harvest the cell colony 4804, the path shown by the solid line. The computing subsystem may also determine various parameters for operating the internal magnetic tool 4802, such as tool orientation, direction, and velocity.

Figure 48G:
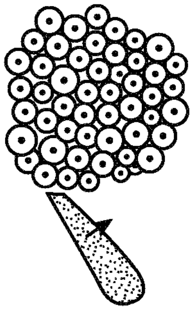

In step (g) illustrated in FIG. 48G, the computing subsystem may activate and control the internal magnetic tool 4802 to follow the path according to the determined parameters to harvest the cell colony 4804. For example, the internal magnetic tool 4802 may have a blade with a low-angle edge that is used for incremental lifting, and that edge approaches the cell colony 4804 to slowly dig under the cell colony 4804 and lift the cells off the cell-bearing surface. The internal magnetic tool 4802 may be moved at a low velocity with maximum magnetic downforce so as to not damage the cells during the lifting process. The computing subsystem may also image the internal magnetic tool 4802 and the cell colony 4804 in real time and make dynamic changes to the path and parameters of the internal magnetic tool 4802. For example, adjustments may need to be done to lift cells that weren't lifted in a first pass, or to compensate for changes or offsets to positioning, or if internal magnetic tool 4802 is accidentally destroying cells.

Figure 48H:
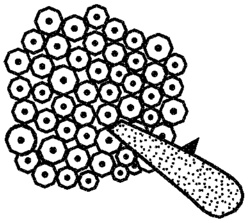
Figure 48I:
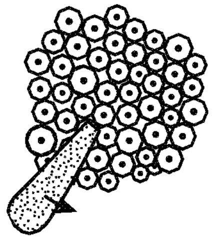
Figure 48J:
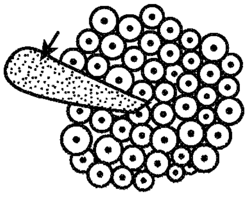
Figure 48K:
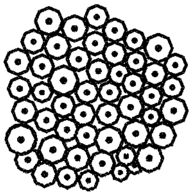

Steps (h)-(j) illustrated in FIGS. 48H-48J, respectively, show the continuation of the lifting process. For example, the internal magnetic tool 4802 may move in a spiral motion around the cell colony 4804, moving closer to the center with each pass. In step (k) illustrated in FIG. 48K, the lift-off process is complete and the fully-detached cell colony 4804 is ready for harvest. The computing subsystem may, for example, flush the cell colony 4804 out of the cell culture chamber into another receptacle. In other implementations, a mechanical tool may be used to push the cell colony 4804 out of the chamber, or gravity may be used as well.

FIG. 49A-I illustrates cross-sectional views of cell editing operations conducted by an internal magnetic tool 4902 during culturing of cell colony 4904 in accordance with various implementations. The cell editing operations shown in FIG. 49 may be similar to the operations shown in FIG. 48, namely removal of undesirable cells from the cell colony 4904 and harvesting of the cell colony 4904. The cell culturing process may be conducted by a cell culture system (e.g., system 110 in FIG. 1). The internal magnetic tool 4902 illustrated in FIG. 49 may be similar to the internal magnetic tool 4A00A in FIG. 45A. The cell colony 4904 may be growing on a cell-bearing surface of a cell culture chamber and may have been selected for retrieval from the cell culture but may have some undesirable cells along its periphery. The cell culture chamber may be liquid-filled, with an adherent cell culture on the upper inside surface (the cell-bearing surface) so that the force of gravity acts downward in FIG. 49.

Figure 49A:
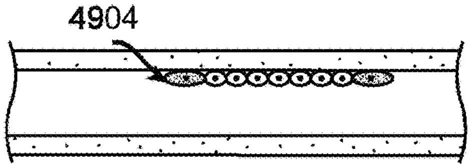
FIGS. 49A-I illustrate cross-sectional views of cell editing operations conducted by an internal magnetic tool during cell culturing in accordance with various implementations.

Step (a) illustrated in FIG. 49A shows the cell colony 4904 in cross-section, with undesirable cells on the periphery marked in gray. An imaging subsystem (e.g., cell imaging subsystem 112) may have imaged the cell colony 4904 and a computing subsystem (e.g., computing subsystem 110) may use various machine learning and image analysis techniques to identify the undesirable cells.

Figure 49B:
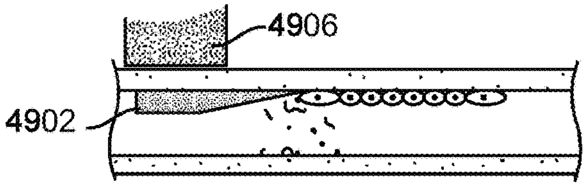

In step (b) illustrated in FIG. 49B, the computing subsystem may control the internal magnetic tool 4902 via the external magnetic component 4906 to remove the undesirable cells. For example, the computing subsystem may determine a path for the internal magnetic tool 4902 to follow to prune the undesirable cells and also determine various parameters for operating the internal magnetic tool 4902, such as tool orientation, direction, and velocity. Then the computing subsystem may activate and control the internal magnetic tool 4902 to follow the path according to the determined parameters to cut out and destroy the undesirable cells. The internal magnetic tool 4902 may have a blade with a high-angle edge that is used for lysing or destroying cells. The computing subsystem may also image the internal magnetic tool 4902 and the cell colony 4904 in real time and make dynamic changes to the path and parameters of the internal magnetic tool 4902. The resulting cell debris from the pruning may drop towards the bottom inside surface of the cell culture chamber.

Figure 49C:
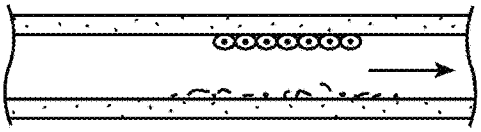
Figure 49D:
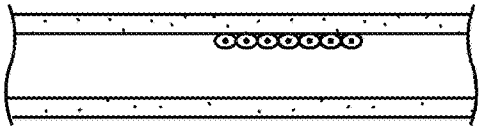
Figure 49E:
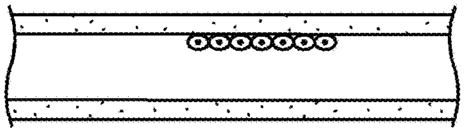

In step (c) illustrated in FIG. 49C, the cell debris may be removed from the cell culture chamber via media flow or some other approaches, which may include but are not limited to use of magnetic tools (as disclosed herein) and/or gravity assistance (e.g., tilting or tipping container appropriately). Step (d) illustrated in FIG. 49D shows the now-pruned cell colony 4904 on the cell-bearing surface. Sometime later, in step (e) illustrated in FIG. 49E, the cell colony 4904 may be ready to harvest. For example, there may have been several rounds of pruning of undesirable cells before the cell colony 4904 is ready for harvest (e.g., iterations of steps (a)-(d)).

Figure 49F:
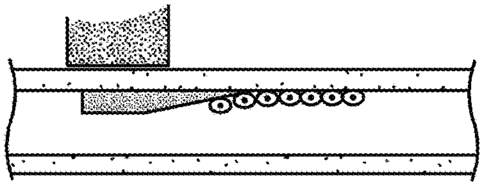

In step (f) illustrated in FIG. 49F, the computing subsystem may determine a path for the internal magnetic tool 4902 to follow to harvest the cell colony 4904, and also determine various parameters for operating the internal magnetic tool 4902, such as tool orientation, direction, and velocity. The computing subsystem may activate and control the internal magnetic tool 4902 via the external magnetic component 4906 to follow the path according to the determined parameters to harvest the cell colony 4904. For example, the internal magnetic tool 4902 may have a blade with a low-angle edge that is used for incremental lifting, and that edge approaches the cell colony 4904 to slowly dig under the cell colony 4904 and lift the cells off the cell-bearing surface. The internal magnetic tool 4902 may be moved at a low velocity with maximum magnetic downforce so as to not damage the cells during the lifting process. The computing subsystem may also image the internal magnetic tool 4902 and the cell colony 4904 in real time and make dynamic changes to the path and parameters of the internal magnetic tool 4902.

Figure 49G:
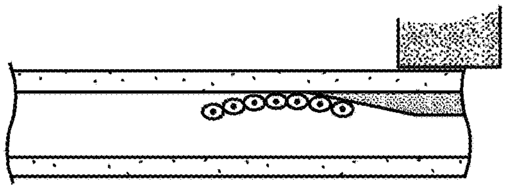
Figure 49H:
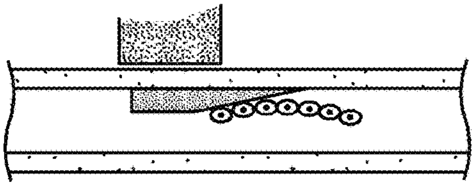
Figure 49I:
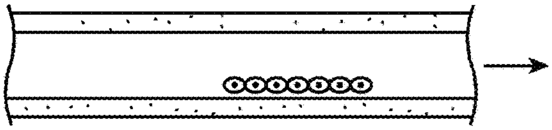

Steps (g)-(h) illustrated in illustrated in FIG. 49G-H show the continuation of the lifting process. For example, the internal magnetic tool 4902 may move in a spiral motion around the cell colony 4904, moving closer to the center with each pass. In step (i) illustrated in FIG. 491, the lift-off process is complete and the fully-detached cell colony 4904 has floated to the inner bottom surface of the cell culture chamber, where it may be harvested. The computing subsystem may, for example, flush the cell colony 4904 out of the cell culture chamber into another receptacle. In other implementations, a mechanical tool may be used to push the cell colony 4904 out of the chamber, or gravity may be used as well.

Figure 50A:
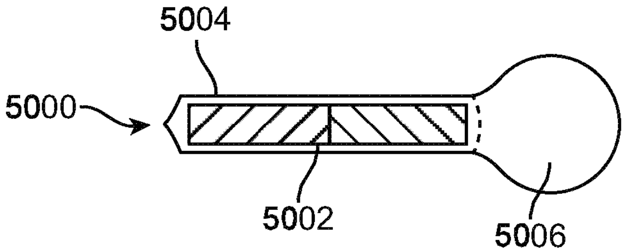
FIGS. 50A-B illustrates an alternate implementation of an internal magnetic tool in accordance with various implementations.
Figure 50A:
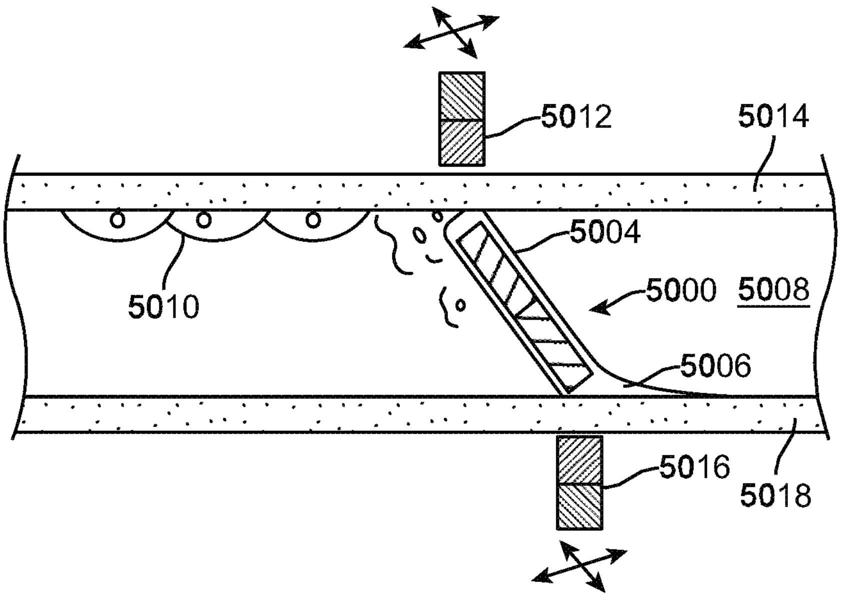
Figure 50B:
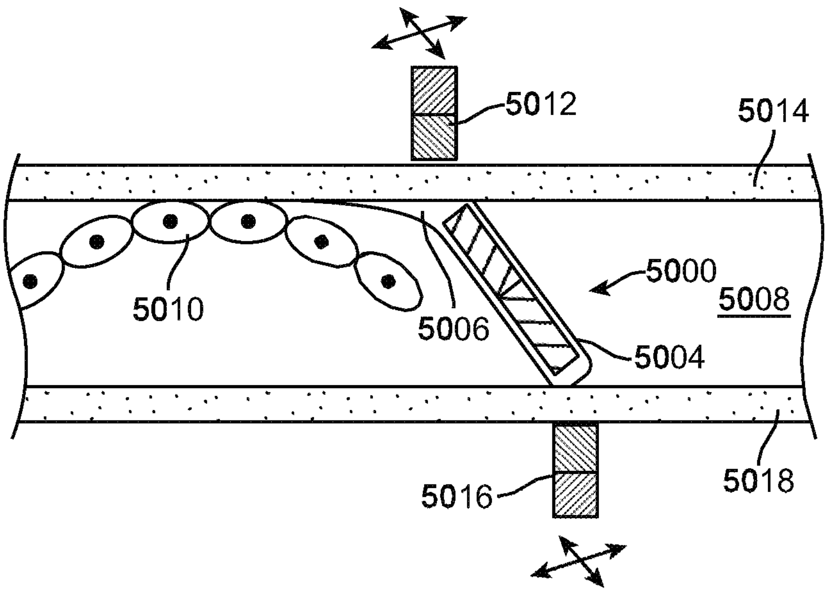

FIGS. 50A-B illustrate an alternate implementation of an internal magnetic tool 5000 in accordance with various implementations. The internal magnetic tool 5000 may be a two-ended tool that includes an embedded permanent magnet 5002, a sharp end 5004 used for precision cell destruction/lysing, and a flexible "scoop" or paddle end 5006 used for detaching cell sheets or colonies (the flexible joint indicated by dotted line). The length of the internal magnetic tool 5000 may be determined by the internal cell culture chamber height and the desired angle of the tool with respect to the surfaces of the cell culture chamber. For example, in a chamber with an internal height of 0.5 mm, a tool with length 0.75-1.0 mm may be employed.

The internal magnetic tool 5000 may be guided by external magnetic components on both sides of the cell culture chamber, as opposed to a single side. One advantage of this arrangement is that the contact region of the internal magnetic tool 5000 with the inside surfaces of the cell culture chamber may be made very small (e.g., smaller than the footprint of internal magnetic tools 4500A and 4500B), and therefore cell culture editing may be much more precise. A further potential advantage is that tools may be flipped while within the cell culture chamber. For example, by flipping the poles of the external magnetic components, the ends of the internal magnetic tool 5000 resident on each surface may be alternated, so that the sharp end 5004 and the flexible end may be applied to either inner surface. A further potential advantage is that the internal magnetic tool 5000 may be disengaged easily from the cell surface in order to form discontinuous tool paths, as described further herein.

FIG. 50A illustrates the use of the internal magnetic tool 5000 for cell removal. The internal magnetic tool 5000 may be located in cell culture chamber 5008 having an upper cell-bearing surface 5014 and a lower surface 5018. A cell colony 5010 is adhered to the cell-bearing surface 5014. The internal magnetic tool is magnetically coupled to two external magnetic components: external magnetic component 5012 is located on the outside of the cell-bearing surface 5014 while external magnetic component 5016 is located on the outside of the lower surface 5018. The external magnetic components 5012, 5016 may be connected to actuators controlled by a computing subsystem of a cell culture system (e.g., system 110 in FIG. 1). The sharp end 5004 of the internal magnetic tool 5000 may be pointed towards the cell-bearing surface 5014 while the flexible end 5006 may be pointed towards the lower surface 5018. The external magnetic components 5012, 5016 translate along the cell-bearing surface 5014 and the lower surface 5018 respectively. The external magnetic component 5012 may control the tool tip location and rotation (e.g., pointing angle) of the sharp end 5004 while the external magnetic component 5016 may control the tool tip location and rotation of the flexible end 5006. The sharp end 5004 may be used for lysing of cells from the cell colony 5010 while the flexible end 5006 may be used for lifting cells from the cell-bearing surface 5014. This configuration allows highly precise editing of the cell colony 5010.

In some implementations the distance between the external magnetic components 5012, 5016 and the surfaces 5014, 5018 may be controlled, allowing for variation of the magnetic force between the external magnetic components 5012, 5016 and the internal magnetic tool 5000. This allows for varying the force applied by the tool tip to the surfaces 5014, 5018 which may be useful for multiple functions. For example, lysing a cell may require more force than lifting a cell from the cell-bearing surface 5012. Also, if the magnetic force is weakened to a certain point the internal magnetic tool 5000 may lose contact with the surfaces 5014, 5018 but may still be controllable by the external magnetic components 5012, 5016. This allows discontinuous tool paths by having the internal magnetic tool 5000 disengage from a surface at one point, float through the interior of the cell culture chamber 5010, and re-engage the surface at another point. In alternate implementations, the polarity of the external magnetic components 5012, 5016 may be switched in order to push the corresponding tool tip away such that it disengages from the surface, and then switched again when the tool tip should be re-engaged.

FIG. 50B illustrates the capability of flipping the internal magnetic tool 5000 within the cell culture chamber 5010. In diagram (b), the polarity of both external magnetic components 5012, 5016 have been switched such that the internal magnetic tool 5000 flips orientation inside the cell culture chamber 5010 with respect to the orientation shown in diagram (a). After flipping, the external magnetic component 5012 may control the tool tip location and rotation of the flexible end 5006 while the external magnetic component 5016 may control the tool tip location and rotation of the sharp end 5004. In this configuration, the flexible end 5006 may be used to lift the cell colony 5010 from the cell-bearing surface 5014 by translating and/or rotating the internal magnetic tool 5000.

Figure 50C:
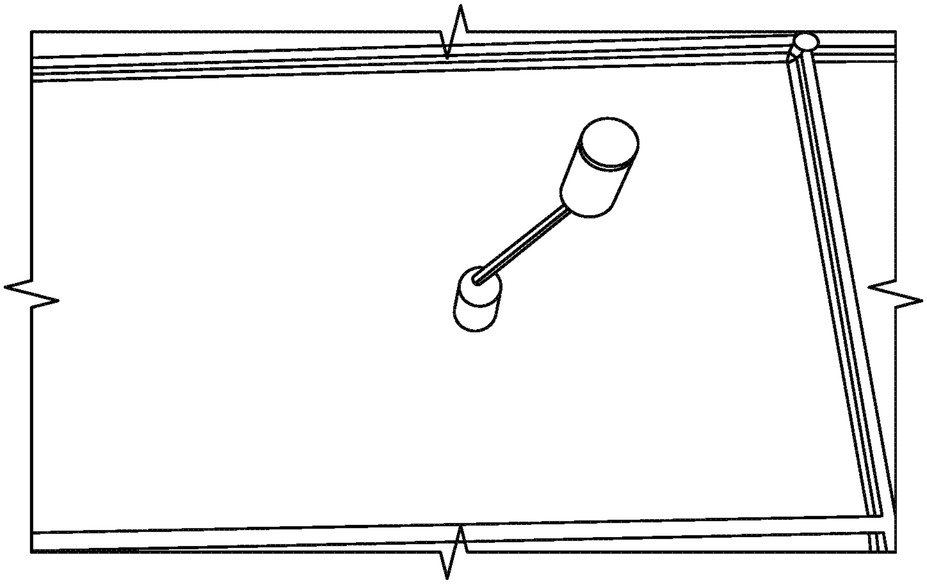
FIG. 50C Illustrates the operating concept of the 2-sided magnetic tool, with actuators on both sides of a cell culture chamber in accordance with various implementations.

FIG. 50C illustrates an exemplary 2-sided magnetic tool, with actuators on both sides of a cell culture chamber, for the purpose of simultaneously controlling the position and tip orientation of a tool for cell culture editing. The prototype is shown in a Corning CELLSTACK adherent cell culture vessel which has a growth area of about 636 $cm^2$ and a chamber height of about 17 mm.

Ultrasound Cell Editing Methods

In many adherent or semi-adherent cell culture processes it may be desirable to selectively lyse cells or regions of cells to control the development of the cell culture. For example, cell lysis may be used to remove cells of the wrong phenotype, to isolate cells or colonies for the purpose of having a clonal cell colony, to lyse and remove cells for the purpose of controlling cell density and confluence, or to selectively lyse cells for the purpose of removing the respective cellular components and contents for downstream analysis.

However, it may be challenging to design a cell editing system and method for use in a cell culture system. For example, any such cell editing approach may have to satisfy several requirements, including (a) selective lysing and removal of cells from a cell culture in a manner compatible with automation, such that cells may be lysed according to image or image time series characteristics that have been acquired using an imaging system, (b) utilizing images to spatially select cells for lysing, and (c) doing so in a non-invasive manner such that the cell culture container does not need to be opened during the cell editing process.

Several approaches for cell editing in a cell culture system include laser-based systems (including a configuration where laser pulses strike an absorbing coating proximate to the targeted cells) and a pass-through magnetic tool system in which a magnetic tool resides inside of the cell culture vessel for the duration of the process, and is actuated by use of external magnetic fields. However, additional cell editing approaches are also contemplated in this disclosure.

One alternate approach disclosed herein uses an imaging system to acquire images of an adherent or semi-adherent cell culture through the cell culture container surface, and then uses targeted focused ultrasound transmitted through the cell culture container wall and focused spatially on specific cells, cell regions, or cell colonies in order to selectively lyse them. Cell lysis by ultrasound is a well-known technique and is applied to bulk volumes of cells in suspension. Typically, a transducer is inserted into an open container with suspended cells, and emits ultrasonic pressure waves to "sonicate" the suspended cells, breaking their membranes. Focused ultrasound has also been used in vivo to disrupt cells, such as high intensity focused ultrasound (HIFU) which may be used for prostate cancer treatment. However, in these procedures the mechanism is largely thermal shock rather than mechanical lysing of cells.

The systems and methods disclosed herein for ultrasound cell lysing may include a cell culture container for adherent or semi-adherent cells, the cell culture container configured to enable label-free imaging of the contained cells, an imaging subsystem that images cells through a wall of the cell culture container, a computing subsystem that processes the images of the cell culture and classifies cells, cell regions or cell colonies, a focused ultrasound system that acts through the wall of the cell culture container to selectively lyse cells according to the classifications provided by the computing subsystem, and a method to remove the material generated by cell lysis. The focused ultrasound subsystem disclosed herein may also include, but is not limited to, electronically-driven spherical transducers, laser-generated focused ultrasound using a spherical absorbing/transducing surface, and phased array transducers.

The cell culture container (e.g., cell culture container 104 in FIG. 1) may be a microwell plate, a cell culture flask, a microfluidic chamber, or other type of container used for cell culture processes. The cell culture container may be fully sealed for sterile processing of cells, for example a cell culture chamber attached to a tubing system for supplying media and reagents and harvesting cell products (and cell debris). For the purposes of enhancing the ultrasound effect on the cells, to maximize cell lysis, microbubbles may be added to the cell culture prior to selective lysis. These microbubbles are used in ultrasound imaging in order to enhance contrast, and may be gas sealed in stable shells. An example of this microbubble material is Sono Vue® from Bracco Diagnostics, which includes a suspension of phospholipid shells filled with sulfur hexafluoride gas with diameters of 2-9 microns.

Figure 51A:
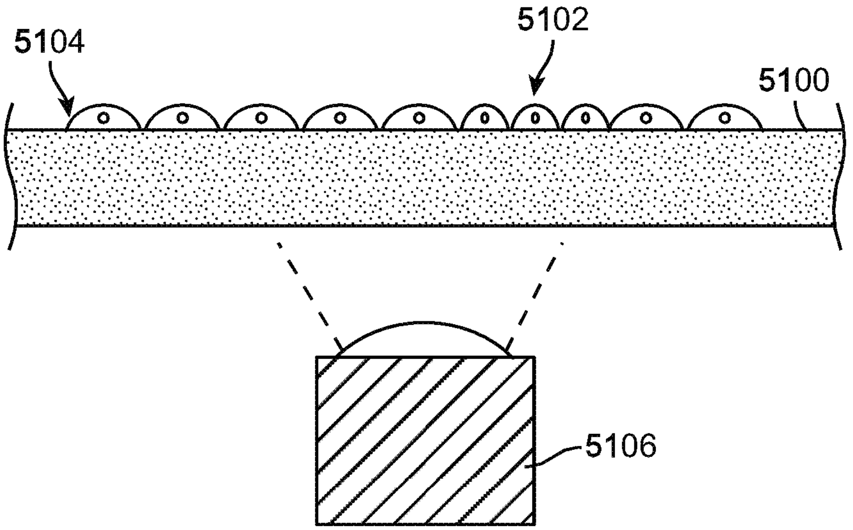
FIGS. 51A-51C illustrates ultrasound lysis of cells in a cell culture system in accordance with various implementations.
Figure 51B:
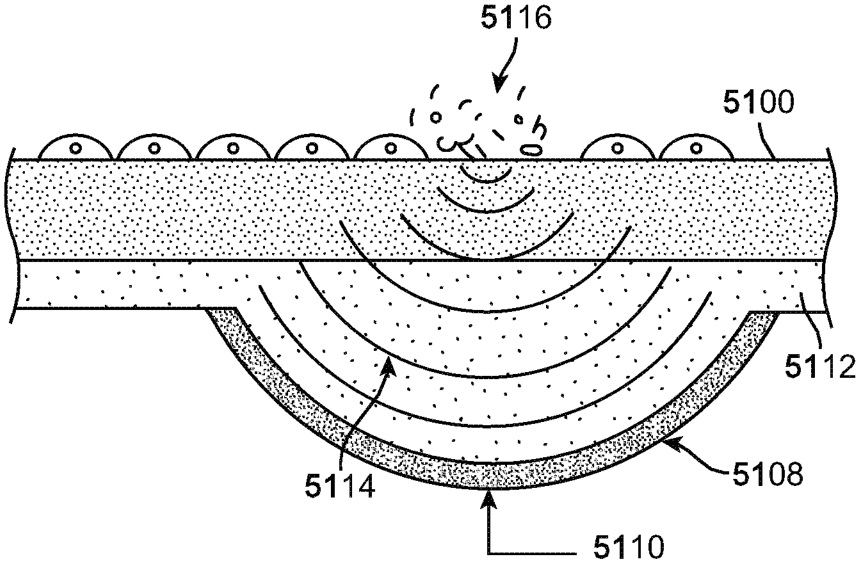
Figure 51C:
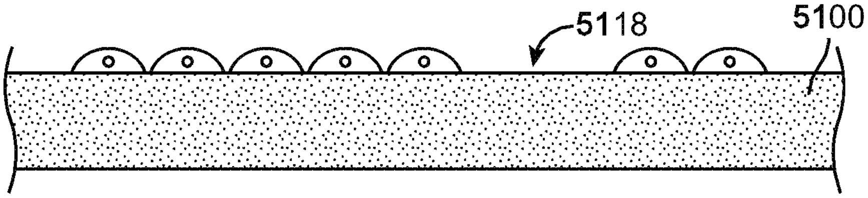

FIGS. 51A-C illustrates ultrasound lysis of cells in a cell culture system in accordance with various implementations. FIG. 51A depicts a cell culture surface 5100 of a cell culture chamber. Inside the cell culture chamber there is fluid media 5102 and an adherent cell culture 5104. The cell culture surface 5100 may be transparent and configured to support the cell culture 5104. The transparency allows imaging of the cells using an imaging subsystem 5106, which may be similar to the imaging subsystem 112 in FIG. 1. The imaging modality used by the imaging subsystem 5106 may include label-free imaging as well as fluorescently-labelled imaging. The images from the imaging subsystem 5106 may be processed by a computing subsystem (e.g., computing subsystem 110), and the cells in the cell culture 5104 are classified by the computing subsystem.

FIG. 51B depicts a focused ultrasound transducer 5108 that is electrically driven through a feed 5110. The electronic signal is controlled via a computing subsystem according to the position of the transducer 5108 relative to the cell culture 5104, and the classifications of the cells, to lyse specific cells or cell regions. A coupling fluid (or gel) 5112 is used to enabled ultrasound transmission into the cell culture surface 5100 and towards the adherent cell culture 5104. In some cases, the coupling fluid 5112 may double as immersion oil for a microscope objective used by the imaging subsystem 5106 to increase the imaging resolution of the imaging subsystem 5106. Generated ultrasonic waves 5114 pass through the coupling liquid 5112, through the cell culture surface 5100, and are focused on a region of the adherent cell culture 5104, resulting in the targeted lysis of local cells 5116.

FIG. 51C shows the cell culture 5104 after lysis and cell debris removal, with the targeted cells removed as indicated by the empty space 5118. Cell debris may be removed by pipetting in the case of an open cell culture container, or by flow methods in a closed container or liquid chamber. The debris may be directed towards a waste container or bag (in the case of a sealed/closed liquid system), or towards a collection container or sample bag if the lysis products will be used for analysis.

Figure 52A:
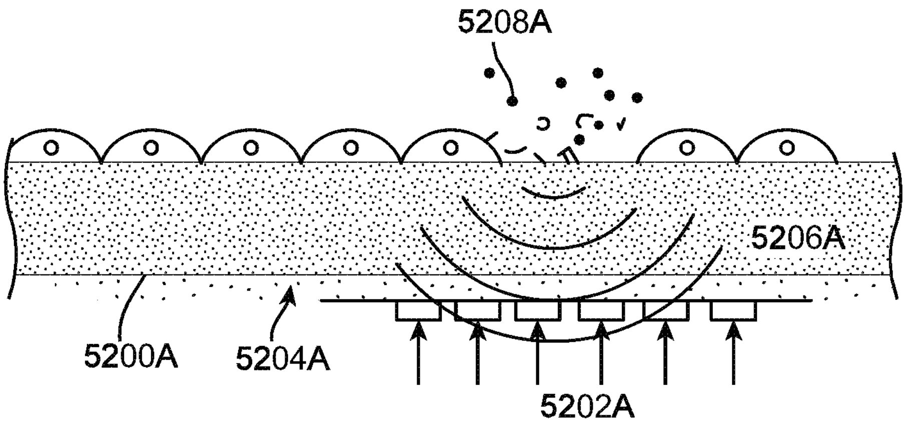
FIG. 52A illustrates an alternate method of ultrasound lysis of cells in a cell culture system in accordance with various implementations.

FIG. 52A illustrates an alternate method (phased-array ultrasound transducer) of ultrasound lysis of cells in a cell culture system in accordance with various implementations. In this implementation, rather than using a shaped surface, ultrasound is focused by use of an array of transducers 5202A, each of which has a settable delay in signal emission (one-time settable using delay lines, or a programmable delay) to form a focused beam out of the combination of emitted signals. An advantage of this configuration is that it may be compact, but even more so that it can allow high-speed steering (in the case of a fully-programmable array) of the focus point across cell culture surface 5200A. A coupling fluid 5204A allows efficient transmission of the resulting ultrasonic signal 5206A into the cell culture surface 5200A and towards a focus point 5208A where cells are lysed.

Figure 52B:
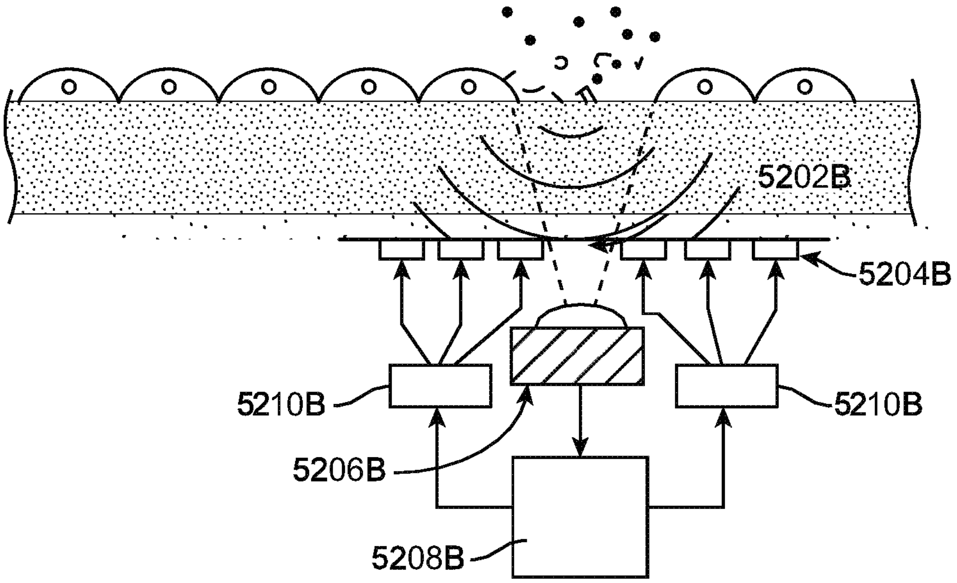
FIG. 52B illustrates a combined imaging and ultrasound lysing system in a cell culture system in accordance with various implementations.

FIG. 52B illustrates a combined imaging and ultrasound lysing system in a cell culture system in accordance with various implementations. The imaging subsystem and ultrasonic transducer may be combined into a single head that can be translated relative to the cell culture for imaging as well as targeted cell lysing. In this example, an aperture 5202B in an ultrasound transducer 5204B allows an imaging subsystem 5206B (e.g., cell imaging subsystem 112) to image the cell culture and/or to establish precise location of the ultrasound transducer 5204B relative to prior images of the cell culture. A computing subsystem 5208B (e.g., computing subsystem 110) then directs ultrasound drivers 5210B based on the computed location and cell/cell region classifications, causing targeted lysis on the cell culture surface.

Washing Systems for a Closed Cell Culture Chamber

Adherent cell cultures grown in a cell culture chamber may require occasional washing for several purposes. For example, washing may be performed to remove weakly adherent or non-adherent cells from the cell culture, remove adherent cells from the cell culture container intact for the purpose of harvesting the cells, or remove cell debris from the cell culture. The cell debris may be weakly adherent to the cell culture container or live cells. Cell debris may be present in the cell culture chamber after cell editing, in which selected cells are damaged or lysed through a number of methods, including but not limited to laser-based cell damage or lysis, ultrasonic cell lysis, or mechanical cell lysis by a tool in the cell chamber.

In open cell culture containers such as microwell plates, petri dishes, and flasks, the washing process may be performed in a number of ways, including using a pipette or other liquid handling device to flush the cell-bearing surface with liquid, thereby dislodging cells or cell debris, or using tilting, rocking, or spinning of the cell culture container to agitate the liquid. However, in closed cell culture chambers, the use of a pipette or similar device to flush the cell surface is not possible. Furthermore, in closed cell culture chambers in which the chamber is substantially filled with liquid (e.g., a microfluidic or millifluidic chamber), rocking or tilting the cell culture chamber has no effect due to the lack of a liquid-gas interface or any compressibility.

The primary methods used for washing cells in closed cell culture chambers in the prior art include repeated tilting of the chamber to induce liquid flow or "sloshing," in cases in which there is a gas-liquid interface on the interior of the chamber. This method only works when there is a gas-liquid interface, but may produce very uneven results. Prior art solutions also include increasing the liquid flow rate and/or changing liquid flow direction in cases in which the cell culture chamber is completely liquid-filled. This method relies on having a pump that can produce sufficiently high flow rates within the cell culture chamber (which typically has a large cross-section compared to the tubing) to induce shear stress on cells or cell debris. However, because of the typical geometries of cell growth chambers, this flow may produce very different shear conditions in different regions, potentially leading to uneven clearing of material and/or reduced cell viability.

Another washing method includes using higher levels of chemical dissociation agents (e.g., enzymes such as Trypsin or recombinant replacements), or longer exposure periods to these agents, to loosen cell-cell and cell-container bonds. However, prolonged exposure to high concentration of these agents reduces cell viability or induces cell death. For these reasons it would be beneficial to have better systems that are applicable to closed adherent cell growth chambers, particularly liquid-filled ones, that enable better non-chemical approaches (or more lightly chemically assisted approaches) for washing cell cultures to remove debris and/or cells. Thus, better ways of performing the washing process inside sealed, liquid-filled cell culture chambers are needed in the art, as such chambers are used to perform high-volume, precision adherent cell culture processes, particularly within a cell culture system.

The systems and methods disclosed herein include several systems for transmitting mechanical force from external actuators through the walls of a sealed, liquid filled cell culture chamber to induce local or global liquid flows that act on adherent or semi-adherent cells or cell debris to separate them from the cell culture-bearing surfaces (or non-cell culture bearing surfaces). The cells or cell debris may be subsequently removed from the cell culture chamber via liquid flow.

One implementation contemplated herein includes a mechanical actuator that pushes against a flexible or semi-flexible wall of a cell culture chamber to constrict a flow path locally, followed by a liquid flow to create a high-velocity flow over the cell culture in the area of the constriction. This high-velocity flow creates shear stresses that detach cells or cell debris from a cell culture-bearing surface inside the cell culture chamber.

Another implementation contemplated herein includes a mechanical actuator that pushes against a flexible or semi-flexible wall of the cell culture chamber to separate two or more regions of the cell culture chamber with one or more constrictions. The actuator may subsequently be moved over the flexible surface to induce flow through the constrictions from one set of regions to another set of regions, in which the resulting high-velocity flow creates shear stress to detach cells or cell debris from a cell culture-bearing surface.

Another implementation contemplated herein includes a mechanical actuator that locally deflects a flexible or semi-flexible wall of a cell culture chamber. As the wall is deflected by the mechanical actuator, liquid moves out of the constricted region of the cell culture chamber due to the reduction in volume, causing a high-velocity flow (e.g., in a radial pattern) out of the constricted region under the actuator, and then back into the region as the actuator is moved away from the chamber well. This motion may be repeated, causing a back and forth flow that applies shear stress to detach cells or cell debris from a cell culture-bearing surface.

Another implementation contemplated herein includes an ultrasonic transducer that is mechanically coupled to one surface of the cell culture chamber and transmits ultrasonic waves through the surface to induce mechanical stresses on the cell culture surface and loosen cells and/or cell debris.

Another implementation contemplated herein includes one or more ultrasonic actuators coupled to a cell culture chamber wall. The ultrasonic actuators create acoustic waves that travel along the wall of the cell culture container. The waves induce local motion in the container wall that in turn create micro-flows within the cell culture chamber, which create shear forces on the cell-bearing surface to detach cells or cell debris.

Unlike the prior art, the implementations disclosed herein enable washing of cells and cell debris from an adherent culture in a sealed cell culture vessel, including liquid-filled chambers, without breaking the seal of the chamber or the supporting liquid systems. This approach maintains sterility of the chamber, and also allows multiple cell culture chambers to be processed in a common environment without the possibility of cross-contamination. It also enables cell culture washing with high local liquid velocities and resulting shear stresses without requiring a liquid and pumping system that by itself can create these velocities in the cell culture chamber. It potentially allows cell harvest or debris removal from 2D adherent cell cultures to be performed with less chemicals or enzymatic dissociation agents (as well as less exposure time to these agents), resulting in healthier cell cultures or products.

Figure 53A:
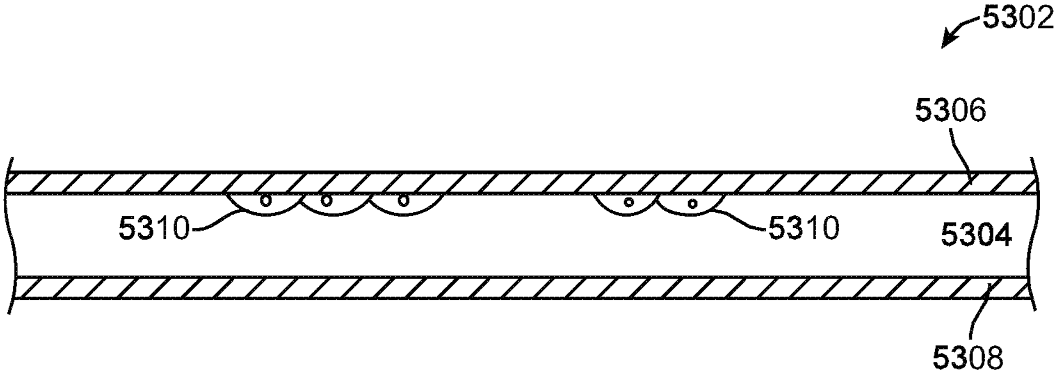
FIGS. 53A-53B illustrate a mechanical method of washing away cells and cell debris from a closed cell culture chamber in accordance with various implementations.
Figure 53B:
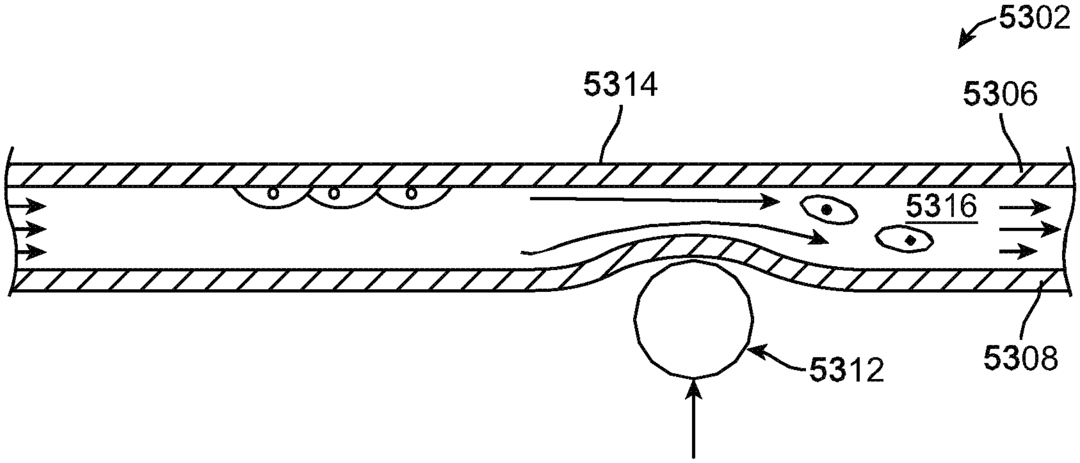

FIGS. 53A-B illustrate a mechanical method of washing away cells and cell debris from a closed cell culture chamber in accordance with various implementations. FIG. 53A illustrates a cell culture chamber 5302 with an adherent cell culture growing inside. The cell culture chamber 5302 may be in a cell culture container (e.g., cell culture container 104 in FIG. 1) of a cell culture system. A cell media-filled cavity 5304 is contained between walls 5306 and 5308. An adherent or semi-adherent cell culture 5310 is adhered to the inside of the wall 5306 (e.g., the upper wall). Both walls 5306, 5308 may be suitable for imaging and/or directed energy editing of the cell culture 5310. Media in the cell culture chamber 5302 may be replenished by slow flow or stopped flow that also removes cell waste products. Dissolved gas ($O_2$ for example) may be supplied as part of the fresh media feed, or through a gas-permeable surface. For example, wall 5308 may be a polymer wall that is mechanically flexible and also gas-permeable.

In FIG. 53B, an actuator 5312 is pushed against a flexible wall of the cell culture chamber 5302, for example the wall 5308, in a specific region of the cell culture chamber 5302. The wall may be pushed inwards to decrease the wall-to-wall spacing within the fluid cavity, creating a constricted region 5314 of the cell culture chamber 5302. Using a media pumping subsystem inherent to a cell culture container containing the cell culture chamber 5302, media may be pumped through the cell culture chamber 5302. In the constricted region 5314, this results in a high-velocity and/or turbulent flow 5316 which creates sufficient shear stress on cells or cell debris to dislodge them from the cell culture surface (e.g., inside of wall 5306), and pull them into the flow 5316.

In some implementations, liquid pumping may be performed in both directions, for example in back-and-forth flow switching, to dislodge material as desired without net use of cell media. The process may be repeated with the constriction at multiple locations within the cell culture chamber 5302. For example, the actuator 5312 may be a roller that pushes against the chamber wall and then slowly traverses the cell culture chamber 5302 along the direction of flow, propagating the constricted region 5314 along the cell culture chamber 5302 while the liquid is pumped back and forth to create rapid flows in the constricted region and dislodge cell material. In general, the liquid flow velocity, duration, and number of repetitions may be controlled and optimized to remove only objects of interest (for example, but not limited to, cell debris remaining adherent or semi-adherent after selective destruction of cells, intact adherent cells, with or without use of disassociation agents, intact semi-adherent cells, intact non-adherent cells, 3D outgrowths of 2D adherent cell cultures, dead or non-viable cells, etc.). The actuator 5312 may be controlled by a computing subsystem (e.g., computing subsystem 110) of a cell culture system. In another implementation, substantially the entire cell culture chamber 5302 may be squeezed using an actuator to reduce flow cross-section across the entire cell culture area, and then apply pumping to the system, resulting in higher flow velocities (higher shear forces) and/or lower liquid volume requirements during washing processes.

The dislodged cells and cell debris may then be washed out of the cell culture chamber 5302 through several approaches. One example may be to lower the volume of fluid media in the cell culture chamber 5302 so that the adherent cell culture 5310 on the upper wall 5306 is not submerged. The dislodged cells and cell debris may settle on the bottom wall 5308. The rate of flow of fresh fluid media through the cell culture chamber 5302 may be increased so that the dislodged cells and cell debris may be flushed out of the cell culture chamber 5302.

In some implementations, there may be no high velocity flow 5316 applied within the cell culture chamber 5302. The motion of the actuator 5312 itself as it pushes inwards on the wall 5308 and then back out creates a rapid fluid flow out of the constricted region 5314 during the pushing action, and then a fluid flow back into the constricted region 5314 as the actuator 5312 is retracted. This process may be used to create local flow velocities and resulting shear forces on cells or cell debris to dislodge them from the growth surface, with the flow velocities determined by the actuator 5312 velocity. Multiple cycles of actuator motion may be used to locally wash the cell culture 5310.

Figure 54A:
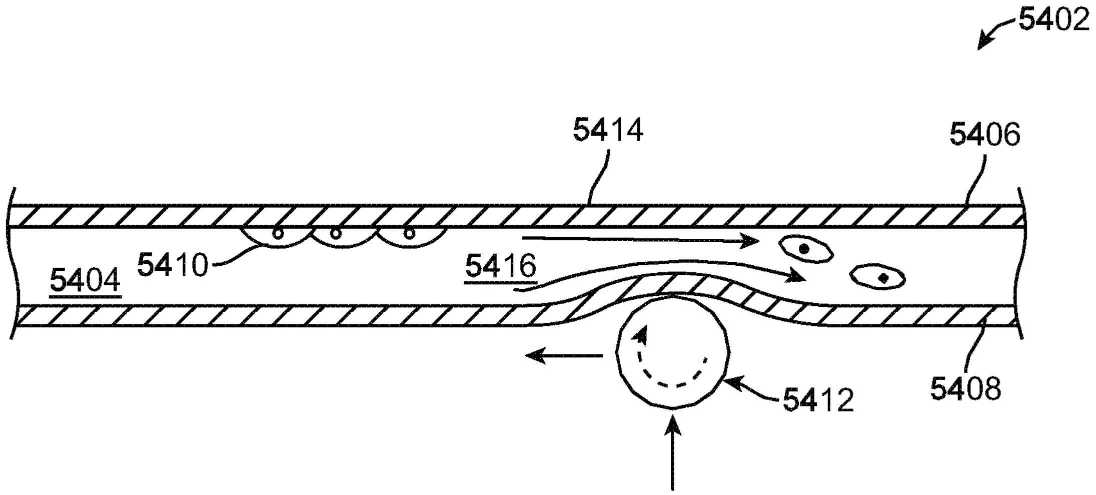
FIGS. 54A-54B illustrate another mechanical method of washing away cells and cell debris from a closed cell culture chamber in accordance with various implementations.
Figure 54B:
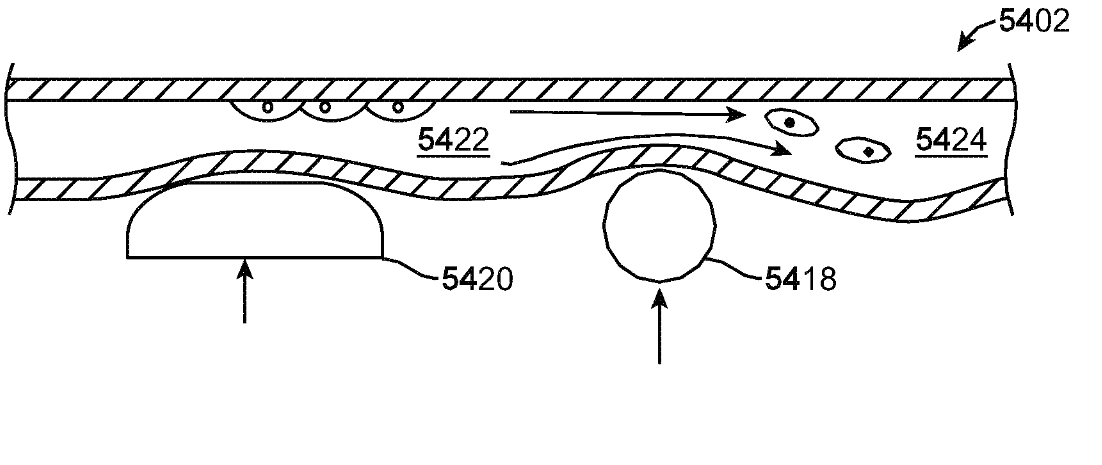

FIGS. 54A-B illustrate another mechanical method of washing away cells and cell debris from a closed cell culture chamber in accordance with various implementations. FIG. 54A illustrates a cell culture chamber 5402 with an adherent cell culture growing inside. The cell culture chamber 5402 may be in a cell culture container (e.g., cell culture container 104 in FIG. 1) of a cell culture system. A cell media-filled cavity 5404 is contained between walls 5406 and 5408. An adherent or semi-adherent cell culture 5410 is adhered to the inside of the wall 5406 (e.g., the upper wall). Both walls 5406, 5408 may be suitable for imaging and/or directed energy editing of the cell culture 5410. During mechanical agitation, the cell culture chamber 5402 may be sealed to prevent liquid flow in/out of the chamber, as shown in FIG. 54A. This may be done with pinch valves in the liquid handling subsystem, for example, or by physical sealing of the cell culture chamber 5402 during this process.

An actuator 5412 is placed against a flexible wall of the cell culture chamber (e.g., wall 5408) and applies a force perpendicular to the wall 5408 to bend the chamber wall inwards and constrict the cavity at a constricted region 5414. The actuator 5412 is then slid or rolled across the cell culture chamber 5402 to propagate the constricted region 5414. Due to the incompressibility of the liquid media, this forces a flow 5416 from one side of the constricted region 5414 to the other, with the velocity of this flow controllable by the amount of constriction as well as the speed of the actuator motion across the cell culture chamber 5402. This flow creates a shear force on the cell-bearing surface and its contents, dislodging cells or cell debris which are subsequently floating in the media. The actuator 5412 may be controlled by a computing subsystem (e.g., computing subsystem 110) of a cell culture system.

FIG. 54B illustrates an alternate implementation of the approach shown in FIG. 54A, using two actuators rather than one. A first actuator 5418 is pushed into the chamber wall to form a constriction in the cell culture chamber 5402, separating the chamber into two non-constricted regions 5422 and 5424. A second actuator 5420 is then also pushed into the chamber wall, deflecting it inwards and reducing available volume in one of the non-constricted regions 5422. This forces liquid through the constriction at high velocity into the other non-constricted region 5424, where the flexible chamber wall expands to accommodate the additional volume. In general, any number of actuators may be used in such a chamber configuration to create washing protocols with high spatial and temporal specificity.

The dislodged cells and cell debris may then be washed out of the cell culture chamber 5402 through several approaches. One example may be to lower the volume of fluid media in the cell culture chamber 5402 so that the adherent cell culture 5410 on the upper wall 5406 is not submerged. The dislodged cells and cell debris may settle on the bottom wall 5408. The rate of flow of fresh fluid media through the cell culture chamber 5402 may be increased so that the dislodged cells and cell debris may be flushed out of the cell culture chamber 5402.

Figure 55A:
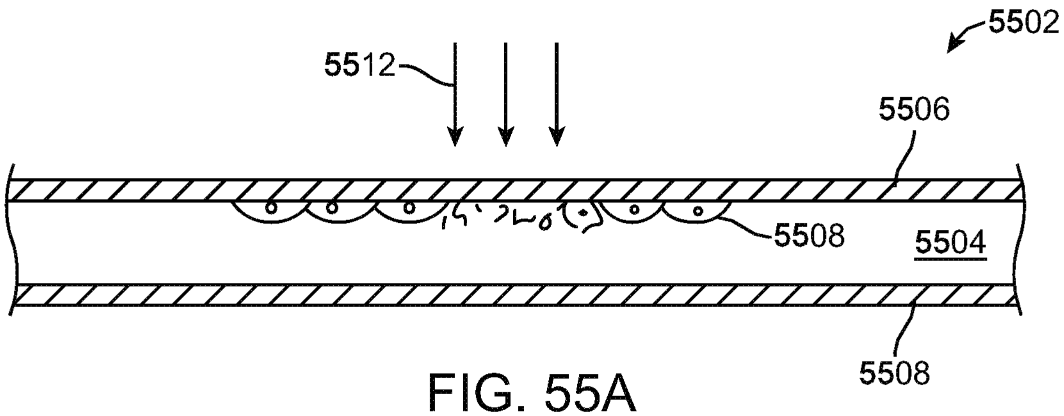
FIGS. 55A-55B illustrate a method for dislodging cells and cell debris in a closed cell culture chamber in accordance with various implementations.
Figure 55B:
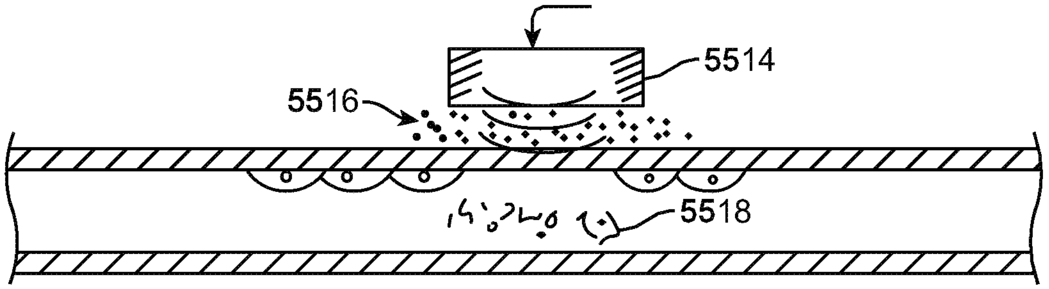

FIGS. 55A-B illustrate methods for dislodging cells and cell debris in a closed cell culture chamber in accordance with various implementations. FIG. 55A illustrates a cell culture chamber 5502 with an adherent cell culture growing inside. The cell culture chamber 5502 may be in a cell culture container (e.g., cell culture container 104 in FIG. 1) of a cell culture system. A cell media-filled cavity 5504 is contained between walls 5506 and 5508. An adherent or semi-adherent cell culture 5510 is adhered to the inside of the wall 5506 (e.g., the upper wall). Both walls 5506, 5508 may be suitable for imaging and/or directed energy editing of the cell culture 5510.

A directed energy source 5512 is used to disrupt selected cells in the cell culture 5510, damaging them or lysing them. The directed energy source 5512 may apply energy towards an outer wall of the cell culture chamber 5502 (e.g., the outside of wall 5506) in a direction perpendicular to the plane of the wall. The directed energy source 5512 may be directed towards specific parts of the cell culture 5510 based on imaging of the cell culture 5502 and calculations regarding the cell culture 5502 by a computing subsystem (e.g., computing subsystem 110). The calculations may include, for example, cell density calculations, cell phenotype classifications, clonal colony separation distances, and/or predictions of cell/colony/regional outcome in a cell culture process. In other implementations, the directed energy source 5512 may target regions in a pattern (for example, to reduce overall cell density), or target regions of the cell culture chamber 5502 that are non-optimal for the target cell culture process. As a result of this directed energy cell targeting, some cell components may be ejected or float into media, while others may still be adherent or semi-adherent after the energy application.

FIG. 55B depicts an implementation for detaching (cells or) cell debris from the adherent culture in which the directed energy source is an acoustic transducer 5514. The acoustic transducer 5514 may be coupled to the cell culture chamber wall using a coupling gel or fluid 5516 and acoustic/mechanical waves are transmitted perpendicular to the chamber wall. The acoustic transducer 5514 may be applied to either the cell-bearing wall of the cell culture chamber 5502, or the wall opposite the cell-bearing wall. The acoustic waves cause mechanical oscillation of the wall in the affected region 5518, resulting local liquid flows that dislodge cell debris into the media. The acoustic transducer 5514 may be controlled by a computing subsystem (e.g., computing subsystem 110) of a cell culture system.

Figure 56:
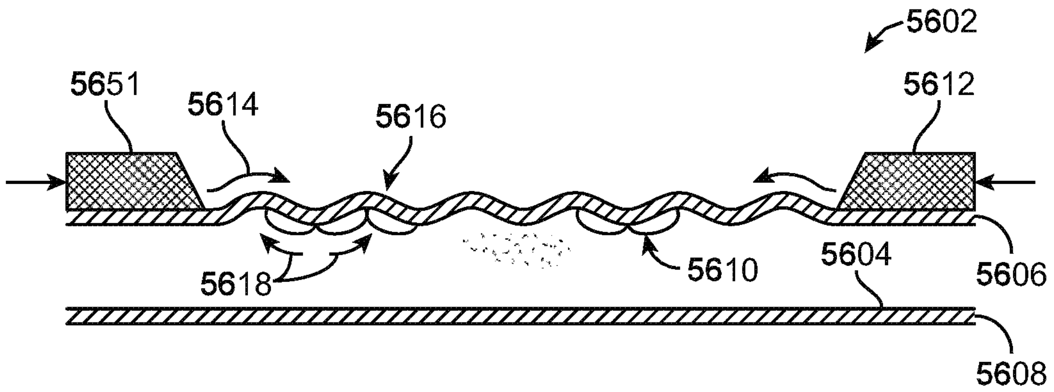
FIG. 56 illustrates another method for dislodging cells and cell debris in a closed cell culture chamber in accordance with various implementations.

FIG. 56 illustrates another method for dislodging cells and cell debris in a closed cell culture chamber in accordance with various implementations. FIG. 56 illustrates a cell culture chamber 5602 with an adherent cell culture growing inside. The cell culture chamber 5602 may be in a cell culture container (e.g., cell culture container 104 in FIG. 1) of a cell culture system. A cell media-filled cavity 5604 is contained between walls 5606 and 5608. An adherent or semi-adherent cell culture 5610 is adhered to the inside of the wall 5606 (e.g., the upper wall). Both walls 5606, 5608 may be suitable for imaging and/or directed energy editing of the cell culture 5610. Acoustic transducers 5612 are coupled to one wall of the cell culture chamber 5612 (e.g., wall 5606). The acoustic transducers 5612 transmit acousto-mechanical waves 5614 across the wall to cause local distortions 5616 of the wall perpendicular to the plane of the wall. The acoustic transducers 5612 may be controlled by a computing subsystem (e.g., computing subsystem 110) of a cell culture system.

The local changes in volume within the cell culture chamber 5602 cause microflows 5618 over the cell-bearing surface on the wall 5606, with associated shear forces on cells or cell debris that dislodge cells or cell debris into the media volume. Typically, a "standing wave" in the chamber wall will be induced by the acoustic transducers 5612, in which at a particular frequency some sections of the wall will experience the maximum upwards and downwards displacement, while other points of the wall ("nodes") will be relatively stationary. To uniformly treat the chamber, a series of frequencies may be employed by the acoustic transducers 5612. In some implementations, the acoustic transducers 5612 may be translated across the surface of the wall. In alternate implementations, one or more mechanical actuators may be pushed against the wall to change the effective resonances of the wall and change the resulting standing wave patterns. In alternate implementations, an array of acoustic transducers may be coordinated in frequency and amplitude to target specific regions of the wall for maximum deflection. An example of such a multi-transducer system is described in Hudin, Charles et al., "Localized Tactile Stimulation by Time-Reversal of Flexural Waves: Case Study With a Thin Sheet of Glass," IEEE World Haptics Conference, April 2013, which is hereby incorporated by reference in its entirety.

Methods for Controlling Cell Culture Systems

Current cell culture processes rely either on timed processes without observation or, in some 2D cell culture processes, occasional imaging and largely human observation of the cell culture in order to monitor progress, assess quality, and/or make "editing" decisions which are largely carried out manually. Examples of how cell cultures may be edited include passaging cells when a certain density is reached, removing cells that are differentiating, or transferring colonies that have the "correct" morphology as seen by a human observer.

There is a strong desire in the industry to automate cell culture processes, and accordingly there has been development in image processing techniques to attempt to replicate expert observations of cell cultures. For example, a number of image processing systems have been demonstrated that assess iPSC colonies based on their overall morphology, in order to guide decisions on colony selection. These systems essentially replicate current human observations, which may be done at a single point in time or at multiple timepoints but without correlating information between images. Decisions may be based on the overall image (pixel data) of a cell colony, corresponding roughly to shape and density. These systems generally do not incorporate cell-level data or statistics, nor do they incorporate time series data or statistics.

There are few, if any, models that relate cell-level and time-series statistics to outcome data for cell culture processes (e.g., reprogramming, differentiation, gene editing expansion). As a result, the ability to predict and control cell cultures is extremely limited using current image analysis techniques, even if appropriate feedback control measures are put into plate (for example, editing the cell culture with a mechanism capable of removing cells, or transferring cells or colonies). Even if large scale times-series data could be collected, the volume of data that may be generated would make data storage and analysis difficult. Large-scale automated biological manufacturing must address these issues to be economically viable.

Figure 57A:
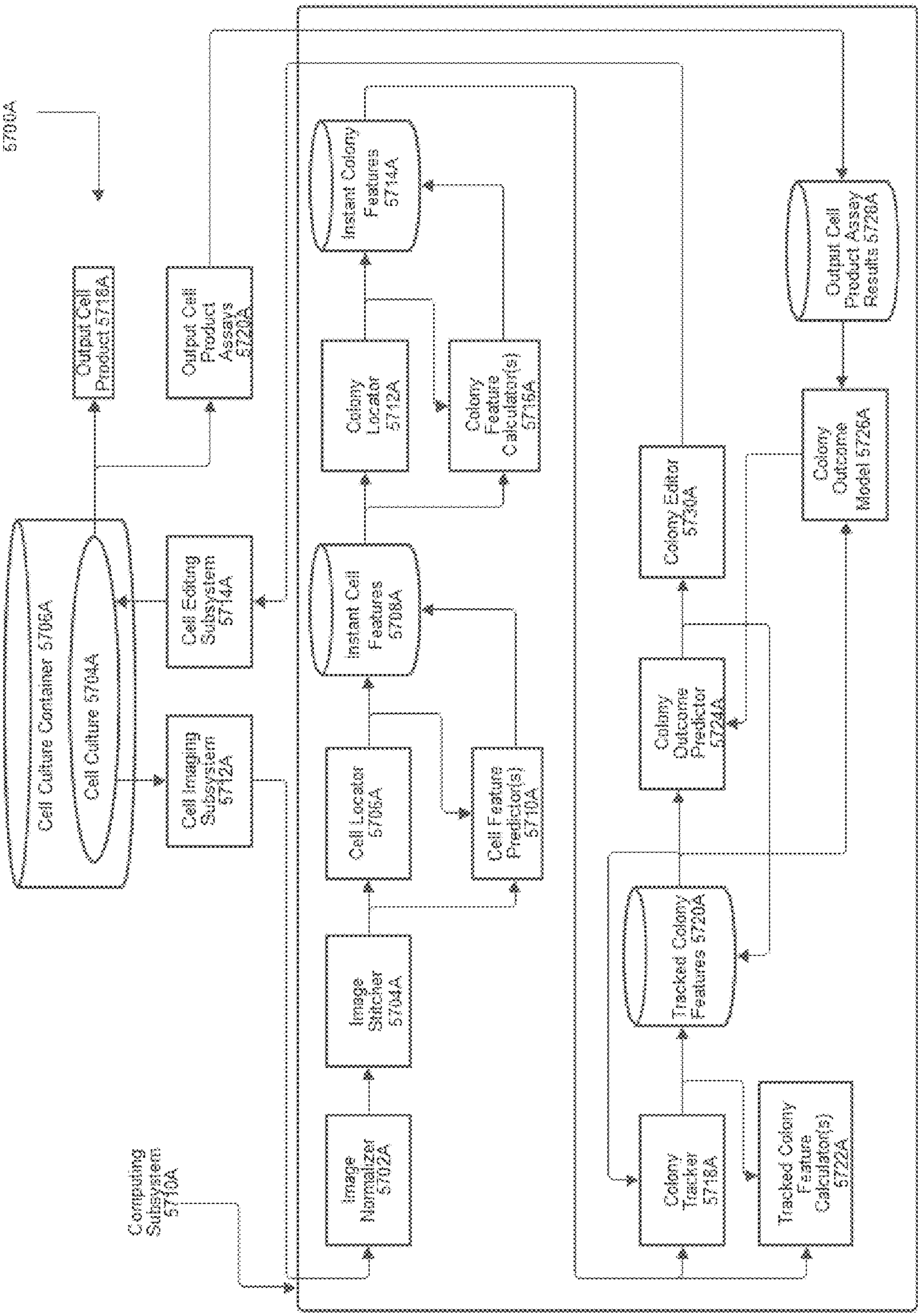
FIG. 57A is a block diagram of a computing subsystem in a cell culture system in accordance with various implementations.

The various implementations disclosed herein include systems and methods for efficiently collecting and analyzing data from a cell culture and utilizing the data to automate cell editing decisions on the cell culture. These systems and methods solve the shortcomings of the prior art and allow for dynamic, automated, easily expandable cell monitoring and editing. FIG. 57A is a block diagram of a computing subsystem in a cell culture system 5700A in accordance with various implementations. The cell culture system 5700A may be similar to the cell culture system 100 described with reference to FIG. 1. For example, the cell culture system 5700A may include a cell culture 5704A in a cell culture container 5706A that undergoes a cell culture process to produce output cell products 5718A. The cell culture system 5700A may also include computing subsystem 5710A, cell imaging subsystem 5712A, and cell editing subsystem 5714A that collectively monitor and controls the cell culture process. Output cell product assays 5720A may be performed on the output cell products 5718A.

The cell culture container 5706A may be configured to enable label-free imaging access to the cell culture 5704A held within it. In an example implementation, the cell culture container 5706A may include a 96-well microplate with an imaging-compatible coverslip (glass, or optical-quality polymer) that is used to contain a cell culture 5704A of somatic cells being reprogrammed to iPSCs through the use of episomal vectors expressing the Yamanaka factors.

Figure 58B:
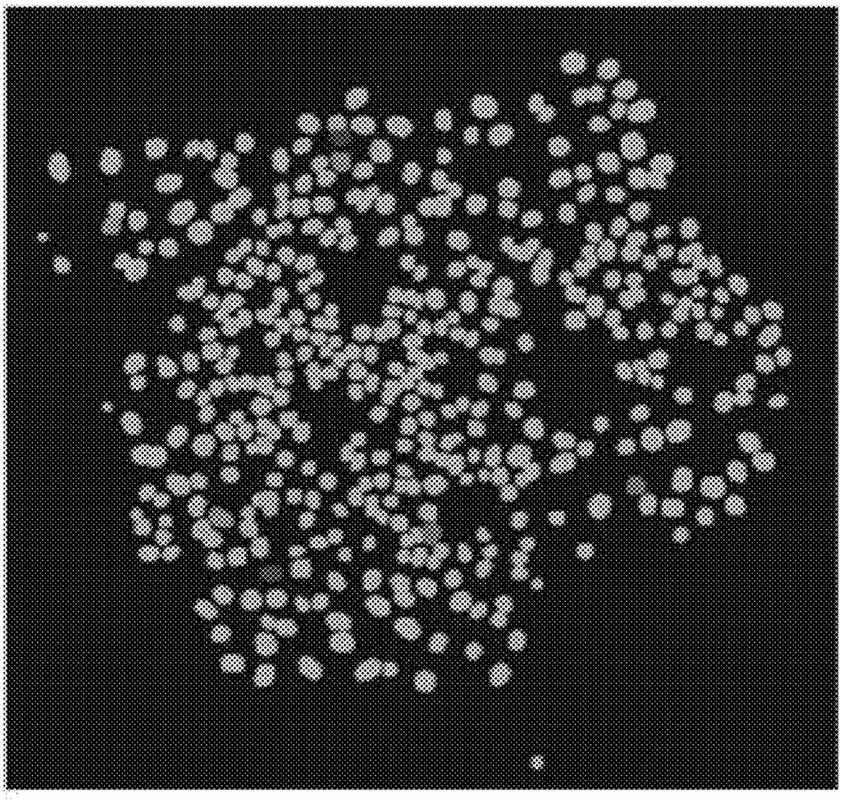
FIG. 58B shows an exemplary output of a deep learning neural network that has been trained to predict nuclear stains from brightfield z-stacks, after thresholding in accordance with various implementations.
Figure 58A:
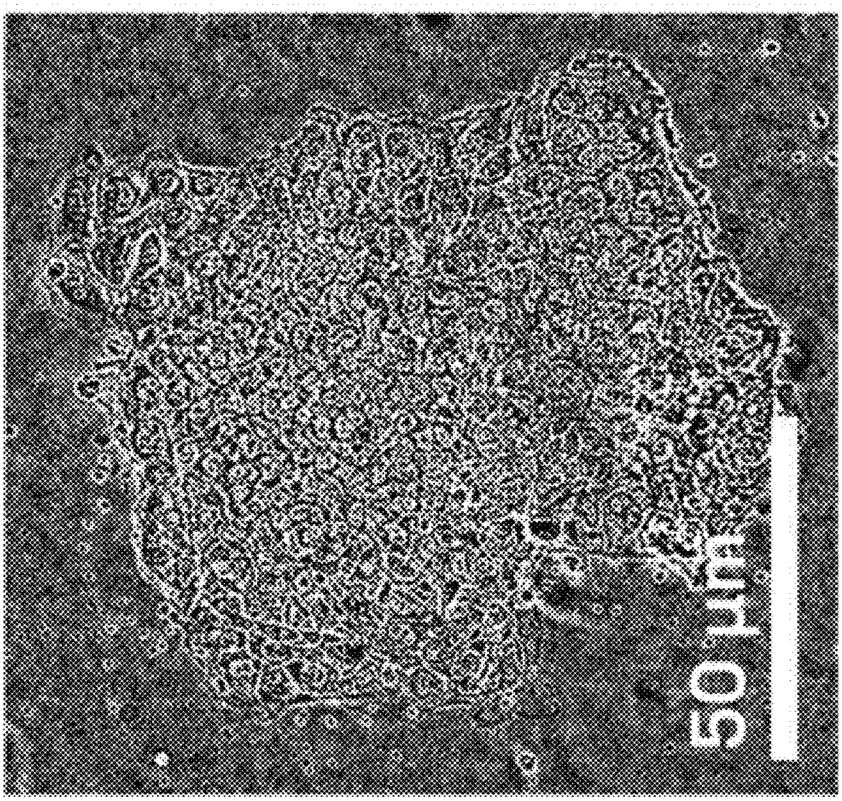
FIG. 58A shows an exemplary normalized brightfield z-stack image of a hiPSC colony in accordance with various implementations.

The cell imaging subsystem 5712A may be configured to acquire label-free images of the cell culture 5704A over time (for example, every 24 hours, or in another example, at a rate equal to more than two times the cell doubling rate). The cell imaging subsystem 5712A may employ imaging modes including but not limited to brightfield imaging, darkfield imaging, phase contrast imaging, differential interference contrast imaging, quantitative phase imaging, Fourier Ptychographic imaging, or combinations thereof. The cell imaging subsystem 5712A may acquire multiple images over the cell culture, with those images subsequently merged into a single larger image. In some implementations, the cell imaging subsystem 5712A may acquire a Z stack of images, with the Z stack subsequently used to better determine cell locations and cell data. An example of a normalized brightfield z-stack image of a hiPSC cell culture is shown in FIG. 58A. In some implementations, the cell imaging subsystem 5712A may use programmable illumination to provide illumination at multiple modes, angles, and/or colors. The cell imaging subsystem 5712A may employ CMOS, CCD, or other image sensors to capture images. The sensors may be area sensors or line sensors.

An example implementation of cell imaging subsystem 5712A may include a broadband LED-based brightfield illuminator that is configured to illuminate the cell culture 5704A in the cell culture container 5706A. The brightfield illuminator may have a 10× microscope objective (NA=0.3) that is mounted on a Z translation stage and a 5-megapixel 12-bit monochrome CMOS camera that is used to capture images of the cell culture at 3 Z levels near optimal focus for the cell culture 5704A (in this example, at Z=−5 microns, Z=0, and Z=+5 microns).

The images acquired by the cell imaging subsystem 5712A are generally of a resolution that at least allows the resolution of individual cells or nuclei within the cell culture. For example, for a 2D adherent cell culture, images may be acquired at a resolution equal to at least several times lower than the mean cell nuclear diameter, or the mean nuclear spacing, whichever is smaller. In an example implementation, when monitoring iPSC reprogramming from blood cells the nuclear diameters average around 9 microns, and mean nuclear spacing may become as low as 5 microns in very dense iPSC colonies. In this example, an imaging resolution of approximately 2 microns or lower is desirable in order to subsequently identify cell nuclei. In some implementations, the imaging resolution used to identify cells or cell components (e.g., organelles) is no more than about 10 microns, about 9 microns, about 8 microns, about 7 microns, about 6 microns, about 5 microns, about 4 microns, about 3 microns, about 2 microns, about 1 microns, or lower. In some implementations, the imaging resolution used to identify cell colonies is no more than about 25 microns, about 20 microns, about 15 microns, about 14 microns, about 13 microns, about 12 microns, about 11 microns, about 10 microns, about 9 microns, about 8 microns, about 7 microns, about 6 microns, about 5 microns, about 4 microns, about 3 microns, about 2 microns, about 1 microns, or lower.

The cell imaging subsystem 5712A may transmit the resulting image data to the computing subsystem 5710A via electronic or optical methods, which may be wired or wireless. The computing subsystem 5710A may include a number of software and/or hardware modules that perform the image analysis and cell editing determinations. For example, all of the components in the computing subsystem 5710A as illustrated in FIG. 57A may be implemented as software applications or routines. In another example, some of the components may be implemented in software while others may be implemented in hardware or a combination of software and hardware.

The computing subsystem 5710A may include an image normalizer 5702A that is configured to normalize all the received cell culture images. Normalization may include removal of local image artifacts or lighting conditions. For example, in the case of non-uniformity in illumination over a single image field, the image normalizer 5702A may remove this non-uniformity by means of bandpass filtering, local mean subtraction or division, or division by/reduction by a pre-measured image field. In another example, each image may be low-pass filtered to produce an image of the local lighting, in which the cutoff frequency for this low-pass is chosen to remove most or all cell-related features. Subsequently, in this example, the original image is divided by the low-pass result, producing an image that has been normalized to remove effects from local illumination or light capture conditions.

An image stitcher 5704A may receive the normalized images and is configured to produce a contiguous image from multiple images of the cell culture 5704A. For example, a single well of a microwell plate may require around 50 image frames to capture all areas of the cell culture with sufficient resolution. The image stitcher 5704A re-assembles these tiles into a single contiguous image for storage and subsequent processing. The resulting contiguous image may have dimensions beyond 2-dimensional axes. Examples of other axes may include but are not limited to Z axis (from multiple Z slice images), illumination or capture color channel, illumination or capture angle and combinations to make 3- or higher-dimensional data volumes.

An important consideration is the sheer data volume that may be generated at the point. In a relatively simple example in which a single well of a 96-well microplate is imaged at 5 Z positions, with imaging performed at 1 micron resolution and with an output format of 16 bits, the resulting data volume for a single imaging pass is roughly 50 Megabytes. This results in almost 5 Gigabytes of data for a single pass over the plate. Cell culture processes performed herein may last upwards of 30 days, with images captured daily or more, so data volumes of hundreds of Gigabytes are possible. This amount of data would be extremely difficult to analyze or model directly against the biological results of the cell culture process. As a result, most current approaches have used only snapshots of image data for this purpose. However, this sampling or single-timepoint approach loses a vast portion of the potentially relevant data in the cell culture. The computing subsystem 5710A includes a number of modules designed to distill this data into a much smaller amount of information that nonetheless captures all the critical features of the cell culture 5704A.

For example, the computing subsystem 5710A may include a cell locator 5706A that performs the first step towards transforming large volumes of imaging data into a much more compact representation of the cell culture 5704A. The cell locator 5706A may be configured to receive the stitched image of the cell culture 5704A and to first segment the images to identify cells or nuclei, and then to extract their center coordinates and potentially nuclear envelopes from the segmented image. The cell locator 5706A may utilize conventional image processing and/or neural network-type processing to perform these functions. In an example, image information from five or more Z slices may first be combined into three images. These three images are then input, in tile form, into a convolutional neural network that has been pre-trained with sets of label-free images and corresponding fluorescent nuclear-stained images. An example of a convolutional network architecture used for this task is U-Net. The network produces a single image corresponding to the predicted corresponding nuclear fluorescence image. This image is subsequently thresholded, and watershed morphological image processing is used to determine the centroid of each nucleus, as well as the corresponding nuclear envelope. As an example, FIG. 58B shows an output of a deep learning neural network that has been trained to predict nuclear stains from brightfield z-stacks.

The cell location data generated by the cell locator 5706A may be stored in an instant cell features database 5708A. "Instant" in this case means location data from a single imaging timepoint. The data stored in the instant cell features database 5708A may include, for each cell, the coordinates of the cell in the observed portion of the cell culture 5704A and the time at which the data was obtained. It may also include other data such as cell or nuclear envelope information, which may either be a polygon representing the envelope or a feature description of the shape.

Additional cell features may be extracted and added to the instant cell features database 5708A by one or more cell feature predictors 5710A. The cell feature predictors 5710A may make further predictions at the cell or regional level based on prior training. For example, the cell feature predictors 5710A may be trained with a series of brightfield images together with corresponding fluorescently-labeled images staining for cell pluripotency, the images received from the image stitcher 5704A. The cell feature predictors 5710A may then produce an image of this predicted fluorescence, and use the previously-extracted XY coordinates for each cell to calculate the local mean "virtual" fluorescence, and add the resulting feature to the cell record in the instant cell feature database 5708A. Other cell features may be calculated directly from the instant cell feature database 5708A and added to the cell records for convenience (for example, a calculation of the local cell density at various scales).

The cell locator 5706A and cell feature predictor 5708A may utilize a range of processing algorithms including, but not limited to: predictive models for semantic segmentation trained with supervised, unsupervised, and semi-supervised methods based on learned representations derived from morphological features by the application of deep learning models (e.g., multilayer perceptrons and convolutional neural networks, including fully-connected networks, such as Mask R-CNN, networks with expansive-path/contractive-path architectures (such as U-Net), with and without residual connections, trained with a multiplicity of objective functions (such as focal loss, cross-entropy loss, and mean square error loss)), using various optimizers in sequence and/or in combination (such as stochastic gradient descent with and without momentum, RMSProp, Adagrad, and Adam) with various learning rate schedules, and ensembles of models trained with the foregoing methods, together with image-processing algorithms for the generation of training examples for the supervised and semi-supervised training regimes, as well as image-based post-processing and refinement of the semantic segmentation masks derived from the deep-learning models.

A colony locator 5712A may be configured to use the instant cell locations stored in the instant cell feature database 5708A to calculate the bounds of colonies within the cell culture 5704A. A colony of cells may include any subset, cluster, or region of the cell culture 5704A. This process may be performed using local density calculations and may also use additional features extracted by cell feature predictors 5710A (for example, a prediction of pluripotency). The colony locator 5712A establishes the bounds of each colony, typically in the form of a polygon.

Each colony record is then stored in an instant colony features database 5714A. Additional colony properties may be calculated using colony feature calculator(s) 5716A. For example, various statistics regarding the cells contained in the colony may be determined or estimated, including count, density, mean virtual fluorescence predictions, and other measures. In addition, geometric features of the colony may be calculated from the cell locations and/or outline polygon.

As a time series of images is collected, a colony tracker 5718A associates successive instant colonies with one another, in order to produce persistent records of colonies, which are stored in a tracked colony features database 5722A. For example, the colony tracker 5718A may determine that a cell colony that is at roughly the same location between two time-series images is the same colony. The colony may then be assigned a number or some other indicator, and information about the colony at each point in time may be associated with each other and stored together. The tracked colony features of a colony may include a series of instant colonies in the instant colony features database 5714A, such that a time-series of instant colony feature may be reconstructed. However, it may be desirable to pre-compute and store a range of features for tracked colonies, including centroid trajectory, cell count history, area history, shape factor history, etc. These features, together with cell statistic features, may be calculated using one or more tracked colony feature calculators 5722A, and added to the appropriate tracked colony record in the tracked colony features database 5722A. FIGS. 58C-H provide an illustrative example of brightfield image z-stack slices of a hiPSC colony proliferating over about 65 hours and the corresponding image with calculated polygons delineating determined colony areas.

The databases in the computing subsystem 5710A (e.g., the instant cell features database 5708A, the instant colony features database 5714A, and the tracked colony features database 5722A) may be relational in a manner that allows features to be traced back to their origin. In other words, tracked colonies are related to the instant colonies that make them up, which are related to the instant cell features that compose them, which can be traced back to specific regions of pixels in the image data.

At this point the vast volume of image time series data has been reduced to a small set of features per tracked colony. This allows a colony outcome predictor 5724A to operate efficiently, and importantly to be trained with a reasonably small dataset. The colony outcome predictor 5724A is configured to use the tracked colony features in the tracked colony features database 5722A to predict outcomes for the colony in terms of phenotype, functionality, genotype, pluripotency, purity, proliferation rate or other product characteristics. The colony outcome predictor 5724A may calculate a score for each colony, the score representing the likelihood that the colony is or will produce high quality cell output products 5718A. The colony outcome predictor 5724A may be driven by a statistical cell outcome model 5726A that has been optimized with a set of tracked colony features from the tracked colony features database 5722A and corresponding output cell product assay results 5728A, which are in turn generated for each output cell product 5718A using output cell product assays 5720A. The colony outcome predictor 5724A and statistical outcome model 5726A may use one of a number of machine learning methods including, but not limited to, logistic and multinomial regression, ordinal logistic regression, support vector machines, classification and regression trees, random forests, boosted trees, principal components analysis, independent components analysis, k-means, hierarchical, density-based, and neighborhood-based clustering, autoregressive models, gaussian process fitting, hierarchical Bayesian models, probabilistic graphical models, methods from topological data analysis such as persistent homology, deep learning models, including multilayer perceptron models and recursive neural networks, reinforcement-based models such as genetic algorithm models and virtual ant colony methods, as well as ensembles and cascades of these methods together with heuristics and rules-based methods to predict quantitative and qualitative colony outcomes based on the extracted features stored in the tracked colony database 5722A and output cell product assay results 5728A.

In the case where colonies or regions of cells should be removed from the cell culture 5704A in order to make space for cells/regions with higher predicted scores and/or to ensure clonality of the product, a colony editor 5730A may be configured to select regions or colonies to be removed from the cell culture 5710A. The colony editor 5730A may drive the editing subsystem 5714A that is capable of removing cells, colonies, or regions of cells. The colony editor 5730A may also terminate a cell culture in order to dispose of it or to harvest output cell products 5718A. In some implementations, the colony editor 5730A may also control various actuators or other controls (e.g., controls 116) to manipulate other environmental parameters within the cell culture container 5706A. For example, the colony editor 5730A may control functions such as shifting reagents or changing parameters such as temperature, pH, $O_2$, nutrients, and media feed rate. The result of this editing operation should be that the net predicted score for the cell culture 5704A is raised, and/or space in the cell culture container 5706A is opened for the remaining (predicted) higher-scoring cells.

Figure 57B:
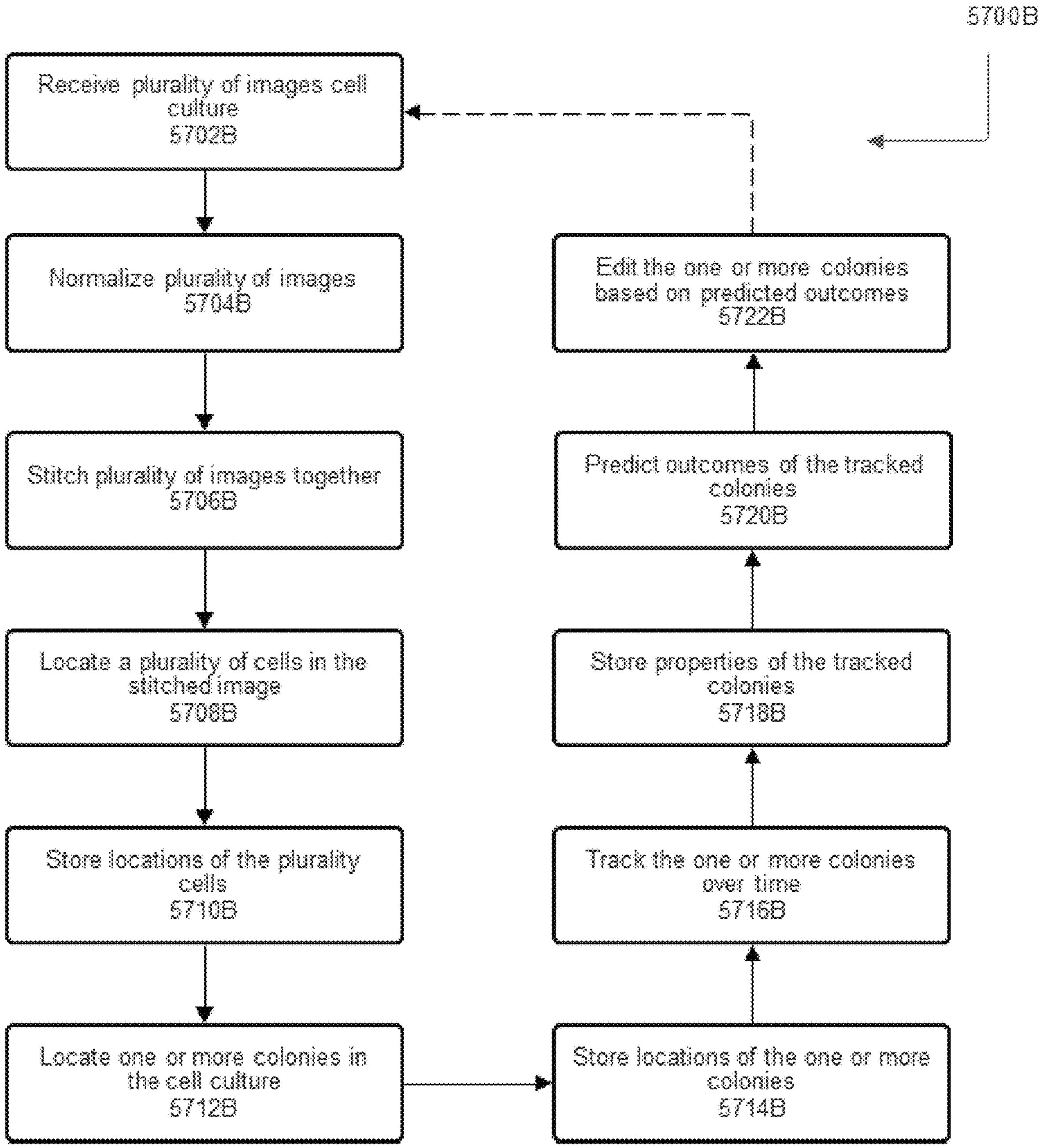
FIG. 57B is a flow chart of a method of controlling a cell culture in accordance with various implementations.

FIG. 57B is a flow chart of a method 5700B of controlling a cell culture in accordance with various implementations. The method 5700B may be performed by a computing subsystem of a cell culture system (e.g., computing subsystem 110 in cell culture system 100). The method 5700B may also the cell culture system to automatically monitor and edit the cell culture during a cell culture process.

In block 5702B, the computing subsystem may receive a plurality of images of the cell culture in a cell culture container. The images may be received from a cell imaging subsystem (e.g., cell imaging subsystem 112) that collects the plurality of images. The plurality of images may collectively image the cell culture. The cell imaging subsystem may utilize one of a variety of imaging methods to capture the images, including brightfield imaging, phase imaging, darkfield imaging, transmission imaging, reflection imaging, quantitative phase imaging, holographic imaging, two-photon imaging, autofluorescence imaging, Fourier ptychographic imaging, defocus imaging or any other implementations known to persons of ordinary skill in the art. Before image analysis of the plurality of images, the computing subsystem may perform a number of preprocessing steps, as described with reference to blocks 5704B-5706B.

In block 5704B, the computing subsystem may normalize the plurality of images. Normalization may include removal of local image artifacts or other irrelevant lighting effects or conditions from the images in order to obtain clear images of the cell culture.

In block 5706B, the computing subsystem may stitch together the plurality of images in order to form a single image of the cell culture. The stitched image may be 2D image of the cell culture, or may include 3-dimensional aspects as well. Each of the plurality of images may be associated with location data that may be used to stitch the images together properly.

In block 5708B, the computing subsystem may locate a plurality of cells in the stitched image. The stitched image may represent the state of the cell culture at a specific point in time. A variety of image processing and/or neural network-type processing may be used to locate the plurality of cells. The location of a cell may be represented as coordinates of the nucleus or center of the cell, and may also include nuclear envelope information as well. A cell feature predictor may be utilized, which uses prior imaging data as well as training set data that allows the computing subsystem to distinguish individual cells from other cells and background images, and to determine a coordinate representing the location of the cell. The cell feature predictor may improve over time as more data is analyzed so that the predictor becomes more accurate.

In block 5710B, the location of the plurality of cells may be stored. For example, the location data may be stored in an instant cell feature database which records the location of each cell at each instant of time at which the plurality of images (and the resulting stitched image) are collected.

In block 5712B, the computing subsystem may identify one or more cell colonies in the stitched image. A cell colony may be any grouping, subset, or region of the cell culture. A colony feature calculator may be utilized to distinguish cell colonies from each other and from background images. The colony feature calculator may utilize cell location data, prior imaging data as well as training set data to accurately identify distinct cell colonies within the stitched image. A cell colony may be defined by shape and location data, as well as other data conveying information about the cell colony.

In block 5714B, information about each cell colony may be stored. For example, the cell colony data may be stored in an instant colony features database which records the location and properties of each cell colony at each instant of time at which the plurality of images (and the resulting stitched image) are collected.

In block 5716B, the computing subsystem may track the one or more colonies over time. This may include iterating the steps in blocks 5702B-5714B at a number of points in time in order to collect time-series cell colony data. The computing subsystem may utilize a tracked colony feature calculator to determine the cell colonies in the images over time. All data associated with the same cell colonies may be associated with each other in order to produce time-series data about the growth and changes of the cells and cell colonies over time. The tracked colony feature calculator may utilize instant colony feature data, prior imaging data, and training set data to accurately identify the same colonies over time.

In block 5718B, the times-series data about each tracked colony may be stored in a database. For example, the tracked cell colony data may be stored in a tracked colony features database which records the location and properties of each cell colony over time.

In block 5720B, the computing subsystem may predict outcomes of each tracked colony in the cell culture. For example, the computing subsystem may generate an outcome score based on the time-series tracked cell colony data. The outcome score may represent the likelihood that a particular cell colony may successfully produce the desired output cell product at a future time. A cell outcome model may be utilized to generate the outcome score. The outcome score may be based on a number of data sources, including the time-series tracked colony data of the current cell culture, tracked colony data from prior cell culture processes of the same type, output cell product assay data, and training set data.

In block 5722B, the computing subsystem may edit one or more of the tracked colonies based on the predicted outcome for the tracked colonies. For example, if an outcome score of a cell colony indicates that it is a low quality colony that is unlikely to produce the desired output cell product, the computing subsystem may instruct a cell editing subsystem (e.g., cell editing subsystem 114) to remove the low quality colony. In another example, the computing subsystem may determine that two cell colonies will soon overlap and instruct the cell editing subsystem to remove the cell colony with a lower outcome score in order to provide more space for the remaining cell colony to grow. Editing may encompass other functions that effect cell colony growth, such as transferring cargo into and out of cells, or changing environmental parameters of the cell culture container.

The method 5700B may repeat itself iteratively throughout the cell culture process until the output cell product is completely harvested, or the cell culture is disposed of in its entirety. In this manner, the method 5700B provides automated and dynamic tracking, prediction, and control of the cell culture process. This eliminates the need for manual human intervention and lessens the potential for contamination from these interventions, and also increases the speed at which cell cultures are processed. Finally, by reducing high density imaging data into low density cell colony data, the method 5700B reduces the need to store, transfer, and analyze large quantities of data.

Figures 58C, 58D, 58E, 58F, 58G, 58H:
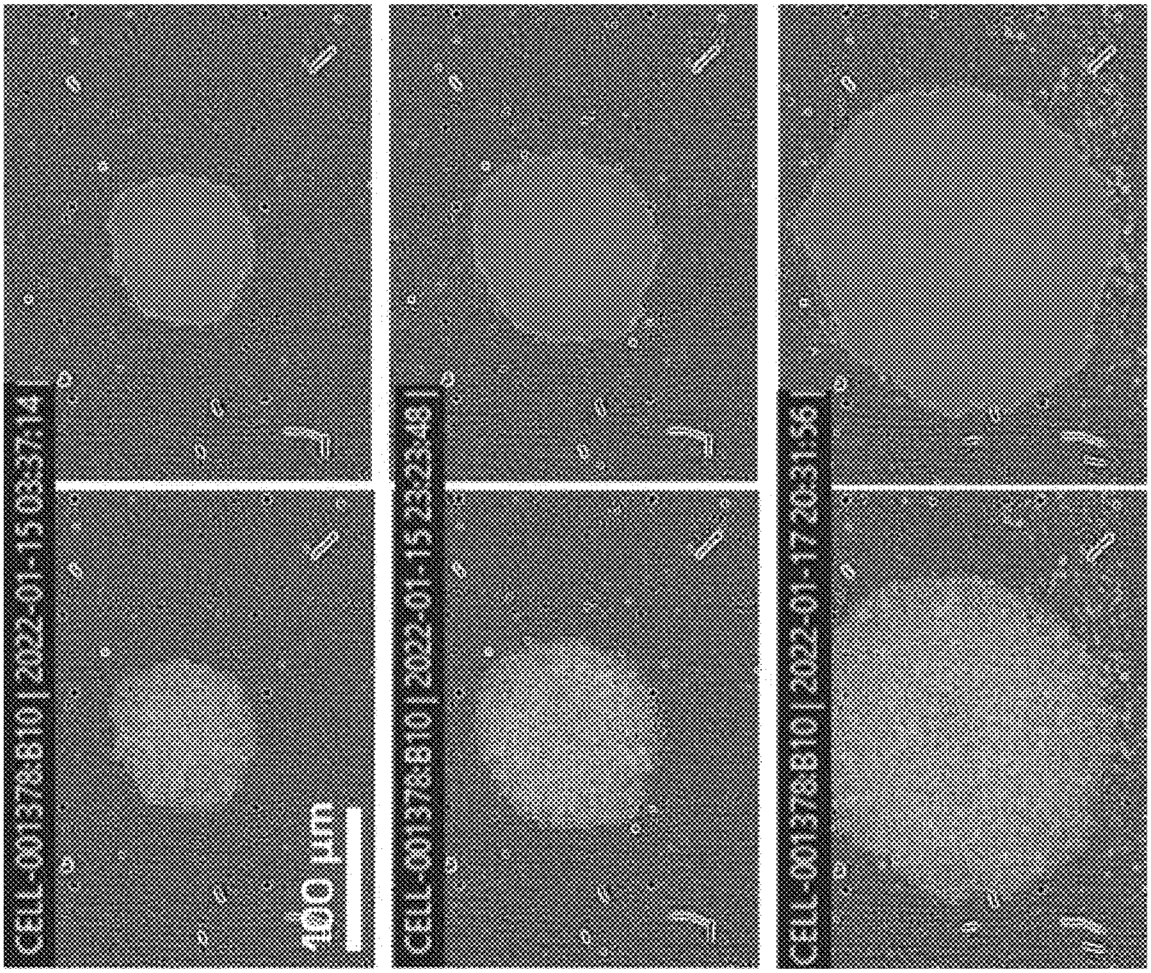
FIG. 58C shows a first exemplary brightfield image z-stack slice of a hiPSC colony proliferating over about 65 hours in accordance with various implementations.
FIG. 58D shows the image of FIG. 58A with polygons delineating determined colony areas in accordance with various implementations.
FIG. 58E shows a second exemplary brightfield image z-stack slice of a hiPSC colony proliferating over about 65 hours in accordance with various implementations.
FIG. 58F shows the image of FIG. 58C with polygons delineating determined colony areas in accordance with various implementations.
FIG. 58G shows a third exemplary brightfield image z-stack slice of a hiPSC colony proliferating over about 65 hours in accordance with various implementations.
FIG. 58H shows the image of FIG. 58E with polygons delineating determined colony areas in accordance with various implementations.

The computing system shown in FIG. 57A may be used to implement the method shown in FIG. 57B in order to generate images such as those shown in FIGS. 58A-58H. FIG. 58A shows an exemplary normalized brightfield z-stack image of a hiPSC. FIG. 58B shows an exemplary output of a deep learning neural network that has been trained to predict nuclear stains from brightfield z-stacks, after thresholding. FIG. 58C shows a first exemplary brightfield image z-stack slice of a hiPSC colony proliferating over about 65 hours. FIG. 58D shows the image of FIG. 58A with polygons delineating determined colony areas. FIG. 58E shows a second exemplary brightfield image z-stack slice of a hiPSC colony proliferating over about 65 hours. FIG. 58F shows the image of FIG. 58C with polygons delineating determined colony areas. FIG. 58G shows a third exemplary brightfield image z-stack slice of a hiPSC colony proliferating over about 65 hours. FIG. 58H shows the image of FIG. 58E with polygons delineating determined colony areas.

Unsupervised Attribute Classification

In many adherent or semi-adherent cell culture processes it is desirable to classify cells or regions of cells automatically to control the development of the cell culture. Once cells are classified according to various attributes, decisions may be made regarding the cell culture process. For example, cells of the wrong phenotype or cells with undesirable mutations or behavioral patterns may be identified and removed from the cell culture.

Such a classification system should have several capabilities to function within a cell culture system, particularly a system that is automated. For example, the automated classification system should be able to extract visual data patterns from image or image timeseries data that correlate to high quality cells or cell colonies. Measures of high quality may be defined based on biological quality control (QC) assays and expert interpretation of such QC assay data in the context of desired biological processes (e.g., differentiation to iPSC cells, reprogramming of iPSC cells, or differentiation to dopaminergic neurons). High quality may also be defined based on cell staining/fixing and imaging cells in such labeled modalities that capture and highlight a desired property of the cell.

Correlations of image data to attribute classifications may be learned in an offline manner from data collected for training purposes, or in an online manner from data collected during cell manufacturing process, or a combination of offline learning and online continuous updates to learned correlations. An automated classification system with online and/or offline learning should learn to map the visual data patterns acquired from label-free image or image timeseries data to data patterns acquired from biological QC assays and labeled-image data.

An automated classification system that is integrated into a cell culture system should be configured to extract the relevant visual data patterns from label-free image or image timeseries data captured in non-invasive ways and without staining or fixing the cells. The automated classification system should also be configured to extract the relevant visual data patterns from label-free image or image timeseries data without the need for manual expert guidance or supervision such as annotation, labeling, or delineation of cells or regions of cells. In addition, a cell culture system utilizing an automated classification system should be configured to control a submodule for selective lysing and removal of cells from a cell culture and carry out biological QC assay data collection based on the output of the online learning system. For example, the cell culture system may lyse cells in a spatially selective manner according to image or image time series characteristics that have been acquired using a cell imaging subsystem.

The automated classification system should also be configured to extract visual data patterns from label-free image or image timeseries data which are relevant to the task of quality assessment of cells or cell colonies or cell groups. Finally, the automated classification system should be configured to classify cells in a non-invasive manner such that the cell culture container does not need to be opened during the process.

The systems and methods disclosed herein provide ways of controlling a cell culture system using an automated classification system with unsupervised learning and inference aspects. In unsupervised learning, relevant visual patterns of imaging data are discovered automatically from a large amount of data and no human supervision is required. In this framework, a large dataset of label-free images may be collected by the imaging subsystem from many cell cultures of a given cell type undergoing a particular biological process. An unsupervised learning engine may be configured to output visual categories that correspond to clusters of spatio-temporal features automatically discovered in that dataset. These visual categories may be indicative of attributes or cell quality of the cell culture (e.g., dense or sparse cell growth, cell morphology, cell division rate, cell motility). The visual categories may be associated with one or more categories of cell quality attributes based on expert interpretation of observed image patterns in members of the output visual categories or based on QC or labeled-image data collected from the members of the output visual categories. An unsupervised inference engine may then generate cell quality attribute maps that annotate the cell culture images automatically. This information may be used by the cell culture system to make decisions about altering cell culture parameters, destroying certain cells or cell regions, collecting additional cells and/or cell contents for assays or testing, and other actions. The unsupervised learning engine for visual classification may use one of a number of machine learning methods including, but not limited to, principal component analysis, autoencoders, variational autoencoders, generative adversarial networks and deep metric learning.

The unsupervised classification system has several advantages over prior art solutions. For example, the unsupervised learning engine may be retrained relatively quickly when there are changes in the cell culture system's imaging protocols and/or hardware. If manual annotation/labeling were used, it would have to be repeated each time system protocols or hardware change. In addition, the unsupervised system is capable of handling multiple imaging modalities, z-slices, or t-slices by changing the number of input channels and thereby increasing the dimensionality of the input space to be encoded in an unsupervised manner. The amount of training data that the unsupervised learning engine utilizes increases substantially as the space dimension increases and so there is a trade-off in configuring the input channels and the training data needs. However, an automated cell culture system can collect large amounts of image data relatively quicker if manual annotation or supervision is not required to label each training sample.

Furthermore, the visual categories learned in unsupervised ways may be as granular as desired and the learning engine may be tuned to pick up on very subtle spatio-temporal differences in cell regions. Such emerging categories may be mapped into colony/cell behavior attributes that relate to desired/undesired aspects of the cell culture. Multiple visual categories may be mapped to the same behavioral attribute and so over-categorization in the visual domain is harmless. In this way, subtle behavioral changes may be caught by the system that may overwise not be possible to catch through human observation of the imaging data. Previously unknown spatio-temporal patterns may also be discovered in a completely automated and unsupervised manner.

Finally, unsupervised model parameters may be learned for each cell type by collecting data from cultures of that cell type. Introducing a new cell type into the system would be relatively easy in the sense that manual annotations are not needed to categorize visual patterns from this new cell type. The system would train on label-free images of the new cell type and have new emergent visual categories for the new cell type.

Figure 59:
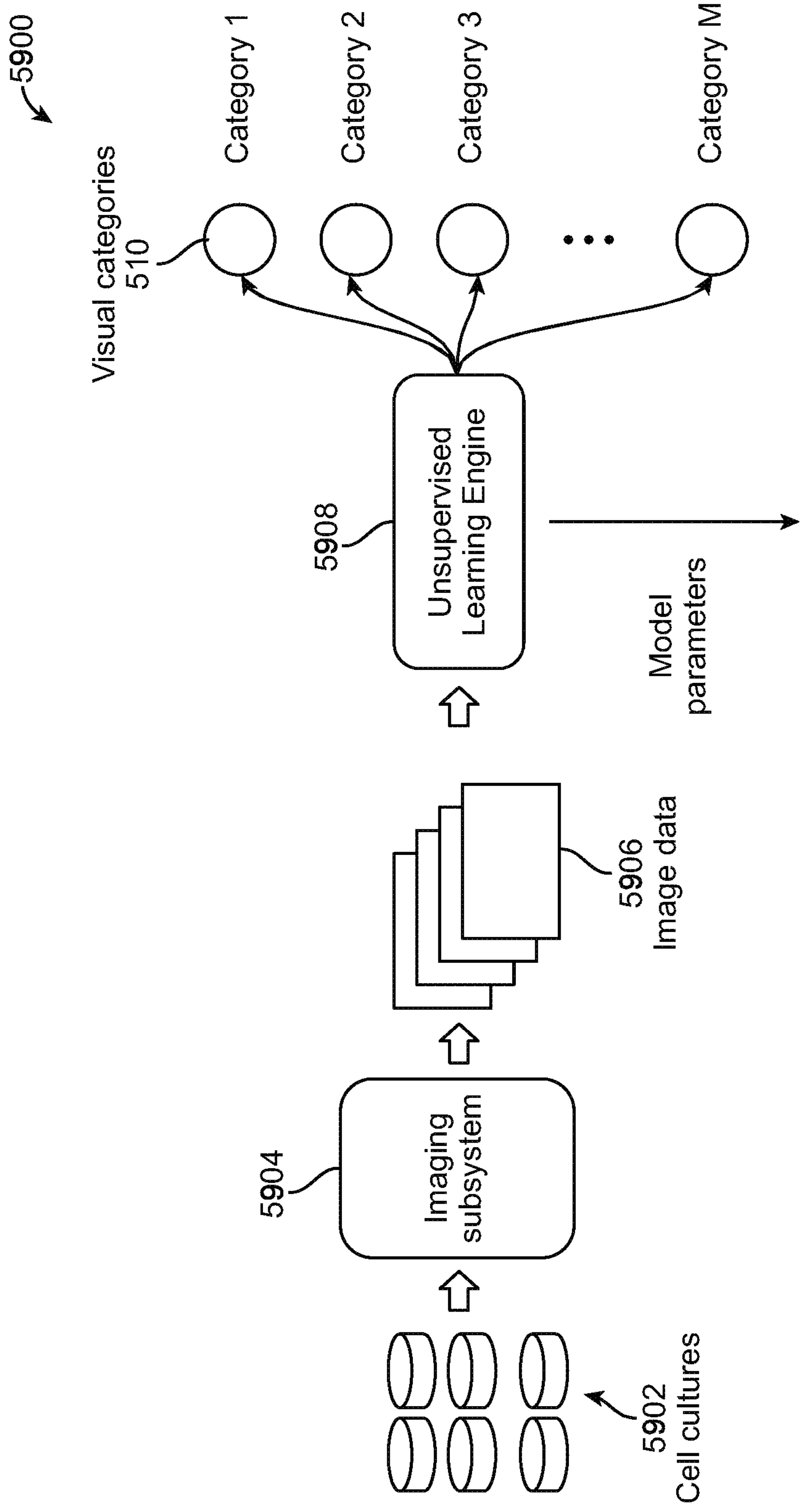
FIG. 59 is a block diagram of an automated classification system in a cell culture system in accordance with various implementations.

FIG. 59 is a block diagram of an automated classification system 5900 in a cell culture system in accordance with various implementations. The automated classification system 5900 may include different subsystems of the cell culture system such as an imaging subsystem (e.g., cell imaging subsystem 112), a lysing or removal subsystem (e.g., cell editing subsystem 114), and a computing subsystem (e.g., computing subsystem 110). FIG. 59 illustrates the operation of the automated classification system 5900 during the learning phase. One or more cell cultures 5902 are cultured in the cell culture system. The cell cultures 5902 may contain cells of the same cell type, and each cell culture 5902 may include one or more cell colonies, regions, or groups. An imaging subsystem of the automated classification system 5900 (e.g., cell imaging subsystem 112) may image the cell cultures 5902 to produce image data 5906. The image data 5906 may be label-free images of the cells, cell colonies, or cell regions.

An unsupervised learning engine 5908 may take the image data 5906 and produce a plurality of visual categories 5910 (e.g., categories 1 through M). The unsupervised learning engine 5908 may be part of the computing subsystem (e.g., computing subsystem 110). The unsupervised learning engine 5908 may identify similar visual features or patterns from the image data 5906 and generate visual categories 5910 for each similar visual feature/pattern that appears throughout the image data 5906. The visual categories 5910 may include, but is not limited to, low intercellular spacing, high intercellular spacing, high density of nucleoli, and cells at different stages of growth (e.g., undifferentiated, differentiated), cells with different cell division rates, and cells with different phenotypes. Each cell type may have different visual features, thus for each cell type there may be an associated plurality of visual categories 5910. In unsupervised learning, the visual categories 5910 may be discovered automatically from the image data 5906 without human or other kinds of supervision. The image data 5906 may be divided into image patches of a pre-determined size and each image patch may be passed through the unsupervised learning engine 5908 to train a classification model.

Cell colonies from each cell type present unique visual features that correlate to desired or undesired growth and behavior for individual members or cell groups of that cell type. For example, researchers have identified several visual features that correlate to the typical morphology of healthy, undifferentiated iPSC colonies such as prominent nucleoli, less intercellular spacing, and no spontaneously differentiated cells. Label-free images of iPSC colonies may be represented as smaller image patches and each image patch may be broadly manually labeled as good, moderate, or poor quality in terms of the visual appearance of the cells in that image patch. Thus, each visual category 5910 may be manually associated with one or more attribute categories that provide information about the attributes of the cells in that visual category. The attribute categories may include quality attributes (e.g., high quality, medium quality, low quality cells) or other attributes of cells or cell colonies/regions that may be relevant to cell culture process decisions (e.g., whether to remove certain cells from a cell culture or extract cells for assay profiling).

The unsupervised learning engine 5908 may generate model parameters that are passed to an unsupervised inference engine 5912. The unsupervised inference engine 5912 may be part of the computing subsystem (e.g., computing subsystem 110). The model parameters may include the visual categories 5910 and associated attribute categories. The unsupervised inference engine 5912 may take the model parameters and the image data 5906 as input and generate labeled images annotated with the attribute categories. For example, the unsupervised inference engine 5912 may identify the visual categories 5910 within the image data 5906, identify instances of the visual categories 5910 within each image, and annotate those sections of the image with the associated attribute category. The output of the unsupervised inference engine 5912 may be attribute maps of the cell cultures 5902, in which different cells and cell region/colonies are labeled according to their attributes. This output may be used by the cell culture system to determine whether certain cells or cell regions/colonies should be edited (e.g., removed), to identify cells that may be assayed for additional information, whether parameters of the cell culture growth process should be changed, or other decisions.

Figure 60:
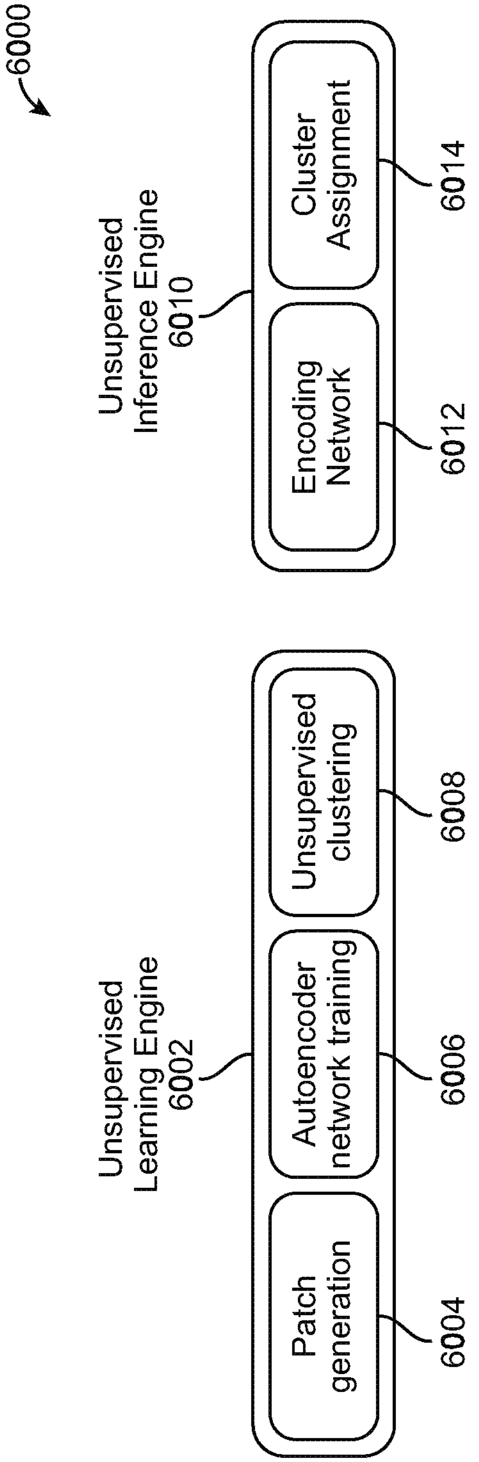
FIG. 60 is a block diagram of components in an automated classification system in accordance with various implementations.

FIG. 60 is a block diagram of components in an automated classification system 6000 in accordance with various implementations. The automated classification system 6000 may be similar to the automated classification system 5900 in FIG. 59 and may include two main engines: an unsupervised learning engine 6002 and an unsupervised inference engine 6010. The unsupervised learning engine 6002 may include a patch generation module 6004, an autoencoder network training module 6006, and an unsupervised clustering module 6008. The unsupervised inference engine 6010 may include an encoding network module 6012 and a cluster assignment module 6014.

The patch generation module 6004 may be configured to receive label-free images and divide them into image patches. The size of the patch may be predetermined (e.g., 64 pixels by 64 pixels), and it should be large enough to capture sufficient visual feature patterns but small enough to limit the input space dimension. The patch may have dimensions in the X and Y planes (e.g., 2D image plane of the cell culture surface), but may also encompass the Z dimension (focus level) and T (timepoint), and wavelength cases where hyperspectral, Raman, autofluorescence, or fluorescently-labelled imaging is used.

The autoencoder network training module 6006 may be configured to learn a low dimensional encoding space from the much higher dimensional input image patch space. Autoencoding networks are a class of algorithms in machine learning that are used for various computer vision tasks to discover latent state spaces that relate to the task. Variational auto-encoders (VAEs) and Generative Adversarial Networks are two example neural network architectures that are commonly used. Similarly, there are well established unsupervised clustering techniques such as k-means or tSNE that may be applied to the data mapped to the encoding space to create visual clusters.

Cells at various states of the cell culture process may exhibit behavior that creates homogenous visual/temporal patterns among the cells of the same state. This allows the autoencoder network training module 6006 to efficiently represent this state information as an abstraction over the much higher dimensional image space. Cells which are in different states (e.g., one state may be desirable, such as having prominent or abundant nucleoli, but another state may be undesirable, such as large inter-cellular spacing indicative of spontaneous differentiation) will exhibit different spatio-temporal patterns and would be encoded into different portions of the encoding space. Autoencoders have the ability to effectively discover such underlying abstractions or states in datasets and create very efficient (low-dimensional) encoding spaces.

In some implementations, each image patch may have multiple data channels that correspond to various image modalities given by the imaging subsystem (e.g., z-slices or t-slices) and/or timeseries image data. Thus, the number of input channels to autoencoders may be increased to include timeseries images of the patch and thus enable spatio-temporal encoding of patches. Such spatio-temporal encoding may capture cell stacking behavior, mobility, proliferation, and change characteristics in various portions of a cell colony, which may correlate with unhealthy growth, mutation, or non-clonal origin.

The unsupervised clustering module 6008 may be configured to apply unsupervised clustering (e.g., k-means) to the encoded features of the lower dimensional image patch data generated by the autoencoder network training module 6006 to identify visual categories. In other words, the unsupervised clustering module 6008 may identify similar visual features across image data and classify those features into the same category. By using an unsupervised approach, a large number of visual patch classes may be learned across many cell culture images and may reveal previously unknown visual patterns that correlate with various colony attribute indicators.

The visual categories generated by the unsupervised learning engine 6002 may be associated with attribute categories through human intervention. For example, a person may review each visual category and assign one or more cell quality attributes to the visual category. The attributes may include healthy behavior measures or other attributes relevant to determining the successfulness of the cell culture process. Additional information may also be used to help associate visual categories with cell quality attribute categories. For example, assay profiles of the imaged cells or labeled images of the cells (e.g., via staining) may provide additional information for determining attributes of the cells.

The unsupervised inference engine 6010 may take as input the label-free images of the cell culture and product an output cell quality attribute map (i.e., labelled image). The encoding network module 6012 in the unsupervised inference engine 6010 may be configured to use model parameters learned by the autoencoder network training module 6006 during learning phase. The cluster assignment module 6014 may be configured to use the model parameters learned by the unsupervised clustering module 6008 during the learning phase. The output of the unsupervised inference engine 6010 may be an attribute map or image of the cell culture that is annotated with the cell attribute categories in the appropriate locations. The output may be used by the cell culture system to make cell editing, assay, and other cell culture process decisions.

Figure 61:
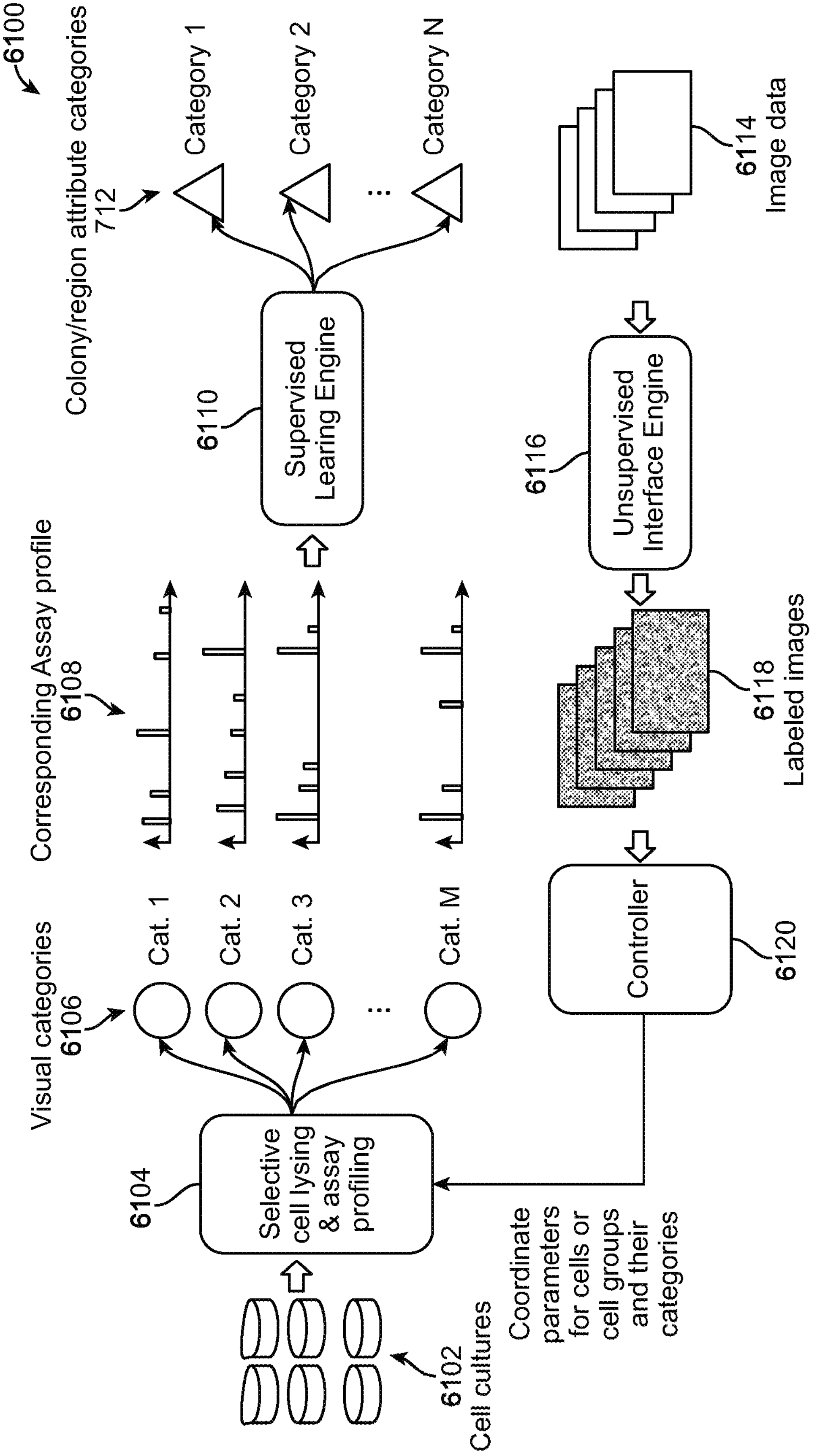
FIG. 61 is a block diagram of an automated classification system learning to associate visual categories to cell attribute categories by means of a cell lysing and assay methodology in accordance with various implementations.

FIG. 61 is a block diagram of an automated classification system 6100 learning to associate visual categories previously discovered by an unsupervised learning engine from label-free images to cell attribute categories by means of a cell lysing and assay methodology in accordance with various implementations. The automated classification system 6100 may include different subsystems of the cell culture system such as an imaging subsystem (e.g., cell imaging subsystem 112), a cell lysing or removal subsystem (e.g., cell editing subsystem 114), and a computing subsystem (e.g., computing subsystem 110). FIG. 61 illustrates the operation of the automated classification system 6100 during the attribute association phase being trained on QC assay data of samples collected from each visual category. One or more cell cultures 6102 are cultured in the cell culture system. The cell cultures 6102 may contain cells of the same cell type, and each cell culture 6102 may include one or more cell colonies, regions, or groups. The cell culture system may be configured to perform selective cell lysing and assay profiling functions 6104 (e.g., using the cell editing subsystem 114) of the cell cultures 6102 to acquire assay profile data 6108 of each visual category (e.g., categories 1 through M). For example, select cells may be dislodged and flushed from the cell cultures 6102 and assays are performed on the extracted cells.

Specifically, an unsupervised inference engine 6116 initialized with model parameters learned by an unsupervised learning engine may take as input label-free image data 6114 of the cell cultures 6102 and produce labeled visual category maps 6118. The labeled images 6118 may be provided to a controller 6120 which determines the coordinates for cells and cell regions/colonies expressing same visual categories. The controller 6120 may control a cell editing subsystem (e.g., cell editing subsystem 114) to selectively remove cells expressing same visual categories from the cell cultures 6102, for lysing and assaying, or other cell culture processes. For example, for each visual category 6106 the cell culture system may select a representative group of cells from the cell culture 6102 and lyse those cells and perform assays on them. In this way, a certain amount of assay profile data can be collected for each visual category in 6106 that is statistically sufficient to run further analysis.

Given sufficient assay profile data from each visual category, a supervised learning engine 6110 may be utilized to associate cell colony/region attribute categories 6112 to the visual categories 6106 with the aid of human intervention. For example, a portion of the assay profile data 6108 from all of the visual categories 6106 may be reviewed and categorized into attribute categories 6112 manually. This manually annotated subset may be used to train a classifier that learns to map assay profile data 6108 to the attribute categories 6112. The attribute categories 6112 may include any number of desirable or undesirable attributes in the context of the cell culture process on the specific cell type. Once a classifier is trained, each assay data sample from a given visual category 6106 may be classified and a consensus voting among all sample data from this visual category may determine the association of that visual category to one of the attribute categories 6112. Note that an off-the-shelf assay data classifier may be used by this attribute learning method and/or the classifier does not need to be trained on the data collected via the procedure described herein. Furthermore, the classifier may also be a simple rule-based algorithm which operates based on pre-configured rules specified by biology experts, for example checking for expression of a certain protein more than a specified quantity.

Figure 62:
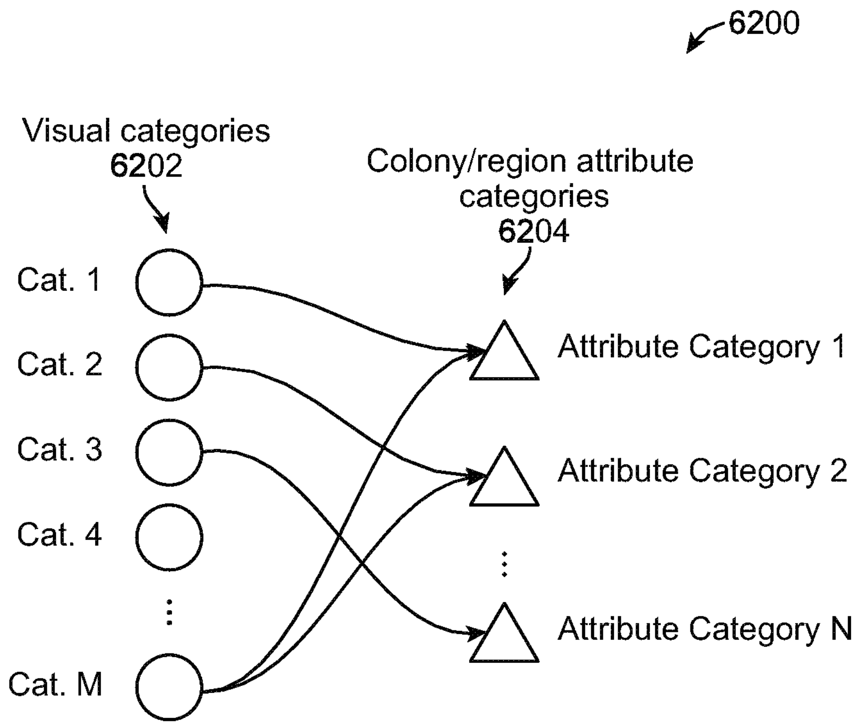
FIG. 62 is a block diagram showing an example association of visual categories to attribute categories in accordance with various implementations.

FIG. 62 is a block diagram showing an example association of visual categories 6202 (1 through M categories) to attribute categories 6204 (1 through N) in accordance with various implementations. This mapping may be similar to the association performed by an automated classification system when learning from label-free (FIG. 61) or labeled (FIG. 63) image data. In other words, each visual category 6202, along with assay profile information if available, may be mapped to one or more attribute categories 6204. This association may be supervised, i.e., done with human intervention. Note that a large number of visual categories may be associated to only a few cell attribute categories (i.e., M>>N).

Figure 63:
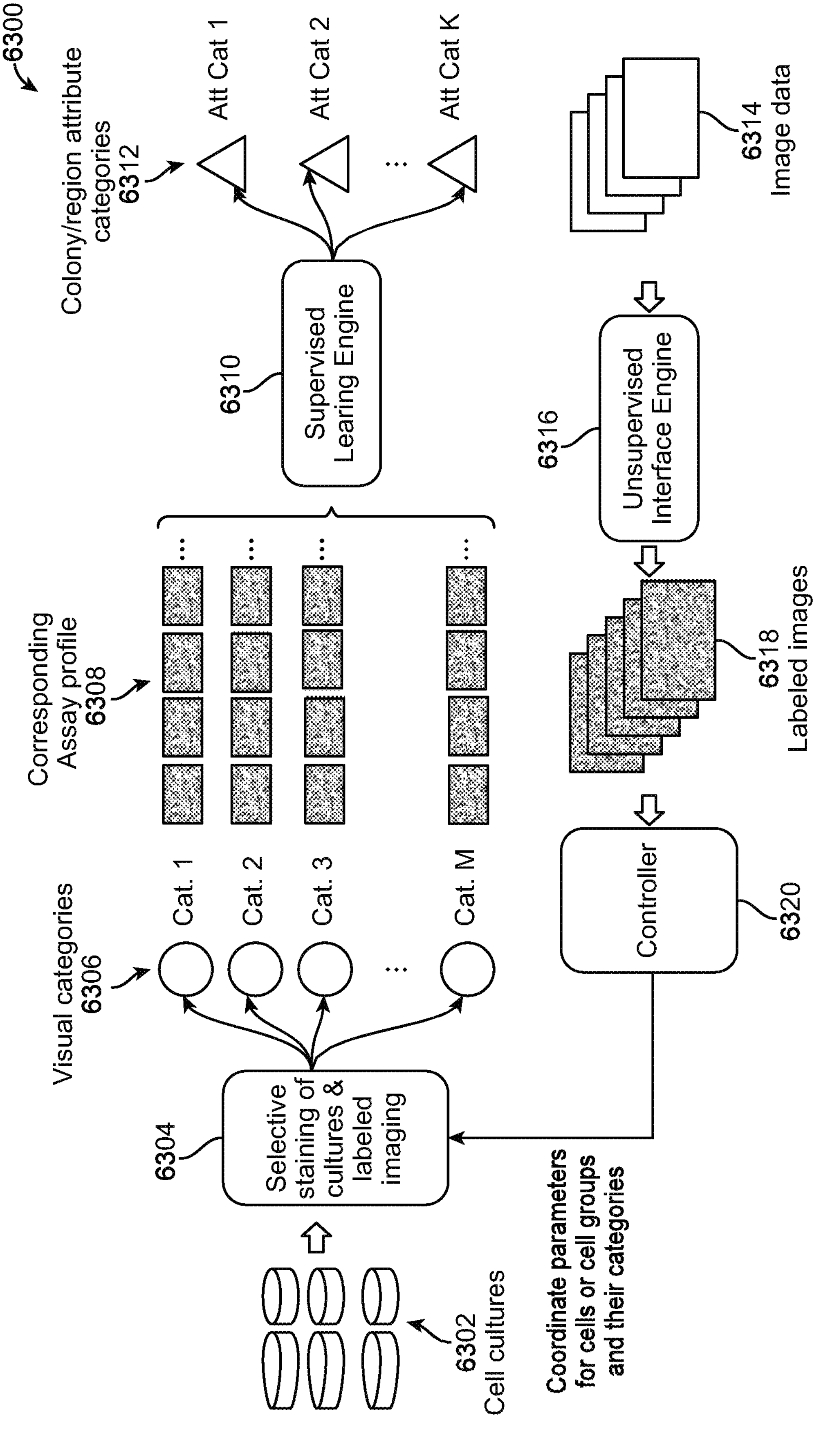
FIG. 63 is a block diagram of an automated classification system learning the association of visual categories to cell attribute categories via selective staining and labeled imaging in accordance with various implementations.

FIG. 63 is a block diagram of an automated classification system 6300 learning the association of visual categories to cell attribute categories via selective staining and labeled imaging in accordance with various implementations. The automated classification system 6300 may include different subsystems of the cell culture system such as an imaging subsystem (e.g., cell imaging subsystem 112), a cell lysing and removal subsystem (e.g., cell editing subsystem 114), and a computing subsystem (e.g., computing subsystem 110). FIG. 63 illustrates the operation of the automated classification system 6300 during the attribute association phase being trained on labeled image data collected from samples of each visual category. One or more cell cultures 6302 are cultured in the cell culture system. The cell cultures 6302 may contain cells of the same cell type, and each cell culture 6302 may include one or more cell colonies, regions, or groups.

Specifically, an unsupervised inference engine 6316 initialized with model parameters learned by an unsupervised learning engine may take as input label-free image data 6314 of the cell cultures 6302 and produce labeled visual category maps 6318. The labeled images 6318 may be provided to a controller 6320 which determines the coordinates for cells and cell regions/colonies expressing same visual categories. The controller 6320 may control a cell staining and labeled imaging subsystem (e.g., may be part of the cell imaging subsystem 112) to perform selective staining of cell cultures and labeled imaging 6304 of the cell cultures 6302 to acquire labeled images 6308. For example, for each visual category 6306 the cell culture system may select a representative group of cells from the cell culture 6302, stain them, and then image the stained cells. In this way, a certain amount of labeled image data can be collected for each visual category in 6306 that is statistically sufficient to run further analysis.

A supervised learning engine 6310 may be configured to generate cell colony/region attribute categories 6312 from the labeled images 6308 with the aid of human intervention. For example, a portion of the labeled images 6308 from all visual categories 6306 may be assigned to one of the cell attribute categories 6312 by experts manually. The attribute categories 6312 may include any number of desirable or undesirable attributes in the context of the cell culture process on the specific cell type. This subset of manually annotated data may be used to train an image classifier that learns to map a label image into one of the attribute categories 6312. Each labeled image sample from a given visual category 6306 may be classified and a consensus voting among all sample data from a visual category may determine the association of that visual category to an attribute category. In alternate implementations, the learning engine 6310 may be unsupervised after training based on labeled images. Note that for the supervised learning engine 6310, if available, an off-the-shelf image classifier that maps labeled images to attribute categories may be used if a standard staining and labeled-image collection procedure is used for the biological process in question. Similarly, if appropriate, a simple rule-based classifier may also be configured for the supervised learning engine 6310 to measure the existence of certain stains in a minimum number of pixels in the labeled images.

Figure 64:
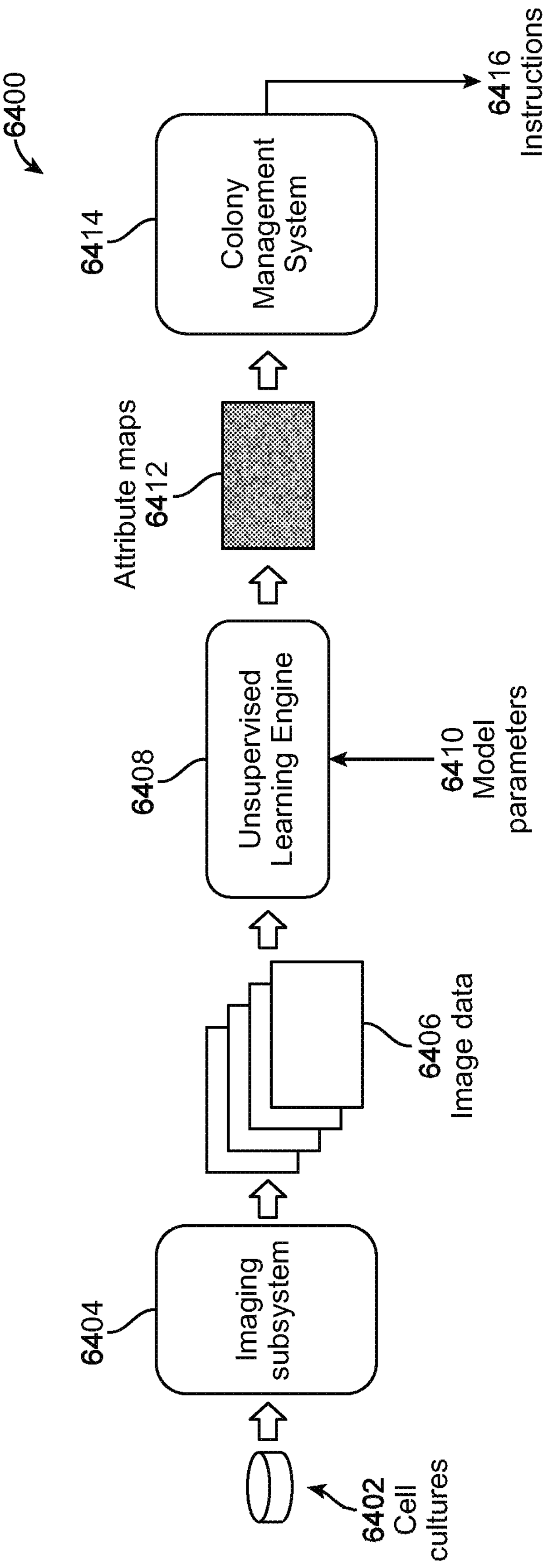
FIG. 64 is a block diagram showing manufacturing of cells using an automated classification system in accordance with various implementations.

FIG. 64 is a block diagram showing manufacturing of cells using an automated classification system 6400 in accordance with various implementations. After the automated classification system 6400 has completed learning/training as described with reference to FIGS. 59-63, the automated classification system 6400 may be utilized in a cell manufacturing process. The automated classification system 6400 may be part of a cell culture system (e.g., cell culture system 100). A cell culture 6402 grown in a cell culture container (e.g., cell culture container 104) may contain cells of a certain type. An imaging subsystem 6404 (e.g., cell imaging subsystem 112) may collect image data 6406 of the cell culture 6402 during the growth process.

The image data 6406 is fed into an unsupervised inference engine 6408, along with model parameters 6410 generated by an automated classification system that has been trained as disclosed with reference to FIGS. 59-63. For example, the model parameters 6410 may include visual categories for the cell type grown in the cell culture 6402 and, for each visual category, its associated attribute categories. The unsupervised inference engine 6408 generates attribute maps 6412, which may be images of the cell culture 6402 in which cells or cell colonies/regions are labeled with various attributes according to their visual characteristics as well as other information (e.g., information obtained from assays or stained images). A colony management system 6414 (e.g., computing subsystem 110) may utilize the attribute maps 6412 to make decisions about cell culture processes like cell editing, additional selective cell lysing and assay profiling, and modifying environmental parameters of the cell culture growth process. The colony management system 6414 may generate instructions 6416 which are used to control other components in the cell culture system (e.g., cell imaging subsystem, cell editing subsystem, container sensors and controls).

Figure 65:
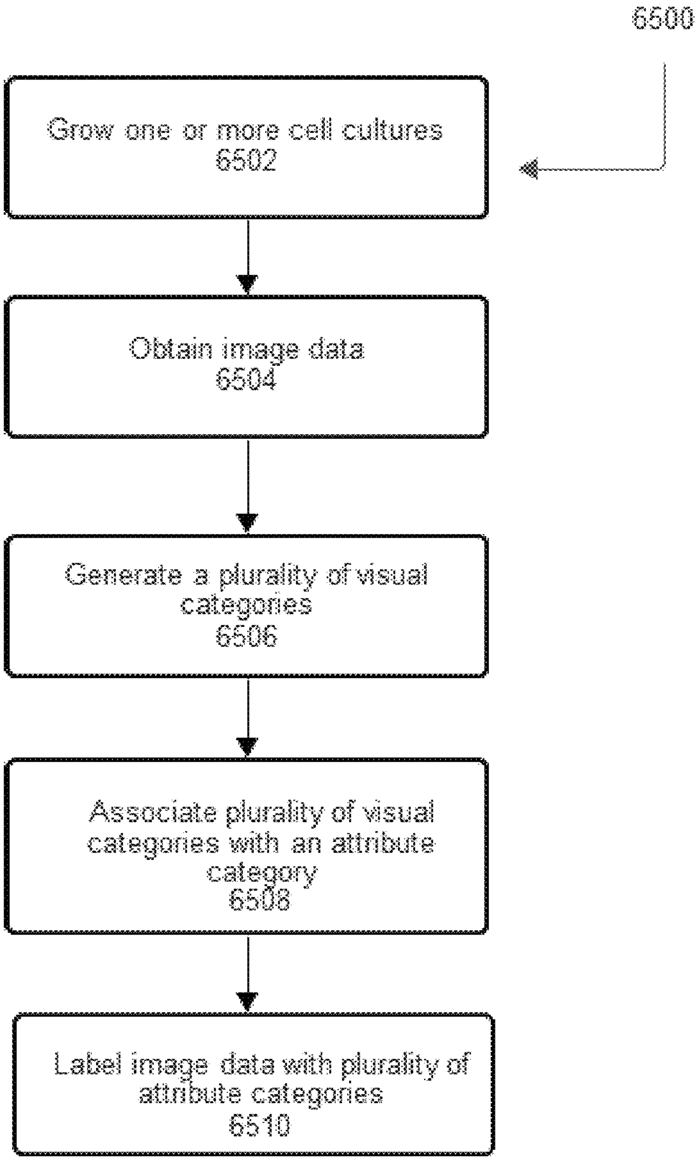
FIG. 65 is a flow chart of a method of classifying image data in a cell culture system in accordance with various implementations.

FIG. 65 is a flow chart of a method 6500 of classifying image data in a cell culture system in accordance with various implementations. The method 6500 may be performed by one or more components in a cell culture system (e.g., cell culture system 100), such as an automated classification system as disclosed with reference to FIGS. 59-63. The method 6500 may be performed during the learning or training phase of the automated classification system.

In block 6502, the cell culture system grows one or more cell cultures. The cell cultures may be grown in cell culture containers (e.g., cell culture containers 106) and be of the same cell type. The cell culture containers may allow for label-free imaging and editing in a closed system (e.g., a closed cassette). In block 6504, the cell culture system may obtain image data of the one or more cell cultures. The image data may be collected by a cell imaging subsystem (e.g., cell imaging subsystem 112) that collects a plurality of images. The image data may be label-free, meaning there is no staining of the cell cultures involved when obtaining the image data. The image data may include multiple imaging modalities, as well as time-series image data.

In block 6506, the cell culture system may generate a plurality of visual categories from the image data. The cell culture system may utilize an unsupervised learning engine within a computing subsystem (e.g., computing subsystem 110) to generate the plurality of visual categories, as disclosed with respect to FIGS. 59-63. For example, the unsupervised learning engine may divide the image data into a plurality of image patches, reduce the image patch data into a lower dimensional encoding space, and then identify repeating visual patterns in the reduced data set that may be classified into visual categories.

In block 6508, the cell culture system may associate the plurality of visual categories with a plurality of attribute categories. The cell culture system may also collect additional data such as assay profiles and labeled image data and utilize this information to associate a visual category with one or more attribute categories. The association may be aided by human intervention in which a person may review the visual patterns and other collected information for a particular visual category, and then determine the attributes that the visual category is indicative of.

In block 6510, the cell culture system may label the image data with the plurality of attribute categories, producing annotated attribute maps of the one or more cell cultures. This information may be used by the cell culture system to make decisions about cell editing, cell culture growth, further testing, or other actions. In this manner, the method 6500 provides an automated method of training the cell culture system to identify visual patterns in observed cell cultures and associate them with attributes that indicate information about cell quality, growth progress, and other factors relevant to producing a desired output cell product.

Figure 66:
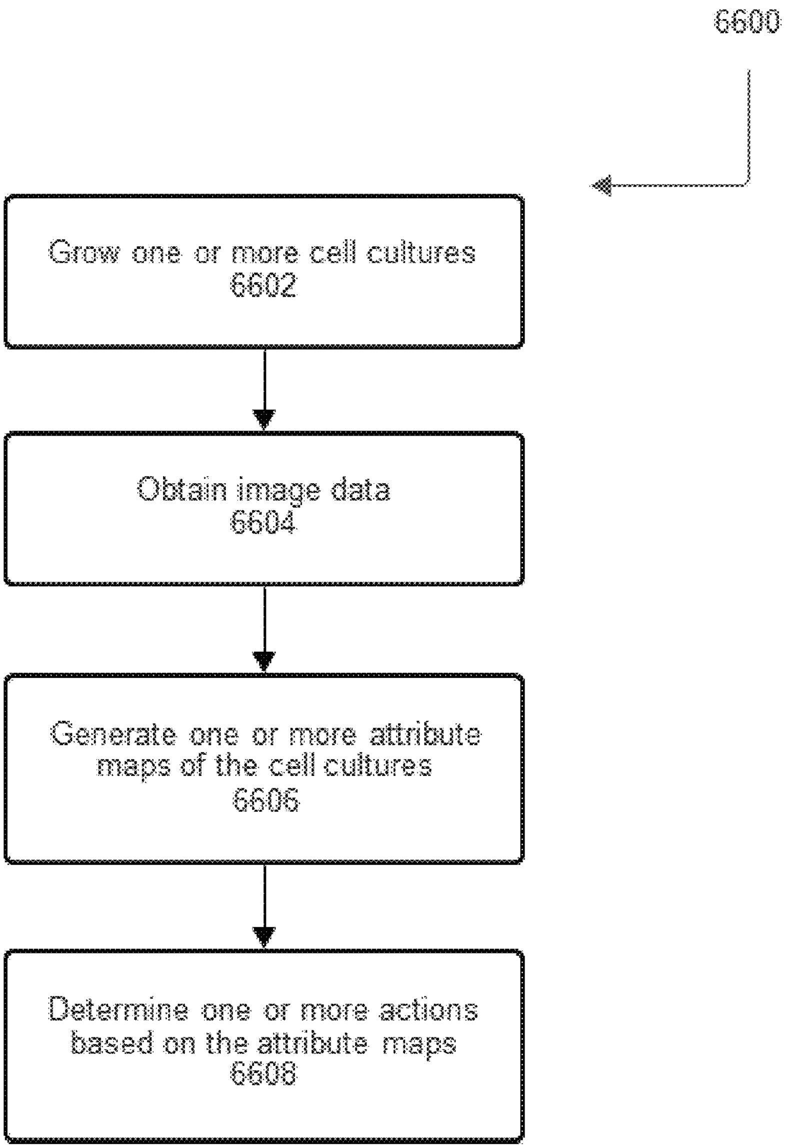
FIG. 66 is a flow chart of a method of growing cells in a cell culture system in accordance with various implementations.

FIG. 66 is a flow chart of a method 6600 of growing cells in a cell culture system in accordance with various implementations. The method 6600 may be performed by one or more components in a cell culture system (e.g., cell culture system 100), such as an automated classification system as disclosed with reference to FIGS. 59-63. The method 6600 may be performed during the manufacturing phase after the automated classification system has completed learning/training as described with reference to FIGS. 59-63 and 65.

In block 6602, the cell culture system grows one or more cell cultures. The cell cultures may be grown in cell culture containers (e.g., cell culture containers 104) and be of the same cell type. The cell culture containers may allow for label-free imaging and editing in a closed system (e.g., a closed cassette). In block 6604, the cell culture system may obtain image data of the one or more cell cultures. The image data may be collected by a cell imaging subsystem (e.g., cell imaging subsystem 112) that collects a plurality of images. The image data may be label-free, meaning there is no staining of the cell cultures involved when obtaining the image data. The image data may include multiple imaging modalities, as well as time-series image data.

In block 6606, the cell culture system may generate one or more attribute maps from the image data, in which each attribute map comprises an image of a cell culture annotated with cell attributes. An unsupervised inference engine may take as input the image data and store model parameters such as visual categories and associated attribute categories. The visual categories and attribute categories may be generated by an unsupervised learning engine within a computing subsystem (e.g., computing subsystem 110) as disclosed with respect to FIGS. 59-63 and 65. The unsupervised inference engine may be configured to identify visual patterns in the image data corresponding to the visual categories and label them with the appropriate attribute.

In block 6608, the cell culture system may determine one or more actions based on the one or more attribute maps. The actions may include, for example, editing select cells in the one or more cell cultures, collecting assays on select cells in the one or more cell cultures, or changing parameters of cell growth of the one or more cell cultures. In this manner, the method 6600 provides automated attribute classification of cells during cell culture manufacturing, which may be useful in guiding and optimizing the manufacturing process, particularly in an automated cell culture system.

Closed Cassette Systems

There is currently no bioreactor or other system in the art for clinical-grade manufacturing of cells that (1) allows 100% non-contact measurement of cells in culture to monitor and control the biomanufacturing process, and (2) is sealed in a manner that allows parallel manufacture in a non-sterile facility, and further, in some cases, allows editing of cell cultures based on image-derived characteristics (e.g., in a cell culture system).

Such a system would enable a wide range of cell biomanufacturing processes at a scale, consistency, yield, and cost that are not currently achievable. This capability is particularly important to translate emerging patient-specific therapies from the laboratory to clinical trials and ultimately to larger patient populations.

The systems and methods disclosed herein include a cell culture container that includes a closed media path and at least one culture chamber suitable for aseptic cell manufacturing in a non-sterile facility. The at least one cell culture chamber has at least one growth surface for cells that is optically accessible for label-free imaging by transmission and/or reflection illumination. The cell culture chamber may be liquid-filled and substantially free of any gas layer, and the growth surface may be is inverted for at least part of the cell culture process in order to gravitationally separate debris and/or non-adherent cells from the culture surface. The cell culture container may provide a sterile-sealed closed loop liquid system to support cell cultures grown in the cell culture container.

In some implementations, the liquid system disclosed herein can be referred to as a liquid handler. A liquid handler can be coupled to the one or more cell culture chambers, and configured to (i) provide input fluid media to the one or more cell culture chambers; (ii) receive output fluid media from the one or more cell culture chambers; and (iii) mix a circulated fluid within the one or more cell culture chambers, wherein the circulated fluid comprises the input fluid media, the output fluid media, or both.

In some implementations, the cell culture container may include a mechanism for selectively removing cells from the cell culture surface without opening the media path, with the removed cells or cell fragments separated at least in part by using the inverted configuration. In some implementations, time-series imaging of the cells on the cell culture surface and image processing of the resulting images may be used to predict the outcome of a cell culture process. This prediction may be used to manage the manufacturing process by discarding the cell cultures with poor predictions, and/or starting back-up cultures, selectively remove cells within the cell culture chamber in order to improve the predicted outcome, and manage the media inside the closed system, for example the addition of fresh media, in order to improve or maintain the predicted outcome. In some implementations, the cell culture container may include a mechanism for agitating liquid in the cell culture chamber without opening the media path in order to dislodge debris or cells from the growth surface.

The various implementations disclosed herein may be used for scaling out 2D cell culture processes in a manner compatible with good manufacturing practice (GMP) requirements for cells and tissue to be used in patients. Furthermore, the disclosed implementations allow long-term processes to be run, observed, and controlled in a sealed system, in order to allow dozens or hundreds of patient samples to be processed in parallel in a single facility, without the risk of cross-contamination. The disclosed implementations may be used for reprogramming of somatic cells into induced pluripotent stem cells (iPSCs), for differentiation of stem cells into cells and/or tissue for screening or transplantation, for expansion of cells, for gene modification of cells, and other applications requiring multi-day processes where cells are maintained with nutrients, factors, vectors to be delivered, etc.

Figure 67:
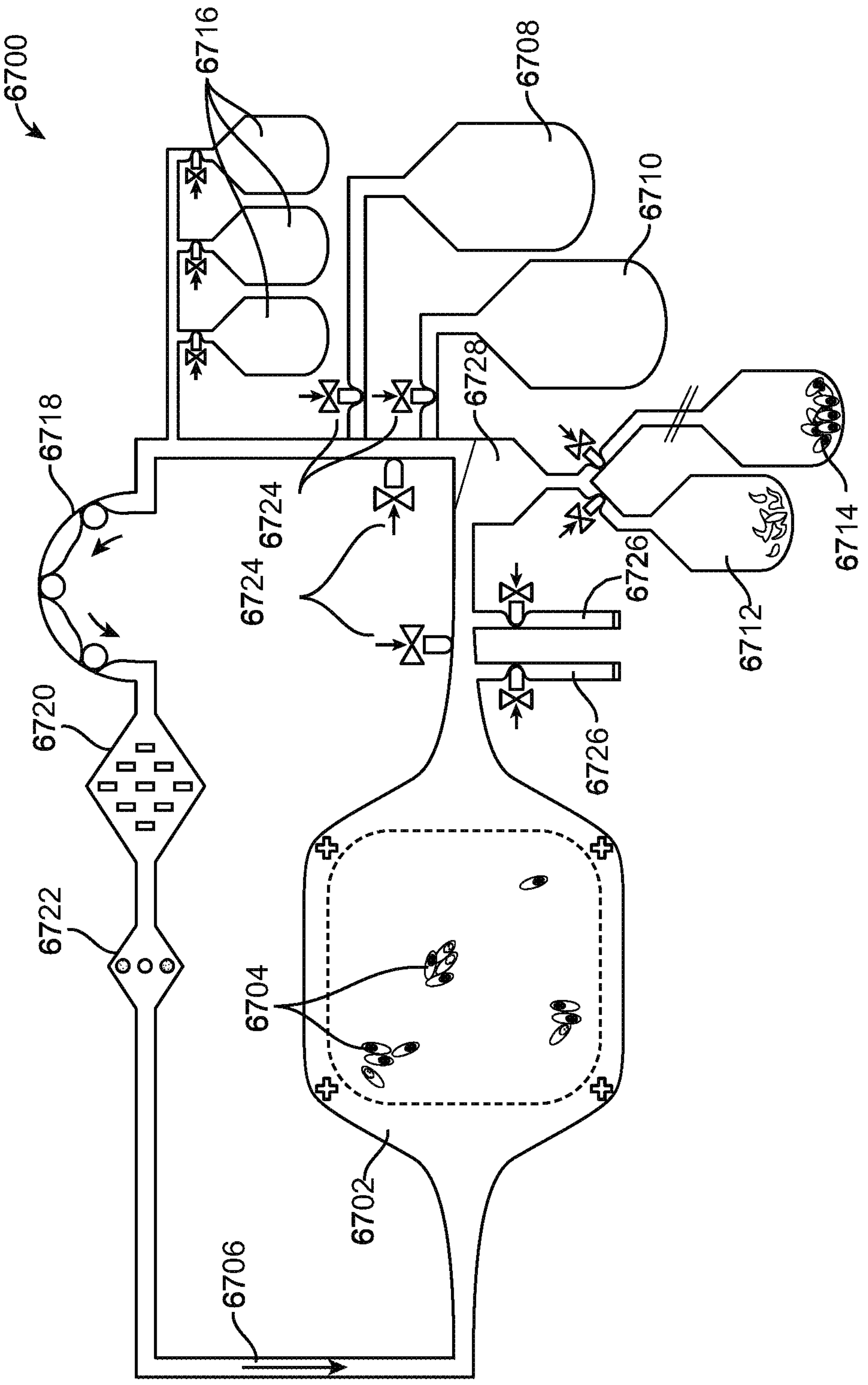
FIG. 67 is a diagram of a closed cassette system for use in a cell culture system in accordance with various implementations.

FIG. 67 is a diagram of a closed cassette system 6700 for use in a cell culture system in accordance with various implementations. The closed cassette system 6700 may be an implementation of the cell culture container 106 shown in FIG. 1. The closed cassette system 6700 may include a cell culture chamber 6702 supporting the growth of an adherent cell culture 6704. In some implementations, the closed cassette system 6700 may include more than one cell culture chamber 6702. A closed liquid loop 6706 provides the cell culture chamber 6702 with fluid media and allows for media and reagent exchange. The closed liquid loop 6706 may be an aseptically-sealed liquid system (also referred to as a fluidic system), built for example using planar microfluidic channels and/or sterile tubing that may be sterile-welded and pre-sterilized using gamma and/or UV radiation. The closed liquid loop 6706 enables the growth and maintenance of the cell culture 6704 over an extended period of time for the purpose of reprogramming, differentiating, gene-editing and/or expanding the cells.

The closed liquid loop 6706 may include a plurality of reservoirs, typically sterile bags that may deflate or inflate over the course of the cell culture process. The reservoirs may include a fresh media reservoir 6708 which supplies cell culture nutrients, vitamins, and other factors, and a waste reservoir 6710 into which spent media is pumped during complete or partial media exchanges. Additional reagents or buffers (for example for pH control) are shown as reservoirs 6716. There may also be a debris collection reservoir 6712 and cell collection reservoir 6714. Debris and/or cells are cleared from the cell culture chamber 6702 and moved to the debris collection reservoir 6712 to remove them from the media loop through the use of a filtration feature 6728. Debris are typically discarded, while the cells captured in the cell collection reservoir 6714 are the output cell product (e.g., output cell product 118 in FIG. 1) of the cell culture process.

A pump 6718 circulates liquid through the closed liquid loop 6706. The pump 6712 shown in FIG. 67 is a peristaltic-type pump, but in general the closed cassette system 6700 may use other configurations compatible with a closed system. In the case of a peristaltic pump, it may act upon tubing or a channel in a planar microfluidic system. The pump 6718 may run forwards as well in reverse. Reverse pumping may be used to clear the cell filtration unit and pump the filtered solids (debris and/or cells) into the debris collection reservoir 6712 or cell collection reservoir 6714. The closed liquid loop 6706 may additionally be pumped in reverse to ensure even distribution of media within the cell culture chamber 6702. The pump 6718, in conjunction with actuated valves 6724 (only some of which may be shown in FIG. 67), controls all the liquid protocols on the closed cassette system 6700.

The closed cassette system 6700 may also include a mixing and exchange section 6720, which is shown schematically in FIG. 67. The mixing and exchange section 6720 may perform two functions. First, it serves to promote mixing in the circulated liquid to ensure homogeneity once it reaches the cell culture chamber 6702. For example, if a small amount of fresh media has been added, the mixing and exchange section 6720 serves to mix it with the existing media. The mixing and exchange section 6720 may have a liquid feedback mechanism to provide a greater mixing factor.

A second function of the mixing and exchange section 6720 may be gas exchange. For example, the dissolved oxygen level in the fluid media may be an important factor in certain bioprocess. When outfitted with gas exchange surfaces/mechanisms, the mixing and exchange section 6720 may be used to control the dissolved oxygen and other gas concentrations in the circulated media. In cases in which pH is controlled indirectly (rather than by addition of liquid), the mixing and exchange section 6720 may be used to control dissolved $CO_2$. In cases in which cavitation mechanisms (e.g., laser, ultrasound, or other) are used to edit cell cultures 6704 within the cell culture chamber 6702, the mixing and exchange section 6720 may be used to control overall dissolved gas concentration, potentially with an inert gas that has no other effect on cell culture, for the purpose of maintaining a stable threshold and predictable energy transfer for cavitation.

Temperature may be separately controlled for the mixing and exchange section 6720, or even within different parts of the mixing and exchange section 6720, to control gas solubility for the purpose of facilitating gas exchange. Additionally, external gas pressure may be controlled in one or more parts to facilitate gas exchange. For example, in a first portion of the mixing and exchange section 6720 the media temperature may be raised and external gas pressure is at below atmospheric pressure, in order to maximize outgassing (for example, to remove $CO_2$, which is a product of the live cell culture). In a second section of the mixing and exchange section 6720 temperature is lowered and external gas pressure is at above atmospheric pressure to maximize transfer of $O_2$ or other gases into dissolved form in the liquid media to support cell culture. One or more bubble-trapping and removal stages (not shown) may be integrated into the closed liquid loop 6706 to trap and remove, via a gas-permeable membrane and reduced external gas pressure, any gas that comes out of solution so it does not interfere with the cell culture or liquid loop functions.

The closed cassette system 6700 may also include a sensing section 6722, which is shown schematically in FIG. 67. The sensing section 6722 may be used to monitor media conditions in a non-invasive manner. In the example shown in FIG. 67, the sensing section 6722 includes two colorimetric patches (top and bottom circles) inside the closed liquid loop 6706. The optical characteristics of the patches may vary with pH and dissolved oxygen, respectively, and may be read using an external light source and detector. Other media property and components may be monitored with similar patches.

In the center of the sensing section 6722, a circular outline is shown that represents a clear optical path for transmission, reflection, or scattering measurements performed without the aid of inserted materials. For example, spectroscopic transmission measurements in the ultraviolet (UV), visible, near infrared (NIR), mid-wave infrared (MWIR) or long-wave infrared (LWIR) may be performed to assess media contents, including but not limited to nutrients, waste products, vitamins, and bioprocess byproducts. Alternatively, Raman spectroscopic measurement may be made of the media and its contents. In addition, scattering measurements at one or more wavelengths and scattering angles may be made to assess media contents. The measurements made in the sensing section 6722 may be used in a closed-loop control of the closed cassette system 6700. For example, data from the sensing section 6722 may be used to make decisions about adding fresh media, adding liquid to control pH, or changing gas exchange rates or composition. In addition, these measurements, in conjunction with imaging-based measurements, may be used to track the cell culture bioprocess and predict outcomes using statistical models (or to train these statistical models, based on endpoint results).

The closed cassette system 6700 may also include a plurality of ports 6726, positioned at various points along the closed liquid loop 6706. These may be single-use ports (e.g., for filling or inoculating the cell culture chamber 6702 or entire closed cassette system 6700, or for harvesting output cell product) that are sterile welded after use. Such ports may also be fitted with one-time sterile connectors.

In typical usage of the closed cassette system 6700, incremental exchange of media is performed over time, either on a fixed time schedule, or more preferably based on some combination of time and observed cell culture characteristics (total cell count, etc.). Media exchange may be monitored by a computing subsystem (e.g., computing subsystem 110) of a cell culture system that utilizes the closed cassette system 6700. Such incremental exchange may be performed by closing the valve in the flow loop situated between the waste outlet (e.g., outlet leading to the waste reservoir 6710) and fresh media inlet (e.g., inlet from the fresh media reservoir 6708), opening the waste inlet, opening the fresh media inlet, and then activating the pump 6718 in the forward direction for a given duration. In this manner, any amount from a small fraction up to the entirety of the media in the closed cassette system 6700 may be replaced, depending on the pumping duration and speed. The closed cassette system 6700 may include other components not shown in FIG. 67, such as additional pumps, valves, reservoirs, and sensors.

In some implementations, the closed cassette system 6700 comprises multiple one-time connector ports for fresh media replenishment during longer processes. In some implementations, the media composition is constant over time. In some implementations, the media composition changes over the processing time. In some implementations, the media composition changes based on a reprogramming phase, a differentiation process, or both. In addition, add multiple one-time disconnect ports for waste media, to remove waste media and debris over time. Both of these allow a compact cassette format that nevertheless enables long-term processes or processes that have high media requirements.

In some implementations, dissolved oxygen in the fluidic system of the cassette is controlled depending based on a reprogramming process or a differentiation process. For example, hypoxic conditions can often make iPSC reprogramming more efficient.

In some implementations, for the closed liquid loop 6706, the process module monitors dissolved oxygen via an optically-interrogated sensor patch, and oxygen levels are dynamically adjusted based on the measured data. The process module may comprise connectors for two or more gas lines (e.g., oxygen connector, nitrogen connector, oxygen/nitrogen connector). In some implementations, the process module comprises an on-board valve for mixing gases in specific concentrations. The mixed gasses can flow via a pluggable connector or an open port that between the cassette 6700 and the process module to a gas exchange section. In one example, a surface of the growth chamber is gas-permeable, wherein the atmosphere surrounding the growth chamber(s) is directly controlled by the process module.

In some implementations, the connector is a one-time aseptic connection (e.g., for a non-ultraclean/sterilized environment). In some implementations, the one-time connector allows tubes to be connected aseptically using removal membranes (e.g., Sartorius Opta SFT Aseptic Tube Connectors). In some implementations, a plurality tubes are connected to form one-time connector formed by aseptic tube welding by a welding tool (e.g., by a Terumo TSCD-II Sterile Tubing Welder). In some implementations, at least a portion of the plurality of tubes comprise a thermoplastic elastomer (TPE), such as PVC, where tubes, including liquid-containing tubes. In some implementations, the one-time aseptic connection comprises a one-time crimped disconnector inserted into tubing with a tubing insert, and crimped by a crimping tool (e.g., Sartorius Quickseal Disconnectors).

In addition, non-aseptic connectors, such as Luer lock connectors, may be used to connect or disconnect media, waste, reagent, or other bags from the cassette in a well-sterilized flow hood environment.

Figure 68A:
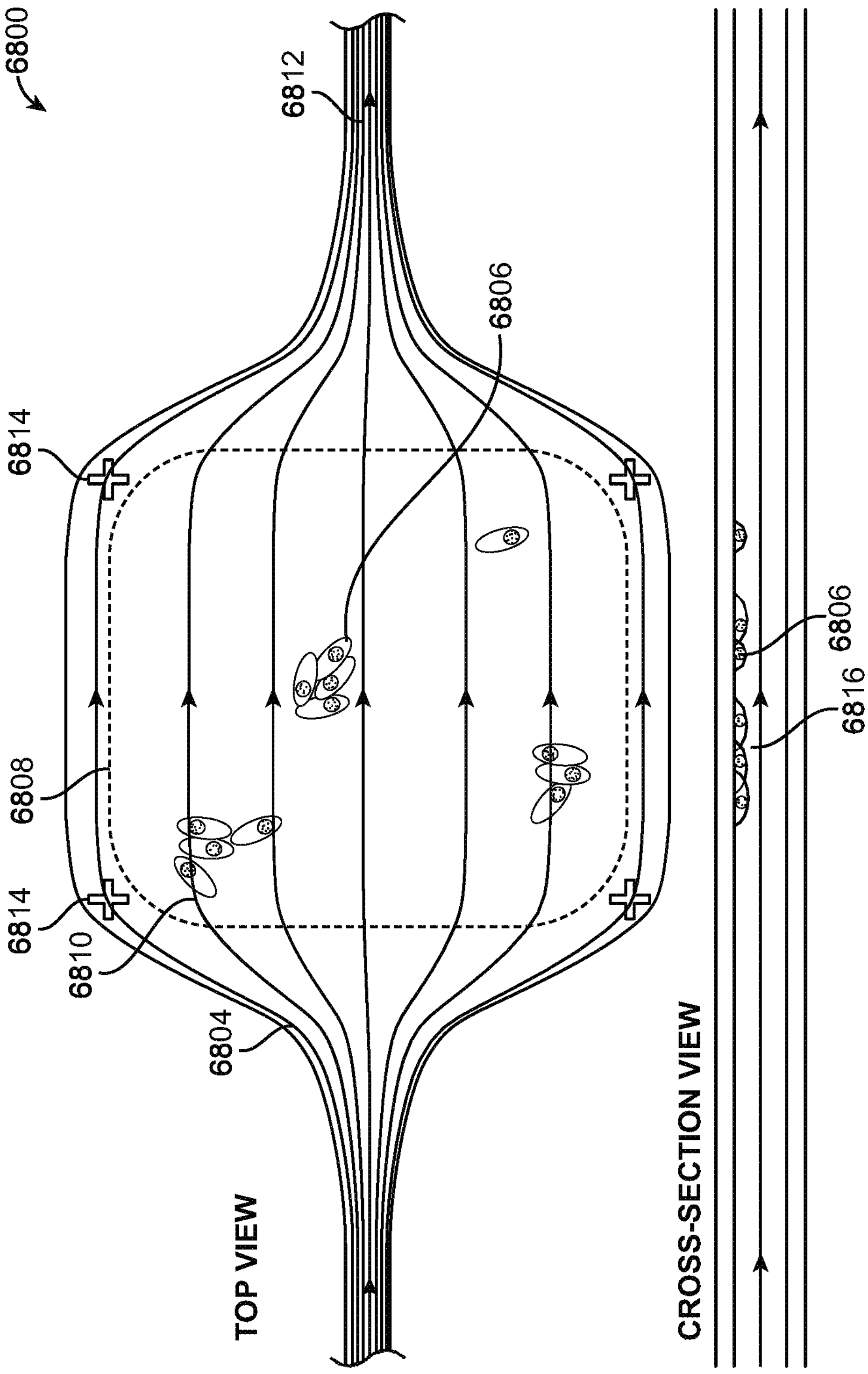
FIG. 68A is a diagram of a cell culture chamber in a closed cassette system in accordance with various implementations.

FIG. 68A is a diagram of a cell culture chamber 6800 in a closed cassette system in accordance with various implementations. The cell culture chamber 6800 may be similar to cell culture chamber 6702 in FIG. 67. FIG. 68A shows both a top view and a cross-section view of the cell culture chamber 6800. The cell culture chamber 6800 includes at least one inlet channel 6802 that is used to deliver media into the cell culture chamber 6800. This media may come from a closed liquid loop of the closed cassette system. The media may include fresh media and/or reagents are incrementally added and mixed into the fluid flow of the closed liquid loop. The fluid flow, which is typically slow and laminar, is expanded gradually through an expansion section 6804 into the cell culture chamber 6800. Additional features may be added to make the overall flow profile uniform. The target is to establish a uniform, very low velocity flow in the target cell growth region 6808. In many cases, the goal is to minimize continuous and/or directional shear stress on the cells in culture, preferably keeping it to <5 dyne/cm$^2$, and preferably <1 dyne/cm$^2$. In some implementations, the shear stress exerted on the cells in culture is less than about 10 dyne/cm$^2$, 9 dyne/cm$^2$, 8 dyne/cm$^2$, 7 dyne/cm$^2$, 6 dyne/cm$^2$, 5 dyne/cm$^2$, 4 dyne/cm$^2$, 3 dyne/cm$^2$, 2 dyne/cm$^2$, or 1 dyne/cm$^2$. Media is removed from the cell culture chamber 6800 via outlet channel 6810. It should be noted that for portions of the cell culture process, the flow direction may be reversed (i.e., media enters from the outlet channel 6810 and exits from the inlet channel 6802).

Cells 6806 are cultured within the cell culture chamber 6800, potentially confined via surface treatment and/or an editing system to target cell growth region 6808. Within this region, the cells are observable via a label-free imaging system (e.g., cell imaging subsystem 112). The imaging may operate in one or more known modalities, including but not limited to transmission imaging, reflection imaging, brightfield, darkfield, phase, differential interference contrast (DIC), quantitative phase imaging (QPI), Fourier ptychographic imaging in transmission or reflection, holographic imaging, or combinations of these. All the cells 6806 may be imaged over time to monitor the progression of the cell culture and make predictions with respect to quality and yield. For this purpose, registration marks 6812 visible to the cell imaging subsystem may be provided to provide stable spatial references over time and accurately monitor cell behavior at a colony or even cell level.

The cells 6806 may be an adherent cell culture adhered to the top surface of the cell culture chamber 6800, as shown in the cross-section view of FIG. 68A. The cells 6806 may initially be cultured on the bottom surface of the cell culture chamber 6800 until they adhere to the surface, and then the cell culture chamber 6800 may be inverted so that the cells 6806 reside on the now-top surface as shown in the cross-section view. Inversion, enabled by a growth chamber that is completely filled with media, may be utilized to separate non-adherent cells, cell debris, and other debris or particles of density greater than the cell media from the adherent cell culture. For example, when reprogramming suspension somatic cells into iPSCs (which are adherent), inversion of the cell culture chamber 6800 may gently separate somatic cells that are not successfully reprogrammed from the reprogrammed iPSCs using gravity. The somatic cells that fall to the bottom surface may then be washed out of the cell culture chamber 6800. In the reverse case, in which stem cells are differentiated into suspension cells, successfully differentiated cells may be gently separated by inverting the cell culture chamber 6800.

In another example, the cell culture chamber 6800 may be used to grow adherent cells that are genetically reprogrammed or have episomal vectors delivered to them for non-integrating expression, in which the programming includes an antibiotic resistance. The antibiotic may subsequently be used to kill the undelivered cells. The debris from these cells may then fall away from the top growth surface of the cell culture chamber rather than potentially contaminating the remaining successfully delivered (hence antibiotic-resistant) cells. In another example, an editing mechanism (e.g., a laser) may be used to lyse or damage specific cells on the growth surface by means of mechanical force, heat, ultrasound, electrical fields or photodamage in a manner compatible with a closed cassette, and the damaged/destroyed cell debris is gravitationally separated from the untouched live cells, such that it does not settle on the live cells. In another example, a matrix or coating is used under the cells that may be selectively altered/removed to release the attached cells. This alteration being performed in a manner that is compatible with a closed container. The separation mechanisms described herein may be used to remove unwanted cells, or to remove wanted (product) cells, or to remove select cells for analysis.

Figure 68B:
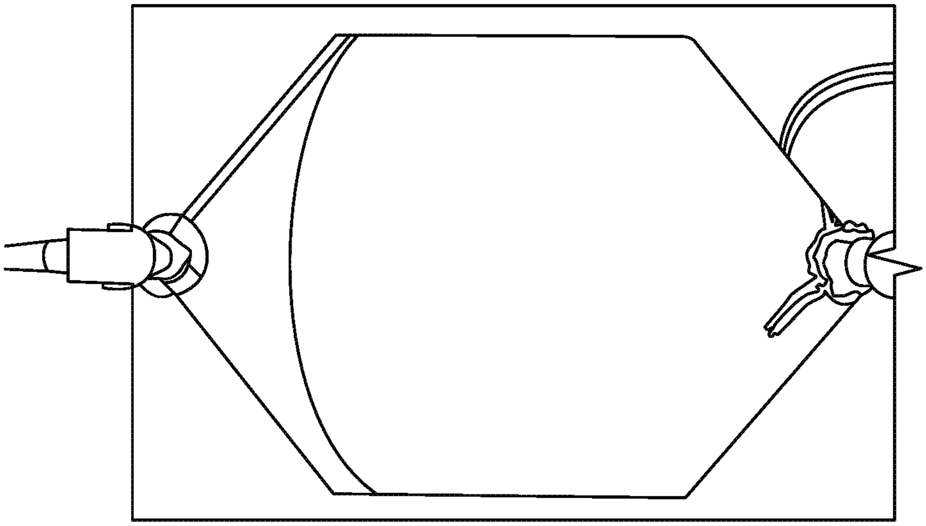
FIG. 68B is an image of an exemplary cell culture chamber in accordance with various implementations.
Figure 68C:
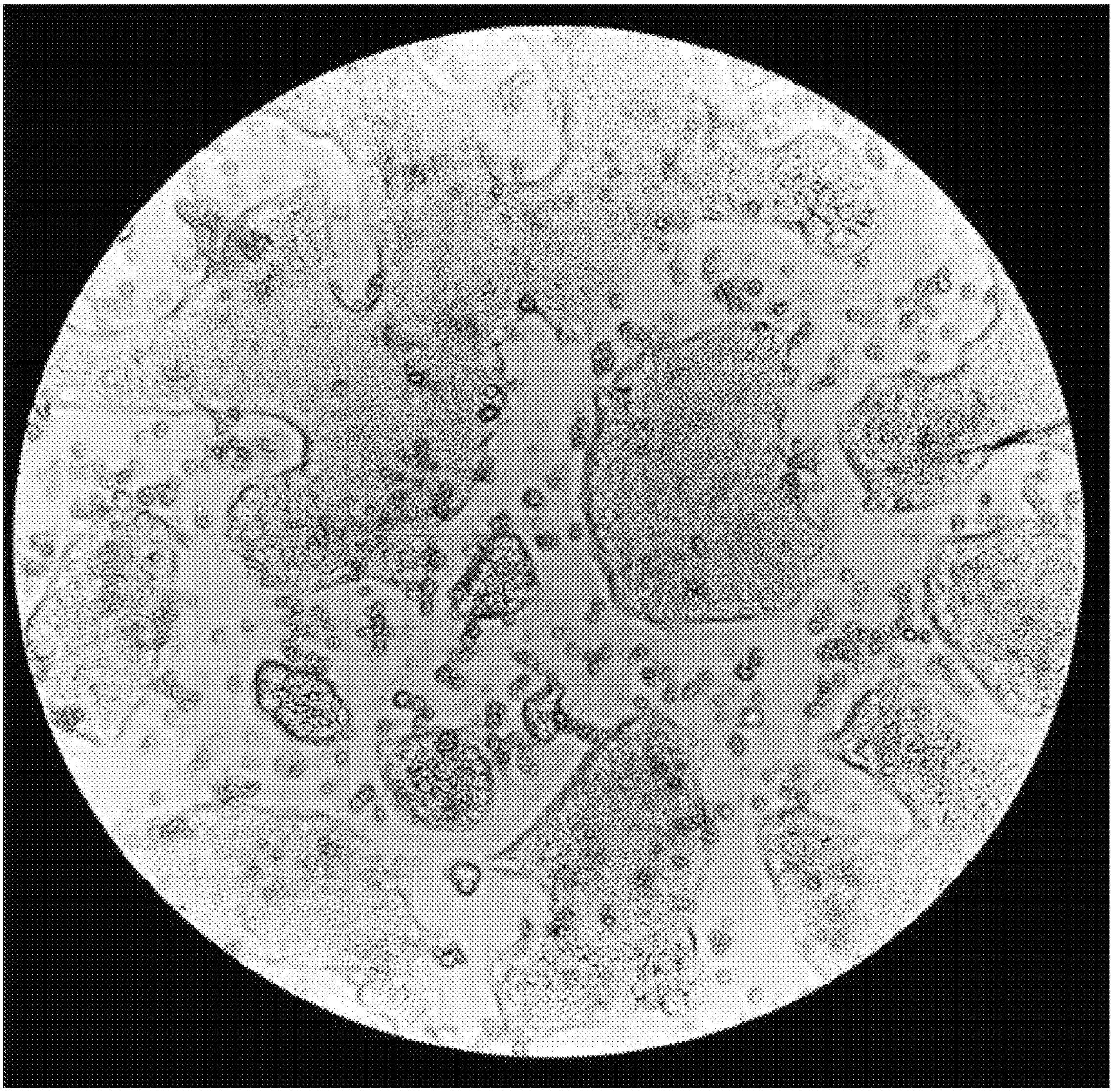
FIG. 68C shows an exemplary hiPSCs grown under continuous media flow in a liquid-filled chamber with a height of less than about 1 mm height in accordance with various implementations.

As an illustrative and non-limiting example, a prototype adherent cell growth chamber as shown in FIG. 68A supports over 50 $cm^2$ of cell culture area on a single surface, and has liquid filled height of approximately 0.5 mm, with a total volume of approximately 3 ml for very high efficiency cell culture. This prototype chamber can be modified for highest-uniformity liquid flow (elimination of angled corners in particular). The chamber in this particular example includes two pieces of 110×74 mm 0.17 mm thick borosilicate glass coverslips, one with two liquid ports cut through it, separated by an 0.5 mm thick silicone gasket with adhesive surfaces that has been cut to define the chamber. Tubing connectors are attached to the liquid ports. FIG. 68B is an image of an exemplary cell culture chamber. This chamber supports over 50 $cm^2$ of cell culture area on a single surface, and has liquid filled height of approximately 0.5 mm, with a total volume of approximately 3 ml for very high efficiency cell culture. This chamber has not yet been modified for highest-uniformity liquid flow (elimination of angled corners in particular). The chamber consists of two pieces of 110 mm×74 mm 0.17 mm thick borosilicate glass coverslips, one with two liquid ports cut through it, separated by an 0.5 mm thick silicone gasket with adhesive surfaces that has been cut to define the chamber. Tubing connectors are attached to the liquid ports. FIG. 68C shows an exemplary hiPSCs grown under continuous media flow in a liquid-filled chamber with a height of less than about 1 mm height.

Figure 69:
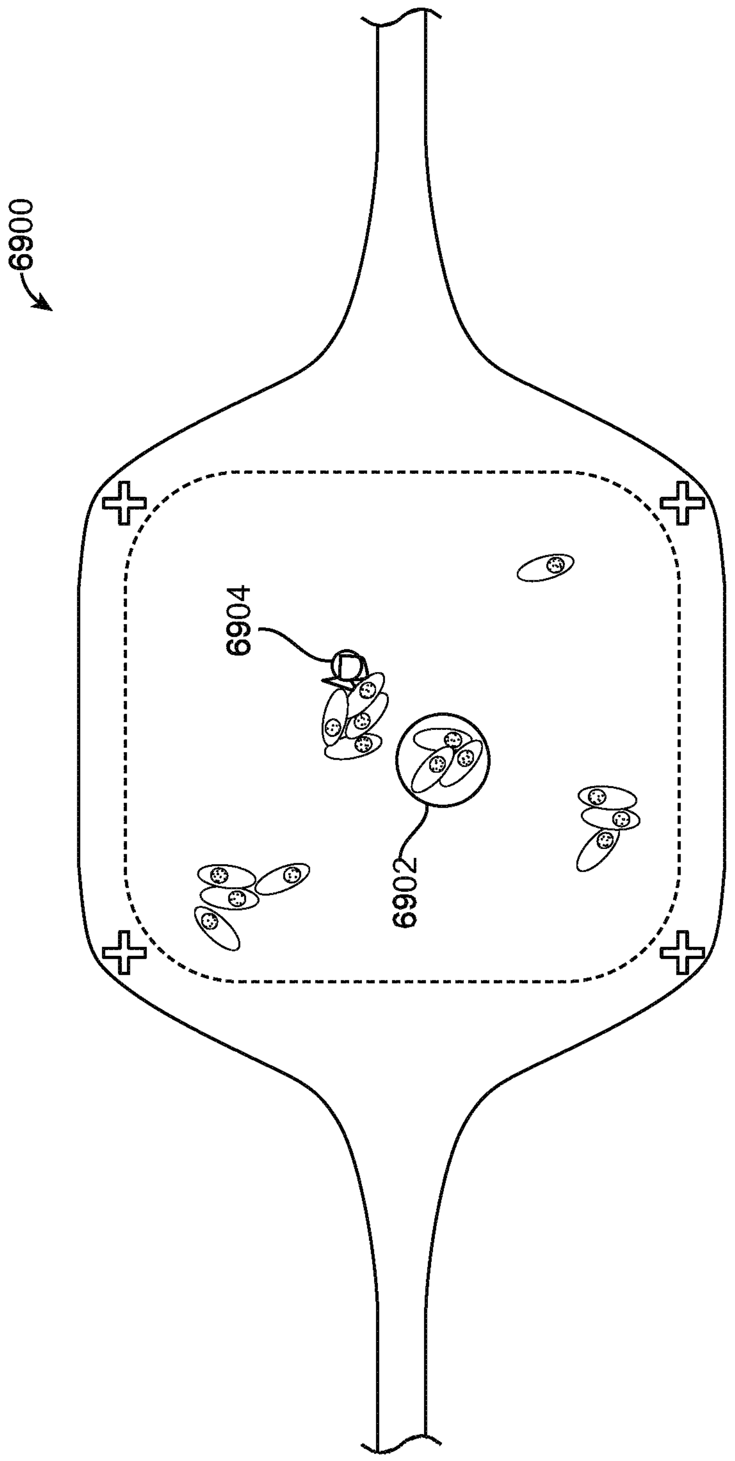
FIG. 69 is a diagram illustrating removal of cells from a cell culture chamber in a closed cassette system in accordance with various implementations.

FIG. 69 is a diagram illustrating removal of cells from a cell culture chamber 6900 in a closed cassette system in accordance with various implementations. The cell culture chamber 6900 may be similar to cell culture chamber 6702 in FIG. 67. Cell colonies 6902 or individual cells 6904 may be selectively lysed via a steered pulsed. For example, in an iPSC reprogramming process colonies may be kept separated to ensure clonality. A cell imaging subsystem (e.g., cell imaging subsystem 112) may collect images of the cell culture chamber 6900 and a computing subsystem (e.g., computing subsystem 110) may utilize various machine learning processes to determine whether one or more of the cell colonies 6902 may be in danger of merging. The computing subsystem may then control a cell editing subsystem (e.g., cell editing subsystem 112) to remove at least one of the cell colonies 6902. Additionally, individual cells or groups of cells may be determined by a human viewer or a computer algorithm to be spontaneously differentiating, in which case they may be removed via the cell editing subsystem as shown herein.

Figure 70:
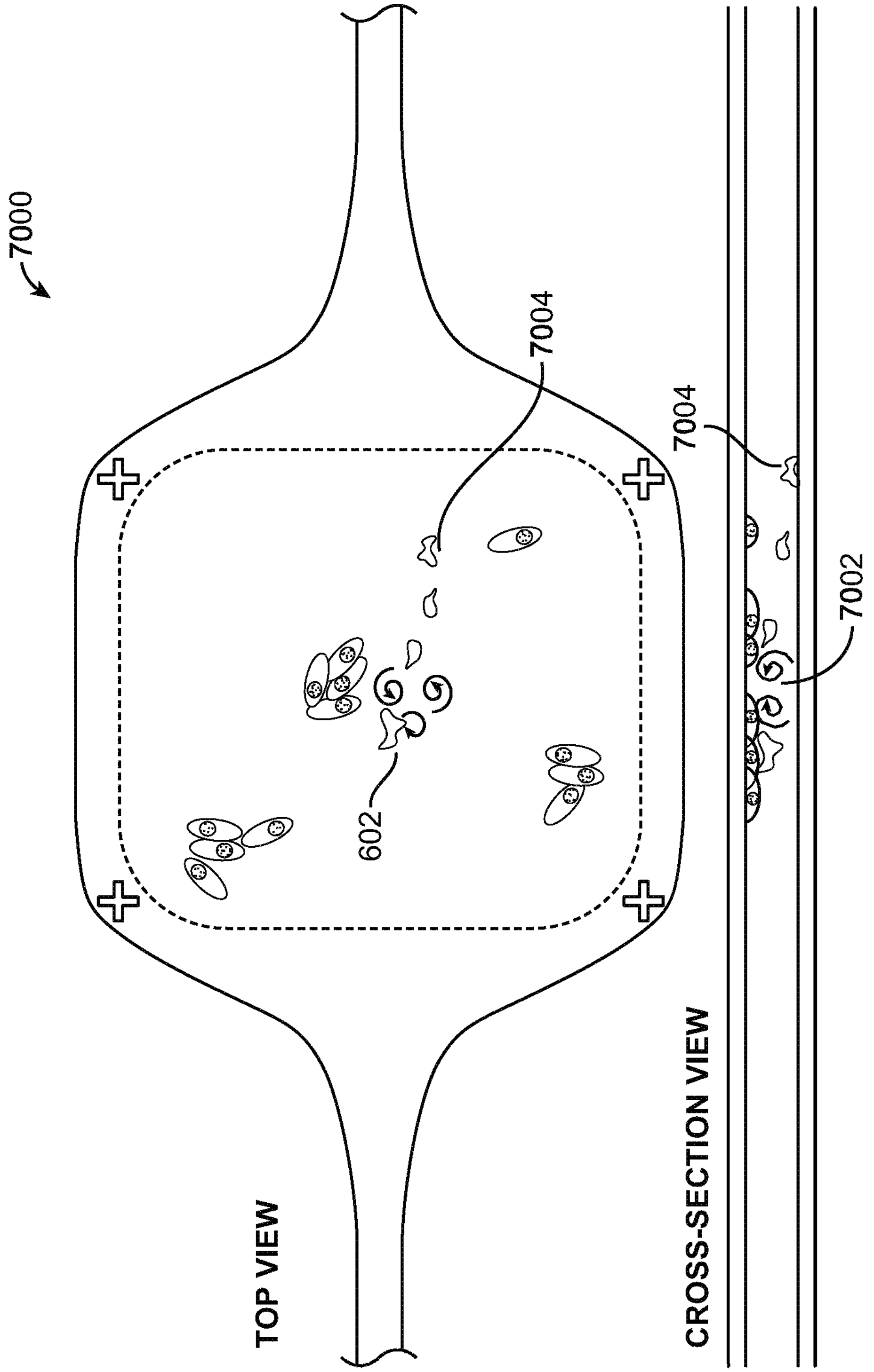
FIG. 70 is a diagram illustrating agitation of cells from a cell culture chamber in a closed cassette system in accordance with various implementations.

FIG. 70 is a diagram illustrating agitation of cells from a cell culture chamber 7000 in a closed cassette system in accordance with various implementations. The cell culture chamber 7000 may be similar to cell culture chamber 6702 in FIG. 67. FIG. 70 shows both a top view and a cross-section view of the cell culture chamber 7000. The systems and methods disclosed herein may allow for agitating or mixing of liquid within the cell culture chamber 7000 without opening the closed cassette system. In this case, the agitation mechanism may be used to detach cell debris from the culture growth surface so that the debris then settles on the opposite surface of the cell culture chamber 7000 (e.g., the bottom surface). The turbulent mixing effect of the mechanism is indicated in the top view and cross-section view by arrows 7002.

The agitation mechanism may include a number of physical modes, including but not limited to: magnetic mixing in which one or more magnets are resident inside the cell culture chamber 7000, and an external magnetic actuator is used to translate and/or rotate these magnets to achieve local mixing and agitation; mechanical actuators acting on the upper and/or lower surfaces of the cell culture chamber, potentially in conjunction with liquid flows or stoppage; laser-based techniques where a pulsed laser is used to induce cavitation inside the cell culture chamber 7000 in order to produce local mechanical forces and mixing (the focus of this laser may be on the surface opposite the cell culture, for example); or ultrasound transmission into the cell culture chamber 7000 that may be uniformly distributed or focused on specific regions where debris needs to be dislodged. As a result of the agitation, the detached cells and/or cell debris 7004 settles on the lower surface. From there the cell debris 7004 may be removed by one or more mechanisms including the above, but also liquid flow and gravitational techniques (e.g., tilting).

Figure 71:
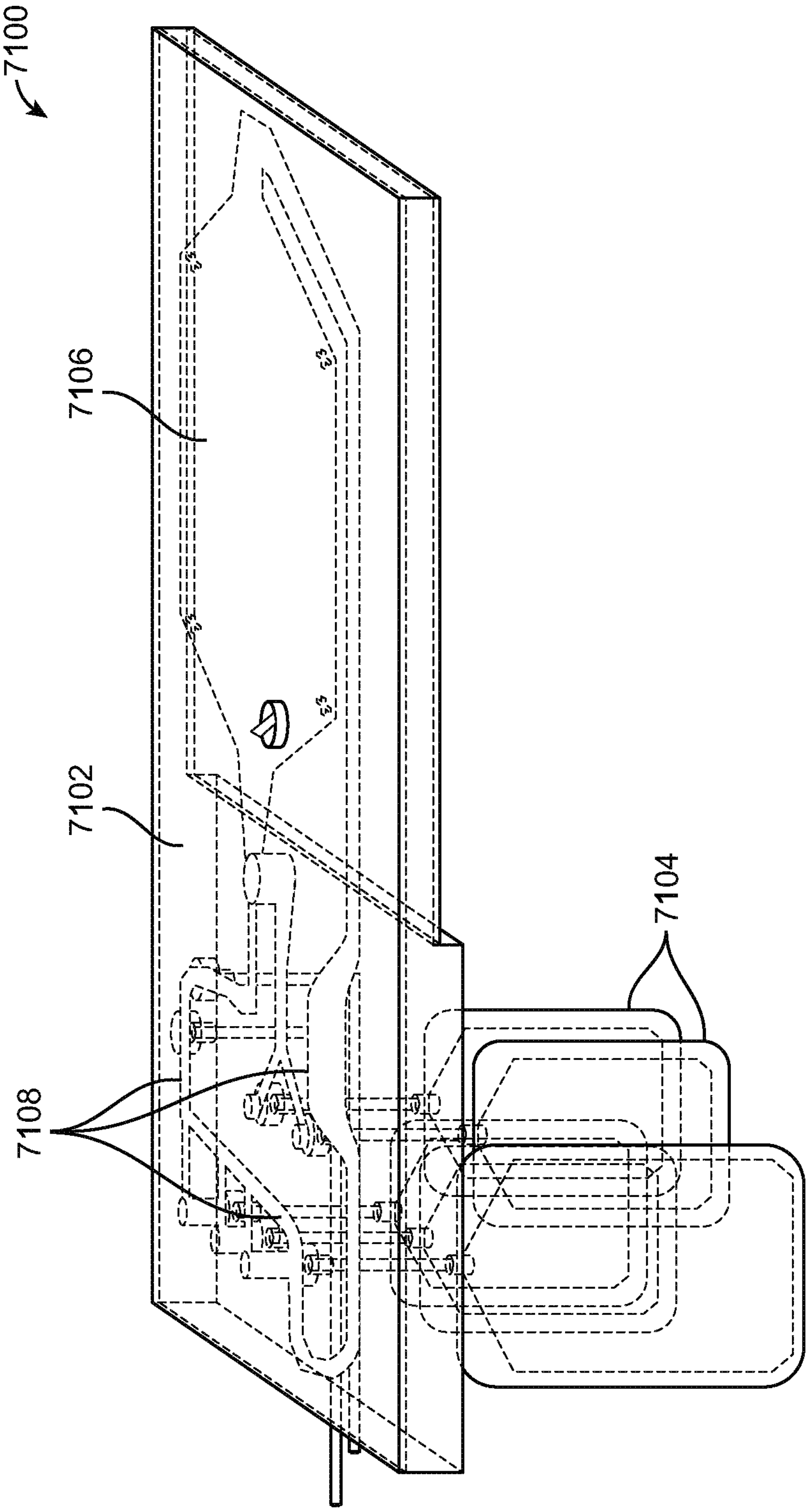
FIG. 71 is a diagram of a single-use portion of a closed cassette system for use in a cell culture system in accordance with various implementations.

FIG. 71 is a diagram of a single-use portion 7100 of a closed cassette system for use in a cell culture system in accordance with various implementations. The single-use portion 7100 may be configured to support a single cell culture process before being discarded. The single-use portion 7100 may include a chamber, fluidics, and supply and waste bags and associated tubing, similar to those shown in FIG. 67. All of the components of the single-use portion 7100 may be sterilized, filled under aseptic conditions, and then used in a cell culture process. After use, the bags containing the output cell product are removed using a sterile weld, and the remainder of the single-use portion 7100 may be disposed of properly.

The single-use portion 7100 may include a body 7102 housing fluidic system 7108 as well as cell culture chamber 7106. The body 7102 may be transparent or semi-transparent to allow for visual or automated imaging of the fluidic components and channels, for example to verify that there is no contamination, blockage, bubbles, etc. Bags 7104 are attached to the single-use portion 7100. The bags 7104 may contain media reagents as well as waste products and cellular products. The fluidic system 7108 in the single-use portion 7100 may include channels for circulating liquid, valve sections, pump sections, gas concentration control fluidics, non-invasive sensing patches, etc.

Figure 72:
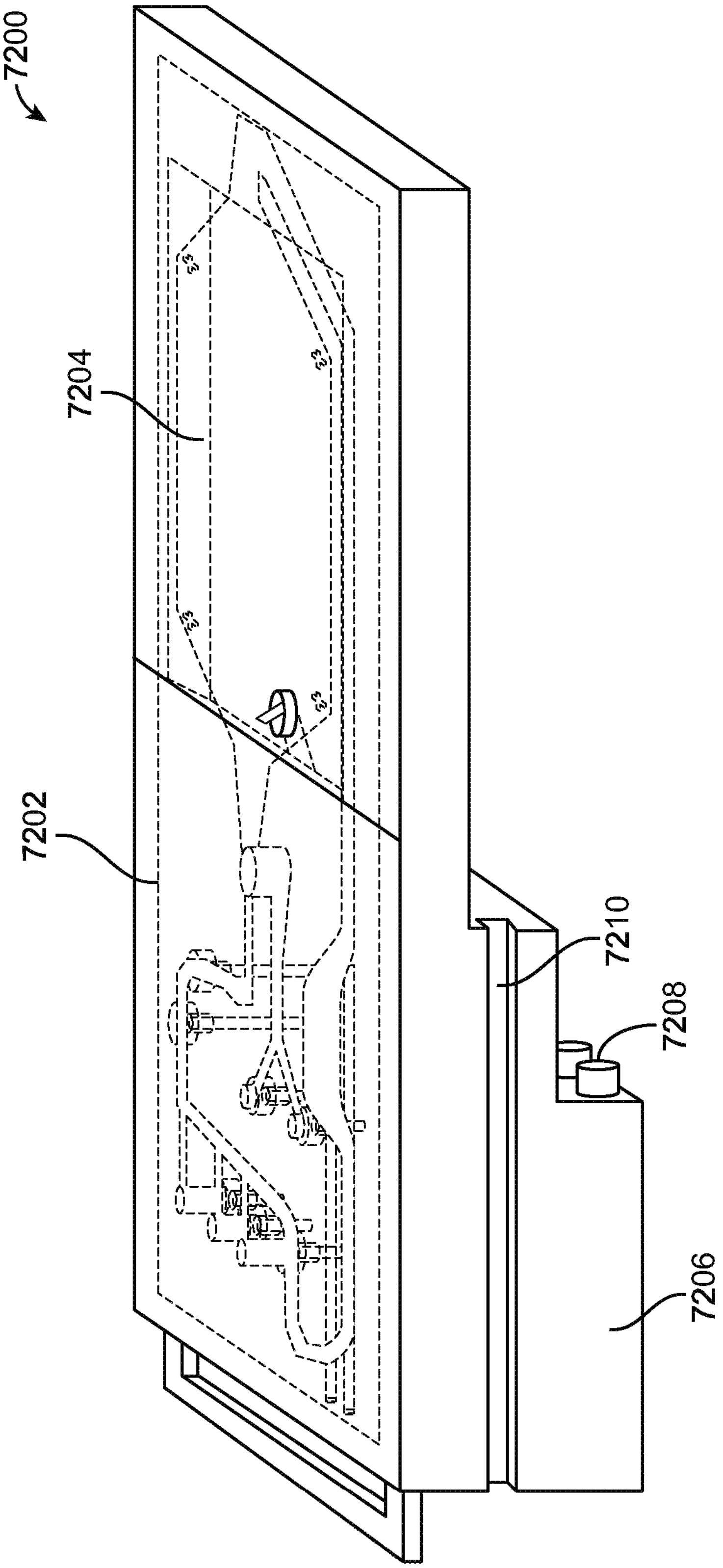
FIG. 72 is a diagram of a permanent portion of a closed cassette system for use in a cell culture system in accordance with various implementations.

FIG. 72 is a diagram of a permanent portion 7200 of a closed cassette system for use in a cell culture system in accordance with various implementations. The permanent portion 7200 may include a reusable housing 7202 that encloses the single-use portion of the closed cassette system (e.g., single-use portion 7100). The combination of the permanent and single-use portions may form a complete closed cassette system (e.g., closed cassette system 6700). The permanent portion 7200 may also include at least one clear window 7204 to allow complete imaging of the cell culture chamber located in the single-use portion. In some implementations, the window 7204 may be on both sides of the cell culture chamber in order to allow transmission imaging. In other implementations, the window 7204 may only be located on one side of the cell culture chamber when reflective imaging is sufficient (i.e., light source and sensor on same side of chamber).

A compartment 7206 houses the supply, waste and product bags of the single-use portion and may provide one or more temperature-controlled chambers for long-term storage (for example, cellular products may be held at 37° C., while some reagents are held at 4° C. until use). In some implementations, the permanent portion 7200 may also include actuators for actuating valves and pumps on the single-use portion of the closed cassette system. For example, spring-loaded solenoids may apply pressure to the tubing on the disposable fluidics to keep valves closed in their unactuated state, and when an electrical current is provided, the solenoid opens the valve by releasing pressure. Similarly, pumps may be driven by electromechanical systems within the permanent portion, for example by driving a series of cylindrical rollers in a semicircle along the path of tubing on the single-use portion to initiate peristaltic pumping.

A mechanical rail 7210 may integrated in the permanent portion 7200 to provide alignment within one or more pieces of equipment. For example, the closed cassette system may reside in equipment that also includes imaging systems, power systems, central computing systems, heating and cooling systems, cassette movement systems, and other components to support parallel cell culture processing on multiple closed cassette systems. In one implementation, such equipment may include a server rack, and the mechanical rail 7210 may allow the closed cassette system to slide in and out of the server rack. The permanent portion 7200 may also include pluggable connectors 7208 that interface with connectors on the equipment (e.g., server rack). The pluggable connectors 7208 may include, but are not limited to, electrical connectors to power on-board electronics and actuators, data connectors to collect sensor and status information centrally, liquid connectors for circulating liquid for temperature control, and gas connectors to supply gas for maintaining gas concentrations in the cell culture media.

Figure 73:
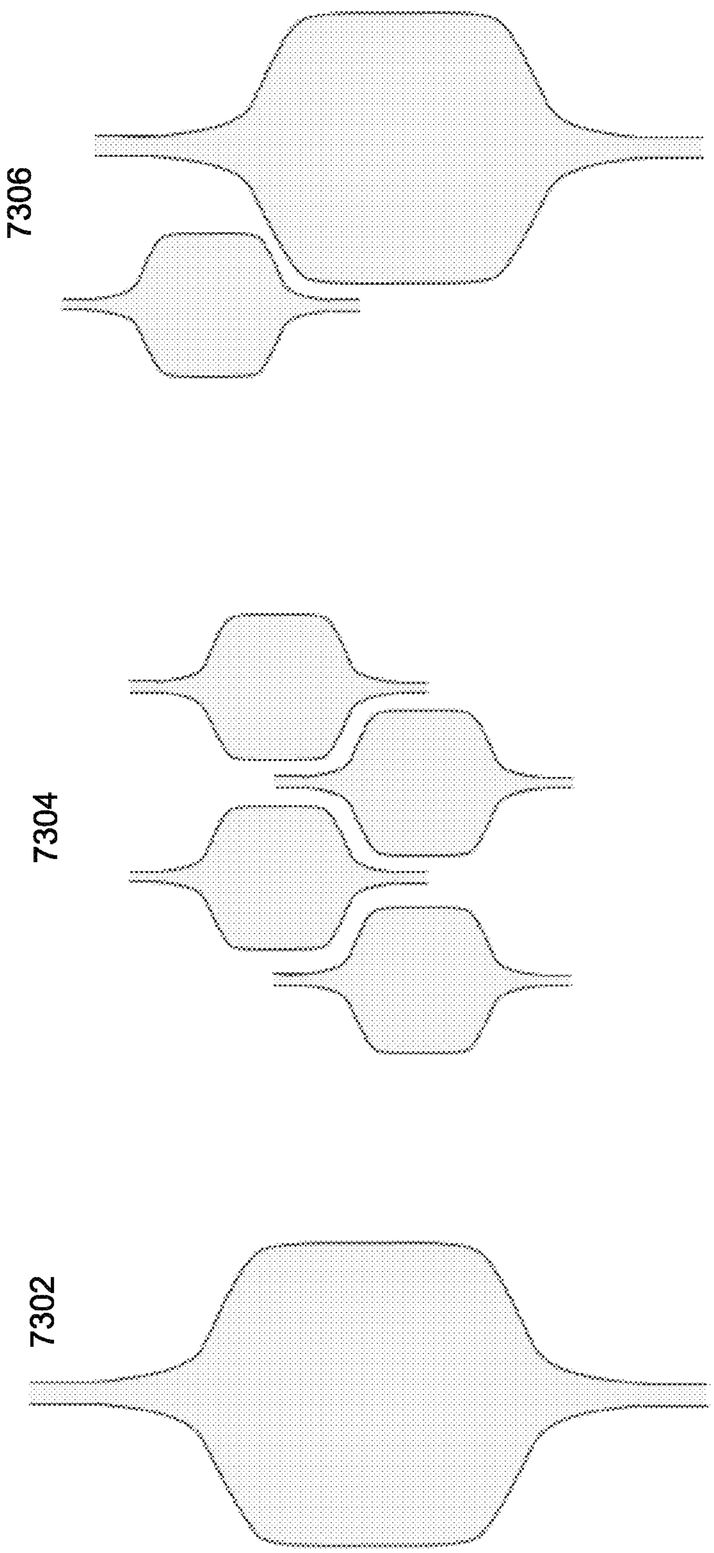
FIG. 73 illustrates various cell culture chamber configurations in a closed cassette system for use in a cell culture system in accordance with various implementations.

FIG. 73 illustrates various cell culture chamber configurations in a closed cassette system for use in a cell culture system in accordance with various implementations. These configurations may include a single large chamber configuration 7302, a multiple small chamber configuration 7304, a small and large chamber configuration 7306, and other configurations not shown in FIG. 73 but known to persons of skill in the art. The single large chamber configuration 7302 may be used for cell expansion, for example. The multiple small chamber configuration 7304 may be used in cases in which multiple clonal populations are desired in order to have a diversity of product, for example. The small and large chamber configuration 7306 may be used to first prime cells in a small chamber using relatively little reagent (this may include delivery of compounds into the cells), followed by reprogramming or differentiation and expansion in the larger chamber. In all of these configurations, it is possible using appropriate valving and/or filtration to keep cells from inadvertently moving from one chamber to another. However, as in the last example, the fluidics may be configured to explicitly allow movement from one chamber to another through valving filtration and pumping operations.

Modular Bioprocessing System

Bioprocessing is the process of using living cells or their components to obtain a desired output. Current bioprocessing equipment is available largely in two types. The first type are large-scale bioreactors derived originally from the chemical industry and repurposed for cell-based processes such as protein or viral production. These bioreactors typically using large steel tanks, but more recently have been fitted with one-time-use bags or scaled down to glass-based stirred bioreactors. These systems are usually surrounded with bespoke, sealed tubing and other modifications to make the bioreactors suitable for handling biological materials. The second type of bioprocessing equipment are small-scale systems derived from manual R&D laboratory instruments, typically including benchtop instrumentation and utilizing microwell plates or small flasks. In some cases, small scale systems have been scaled up to larger containers, and custom systems have been developed in order to transport, fill, and handle stacks of plastic containers containing cell cultures.

In the case of large scale bioreactor systems, the amount of data collected during the bioprocess is often minimal. There has been a largely stalled push to get more measurement and control in tank bioreactor-style systems. However, the proposed measurements, even if implemented, would be minimal representations of the state of the bioreaction, typically measurements of nutrients, waste products, cell mass/density, pH, $O_2$, temperature, and a few other factors that allow for better control of the process. Some additional sampling-based measurements allow for more detailed, but less frequent, measurement of the cell mixture. However, the physical volumes of these systems are large, and the data volume is quite low.

Recent autologous cell and gene therapy processes, such as CAR-T therapies, have taken a similar approach, simply miniaturized. It has become increasingly clear that the absence of higher-bandwidth measurement, monitoring, and feedback control are a challenge in these therapies, where patient-to-patient variations can lead to poor consistency and yield. On-time delivery of therapies is crucial, and these drawbacks may lead to significant delays. Some bioprocessing equipment suppliers have sought to build automated, modular units to address these issues, but although these provide the ability to perform cell processes in non-sterile facilities, they still keep to the convention of separating biological equipment from the data infrastructure, and are built with only human operators in mind.

On the other hand, in the small scale system model, derived from R&D laboratory equipment, there is at least the potential to gather more data on the actual cell culture conditions by use of imaging, because many formats were developed specifically to allow microscopy and other optical measurements. However, imaging measurements of cell culture are done almost only as "spot checks" rather than to quantitatively assess the cells or guide process parameters. High content imaging has largely remained in the domain of R&D or is used in quality control assays at the end of a cell culture process. For example, immunofluorescent-labelled imaging may be used on a small sample that seeks to reflect the whole product.

Bioprocessing systems should ideally collect detailed, fine-grained information about the progression of the process, the state of cells and cell colonies, and potential problems with purity or yield far in advance of final quality control assays. This fine-grained data, together with appropriate control algorithms, may be used to control and optimize both process parameters (such as nutrient flow, product harvest, vitamin or gas concentrations, temperature, pH, etc.) and to actively guide the cell cultures by use of selecting cell removal or editing based on imaging results. In addition, other optical techniques such as spectroscopy may be employed in such formats to extract data related to biochemical constituents within the cell media or cell mass.

With such expanded use of online imaging and spectroscopic techniques, the amount of data generated per biological sample in process explodes. Take for example the equivalent of a T-225 flask (225 $cm^2$ growth area) used in a process for differentiating cells from induced pluripotent stem cells (iPSCs). Using brightfield imaging with a 5-layer Z stack, at a cycle time matching the rough cell division (18 h), a resolution of 1 micron, and a standard 16 bits per pixel, the daily raw data stream of imaging alone is 150 Gigabytes. This imaging data must be collected, processed, interpreted, and made into actionable information relevant to bioprocess prediction and control. Scale up to a facility in which hundreds of patient samples are processed in parallel, and the scale and reach of the data infrastructure alongside the bioprocessing infrastructure becomes clear: many terabytes per day flow through the biomanufacturing environment. Small scale data storage means are no longer useful. An infrastructure in which biology and data coexist and work together is required.

Another issue in bioprocessing is the ability to automate processes efficiently. The current approach includes setting instruments on benches (similarly to how they would be situated in a manual R&D laboratory), placing one or more robots between the instruments, and then training the robots to very precisely find the correct locations to place or pick consumables to/from the various instruments. Any movement (swap-out for repair, etc.) of an instrument requires retraining. Almost every instrument has a slightly different mechanical interface, usually designed primarily with manual R&D lab operations in mind, with mechanical interfaces to robotic systems as an afterthought. As a result, building an automated system with even just a few instruments becomes a major undertaking for which specialized contractors are hired, custom benches are fabricated, and the reach of a central robot arm must be carefully calculated. Once built, the setup offers limited expandability. As a result, the up-front investment in time, dollars, and real estate footprint for incremental capacity can be very significant.

Some companies have attempted to remedy the expandability issues with large-scale transport system for microplates and extensive custom automation hardware. Others have built more linear robotics that move along shelving constructed specifically for each piece of equipment, with appropriate widths, heights, etc. for shelves. However, these systems rely on specific positioning of instrumentation to properly interface with the robotics, and where the robotics are required to be highly flexible, with multiple degrees of freedom, and therefore quite expensive.

Additionally, because of the format of these systems and the constraints of the type of robotics and automation that is required the systems end up having a large, planar footprint. The result resembles a warehouse where bulk goods of various shapes and sizes are simply placed on shelving of varying proportions. When faced with these analogous issues, large warehouse operators have tried to standardize shelving and storage, and then try to automate the storage and retrieval process and adopt a vertical format for space and transport logistical efficiency. Similarly, in order to scale up biology, and in particular bioprocessing and biomanufacturing, a more modular, standardized, expandable, and data-integrated system that minimizes footprint and transport complexity is needed.

The systems and methods disclosed herein utilizes industry standard data and communications infrastructure and equipment to serve as the basis and backbone for a highly modular bioprocessing system. The bioprocessing modules used in these systems may be closed cassettes that are fully imageable for monitoring and control purposes, including the ability to actively edit cell cultures by removing cells or cell colonies during the course of the process. The present implementations may utilize such cassette-based systems, but may also utilize existing microwell plate, flask, and larger (closed) container formats.

The bioprocessing modules may be sized to fit within standard server rack units, with heights measured in standardized units of U (1U, 2U, 4U, etc.) and widths the same as computing, storage, and communications equipment. The modular bioprocessing system also includes common modules that may be shared between multiple bioprocessing modules on the same rack, such as data storage modules, computing modules, power supplies, communications modules, environmental control modules, laser modules, liquid handler modules, and imaging modules. This not only allows for a highly modular, incrementally expandable format for bioprocessing facilities, but also allows for very tight integration between bioinstrumentation and data processing to address the high volumes of data and communication in fully-monitored, closed-loop bioprocessing. Other advantages of such a system include fast setup and delivery, easier automation, incremental expansion, use of existing modular units for power, environmental management, and direct integration with data infrastructure and modules.

The modular bioprocessing systems may have standardized dimensions, such as 19 inch width enclosures, various depths including but not limited to 24", 36" and 48", and various heights up to the industry-standard 42U (in which 1U=1.75"). All instrumentation and equipment in the various implementations may mount into these racks and have heights in 1U increments, so positioning may be calculated purely from rack position index. The front-facing panel of the instrumentation modules may have a loading area to load/unload the micro plate, flask, cell culture vessel, or cell culture cassette for which the system is designed. The modular bioprocessing system may also include vertical transport mechanisms to move cell culture containers (e.g., microwell plates) in and out of bioprocessing modules and onto/off of horizontal transport mechanisms designed to move cell culture containers between modular bioprocessing systems and other locations. These mechanisms may be automated in order to form a fully automated bioprocessing facility, but may also allow for easy human interaction with the system.

The systems and methods disclosed herein include a modular bioprocessing system that includes a rack, one or more bioprocessing modules configured to fit within the rack, the one or more bioprocessing modules configured to accept one or more cell culture containers, and a plurality of common modules configured to fit within the rack, the plurality of common modules shared by the one or more bioprocessing modules. This system has many advantages over current bioprocessing designs, which may include, but are not limited to, easy setup, alteration, and expansion in capacity, and easy integration with data, communication, and power systems.

Figure 74:
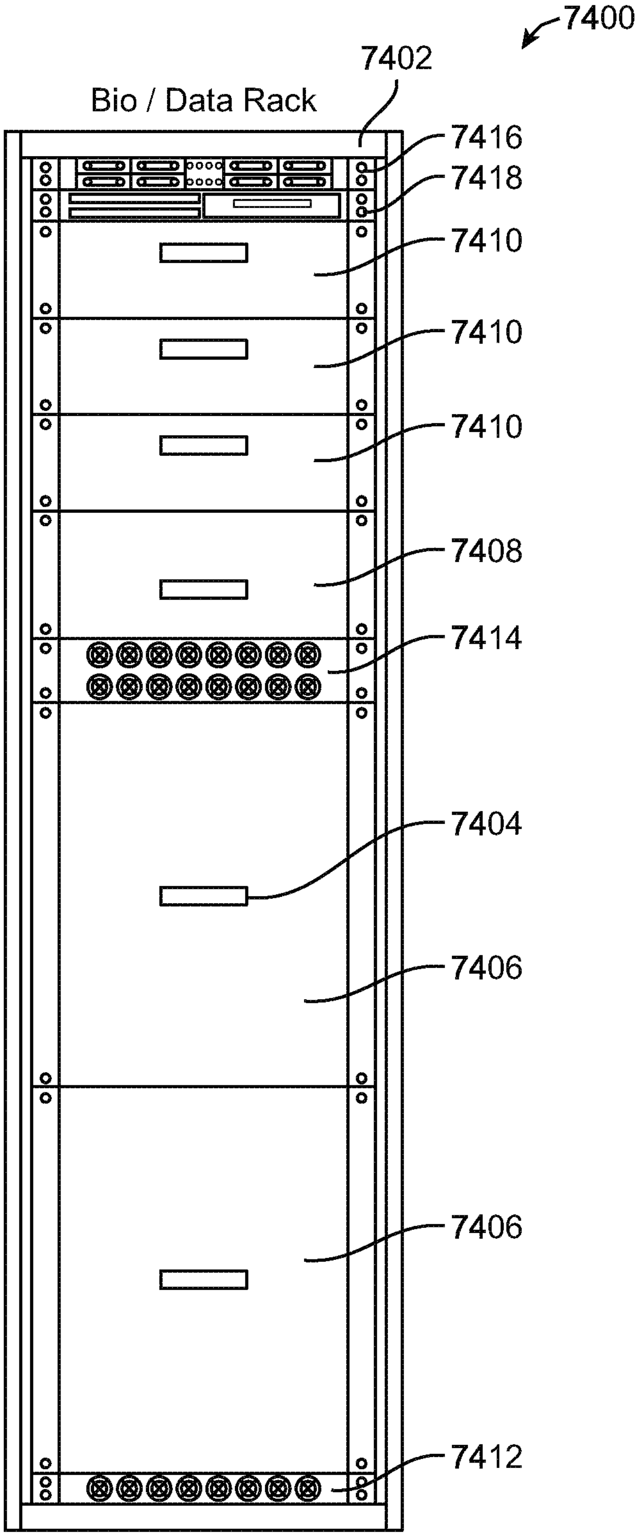
FIG. 74 is a diagram of a modular bioprocessing system in accordance with various implementations.

FIG. 74 illustrates a modular bioprocessing system 7400 in accordance with various implementations. The modular bioprocessing system may be an implementation of a cell culture system (e.g., cell culture system 100), or may be part of a larger cell culture system that includes one or more modular bioprocessing systems. The modular bioprocessing system 7400 may include a rack 7402 for holding all the modular elements in the modular bioprocessing system 7400, including both data processing and communications modules, as well as bioprocessing modules. The rack 7402 may have standardized server rack sizes. For example, server rack height may be measured in units of U (1U=1.75 inches). For example, a rack with a size of 42U has a usable height of 73.5 inches. The rack 7402 may also have standard depth and width dimensions. This allows for a number of standard-shaped modular elements to be placed in the rack 7402, rather than requiring custom-sized components.

The modular bioprocessing system 7400 may also include one or more container interfaces 7404 for accepting and holding cell culture containers. These cell culture containers may include, but are not limited to, standard microwell plates (for example 6-, 12-, 24-, 48-, 96-, 384- . . . well plates), cell culture flasks, microfluidic chambers, or custom cassettes for cell cultures. In FIG. 74, an implementation that uses standard microwell plates is shown. In this case, the container interface 7404 include a plate holder that extends from the front of each bioprocessing module for loading/unloading microwell plates. The microwell plates are then retracted into each bioprocessing module for processing or storage.

The modular bioprocessing system 7400 may also include one or more bioprocessing modules 7406. Each bioprocessing module 7406 may be a closed container (i.e., the internal components are not exposed to external components that may contaminate the container) that includes a cell culture container holding a biological sample to be processed (e.g., differentiated cells that are processed into iPSCs or vice versa) and components that support the growth, editing, cleaning, imaging, sensing, and other functions for processing the biological samples. The bioprocessing modules 7406 may include, but are not limited to, closed cassettes that are fully imageable for monitoring and control purposes, microwell plates, flasks, and other closed container formats. Each bioprocessing module 7406 may maintain independent environmental conditions corresponding to different cell processes or cell process stages or states. For example, the temperature for each module may be set differently, pH may be controlled, or the dissolved oxygen level may be set differently in each module in order to maintain a hypoxic environment for some cell culture processes or stages of processes.

The modular bioprocessing system 7400 may also include one or more liquid handler modules 7408 that is configured to change media in the bioprocessing modules 7406. Appropriate tubing and containers for media and waste may be connected to the rear (utility) side of the liquid handler module 7408 and connected to the bioprocessing modules 7406. A single liquid handler module 7408 may support one or more bioprocessing modules 7406. For example, bioprocessing modules 7406 that contain the same biological samples undergoing the same process may share a liquid handler module 7408. In other implementations, there may be a one-to-one correspondence between bioprocessing modules 7406 and liquid handler modules 7408. The liquid handler modules 7408 may include relatively simple media exchange modules, which withdraw waste media from cell culture containers, and refill with fresh media. Such media exchange functionality may further include centrifugation in the case of suspension cell cultures. Other modular liquid handling implementations may include the ability to add multiple reagents to wells within microplates in various combinations, for the purpose of drug screening or high-throughput cell process development. Other modular liquid handling implementations may include the ability to simultaneously load multiple cell culture containers and affect transfers between these containers, for example to distribute cell samples among multiple wells for subsequent quantitative polymerase chain reaction (qPCR analysis), which may also be implemented in the present application via a modular unit.

The modular bioprocessing system 7400 may also include one or more imaging modules 7410 that are configured to capture time series images of biological samples cultured in the bioprocessing modules 7406. Different imaging modules 7410 may have different capabilities. For example, two label-free (brightfield, phase, quantitative phase, transmissive or reflective darkfield, etc.) modules may be used to capture label-free time series images of cell cultures over days, and a single fluorescent imaging module may be used to capture high-content multi-channel fluorescently-labelled cell culture images at an endpoint. In some implementations, one imaging module 7410 may be configured to capture multiple types of images. The imaging modules 7410 may be configured to automatically capture images based on a schedule, the schedule set by a control module within the modular bioprocessing system 7400 or by an external controller that controls multiple modular bioprocessing systems.

One of the advantages of the modular bioprocessing system 7400 is that modules may share resources, similar to how resources may be shared in data server rack configurations. For example, the modular bioprocessing system 7400 may include a power supply module 7412 provides power (for example, 24V DC) to all modules in the system, with redundancy. Similarly, the modular bioprocessing system 7400 may also include an environmental control module 7414 that is configured to provide heating and cooling capacity via liquid to all modules in the system. For example, the environmental control module 7414 may maintain cell cultures at 37° C., reagents to be maintained at 4° C., and data/computing modules to be cooled to appropriate operating temperatures even under high loads. The modular bioprocessing system 7400 may utilize standardized liquid connectors and distribution manifolds used in cooling CPU/GPU server racks because of the standardized setup of the rack 7402 and other modules.

The modular bioprocessing system 7400 may also include one or more data storage modules 7416 and computing modules 7418. The data storage module(s) 7416 may be configured to store images collected by the one or more imaging modules 7410, sensor data collected by various sensors in the modular bioprocessing system 7400, and data and applications used by the computing modules 7418. The computing module(s) 7418 may be configured to perform various data processing and analysis functions related to bioprocessing the cell cultures in the bioprocessing modules 7406. For example, the computing module(s) 7418 may perform image pre-processing, registration, normalization, and stitching functions for the imaging modules 7410, reducing or eliminating the need for dedicated processors or computing modules for each imaging module 7410, and potentially significantly distilling or compressing imaging data before it is transferred to a centralized location (either on-premises, in another location including cloud resources, or both in a hybrid architecture). The computing module(s) 7418 may also perform other data processing, input/output, and communications functions for the modular bioprocessing system 7400.

The modular bioprocessing system 7400 may be communicatively connected to a central controller, such as a central server that controls one or more modular bioprocessing systems 7400. For example, there may be multiple modular bioprocessing systems 7400 located in a room, and there may be wired and/or wirelessly connected to a central server that controls the operation of each modular bioprocessing system 7400. The central server may also collect data from each modular bioprocessing system 7400, and may also provide a user interface for a person to view data (e.g., imaging data) collected from any modular bioprocessing system 7400, monitor the status of any bioprocessing module, and control any of the modules in any modular bioprocessing system 7400. The central server may implement many functions, including scheduling automated processing schedules of cell cultures, alerting users of emergency conditions in any modular bioprocessing system 7400, and presenting real-time operational data for any modular bioprocessing system 7400.

The modular bioprocessing system 7400 shown in FIG. 74 is a full-height rack. However, it should be clear from the modular nature of the system that smaller systems are feasible. For example, a minimal system for continuous cell culture measurement may include one bioprocessing module 7406, one liquid handler module 7408, one imaging module 7410, plus shared systems. The system may fit into a very compact rack suitable for even the densest environments such as university laboratories. The modular bioprocessing system 7400 may include other components not illustrated in FIG. 74, and may include variations known to persons of ordinary skill in the art.

Figure 75:
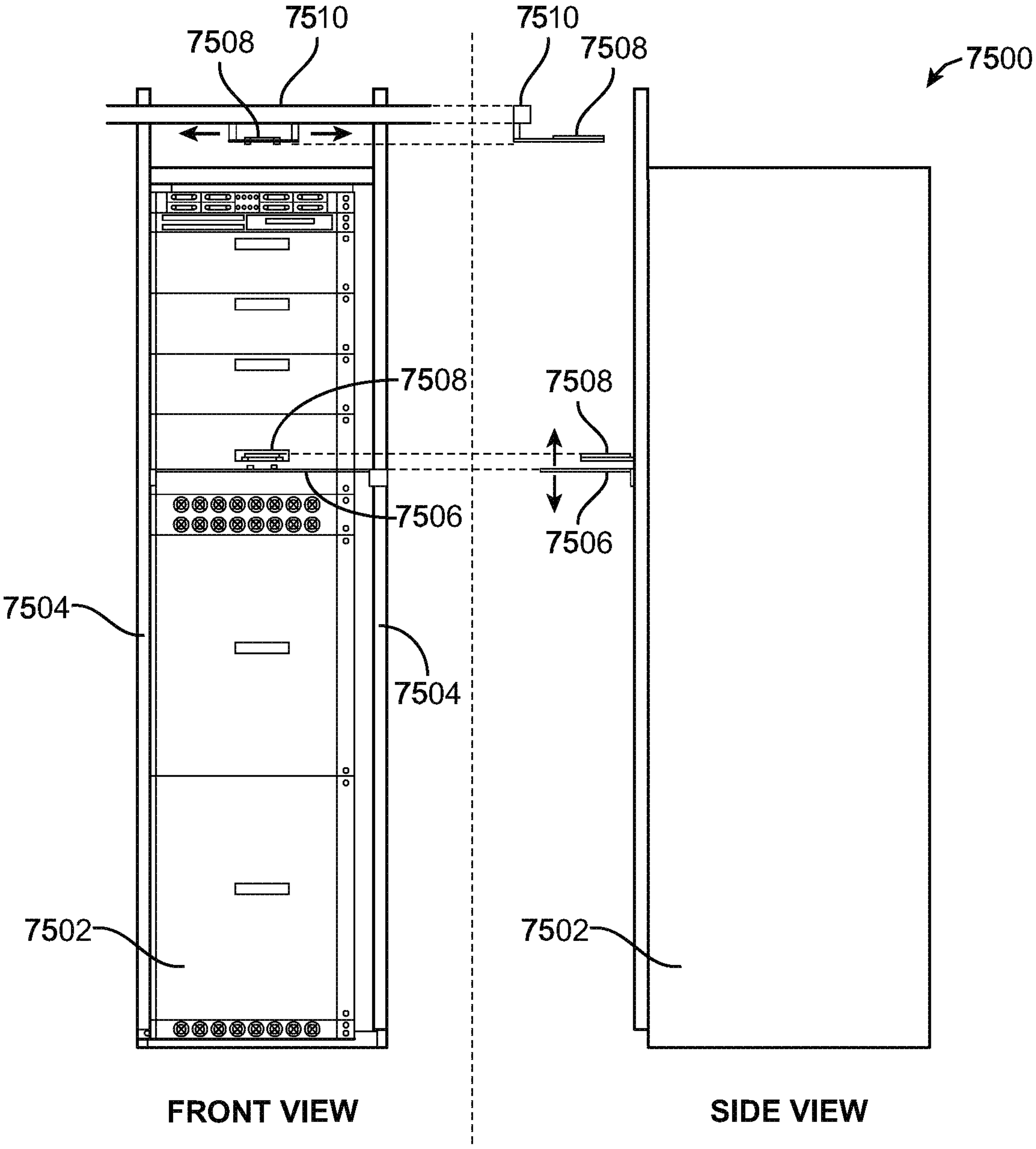
FIG. 75 illustrates container transportation functionality in a modular bioprocessing system in accordance with various implementations.

FIG. 75 illustrates container transportation functionality in a modular bioprocessing system 7500 in accordance with various implementations. Because of the modular nature and vertical format of the various implementations, a highly simplified cell culture container transport mechanism is possible. Moreover, the transport is compatible with side-by-side work with human operators, unlike robotic transport systems where a potentially hazardous robot arm sits in the center of a cluster of bioinstruments. The standardized modular format disclosed herein dramatically simplifies the requirements for such an automated transport system, since it defines discrete vertical rack locations for container pickup/drop-off, and a fixed horizontal position, allowing a single-axis, low-precision actuator (track system) to be utilized, with low-cost sensors to confirm container pick-up and drop-off at individual modules or on an overhead transport system.

The modular bioprocessing system 7500 may be similar to the modular bioprocessing system 7400 shown in FIG. 74. The modular bioprocessing system 7500 may include one or more bioprocessing modules 7502 that host cell culture containers. The example shown in FIG. 75 uses microwell plates 7508 as cell culture containers, but any suitable cell culture container is compatible with the described implementation, such as closed cassettes. A set of rails 7504 may be mounted on the rack front, allowing vertical motion control of a vertical transporter 7506 mounted on the rails 7504. A bioprocessing module 7502 may eject a microwell plate 7508 from the front of the module onto an extended container interface (e.g., container interface 7404). The vertical transporter 7506 may approach the container interface from the bottom to retrieve the microwell plate 7508 from a bioprocessing module 7502 that is presenting it. The vertical transporter 7506 may then transport the microwell plate 7508 to another location along the vertical axis of the rack and/or allow a person to collect the microwell plate 7508. Alternatively, the vertical transporter 7506 may approach an extended container interface from the top when it is delivering a microwell plate 7508 to a bioprocessing module 7502, and the microwell plate 7508 remains on the extended container interface as it passes. The container interface may then retract the microwell plate 7508 into the associated bioprocessing module.

For single-rack installations, or multi-rack installations where the racks are independent, this vertical transport is sufficient to completely automate the bioprocessing system, again with an extremely compact footprint compared to existing bio-automation configurations. In the case of multi-rack systems where automated microplate exchange is desired between racks, or between individual racks and a fill/harvest or other central location, a horizontal track-based transporter 7510 is provided. The horizontal transporter may transport cell culture containers in a horizontal axis of the rack. The horizontal transporter 7510 provides a mechanical interface similar or identical to the container interfaces, in order to hold the microplate wells 7508 for transport. The vertical transporter 7506 may load microwell plates 7508 onto the horizontal transporter 7510 by approaching from the top, or picks up a plate from the horizontal transporter 7510 by approaching from the bottom. Neither the vertical nor horizontal transport system interfere with human operator access to the front (or back) of the modules, so plates may be manually retrieved or added by human operators in concert with automated transport. Moreover, the automated transport works with minimal footprint, and may use low mechanical force to increase safety.

Figure 76A:
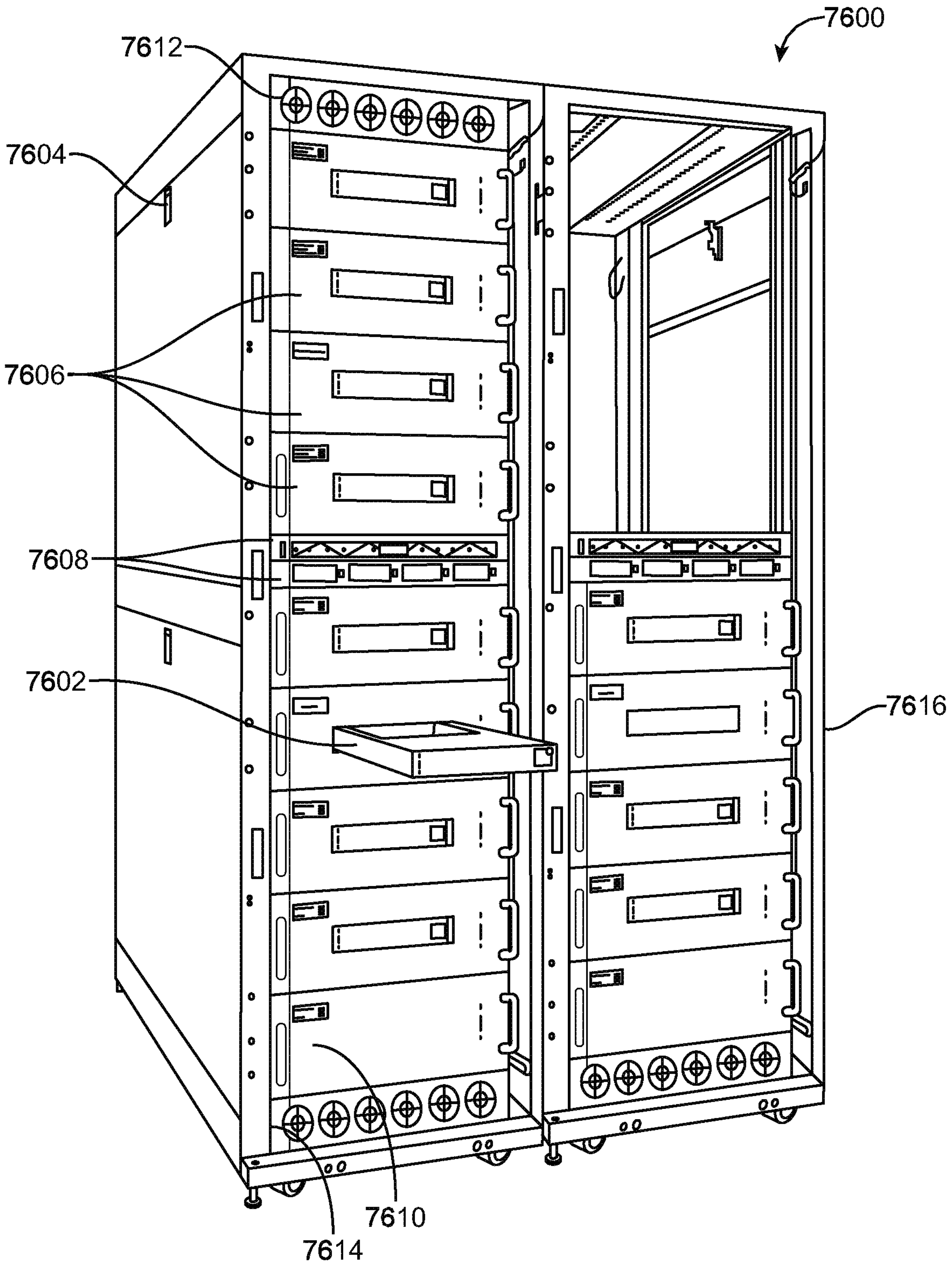
FIG. 76A is another diagram of a modular bioprocessing system in accordance with various implementations.

FIG. 76A is another diagram of a modular bioprocessing system 7600 in accordance with various implementations. In this implementation, the cell culture container is implemented as a cassette 7602 that may be used for various cell culture processes, including but not limited to cell reprogramming, cell differentiation, cell gene editing, and/or cell-based bioproduction. The cassette 7602 is sealed in order to allow sterile processing of multiple samples in the same environment, for a high degree of control and consistency, and potentially for good manufacturing practice (GMP) compliance for therapeutic (patient-bound) products. An example of the application of this implementation is the production of patient-specific human induced pluripotent stem cells (hiPSCs), and subsequent differentiation of hiPSCs into replacement cells for cell therapies. In such an application, complete isolation of patient samples from one another is required, and accomplished using a cassette-based system where required media and reagents, as well as waste reservoirs, are contained within a sealed liquid system on the cassette 7602. In this example, the cassette 7602 may include a cell culture chamber that is fully imageable, and the cell culture chamber is configured to allow selective laser ablation of cells from the cell culture, with subsequent removal of resulting debris by on-board liquid handling subsystems. Using this combination of elements, a high degree of control and therefore predictability and yield is possible to achieve in a sealed cell culture.

The cassettes 7602 may be inserted into bioprocessing modules 7606 mounted in a rack 7604, which may have standard server rack dimensions. The cassette hosts 7606 may provide a number of functions, such as (a) incubating the cells in the cassette inserted into the host; (b) actuating on-cassette liquid handling systems for media replenishment, reagent additions, waste removal; (c) monitoring media conditions in the cassette, for example dissolved oxygen and pH, and making adjustments as necessary; (d) providing gas exchange with the on-cassette circulated media to adjust oxygen and other dissolved gas levels; (e) imaging the cells within the cassette; (f) selectively destroying and ablate cells within the growth chamber using a laser system; and (g) editing cells (e.g., inserting cargo into a cell or removing cargo from a cell) within the growth chamber using a laser system. In this manner, a single bioprocessing module 7606 may monitor and control a long-duration cell culture process without removal or transport of the cassette 7602, reducing the potential sources of variability in the process. The bioprocessing modules 7606 in a rack operate independently but may share a number of resources, as described below.

Shared computing, storage, and communications modules 7608 may be used to process imagery acquired by each bioprocessing module 7606 for normalization, registration, stitching, and other functions. The resulting images/data may be further processed using a machine learning system that is located either locally or remotely (e.g., elsewhere on the premises or in the cloud). Algorithmic choices or predictions may then be computed internally or transmitted back to this computing infrastructure to drive selective laser removal of cells within each bioprocessing modules 7606 and associated cassette 7602. For example, a shared pulsed laser module 7610 may provide laser energy to multiple bioprocessing modules 7606 via standard fiber optic connectors located on the rear of the rack 7604. The energy may be split among the bioprocessing modules 7606 via a tree of static fiber optic splitters or switched from unit to unit via an optical switch, or via some other method. In some implementations, there may be more than one laser module in the modular bioprocessing system 7600. In some implementations, a single laser module may be used for modules in multiple racks within the modular bioprocessing system 7600.

A shared environmental control module 7612 may be used to provide cell culture temperature control (usually 37° C.), reagent cooling (often 4° C.), laser cooling, and cooling for the data storage and computing modules, especially in the case where local central processing units (CPUs) or graphics processing units (GPUs) perform large workloads for image processing or machine learning operations. A shared power supply 7614, in some implementations a power supply with built-in redundancy, may be used to provide reliable DC current to the bioprocessing modules 7606, laser module 7610, and potentially the data storge and computing modules, so that there is no need for individual power supplies.

The various implementations allow for small system configurations, as shown by the half-height setup 7616 with very small footprint and setup time, and incremental addition of bioprocessing modules 7606 for additional capacity as demand requires. The modular configuration also enables a high degree of redundancy and reliability because spare modules may be added or brought online very quickly to compensate for any failures. In the example shown in FIG. 76A, a small modular system, even in a half-height rack, may take the place of several high-grade cleanrooms (often located in expensive urban spaces) for GMP cell culture, and negate the need for extensive suiting-up for personnel for daily cell culture observation and manual modification/transfer steps.

The modular bioprocessing system 7600 illustrated in FIG. 76A may be fitted with a transport system similar to the one described with reference to FIG. 75, with simple, human operator-compatible vertical as well as horizontal transport for large multi-rack facilities. The modular bioprocessing system 7600 may include other components not illustrated in FIG. 76A, and may include variations known to persons of ordinary skill in the art.

Figure 76B:
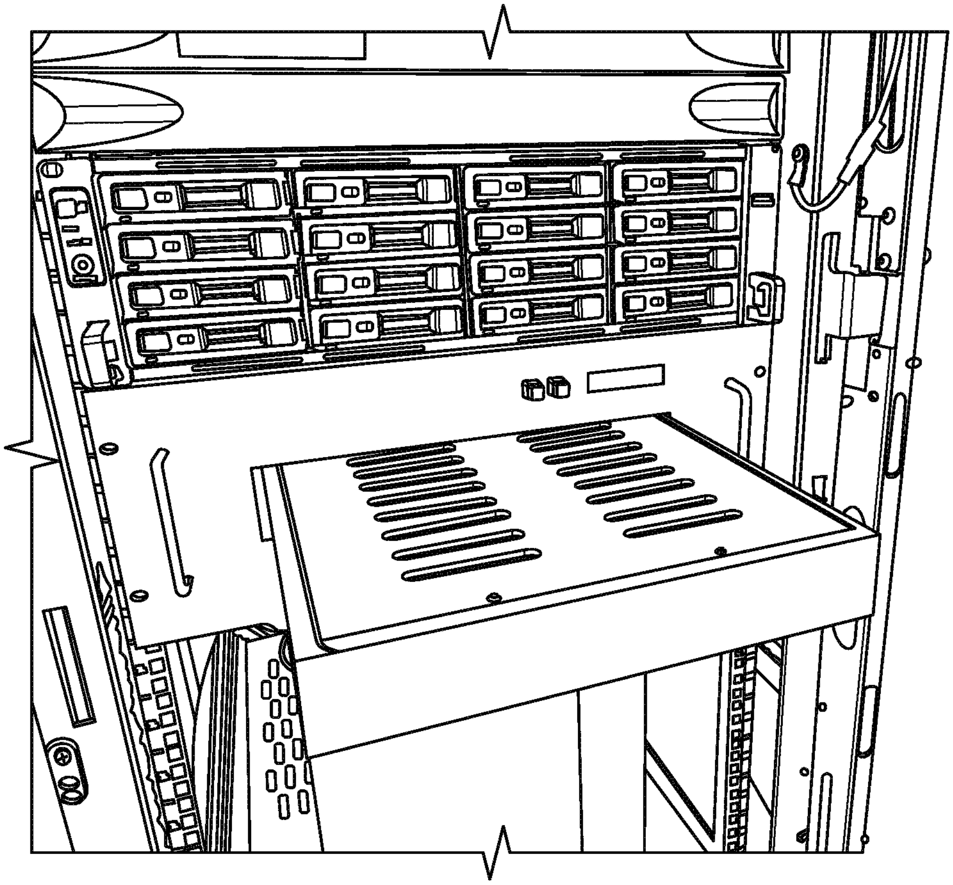
FIG. 76B shows an exemplary prototype process module (lower, with handles) and partially inserted cell culture cassette, which is shown co-located with RAID storage array (with 16 drive bays visible) and backup power module (above, marked Tripp Lite), in accordance with various implementations.

FIG. 76B shows an exemplary prototype process module (lower, with handles) and partially inserted cell culture cassette, which is shown co-located with RAID storage array (with 16 drive bays visible) and backup power module (above, marked Tripp Lite).

Hot-Swap Redundant Cell Culture Systems

Many cell culture processes, including gene editing, reprogramming (for example, reprogramming cells into iPSCs), expansion, differentiation, and bioproduction, may require lengthy, complex processes. Cell culture systems that run these processes may be complex and have many different subsystems, such as environmental sensors and controls, media/waste and reagent transfer subsystems (pumps, valves, sensors), imaging subsystems, and cell editing and/or manipulation subsystems (including directed-energy systems for intracellular delivery or selective cell destruction or removal, cell culture washing systems, etc.). This complexity makes these systems prone to failures due to the failure of a single component, subsystem, or software. In current systems, this usually results in the loss of the cell culture, which may be extremely expensive and also have a large impact on patients awaiting the cell product.

Implementations disclosed herein, for example in FIGS. 74-76, describe the use of a distributed, modular system, in which cell cultures are processed simultaneously in multiple modules that each encompass a range of functionality. These implementations reduce the chance of mass failures due to shared equipment (for example, robotic arms, imaging systems, liquid handling systems, cell editing systems). These implementations also prevent bottlenecks, for example if a transport robot that is used to move cell cultures around the system fails or becomes misaligned, or a central shared imaging subsystem fails due to a software issue. However, even modular systems may fail, and though this failure impacts only a single cell culture in process, it would be highly desirable that the failure of a cell culture module does not result in the failure, destruction, or denaturing of the cell culture being handled by the module.

In some cases, cell culture processes may require a diversity of processes that cannot practically be accomplished within a single cell culture system. Current systems require at least tubing and other reconfigurations, if not cell material transfers, to achieve such change-overs, resulting in more complex processes, more manual steps, higher probabilities of damage to the cell culture, or contamination.

The systems and methods disclosed herein include a cell culture system in which components may easily be switched out and replaced so that the cell culture system may easily be adapted for different cell culture processes and also to allow for easy repairs. The cell culture system may include a cell culture container (e.g., a closed cassette system) that includes at least one cell culture chamber and supporting components. All fluidic paths, including the cell culture chamber(s), may be sealed for at least a portion of the cell culture process to ensure sterility and prevent cross-contamination. The cell culture container may also include on-board media, reagents, buffers, product, and/or waste reservoirs and tubing components. The cell culture chamber(s) may be configured to allow imaging of the cell culture and allow directed-energy editing (e.g., intracellular delivery or lysis) of the cell culture.

The cell culture container (which may be a closed cell culture cassette in some implementations, as described with reference to FIGS. 67-73) may be quickly connected and disconnected to external components through connection plugs so that the cell culture container may be plugged into, or removed from, a modular bioprocessing system which manages the cell culture container and cell culture conditions. These connections may include electronic connections (e.g., for power, sensor readouts, valve or pump actuation), communication connections (e.g., for processor-to-processor communication), and liquid or gas connections (e.g., for temperature control of the cell culture and/or media, reagent, buffer, waste, product containers on board the cell culture container, or dissolved gas control). The liquid path inside the cell culture container may be self-contained and non-accessible to preserve a closed loop and keep the cell culture container sterile.

The cell culture system may also include process module(s) that receive one or more cell culture containers and provide cell culture support functions. The process modules may be configured so that the cell culture containers may hot-plug into the process module using the connectors to provide monitoring and support to the cell culture containers. The process module and cell culture containers may be designed so that if the process module fails or malfunctions, the cell culture containers may be removed from the process module via a simple mechanism, for example a mechanical unlock and subsequent pull.

In some implementations, the process module disclosed herein can be referred to as a cell culture process module, a cell culture process system/subsystem, a cell culture process mechanism, or a docking station. The cell culture process modules includes physical devices that are configured to provide cell culture support functions such as, for example, media monitoring and replenishment, and gas monitoring, mixing, and replenishment. A cell culture process module may be configured to receive one or more cell culture containers (e.g., cell culture cassettes). The cell culture process module configured to receive one or more cell culture containers may be referred to as a docking station. For example, a cassette may be received by the cell culture process module such that it "docks" with a receiving space of the cell culture process module hosting the cassette, as illustrated in FIG. 76A. The cell culture process module may operate in combination with the cell culture cassette to handle one or more cell culture support functions. For example, the cell culture cassette may include a fresh media reservoir, and the cell culture process module may fluidically connect with the cell culture chamber and the media reservoir of the cell culture cassette and then transfer fresh media into the cell culture chamber.

The cell culture system may also include a computing and communication system that monitors and tracks the status of each cell culture container as it undergoes a cell culture process recipe. The system may essentially maintain a "digital twin" of the cell culture container (e.g., a dynamic digital profile of the cell culture) that may be stored on the cell culture container, and/or on a remote server. This allows a cell culture container to be removed from one process module and inserted into another without any data entry, and allows the receiving process module to quickly resume the cell culture process with appropriate conditions (temperature, media exchange, reagent or buffer additions, dissolved gas control, flow rate/liquid shear control, washing or agitation, etc.). For example, the cell culture container may contain non-volatile memory such as FLASH memory that contains a record of the cell culture process recipe, as well a history of what steps have been performed, and conditions on the cell culture container. Thus, if the cell culture container is removed from one process module and inserted into another, the process module may read this memory and proceed with the current or next steps of the cell culture protocol under the correct conditions. In some implementations, the cell culture container includes a barcode or an electronic tag (which could include nonvolatile memory on board) that presents a container ID to the process module, and the process module retrieves a process recipe and history from a server when the container is inserted, so that it may immediately resume the process.

Figure 77:
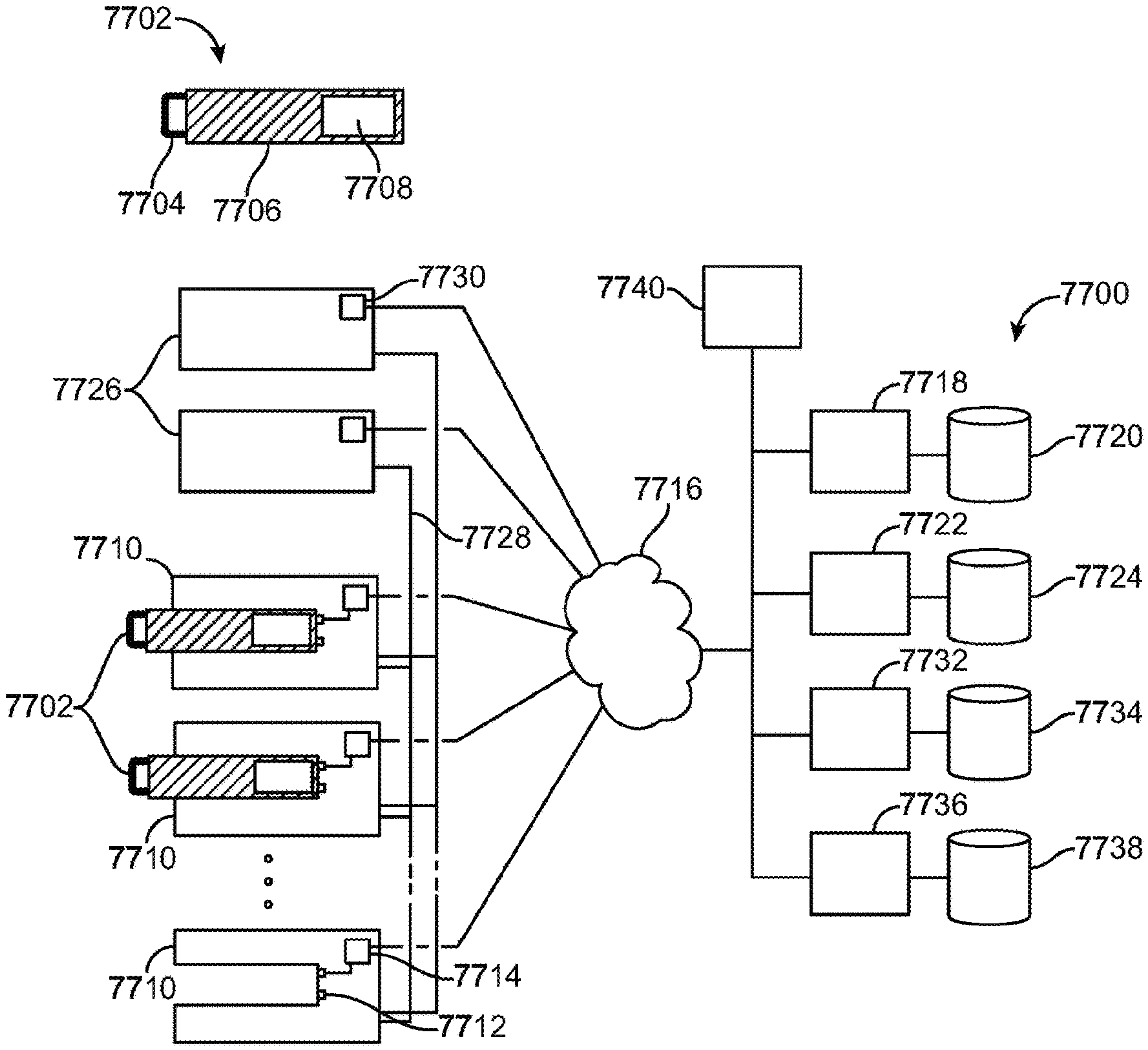
FIG. 77 is a diagram of a modular cell culture system in accordance with various implementations.

FIG. 77 is a diagram of a modular cell culture system 7700 in accordance with various implementations. The modular cell culture system 7700 may support a number of cell culture containers, which may be formatted as a closed cell culture cassette 7702 (e.g., closed cassette system 6700). The cassette 7702 may have a housing that includes a handle 7704. The housing encloses one or more compartments 7706 for carrying cell culture media, reagents, waste, cell products, etc., as well as a liquid handling system to circulate media, waste, debris, cell products, etc., into and out of a one or more cell culture chambers 7708. The cell culture chambers 7708 may be suited for culturing of suspension and/or adherent cells. The cell culture chambers 7708 may further be configured for imaging of the cell culture (e.g., label-free imaging through a transparent surface of the cell culture chambers 7708) and directed energy editing of the cell culture (e.g., using cell editing subsystem 114).

The modular cell culture system 7700 may include a series of cell culture process module 7710, each of which are configured to receive the cassettes 7702. Each process module 7710 may be configured to manage the cell culture functions on the cassette 7702 docked in that particular process controller 7710. These functions include, but are not limited to, temperature controls (e.g., for cell cultures, and for media, reagents, products, and waste, which may each be controlled independently or in groups), cell media and/or reagent addition and circulation, cell culture washing or harvest, control of dissolved gas concentrations, control of pH, imaging of the cell culture, and directed energy editing of the cell culture (e.g., laser editing).

The process module 7710 interfaces to the cassette 7702 via plug sockets 7712 for electrical, communications, gas, temperature control and other connections. These plug sockets 7712 may be configured such that a cassette 7702 may be quickly loaded or unloaded from the process module 7710 without manual connection or disconnection of wires or tubes, or in some cases even without execution of software programs and associated functions in the containing cell culture module, so a "hot swap" may be performed to move cassettes 7702 from one process module 7710 to another. An on-board computer 7714 in the process module 7710 may connect electronically with an on-board computer or memory of the cassette 7702, or read a barcode on the cassette to ascertain the identity and retrieve the current operating state of the cassette 7702.

The process module 7710 communicates via a communications network 7716 to a cassette data monitoring system 7718 which maintains a cassette state database 7720. The cassette state database 7720 stores a "digital twin" for each cassette 7702 in the modular cell culture system 7700, the digital twin reflecting the current cassette status and intended cell culture process. Thus, if a cassette 7702 is pulled from one process module 7710 and inserted into another, the receiving process module 7710 can immediately resume the desired cell culture program for the cassette 7702. This allows a cassette 7702 to be moved quickly in case of a malfunction in a process module 7710 or supporting infrastructure, or moved around a facility depending on the stage of a cell process. The process modules 7710 may also communicate with a module monitoring system 7722 which maintains a process module "digital twin" database 7724 to monitor critical module functions and detect any deviations. Additionally, the module monitoring system 7722 may be used when a process module 7710 is moved from one process cluster or facility to another, or from one set of supporting systems to another.

The modular cell culture system 7700 may include supporting subsystems 7726 that are shared by multiple process modules 7710. Supporting subsystems 7726 may include, but are not limited to, environmental control systems (e.g., for providing warming for cell cultures and/or cooling for media, reagents, products, and computing or optical subsystems), laser systems for directed-energy editing of cell cultures, cell culture imaging, autofocus or registration functions, and/or spectral sensing of media or cell cultures, power supply systems (e.g., an internally redundant 24 VDC power supply), and computing systems for computing or storage associated with imaging, spectral sensing, cell culture editing, etc. (which may also have internal redundancies). The supporting subsystems 7726 are connected to the process modules 7710 via pluggable or quick connectors 7728 to facilitate easy connection or disconnection of the process modules 7710 from a local cluster, for example a cluster of process modules 7710 on a server rack along with supporting subsystems 7726. The supporting subsystems 7726 typically have embedded computers or sensing/computing modules 7730 to monitor and/or control these subsystems.

One or more supporting subsystem monitoring services 7732 may monitor the supporting subsystems 7726 and tracks performance in a supporting subsystem database 7734, again establishing a "digital twin" for each supporting subsystem 7734 for redundancy and quick-resume functions. If a supporting subsystem 7726 indicates a problem it may be quickly replaced and cell processes continued, or the affected cassettes 7702 may be moved to process modules 7710 on another set of functioning supporting subsystems 7726, and/or one or more process modules 7710 may be moved to a new set of functioning supporting subsystems 7726.

The modular cell culture system may also include a cell culture monitoring system 7736 configured to tracking the cell culture state in each cassette 7702 (and in turn the cell culture chambers in each cassette) and maintains a cell culture database 7738 that stores a "digital twin" of each cell culture (which may include time series images, cell or colony feature databases, sensor data streams, etc.). Finally, an overall monitoring and control system 7740 may be configured to monitor the overall modular cell culture system 7700, by communicating with the monitoring systems 7718, 7722, 7732 and 7536, and coordinates responses to failures or states requiring attention, for example transfer of cassettes 7702 from one process area to another. The modular cell culture system 7700 may include other components not illustrated in FIG. 77.

The process modules 7710 may have different configurations corresponding to different cell culture processes, or stages of these processes. Thus, the ability to pull cassettes 7702 from one process module 7710 and place them in another while maintaining continuity in cassette conditions, environmental parameters, and cell culture data and processes enables very efficient, failure-free multi-stage cell culture processes. In addition, the modular cell culture system 7700 is very flexible as it can accommodate different cell culture processes performed in parallel, which increases throughput while minimizing delays in equipment failures or other issues.

Figure 78:
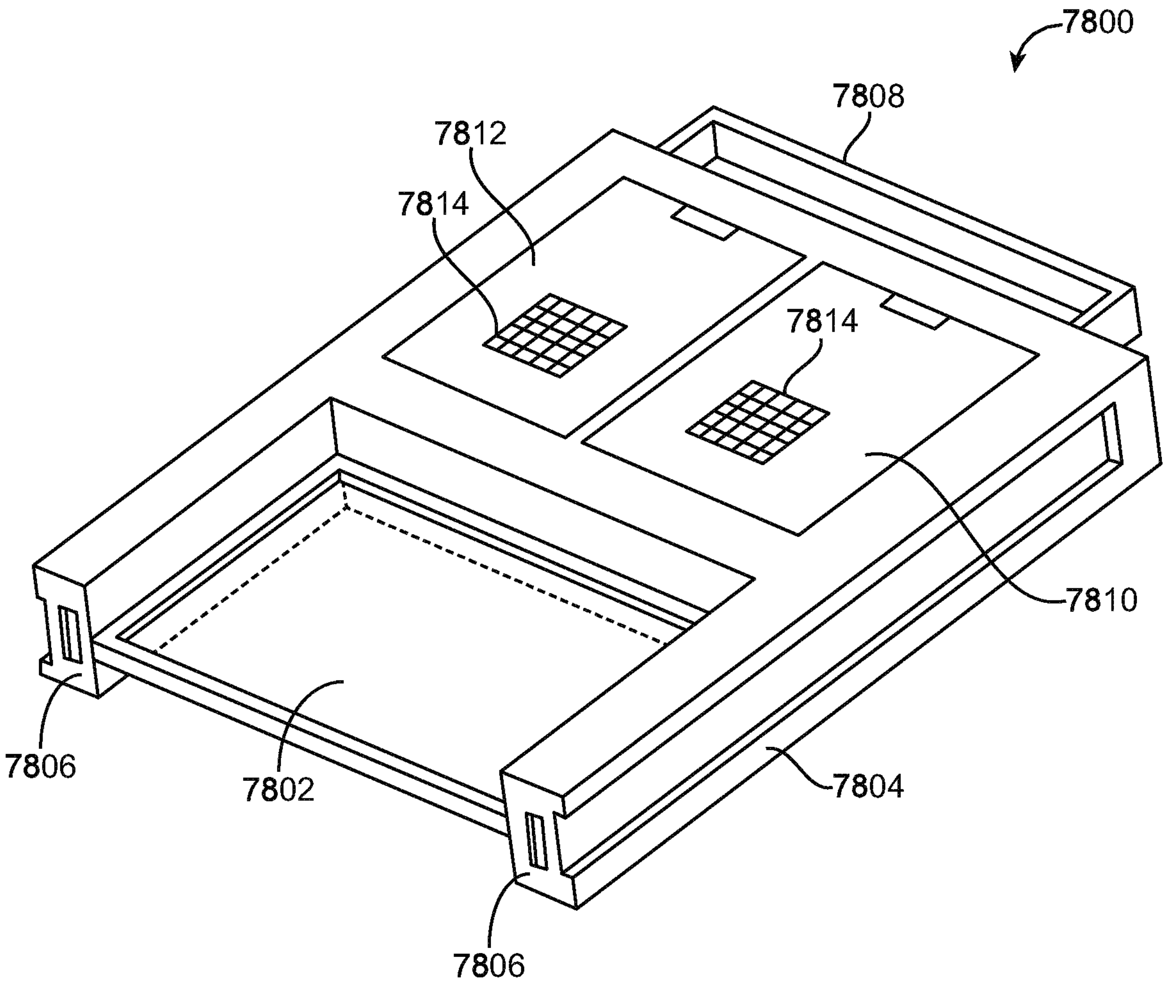
FIG. 78 is a diagram of a cell culture cassette compatible with a modular cell culture system in accordance with various implementations.

FIG. 78 is a diagram of a cell culture cassette 7800 compatible with a modular cell culture system in accordance with various implementations. The cell culture cassette 7800 is an example implementation of a cell culture container (e.g., cell culture container 106) in a cell culture system. The cassette 7800 may be primarily designed for 2D adherent cell cultures. The cassette 7800 may include a 2D liquid cell culture chamber 7802 with transparent upper and lower surfaces, which may be used for imaging and directed-energy editing of the cell culture. Mechanical guide rails 7804 serve to align the cassette 7800 to the process module as it is inserted. As it is inserted, connectors 7806 plug into complementary connectors on the process module. These connectors carry electrical signals, including but not limited to any required power, communications, signals from sensors aboard the cassette, and controls signals to actuators aboard the cassette. The connectors 7806 may also include non-mechanical elements such as gas or liquid ports. For example, cooling or warming liquids may flow in a loop through the connectors 7806, or gases for maintaining proper dissolved gas concentrations may flow in a loop through the connectors 7806. In these cases, quick-connect fittings may be used to seal the connections upon disconnection of the cassette 7800, and open them when the cassette 7800 is inserted.

The connectors 7806 may be disengaged mechanically through a locking mechanism accessible from the front of the cassette 7800 or process module (possibly on or near handle 7808), or electromechanically by the process module. The cassette 7800 may be removable from the process module regardless of software, electrical, or other failures in the process module, so the cassette 7800 may be quickly withdrawn using handle 7808 and placed in another process module. In the example shown in FIG. 78, the cassette 7800 may include two independent storage compartments for maintaining liquids associated with the cell culture, including but not limited to cell media, reagents, buffers, cell products, and waste, which may be stored in sealed bags or other containers. For example, one compartment 7810 may store media and reagents at 4° C., while another compartment 7812 may store cell products at 37° C. Temperature control ports 7814, which are sealed when the cassette 7800 is not in a process module, may be pushed open by the insertion of the cassette 7800 into the process module. This allows the process module to push temperature-controlled air through the compartments 7810, 7812 perpendicular to the plane of the cassette 7800. Thus, each compartment 7810, 7812 may be precisely temperature-controlled in a closed-loop fashion while in the process module, but when the cassette 7800 is pulled from the process module the ports 7814 may close automatically, such that temperature within compartments 7810, 7812 may maintained passively while the cassette 7800 is in transit or awaiting transfer to another process module.

In some implementations, the cassette 7800 may be designed to allow an optical system to access the cell culture chamber 7802 for the purpose of imaging the cell culture (e.g., cell imaging subsystem 112) and/or editing the cell culture through a cell editing mechanism such as using directed energy (e.g., cell editing subsystem 114). The directed energy editing may take the form of laser light, ultrasound, magnetic tools inside the cell culture chamber 7802 that are directed by external magnetic actuators, or other methods. The cell imaging and cell editing subsystems may interact with the cassette 7800 without physical entanglement such that it may be manually withdrawn from the process module without damage to the cassette 7800 or process module when any subsystem fails. The cell imaging and cell editing subsystems may also be configured to return to an "off" mode in case of a software, power, or mechanical failure in the process module, for example cutting off laser illumination, cutting off imaging illumination, and retracting magnetic actuators though a "active-on" solenoid or compressed-air mechanism.

In the case that a failure is detected in the process module, an "eject" sequence may be activated which unlocks the cassette 7800 and pushes it partially out of the process module. The partial ejection may include disengaging all ports and connectors 7806, to close all valves on board the cassette 7800, to stop pumping on board the cassette 7800, and to seal all temperature control ports 7814 (liquid or gas). This may be achieved, for example, by solenoid and spring actuators that are retracted electromagnetically when the process module is active and running properly and a cassette 7800 is inserted, but when there is a failure detected in the process module, or power is lost, spring back to eject the cassette 7800 into retraction position. In this position, the cell culture is effectively in a "safe" mode where liquid is not flowing and temperatures are maintained passively until it may be moved to an active process module.

Figure 79:
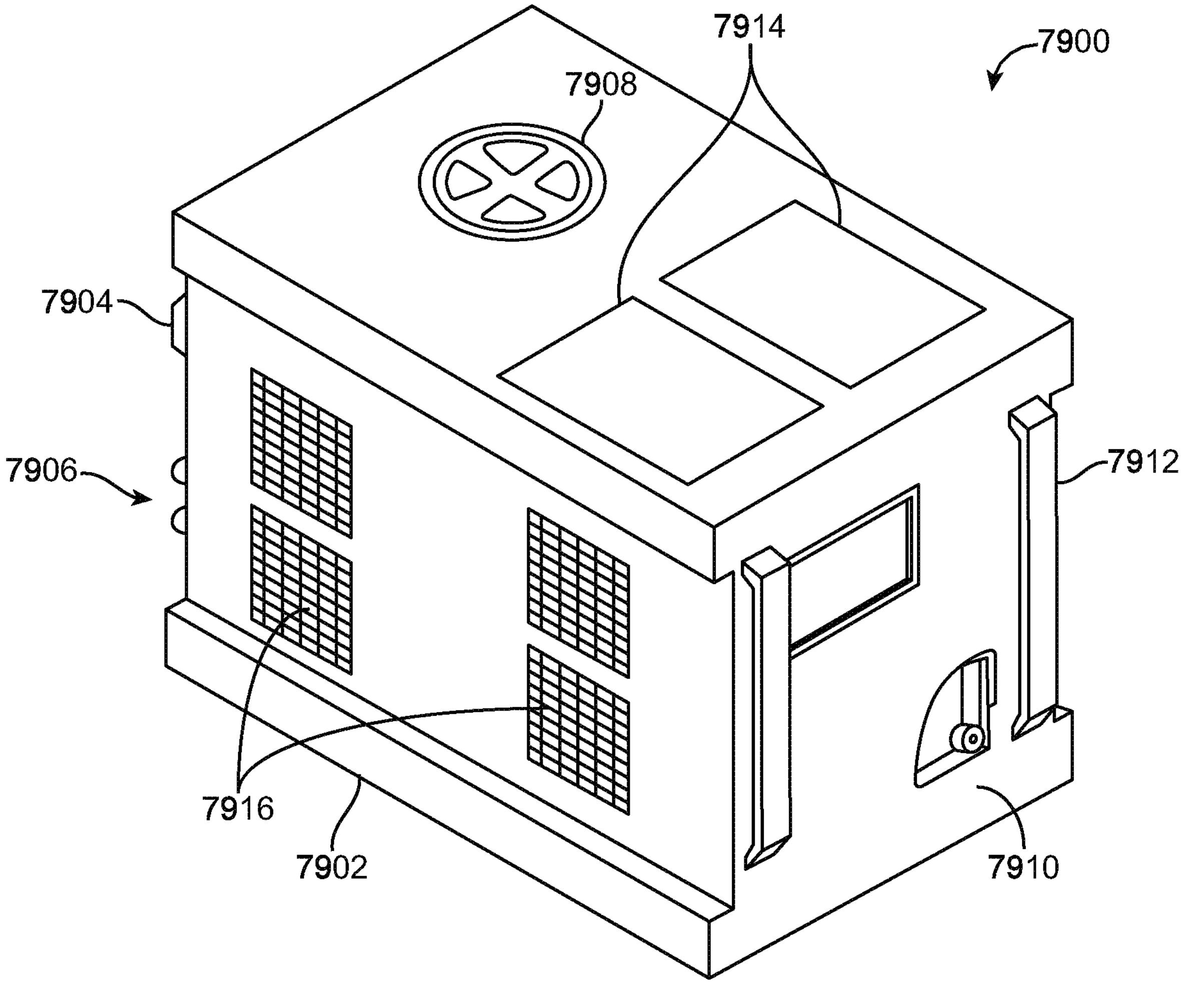
FIG. 79 is another diagram of a cell culture cassette compatible with a modular cell culture system in accordance with various implementations.

FIG. 79 is a diagram of a cell culture cassette 7900 compatible with a modular cell culture system in accordance with various implementations. The cell culture cassette 7900 is an example implementation of a cell culture container (e.g., cell culture container 106) in a cell culture system. The cassette 7900 may be primarily designed for suspension cell cultures held in a miniature stirred tank bioreactor, with a sterile tubing set connecting it to cell media, buffers, reagents, and also waste and cell product bags that are all stored on-board. Guide rails 7902 allow the cassette 7900 to be inserted into a corresponding process module and assure mechanical alignment of plug connector ports including electrical/communications connectors 7904 and gas/liquid quick-connectors 7906. In some implementations, when inserted, a magnetic actuator on the process module aligns with a follower magnetic component 7908 which is connected to the stirrer in the cell culture vessel. However, in general any number of non-contact methods of stirring the interior of the cell culture vessel may be implemented in the cassette 7900. For example, other implementations may include magnetic couplings to actuate valves on the cassette 7900, operate peristaltic pumps on the cassette 7900, or move actuators within the sealed cell culture vessel for the purpose of washing cell cultures, circulating media, or removing cells or debris from surfaces.

A latch 7910 may be used to lock the cassette 7900 in place in the process module, and may be mechanically coupled to a number of components to open/close them appropriately, including but not limited to the gas/liquid ports 7906. The latch 7910 may be opened prior to retrieving the cassette 7900, assisted by handles 7912. A display on the cassette 7900 may display the current status of the cassette 7900 and cell process, and may include touchscreen functions.

In the implementation shown in FIG. 79, two compartments 7914 are configured to carry media, reagents, buffers, cell sources, and waste, cell products, etc. However, in general there may be any number of compartments 7914. The compartments 7914 may be temperature controlled via air ports 7916 on the side of the cassette 7900. For example, the air ports 7916 may be used for entry (top) and exit (bottom) of temperature-controlled air from the process module to keep the left-side compartment to 4° C. temperature. The air ports 7916 may be configured to close when the cassette 7900 is not fully-docked to the process module, to maintain the internal temperature of the compartments 7914 as long as possible. Similarly, the air ports 7916 corresponding to the bioreactor may be used in either in top-to-bottom or side-to-side configuration to move air through the bioreactor enclosure and maintain its temperature, typically at 37° C.

Figure 80:
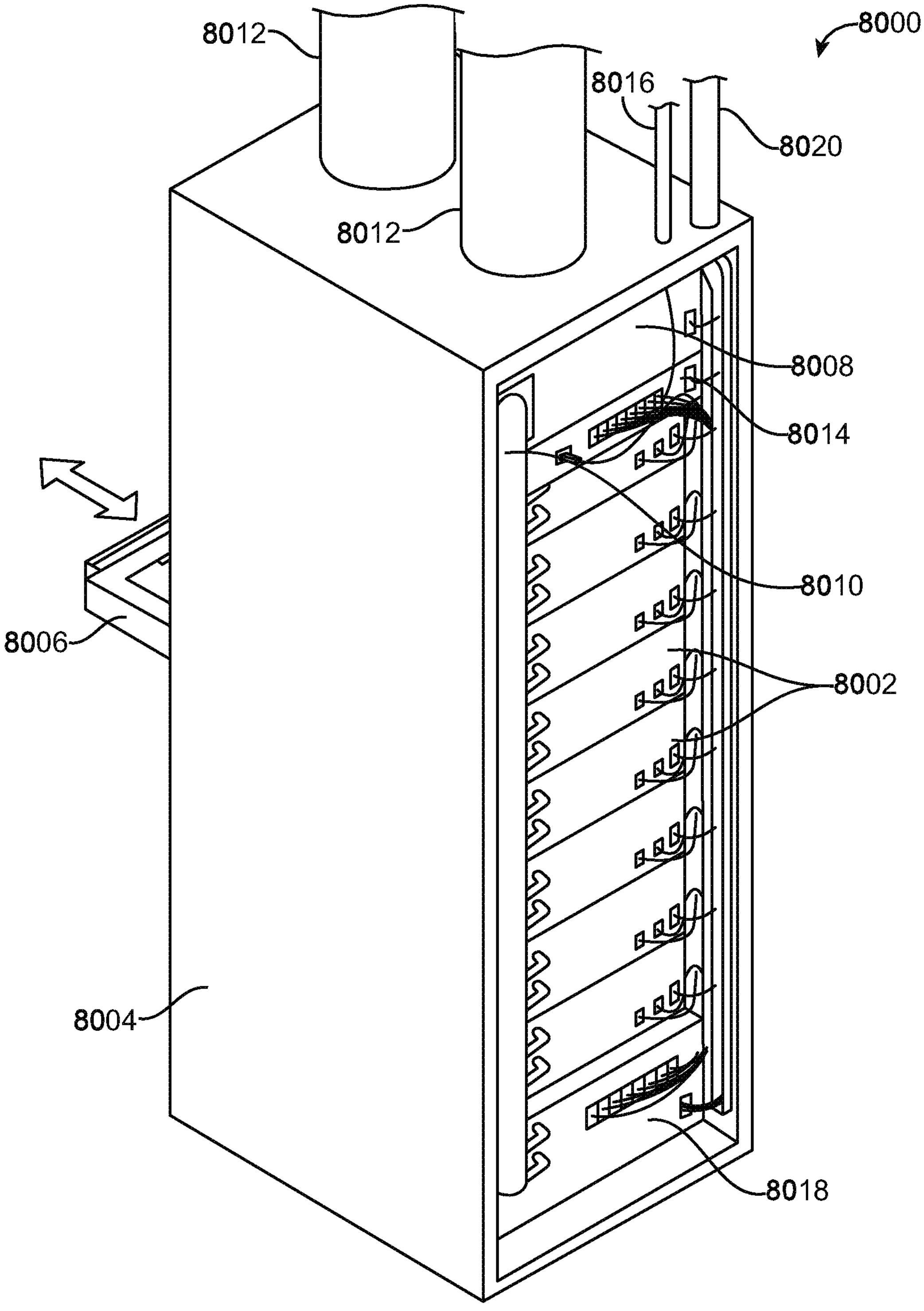
FIG. 80 is a diagram of a rack-style modular cell culture system in accordance with various implementations.

FIG. 80 is a diagram of a rack-style modular cell culture system 8000 in accordance with various implementations. The modular cell culture system 8000 may include any number of cell culture process modules 8002 (eight shown in FIG. 80) and several supporting modules mounted in a server-style rack 8004. The process modules 8002 may be configured to receive a cell culture cassette 8006 (shown in insertion/retraction position in FIG. 80), which may be similar to cassette 7800 in FIG. 78 for 2D adherent cell cultures.

The modular cell culture system 8000 may include a shared environmental control module 8008. In an example implementation, the shared environmental control module 8008 may circulate refrigerant and two temperatures, for example 0° C. and 40° C., along liquid manifolds contained in an environmental control column 8010. The environmental control column 8010 provides process modules 8002 with thermal "rails" to maintain temperatures for cell culture and various media, reagent, waste, or cell product compartments. It also provides components that generate significant heat (for example, computing modules, if present, or shared laser modules) with cooling, while maintaining a compact footprint (as opposed to air-cooling each one). The environmental control module 8010 may exchange heat between the return streams, and may also include high-flow air circulating through it for heat exchange purposes, through ducts 8012.

The modular cell culture system 8000 may also include a computing and communications module 8014 that provides local computing, storage and network communications (e.g., computing subsystem 110). In an example implementation, multimode fiber and optical transceivers may be used to provide communication between the computing and communications module 8014 and individual process modules 8002, ensuring high bandwidth during cell culture imaging. The computing and communications module 8014 may also provide local processing and storage of the images, and potentially computing of cell culture editing functions. The computing and communications module 8014 may also be connected to external networks via fiber optics or other communications links that pass through a duct 8016. External networks may store "digital twins" of process modules 8002, cassettes 8006, and supporting modules 8008, 8014, 8018 in the modular cell culture system 8000. These digital twins may aid in monitoring and tracking cell culture, cassette, and process module status and performance versus nominal, and provide hot-swap capability in the case of failure of a process module or any supporting system.

The modular cell culture system 8000 may also include a cell editing subsystem, such as a shared pulsed laser system 8018. Pulsed laser light from the pulsed laser system 8018 may be transmitted via optical fiber to each process module 8002. For example, the pulsed laser system 8018 may include a nanosecond pulsed laser with 532 nm or 1064 nm emission. The laser light may be split into eight equal power beams (may be achieved using free-space optics, or fiber optic couplers), and coupled into polarization-maintaining single-mode fiber. These fibers are routed to respective process modules 8002. Each process module 8002 may be configured to synchronize to the pulse timing (for example, 500 kHz) and then apply modulation (for example, with an acousto-optic modulator) and beam steering for the purpose of directed-energy cell culture editing. In other implementations, laser sources may be shared for other purposes, such as illumination for fluorescent, auto-fluorescent, two-photon imaging, Raman spectroscopy, or other sensing modalities within the cell culture modules. The modular cell culture system 8000 may also include a shared DC voltage power rail to provide power to the entire rack 8004 and supported equipment, fed by power duct 8020. In alternate implementations, DC power supplies may be mounted on the rack 8004 itself as rack-mounted equipment (potentially with connections for cooling).

Methods of Manufacturing Semi-Adherent Cells and Cell Products

The immune system is divided into two systems: the innate immune system, which acts rapidly and generally, and the adaptive immune system, which represents an acquired immune response and is much slower and specific. In recent years, cell-based immuno-oncology therapies, including but not limited to adoptive cell immunotherapies, have risen dramatically. Immune system cells are naturally capable of recognizing and eliminating entities which do not belong in the body, so they are effective vehicles to treat various diseases. These strategies may involve modifications of the immune system cells to improve recognition and elimination of tumors. Examples include tumor infiltrating lymphocytes (TILs), chimeric antigen receptor (CAR) T-cells, T-cell receptor (TCR) therapies, and activated dendritic cells (DCs), macrophages, or some mix of these or other immune-related cells. It is widely recognized that the safest and most effective therapies would be autologous, which are derived from the patient's own cells which respond uniquely to tumor cells, reducing or eliminating toxicity and need for immunosuppression.

However, there are several hurdles to utilizing autologous immune cell treatments. Cells may be difficult or painful to isolate (especially in numbers viable for therapeutic doses), dysfunctional, functionally compromised, variable in capability, difficult to consistently genetically modify, have limited in vivo survivability and migratory capability, require repeated harvesting or dosing, and are challenging to manufacture under good manufacturing practice (GMP) conditions, among other limitations.

As an example, dendritic cells (DCs), the most powerful of the antigen presenting cells, are widely considered the bridge between the innate and adaptive immune systems by identifying threats and acting as messengers. DCs signal to T-cells via surface receptors and secreted cytokines to dictate various T-cell responses. Due to their unique role in the immune system, DCs have powerful therapeutic potential both in inducing immunity, such as with oncology, and in tolerance, such as with autoimmune diseases. They are a rare cell type in human blood, <0.1% of blood, which makes it challenging to harvest adequate primary cell numbers for therapy. Additionally, there are various DC subsets including conventional DC Type 1 (cDC1), conventional DC Type 2 (cDC2), plasmacytoid DCs (pDCs), and monocyte-derived DCs (moDCs), which are specialized for various conditions and applications. DCs are sensitive to an immuno-suppressive tumor microenvironment and thus their activation may be suppressed in vivo. Furthermore, DCs require an autologous approach to maximize functionality as T-cells recognize peptides bound to MHC receptors on DCs, particularly class II receptors, but there can be variability in the primary cell source.

Due to limited source material and cell sensitivity, the majority of clinical trials to date have involved autologous moDCs. This subset is far from optimal, most commonly found in inflammatory conditions, with limited cross-presentation and migratory capability. The rarest of the DC subsets, cDCIs, represent <0.03% of peripheral blood mononuclear cells and are highly effective at cross-presentation to T-cells. However, this subtype has yet to be clinically explored in earnest largely due to limited in vivo numbers, difficulty of isolation in blood, and the ease with which moDCs can be derived. Further, it is plausible that all DC subsets could be further optimized through genetic or non-genetic modification, including but not limited to cell viability in vivo, migratory capabilities, cross-presentation capability, and maturation or activation level.

Large-scale manufacturing of induced pluripotent stem cells (iPSCs) which can then be differentiated to the immune cells of interest represent an elegant solution to issues noted above. They can be cultured unlimitedly in vitro, successfully differentiated towards the lymphoid lineage, are easily amenable to genetic transformations in vitro, and consistency may be achieved through fully modified and quality controlled clonal lines. The terminally differentiated product may be edited in order to optimize for purity and functionality. Thus, what is needed in the art are systems and methods for large scale generation of semi-adherent cells, which include immune cells, particularly as an extension of large scale manufacturing of iPSCs.

The systems and methods disclosed herein include an automated research and clinical-grade manufacturing system for various semi-adherent cells (e.g., immune cells such as dendritic cells) which (1) allows 100% non-contact measurement of semi-adherent cells and semi-adherent cell-based therapies in culture, starting first from a primary cell source, reprogramming to a progenitor cell type such as human induced pluripotent stem cell (hiPSC) or CD34+ hematogenic progenitor cells, in order to monitor and control the biomanufacturing process; (2) enables selective combination, segregation and isolation of the various cell populations or subpopulations and maturity levels as specified for the end product; (3) enables genetic modification of cells or their precursors to optimize the end product; and (4) is sealed in a manner that allows parallel manufacture in a non-sterile facility, and further, in some cases, allows editing of cell cultures based on image-derived characteristics.

Such a system would enable a wide range of cell biomanufacturing processes at a scale, consistency, yield and cost that are not achievable in the prior art, including through selectivity in subset, generation of enough viable cells for a therapy (estimated ~$10^5$ to $10^8$ cells per dose over approximately 1-10 injections), the elimination of any cells or material which lowers the quality of the final product (including but not limited to unwanted cells or undifferentiated cells), enabling of multiple and/or reduced dosing due to autologous nature of therapy, and the correct maturation or activation level. This capability is particularly important to translate emerging patient-specific dendritic cell therapies from the laboratory to clinical trials and ultimately to larger patient populations. An automated system would not require any handling, enable genetic manipulation of a sensitive cell population, and avoid undesired biological consequences, such as cell activation prior to need. The system may be applicable to numerous immune cells and more generally to any kind of semi-adherent cells.

Figure 81A:
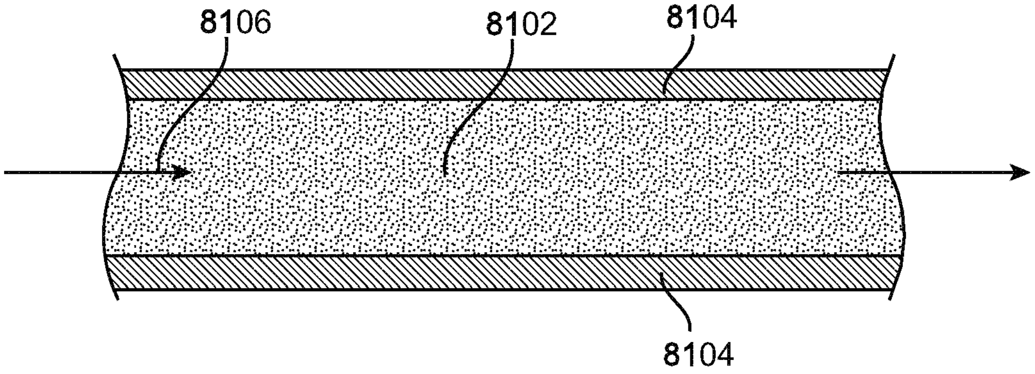
FIGS. 81A-81C are diagrams illustrating cell culturing in a closed cell culture cavity in accordance with various implementations.

FIGS. 81A-83C are diagrams illustrating cell culturing in a closed cell culture chamber in accordance with various implementations. FIG. 81A shows a microfluidic cell culture cavity 8102 in a cell culture chamber, which may be part of a closed cell culture container (e.g., cell culture container 106 in FIG. 1) in a cell culture system. The cell culture cavity 8102 may be enclosed by top and bottom surfaces 8104 and side surfaces (not shown in FIG. 81A). The cell culture cavity 8102 may be connected to one or more fluid reservoirs (not shown) to enable fluid flow into and out of the cell culture cavity 8102, for example to refresh fluid media in the cell culture cavity 8102 or to flush one or more cells or debris from the cell culture cavity 8102. There may be a perfusion flow 8106 of fluids through the cell culture cavity 8102. The parameters of the perfusion flow 8106 may be controlled by a control system (e.g., computing subsystem 110 in FIG. 1). For example, the computing subsystem may control the flow rate of the perfusion flow 8106 and may turn the perfusion flow 8106 on and off to enable various functionalities as further described herein. In some implementations, the computing subsystem comprises a computer processor.

Figure 81B:
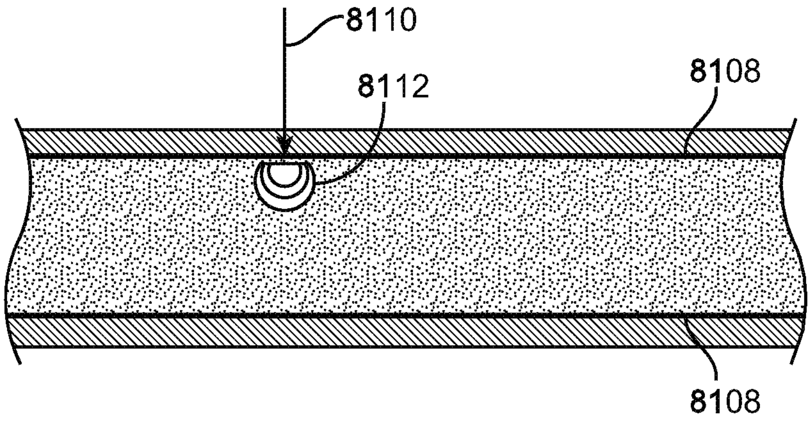

FIG. 81B shows the cell culture cavity 8102 of FIG. 81A, except that the top and bottom surfaces 8104 of the cell culture cavity 8102 may be coated with an absorption layer 8108 on the outside of the cell culture cavity 8102. The absorption layer 8108 may be configured to absorb pulsed laser light 8110 impinging on the cell culture cavity 8102 while allowing other light to pass through in order to image the contents of the cell culture cavity 8102. When a pulsed laser light strikes impinges on the cell culture chamber 8102, it may create microbubbles 8112 on the inside of the cell culture chamber 8102. The microbubbles 8112 may collapse to create shockwaves within the cell culture chamber 8102, which may be used to impart mechanical forces in the local environment. For example, the microbubbles 8112 and subsequent shockwaves may be used to mix the fluid media, knock adhered cells loose from the impinging surface, destroy adhered cells, or weaken cell membranes to allow transport of pay loads into and out of cells. The pulsed laser light 8110 may be controlled by a computing subsystem or other control system in a cell culture system.

Figure 81C:
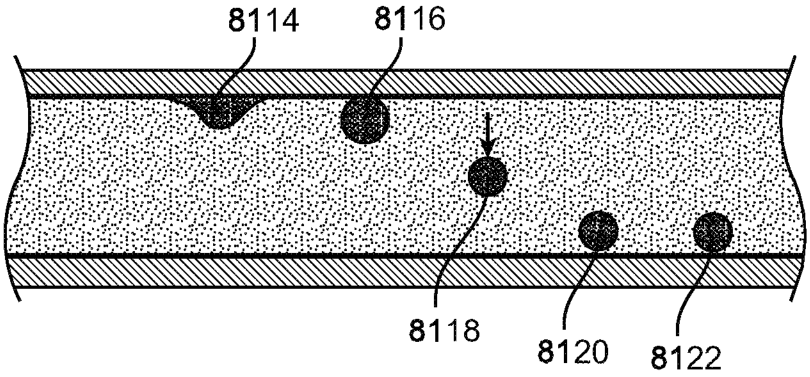

FIG. 81C shows the cell culture cavity 8102 of FIG. 81A with adherent cells 8114 growing on the top surface of the cell culture cavity 8102. The adherent cells 8114 may be immune system cells, such as macrophages. The cell culture cavity 8102 may be oriented so that the force of gravity acts downwards in FIG. 81C. This may be termed an inverted orientation. For example, cells may be initially cultured on the bottom surface of the cell culture cavity 8102. When the cells become adherent cells 8114, the cell culture cavity 8102 may be inverted or flipped such that the adherent cells 8114 rest on the now top surface of the cell culture cavity 8102 as shown in FIG. 81C.

The cell culture cavity 8102 may also include semi-adherent cells 8116, which may be monocytes or dendritic cells for example. Semi-adherent cells 8116 may have a weaker adherent bond to the top surface of the cell culture cavity 8102 than adherent cells 8114. The cell culture cavity 8102 may also include non-adherent cells 8118 that have detached from the top surface. The non-adherent cells 8118 may be, for example, T cells or dendritic cells that have been naturally or artificially released from the top surface. For example, pulsed laser light 8110 may be used to knock cells loose from the top surface so that they become non-adherent cells 8118.

The cell culture cavity 8102 may also include bottom resting non-adherent cells 8120. The non-adherent cells 8120 may be non-adherent cells 8118 that come to rest on the bottom surface due to gravity. The cell culture cavity 8102 may also include re-adhered cells 8122, which are bottom resting non-adherent cells 8120 that adhere to the bottom surface of the cell culture cavity 8102 if they are allowed to remain there for a period of time.

Figure 82A:
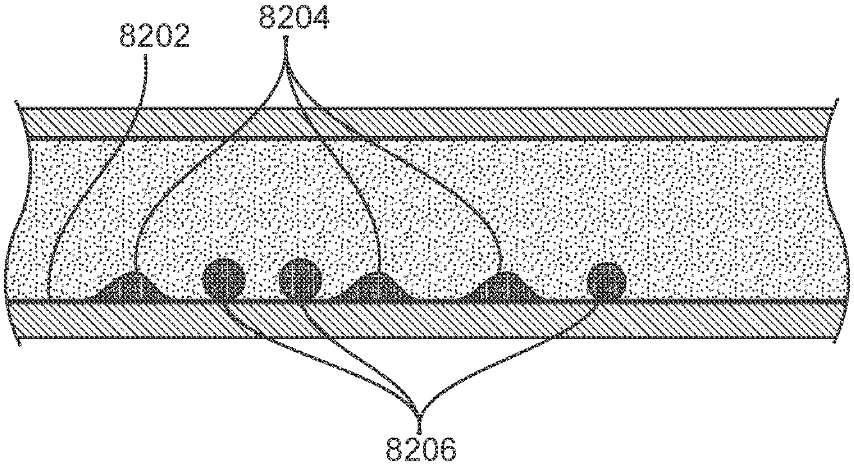
FIGS. 82A-82B are diagrams illustrating adherence of cells in a closed cell culture cavity in accordance with various implementations.
Figure 82B:
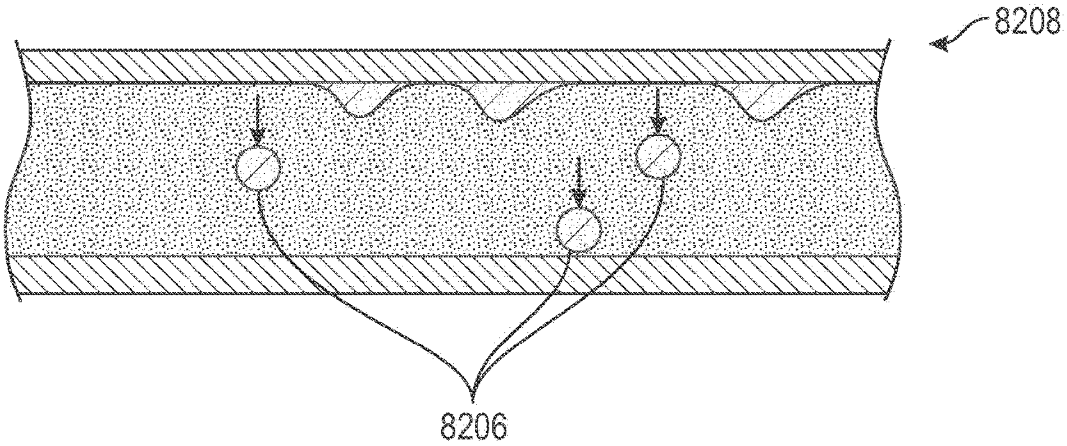

FIGS. 82A-82B are diagrams illustrating adherence of cells in a closed cell culture cavity in accordance with various implementations. FIG. 82A illustrates a closed cell culture cavity, which may be similar to cell culture cavity 8102 in FIGS. 81A-81C. The cell culture cavity may include an adhering surface 8202, which is the bottom surface as shown in FIG. 82A. Adherent cells 8204 may be adhered to the adhering surface 8202. The adherent cells 8204 may be various types of immune cells, such as macrophages, dendritic cells, and T cells, and may have varying degrees of adherence to the adhering surface 8202. The adherent cells 8204 may be introduced to the cell culture cavity and given some time to adhere to the adhering surface 8202. The cell culture cavity may also include one or more non-adherent cells 8206 that come to rest on but are not adhered to the adhering surface 8202 due to gravity.

At a certain time, the cell culture cavity may undergo inversion 8208 such that the adhering surface 8202 is now the top surface and the force of gravity acts downward, as shown in FIG. 82B. A computing subsystem may invert the cell culture cavity in response to certain criteria. For example, inversion may happen after imaging shows that a certain number or percentage of cells are adhered, or when adhered cells show certain properties, or at a predetermined point in time from the start of the cell culturing process. The cell culture chamber containing the cell culture cavity may be connected to one or more actuators that carry out the inversion motion and that are controlled by a computing subsystem. After inversion 8208, the adhered celled 8204 may remain on the adhering surface 8202 while the non-adherent cells 8206 may fall to the opposite surface due to gravity.

Figure 83A:
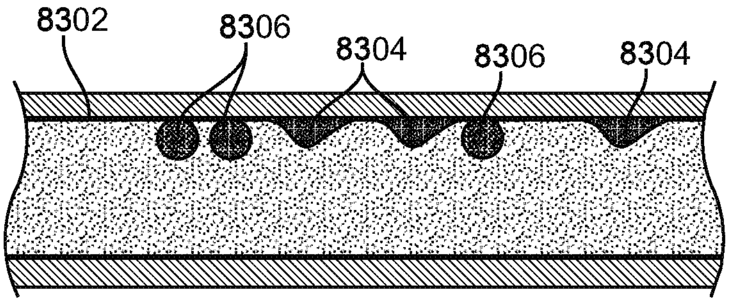
FIGS. 83A-83E are diagrams illustrating separation of adherent and semi-adherent cells in a cell culture cavity in accordance with various implementations.
Figure 83B:
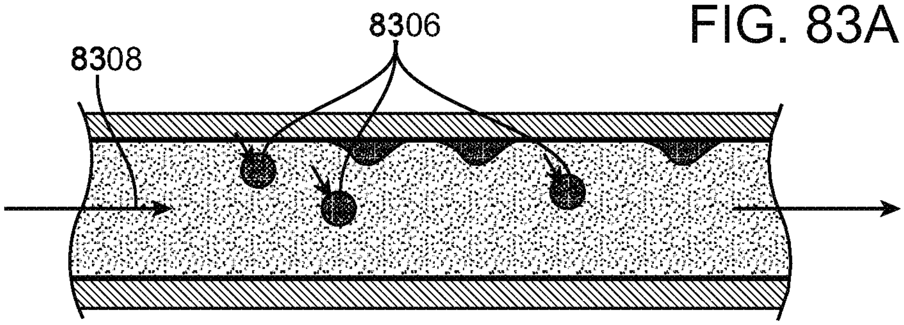

FIGS. 83A-83E are diagrams illustrating separation of adherent and semi-adherent cells in a cell culture cavity in accordance with various implementations. FIG. 83A illustrates a closed cell culture cavity, which may be similar to cell culture cavity 8102 in FIGS. 81A-81C. The cell culture cavity may be part of a cell culture system (e.g., cell culture system 100). The cell culture cavity may include an adhering surface 8302 upon which rest adherent cells 8304 and semi-adherent cells 8306. The adherent cells 8304 and semi-adherent cells 8306 may include various immune cells, such as T cells, dendritic cells, and macrophages. The cell culture cavity may be in an inverted orientation such that the force of gravity points downwards in FIGS. 83A-83E, as described with respect to FIG. 82B. The adhering surface 8302 may also have an absorption layer on top of the adhering surface 8302, on the outside of the cell culture cavity, that absorbs pulsed laser light impinging on the outside of the cell culture cavity.

The semi-adherent cells 8306 may be detached from the adhering surface 8302 and separated from the adherent cells 8304 using a variety of cell editing mechanisms, as illustrated in FIGS. 83B-83E. The mechanisms may include directing energy towards the adherent cells 8304 to dislodge them. The energy delivered may include, for example, laser radiation, mechanical forces, and ultrasound. For example, in FIG. 83B a fluid flow 8308 through the cell culture cavity may create lateral forces that detach the semi-adherent cells 8306 from the adhering surface 8302. The fluid flow 8308 may be controlled by a computing subsystem and may be performed at specific times or based on conditions within the cell culture cavity as measured by an imaging subsystem or by cell media measurements conducted by other components in a cell culture system. The detached semi-adherent cells

8306 may be pushed by the fluid flow 8308 to another location in order to separate them from the adherent cells 8304.

Figure 83C:
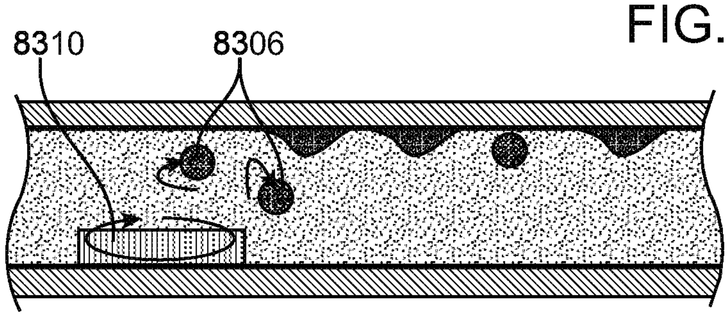

In another implementation as shown in FIG. 83C, an agitation tool 8310 may be used to create local fluid flows that detach the semi-adherent cells 8306. For example, the agitation tool 8310 may be a magnetic tool that is capable of translation across the bottom surface of the cell culture cavity and rotation as well. Rotation of the magnetic tool may create local forces that act on the semi-adherent cells 8306 and detach them from the adhering surface 8302. The magnetic tool inside the cell culture cavity may be magnetically coupled to another magnetic tool outside the cell culture cavity, which may be used to move the internal magnetic tool. A computing subsystem may be configured to determine the location of the magnetic tool using imaging tools and control the external magnetic tool using one or more arms or actuators. In general, the agitation tool 8310 may be any tool that is controllable in order to loosen and detach semi-adherent cells 8306 from the adhering surface 8304. The detached semi-adherent cells 8306 may then be pushed by the agitation tool 8310 or another mechanism to another location in order to separate them from the adherent cells 8304.

Figure 83D:
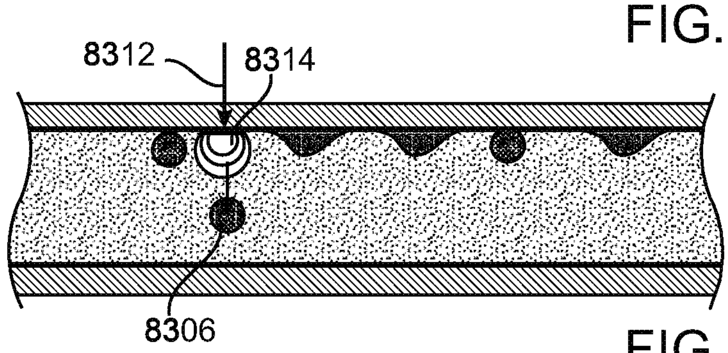

In another implementation as shown in FIG. 83D, pulsed laser light 8312 may impinge the outside of the adhering surface 8304. The pulsed laser light 8312 may generate one or more microbubbles 8314 within the cell culture cavity. The microbubbles 8314, when collapsed, may create a shockwave that detaches the semi-adherent cells 8306 from the adhering surface 8302, as described with respect to FIGS. 81A-81C. The detached semi-adherent cells 8306 may then be pushed to another location in order to separate them from the adherent cells 8304.

Figure 83E:
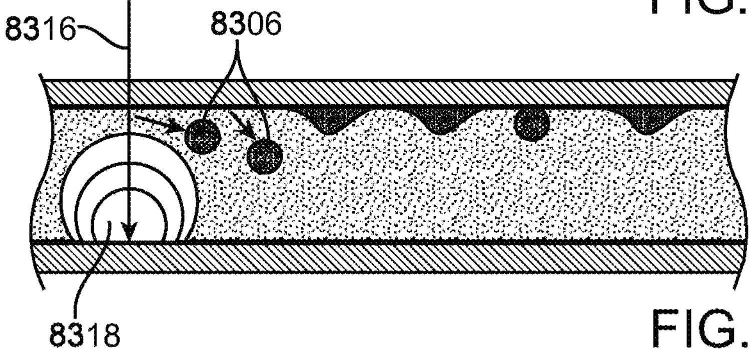

In another implementation as shown in FIG. 83E, pulsed laser light 8316 may impinge the bottom surface of the cell culture cavity. The pulsed laser light 8316 may come from the top as shown in FIG. 83E, but may also come from the bottom of the cell culture cavity (not shown in FIG. 83E). If the pulsed laser light 8316 originated from the top, the adhering surface 8302 may not have an absorption layer, or may have an absorption layer that is configured to not absorb pulsed laser light 8316 (e.g., at specific wavelengths). The pulsed laser light 8316 may generate one or more microbubbles 8318 within the cell culture cavity. The microbubbles 8318, when collapsed, may create a shockwave that detaches the semi-adherent cells 8306 from the adhering surface 8302, as described with respect to FIGS. 81A-81C. The detached semi-adherent cells 8306 may then be pushed to another location in order to separate them from the adherent cells 8304.

Figure 84A:
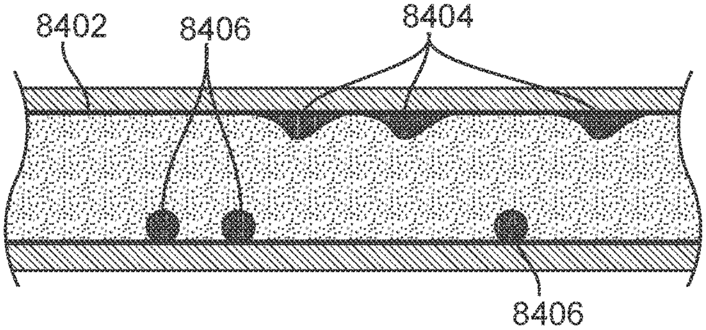
FIGS. 84A-84E are diagrams illustrating removal of semi-adherent cells in a cell culture cavity in accordance with various implementations.
Figure 84B:
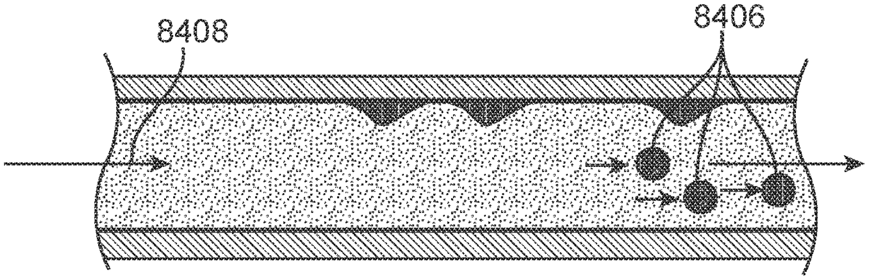

FIGS. 84A-84E are diagrams illustrating removal of semi-adherent cells in a cell culture cavity in accordance with various implementations. FIG. 84A illustrates a closed cell culture cavity, which may be similar to cell culture cavity 8102 in FIGS. 81A-81C. The cell culture cavity may be part of a cell culture system (e.g., cell culture system 100). The cell culture cavity may include an adhering surface 8402 upon which rest adherent cells 8404. Semi-adherent cells 8406 may have been previously detached from the adhering surface 8402, as described with respect to FIGS. 83A-83C. The adherent cells 8404 and semi-adherent cells 8406 may include various immune cells, such as T cells, dendritic cells, and macrophages. The cell culture cavity may be in an inverted orientation such that the force of gravity points downwards in FIGS. 84A-84E, as described with respect to FIGS. 82A-82B. The adhering surface 8402 may also have an absorption layer on top of the adhering surface 8402, on the outside of the cell culture cavity, that absorbs pulsed laser light impinging on the outside of the cell culture cavity.

The semi-adherent cells 8406 may be removed from the cell culture cavity using a variety of approaches, as illustrated in FIGS. 84B-84E. For example, in FIG. 84B a fluid flow 8408 through the cell culture cavity may push the semi-adherent cells 8406 to another location, for example a second cell culture cavity, a waste receptable, or a collection receptable. In some implementations, the cell fluid media containing the semi-adherent cells 8406 may be filtered as it is moved to another location. The filtering may be done, for example, to separate cell from cell debris, or separate cells by size, volume, mass, or other characteristics. The cell fluid media may be filtered using a number of methods, including but not limited to tangential flow filtration, ultrasonic separation, inertial microfluidic focusing, and deterministic lateral displacement using microfluidic features. A computing subsystem may be configured to control the fluid flow 8308.

Figure 84C:
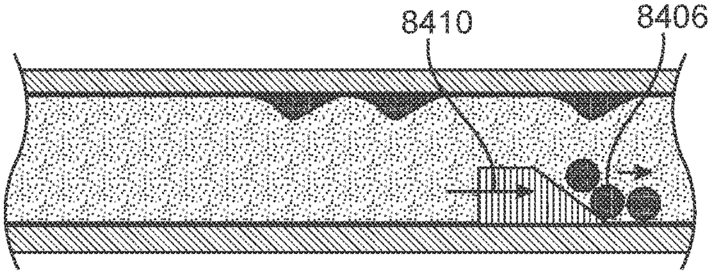

In another implementation as shown in FIG. 84C, a collection tool 8410 may be used to push the semi-adherent cells 8406 to another location. The collection tool 8410 may be the agitation tool 8310 described with respect to FIG. 83C, or may be a separate tool. For example, the collection tool 8410 may be a magnetic tool that is controlled by an associated magnetic component located outside the cell culture cavity. The collection tool 8410 may rest on the bottom surface and may push the semi-adherent cells 8406 that are resting on the bottom surface towards another location. The collection tool 8410 may be controlled by a computing subsystem.

Figure 84D:
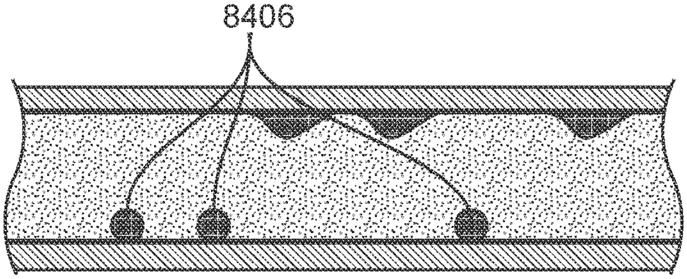
Figure 84E:
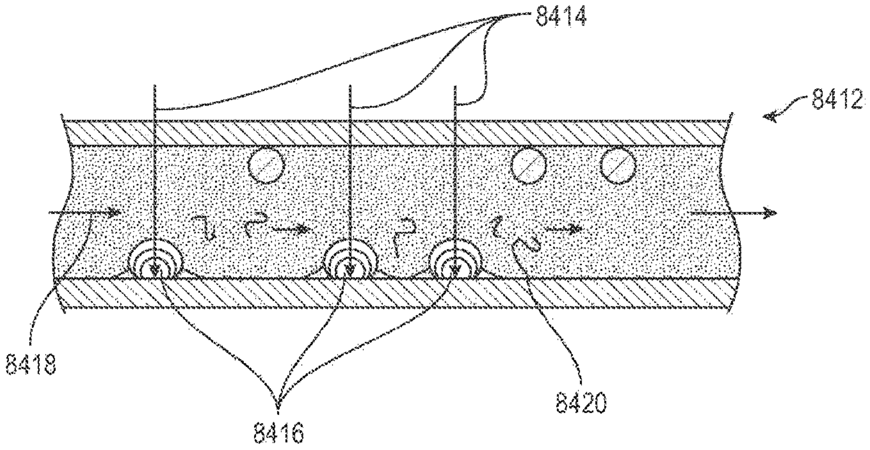

In another implementation as shown in FIGS. 84D-84E in which the adherent cells 8404 may be destroyed, the semi-adherent cells 8406 may have adhered to the bottom surface of the cell culture cavity. The cell culture cavity may undergo inversion 8412 such that the semi-adherent cells 8406 are now on the top surface, as shown in FIG. 84E. The adhering surface 8402 containing the adherent cells 8404 may now be the bottom surface. One or more laser pulses 8414 may target the adherent cells 8404. For example, a computing subsystem may determine the location of the adherent cells 8404 using an imaging subsystem, and control a laser to target the adherent cells 8404. The laser pulses 8414 may come from the top (as shown in FIG. 84E) of the cell culture cavity, or from the bottom. The laser pulses 8414 may create one or more microbubbles 8416 that lyse, or destroy, the adherent cells 8404. After the adherent cells are lysed into cell debris 8420, a fluid flow 8418 may push the cell debris out of the cell culture cavity. The computing subsystem may control the fluid flow.

Figure 85A:
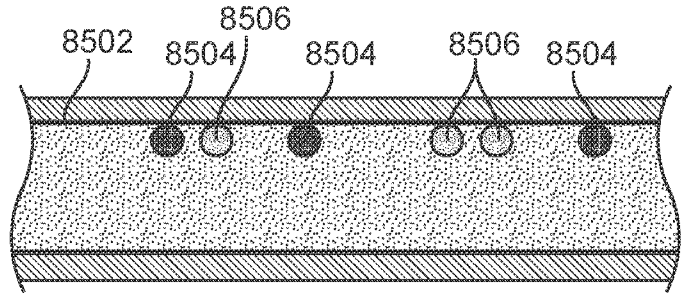
FIGS. 85A-85E are diagrams illustrating selective separation of semi-adherent cells in a cell culture system in accordance with various implementations.

FIGS. 85A-85E are diagrams illustrating selective separation of semi-adherent cells in a cell culture system in accordance with various implementations. The semi-adherent cell culturing process may include multiple steps, some of which were described in detail with respect to FIGS. 81A-81E. FIG. 85A illustrates a closed cell culture cavity, which may be similar to cell culture cavity 8102 in FIGS. 81A-81C. The cell culture cavity may be part of a cell culture system (e.g., cell culture system 100). The cell culture cavity may include an adhering surface 8502 upon which rest a first plurality of cells 8504 having a first cell type/state and a second plurality of cells 8506 having a second cell type/state. The first and second plurality of cells 8504, 8506 may be one or more kinds of immune cells, such as T cells, dendritic cells, myocytes, and macrophages. The first and second cell types/stages of the first and second plurality of cells 8504, 8506 may be different types or stages of semi-adherent cells. For example, the first cell type/stage may be a dendritic cell and the second cell type/stage may be a monocyte. In another example, the first cell type/stage may be an immature dendritic cell and the second cell type/stage may be a mature dendritic cell. The cell culture cavity may be in an inverted orientation such that the force of gravity points downwards in FIGS. 85A-85E. The adhering surface 8502 may also have an absorption layer on top of the adhering surface 8502, on the outside of the cell culture cavity, that absorbs pulsed laser light impinging on the outside of the cell culture cavity.

Figure 85B:
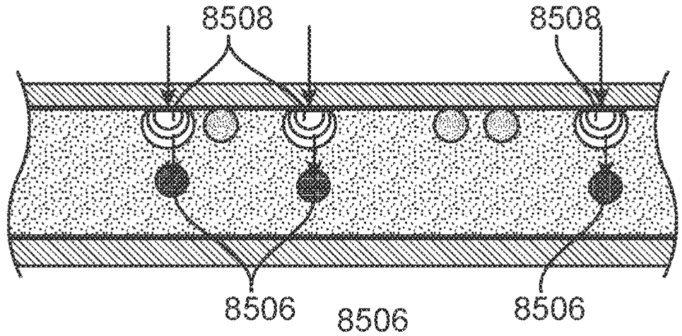

In FIG. 85B, pulsed laser lights may be applied to the locations of the first plurality of cells 8504. For example, an imaging subsystem of the cell culture system may identify the locations of each cell in the cell culture cavity, and identify which cells are of the first cell type/stage versus the second cell type/stage using image analysis and/or machine learning. A computing subsystem may control a laser to target the locations of the first plurality of cells 8504 with pulsed lasers. The pulsed laser lights create microbubbles 8508 within the cell culture cavity. The microbubbles 8508 and their subsequent collapse may cause the first plurality of cells 8504 to be dislodged from the adhering surface 8502. In other implementations, other methods of dislodging the first plurality of cells 8504 may be used, as described in detail with respect to FIGS. 83A-83E.

Figure 85C:
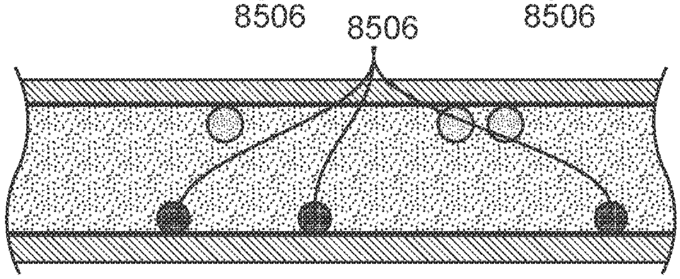

In FIG. 85C, the first plurality of cells 8504 that have been dislodged may settle on the bottom surface of the cell culture cavity due to gravity. The first plurality of cells 8504 may be rest there for a period of time until they re-adhere to the bottom surface.

Figure 85D:
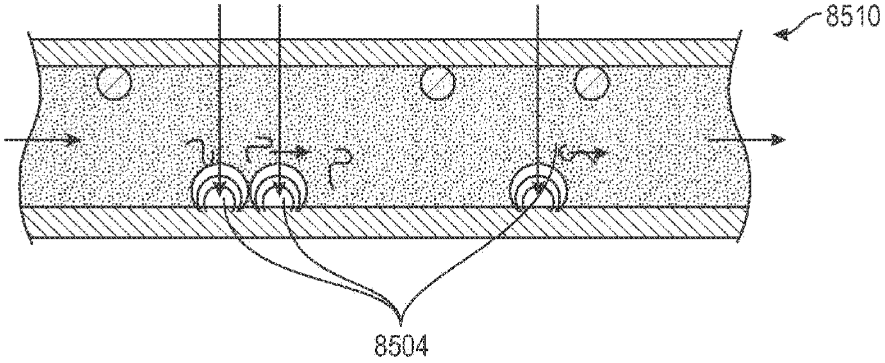

In FIG. 85D, the cell culture cavity may undergo inversion 8510 so that the adhering surface 8502 with the second plurality of cells 8506 is now on the bottom while the surface with the first plurality of cells 8504 is on the top. A computing subsystem may apply pulsed lasers to the locations of the first plurality of cells 8504 to lyse them and a fluid flow may push the resultant cell debris out of the cell culture cavity, as described in detail with respect to FIGS. 84A-84E.

Figure 85E:
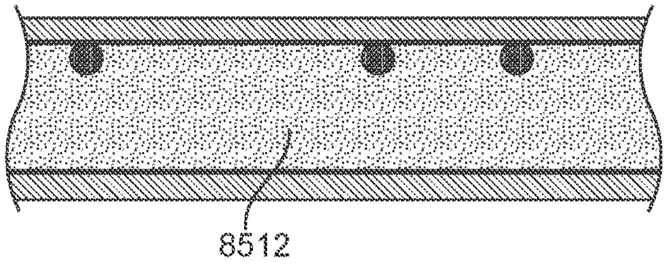

In FIG. 85E, the cell culture cavity with only the second plurality of cells 8506 on the top surface remain. The second plurality of cells 8506 may undergo additional cell culturing until two or more cell types/stages are grown. At that point, the process of separation, inversion, and removal described with respect to FIGS. 85A-85E may be repeated. This process may allow for selective separation and removal of certain cell types or stages during cell culturing, and may be particularly useful for the culturing of semi-adherent cells, such as immune cells (e.g., dendritic cells, T cells, monocytes, and macrophages).

Figure 86:
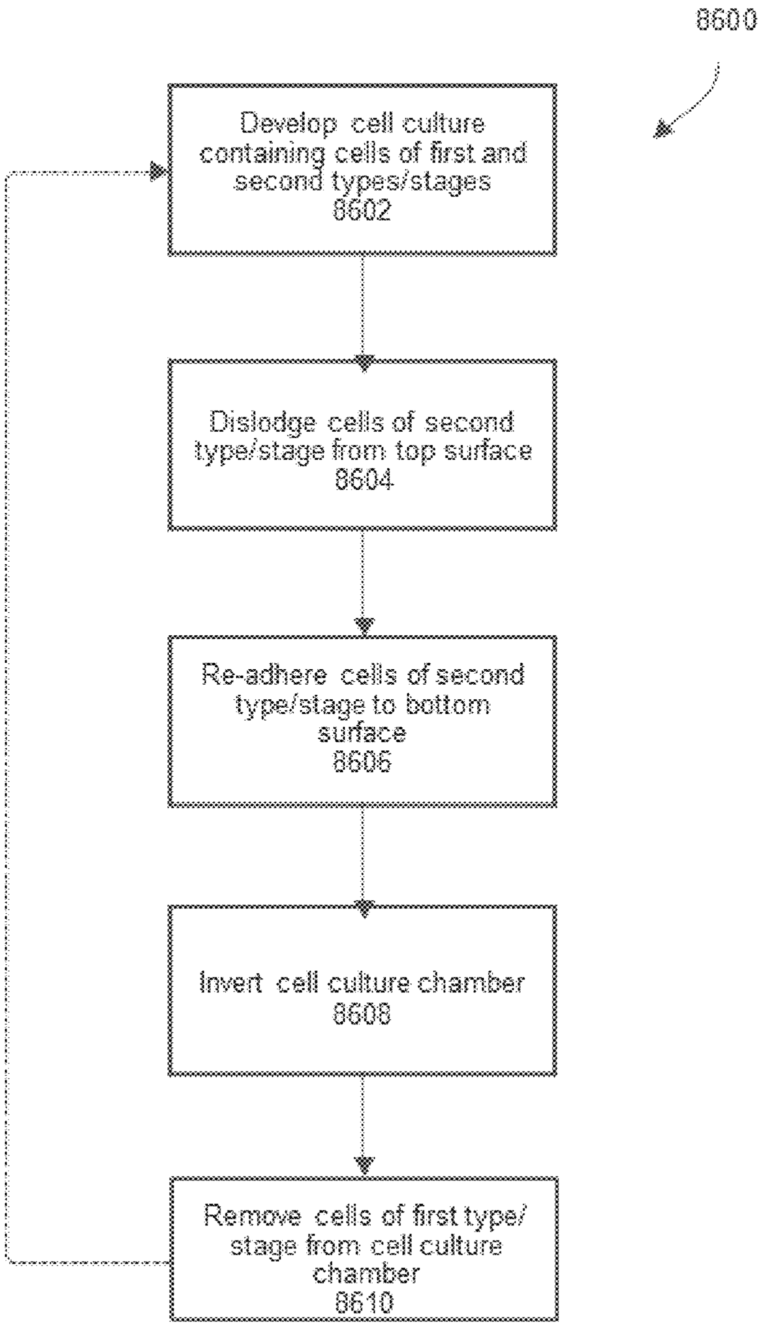
FIG. 86 is a flow chart illustrating a method of cell culturing in a cell culture system in accordance with various implementations.

FIG. 86 is a flow chart illustrating a method 8600 of semi-adherent cell culturing in a cell culture system in accordance with various implementations. The method 8600 may be performed by a cell culture system (e.g., cell culture system 100 in FIG. 1). The method 8600 may be similar to the process described with respect to FIGS. 85A-85E.

In block 8602, a cell culture may be developed in a cell culture container (e.g., cell culture container 106). The cell culture cavity in the cell culture container may contain cells of at least a first and second cell type/stage. The first and second cell types/stages may include various types of immune cells, such as T cells, dendritic cells, and macrophages. The first and second cell types/stages may be different types or stages of semi-adherent cells. For example, the first cell type/stage may be a dendritic cell and the second cell type/stage may be a monocyte. In another example, the first cell type/stage may be an immature dendritic cell and the second cell type/stage may be a mature dendritic cell. The cells of the first and second cell types/stages may adhere to a top surface of the cell culture cavity, with the force of gravity acting downwards from the top surface to the bottom surface.

In block 8604, the cell culture system may dislodge cells of the second cell type/stage from the top surface. An imaging subsystem of the cell culture system may identify the locations of each cell in the cell culture cavity, and identify which cells are of the first cell type/stage versus the second cell type/stage. The cell culture system may utilize a number of methods to dislodge cells of the second cell type/stage, including using agitation tools, pulsed laser lights, and fluid flows as illustrated in FIGS. 83A-83E. The dislodged cells of the second cell type/stage may settle on the bottom surface of the cell culture cavity. In block 8606, the cells of the second cell type/stage may be given time to re-adhere to the bottom surface of the cell culture cavity.

In block 8608, the cell culture system may invert the cell culture cavity. For example, the cell culture system may include one or more actuators connected to the cell culture chamber containing the cell culture cavity that may act on the cell culture chamber to invert it. When inverted, the bottom surface containing the re-adhered cells of the second cell type/stage may now be the top surface and the top surface containing cells of the first cell type/stage may now be the bottom surface.

In block 8610, the cell culture system may remove the cells of the first cell type/stage from the cell culture cavity. The cell culture system may utilize a number of methods to remove cells of the first cell type/stage from the bottom surface, including using collection tools, pulsed laser lights, and fluid flows as illustrated in FIGS. 84A-84E. Once removed, the method 8600 may return to block 8602 and continue culturing of the cells of the second or more cell type/stage until multiple cell types/stages are grown, in which case the cell culture system may separate the different cell types/stages and selectively remove some of them. In this manner, the method 8600 enables automated, controlled culturing of cells, which may be particularly useful for large scale derivation and manufacturing of semi-adherent cells.

For the particular application of derivation and manufacturing of immune cells, the cell culture system may enable end-to-end large-scale production of immune cells from an input cell type. Starting with virtually any input cell type, such as fibroblasts or CD34+ cells, the cell culture system may reprogram the input cells into iPSCs using methods described herein, and then expansion of iPSCs to useful therapeutic doses. The iPSCs may then be directed to differentiate and eventually mature towards various cells of the myeloid lineage, including dendritic cells. During this differentiation process towards a predefined end product, the cell culture may pass through various cell types and cell clusters of varying levels of adherence. The iterative computer guided, time controlled, laser-based, inversion aided process described herein will enable selection throughout the differentiation and maturation process resulting in a highly functional, highly pure end product based on phenotypes recognized by a computer, such as the presence or lack thereof of dendrites or adherence level. For example, early in the differentiation process, non-adherent or semi-adherent cells may be flowed from the first cell culture cavity to a second cell culture cavity and allowed to settle in the second cell culture cavity for the next stage of differentiation. As another example, adherent cells such as macrophages for a purely dendritic cell-based product or non-functional cells such as immature dendritic cells after the cell culture was supplemented with a maturation cocktail may be removed from the cell culture cavity during the differentiation process.

Selective Material Extraction and Analysis

During a cell culture process, it may be beneficial to selectively collect and sample cells in the cell culture to determine its characteristics. The characteristics may be used in different applications. For example, a computing subsystem (e.g., computing subsystem 100) may associate characteristics of the sampled cells with the cell regions or colonies that the cells came from. It may also be important to image live cells at multiple timepoints to enable the measurement of trends at the subcellular, cellular, cell neighborhood, or colony level. Another application of selective cell sampling and characterizing is to monitor the cell culture state, for example during a cell-based process or in a bio production system, and doing so in a selective manner in order to obtain a representative sample of cell material. This may allow a cell culture system to determine whether the cell culture process should be continued, altered, or stopped based on the attributes of the harvested cells. The information may also be used in machine learning models to improve future cell culture processes.

The characteristics of the cells that may be observed or measured from label-free images may include, but are not limited to, morphology, presence/count/size of subcellular components, density, refractive index, absorption or absorption spectrum, polarization-dependent absorption or refractive index, degree of attachment to substrate or surrounding cells, proliferation rate, velocity, projection of cell outgrowths such as neurites, interaction with other cells, and spectroscopic characteristics including but not limited to Raman spectra, infrared spectra, autofluorescence, etc. The measured or observed characteristics may also include parameters measurable by fluorescent labelling, such as surface markers or other components known to the industry. The measured or observed characteristics may also include phenotypic, genomic, epigenetic, transcriptomic, proteomic characteristics of those cells.

The selective cell extraction and analysis should be done in situ on live or recently live cell cultures in a cell culture vessel suitable for long-term cell processes, and observation should be conducted via imaging. The cell extraction process should be minimally invasive so that the remaining cells can remain in culture and continue the cell process. In addition, it should be compatible with a closed or semi-closed cell culture system such as a flask or microfluidic cell culture chamber, or other 90D cell culture vessel that does not allow manual access to the cell culture region. The selective cell extraction and analysis should also be compatible with existing analysis techniques, including but not limited to qPCR, RNA sequencing, DNA sequencing, karyotyping, DNA methylation sequencing, chromatin accessibility measurements such as ATACseq/MNase-seq/DNase-seq, and proteomic measurements including but not limited to microarrays, liquid chromatography, and mass spectroscopy.

There are several current approaches in the art for sampling cells during a cell culture process. One example is laser microdissection. This is a well-established technique by which samples are "cut out" of cell or tissue sheets and retrieved for analysis. Often the technique is used on preserved intact tissues, or when cells have been secured to a foil for extraction. The disadvantages of this technique are that it is generally relevant to continuous tissues only, not where there are individual cells, and requires mechanical extraction of the cut-out cell sheets, which is performed in a number of ways—all of which are generally incompatible with a long-term cell culture system, particularly one that is semi-closed (like a tissue culture flask) or entirely closed (like a microfluidic cell culture vessel).

Another approach is foil-based, in which tissue is attached to a foil which absorbs laser radiation and may be cut, allowing sections to be cut and then retrieved mechanically. Another approach is membrane retrieval, in which after cutting of the tissue section of interest, a "stamp" that contains a textured membrane is lowered onto the tissue surface to make contact with the section of interest and retrieve it. There is also ejection/gravity, in which a section of tissue is suspended (on a foil) in air, and sections that are laser-cut drop off into a collection chamber. Another method is called fluorescent in-situ hybridization (FISH), including both DNA-FISH and RNA-FISH. This technique allows a number of pre-determined DNA sequences or RNA sequences to be labelled and imaged in situ. However, cells must be fixed prior to hybridization and labelling, the number of sequences that can be examined is generally limited, and high-resolution fluorescence microscopy is required to image the fluorophores. Yet another approach is micropipette-based extraction of cells, or cellular components. These techniques are able to target individual cells, or small groups of cells, and are able to work on live cell cultures.

There are also spatial transcriptomic techniques for cell sampling. These techniques rely on a specialized surfaces that has been pre-coded with DNA sequences to allow tracing of the spatial origin of RNA molecules. To date these techniques have been developed primarily for tissue sections that have been preserved in a thin slice, for use in pathology or ex-vivo studies. The drawbacks of this approach are that they do not apply to in situ measurement of live cell cultures, and that they are currently restricted to RNA sequencing.

In short, while existing methods address situations where preserved tissue samples are used, or may act on recently-live cells but with expensive instruments and consumables, there are few viable options for using standard analytical methods in conjunction with dynamic live cell imaging. Particularly, no current approach is suitable for performing such measurements inside of closed or semi-closed cell culture vessels, and potentially within the course of a cell process (without damaging the remaining live cells). Thus, what is needed in the art are methods of extracting and sampling cells during a cell culture process in a closed, automated cell culture system while not disturbing the cell growth process.

The systems and methods disclosed herein include a system for selective cell extraction and sampling which is compatible with a cell culture system (e.g., cell culture system 100). The system may include a cell culture chamber suitable for long-term cell culture and imaging, a coating on the cell culture chamber for laser absorption (but transmits imaging light), an imaging subsystem configured to image cells resident on the coated surface, a computing subsystem for selecting one or more cells for analysis, and a cell editing subsystem that utilizes laser pulses that strike the coating, causing an explosive microbubble and cavitation. The cells are de-adhered from the coated surface as a result of the microbubbles and are harvested via liquid extraction, and/or cells are lysed by the microbubbles and their components are harvested via liquid extraction. The cells and/or cell components may then be analyzed via a range of analytical techniques. In some implementations, the analyzed cells may be selected by their image characteristics, including time series image characteristics and/or analysis thereof. In some implementations, a series of laser processes and liquid removal processes may be used to sample multiple subpopulations.

Additional methods of targeted cell extraction or cell lysis are contemplated in this disclosure. For example, cells may be extracted using magnetic tools operable in a live cell culture container, including a closed fluidic chamber or cassette. The magnetic tool may be controlled by an external component actuating the in-chamber component, the external component guided by a computing subsystem based on imaging data. In an alternate example, focused ultrasound operable in a live cell culture container, including a closed fluidic chamber or cassette, may be used to extract cells. An external transducer transmitting focused sound waves through the container wall may be used to focus on cells of interest and loosen them from the cell culture surface. The transducer may be controlled by a computing subsystem based on imaging data.

Cell lysis may take place in situ, and resulting debris are removed from the container with the surrounding liquid. If cell lysis is done in situ, the cell culture fluid media may be replaced with an "extraction and measurement" media prior to lysis. This extraction media may be free of potential contaminants, components that will interfere with the downstream measurements, or sample-degrading components such as RNAse. In some implementations when cell lysis takes place in situ, the cells may be fixed prior to the process, and reverse transcription of RNA to cDNA may be performed in situ. This "freezes" the state of the cell culture, preserves mRNA information, and allows for a multi-part selective harvest of material over a longer period if needed.

Cells may be selectively harvested intact through this selective method, with lysis done prior to analysis, enabling single-cell measurements. Once cells or cell debris have been selectively separated from the cell culture, harvest may be done in a number of ways, including but not limited to, pipetting (including automated pipetting systems) for open cell culture containers such as microwell plates, and liquid replacement and outflow in closed fluidic chambers, in which the liquid exiting chamber flushes the extracted cells with it.

There may be several approaches for selecting cells for extraction. For example, one approach is random sampling of cells from a cell culture. This may include random area selection for cells or cell components in a high-confluency cell culture (e.g., choosing random 90D patches to act upon with transducer and then harvesting the material) or random area selection from within cell-bearing areas, based on an image of the cell culture. Using such an image, regions of different local densities may be randomly sampled to obtain a representative sample. In another approach, the sampling may be guided by manual annotation of images of the cell culture, with humans observing the cell culture image and selecting regions of interest, and the cell editing subsystem acting upon these areas prior to sample extraction.

In another approach, the sampling may be guided by image characteristics as measured by a computing subsystem (e.g., computing subsystem 100). The relevant image characteristics may include (1) outputs of image processing subsystems that measure local density, morphology, order, orientation, etc.; (2) outputs of machine learning models whose input is the images of the cell culture and whose output is a spatial map classifying the cell culture at the cell, neighborhood, region, colony or other level (the machine learning model may be, for example, a supervised model that has been trained with labelled data or an unsupervised model that classifies spatial regions into a series of clusters based on image data alone); (3) outputs of a computing subsystem that locates each cell in the cell culture and computes local characteristics such as cell morphology, density, colony membership, etc.; and (4) outputs of a computing subsystem that locates each colony and computes colony characteristics, including time series characteristics.

Figures 87A, 87B, 87C, 87D, 87E:
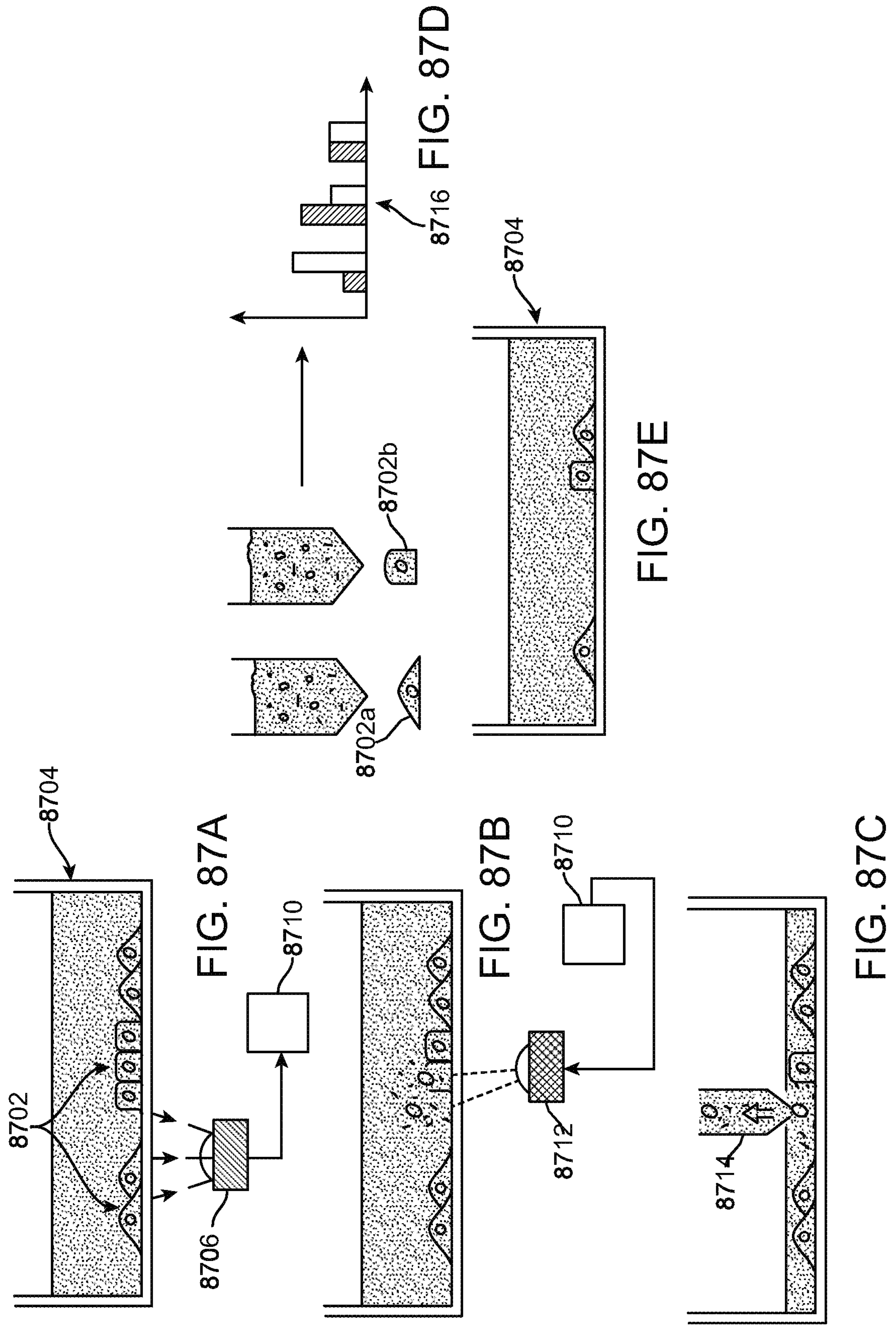
FIGS. 87A-87E are diagrams illustrating selective cell extraction and analysis of adherent cells in accordance with various implementations.

FIGS. 87A-E are diagrams illustrating selective cell extraction and analysis of adherent cells in accordance with various implementations. In FIG. 87A, cells 8702 undergo a cell culture process in a cell culture container 8704. The cells 8702 may be adhered to a surface of the cell culture container 8704, the surface configured to allow imaging (e.g., a transparent surface). The cells are imaged using an imaging subsystem 8706 (e.g., cell imaging subsystem 112), which transmits data to a computing subsystem 8708 (e.g., computing subsystem 110). In one example, the computing subsystem 8708 may classify the regions of cells using an unsupervised clustering model which classifies cell regions by texture, morphological characteristics, and time series characteristics (e.g., changes of properties over time, optical flow measurements). Similarly, the computing subsystem 8708 may identify individual colonies, and categorize cells by colony membership.

In FIG. 87B, the computing subsystem 8708 may select a first group of cells for lysing using any of the methods described herein (e.g., unsupervised clustering models). The computing subsystem 8708 may control a cell editing subsystem 8712 (e.g., cell editing subsystem 114) to lyse the selected cells using a non-contact lysis method. For example, the cell editing subsystem 8712 may be a steered pulsed laser system that interacts with a coating on the internal surface of the cell culture container 8704 to form explosive microbubbles and lyse the targeted cells. Prior to this lysing process, the cell media in the cell culture container 8704 may be exchanged for a specialized, temporary lysis and material harvest buffer that is RNAse free and/or may contain compounds to accelerate cell dissociation upon lysis.

In FIG. 87C, liquid is withdrawn from the cell culture container 8704. The liquid contains the components of the cells that were targeted and lysed by the cell editing subsystem 8712. In the example shown in FIG. 87C, an automated pipetting system 8714 is used to withdraw the liquid from the cell culture container 8704. The automated pipetting system 8714 may optionally position the pipette to draw liquid from the specific region where cells were lysed, and withdraw only a portion of the total liquid in the cell culture container 8704, in order to maximize the concentration of the cellular constituents within the harvested liquid. The automated pipetting system 8714 is only one possible method of liquid extraction. In general, multiple liquid extraction methods may also be utilized to withdraw liquid containing the lysed cell components. The lysing and extraction process illustrated in FIGS. 87B-C may be repeated multiple times for each distinct cell population that has been identified.

In FIG. 87D, extracted cell samples may be processed for analysis according to one or more pre-existing analysis techniques. For example, two cell samples 8702*a* and 8702*b* may have been extracted. In one example, each sample 8702*a*, 8702*b* is analyzed by qPCR, and levels of expression for a series of target genes, along with housekeeping genes that normalize for cell quantity, are measured and compared to each other as well as reference readings. The data analysis is represented in FIG. 87D by chart 8716. This approach may allow analysis of multiple cell phenotypes that are linked to image or image timeseries characteristics. This information may be used in future predictive model and process optimization operations by a cell culture system. For example, a cell culture system may selectively lyse cells and remove them from the cell culture container for analysis. The cell culture system may utilize the resulting information to monitor progression and success of similar cell cultures with imaging alone and the use of a machine learning model (now trained with the qPCR data and other information), and may also use the information to optimize the cell culture process given certain output cell target attributes.

Various cellular components obtained through the extraction techniques disclosed herein can be used as biomarkers suitable for downstream analysis. Examples of cellular components include cell surface proteins (particularly surface biomarkers), cytoplasmic proteins, cytoplasmic RNA, nuclear proteins, mitochondrial DNA/RNA, nuclear DNA/RNA, and extracellular vesicles (EVs) and their associated materials (endosome, exosome, and their associated contents). RNA could include total RNA, run-on RNA transcripts, enhancer RNAs, general non-coding RNAs (including but not limited to lncRNAs, lincRNAs, snoRNAs, miRNAs, and similar), mRNAs, or any combination thereof.

Various capture technologies can be used to obtain the target cellular component(s). Bead capture can be used to capture cellular components after laser cell lysis. In some cases, the primary capture method uses magnetic beads targeting a given cellular component. Examples include DNAs/RNAs capture using SPRI paramagnetic beads (such as AmpureXP), and antibody-conjugated protein capture superparamagnetic beads (such as protein A/G dynabeads pre-conjugated to an antibody targeting a protein of interest). Alternative bead/slurry methods could also be utilized when appropriate, such as coated agarose-based bead capture for isolation of targeted molecules. Capture may also be achieved through collection of total lysed material in an appropriate buffer for further downstream analysis, followed by gradient ultracentrifugation to isolate the components of interest (in the case of EVs, for example).

The captured cellular component(s) can be analyzed according to various available analytical methods. For RNAs, suitable methods include all forms of applicable NGS, including but not limited to total RNAseq, mRNAseq, scRNAseq, enhancer RNAseq, and exome capture sequencing approaches. More targeted qPCR-based evaluations and/or arrays may be used to evaluate isolated RNAs on a smaller scale as well. For DNAs, suitable methods include all forms of applicable NGS, including but not limited to ATACseq, ChIPseq, scATACseq, whole exome sequencing, whole genome sequencing, or targeted DNA region or portion sequencing. More targeted qPCR-based evaluations and/or arrays may be used to evaluate isolated DNAs on a smaller scale as well.

For proteins, analysis may be performed using an extremely wide and diverse array of downstream applications depending on the quantity and purity that can be isolated. Mass-spectrometry analysis based or antibody probe based methods can be used to evaluate, for example, the identity and/or quantity of select protein biomarkers. Alternatively, any of a vast number of other protein analytics methods could be applied as necessary (e.g., Western Blot, ELISA, immunostaining, etc.).

Following the selective extraction of cell material, the cell culture process may continue in the cell culture container 8704, as shown in FIG. 87E. Thus, the implementations disclosed allows harvest of cell material (often a very small fraction of the overall growth) from a live cell culture and therefore allows the remaining cells to progress to an endpoint of the cell culture process without interruption. In some implementations, the selective harvest and analysis may be performed at multiple points during the cell culture process. The methods disclosed herein may be used for cell processes including, but not limited to, stem cell reprogramming (e.g., iPSCs), stem cell differentiation, trans-differentiation, cell maturation, cell gene editing, clonal growth and selection, etc. The methods disclosed herein may be used for the purpose of training image-based models for predicting cell process outcomes, or may be used directly to select optimal regions, colonies, clones, cell cultures for further processing.

Figure 88A:
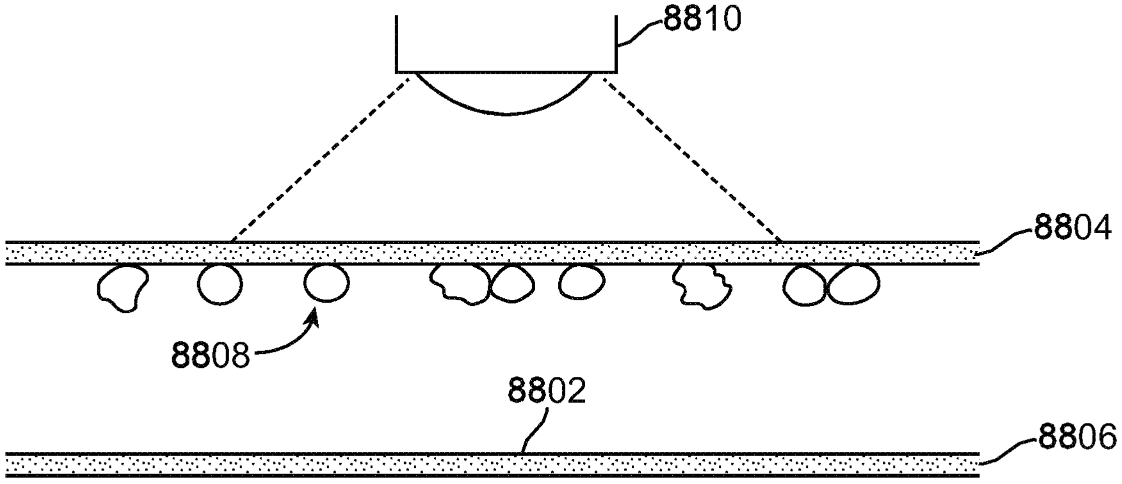
FIGS. 88A-88C are diagrams illustrating selective cell extraction and analysis of semi-adherent cells in accordance with various implementations.
Figure 88B:
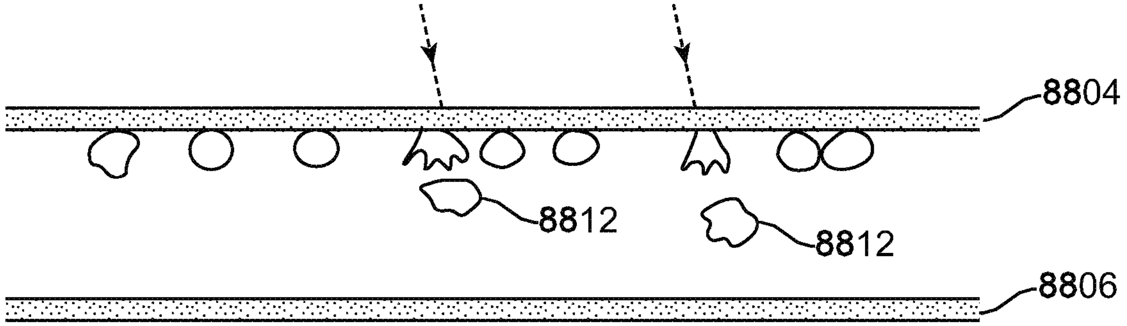
Figure 88C:
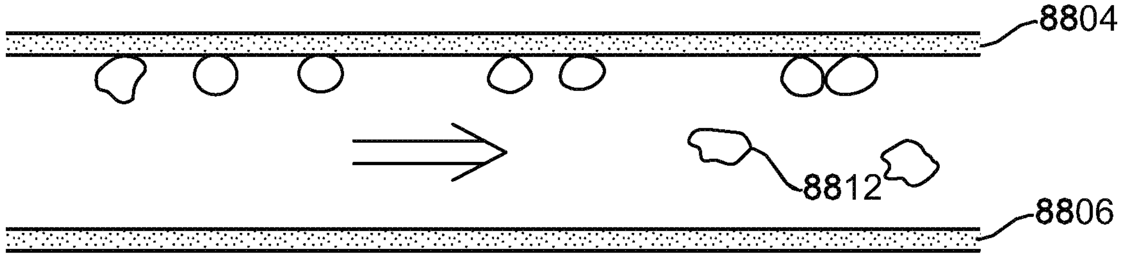

FIGS. 88A-C are diagrams illustrating selective cell extraction and analysis of semi-adherent cells in accordance with various implementations. The semi-adherent cells may be grown in a cell culture container having a closed liquid chamber, and the cells may be selected for extraction based on imaging or imaging time series characteristics. In FIG. 88A, a closed liquid chamber may include a volume of liquid media 8802 bounded by an upper surface 8804 and a lower surface 8806. The upper and lower surfaces may be transparent so that cells within the closed liquid chamber may be imaged using transmitted-light imaging (e.g., bright-field imaging, Zernike phase imaging, darkfield imaging, differential interference contrast imaging, quantitative phase imaging, etc.).

In the example shown in FIG. 88A, cells 8808 have been introduced into the closed liquid chamber when it was inverted (i.e., the upper surface 8804 is below the lower surface 8806), and due to their semi-adherence, attach weakly to the upper surface 8804 when the chamber is inverted back to the orientation shown in FIG. 88A. When the closed liquid chamber is inverted to the orientation shown in FIG. 88A, any cells or debris that are not adhered to the upper surface 8804 drop towards the lower surface 8806 and may be washed out of the closed liquid chamber by pumping liquid through it.

An imaging subsystem 8810 (e.g., cell imaging subsystem 112) may image the cells 8808 that are attached to the upper surface 8804 at one or more timepoints. A computing subsystem (e.g., computing subsystem 110) may calculate characteristics of individual cells based on size, morphology, intracellular components, polarization dependence, refractive index, phase, cell division, or other characteristics captured by the images. In some implementations, fluorescent labels may be applied as well to indicate presence of specific surface markers. In some implementations, time series trends of one or more of the measured characteristics are used. As a result of these observations, cells are grouped by classifications. The cells may be grouped automatically by the computing subsystem or manually by a human operator who can look at the distribution of these characteristics (e.g., one or more scatter plots) and select one or more clusters of cells of interest.

A non-invasive selective cell harvesting system (e.g., cell editing subsystem 894) may be used to dislodge selected cells 8812 with a specific classification from the upper surface 8804, as shown in FIG. 88B. For example, the cell harvesting system may be a pulsed laser system which creates microbubbles when it strikes an absorbing film on the upper surface 8804. The microbubbles detach the selected cells 8812 from the upper surface 8804, causing them to fall away from the upper surface 8804 into the liquid media 8802 contained within the cell chamber.

The selected cells 8812 are then harvested from the closed liquid chamber by exchanging the liquid media 8802 in the chamber as shown in FIG. 88C. The media exchange may be done as part of a regular media change. The selected cells 8812 are then collected for analysis. Because the selected cells 8812 are intact when extracted, both bulk analysis techniques as well as single-cell techniques such as single-cell RNAseq may be used on the harvested cells.

Figure 89A:
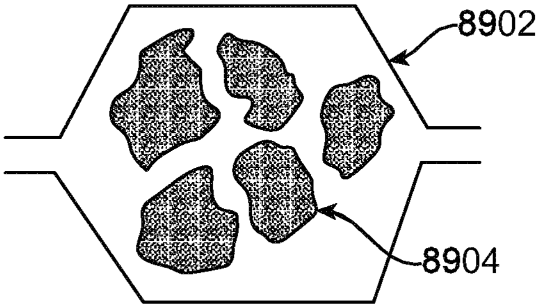
FIGS. 89A-89C are diagrams illustrating a cell culture process with selective cell extraction and analysis in accordance with various implementations.
Figure 89B:
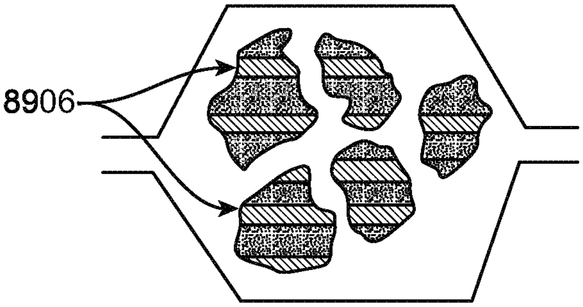
Figure 89C:
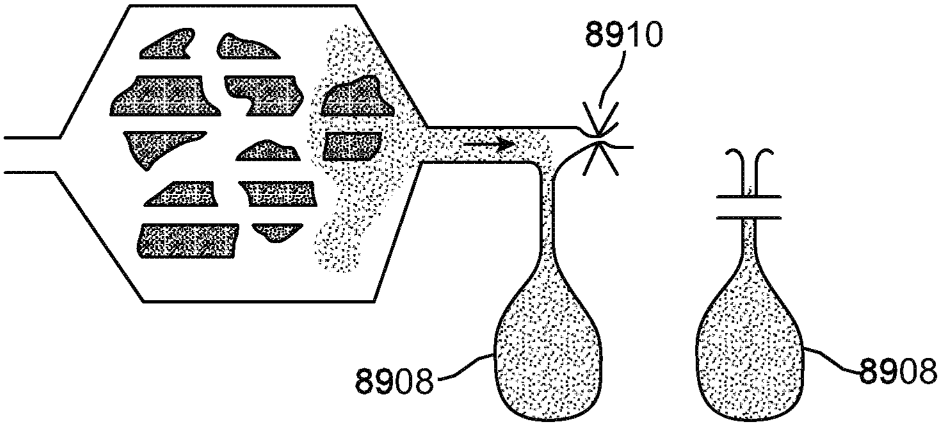

FIGS. 89A-C are diagrams illustrating a cell culture process with selective cell extraction and analysis in accordance with various implementations. FIG. 89A illustrates a perfused cell culture chamber 8902 in which a cell culture 8904 is growing. For example, the cell culture 8904 may be an adherent cell culture in a continuous perfusion 2D reactor and may be approaching maximum specified cell confluency. The cell culture 8904 may be imaged periodically to assess confluency, and optionally to locate cells/colonies for treatment. The number of cells may be periodically reduced via a non-invasive cell editing method (for example, using the laser, ultrasonic or magnetic tool techniques described herein) to prevent overgrowth of cells. This may be useful for certain cell culture processes, for example during clearing of episomal or viral vectors from cells, in which each cell division reduces the load of vectors in the cell population.

In FIG. 89B, a subset of the cells 8906 in the cell culture may be targeted for lysis. The selected subset of cells 8906 is shown as dark bands as shown in FIG. 89B. The cells may be selected in a pre-set pattern as shown in FIG. 89B, or may be based on the configuration of cells in the cell culture 8904. For example, cells may be selected from regions of the cell culture 8904 that are most dense, or regions that are approaching the bounds of the cell culture chamber 8902 (where conditions are more variable), or some combination of these or other factors.

The selected subset of cells 8906 may be lysed, as shown in FIG. 89C, and the lysed cells are suspended in the fluid media in the cell culture chamber 8902. The fluid media may be exchanged or flushed, and at least a portion of the spent fluid media containing the lysed cell debris may be collected by a sampling bag 8908 or some other collection mechanism. In the case of collection via the sampling bag 8908, a pinch valve 8910 in the primary fluid path may be closed to direct the fluid media into the sampling bag 8908. The sampling bag 8908 may be subsequently detached with a sterile tube welder, which enables sterile detachment of the sample bag 8908 from the cell culture system. The contents of the sampling bag 8908 may then be sent to analysis. In alternate implementations, an analysis system may be directly connected to the cell culture system to allow online measurements of the resulting cellular matter without detachment of a sample bag or container. Such an online system may perform further fractionization/homogenization of the cell debris, filtration, preparation steps and then analysis of the cell contents.

Using the example of iPSC reprogramming in which a reprogramming vector is cleared over time, the measurement enabled by the system may include, for example, a qPCR measurement of the contents of the sampling bag 8908 to measure RNA expression levels of: (1) one or more housekeeping genes (e.g., GAPDH) in order to normalize for the cell count; (2) one or more components of the reprogramming vector, for example OCT4 if the episomal reprogramming vector contained it, in order to monitor clearance of the vector; and (3) one or more non-vector gene expressions to measure pluripotency markers of the cells, for example SSEA4 if not included in the vector. The vector-specific measurement could assess progress in clearing the vector from the cells (a necessary condition for completion of the process). The endogenous gene expression is used to verify that the cell culture remains highly pluripotent and is not differentiating. Optionally, regions that are potentially differentiating may be selectively harvested in a separated iteration from regions that are thought to be pluripotent, and this may be confirmed by analysis of the cell lysis product.

Figure 90:
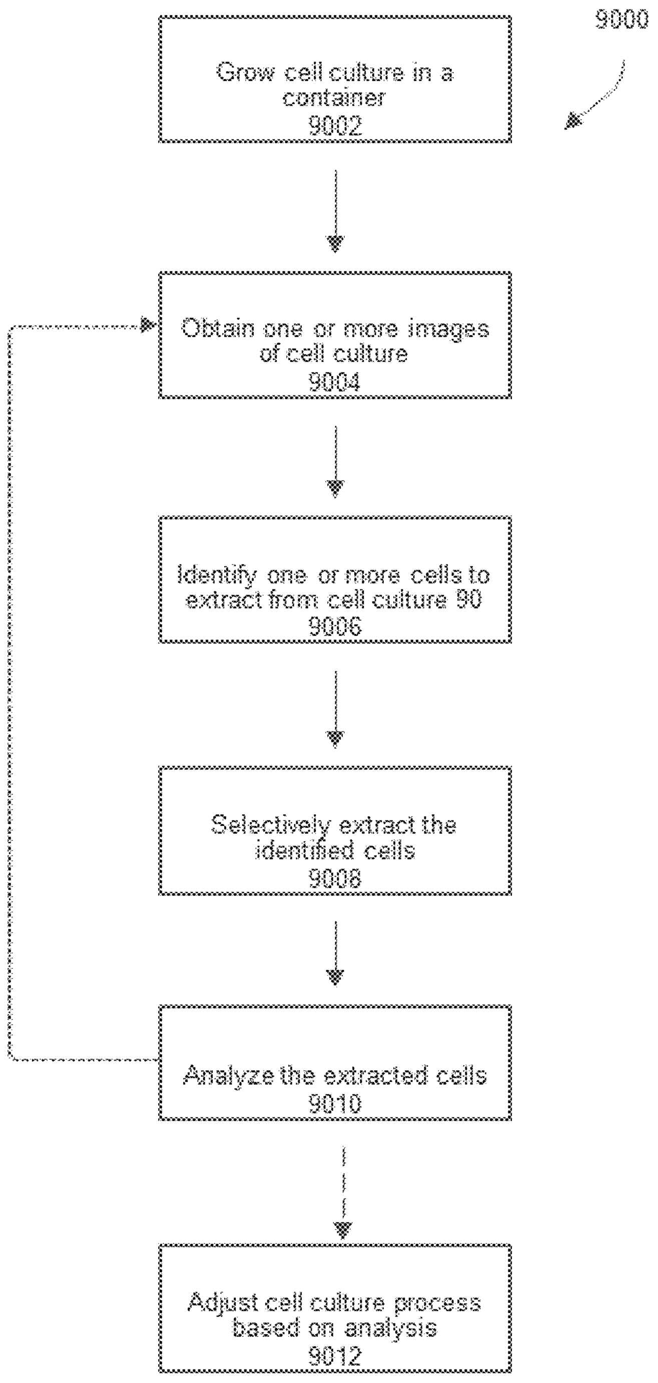
FIG. 90 is a flow chart illustrating a method of cell extraction and analysis in accordance with various implementations.

FIG. 90 is a flow chart illustrating a method 9000 of cell extraction and analysis in accordance with various implementations. The method 9000 may be performed by a cell culture system (e.g., cell culture system 100 in FIG. 1). In some implementations, the method 9000 may be performed by a mix of an automated cell culture system and manual effort by humans.

In block 9002, a cell culture may be grown in a cell culture container (e.g., cell culture container 106). The cell culture may be adherent or semi-adherent cells adhered to a cell growth surface of the cell culture chamber in the cell culture container. The cell growth surface may be transparent to enable imaging of the cell culture. The cell culture container may be a closed system, such as a closed cassette.

In block 9004, the cell culture system may obtain one or more images of the cell culture. For example, the cell culture system may include a cell imaging subsystem (e.g., cell imaging subsystem 112) that is configured to take one or more images of the cell cultures. In some implementations, the images may be a time-series of images of the cell culture.

In block 9006, the cell culture system may identify one or more cells to extract from the cell culture. For example, a computing subsystem (e.g., computing subsystem 110) may identify and select one or more cells to extract based on the collected images. The computing subsystem may utilize one or more characteristics derived from the cell images to determine which cells to extract. The characteristics may include direct measurements or observations from the images as well as the output of various machine learning models or other algorithms that process the image. For example, the computing subsystem may classify the regions of cells using an unsupervised clustering model which classifies cell regions by texture, morphological characteristics, and time series characteristics (e.g., changes of properties over time, optical flow measurements). Similarly, the computing subsystem may identify individual colonies and group cells by colony membership. The computing subsystem may then select one or more cells from each cell region or colony so that cells having different characteristics may be extracted and sampled. In some implementations, the identification of cells may be done manually by a person rather than by the cell culture system.

In block 9008, the cell culture system may selectively extract the identified cells. For example, a cell editing subsystem (e.g., cell editing subsystem 114) may be used to lyse or otherwise dislodge the identified cells from the cell growth surface of the cell culture chamber. The cell editing subsystem may utilize, for example, lasers, ultrasound, or magnetic tools among other approaches, to dislodge the identified cells without destroying them. Before extraction, the fluid media in the cell culture chamber may be changed to a specialized, fluid that accelerates cell dissociation upon lysis. The dislodged cells may then be extracted from the cell culture chamber using a fluid media exchange/flush, automated pipetting system, or other means.

In block 9010, the cell culture system may analyze the extracted cells. For example, qPCR assays and other tests/assays/measurements may be conducted to determine various properties and characteristics of the extracted cells. The cell culture system may periodically repeat the steps shown in blocks 9004-9010 to extract and sample cells at different points in the cell culture process.

In block 9012, the cell culture system may adjust the cell culture process based on the analysis of the extracted cells. For example, the cell culture system may determine that a sampled cell from a particular cell colony is outside the preferred cell growth parameters and thus the cell colony should be destroyed. In another example, the cell culture system may determine that a sampled cell from a particular cell colony may need additional nutrients and may initiate a fluid media exchange to freshen the media in the cell culture chamber. In general, the cell culture system may change a number of environmental or growth parameters, destroy certain cells, or take other actions based on the results of the analysis. The cell culture system may also incorporate the data into a machine learning model to improve future cell culture processes. In this manner, the method 9000 provides a way for selective extraction and analysis as to benefit the operation of a cell culture system and to provide dynamic cell growth feedback.

Wavelength-Selective Films for Cell Culture Imaging and Control

With the industrialization of cell-based processes such as bioprocessing and cell therapies, the need for tools to manipulate cells within a cell culture has grown rapidly. High variability in cell culture processes has driven the need for tools that can be responsive to real-time cell culture conditions, not only at the vessel level but also at the local level. Information about cell culture conditions may be useful for making various cell culture process decisions, such as the addition of media, reagents, buffers, or other compounds to the cell culture as a whole, or decisions to terminate a cell culture, either positively for harvest or negatively for disposal.

One preferred method for monitoring cell cultures at a local level, whether it be a region, colony, local cluster of cells, or at the single cell level is by imaging. The imaging may be conducted either by fluorescently-labeled imaging or using label-free imaging such as brightfield, phase contrast, darkfield or other transmission/scattering based techniques. These techniques, in particular the label-free techniques, require cell culture vessels and/or inserts into these vessels that by their construction enable high-fidelity imaging, meaning that they transmit light with high efficiency, and without imparting diffraction or other spatial artifacts that would interfere with the contained imaging cell cultures.

At the same time, a range of tools for active cell culture manipulation have been developed, intended to replace mostly open-loop cell culture control (in which only vessel-level changes are applied in bulk to the contained cells), or manual processes such as pipette scratching of cells, or manual transfer of cell colonies from one vessel to another. These tools include tools for selective cell removal, as well as tools for selective intracellular delivery of compounds to cells in a cell culture. A wide range of such tools used to manipulate cells are described in Stewart, Martin P. et. al., "Intracellular Delivery by Membrane Disruption: Mechanisms, Strategies, and Concepts," Chem. Rev. 118, 16, 7409-7531 (2018), which is hereby incorporated by reference in its entirety.

One known method for selective cell manipulation is using optical energy. For example, optical cell trapping may be used to individually move cells, and optoporation may be used to focus light on individual cell membranes to porate them for the purpose of compound delivery, cell content extraction, or cell destruction. However, cells are highly transmissive over a wide range of wavelengths from the ultraviolet (UV) to the near infrared (NIR), meaning extremely high power and energy densities are required to accomplish these operations. The devices that generate this optical energy may include lasers with very high pulse energies (and often associated low pulse rates) and/or focusing objectives with high numerical apertures (and therefore very limited fields of view), resulting in very low throughputs. This has made direct optical manipulation of cells suitable mostly for research only, and not for large-scale application in bioprocessing, gene or cell therapies, or high-throughput drug discovery or screening.

As a result, many efforts have been made to enhance optical energy absorption in the proximity of target cells within cell cultures. Some approaches include optoporation, UV killing (selective cell killing in a cell culture using UV lasers), photothermal and/or photochemical (photoacid), photomechanical, photomechanical or photothermal with gold nanoparticles mixed into cells, photomechanical with gold pyramids, and photomechanical with a metal film. However, each of these approaches comes with drawbacks that make them ineffective for incorporating into an efficient, automated, closed cell culture system. For example, optoporation requires large power and time requirements and is not scalable; UV killing is likely to genetically alter or damage cells. Photothermal and/or photochemical (photoacid) approaches may result in chemical leaching from the film layer, high collateral damage, and slow cell death. Photomechanical approaches may cause cell death and have very high energy and area requirements. Photomechanical or photothermal approaches with gold nanoparticles mixed into the cells may cause variable effects across the cell culture, may alter cell health/behavior and introduce contaminants, and may necessitate repeated dosing of nanoparticles because cells may grow away from the nanoparticles. Photomechanical approaches with gold pyramids hinder imaging and may alter cell culture growth and differentiation. Photomechanical approaches with continuous metal films introduces significant optical loss and as a result amplifies any film defects in the cell culture images. Therefore, none of these approaches satisfy the requirements for a satisfactory imaging-compatible, high-throughput optical energy transfer system that does not leave exogenous compounds or particles in the resulting cell culture. Thus, there is a need for supporting components that make cell imaging and editing efficient and effective without comprising the underlying cell culture.

A supporting component for cell imaging and editing in cell culture systems should ideally have several attributes and capabilities for efficient, automated cell culture imaging and editing. For example, a cell culture system should be capable of delivering localized optical energy to a cell culture for the purpose of imparting energy to cells (for example, by causing rapid heating of cell media to form explosive microbubbles and cavitation, or causing highly localized heating of cells) for the purpose of destroying specific cells, or for intracellular delivery or extraction of compounds into/from cells. The cell culture system should have a high efficiency of conversion from optical energy to local thermal and/or mechanical energy, such that a significant amount of energy is transferred within a small volume. This allows the use of lower-energy optical sources and/or allows very high throughput (e.g., area and number of cells processed per unit time).

The supporting component should also be capable of imparting optical energy without the addition or leaching/escape of exogenous compounds or particles into the cell culture, which may alter the behavior of the cell culture, be deleterious to the health of the cells, or leave residual compounds in cells to be used in downstream applications.

In addition, the supporting component should use materials that are known to be biocompatible and non-toxic, and have a surface that in its base configuration is free of mechanical features that could perturb cell growth or differentiation.

The supporting component should also achieve energy absorption and conversion using an absorbing layer that, while meeting the criteria above, allows high-fidelity imaging of the cell culture through this supporting component, meaning that it imparts low optical extinction (absorption and/or scattering) at desired imaging wavelengths and does not result in image artifacts at the desired imaging resolution. The supporting component should also be configured to enable energy absorption in cell culture chambers ("consumables") that are constructed with materials typically used for cell culture and/or high-throughput cell screening or high-content cell imaging, such as polymers or glass.

The systems and methods disclosed herein include a supporting component as described above embodied as a unique optically-resonant film that is permanently attached to a cell culture chamber, or component within a cell culture chamber. The resonant optical film may be designed and configured to simultaneously achieve high-efficiency coupling of optical energy into the local cell environment at wavelengths that are not directly harmful to cells, and allow high-fidelity transmission and fluorescence imaging of the contained cell cultures, while obviating the need for addition of exogenous dyes, particles, or other constructs to the cell culture to achieve energy delivery.

The resonant optical film may be located on one surface of the cell culture chamber or may be on the surface of an insert that is placed into the cell culture chamber. The resonant optical film may be configured to preferentially absorb light at one wavelength range (absorption range) while maintaining high transmission at another wavelength range (imaging range) using a resonant optical film design that is resonant at the laser absorption range.

In some implementations, the resonant optical film may absorb more than 5%, 10%, 15%, 20%, or 30% of light at a cell processing optical wavelength, while absorbing less than 5%, 10%, 15% or 20% of light at a cell imaging optical wavelength. In some implementations, the resonant optical film may not have inherent features with median dimensions larger than 10%, 20%, or 50% of the cell imaging optical wavelength, with the exception of fiducial markings imparted on it. In some implementations, the resonant optical film may be located on a wall of a cell culture chamber, or may be situated on a foil in the cell culture chamber. In some implementations, the foil may be a membrane with pores.

In some implementations, the resonant optical film may be configured to have a resonant absorption at 532 nm and/or 1064 nm. In some implementations, the resonant optical film may be configured to withstand laser pulses of less than 25 ns of 0.05, 0.1, 0.2, or 0.4 J/cm^2 energy with less than a certain percentage of change in optical transmission at the cell imaging wavelength. In some implementations, the resonant optical film may include gold nano-islands with mean diameter less than 20, 30, 40, or 50 nm as measured along at least one axis. The nano-islands may be permanently attached to an optically transparent material, which may include glass, cyclic olefin copolymer, polystyrene, polycarbonate, polyethylene terephthalate or other materials suitable for cell culture.

Figure 91:
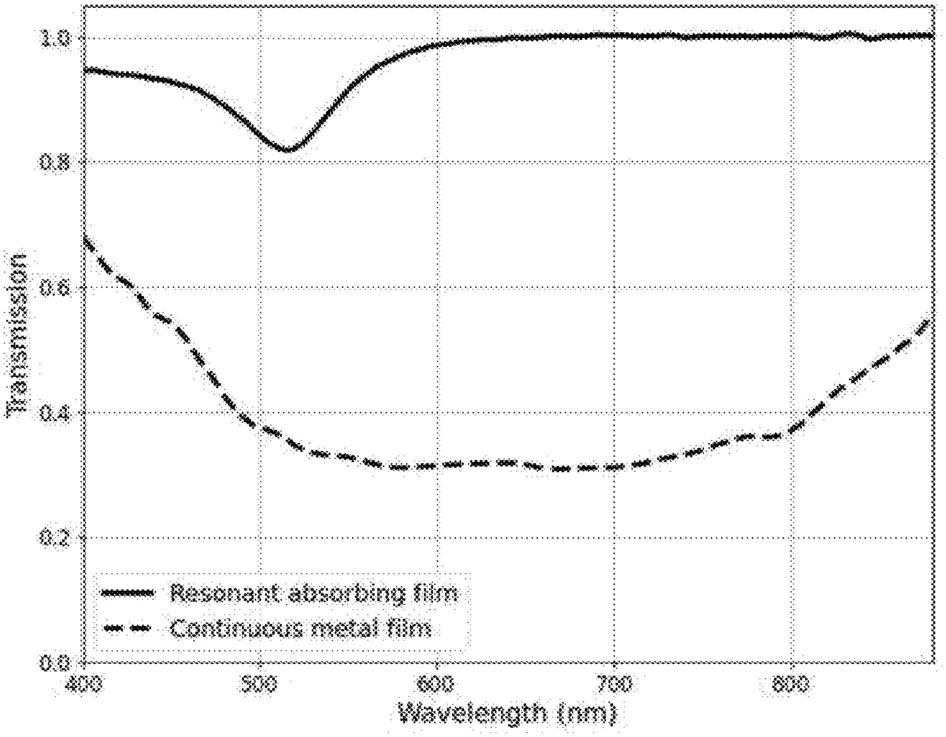
FIG. 91 is a graph illustrating the absorption/transmission behavior at different wavelengths of a resonant optical firm in accordance with various implementations.

FIG. 91 is a graph 9100 illustrating the absorption/transmission behavior at different wavelengths of a resonant optical firm in accordance with various implementations. The graph 9100 shows data from two different laser-absorbing semi-transparent films developed for the purpose of transferring laser energy to a cell culture for both cell imaging and cell editing purposes. The dashed line shows the optical transmission of an optical film on a cell culture chamber, namely a previously disclosed 20 nm Titanium film. This film provided some transmission across the entire VIS/NIR band, allowing imaging of a live cell culture. However, the optical transmission of the film was only 30-35%, resulting in low transmission efficiency, therefore requiring longer exposure times and/or more intense illumination. For epifluorescent imaging, there were 65-70% losses on both the excitation and emission paths to and from the sample, meaning a compound efficiency of only 9-12%, again requiring long exposure times and/or more intense illumination. The titanium optical film absorbed 532 nm nanosecond pulsed laser light and transferred energy to targeted cells via explosive bubble formation and collapse. A fluence of approximately 250 $mJ/cm^2$ was required to lyse and remove cells.

The solid line in the graph 9100 shows a transmission spectrum of a resonant optical film on the cell culture chamber surface in accordance with various implementations. In this instance, the resonant optical film is a 4 nm layer of gold on a 170 micron thick borosilicate coverslip sufficiently large to form the cell culture surface of a 96-well SBS microwell plate, and then annealed in order to consolidate the material into small islands that exhibit plasmonic resonance at roughly 520-540 nm. The resulting extinction can be seen by the dip at this wavelength, at which the film absorbs light from a 532 nm pulsed laser. The resonant optical film achieves cell lysis at similar laser fluences (~250 mJ/cm^2) as the titanium film. However, the transmission through the resonant optical film, and therefore the imaging efficiency, are superior, with virtually 100% transmission at wavelengths longer than 625 nm, meaning over 3 times as much light transmission for transmission-type imaging, and a roughly 10× improvement in round-trip efficiency for epifluorescent imaging. This efficient transmission is beneficial for long-term imaging of cell cultures, as the lower illumination power or shorter illumination/exposure times that are enabled reduce exposure of cells to light and minimize any effects on cell metabolism or health. In addition, the low reflectivity of the coating (near zero at imaging wavelengths) prevents a double-pass of light through the cell culture, further reducing any of these effects. This near-full transparency at imaging wavelengths also means that alterations to the optical film do not cause changes in the images observed, assuming a band-limited light source (or image sensor) is used to capture a transmission image of the sample.

Figure 92:
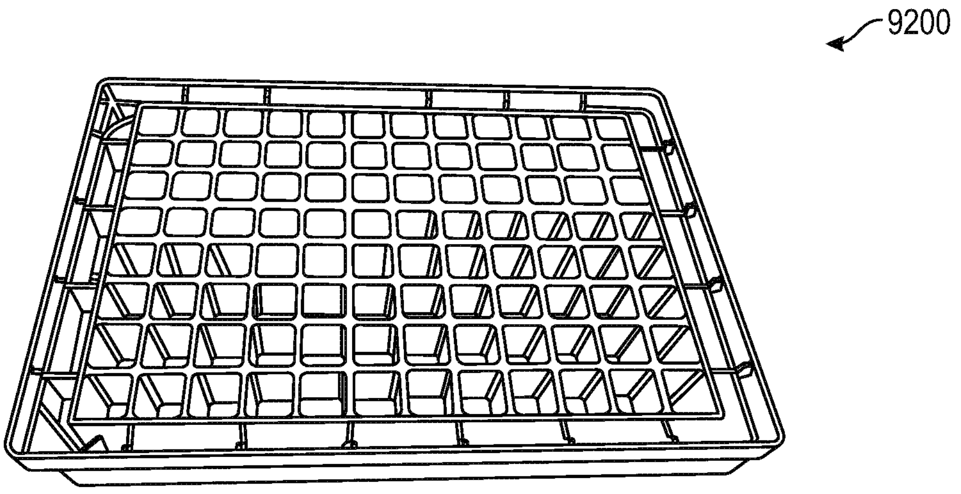
FIG. 92 is an image of a microwell plate with a resonant optical film on the cell-bearing surface in accordance with various implementations.

FIG. 92 is an image of a microwell plate 9200 with a resonant optical film on the cell-bearing surface in accordance with various implementations. The microwell plate 9200 depicted in FIG. 92 is a 96-well SBS-standard format microwell plate fitted with a resonant optical absorbing film on the cell-facing surface. As may be seen in the bottom left wells, the coverslip and film are highly transmissive over most wavelengths, allowing high-quality imaging. The film may have a pink-ish hue due to the enhanced absorption in the green wavelength range.

The microwell plate 9200 is an example implementation of a cell culture chamber, but in general many cell culture chambers known in the art may be used. For example, microwell plate 9200 is not limited to 96 wells, but may include single-well plates to 6, 12, 24, 96, 384, 1536 and other numbers of wells on the microwell plate, as well as well plates with microwells within each well for the purpose of isolating cells or cell clusters. In addition, the cell culture chamber may include well plate inserts such as transwell membranes constructed with a permeable polymer membrane and coated with the resonant optical firm to allow cells to be cultured on a permeable membrane between two layers of media (often with different contents), and to be manipulated using optical radiation that is absorbed by the resonant optical film for the purpose of lysis or compound delivery.

In alternate implementations, the cell culture chamber may include petri dishes, flasks, or other large cell culture chambers with resonant absorbing films to allow for larger-format cell cultures. In such cases, the coating may be applied directly to the chamber wall(s), or it may be inserted into the cell culture chamber using a coating-bearing sheet made of thin glass or polymer that is attached to a chamber wall. Alternate implementations of cell culture chambers may also encompass closed fluidic chambers in which media flows through the chamber, such as microfluidic or macro-scale fluidic flow chambers that allow automated media perfusion of cell cultures.

Figure 93A:
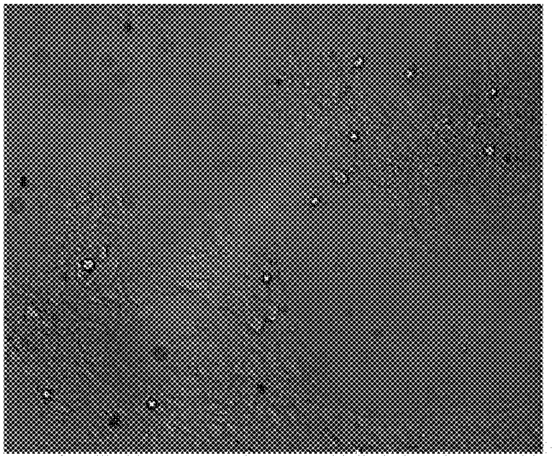
FIGS. 93A-93C are images of cells undergoing cell editing and washing in a cell culture chamber having a resonant optical film in accordance with various implementations.
Figure 93B:
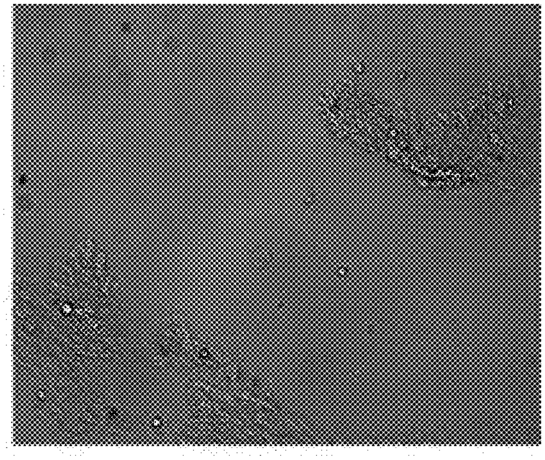
Figure 93C:
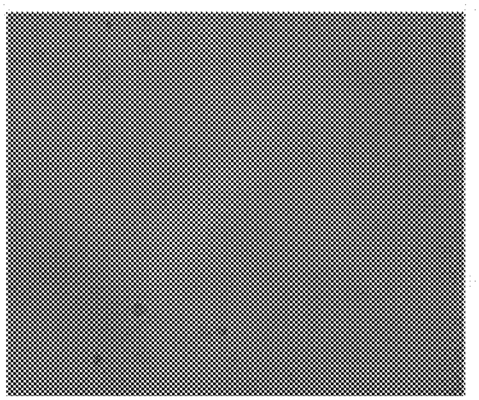

FIGS. 93A-C are images of cells undergoing cell editing and washing in a cell culture chamber having a resonant optical film in accordance with various implementations. FIG. 93A shows human induced pluripotent stem cells (hiPSCs) grown in a region of a cell culture chamber, with a laser-absorbing resonant optical film on the cell culture chamber surface. Imaging, performed with a 10× objective, shows a high level of detail in the cell culture. FIG. 93B shows the same region of cells immediately following pulsed laser illumination with ~40 nJ pulses, 15 nsec pulse width at 532 nm, in which pulses were applied in a grid of 4×4 microns over the field of view. Cell lysis is evident from detachment of some cells, and extensive blebbing observable along the periphery of the cell clusters. FIG. 93C shows the same area following washing of cell debris from the cell culture chamber. Cells within the field of view have been removed completely, without marking evident on the resonant optical film. Some cells at the edges of the scanned area are visible, where they remain attached to intact regions outside of the scanned area. Despite spots from out-of-focus dust, the surface displays a feature-free quality that is important for highly-repeatable imaging of cell cultures, especially when these images are used for image processing routines and ultimately for automated management of the cell culture in a cell culture system (e.g., cell culture system 100). The resonant optical film is compatible with a pulsed laser system as the cell editing subsystem. In addition to the use of pulsed laser systems to produce microbubbles for cell lysis or intracellular delivery, continuous-wave sources (whether lasers or other sources) may be used to impart thermal energy selectively to a cell culture using the resonant optical film.

Figure 94:
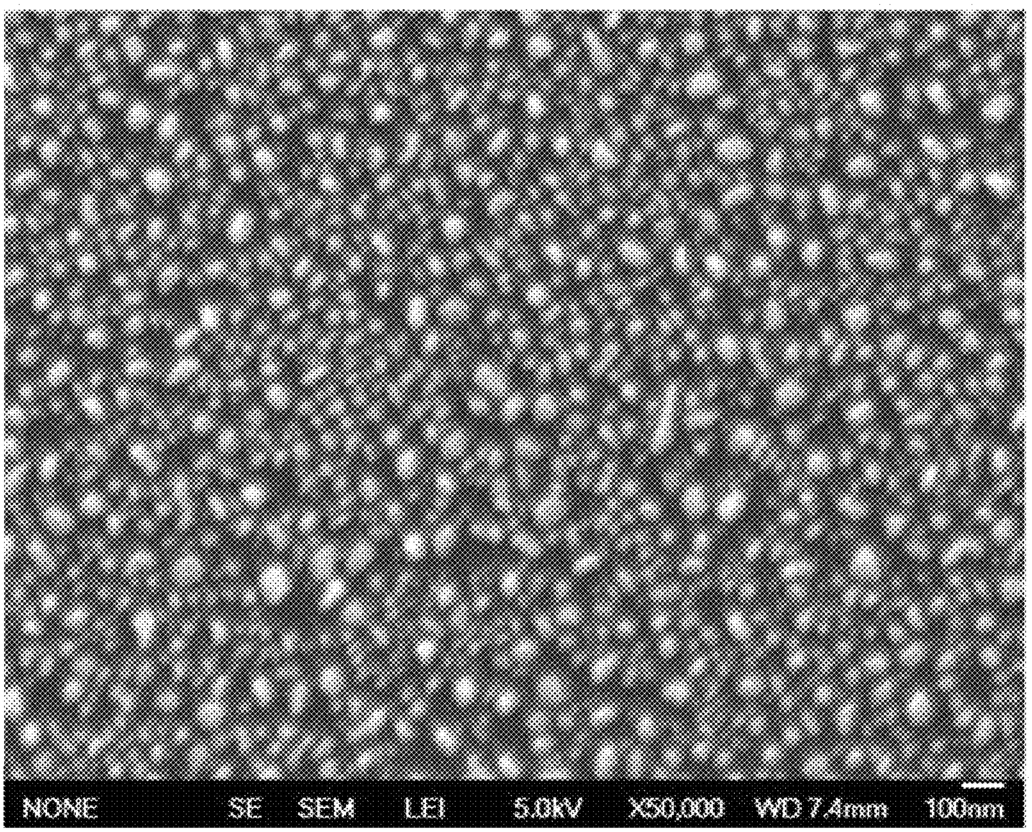
FIG. 94 is an image of a resonant optical film surface in accordance with various implementations.

FIG. 94 is an image of a resonant optical film surface 9400 in accordance with various implementations, taken by a scanning electron microscope (SEM). The resonant optical film surface 9400 was fabricated using gold deposition and subsequent film annealing at approximately 500° C. to form islands that exhibit plasmonic resonance at around 520-540 nm. As can be seen from the image, the maximum feature size is around 100 nm, with the median feature size closer to 25 nm. As a result, the film has very low scattering or absorption at the desired imaging wavelengths (roughly ≥600 nm) and with no visible features at 10× magnification.

The resonant optical film described herein may be fabricated using several approaches. The first is using thin semiconductor films. Thin semiconductor films may work near the edge of the bandgap, where film thickness is tuned such that one optical resonance is at the laser wavelength (where the material absorption is relatively high) and at least one other optical resonance point at a wavelength where the inherent absorption is lower (the point at which imaging will be performed). For example, multiple forms of silicon have absorption coefficients that drop rapidly over the visible wavelength range. Deposition of thin layers of silicon onto a substrate material such as glass or plastic therefore results in a transmission spectrum with peaks and valleys in the visible and NIR wavelength range where there are optical resonances. These resonances may then be used to preferentially absorb optical radiation for manipulation of cells (at shorter wavelengths) and transmit optical radiation for imaging cells (at longer wavelengths).

An example of such a resonant film may be found in Zhou, Jaiping et al., "Si surface passivation by SiOx: H films deposited by a low-frequency ICP for solar cell applications," Journal of Physics D Applied Physics 45(30):395401 (2012), which is hereby incorporated by reference in its entirety. The Zhou reference discloses a transmission spectrum of a hydrogenated amorphous silicon layer with transmission maxima at ~520 nm and ~600 nm. The optical film disclosed in Zhou may be modified for use in the present implementations, for example by using a slightly thicker layer to achieve a resonance at the 532 nm frequency-doubled Er: YAG laser line, and another resonance at just over 600 nm, where high power density LED illuminators are readily available for transmission imaging.

Figure 95:
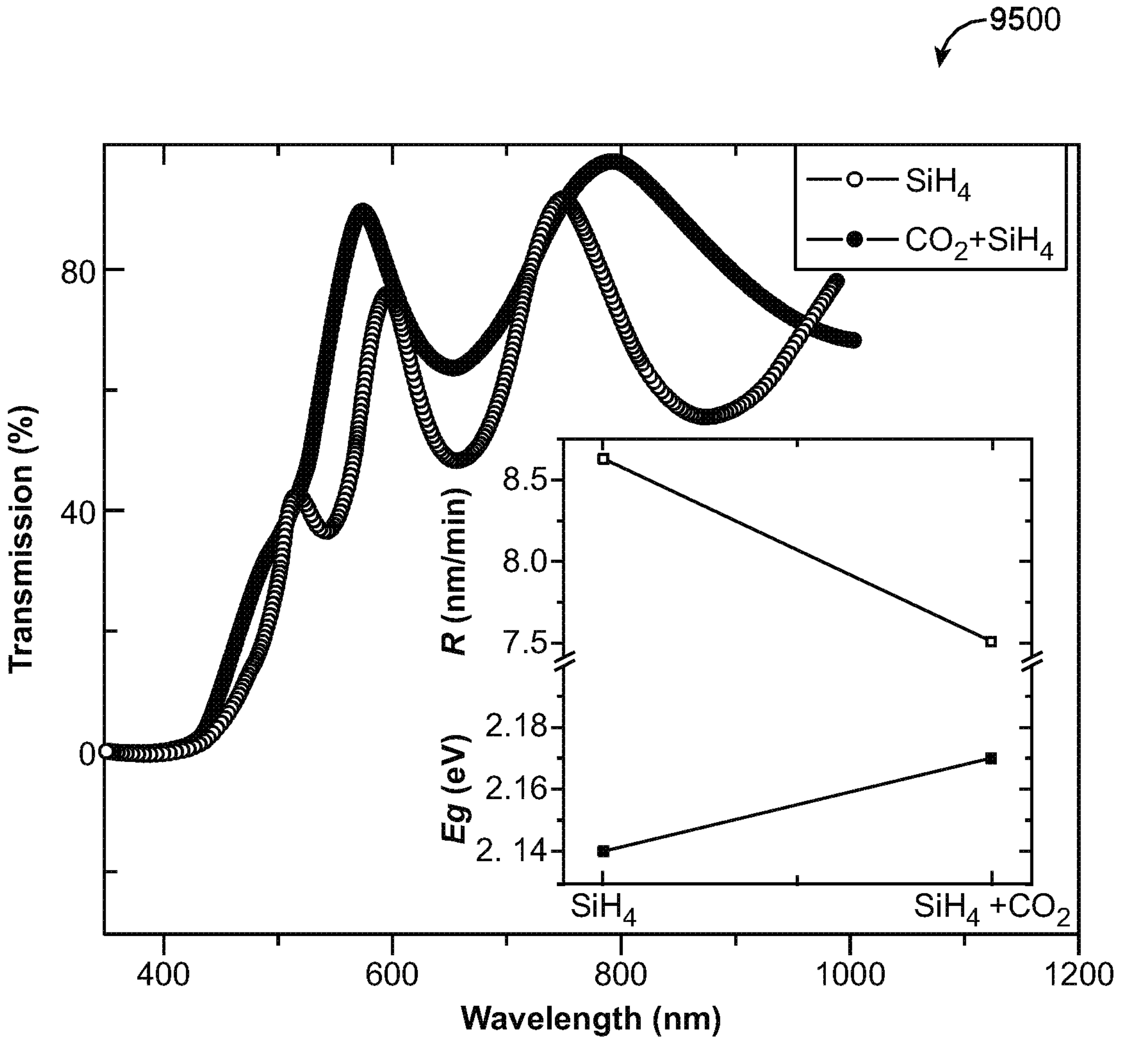
FIG. 95 is a graph showing the transmission spectrum of an optical film which has resonances at specific wavelengths.

FIG. 95 is a graph 9500 showing the transmission spectrum of the film disclosed in the Zhou reference, which has resonances at specific wavelengths and progressively higher absorption at short wavelengths. Such a resonant, partially-absorbing layer may be deposited directly on a coverslip material (borosilicate glass or polymer). It may then be capped with a dielectric layer such as silicon dioxide or silicon nitride to form a consistent index difference interface at high contrasts (to enhance reflection) and prevent deterioration or modification of the semiconductor layer by cell media components. In an example implementation, a layer of amorphous silicon is deposited by plasma-enhanced chemical vapor deposition (PECVD) onto an optical-grade sheet of cyclic olefin copolymer (COC) to form a layer of approximately 400 nm. This layer is then recrystallized using a Xenon flash lamp to convert the amorphous Silicon into microcrystalline silicon, which exhibits a lower optical absorption at over 500 nm and has a higher thermal conductivity. The deposition layer thickness is tuned such that it results in a half-wave multiple of 532 nm (the laser wavelength) after annealing. Finally, the silicon layer is capped with a thin (10-20 nm) layer of silicon dioxide to protect the silicon and provide a biocompatible surface. The resultant resonant optical film will have a resonance at 532 nm where the material has sufficient absorbance to capture laser light and transmit this energy in the form of heat to the cell media above it. Additionally, it has other resonant transmission peaks where the transmission is 75% or higher at longer wavelengths, for example 620-650 nm, which is suitable for transmission microscopy of cell cultures.

Another approach for fabricating optical films as disclosed herein may include plasmonic resonant absorbing films. One class of these films useful in the present implementations is patterned conductive structures on a transparent substrate (coverslip or insert into a cell culture chamber). Metal structures with appropriate (usually high) conductivity, dimensions, and spacing can have plasmonic resonances that may couple with specific wavelengths. Films that are useful in the present implementations should (a) have high uniformity and consistency in the distribution of absorption; (b) have no residual particles or materials in cell culture products; and (c) prevent aggregation of materials such as nanoparticles that could become visible in cell culture imaging. Films with resonant structures that are inherently and uniformly attached to a surface in the cell culture chamber may satisfy these qualities. For example, gold nanostructures with dimensions on the order of tens of nanometers have resonances in the visible spectrum from roughly 520 nm upwards, and can be used to absorb laser wavelengths while transmitting wavelengths for imaging.

Patterned films for use in the present implementations may be formed in a number of ways. One set of fabrication techniques include pre-defined patterning. One example of pre-defined patterning is photolithographic patterning, in which a lift-off process is used in which photoresist is applied onto the substrate, exposed using a photomask, developed, and removed from selected areas. Metal such as gold is then deposited onto the substrate (where exposed) or photoresist using deposition techniques including, but not limited to, evaporation or sputtering. The remaining photoresist is then removed from the substrate, along with any gold that was deposited on top of it. A variation of photolithographic patterning is optical interference based photolithography, in which instead of a mask being used to expose photoresist, an interference pattern is used to produce a periodic pattern.

Another example of pre-defined patterning is nano-imprinting, in which a template is used to pattern photoresist on the substrate, and then the photoresist is processed as in the photolithography approach. A representative technique for such patterning is given in Lopatynskyi, Andrii M. et al., "Au nanostructure arrays for plasmonic applications: annealed island films versus nanoimprint lithography," Nanoscale Research Letters 10:99 (2015), which is hereby incorporated by reference in its entirety. Further examples of pre-defined patterning include: e-beam lithography, in which the plasmonic features are patterned by electron beam writing in photoresist (described in Chen, Yifeng, "Nanofabrication by electron beam lithography and its applications: A review," Microelectronic Engineering Vol. 135, pp. 57-72 (2015)); ion beam lithography (described in Wat, F., et al., "Ion Beam Lithography and Nanofabrication: A Review, Int. J. Nanoscience, Vol. 4, No. 3, pp. 269-286 (2005)); colloidal mask deposition, in which self-organizing particles such as microspheres are layered onto the substrate and temporarily attached (for example, spheres that form a hex-packed layer on the substrate surface), and metal is then deposited onto the substrate only where there are gaps in these spheres (described in Sanchez-Esquivel, Hector et al., "Spectral dependence of Nonlinear Absorption in Ordered Silver Metallic Nanoprism Arrays," Scientific Reports 7(1) (2017)); and self-assembled polymers or other layers (described in Segalman, Rachel A., "Patterning with block copolymer thin films," Materials Science and Engineering R 38, 191-226 (2005)), which may be used to pattern metallic films into plasmonic resonant structures either by applying such a structure to the substrate, depositing metal, and then removing the structure (acting as a mask for deposition, or "lift-off" mask) to yield metal structures, or by applying such a structure to a substrate with an existing metal film, using the structure as a mask for etching the metal film, and then removing the structure to yield a structured metal film. Each reference listed above are incorporated by reference in their entirety.

Another set of fabrication techniques for patterned films include self-forming patterned metal films. In this technique, a film of metal is first deposited on the substrate (for example, a layer of gold onto a borosilicate glass), and then annealed to form semi-random islands based on surface energy alone. While the islands are random, the distribution of island sizes and spacing is controllable and repeatable, and as a result the optical properties of the films are consistent from spot to spot and from sample to sample. Metal is deposited by mechanisms including but not limited to evaporation, e-beam evaporation, and sputtering, and then annealed to form islands by one or more methods. The annealing methods may include oven annealing (in which the substrate and film are placed in an oven, for example a nominal 3 nm gold film annealed for 8 hours at 500° C., in a nitrogen environment) and optical annealing (in which the substrate and as-deposited film are exposed to intense light, for example laser light or intense flash lamps, in order to heat the film and cause it to form plasmonic islands). For example, using optical annealing a 532 nm laser may be used to anneal the film with repeated pulses. Such optical annealing may be done in a gas environment, or in a liquid environment for the purpose of dissipating heat and removing any particulates that form, and generally reflect the ultimate operating environment of the plasmonic film during this pre-treatment. In alternate implementations, the islands may be created via direct deposition of metal onto a substrate under appropriate conditions, for example sputtering gold onto a borosilicate glass at elevated temperature. This may allow the film to re-form into islands as it is deposited, which may directly yield a plasmonic resonant film. An example is described in Tvarozek, V. et al., "Plasmonic behaviour of sputtered Au nanoisland arrays," Applied Surface Science Vol. 395, pp. 241-247 (2017), which is hereby incorporated by reference in its entirety. In some implementations, high-conductivity metals such as gold, which form the plasmonic structures, may be co-deposited with other materials such as titanium to promote adhesion to the substrate material.

Another set of fabrication techniques for patterned films include deposition of metallic nanoparticles and then permanent attachment to an optically clear substrate. In this approach, pre-formed nanoparticles in a liquid are applied and attached to the substrate material, for example as described in Ahmed, Syed Rahin et al., "In situ self-assembly of gold nanoparticles on hydrophilic and hydrophobic substrates for influenza virus-sensing platform," Scientific Reports 7, 44495 (2017), which is hereby incorporated by reference in its entirety. For cell manipulation applications (as opposed to sensing applications such as the one described in Ahmed), the resonant optical film is configured to absorb a significant amount of energy, and may need to operate over a period of days or weeks without detachment of constituent materials. For that reason, both chemical and thermal methods may be used to create a strong attachment between the nanoparticles and surface. For example, the deposition of metallic nanoparticles and permanent attachment may be followed by a thermal annealing process in which the nanoparticles re-shape and increase contact area with an underlying glass or polymer substrate.

It should be understood that the disclosed implementations of resonant optical films and methods of constructing them is not exhaustive, and that the present implementations are not dependent on a specific implementation. Rather, in general the present implementations utilize a combination of resonant optical films within a cell culture chamber that achieves the goal of efficient cell culture imaging and editing within a cell culture system, particularly one that is automated. The properties of the resonant optical film should be conductive to accurate and easy imaging.

Surface Enhanced Raman Spectroscopy of Cell Cultures

Chemometric monitoring of bioprocessing systems, such as bioreactors, is a growing field because it allows for closed-loop monitoring and control of biological processes to increase yields. Label-free methods that can monitor media components, cells or cell components, or cell products, are particularly useful because they may be applied to bioprocessing systems non-invasively and without perturbing the cell culture.

Vibrational spectroscopy, and in particular Raman spectroscopy, have made inroads in bioprocessing and automated cell culture control because they are able to measure media constituents and cells/cell products without exogenous labels, and in situ without breaking system sterility (e.g., through a clear surface, or fiber optic probe). However, conventional Raman spectral signals are very weak due to the very low probability of inelastic scattering within a sample such as cell media. This can limit the constituents or concentrations that such systems can measure, and usually require high excitation laser powers, high-NA objectives and related corrections, very high sensitivity spectrometer systems, and/or long integration times and extensive baselining procedures.

The systems and methods disclosed herein include the use of surface-enhanced Raman Spectroscopy (SERS) in bioprocessing systems, for example in automated or semi-automated cell culture systems. The cell culture system may include a cell culture container enclosing cells undergoing a cell culture process. The cell culture system may also include an imaging subsystem for imaging cells in the cell culture container, a computing subsystem for analyzing cell images and other information to monitor the progress of the cell culture process, and a cell editing subsystem for manipulating and removing the cells in the cell culture container (e.g., using pulsed lasers).

The cell culture container may include a semi-transparent, resonant plasmonic film that allows imaging of the cell culture by the cell imaging subsystem at one or more select wavelengths. The cell editing subsystem may use a pulsed laser focused on the resonant film and at roughly the resonant absorption wavelength of the film to create transient microbubbles for the purpose of achieving mechanical effects on cells, including cell lysis or removal and cell membrane poration.

In the systems and methods disclosed herein, the film of the cell culture container may also be used to enhance Raman scattering signals, particularly SERS signals. Particularly, when the cell editing subsystem focuses an excitation laser onto the film, the film may scatter the light at wavelengths shifted from the laser wavelength. The magnitude of the scattered light at these shifted wavelengths is indicative of the chemical composition of the cell media, biofilm, cellular matrix, cell membrane or other substances in the immediate proximity of the film.

In some implementations, the cell editing subsystem may also be used to clean the film surface prior to or during SERS measurements using the film. For example, a laser may remove biofouling or other materials from the surface of the film prior to measuring the local media environment using SERS. In another example, SERS may be used to measure prior to and after laser clearing to get a measurement of biofilms accumulated on the film.

In some implementations, the cell editing subsystem may use pulsed lasers to create explosive microbubbles that locally mix media to ensure good sampling of media by subsequent SERS measurements. In some implementations, the cell editing subsystem may use the microbubbles formed by the lasers to lyse or temporarily porate cell membranes of nearby cells prior to SERS measurement to measure cell contents. This microbubble poration may be combined with the laser clearing operation, or the SERS measurement may be alternated with ramped pulsed laser energy to clear the film, measure a baseline, and then measure cell contents. In some implementations, the laser in the cell editing subsystem may have multiple uses, such as for biofouling clearing and Raman excitation.

In some implementations, the cell culture system may use SERS to monitor media components, including but not limited to nutrients, metabolic and waste products, and vitamins. In some implementations, the cell culture system may use SERS-derived cell media data together with cell culture imaging-derived data in a model that predicts cell culture state. In some implementations, the cell culture system may use SERS-derived data from cell regions in conjunction with transcription data in models to predict transcriptomes from SERS data.

The use of SERS in the systems and methods disclosed herein can address the issue of low signal levels with conventional spectroscopy. SERS uses an arrangement of conductive particles to enhance local field strengths when illuminated by the excitation source (typically a laser), and as a result can produce Raman scattering signals that are many orders of magnitude larger than conventional Raman. An overview of SERS techniques applied to biological systems is given in Kogler, Martin, et al., "Comparison of time-gated surface-enhanced Raman spectroscopy (TG-SERS) and classical SERS based monitoring of *Escherichia coli* cultivation samples," Biotechnology Progress 34(6): 1533-1542 (November 2018), which is hereby incorporated by reference in its entirety. As a result, SERS is used extensively for one-time measurements of samples that are placed onto a SERS substrate, and sometimes allowed to dry or settle onto the substrate.

However, when SERS is applied to time series monitoring of biological systems, the settling or attachment of material to the SERS surface can have both positive and negative effects on the desired measurements. For example, materials such as live cells, dead cells, debris, media components, cell excretions (such as extracellular matrices or other proteins), exosomes, and the like may accumulate on the SERS surface. If the SERS system is used to monitor media constituents (nutrients, waste products, vitamins, growth factors, proteins, etc.) this accumulation ("biofouling") on the SERS surface may dominate the spectral signal and obscure the desired measurement. Conversely, the accumulation of biological material on the SERS substrate may allow analysis via spectroscopy of this material, which may be indicative of the state of the biological system. For example, the excretion of proteins or exosomes by cells that accumulate on the surface may be measured. However, continued accumulation past a certain point reduces accurate time series analysis of secretions and therefore reduces the ability to monitor the status of the biological system over time.

Accordingly, there is a need in the art to clean biofouling from the SERS surface when SERS is used in biological systems so that media measurements remain accurate, and also a need to directly measure the accumulation of biological material on the surface over time, with a series of timepoints or intervals. Further, it would be desirable to couple such a SERS system with imaging systems so that the SERS surface and any cells growing on it, or debris residing on it, may be imaged.

An electrically-based system for performing such cleaning has been proposed, in which a conductive layer is used on conjunction with the SERS substrate. See Meier, T.-A., et al., "Fast electrically assisted regeneration of on-chip SERS substrates," Lab on a Chip 15, 2923 (2015), which is hereby incorporated by reference in its entirety. However, this electrical means require feed-throughs into the biological chamber, which may compromise integrity or sterility, and requires additional materials in the biological chamber, which may introduce cytotoxic effects. Finally, the required voltages are on the order of 100V for even a small chip, which makes the approach impractical for most applications, and the resulting electrical fields may cause other biological or biochemical side-effects (electrophoretic or cell electroporation included). Instead, it is desirable to achieve the aforementioned solution without the need for additional feedthroughs into the biological container, and without the need for additional materials.

Accordingly, implementations of the systems and methods disclosed herein provide mechanisms for removal and/or reduction of biofouling that enables accurate measurements over time without compromising cell culture sterility. In some implementations, the systems and methods disclosed herein include an editing subsystem that allows for measurement of the accumulation of biological material and/or cell culture media components.

Figure 96:
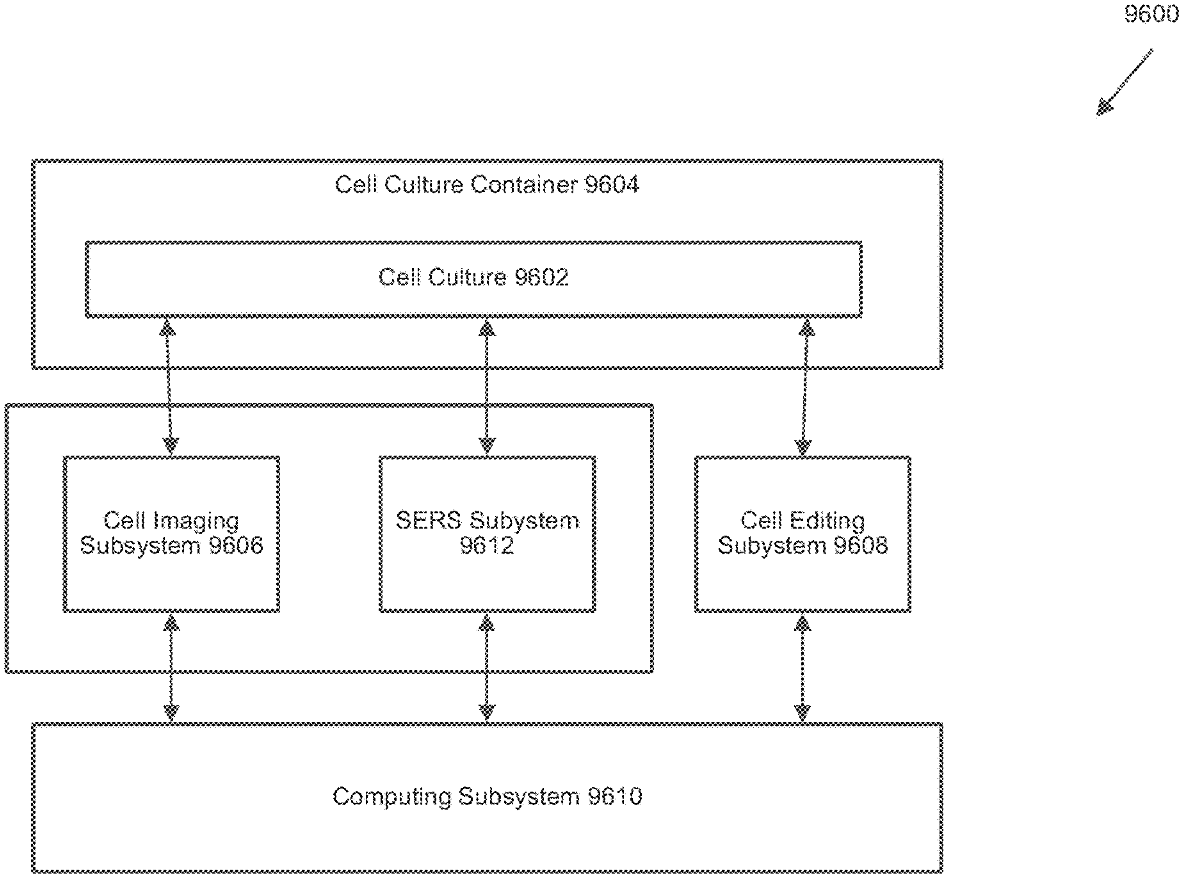
FIG. 96 is a block diagram of a cell culture system in accordance with various implementations.

The systems and methods disclosed herein contemplate the use of SERS in bioprocessing systems, for example in automated or semi-automated cell culture systems. FIG. 96 is a block diagram of a simplified cell culture system 9600 in accordance with various implementations. The cell culture system 9600 includes one or more cell culture containers 9604, each cell culture container 9604 supporting a cell culture 9602. The cell culture 9602 may start as source cells that undergo a cell culture process to produce an output cell product. The cell culture 9602 may be used for a number of cell culture processes performed and monitored by the cell culture system 9600, including but not limited to: cell reprogramming (into pluripotent or multipotent forms), cell differentiation, cell trans-differentiation, cell expansion, cell sorting, clonal isolation, cell gene editing, cell-based protein production, cell-based viral production, combinations thereof, or any other implementations known to persons of ordinary skill in the art.

The cell culture container 9604 may include one or more cell culture chambers to hold the cell cultures, and may take the form of microwell plates, flasks, stackable cell culture containers, closed cassette systems, microfluidic chambers, purpose-built bioreactor vessels, or any other implementations known to persons of ordinary skill in the art. The cell culture container 9604 may be in a format that allows for observation of the cell culture 9602 at regular intervals using an imaging subsystem 9606. For example, the cell culture container 9604 may include a closed cassette system having a transparent or semi-transparent surface that allows for light or laser-based imaging and editing. The cell culture container 9604 may include a semi-transparent, resonant plasmonic film that allows imaging of the cell culture by the cell imaging subsystem at one or more select wavelengths. This film may also be used to enable SERS measurements of the contents within the cell culture container.

The imaging subsystem 9606 may be configured to provide label-free imaging suitable for long-term cell culture observation, although some implementations may include fluorescent imaging capability for immunofluorescent or other labeled images. Label-free modalities employed by the imaging subsystem 9606 may include, but are not limited to, brightfield imaging, phase imaging, darkfield imaging, transmission imaging, reflection imaging, quantitative phase imaging, holographic imaging, two-photon imaging, autofluorescence imaging, Fourier ptychographic imaging, defocus imaging or any other implementations known to persons of ordinary skill in the art.

The cell culture system 9600 further includes a cell editing subsystem 9608 for editing the cell culture 9602. The cell editing subsystem 9608 may edit the cell culture 9602 at a regional, colony-specific, and/or cell-specific level. Editing, in this context, may include selective destruction and/or removal of cells or cell regions, and non-destructive operations on cells (including intracellular delivery of compounds into cells or extraction of compounds from cells). The mechanism by which the cell editing subsystem 9608 acts upon cells in the cell culture may include, but not be limited to, mechanical mechanisms, ultrasound mechanisms, electric field mechanisms, optical mechanisms, combinations thereof, or any other implementations known to persons of ordinary skill in the art.

Optical mechanisms for cell editing may include, but are not limited to, optical systems that deposit energy directly into cells or surrounding media in the cell culture, optical systems that deposit energy into particles or dyes that are added to the cell culture media (including but not limited to particles functionalized in a manner to attach to specific cells, or that are taken up by cells), or optical systems that deposit energy into particles or films that are on surfaces proximate to portions of the cell culture, or any other implementations known to persons of ordinary skill in the art. For example, one optical mechanism is a pulsed laser that can impart energy to the contents of the cell culture container 9604. Optical mechanisms may operate on the cell culture by a number of means including, but not limited to, elevating the local temperature to a point where cells are destroyed due to heat damage, elevating local temperature to cause boiling and/or bubble formation to cause portions of the cell culture to detach from a surface, or elevating local temperature rapidly in order to cause rapid bubble formation and then subsequent collapse to affect mechanical forces on the local cell membranes, or combinations thereof.

The computing subsystem 9610 of the cell culture system 9600 may be configured to control the other components of the cell culture system 9600 to perform the specified cell culture process on the cell culture 9602. The computing subsystem 9610 may be configured to gather data from a range of sources, organizes the data in a manner that allows it to make predictions of success/quality/functionality of the cell culture 9602, and in many cases do so on a cell-by-cell, colony-by-colony, or region-by-region basis. For example, the computing subsystem 9610 may be configured to predict which regions of cells are most likely to yield superior cell products, and which regions are less likely to yield good product. In another example, the computing subsystem 9610 may use cell data derived from imaging in conjunction with sensor data and assay data to pre-emptively adjust cell culture conditions. Similarly, the computing subsystem 9610 may use cell data obtained from imaging, potentially in conjunction with cell media sensor data, to determine when the cell culture 9604 is ready for harvest.

The computing subsystem 9610 may control the cell editing subsystem 9608 to make edits to the cell culture 9602 according to cell management algorithms (for example, to maintain a certain cell density, to maintain certain exclusion areas within the cell culture container), in a timed manner (for example, delivering gene-activating or gene-editing compounds to cells at a specific interval), and/or as a result of predictions made by the computing subsystem 9610 (for example, removal of cells predicted not to yield the desired phenotype or optimal level of function). "Editing" includes a variety of individual functions such as destruction of cells and/or colonies (including inducing apoptosis, lysing, physically removing) as well as selective delivery of compounds into cells and/or regions of cells via intracellular delivery mechanisms, or selective extraction of compounds from the cells via intracellular delivery mechanisms.

The cell culture system 9600 may also include a SERS subsystem 9612 configured to perform SERS measurements of the cell culture container 9604. Information derived from SERS measurements may be used to monitor media components in the cell culture container 9604, including but not limited to nutrients, metabolic and waste products, and vitamins. In some implementations, the cell culture system 9600 may use SERS-derived cell media data together with cell culture image data from the imaging subsystem 9606 in a model that predicts cell culture state. In some implementations, the cell culture system 9600 may use SERS-derived data from cell regions in conjunction with transcription data in models to predict transcriptomes from SERS data. In some implementations, components and/or functionality of the SERS subsystem 9612 may be combined with the cell imaging subsystem 9606 in a single subsystem. The cell culture system 9600 may have additional functionality and components not shown in FIG. 96.

Figure 97A:
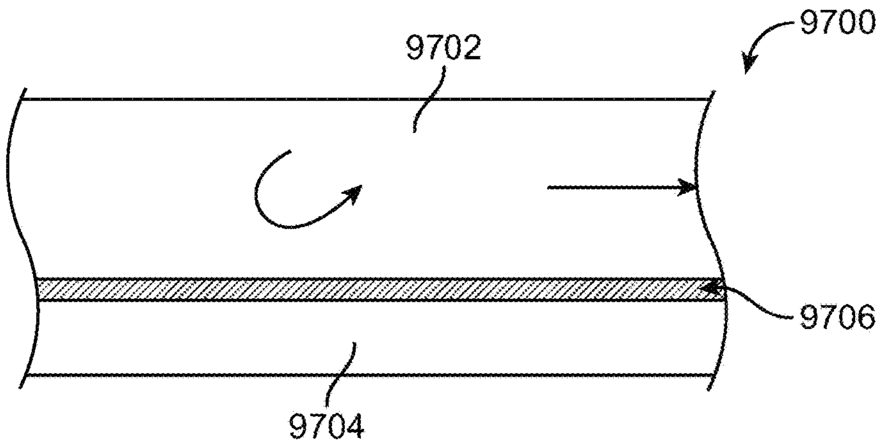

FIGS. 97A-D are diagrams depicting use of a SERS subsystem (e.g., SERS subsystem 9612) to measure contents in a cell culture container 9700 in accordance with various implementations. In FIG. 97A, the cell culture container 9700 includes a fluid media 9702 enclosed by walls (only a lower wall 9704 is shown in FIG. 97A). The lower wall 9704 may be transparent to allow for imaging of the contents of the cell culture container 9700. The fluid media 9702 may be circulated and periodically refreshed. A film or layer 9706 is in contact with the fluid media 9702 and is designed to enhance Raman scattering for SERS or resonant SERS (in which the Raman excitation wavelength matches a resonant wavelength of the film 9706). The film 9706 may reside on one of the walls of the cell culture container 9700, for example the bottom of a microwell plate container or the window of a bioreactor. Alternatively, the film 9706 may reside on a standalone substrate that is inserted into the cell culture container 9700, located such that it may still be interrogated by cell editing and imaging subsystems. The film 9706 may also be semi-transparent to allow for imaging of the contents of the cell culture container 9700.

Figure 97B:
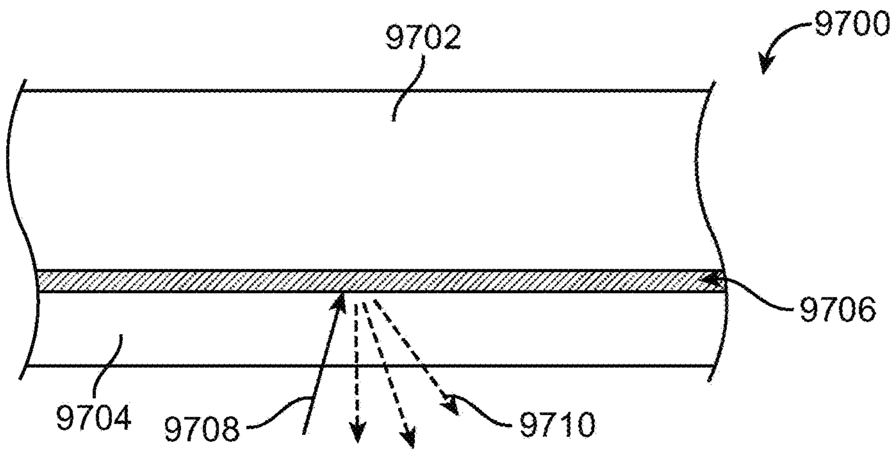

FIG. 97B illustrates an example operation of a SERS subsystem to measure biochemical constituents in the fluid media 9702 of the cell culture container 9700. An excitation source 9708 (e.g., a laser) is focused through the clear wall 9704 and strikes the film 9706, causing light scattering including inelastic light scattering 9710. The scattered light 9710 may be captured and measured spectroscopically. The light measurement component of the SERS subsystem may block the wavelength of the excitation source 9708 so as to measure only light that has been scattered inelastically (i.e., at wavelengths other than the incoming excitation wavelength).

Figure 97C:
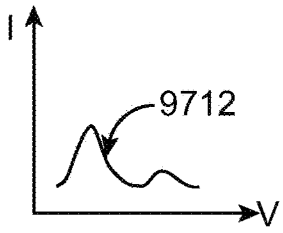

FIG. 97C is a chart showing an intensity spectrum 9712 of scattered light collected by a SERS subsystem after reflection from the film 9706. The spectrum 9712 is shown with a frequency shift (typically given in wavenumbers ν, in units of $cm^{-1}$) on the X-axis and intensity I on the Y-axis, and peaks correspond to characteristic vibrational modes of the molecules sensed by the SERS subsystem.

Figure 97D:
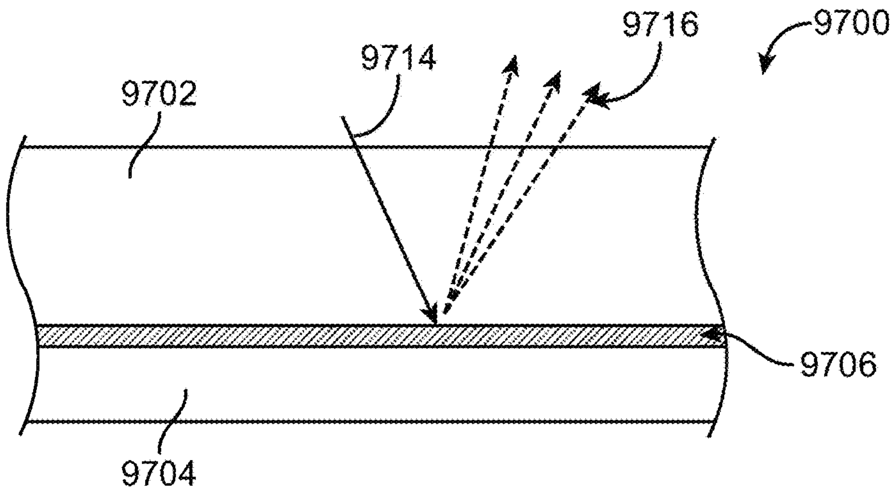

FIG. 97D illustrates an alternative implementation of the SERS subsystem in which an excitation source 9714 is incident on the film 9706 on the opposite side as opposed to the configuration illustrated in FIG. 97B (i.e., after traveling through the fluid media 9702 rather than through the lower wall 9704). The inelastically scattered light 9716 also travels through the fluid media 9702 before it is captured by the light measurement component of the SERS subsystem.

Figure 98A:
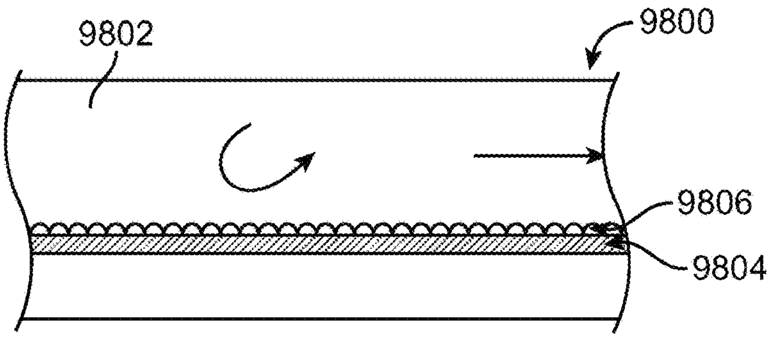

FIGS. 98A-F are diagrams depicting laser clearing of a cell culture container film during SERS measurement in accordance with various implementations. FIG. 98A depicts a cell culture container 9800 containing fluid media 9802. The fluid media 9802 may be circulated and periodically refreshed. The cell culture container 9800 includes a film 9804 designed to enhance Raman scattering for SERS or resonant SERS. The film 9804 may reside on one of the walls of the cell culture container 9800, for example the bottom of a microwell plate container or the window of a bioreactor. Alternatively, the film 9804 may reside on a standalone substrate that is inserted into the cell culture container 9800. The film 9804 may also be semi-transparent to allow for imaging of the contents of the cell culture container 9800. During a cell culture process, the film 9804 may adsorb molecules or analytes, and/or be covered with cell debris, extracellular matrix, or cell growth byproducts. These materials (termed "biofouling") form a layer 9806 on the film 9804.

Figure 98B:
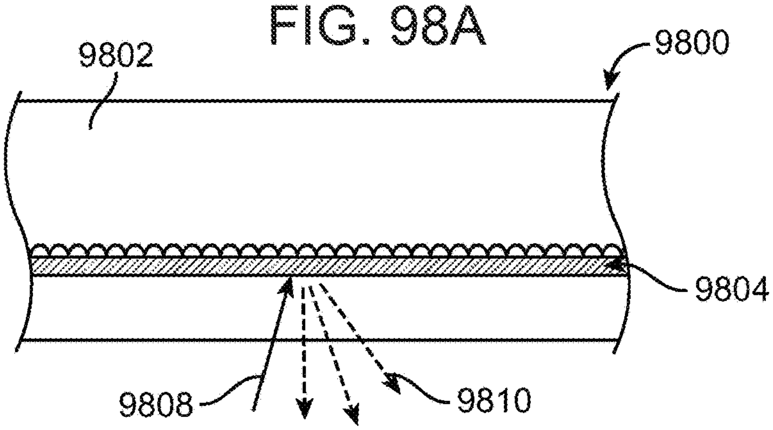

FIG. 98B illustrates a SERS measurement on the cell culture container 9800. A SERS subsystem emits excitation light 9808 that impinges on the film 9804, which results in inelastic scattered light 9810 that is collected and spectrally measured to ascertain the chemical composition of material proximate to the film 9804. In this scenario, the signal from the scattered light 9810 may represent information that is a combination of the biofouling layer 9806 and components of the liquid media 9802.

Figure 98C:
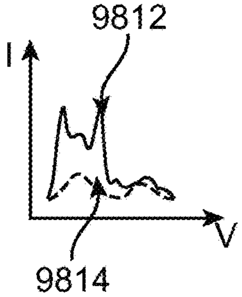

FIG. 98C is a chart showing an intensity spectrum 9812 of the scattered light 9810 collected by a SERS subsystem after reflection from the film 9804, with intensity on the Y-axis and wavenumber on the X-axis. The intensity spectrum 9812 may be a combination of the signal from the liquid media components (shown as media spectrum 9814) and the biofouling layer 9806 components. Thus, the compound intensity spectrum 9812 cannot be used to accurately determine characteristics of the liquid media components.

Figure 98D:
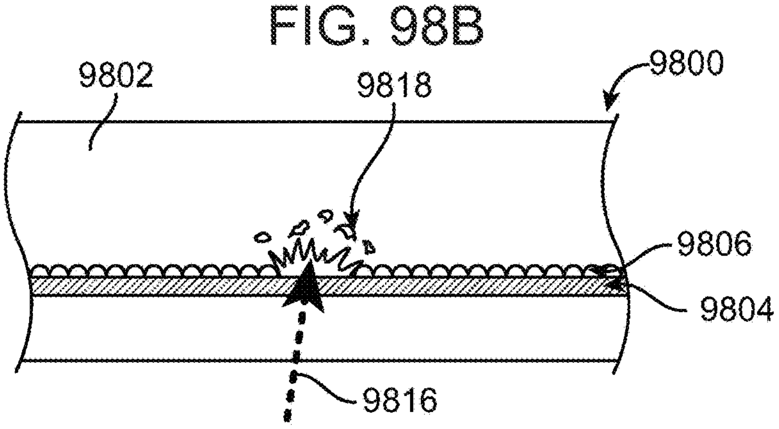

FIG. 98D illustrates optical clearing of the biofouling layer 9806 in the cell culture container 9800 in accordance with various implementations. One or more laser pulses 9816 are directed at the film 9804. These laser pulses 9816 are at a wavelength and duration configured to be absorbed by the film 9804 and create sufficient local energy to cause explosive microbubbles 9818 to form at the film surface. The explosive expansion and subsequent collapse of the microbubbles 9818 ablates a portion of the biofouling layer 9806 from the surface of the film 9804.

Figure 98E:
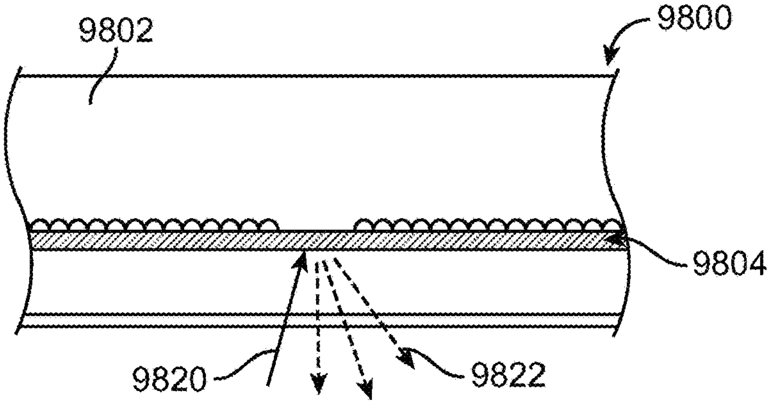

FIG. 98E illustrates a SERS measurement on the cell culture container 9800 after the optical clearing operation on the biofouling layer 9806. The SERS subsystem emits excitation light 9820 that impinges on the film 9804 at the spot where it was optically cleared, and the resultant scattered light 9822 is collected and spectrally measured to ascertain the chemical composition of material proximate to the film 9804.

Figure 98F:
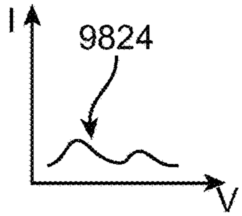

FIG. 98F is a chart showing an intensity spectrum 9824 of the scattered light 9822 collected by a SERS subsystem after reflection from the film 9804 after optical clearing. The intensity spectrum 9824 is now representative of the surrounding cell media, without the biofouling molecular signals that previously dominated. Thus, an accurate representation of the cell media state can be measured, for example for measuring levels of nutrients, waste, vitamins, proteins, cell products, etc. Moreover, by using the intensity spectrum 9812 prior to clearing as well as the intensity spectrum 9824 post-clearing, the differential spectrum resulting from the biofouling may be calculated. The biofouling or biolayer signal may be indicative of longer-term biological state or cell culture state, as it represents the accumulation of material over time. In such a manner even molecular species that are at low concentration but that tend to accumulate on the surface of the film 9804 over time may be measured with high sensitivity. The rate of accumulation/adsorption may also be measured by repeated accumulation, measurement, clearing, measurement, accumulation, etc.

FIGS. 99A-C are diagrams depicting poration of cells in a cell culture container 9900 during SERS measurement in accordance with various implementations. FIG. 99A illustrates the cell culture container 9900 containing fluid media 9902 and cells 9904 resting or adherent on a film 9906. The cells 9904 may be adherent cells that adhere to the surface of the film 9906, or suspension cells that are resting on the film 9906. A SERS measurement (with excitation light 9908 and captured scattered light 9910) may be made, which measures the local chemical environment under one or more of the cells 9904. However, since SERS measures chemical composition in a manner extremely local to the resonant structure, it will not measure cellular composition. Rather, what is measured is the conditions of the fluid media 9902 as it is affected by cell condition and metabolism, and perhaps components of the cell membrane that are in direct contact with the film 9906. These measurements may in many cases be sufficient to characterize a cell or clusters of cells. However, in other cases it may be desirable to measure cellular contents.

FIG. 99B illustrates the use of a pulsed laser mechanism 9912, together with the film 9906, to create an explosive microbubble 9914 under a target cell or cells. The same laser pulses 9912 may clear any biofouling from the film 9906, as previously described. The expansion and collapse of the microbubble 9914 generates energy that causes the membranes of nearby cells to partially porate, making it easier for biological materials to enter and exit the cells. In some cases, the pulsed laser mechanism 9912 may emit sufficient intensity to cause destructive lysing of cells via the microbubble 9914, meaning that all the contents of the cell are released into the fluid media 9902.

FIG. 99C illustrates SERS measurement of cells in the cell culture container 9900 after partial poration. When a cell membrane is partially porated, some cell contents escape into the surrounding fluid media. A SERS measurement (with excitation light 9908 and captured scattered light 9910) is then able to capture information about the cell contents, and thus the internal contents of cells can be released and measured on demand. Such functionality may be used to manage cell cultures, in which SERS measurements may be used to profile cells or regions of cells and the cell editing subsystem may be used to selectively lyse or remove certain cells based on these measurements. The SERS measurements may be combined with label-free imaging to make predictions/assessments of which cells to retain and which cells to lyse or remove. In combined imaging and SERS implementations, the film 9906 may be transmissive for label-free imaging such as by brightfield, phase, darkfield, differential interference contrast, differential phase contrast, phase-from-defocus, Fourier Ptychographic imaging, or other imaging techniques including but not limited to various quantitative phase imaging techniques.

FIG. 100 is a block diagram of an example SERS subsystem 10000 for use in a cell culture system (e.g., cell culture system 9600) in accordance with various implementations. The SERS subsystem 10000 may include a controller 10002 (e.g., computer or microprocessor) that controls a laser 10004 that produces pulsed light 10006 for the purpose of clearing a SERS substrate, such as a resonant plasmonic film in a cell culture container. The pulsed light 10006 is redirected by optical component 10008, which may either be a dichroic filter (when the clearing light wavelength is different from the SERS excitation wavelength) or polarization beam combiner (when the clearing wavelength is same or similar to excitation wavelength, but differently polarized for the purpose of combining the two beams). The pulsed light 10006 is then redirected again by a Raman filter 10010, which reflects excitation and clearing wavelengths, but passes through inelastically scattered light (higher wavelength than the excitation wavelength).

The pulsed light 10006 is focused by an objective 10012 onto film 10014, which is located in the cell culture container. The pulsed light 10006 may clear biofouling from the film 10014 in conjunction with SERS measurements. In addition, the pulsed light 10006 may be used to porate or lyse cells that are on or near the surface of the film 10014. Before and/or after this clearing and porating/lysing action, the controller 10002 activates an excitation source 10016, which is typically a laser source. The excitation source 10016 emits excitation light 10018 which passes through the optical component 10008, is reflected by the Raman filter 10010, and is focused onto the film 10014 via the objective lens 10012. The excitation light 10018 may be aligned with the clearing pulsed light 10006 so that that they target the same region. The relative beam sizes of the clearing pulsed light 10006 and the excitation light 10018 may be configured such that the spot size of the excitation light 10018 is smaller than the spot size of the clearing pulsed light 10006 on the film 10014 to ensure the excitation light 10018 samples only regions that have been cleared by the clearing pulsed light 10006.

Some inelastically scattered light 10020 results from the excitation light 10018 interaction with the film 10014 and surrounding molecules. Some of the scattered light 10020 is captured by the objective 10012 and passes through the Raman filter 10010. An additional laser line (rejecting) filter 10022 may be used to remove any residual excitation or clearing laser light from the signal of the scattered light 10020. A lens 10024 then focuses the scattered light 10020 to the entrance of a spectrometer 10026. The acquisition of the spectrum of the scattered light 10020 is controlled by the controller 10002. This may include triggering to coincide with excitation illumination, including systems where very short exposure time is used to generate time-resolved Raman spectra to distinguish Raman spectral signals (which are ultra-short duration) from autofluorescent signals (which have a longer overall duration). Such a time-resolved setup may be particularly useful when shorter excitation wavelengths (such as 532 nm) are employed: these produce strong Raman spectra, but also excite autofluorescence in many materials. The spectrometer 10026 may generate an output spectra 10028 from the scattered light 10020, which may be supplied to a downstream computing system for analysis (e.g., computing subsystem 110, 9600), usually as an array of intensities versus wavelengths or wavenumbers as depicted schematically by graph 10030.

FIG. 101 is a block diagram of another example SERS subsystem 10100 for use in a cell culture system (e.g., cell culture system 9600) in accordance with various implementations. In this implementation, a single laser source may be used for both film clearing and SERS measurement operations, and images of the biological sample may be captured alongside a spatially-resolved SERS spectrum. In addition, the multi-use laser may also be configured to porate or remove cells proximate to the film.

The SERS subsystem 10100 includes a controller 10102 (e.g., computer or microprocessor) that controls a laser source 10104 used for both film clearing and Raman excitation operations. The laser source 10104 may generate clearing pulses 10106 generally being of higher peak energy than Raman excitation light 10108. Both the clearing pulses 10106 and the excitation light 10108 are steered in two axes by steering mechanisms 10110 so that they impinge a film 10116 within the field of view of an objective 10114 after being reflected by a Raman filter 10112. The film 10116 may be located in a cell culture container containing fluid media and a cell culture. Cells and/or biofouling may be resting on the film 10116.

Scattered light 10118 from the film 10116 is collected by the objective 10114, and the inelastically scattered portion (shifted wavelength) of the scattered light 10118 passes through the Raman filter 10112. In some implementations, the scattered light 10118 may pass through an optional filter 10120 to remove any remaining laser light from the beam. In alternate implementations, this functionality may be part of the next component in the beam path, optical switch 10122. The optical switch 10122 allows light to be diverted either to a spectroscopy path (leftward direction in FIG. 101) or an imaging path (downward direction in FIG. 101). The optical switch 10122 may be toggled by the controller 10102 depending on the desired mode. In implementations in which the laser cleanup filter (i.e., filter 10120) is integrated into the optical switch 10122, there may be an optical component in the optical switch 10122 that passes through laser light to the imaging path, and not reflect it into the spectroscopy path. This may be useful for calibration and other purposes in which a small fraction of the steered laser light passes through to the image sensor, for the purpose of XY calibration in the scanning system, and potentially focusing of the laser system on the film 10116 via spot size imaging.

In Raman spectroscopy or measurement mode, the optical switch 10122 diverts the inelastically scattered light 10118 to a tube lens 10124, which directs light into a spectrometer 10126. By virtue of the steering system, the SERS subsystem 10100 may build up a hypercube of spectral data on a “pixel” (XY dimension) basis, in which each pixel has a spectrum (such as the one represented by graph 10128) associated with it. In the imaging mode, the SERS subsystem 10100 allows imaging of the same region. For example, imaging light 10130 may be acquired using an illumination source (not shown), in which light passes through a biological sample on the film 10116, is collected by the objective 10114, and then passes through filters 10112 and 10120. The optical switch 10122 is switched to allow the imaging light 10130 to pass through and is focused by a tube lens 10132 onto an image sensor 10134. The image sensor 10134 is triggered by the controller 10102 and produces a pixel image 10136. In some implementations, the illuminating wavelength for imaging may be configured to not require an optical switch, but rather accomplish the splitting of spectroscopy light from imaging light using a bandpass or dichroic filter.

The combination of spectroscopy and imaging capabilities allows imaging of cell cultures and acquisition of corresponding spatially-resolved Raman spectra, which supports a number of system modalities. For example, the SERS subsystem 10100 may acquire an image of the cell culture using one of several imaging modalities (including reflection, transmission, fluorescence, etc.) and also acquire a spatial SERS map of the cell culture. The SERS measurement may be made both before and after a clearing function of the laser (which may include clearing of biofouling on the film and/or poration of the cells for analysis of intracellular contents by SERS). The clearing function and SERS measurement may be performed on all or part of the imaged area. For example, the clearing and measurement may be performed only in regions of interest that are generated by image processing of the imaging data. The two image sources may then be combined for use in a predictive model (e.g., run by a computing subsystem) that makes predictions on success or fate of certain cell regions. Finally, the clearing laser may be used to lyse cells that are deemed not progressing along the desired trajectory.

In some implementations, the SERS subsystem 10100 may be used to train imaging-based algorithms using SERS training data, in which SERS has been pre-correlated with cell fates, phenotypes, etc. For example, one model may have been trained with spatial SERS data (medium throughput, inexpensive) and then corresponding transcriptomic data (low throughput, expensive). Then the SERS subsystem 10100 may be used to correlate spatial features in the image data to transcriptomic profiles via the SERS measurement.

FIG. 102 is a block diagram of another example SERS subsystem 10200 for use in a cell culture system (e.g., cell culture system 9600) in accordance with various implementations. The SERS subsystem 10200 includes a semi-transparent SERS and laser-absorbing film 10202 situated inside a cell culture container with cells 10204 settling or adhering to the surface with the film 10202. The cell culture container may be translated relative to the optical subsystem of the SERS subsystem 10200, indicated by arrow 10206. As continuous translation of the cell culture container occurs, a single linear region of interest (ROI) 10208 is interrogated by the optical subsystem in either or both an imaging mode and a measurement mode. The imaging mode may be suitable for quantitative phase image (QPI) reconstruction, and the measurement mode may use SERS to measure the local spatial biochemical content of the cell culture, with the potential addition of biofouling clearing functions, cell poration, and cell lysis functions as described herein.

When the SERS subsystem 10200 is in imaging mode, illumination for transmission imaging may be provided at multiple wavelengths, each one of which corresponds to a unique distribution of illumination angles $\theta_1$ through $\theta_n$. Illumination of a sample at multiple known angle distributions may be used to reconstruct the phase of the sample using differential phase contrast (DPC) or Fourier Ptychography algorithms. The use of wavelength multiplexing allows single-shot acquisition of multiple illumination conditions within the ROI 10208 during continuous motion. For each wavelength/angle distribution, some light is diffracted into an objective 10210, passes through a Raman filter 10212, is focused by lens 10214 through a slit 10216 that defines the ROI 10204 and prepares the light for spectral analysis, and then re-collimated by a lens 10218. The collimated light is then diffracted by a grating 10220, which is shown as a reflective grating in FIG. 102 but may also be a transmission grating or dispersive prism.

After the collimated light is dispersed by wavelength by the grating 10220, it is focused using tube lens 10222 onto an image sensor 10224. The linear ROI 10204 is imaged onto the image sensor 10224 at multiple rows, each corresponding to one of the illumination wavelengths, and therefore corresponding to a specific known illumination angle distribution. The image sensor 10224 may be a machine vision CMOS image sensor that is configured to only image selected rows, and if the number of selected and digitized rows is small compared to the overall number of rows, the image sensor 10224 may run at very high frames rates, since data conversion and output is generally the bottleneck, not exposure time. As a result, the optical subsystem may be translated at high speed relative to the sample, with the images (one per illumination condition per wavelength) being built up row by row into 2D planes 10226. The resulting stack of 2D planes 10226 correspond to different illumination conditions and may be used directly by a model, for example a deep learning network, or the 2D planes 10226 may be processed into a representation of phase delay and amplitude by methods such as differential phase contrast or Fourier Ptychography. Graph 10228 shows a representation of different imaging wavelengths $\lambda_1$-$\lambda_n$ used to encode illumination angles in a plot of intensity versus wavelength. The dashed line 10230 indicates the transmission of the Raman filter 10212, which is configured to reflect excitation/clearing laser light and prevent it from interfering with image sensing.

When the SERS subsystem 10200 is in measurement mode, a laser source 10232 (e.g., a 532 nm nanosecond pulsed laser) emits an excitation beam 10234 at an energy sufficient for SERS measurements. The excitation beam 10234 is scanned across the linear ROI 10204 using a scanner 10236 and reflected towards the objective 10210 by the Raman filter 10212. The excitation beam 10234 is focused on the film 10202, where it produces scattered light, including inelastic scattered light (shown in dashed lines) which is captured by the objective 10210, passes through the Raman filter 10212, focused by the lens 10214 through the slit 10216, and then is recollimated into a beam 10238 that impinges on the diffraction grating 10220. This beam path is the same path taken by the imaging light when the SERS subsystem 10200 is in imaging mode.

The beam 10238 is diffracted by wavelength by the diffraction grating and focused by the lens 10222 onto the imaging sensor 10224. The beam wavelengths are spread continuously along the vertical axis of the imaging sensor 10224 (the horizontal axis corresponds to position along the linear ROI 10204), so an output 10240 of the imaging sensor 10224 is Raman intensity as a function of wavelength and Y axis (where Y is perpendicular to the motion of the sample relative to the optical subsystem). In measurement mode, the light scanning uses a continuous section of the imaging sensor 10224 rather than discrete rows (as opposed to the imaging mode) and the signal levels are likewise significantly lower than in imaging mode, so the motion of the sample relative to the optical subsystem should be slower if high spatial resolution was desired.

The composite wavelength data for a single linear ROI is shown by graph 10242. These images are compiled per X location as the SERS subsystem 10200 scans to form a "data cube" with X, Y, and frequency dimensions. In measurement mode, the SERS subsystem 10200 may be used to measure cell media, accumulated biofilms or other compounds, cell components, or intracellular components that have been extracted using the methods described above. Graph 10244 shows a spectrum of the SERS subsystem 10200 operating in measurement mode, and includes the excitation wavelength 10246, the inelastically scattered light spectrum 10248, and the transmission of the Raman filter 10250 (which excludes the excitation wavelength from the measurement system).

In some implementations, the SERS subsystem 10200 may have additional functionalities or modes. For example, the laser 10232 may emit laser pulses at higher energy levels to clear biofouling from the surface of the film 10202 prior to measurement of media, or after measurement of biofilm, or both. In another example, the laser 10232 may emit laser pulses to reversibly porate or lyse cells on or near the film 10202 for the purpose of measuring cell contents using the SERS subsystem 10200. In another example, the laser 10232 may emit laser pulses to reversibly porate cells for the purpose of delivering compounds into them (e.g., intracellular delivery). In another example, the laser 10232 may emit laser pulses to lyse cells for the purpose of removing them from the cell culture, thereby selectively expanding other cells in the cell culture, which may be done based on measurements made by the imaging mode and/or spectroscopy modes described herein.

Led Imaging Array for Customizable Imaging Modalities

Automating imaging and microscopy systems (e.g., for use in an automated cell culture system) is difficult, particularly for setups that use multiple (non-complimentary) imaging modalities. Such platforms may explore or utilize a range of microscopy techniques, such as transmission imaging, reflection imaging, brightfield imaging, darkfield imaging, phase imaging, differential interference contrast (DIC) imaging, quantitative phase imaging (QPI), transmission Fourier ptychographic imaging, reflection transmission Fourier ptychographic imaging, holographic imaging, differential phase contrast imaging, or any combination thereof. To switch between these imaging modalities, the illumination hardware is usually manually reconfigured to suit the specific requirements. Alternatively, multiple imaging setups may be used, each customized for a specific imaging modality. Each of these approaches are cumbersome and time-consuming when one wants to frequently switch between imaging modalities or switch quickly.

The systems and methods disclosed herein include an adaptable imaging subsystem that supports several complex imaging modalities without time-consuming hardware modification of the system. The imaging subsystem utilizes a light emitting diode (LED) array that is configured to provide real-time customizable illumination patterns for non-complimentary imaging techniques. Mounting an LED array underneath a sample (e.g., in the case of transmission microscopy) may provide a way to control illumination wavelength, intensity, and patterning using one piece of standardized equipment rather than multiple unique imaging setups.

Such a system confers several advantages over the prior art. For example, assuming the LEDs are sufficiently small, the brightness and directionality of light penetrating a sample may be customized with high precision, especially when compared to a traditional illumination setup that emits collimated or focused light at one wavelength. Furthermore, instead of translating the sample on a motorized stage, which may displace cells in live culture, the imaging subsystem described herein has the sample fixed with the optics translated in 2D or 3D space. The optical system may capture any area of the sample because the LED array is larger than the sample footprint, thus individual LEDs can be addressed to illuminate the region directly below the objective (or off-center depending on the imaging technique). Besides avoiding sample disturbance, this configuration promotes a more optimal mechanical design that translates less mass and thereby creates an inherent inertial advantage for faster acquisitions.

In addition, unlike conventional microscopy systems, the imaging subsystem described herein allows the creation of arbitrary patterns that may be used for machine learning or computer vision applications. For instance, depending on the type of LEDs in the array, which determine the directionality of light, a user can generate equidistant shapes (e.g., crosses) that a computer vision system can reference as fiducial markers. This would potentially save massive costs associated with fabricating physical fiducials into the bottom of sample containers.

FIG. 103 illustrates an example imaging subsystem 10300 in accordance with various implementations. The imaging subsystem 10300 includes a sample 10302, which may include one or more cells (e.g., cell culture 102) growing in a cell culture chamber or container (e.g., well plates or cell culture chamber 104). In some implementations, the sample 10302 may include adherent cells grown on a surface of an open or sealed container, the growth surface being transparent for imaging purposes. Light is emitted from an LED array 10304 below the sample 10302 and light transmitted through the sample 10304 is captured by an objective 10306. The objective 10306 may be translated around the plane of the sample 802. An advantage of the present implementations over conventional trans-illumination systems is that the illumination source remains mechanically fixed relative to the sample. As a result, the sample 10302 may be mounted in very close proximity to the LED array 10304, allowing for more compact microscopy systems.

The LED array 10304 may be controlled by a controller, processor, FPGA, or other computer device (e.g., computing subsystem 110). Each LED in the array may be individually addressed, and the intensity and color of each LED independently controlled. As the objective 10306 translates across the plane of the sample 10302, individual LEDs may be turned on/off and adjusted to illuminate a specific region of the sample 10302 that is then captured by the objective 10306. For example, the LEDs may be controlled to illuminate a single cell, or a selected colony or cluster of cells to enable targeted imaging of a subset of the sample 10302. In another example, the intensity of the LEDs may be adjusted to enable multiple imaging modalities that may require different lighting intensities, for example to provide anti-aliasing as the relative position of the objective 10306 and the LED array 10304 shift, or to provide equivalent illumination onto a sample area from multiple angles despite the individual LED element angular emission profile being non-uniform. In alternate implementations, the sample 10302 and the LED array 10304 may be translated while the objective 10306 is stationary.

The LED array 10304 may be monochrome or have LEDs of different wavelengths. Multi-wavelength LED arrays may be used in imaging systems that multiplex illuminations and de-multiplex the light captured by the objective 10306 to capture multiple illumination conditions (such as angles) in a single shot. In some implementations, the LED array 10304 may further include bandpass filters that narrow the wavelength band of individual LED elements. The LED array 10304 may be composed of conventional LEDs mounted on a common printed circuit board or flex board, or may use micro-LED technology to provide very high resolution. In some implementations, the imaging subsystem 10300 may utilize a microLED screen.

In some implementations, the LED array 10304 may be configured to generate various light patterns, such as annuli or semi-annuli with arbitrary rotations, for more advanced imaging techniques such as DPC. Examples of such light patterns are shown in FIG. 104. These light patterns may also be used for other computer vision applications, such as generating light-based fiducial marks for orientation rather than creating a physical fiducial mark in the sample.

Fiducial-Mapped Cell Culture Containers

In some implementations of the cell culture systems described herein, imaging of cells within a cell culture chamber is aided by imaging-compatible laser-activated films or coatings for cell processing. In the implementations described herein, the laser film may also include registration features or fiducials for the purpose of establishing precise chamber position relative to systems that interrogate and/or act upon the contained cell culture. These systems may include imaging subsystems, cell editing subsystems, spectroscopy subsystems, magnetic actuator subsystems, ultrasonic or mechanical actuator subsystems, and other subsystems that enable precise measurements of cells as well as action upon the cell culture over time.

FIG. 105 illustrates fiducial markers for use in a cell culture system in accordance with various implementations. FIG. 105 shows a surface 10500 within a cell culture container (e.g., cell culture container 104). This surface may be a barrier surface, such as the bottom window of a multi-well plate, or the window of a fluidic chamber. Alternatively, it may be a separate construction such as a thin polymer foil or film that is inserted into a cell culture vessel, or forms an intermediate later of a cell culture vessel. The surface 10500 may be made of glass (for example, a #1.5 coverslip thickness or 0.17 mm, of Schott D 263 borosilicate glass), or may be made of a clear polymer such as polycarbonate, polyester, polystyrene, cyclic olefin copolymer, PTFE, or other material compatible with biological samples. The foil may further be permeable to various degrees to gases (such as oxygen) or liquids. For example, the foil surface may have well-defined density and size of pores etched into it using track-etching to resemble a material such as a transwell membrane, which allows exchange of liquid and biochemical components while preventing cell migration through the foil.

The surface 10500 has a film 10502 applied for the purpose of patterning fiducial markings. This film 10502 may serve other purposes as described with reference to FIGS. 91-95, including but not limited to absorbing optical radiation for the purpose of manipulating cells locally (by heating, by creation of microbubbles, by creation of plasmas, or other methods) to perform cell operations, such as lysing cells, temporarily porating cells, or removing cells from the surface intact. The film 10502 may also be used to aid in sensing local biochemical conditions, for example by surface plasmon resonance, direct measurement of transmission or reflection spectra which shift with concentrations or binding of substances to the surface, surface-enhanced Raman spectroscopy, or by other surface-based spectral methods known to those of skill in the art.

The film 10502 may be patterned, either in positive (where fiducial is unmodified coating) or negative (where fiducial is modified coating), to form fiducials 10504. The film 10502 may be patterned using a mask during fabrication. For example, a shadow mask may be used during material deposition, or a lift-off photoresist mask may be applied, patterned, and then removed after deposition (along with any coating deposited on the area where photoresist remained). Alternatively, a resist layer may be patterned on the film 10502 and then the film 10502 is etched away from areas not covered by the patterned resist, or the open areas may be modified optically but not removed. In other implementations, the film 10502 may be patterned after deposition using optical means such as a scanning laser that modifies or ablates the film. In the implementation shown in FIG. 105, the fiducials 10504 are patterned in the corners of the surface 10500, but in general the fiducials 10504 may be located anywhere on the surface 10500.

The fiducials 10504 may aid in determining the location of the surface 10500 relative to other systems by imaging or other optical means and calculation of the overall orientation, rotation, and scale of the surface 10500 and therefore cell culture that resides on it. This registration process is used to align imaging and other spatial operations over time, for example to build time series images that are well-aligned in the X, Y planes, or to perform operations such as laser cell removal that are well-registered to the images of the cell culture used to determine which areas/cells to remove. These "corner-type" fiducials 10504 may be patterned in exclusion areas 10506, which are not used for cell culture, so they remain unobstructed. For example, in a microwell plate, these fiducials 10504 may be patterned in wells that are not used for cell culture, but establish the overall orientation and scale over the overall plate for imaging and other operations. In another example, the fiducials 10504 may be patterned in open areas outside of a liquid volume between two surfaces in a fluidic chamber. In another example, the exclusion areas 10506 may be formed actively, by use of a cell removal mechanism (e.g., cell editing subsystem 114) that actively removes cells from exclusion zones. In another example, the exclusion regions 10506 may be pre-coated with a coating that prevents cell attachment or growth to keep these regions clear. Additionally, the fiducials 10504, when located in corners, may be used to establish Z position in the corners or along the edges of the surface 10500 (by measuring goodness-of-focus, or scanning the fiducials with a laser beam and finding Z with sharpest signal), to calculate an overall tilt or shape for the surface 10500, and through a mathematical model predict the Z height at each location within the cell culture area, to automatically adjust Z position in imaging or laser scanning operations within the cell culture region.

FIGS. 106A-C are diagrams further illustrating fiducial markers for use in a cell culture system in accordance with various implementations. In FIG. 106A, fiducials 10604 are patterned in a film 10602 within the working cell culture area of a surface 10600 of a cell culture container (e.g., cell culture container 104). The pattern of the fiducials 10604 may be used to provide real-time alignment in the X, Y, and potentially Z planes without interfering with other system functions including cell imaging and cell manipulation using lasers or other means. The fiducials 10604 may be formed in such a manner that they are clearly observable in transmission or reflection at one wavelength, but much less visible at other wavelengths (e.g., the wavelengths used for imaging the cell culture). Such fiducial markings may be formed using a wavelength-selective film, including but not limited to resonant absorbing or reflecting films. The fiducials 10604 may be distributed evenly across the surface 10600 (e.g., in a grid), but may also be distributed unevenly in a manner which indicates absolute position rather than just local position, or include markings that indicate absolute position on the surface 10600. Fiducials 10604 that indicate absolute position allow "random access" with absolute position repeatability, versus the need to proceed and track fiducials from a fixed fiducial at the corner or edge of the surface, for example.

FIG. 106B illustrates the use of small fiducial marks 10608 to form a pattern 10610 on the coating or film. The individual fiducial marks 10608 may be smaller than the resolution of the imaging subsystem, but nevertheless extractable by the fiducial detection system. The fiducial detection system may use image processing (e.g., a filter or template matching system that can match these feature arrays), or optical techniques to detect the fiducial marks 10608. The fiducial detection system may include using a shorter wavelength than the cell imaging portion of the cell culture system, and may also include focusing at a Z plane relative to the film where light passing through these features and the surrounding film constructively or destructively interferes in a manner in which the imaging system can detect the composite. These sub-features are also sufficiently small such that they are small compared to a laser spot that is used for cell treatments, such as pulsed laser microbubble formation for cell destruction or intracellular delivery functions.

FIG. 106C illustrates an example in which multiple small features are arranged to form a fiducial mark detectable via constructive interference. These features, patterned in film 10612, have a size that is below the resolution limit of the cell imaging subsystem, so do not appear in cell images. Furthermore, by use of a resonant film and appropriate imaging wavelength, there is a minimal overall effect on light transmission in the local area. However, when illuminated at the resonant wavelength of the film 10612, the features cause constructive interference that can be used for fiducial detection for both X-Y localization and tracking, and Z tracking for autofocus purposes.

A system focused on the film 10612 itself will still see only a local aggregate brightening or darkening depending on the film 10612 and fiducial technique used, as shown by the featureless intensity plot 10614. However, when the fiducial imaging system, which operates at specified fiducial detection illumination wavelength(s), is properly focused onto a Z plane where the features constructively interfere (as shown in plot 10616), a clear feature is visible and its location may be used to track XY position across the sample. However, if the focus drifts (e.g., when the cell container is not flat, or tilted) the fiducial signals degrade from a sharp constructive interference as shown in plot 10616 to less constructive interferences as shown in plots 10614 and 10618. As a result, with in situ fiducial markings over the entire cell growth area, it is possible for a system to establish XY location in real time and simultaneously adjust focus by maximizing the constructive interference signal from the fiducials, for example by using a piezoelectric element to adjust Z position of the objective relative to the sample. Note the cell imaging subsystem and fiducial imaging subsystem may be adjusted to focus on different planes, which can be achieved by positioning sensors at different distances from the respective tube lenses in the microscopy system.

FIG. 107 shows a graph 10700 illustrating an example optical extinction spectrum for a film (e.g., the films described with reference to FIGS. 105-106C) used in a cell culture container in accordance with various implementations. The horizontal axis of the graph 10700 represents wavelength and the vertical axis represents optical extinction. The film used in this example has a resonant wavelength 10702 (where it absorbs and/or scatters light), as indicated by curve 10704. In regions where the film has not been deposited (or ablated after deposition) to form fiducial marks, there is minimal extinction, as indicated by the dashed curve 10706. This allows the film to be used at the resonant wavelength 10702 to absorb laser light, for example, and at a range of other wavelengths 10706 for high efficiency imaging. It also allows fiducial markings to be imparted into the film, in which these fiducial markings are detectable with good contrast at the resonant wavelength 10702 by transmission or reflection of light, but where these fiducial markings do not interfere with cell culture imaging because the film is highly transmissive in these wavelengths.

FIG. 108 shows another graph 10800 illustrating an example optical extinction spectrum for a film (e.g., the films described with reference to FIGS. 105-106C) used in a cell culture container in accordance with various implementations. The film used in the cell culture chamber has an extinction spectrum 10802 that may be modified to another spectrum 10804 at fiducial markings. This can be achieved, for example, by depositing an additional, patterned, layer onto the fiducials only. If the base film is composed of resonant metallic islands, a temporary mask (such as a photoresist or shadow mask) may be applied to the film and then an oxide or nitride film deposited such that when the mask is removed, the oxide or nitride is present only in the fiducial markings. As a result of the additional layer's dielectric constant, the layer extinction peak shifts to longer wavelengths. This allows fiducial markings to be detected easily using two sources and/or two detectors operating at wavelengths 10806, 10808. For example, two LEDs (potentially with bandpass filters) may be used to illuminate an area in succession and an imager records images and a difference image is calculated for the purpose of extracting a fiducial image. However, in the cell imaging wavelength band 10810, away from the film resonance, the untreated and treated film extinction is substantially identical, preventing fiducial markings from interfering with high-quality cell imaging.

FIGS. 109-110 are diagrams illustrating the use of fiducial markers during imaging of a cell culture system in accordance with various implementations. In FIG. 109, a film 10902 contains fiducial marks 10904 having different transmission characteristics than the film 10902 (as described herein). A cell imaging illumination source or sources 10906 is used to image cells in a band where transmission through the film 10902 and the fiducial mark 10904 are substantially identical, such that light passing through the film (shown as beam 10908) and the film with fiducial (shown as beam 10910) do not show high contrast differences in the resulting images. The fiducial markings 10904 may additionally be patterned to be very small relative to the resolution required by the cell imaging, as described herein. When a fiducial detection illumination source or sources 10912 transmits light at one or more wavelengths through the film 10902, the light traveling through the fiducials (shown as beam 10914) and light traveling through the film (shown as beam 10916) are differently attenuated. Thus, an imaging/detection system operating by alternating between imaging and fiducial illuminations, or using them simultaneously by wavelength-multiplexing and demultiplexing them, may capture high-quality cell images and clearly detect fiducial markings for XY- and Z-positioning simultaneously.

FIG. 110 illustrates a registration/fiducial detection and tracking system that uses a reflective scheme for fiducial tracking. In FIG. 110, a film 11002 contains fiducial markings 11004. The film 11002 and fiducial marks 11004 transmit cell imaging illumination source emits beams with substantially identical wavelength(s), as indicated by beams 11006, 11008. When epi-illuminated with registration illumination wavelength(s) as shown by beams 11010, the film 11002 and fiducial marks 11004 reflect light differently, as indicated by beams 11012 and 11014 respectively. Thus, the implementations disclosed herein may be implemented in reflective mode, including with fiducials that are made up of many sub-elements that produce an aggregate effect that may be extracted via image processing (template matching or frequency filtering for example) or optical means (constructive interference for example).

FIGS. 111-112 are diagrams illustrating different shapes for cell culture containers and accompanying films in accordance with various implementations. In FIG. 111, the cell culture surface and accompanying film 11100 is non-planar. The film 11100 may include in situ fiducial markings 11102 in the field where cells are cultured, and may be useful because XY motion as measured by linear actuators or encoders 11104 may diverge from the path length along the cell-bearing film 11106. This is particularly helpful when the fiducial markings 11102 are also used to track Z position of the optical system relative to the film and cells. FIG. 11200 shows another implementation of the registration and fiducial system as part of a cylindrical cell culture chamber 11200, such as a roller bottle. In this implementation, a substrate such as a glass or polymer foil with a laser film 11202 is marked with fiducial markings 11204. This enables a system where the cell culture container is rotated around its center axis, and an imaging and/or laser system translated along the longitudinal axis in order to cover the entire cell growth surface to allow accurate repeated positioning and registration of images and laser operations on the cells that have been imaged.

Cell Culture Membrane with Laser Activated Film

Porous membranes may be utilized for certain cell culture operations, including but not limited to expansion, differentiation, co-culture, maturation, filtration, selective migration, and harvest of cell output. In the implementations disclosed herein, such porous membranes may also include a laser-activated layer (such as the films disclosed with reference to FIGS. 91-95) for processing supported cells via laser illumination.

In implementations disclosed herein, the cell culture system may utilize a porous membrane or sheet made of an optically-clear material, typically a foil with a thickness on the order of tens of microns (often a polymer such as polyester or polycarbonate). The pores in this membrane may have a uniform diameter distribution and density of pores per unit area, with pores sized so as to allow transport of certain substances and cell components but not others. Membranes may be formed from a range of materials, including but not limited to polydimethylsiloxane (PDMS), thermoplastic polymers, polyester, polycarbonate, polystyrene, polyethylene glycol, and other materials. They may be formed by known processes including but not limited to track etching, photo nano imprint lithography, nanoimprint lithography, polymer self-assembly, 3D printing techniques, or electrospinning.

There may be an optical coating or film applied to at least once side of the membrane, in which the optical film absorbs laser radiation for the purpose of affecting cells locally. The film may be semi-transparent, or transparent in some wavelength ranges, to allow imaging of cells on or near the surface of the membrane. The film may be resonantly absorbing so as to absorb laser radiation more strongly at one wavelength, while allowing wavelengths for imaging to be passed through with higher transmission. The film may be composed of metallic nanoislands or nanospheres that are attached to the surface of the membrane. The film may contain fiducial markings for the purpose of ascertaining spatial location in XY (in the plane of the membrane) and/or Z (axially perpendicular to the membrane) planes.

FIG. 113 is a diagram of a porous membrane 11300 for use in a cell culture container in accordance with various implementations. The membrane 11300 may be composed of a sheet 11302 of material, which may be a polymer such as polyester or polycarbonate. The membrane 11300 has pores 11304 that allows transport of media, factors, or cell products but prevent cells from passing through the membrane 11300. The membrane 11300 may be spun material with defined pore sizes, or in other cases a track-etched membrane in which radiation and etching is used to define average pore size and density (for example ipCELLCULTURE™ track-etched membrane filters from it4ip SA, Belgium).

The membrane 11300 may also include an optical film 11306 that is designed to absorb laser radiation 11308 for the purpose of affecting cells growing on the membrane 11300. For example, the laser radiation 11308 may be converted by the film 11306 to heat to locally disrupt or destroy cells thermally. In some implementations, pulsed laser radiation 11308 may be absorbed by the film 11306 and cause rapid formation of explosive microbubbles which disrupt or destroy cells mechanically. In either case, cells may be permanently destroyed through necrosis or apoptosis, or experience temporary membrane disruptions/poration that allows intracellular delivery of molecules, or extraction of cellular components for analysis or downstream use. The membrane 11300 and film 11306 may be optically clear and transparent in at least one wavelength range so that high-quality cell imaging may be performed within this wavelength range. In such a case, the film 11306 may further include fiducial marks 11310 for the purpose of registration and focus for imaging and laser operations.

FIG. 114 is a diagram illustrating use of a porous membrane in a multi-well plate 11400 in accordance with various implementations. A well insert frame 11402 is placed into a well of the multi-well plate 11400. The well insert frame 11402 supports a membrane 11404 including a laser film (as described with reference to FIG. 113), which supports the growth of cells 11406. The membrane 11404 also separates a top media compartment 11408 from a bottom compartment 11410. The separated media compartments 11408, 11410 may be used to influence cell behavior or differentiation, or to allow for cases where cells excrete directionally (for example, retinal pigment epithelial cells that expel waste, and form bubbles under a cell sheet if not placed on a porous membrane or support). The membrane with film 11404 may support imaging of the cells 11406 growing on the surface of the membrane 11404, and a laser source 11412 may be used to selectively destroy or disrupt the cells 11406. FIG. 114 illustrates an example using pulsed laser induced explosive microbubble formations to lyse or porate cells, but manipulation of cells through the membrane 11404 is not limited to the approach shown in FIG. 114.

Furthermore, in configurations with two compartments separated by a porous membrane such as illustrated in FIG. 114, electrical measurements may be made between the two liquid compartments. Such measurements may include, for example, a transepithelial/transendothelial electrical resistance (TEER) measurement which can measure the integrity and properties of a sheet of cells grown on the membrane. Such a measurement may be combined with image analysis to correlate image characteristics with electrical properties and may further be combined with laser processing to help elucidate spatial relationships between cell image characteristics and electrical measurements by selectively destroying or temporarily porating cells using a laser system and the laser film on the membrane.

FIG. 115 is a diagram illustrating use of a porous membrane in a cell culture container 11500 in accordance with various implementations. The cell culture container 11500 includes a frame 11502 that holds in place a membrane 11504. The membrane separates the cell culture container 11500 into a lower chamber 11506 and upper chamber 11508. Cells may be cultured on either (or both) sides of the membrane 11504. Both chambers 11506, 11508 may have ports for the purpose of flowing in and out liquid such as cell media and reagents. Cells growing on the membrane 11504 may be imaged, and then a laser source may be used to illuminate selected areas. In the example shown in FIG. 115, the laser source emits laser pulses 11510 that cause explosive microbubble formation for the purpose of destroying selected cells.

The porous membrane described with reference to FIGS. 113-115 may be used for multiple purposes in a cell culture container. For example, some cells ingest compounds from one side and/or excrete on another. A porous membrane may enable cell excretions to be separated effectively and prevent bubbling of cell sheets. In another example, different cell types may be cultured on opposite sides of the membrane, in which one set of cells is supported by the other. This may include cases in which both cell types are adherent, or one cell type is adherent and another is in suspension, or when both are in suspension.

In another example, exogenous compounds including reprogramming or gene editing constructs or compounds may be delivered through one chamber of a cell culture chamber, which may be optimized for minimum volume. These compounds may then be delivered in close proximity to the cells through the membrane. In some implementations, laser pulses may be used to facilitate intracellular delivery of the compounds. In another example, the membrane may enable directional delivery growth factors or nutrients that may facilitate proper development of cells. In another example, when cell constituents or products such as endogenous factors or exosomes are desired, they may be harvested from the cells through the membrane and efficiently extracted by flowing out of the cell culture chamber. This harvest may be promoted by laser action on the film attached to the membrane.

In another example, a device with a porous membrane equipped with a laser activated film may be used to managed suspension cells in culture, either during an all-suspension process or in a process in which cells become adherent. The membrane may be used to create pressure differentials that pull suspension cells onto the surface, where they may be imaged and laser-processed (e.g., destroyed with a laser process, or temporarily porated to affect intracellular delivery). In another example, the pressure differential method may be used hold non-adherent cells in place while the media in the cell culture chamber is exchanged, similar to a tangential-flow filtration system that retains particles in an active flow. In another example, the membrane may facilitate processes in which cells differentiate or activate and become migratory. The pores in the membrane may be traversed by cells that are to be selected (or de-selected), and factors or nutrients may be used to “pull” a subset of cells across the barrier for harvest or removal. This may be done in conjunction with image- and laser-based cell destruction or delivery operations. In another example, a sheet of cells may be separated from the membrane by flowing a medium containing a cell matrix-disassociating compound into the chamber opposite the cell growth chamber. The compound penetrates the membrane through the pores and detaches the cell sheet from the membrane intact. This technique may be used for cell harvesting or destruction/clearing of an entire sheet of cells.

System for Laser Cell Culture Management

Traditionally, laser sources and subsystems used in laser-based cell culture systems were originally built for industrial cutting and marking processes and were repurposed for biotechnology applications. These lasers are expensive, bulky, and require dedicated power and cooling systems. Moreover, they have a limited lifetime compared to other system components, and redundancy for continuous operation is required in cell manufacturing operations. Thus, what is needed in the art are cheap, small, and efficient laser subsystems that may be incorporated into cell culture systems.

The various implementations disclosed herein include systems and methods for sharing a common laser or lasers in a cell culture system. Sharing lasers among a plurality of cell culture containers and/or across a plurality of cell culture processes may enable a reduction in size, cost, and cooling requirements for the laser system as compared to traditional laser systems. In addition, there is also increased redundancy and fast switchover to a new laser source if one laser fails.

FIG. 116 is a diagram illustrating a cell culture system 11600 with shared laser resources in accordance with various implementations. The cell culture system 11600 may be embodied in a standard server rack format, as disclosed with reference to FIGS. 74-76B. For example, the cell culture system 11600 may include several modules located within a server rack frame 11602. The cell culture system 11600 may include one or more computing subsystems 11604 (e.g., computing subsystem 110) co-located with cell process modules to provide image processing, laser patterning, or other computation, storage, and communication services.

The cell culture system 11600 may include a plurality of cell process modules 11606 configured to accept cell culture containers (e.g., cell culture containers 104) with live cell cultures and monitor and manage these cell cultures. For example, the cell process modules 11606 may be configured to accept cassette-based cell culture containers, or alternatively cell culture container formats such as microwell plates, flasks, or roller bottles. The cell process modules 11606 may be configured to maintain environmental conditions (temperature, gas concentrations, etc.) and may manage media and reagent exchange in the cell culture containers. The cell process modules 11606 may also perform imaging and other measurements of the cell cultures in the cell culture containers.

The cell process modules 11606 may be further configured to perform laser-based operations on the cell cultures in the cell culture containers. These operations may include destruction of cells, whether of specific cells as determined by an imaging subsystem, or pre-programmed areas/volumes of cells (e.g., to maintain a certain cell density or to harvest materials from a cell-based process). These cell operations may also include laser-driven intracellular delivery of compounds into live cells or extraction of intracellular components from live cells. These cell operations may be performed in a variety of ways, including but not limited to direct action of the laser on the cells or cell membranes, thermal action of the laser on the cells via an absorbing material, or mechanical action in which laser energy is converted into a mechanical energy such as a microbubble formation. The absorption mechanism by which the laser light is converted into thermal or mechanical energy may be direct plasma formation in the case of short-pulse high-intensity systems. In other cases, conversion may be accomplished through the use of an absorbing material, including but not limited to cell media, dye or particles in the cell media, nanoparticles, labels, or beads that either permeate the cell culture or attach based on specific receptors/structures, or layers of material specifically configured to absorb laser radiation.

To perform these cell operations, laser power in pulsed or continuous wave (CW) form is utilized, sometimes with very specific attributes such as wavelength, power, pulse energy, and duration. As a result, the laser sources for cell operations may be expensive and/or bulky systems that include supporting components for air or liquid cooling, power supplies, and monitoring and control systems. In addition, for high reliability it may be desirable to have backup lasers so that if one laser experiences degradation or malfunction, another laser may be immediately brought online so cell culture management processes are not interrupted.

The implementations disclosed herein overcome the limitations of cost, space, complexity, and reliability that are inherent to cell culture management process modules that each contain their own dedicated laser subsystems by enabling centralization and sharing of a common laser subsystem. The cell culture system 11600 includes a laser subsystem 11608 mounted on the server rack. In the configuration shown in FIG. 116, the output of the laser subsystem 11608 may patched via an optical fiber cord 11610 into an optical multiplexer 11612. The optical multiplexer 11612 accepts two laser inputs 11614 (one of which is connected in the example shown in FIG. 116) and provides laser power for cell process module use on a number of outputs (e.g., eight possible outputs as shown in FIG. 116), six of which are in use as shown in FIG. 116 by optical fiber patch cords 11616. In this manner, a single laser subsystem may be shared among a plurality of cell process modules 11606, significantly reducing the space requirements, cost, and complexity of each cell process module 11606.

FIG. 117 is a diagram illustrating another cell culture system 11700 with shared laser resources in accordance with various implementations. The cell culture system 11700 may include two laser subsystems 11702 for redundancy, but in general the cell culture system 11700 may include any number of laser subsystems. In some implementations, the laser subsystems 11702 may be used to provide different illumination characteristics. For example, a 532 nm nanosecond-pulsed laser may be used provide high peak power pulses for cell lysing operations based on explosive microbubble formation, whereas a CW laser may provide narrow wavelength, stable 532 nm illumination output for Raman spectroscopic measurements, or high continuous power output for thermal operations on the cells or other cell culture components.

In some implementations, it may be desirable to deliver a specific polarization of light to the cell process modules and so the laser subsystem 11702 may be configured to output polarized light (e.g., at a specification of 100:1) and may include polarization-maintaining components such as optical fibers and optical couplers or splitters. A multiplexer 11704 may be configured to accept laser inputs from the laser subsystem 11702 via patch cables 11706 to panel connectors on the multiplexer 11704. In a typical server rack configuration, the patch cables 11706 may be arranged in the rear portion of the server rack along with power cables, tubing for heating/cooling, and tubing for gas distribution to keep the front clear for loading/unloading of cell culture containers.

The multiplexer 11704 may include an optical switch 11708 to select one of the laser inputs. A fiber tap 11710 may be used to divert a small amount of light to a monitor photodiode 11712. The monitor photodiode 11712 may be used to monitor laser power, pulse frequency, etc. to ascertain whether the currently-selected laser is functioning properly, or to detect degradation in function, and to allow switchover to a backup laser. The multiplexer 11704 may include a communications connection to the backup laser module to turn power on and go through a warmup process before switchover, or the backup laser may be running continuously, or kept in "warm" mode and switched over instantaneously.

The majority of the laser power then passes into a distribution subsystem 11714, which may be configured to evenly split the laser power among the cell process modules in the cell culture system 11700. The laser subsystems 11702 may be configured to produce a sufficient amount of laser power so that when it is divided each cell process module still receives sufficient laser power to perform cell operations. The distribution subsystem 11714 may include a series of evanescent fiber couplers with 50/50 output ratios to split the laser light into a number of output ports (eight in the example shown in FIG. 117, but in general there may be any number of output ports). In other implementations in which the ratio of laser power provided to the cell process modules to laser output is higher, the fiber couplers may be replaced by 1×2 optical switches, which may either be mechanical switches or waveguide-based switches such as Mach-Zehnder interferometer-based switches. The splitting or switching function shown in FIG. 117 may also be performed in free space, using 50/50 beam splitters or mechanical optical switches (including a 1×8 switch) for example.

The light outputted by the multiplexer 11704 may be outed to fiber connector ports 11716, which have delivery optical patch fibers 11718 attached when in use and are covered with absorbing terminator caps for eye safety when not in use. In some implementations when switchover redundancy is not required, the multiplexer 11704 multiplexer may be integrated into a single unit with the laser source. The optical patch fibers 11718 deliver laser light to cell process control modules 11720, where the light is used to process cell cultures in cell culture containers 11722. An example implementation of using a laser to perform cell operations on cell cultures may utilize a nanosecond laser source such as the Spectra-Physics SPFL 532 fiber laser, which produces 40 microjoule pulses (5 nsec) at 500 kHz. The cell process modules 11720 may only require ~50 nJ of pulse energy to form explosive microbubbles for cell deletion when using a plasmonic absorber film in the cell culture container. In this configuration, and taking into consideration an ample optical loss budget for connectors, couplers, and cell culture process module components, a single laser unit may be shared by sixteen process control modules (picking a power of 2 accommodated by most optical splitting schemes). This light may be delivered via a single-mode polarization-maintaining (PM) fiber such as ThorLabs PM-S405-XP PANDA fiber to maximize the amount of usable light (and minimize additional components) in the cell process modules 11720. For 50:50 splitting, 1×2 50:50 PM fiber couplers such as the ThorLabs PN530R5F1 may be used, and for monitoring purposes a 99:1 PM coupler such as the PN530R1F1 may be used.

FIG. 118 is a diagram illustrating a cell process module 11800 utilizing shared laser resources in accordance with various implementations. The cell process module 11800 is configured to manage a cell culture in a cell culture container 11802, which may be a cassette with on-board media and reagents, or a standalone container such as a flow cell, a microwell plate, a flask, a dish, a roller bottle, or other container for cell cultures. The cell process module 11800 may manage temperature, pH, media exchange, reagents, pH, etc. of the cell culture containers 11802. The cell process module 11800 may also be configured to use an imaging subsystem (which may be integrated with the laser processing system described herein) to image the cell culture (e.g., cell imaging subsystem 112).

Laser light may be delivered to the cell process module 11800 via an optical fiber connector 11804. A fiber 11806 may be connected to the optical fiber connector 11804 to a moving portion 11808 of an optical engine that moves freely along at least one axis, drive by a translation stage 11810 that simplifies the relay of laser light onto the moving assembly. A controller 11812 may be configured to coordinate coordinates multiple operations of the cell process module 11800, including monitoring photodiodes, motion and scanning, and laser pulse or power modulation. On the moving portion 11808, a fiber collimator 11814 produces a collimated free-space beam (shown as a dotted line in FIG. 118). A beam splitter 11816 allows a small percentage of light (e.g., 1%) to pass to a photodiode 11818.

The photodiode 11818 may be configured to measure the delivered laser pulse energy (or power in the continuous wave case) in real time for the purpose of adjusting the power or energy delivered to a sample. Moreover, in pulsed laser systems, the photodiode 11818 may be configured to feed electronics or firmware that acquires pulse timing from the optical signal, and coordinates internal component timing using this pulse train. This configuration takes advantage of Q-switched pulsed lasers or other lasers that provide a pulsed output with regular intervals, such that once a module is "locked on" to the timing of the pulses, it may synchronize its internal components reliably to the incoming laser pulses. For example, once there is a lock onto the pulse timing, an optical modulator 11820 (for example, an acousto-optic modulator) may modulate pulses on a pulse-to-pulse basis to tailor energy from point to point in the cell culture. The modulator 11820 may also provide steering of the beam along an axis. For example, when using an acousto-optic modulator, RF power controls the amount of light passing to the cell culture, whereas RF frequency may be used to change the output angle of the light to a small degree, allowing high-speed steering along one axis.

The modulated pulses then pass through a combined polarization beam splitter and wave plate 11822 which is configured to divert reflected laser light to a reflected-light monitoring photodiode 11824. The photodiode 11824 may be used to monitor the state of the cell culture container 11802, or coating applied to the cell culture container 11802. The photodiode 11824 may also be used to detect fiducial markings on the cell culture container 11802 or film within the cell culture container 11802 during laser scanning or imaging operations. The photodiode 11824 may also be used to detect focus using reflected laser light. The modulated laser light then is steered by a steering component 11826 that provides steering along at least one axis. The steering component 11826 may include a galvanometric mirror assembly, a spinning polygonal mirror, an acousto-optic deflector, a resonant electrostatically-driven mirror, or other light-steering components and their combinations. The steering axis may be configured such that after the beam passes through one or more lenses 11828 configured to focus light onto a region 11830 within the cell culture container 11802, the beam is steered roughly perpendicularly to the axis of motion of the moving portion 11808 of the optical engine as it is translated by the translation stage 11810.

The motion of the translation stage 11810, the modulation of the beam, and the scanning of the optical engine are all coordinated by the controller 11812. Another axis of motion which adjusts the axial position of the optics relative to the cell culture (the "focus" or "Z" axis) may be simultaneously controlled by positioning the lens 11828 or the cell culture container 11802, or by use of an adjustable lens within the lens assembly (not shown). The laser light that passes through the cell culture container 11802 may be captured on the opposite side. In the implementation shown in FIG. 118, a dichroic or laser band beam splitter 11832 may be used to divert light having the laser wavelength while passing through other light, for example light for illuminating the cell culture for imaging purposes (not shown). This assembly may move in unison with the moving portion 11808 of the optical engine to keep illumination and detection aligned with scanning portions. The laser light from the beam splitter 11832 is received by a photodiode 11834 which may be configured to monitor the transmitted light in real time to estimate the amount of light absorbed or reflected. This may be used to tailor the laser power in the cell process module 11800 to adjust to conditions in the cell culture container 11802. It may also be used to detect fiducial markings within the cell culture container 11802 to ascertain or track XY position or Z focus.

An additional reference photodiode 11836 may be positioned outside of the area of the cell culture container 11802, and with components near the focus plane of the optical engine. For example, a pinhole aperture may be used in combination with a detector to measure the laser power emitted through the entire system, measure the laser spot shape, measure laser spot position, and measure the focus position of the lens system, all for the purpose of tracking in semi-real time to make adjustments to laser power, focus and other beam handling parameters, and steering.

Large Format Managed Adherent Cell Cultures

The various implementations disclosed herein include systems for managing 2D adherent cell cultures using cell culture containers that allow high-quality cell culture imaging, including label-free imaging, in conjunction with tools for selectively removing cells based on those images or series of images (and in some cases predictive models). Additionally, various implementations disclosed herein include tools for implementing selective cell expansion that may operate without opening the cell culture container that seals in a cell culture. This allows the preservation of a sterile environment and prevents cross-contamination between samples. Additionally, various implementations disclosed herein include laser cell editing subsystems for performing various cell operations such as cell removal. In some implementations, lasers may be used in conjunction with a laser-activated film that forms at least one surface of the cell culture container on which cells adhere, in which this laser-activated film may transduce energy delivered by the laser to the selected cells in order to destroy them.

The cell culture containers disclosed herein may include planar formats such as microwell plates, flasks, and fluidic chambers with glass or plastic windows/cell-carrying surfaces. These planar formats may be expandable in 2 dimensions, but only up to a point at which the container becomes prohibitively large for handling and the required translation of the imaging system and tools becomes too large and expensive.

In various implementations disclosed herein, cell culture containers may also include non-planar formats and shapes, which may increase the surface area for cell growth without inhibiting space constraints in a cell culture system. The cell culture container may include formats using a flexible foil that supports adherent cell culture, and may also include a laser-activated thin film for in situ processing of cells. Such flexible, non-planar arrangements may allow for processing of large areas of adherent cell cultures while minimizing the total system volume and cell media volume. These non-planar arrangements may also retain similar functionality to planar arrangements, such as total tracking or traceability of cell culture through imaging and total "editability" of cell culture through a laser processing tool configured to kill unwanted cells and thereby selectively expand cell cultures.

FIG. 119 is a diagram illustrating a flexible foil 11900 used in a cell culture container in accordance with various implementations. The foil 11900 may be composed of a cell-compatible material, preferably transparent for imaging and laser editing, and potentially porous to pass through media or other cell culture constituents. The foil 11900 may include a laser-activated film 11902 that is configured to absorb laser radiation to produce effects on cells cultured on its surface. In such cases the laser-activated film 11902 may be either on the cell-bearing face of the foil 11900, or in the case of a porous foil, may be on the opposite face. The film 11902 may contain fiducial markings 11904 that serve to register imaging and laser operations performed over time on the cell culture growing on the foil 11900. Foil 11900 may be manufactured in a range of sizes including long strips for continuous processing, or for coiling into an efficient volume-filling surface for cell growth in a cell media volume.

FIG. 120 is a diagram illustrating a cylindrical flexible foil 12000 used in a cell culture container in accordance with various implementations. The cylindrical foil 12000 may be used in a roller bottle type cell culture configuration. The cylindrical foil 12000 may be formed using a flexible foil sheet that is rolled into a cylinder by joining its ends. The cylindrical foil 12000 may include a laser-activated film 12002 that may be situated on the inside or outside of the cylindrical foil 12000. The film 12002 may contain fiducial markings 12004 that serve to register imaging and laser operations performed over time on the cell culture growing on the cylindrical foil 12000. While FIG. 120 illustrates the use of a flexible foil to form a cylinder, in general the flexible foil may be formed into a variety of shapes, including belt shapes or formats that include twists to form Mobius strip-like surfaces to accommodate processes in which the cell-bearing surface is on the interior of the loop for one portion of a process and the exterior for another portion. In some implementations, the cylinder may be formed by coating a pre-made cylinder (which may be inflexible) with foil material, for example using atomic layer deposition. The inside of the cylinder would be covered the foil material, while the outside is either shielded from the deposition process, or the foil later removed from the outside.

FIG. 121 is a diagram illustrating a cell culture system 12100 including a roller bottle cell culture container 12102 in accordance with various implementations. The roller bottle 12102 may include a laser-activated film on the interior cell-bearing surface that supports a cell culture 12104. The roller bottle 12102 contains cell culture media 12106 and the roller bottle 12102 may be rotated (as indicated by arrow 12108) to expose the cells growing on the interior surface to the media 12106, effectively "wetting" the cell culture surface for the duration of each rotation by surface tension. The cell culture system 12100 may include an optical subsystem 12110 (e.g., cell imaging subsystem 112 and/or cell editing subsystem 114) that images the cell culture 12104 via an objective 12112. The image data may be used to generate a set of laser processing instructions which are executed via focused laser pulses 12114 on the laser activated film carrying the cell culture, enabling deletion of cells from the surface. The optical subsystem 12110 may be connected to a computing subsystem (e.g., computing subsystem 110) and in some cases one or more laser sources via optical fiber by an umbilical 12116 that allows translation of the optical subsystem 12110 along the length of the roller bottle 12102. Imaging may be performed either in the region completely submerged in cell media, or in a region that is depleted of most media, which will result in differing refractive index profiles. Likewise, laser processing may be done on the portion submerged or the media-depleted portions of the roller bottle 12102 as it rotates—these positions may result in different mechanical and/or thermal effects from laser irradiation. In some implementations, the imaging and laser processing may be done in different zones of the rolling process.

FIG. 122 is a diagram illustrating another view of a cell culture system 12200 including a roller bottle cell culture container 12202 in accordance with various implementations. The roller bottle 12202 may include a laser-activated film on the interior cell-bearing surface that supports a cell culture. The roller bottle 12202 may be rolled using actuators 12204. An optical subsystem 12206, connected by umbilical 12208, may be translated along a line 12210 orthogonal to the rolling motion. The cell culture may be imaged and laser processed through objective 12212. Various timings for imaging, laser editing, and related processes may be used. For example, imaging and laser processing may be performed on successive rotations, with data being processed as a corresponding "line" of cells rotates through media. The cell culture system 12200 may further perform a "washing" step after laser processing in which the bottle is rolled rapidly, potentially both clockwise and counterclockwise, to increase liquid velocity, and therefore shear forces on any attached cell debris to remove it from the surface. The roller bottle configuration illustrated in FIG. 123 may additionally include ports for media exchange in the roller bottle 12202. These ports may either be fixed and attached to flexible tubing that may wind/unwind as the roller bottle 12202 rotates in one direction and then the other. In alternate implementations, it may include tubing ports with slip interfaces such that the roller bottle 12202 may rotate continuously in a single direction and attached tubes remain rotationally stationary to provide a substantially aseptic connection through which media may be exchanged. Such ports may be fitted to one or both ends of the roller bottle 12202.

FIG. 123 is a diagram illustrating a cross-sectional view of a cell culture system 12300 including a roller bottle cell culture container 12302 in accordance with various implementations. The roller bottle 12302 may include an interior cylinder 12304 composed of a cell-bearing foil formed into a cylindrical shape. The interior cylinder 12304 may serve as a cell-bearing structure for an adherent cell culture. In some implementations, the interior cylinder 12304 may rotate independently within a stationary exterior cylindrical structure of the roller bottle 12302. The cell culture system 12300 may include illumination, imaging, and laser processing subsystems that monitor and control the cell culture process. A cell media reservoir 12306 is contained within the roller bottle 12302. The interior cylinder 12304 may be supported by one or more sets of cross-bearing members 12308, which may serve to rotate the interior cylinder 12304 using a plurality of magnetic elements 12310 that couple magnetically to external magnetic components. In this manner the interior cylinder 12304 may be precisely aligned and rotated inside of the sealed bottle.

Cells 12312 are cultured on the interior surface of the interior cylinder 12304, are rotated through the media reservoir 12306, and are imaged and laser processed by an optical system 12314. In some implementations, trans-illumination may be provided from the opposite side of the roller bottle 12302 as shown by illumination source 12316. In some implementations, various off-angle, reflective, dark-field, or epi-illumination illumination sources 12318 may also be present. There are several advantages of a two-cylinder system (i.e., independent interior cylinder that rotates independently from an external stationary cylinder) as shown in FIG. 123. For example, the interior cylinder 12304 may have significantly smaller rotational inertia, allowing for faster acceleration and deceleration of rotational motion. In addition, the external cylinder may have tubing attachments that feed fresh media and reagents, and remove waste media and debris, and these tubing attachments do not necessitate rotating couplings, making them achievable for a sterile cell culture in an aseptic environment. Furthermore, the freestanding foil interior cylinder 12304 allows for the use of a range of materials including porous foils that may promote media perfusion, and or/allow a 2-liquid system internally (e.g., one liquid on the internal side of the interior cylinder 12304 another between the interior and exterior cylinder, separated by a porous foil that carries cells).

FIG. 124 is a diagram illustrating another view of the cell culture system 12300 of FIG. 123 in accordance with various implementations. The interior cylinder 12304 may be fixed in position and may only move along a rotational axis without breaking the seal of the exterior cylinder via magnetic couplings 12310 mounted on the cross-member supports 12308. A motor 12402 on the exterior of the roller bottle 12302 rotates magnets coupled to the magnetic couplings 12310 to support and rotate the interior cylinder 12304 that carries the cell culture 12312. One advantage of the two-part roller bottle cell culture system is that the exterior cylinder may have sterile-connected tubing for the purpose of delivering fresh media and reagents (shown by tube 12404) and removing spent media, cell debris and/or cell products (shown by tube 12406) without complex/non-aseptic attachments that would be required if the exterior cylinder was rotating. In such a manner, a fluidic management system 12408 may be fully aseptically connected to the roller bottle 12302 for long-term cell culture management without any manual operations and without any opening of the cell culture container that would require a sterile environment.

FIG. 125 is a diagram illustrating a roller bottle implementation of a cell culture system 12500 in accordance with various implementations. The cell culture system 12500 includes a roller bottle 12502 having an exterior cylindrical wall 12504 and an interior cylindrical wall 12506 that are concentrical. A cell culture 12508 and cell culture media 12510 may be contained between the exterior cylindrical wall 12504 and the interior cylindrical wall 12506, and adhered to the interior of the exterior cylindrical wall 12504. The exterior cylindrical wall 12504 may include a laser-activated film to aid in cell imaging and performing various cell operations such as removal or poration. The roller bottle 12502 may be rotated so that all the cell cultures 12508 located at various sites around the cylinder are exposed to the cell culture media 12510 for a portion of time. One advantage of the implementation shown in FIG. 125 is that it minimizes the volume of cell culture media used in the cell culture container. Another advantage is that light source 12512 or other tools (imaging systems, sensors, etc.) may be placed on the interior of the roller bottle 12502 for effective monitoring, imaging, and management of the adherent cell culture. The example shown in FIG. 125 includes an imaging and cell editing subsystem 12514 on the exterior of the roller bottle 12502, taking advantage of the transillumination provided by the light source 12512.

FIG. 126 is a diagram illustrating another roller bottle implementation in a cell culture system 12600 in accordance with various implementations. The cell culture system 12600 includes a roller bottle 12602 having an exterior cylindrical wall 12604 and an interior cylindrical wall 12606 that are concentrical and stationary. The roller bottle 12602 also includes a cylinder 12608 on which a cell culture 12610 is adhered and that freely rotates between the exterior cylindrical wall 12604 and the interior cylindrical wall 12606. Rotation of the cylinder 12608 allows the cell culture 12610 to move through cell culture media 12612 and past an illumination system 12614 and optical system 12616, which may include imaging and cell editing subsystems. In this manner, the example shown in FIG. 126 illustrates a combination of flexible lighting, imaging, and sensing configurations that may be achieved. In addition, media efficiency is high due to the double-walled roller bottle configuration, and sterile connections may be made to the roller bottle 12602 for the purpose of exchanging cell media, removing waste and debris, and removing cell products from the system, all in an automated and aseptic manner.

FIG. 127 is a diagram illustrating a cell culture system 12700 including a multi-roll cell culture container in accordance with various implementations. The cell culture system 12700 includes a flexible foil 12702 that supports an adherent cell culture 12704 on one side. The foil 12702 may be rolled and therefore transported from one roll to another as indicated by arrow 12706. An imaging subsystem 12708 (e.g., cell imaging subsystem 112) may be configured to image the cell culture 12704 along a line 12710 as the foil 12702 is transported. The image information may be processed by a computing system (e.g., computing subsystem 112), which outputs a map of regions to be processed by a laser processing system 12712 (e.g., cell editing subsystem 114). The laser processing system 12712 may be configured to, at the appropriate delay (and potentially looking at fiducial markings also measured by the imaging system 12708), scans the cell culture 12704 along line 12714 to remove selected cells. The foil 12702 may be moved from a first roll 12716 to a second roll 12718 and the cell culture 12704 is selectively processed (e.g., cells removed) in the process, allowing for a large-area continuously managed cell culture while maintaining relatively compact and simple imaging and editing systems.

FIG. 128 is a diagram illustrating another view of the cell culture system 12700 including a multi-roll cell culture container in accordance with various implementations. The first roll 12716 and cell culture media 12804 may be contained in a first sealed cell culture chamber 12802. Connector ports 12806 may be used to exchange media in an automated and aseptic manner. The foil 12702 is transported (sometimes, back and forth between the first sealed container and a second cell culture chamber 12808 in a multi-step process) through a measurement and laser processing region 12810, where an optical system 12812 performs imaging and laser processing on the cell culture 12704. In the implementation shown in FIG. 128, a washing system sprays liquid 12814 onto the laser-processed regions of the cell culture 12704 to dislodge and wash away any cell debris through port 12816, prior to the foil 12702 being coiled up in the second cell culture chamber 12808. In such a roll-to-roll system, the cell culture 12704 may be maintained and managed for days or weeks, with cell media exchanged aseptically and with different reagents/components for different parts of the process, if desired. In a final step, cells may be disassociated from the foil 12702 and harvested through a liquid port. Alternatively, a continuous cell culture process may be performed where a fraction of cells are continually harvested from the cell culture system 12700, either by selective washing and/or laser processing (either intact, or lyse, where the cell contents are desired).

FIG. 129 is a diagram illustrating a cell culture system 12900 using flexible foil in accordance with various implementations. The cell culture system 12900 includes a continuous belt of flexible foil 12902 hosting an adherent cell culture 12904. At least part of the foil 12902 resides in a cell culture media 12906 and part of the foil 12902 is transported past an imaging subsystem 12908 (e.g., cell imaging subsystem 112) and a laser processing subsystem 12910 (e.g., cell editing subsystem 114). In an example implementation, based on information computed from the images captured by the imaging subsystem 12908, the laser processing subsystem 12910 ablates cells from the foil 12902 with pulsed lasers that induce ejection of cells and/or cell contents 12912 from the foil 12902, which is inverted in a gas-filled region. These cells or cell contents 12912 may be captured by a receptacle 12914.

In this manner, a very large area of cells may be maintained and periodically measured by imaging and other means, and based on this information processed by the laser subsystem 12910. For example, cell removal may be prompted by detection of the wrong phenotype or cell density, or by detection that cells have accumulated sufficient product internally to harvest. Cells may be adhered to only a portion of the foil 12902 in this configuration, such that they reside in the cell culture media 12906 for the majority of the time in process, and are moved relatively rapidly through the imaging, laser processing and/or washing sections. In some implementations, the foil 12902 may be configured with a twist to form a Mobius strip-like or otherwise twisted configuration allowing cells to be on the interior for a portion of the process and exterior for another. As with other implementations, the cell culture system 12900 may be sealed in a sterile container with media and reagents aseptically connected such that a high-volume process may be run in each system, in an otherwise non-sterile environment.

FIG. 130 is a diagram illustrating a cell culture system 13000 with sequential stations in accordance with various implementations. The cell culture system 13000 may include a sequence of media baths and imaging/laser editing stations that may run an entire cell process in a continuous fashion. The cell culture system 13000 includes a flexible foil 13002 with a laser activated film that supports an adherent cell culture process, and runs an end-to-end cell process with a series of cell media baths 13004 and a series of inspection and laser processing stations 13006. The cell culture process may utilize multiple media/reagent compositions in each cell media bath 13004, and intervening laser cell patterning and/or selection processes may be run at each laser processing station 13006. For example, a complex differentiation process from stem cells to somatic cell types may be performed on the cell culture system 13000, with seeding of source cells and subsequent adherence to the foil 13002, pre-patterning of source cells, in situ de-selection of cells that are differentiating improperly, in-situ de-selection of undifferentiated cells, and finally disassociation of cells and harvest (or, harvest of a continuous sheet of cells for tissue-type applications) may all be performed on a continuous band, and inside of a sterile-sealed system in which imaging and laser apparatuses are performing their functions through a transparent window.

Plasmonic Spectral Monitoring System for Cell Culture Management

The various implementations disclosed herein include cell culture containers for adherent cell culture, complete with mechanisms for imaging the cell cultures and mechanisms for selectively removing cells. Various implementations may also include the use of semi-transparent plasmonic films suitable for both high-quality imaging of adherent cell cultures, as well as measurement of media, biofilms, and cell adhesion through their optical properties. These plasmonic films may also be used for resonant absorption of laser illumination for the purpose of acting upon the contained cell cultures, for example selectively destroying cells or delivering intracellular materials into the cells.

The plasmonic film disclosed herein may be applied directly to the window or wall of a cell culture container that is used to support an adherent cell culture, or may be disposed on a cell culture foil (e.g., the foils disclosed with reference to FIGS. 119-130) that is placed inside a cell culture container. The film may be fabricated to have a resonant peak and with a surface at which energy couples into the surrounding volume, where it interacts with cell media, cell media components, coating materials, proteins, extracellular matrices, cell products, or cellular components including cell membranes and surface proteins (including proteins for cell adhesion that form focal adhesions). Through this energy coupling, the resonant peak of the plasmonic film shifts in amplitude and/or wavelength when interacting with different materials locally, allowing sensing of local conditions. The readout of this film may be done in transmission (where extinction is measured) or reflection mode. The readout may be accomplished using a broad light source and a spectrometer, a broad source and a series of bandpass filters plus a detection system, discrete wavelength sources (such as LEDs) and a single or multiple detection systems, tunable wavelength sources, tunable detectors, hyperspectral imagers, and various other arrangements and combinations. In some implementations, the film's optical properties are measured over a region using a large beam. In alternate implementations, an imaging system is used to image varying properties over a section of the film bearing an adherent cell culture.

The various implementations of the plasmonic film may be used to measure media composition (via refractive index), the presence and thickness of layers of material on the surface (including but not limited to extracellular matrices and non-stick films), and the presence or absence of cell adhesion points. The various implementations of the plasmonic film may be used in conjunction with a laser system that may ablate materials adsorbed on the plasmonic film, allowing measurement prior to, and after, ablation, or the buildup of material over time after ablation. In some implementations, the plasmonic film may be overcoated with material in some regions to shield it with interactions and removed in other regions to provide reference regions for the spectroscopic system.

FIG. 131 is a diagram illustrating a cell culture system 13100 with a plasmonic film in accordance with various implementations. The cell culture system 13100 utilizes fiber-based illumination and detection components to measure the spectral properties of a plasmonic film inside of a cell culture chamber. The cell culture system 13100 includes a spectrometry unit 13102 that communicates with a computing subsystem 13104 (e.g., computing subsystem 110) configured for cell culture management. The spectrometry unit 13102 emits light via an optical fiber bundle 13106 to a collimating lens 13108, which projects light through a cell culture chamber 13110. The cell culture chamber 13110 includes a first window 13112 with a plasmonic film 13114 on its surface, a space containing cell culture and media, and another (top) window.

When the cell culture chamber 13110 is used as a fluidic chamber, the space between the windows is typically filled with cell culture media, allowing a probe beam 13116 from the spectrometry unit 13102 to pass directly through to a capture lens 13118. Additionally, reflected light 13120 from the plasmonic film 13114 may be captured and returned to the spectrometry unit 13102. The measured spectra may be either the extinction spectrum as measured by transmission, or the reflection spectrum as measured by light reflected by the plasmonic film 13102, or a combination of the two. In some implementations, the optical components may orient at an angle other than 90 degrees to the plasmonic film 13114, and in such a case the reflected light may be captured by a separate lens and fiber. Thus, the spectrometry unit 13102 may be configured to capture the absorption spectrum of the cell culture media as it passes through the cell culture chamber 13110. This spectrum may be separated from the spectrum of the plasmonic film 13114 by the use of regions where the plasmonic film 13114 has been ablated or not deposited, for example at "fiducial" markings or regions. With appropriate additives, such as phenol red for example, the spectrometry unit 13102 may measure the pH of the cell culture media as part of the cell culture management system. The spectrometry unit 13102 may also measure the extinction and/or reflection spectra of the plasmonic film 13114.

The plasmonic film 13114 may also serve as a laser-activated film for cell processing, including cell destruction and intracellular delivery by means of thermal and/or mechanical signals generated when the plasmonic film 13114 is illuminated with a laser. The plasmonic film 13114 may be semi-transparent and suitable for transducing laser energy at at least one wavelength, and for high quality transmission imaging of cell cultures at at least another wavelength, as described herein. The plasmonic film 13114 may be constructed so that its spectral properties (e.g., absorption, reflection) are sensitive to the refractive index of the material immediately surrounding it. This change in refractive index is reflected in a change in the amplitude and/or wavelength of one or more spectral features in the transmission and/or reflection from the plasmonic film 13114, and as a result the measurements by the spectrometry unit 13102 provides high sensitivity to changes in cell culture media, or in materials that are settling on, adsorbing to, or attaching to the surface of the plasmonic film 13114. For example, layers of materials such as proteins or an extracellular matrix 13122 that accumulates on the plasmonic film 13114 may cause the spectrum to shift. In this manner the production of proteins by the cell culture may be monitored by the spectrometry unit 13102.

In some implementations, the plasmonic film 13114 may also be used to monitor the deposition or depletion of layers that are deposited in the cell culture chamber 13110 to enhance (or inhibit) cell attachment and growth. For example, the cell culture system 13100 may be configured to monitor the deposition of Laminin, Matrigel, or other matrices. It may also be configured to measure a layer of PEG or other compound used to inhibit cell attachment to specific regions of the cell culture chamber 13110. This information may be used to replenish these layers, or to remove these layers using laser pulses focused on the plasmonic film 13114. Additionally, as an adherent cell culture 13124 proliferates in the cell culture chamber 13110 on top of the plasmonic film 13114, the regions where the cells attach to the plasmonic film 13114 or the matrix disposed on the film experience a local increase in refractive index as a result of the attachment proteins at the adhesion foci. In this manner, the cell culture system 13100 may effectively map adherent cell cultures and level of adhesion per area. This data may be used in conjunction with imaging data obtained through label-free imaging subsystems as described herein.

Figure 132A:
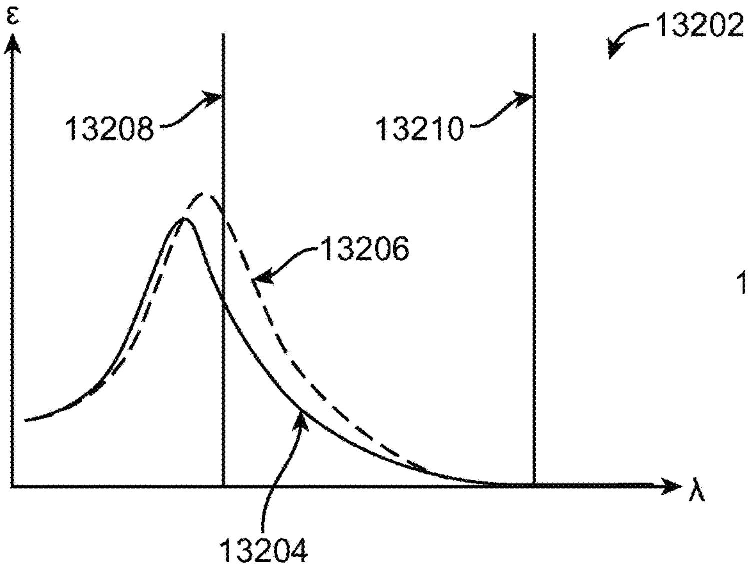

FIGS. 132A-D are diagrams illustrating extinction spectra of plasmonic films in a cell culture system in accordance with various implementations. FIG. 132A shows an example graph 13202 of an extinction spectrum from a plasmonic film with and without the presence of a biofilm. The graph 13202 shows plasmonic film transmission extinction on the y-axis vs. wavelength on the x-axis. A similar plot may be made with reflection (which is a component of extinction) on the y-axis instead. The plasmonic film has a resonant peak which causes a localized extinction loss when exposed to cell media only, as shown by curve 13204. When material accumulates on the plasmonic film, the local refractive index increases and the amplitude and wavelength of the peak shift, as indicated by curve 13206. These changes may be measured by a spectrometer system (which captures the entire spectrum, or at least a portion of it) at one or more wavelengths 13208 near the resonant peak. Another wavelength or wavelengths 13210, away from the resonant peak, may be used as a baseline level for measuring changes in film spectrum. Moreover, these wavelengths away from the extinction peak may be used to image the cell culture through the semi-transparent plasmonic film without interference from changes to the film, or the effects of material in the vicinity of the film. Thus, the accumulation or depletion of biofilm may be measured with transmission or reflection spectrum to monitor the cell culture system and adjust conditions, add reagents, or use the laser processing system to modify the contained cell culture, or the biofilm layers.

Figure 132B:
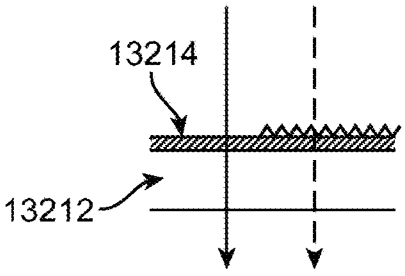

FIG. 132B shows an example of the physical setup corresponding to the spectra in FIG. 132A. A substrate or window 13212 has a semi-transparent plasmonic film 13214 disposed on it. The transmission (solid arrow) without biofilm corresponds to spectrum 13204 and where a biofilm has been deposited, patterned, or accumulated (dashed arrow) the transmitted spectrum corresponds to spectrum 13206. The measurement may also be made entirely in reflection, in which light enters and exits on the same side of the window 13212.

Figure 132C:
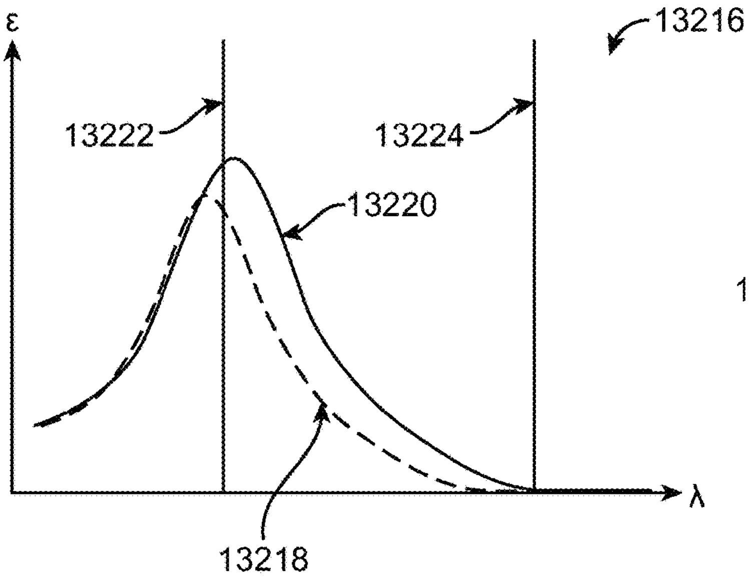

FIG. 132C shows an example graph 13216 of an extinction spectrum from a plasmonic film with and without the presence of cells, specifically cells with adhesion focal points to the film or extracellular matrix situated onto the plasmonic film. The graph 13216 shows the extinction spectrum at locations where an extracellular matrix is attached to the plasmonic film, indicated by curve 13218. The graph 13216 also shows the extinction spectrum at locations where cells attach as well, where the proteins that form the adhesion points of foci further change the refractive index of the local environment around the film, shifting the spectrum as indicated by curve 13220. The mere presence of cells in the area may be measured by imaging, and combined with the spectral shifts measured to indicate the level of adhesion or other cell properties. The change may be measured with a complete spectral measurement, or with two or more wavelengths, for example one wavelength 13222 near the absorption peak and another ("reference") wavelength 13224 away from the resonant peak. This may be accomplished in its entirety, for example, using an imaging system that trans-illuminates the cell culture container with two wavelengths and uses a dichroic filter to separate light after a microscope objective in concert with two image sensors, or sequential illumination by these two wavelengths and a single image sensor to separately image the sample at the two wavelengths.

Figure 132D:
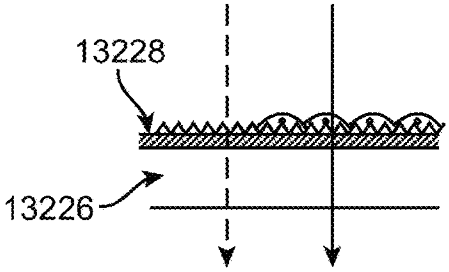

FIG. 132D shows an example of the physical setup corresponding to the spectra in FIG. 132C. A window 13226 supports a plasmonic film 13228. When the plasmonic film is coated with a biofilm such as an extracellular matrix, the transmitted light (dashed line) corresponds to spectrum 13218. When cells are present and adhered to the underlying matrix and/or surface, the transmitted light (solid line) corresponds to spectrum 13220. The measurement may also be made entirely in reflection, in which light enters and exits on the same side of the window 13226.

FIG. 133 is a graph 13300 illustrating extinction spectra of plasmonic films in a cell culture system in accordance with various implementations. The graph 13300 shows plasmonic film extinction spectrum when measured with and without a biofilm present. Measurements were made through a fluidic chamber designed for cell culture, in which one window has a plasmonic film formed from Gold nanoislands. The film is resonant at roughly 532 nm, at which it serves as a laser-activated film for pulsed laser destruction of selected cells, as described herein. The film is further used to measure the deposition of a biofilm, specifically Laminin, which is used as a matrix for cell culture, including induced pluripotent stem cell (iPSC) cell reprogramming and expansion. In this example, a chamber is filled with phosphate-buffered saline (PBS) and the transmission extinction (baselined against a chamber with no plasmonic coating) is measured, as shown by curve 13302. After the addition of Laminin to the chamber by a media change and incubation (and subsequent flushing with PBS), the Laminin attached to the surface of the plasmonic film shifts the extinction spectrum to curve 13304. The effect can be seen in both amplitude shift (horizontal lines 13306), and a shift in wavelength (vertical lines 13308).

FIG. 134 is a diagram illustrating a cell culture system 13400 with a plasmonic film in accordance with various implementations. In the example shown in FIG. 134, a microscopy system is used in conjunction with multiple illumination wavelengths to detect spectral changes in a plasmonic film disposed inside a cell culture chamber. This may be used to measure changes in local biomolecular composition, including but not limited to media composition, biofilm accumulation and cell culture adhesion. The cell culture system 13400 includes a cell culture chamber 13402 containing cell culture media in a cell culture chamber 13404 between two windows 134006 and 13408. A plasmonic film 13410 is placed on the bottom window 13408. The plasmonic film 13410 is in contact with cell culture media in some regions, in other regions it is coated with an extracellular matrix 13412, and in other regions cell culture 13414 is adherent to the matrix 13412 and the plasmonic film 13410.

The cell culture system 13400 includes a microscope illumination subsystem 13416 configured to emit at least two wavelengths: a resonance wavelength 13418 that is in the range of the plasmonic film's resonant extinction peak, and a reference wavelength 13420 which is away from the resonance peak. The reference wavelength 13420 may also be used to perform label-free transmission imaging of the cell culture 13414 in one or more modalities as described herein. An imaging subsystem 13422 (e.g., cell imaging subsystem 112) captures light and produces images of the cell culture 13414 and plasmonic surface at both wavelengths 13418, 13420. A computing subsystem 13424 (e.g., computing subsystem 110) processes these images. For example, the computing subsystem 13424 may be configured to normalize each image to a common intensity, and then subtract one wavelength image from another to produce a differential image that corresponds to the amplitude of the resonant extinction in the plasmonic film 13410. The amplitude depends on the local biochemical composition (e.g., cell culture media, extracellular matrix, cells and adhesion focal points) with other sources of absorption or scattering normalized out.

The resulting images may be transmitted to cell culture control systems, such as a cell editing/laser processing subsystem (e.g., cell editing subsystem 114). The cell culture control system uses the cell images, as well as the differential images corresponding to the plasmonic film absorption, to calculate the state of the extracellular matrix, and in regions with cells, the level, shape, and distribution of cell adhesion foci. The image of adhesion foci may be used in conjunction with other images of the cells (for example, quantitative phase images produced by the same illumination and imaging system) to make predictions of cell function, health, phenotype, cell cycle, metabolism, etc. These predictions may in turn be used to control the cell culture, either at a macroscopic level with media or reagents, or by selective editing of the cell culture. For example, a pulsed laser system may be configured to focus on the plasmonic film to produce explosive microbubbles, which in turn rupture cell membranes and destroy them, allowing them to be removed from the cell culture container 13402. In some embodiments, the cell culture system 13400 may also be configured to image the effect of materials secreted below the cells and in contact with the plasmonic film 13410.

The cell culture system 13400 may also be configured to measure cell adhesion during various other processes. For example, after laser treatment to remove cells, the cell culture system 13400 may be configured to monitor degradation of adhesion points. In regions where the degradation points do not sufficiently degrade, additional laser processing may be applied. The degradation rate and level may further be utilized to time "washing" steps in which cells deleted by the laser process are washed away. Similarly, the cell culture system 13400 may also implement processes for cell harvest or re-suspension, in which enzymes or other means are used to weaken cell-cell and cell-substrate adhesion. Monitoring cell adhesion point density may track the progression of this process, for example to minimize the time cells are exposed to agents or enzymes such as trypsin. In implementations in which laser or other systems are used to break up colonies or sheets of cells in conjunction with enzymes, the information provided by the cell culture system 13400 may allow dynamic use of these breakup tools. For example, additional laser cuts (e.g., to remove cells to allow for more rapid detachment of sub-colonies) may be made to increase the rate of detachment in areas showing resistance to detachment from the substrate.

FIG. 135 is a graph 13500 of absorbance of cell culture media measured within a cell culture container having a plasmonic film in accordance with various implementations. The graph 13500 shows the spectrum of cell culture media, including phenol red, measured at different pH conditions. Phenol red has one absorption peak at a first wavelength 13502, which increases with pH, as indicated by the curves 13504. Another peak, at a second wavelength 13506, increases as pH is lowered. For phenol red-containing cell culture containers, the media spectrum may be measured independently in a region where there is no plasmonic resonant film to assess media status. This may be used by a system controller to assess cell culture (based on rate of change of the pH vs number/density of cells measured via imaging) and/or control media conditions (e.g., by adding fresh media, controlling $CO_2$ concentration, or directly adding acid or base to the cell media to change pH). This spectrum may also be used to normalize measurements made through regions with the plasmonic film to remove absorption effects from the cell culture media in the path.

System for High-Speed Cell Culture Imaging

Various implementations disclosed herein include additional imaging configurations in a cell culture system (e.g., cell culture system 100), including configurations that enable high-speed cell culture imaging. FIG. 136 is a diagram illustrating a high-speed imaging subsystem 13600 for use in a cell culture system in accordance with various implementations. The imaging subsystem 13600 is configured to use annular illumination and an angled image sensor to capture in-motion multi focal plane data for the purpose of quantitative phase reconstruction. The imaging subsystem 13600 images a sample 13602 that is in continuous motion relative to the imaging components. An objective 13604 captures an image of the sample 13602, and a tube lens 13606 focuses this image on an image sensor 13608. The image sensor 13608 is angled such that it samples a plane 13610 that is tilted relative to the sample 13602, around the axis perpendicular to the motion of the sample 13602. Thus, individual rows 13612 on the image sensor 13608 correspond to different Z planes "passing through" the sample 13602 as it translates relative to the imaging components.

The data from the rows 13612 is transmitted to a processor 13614 which accumulates the individual Z planes, shifts the data to account for the sample motion and any rotation of the image sensor 13608 relative to the sample axis of motion, and transmits these corrected Z planes to downstream computing systems (e.g., computing subsystem 110). In the example shown in FIG. 136, the sample 13602 is illuminated by an annular illumination source 13616 that effectively provides a conical illumination of the sample 13602. The illumination source 13616 illuminates the imaged sample area relatively uniformly. The illumination source 13616 may be configured so the cone angle corresponds to roughly the numerical aperture of the objective 13604 such that a combination of high efficiency (e.g., low exposure time), narrow illumination angle range, and high optical resolution may be achieved (because optical resolution is determined by a combination of numerical apertures of both the objective 13604 and the illumination source 13616). When performing quantitative phase image (QPI) reconstruction of the sample 13602 using transport of intensity (TIE) equation, the illumination source 13616 may be substantially monochrome. The illumination source 13616 may include single light emitting diodes (LED) or multiple LEDs, or a superluminescent light-emitting diode (SLED), such as a 635 nm SLED. In some implementations, the illumination source 13616 may stay stationary relative to the sample 13602 (e.g., the sample moves). In implementations in which the illumination source 13616 is an LED array, it may be translated relative to the sample 13602 digitally by shifting the illuminated LEDs along the sample 13602 to match the position of the objective 13604.

FIG. 137 is a diagram illustrating another high-speed imaging subsystem 13700 for use in a cell culture system in accordance with various implementations. The imaging subsystem 13700 includes two LED sources whose light is transformed through a series of optical elements to simultaneously provide illumination to a sample 13702. The sample 13702 may be, for example, a cell culture container (e.g., cell culture container 104) with a plasmonic film on a cell-bearing surface, the plasmonic film having different wavelengths and illumination characteristics (e.g., plasmonic films described with reference to FIGS. 131-135). Light passing through the sample 13702 is captured by an objective 13704 for imaging. A first LED source 13706 emits at a first wavelength corresponding to a resonant extinction peak of a plasmonic film on a surface inside the cell culture container. The light from the first LED source 13706 is collimated by a condenser 13708 and then a field stop 13710 is used to define the area on the sample 13702 that is illuminated. A focusing lens 13712 focuses the light through an aperture stop 13714, before a collimating lens 13716 re-collimates the light. The light is reflected by 45-degree mirror 13718 and then reflected again by dichroic filter 13720. The light is then focused onto the sample 13702 by condenser 13722.

Light passing through the sample 13702 is captured by the objective 13704 and reflected by dichroic filter 13724 into path 13726, which leads to an imaging system for the first wavelength of the first LED source 13706. Because this light is at the resonant wavelength of the plasmonic film, it may be used to image fiducial markings on the plasmonic film to ascertain XY and potentially Z position in real time or at specific points across the sample 13702. It may also be used to assess the state of the plasmonic film, including but not limited to measuring changes in the resonant extinction peak resulting from local refractive index changes that shift the amplitude and/or wavelength of the resonant peak, as described herein. This may be done with a second wavelength system providing a baseline reference. The second wavelength illumination may also be used to allow high-resolution TIE-based reconstruction of the sample 13702 based on semi-coherent conical illumination of the sample 13702.

Light at the second wavelength is provided by second LED source 13728 and collimated by condenser 13730. This light is filtered by bandpass filter 13732 to provide narrow-bandwidth illumination for TIE reconstruction. For example, the bandpass of the filter 13732 may be less than 25%, 20%, 15% or 10% of the second wavelength. Light then passes through a field stop 13734 that defines the size of the illuminated region on the sample 13702. It is then focused by focusing lens 13736 through aperture stop 13738 that limits the etendue of the light, allowing a narrow distribution of illumination angles on the sample 13702 (another requirement for semi-coherence). A collimating lens 13740 then re-collimates the light. The combination of semi-coherent illumination and very fast exposure time required for in-motion image capture of multiple Z planes requires efficiency in the handling of LED light. In the case of annular or cone-shaped illumination this may be difficult when simply spatially filtering collimated light with an annular spatial filter since much of the light is lost by the central blocking portion.

In the example implementation of FIG. 137, this loss is partially remedied using two axicon lenses 13742, 13744 that serve to redistribute the incoming collimated light into a cylindrical beam, with much of the power concentrated in the annulus of spatial filter 13746. The resulting cylindrical beam passes through the dichroic filter 13720 before being focused onto the sample 13702 by the condenser 13722. The light passes through the sample 13702 and is captured by the objective 13704. It then passes through the dichroic filter 13724 and is sent on to an imaging system as indicated by path 13748. The imaging subsystem 13700 may, for example, include a tube lens and an angled CMOS imager configured to capture multiple Z planes while in motion, as described herein.

FIG. 138 is a diagram illustrating another high-speed imaging subsystem 13800 for use in a cell culture system in accordance with various implementations. The imaging subsystem 13800 may be configured to provide multiple angles of illumination to a sample as it passes through the field of view of the imaging subsystem 13800 and use differential phase contrast (DPC) algorithms to reconstruct the phase delay through the sample. The sample is translated through a field of view 13802 of the imaging subsystem 13800. A conical illumination system illuminates the sample from different portions of a cone, typically configured to roughly match the numerical aperture of a microscope objective. The angular distribution is shown in plot 13804, in which the top half of the cone is illuminated, resulting in the phase object in the field of view 13802 showing diffracted light corresponding to that illumination angle. As the sample is translated through the field of view 13802, a series of illuminations 13806 at times t1-tn are provided and a series of images 13808 are captured. This may be accomplished by strobing the illumination source, or short exposure time on an image sensor, or both.

The illumination patterning may be accomplished using multiple light sources that are appropriately masked and multiplexed. In alternate implementations, the patterning may be accomplished using a ring of courses that can be addressed. In other alternate implementations, the patterning may be accomplished by the combination of a cylindrical beam (such as the one described herein with reference to FIGS. 136-137) and a device for modulating which portions of the beam are "on" and "off". For example, this may be accomplished using a mask that rotates at a fixed speed within the optical system in unison with the motion of the sample and the capture of images. For example, a stepper motor driving the rotation of this mask may be driven using a waveform derived from a linear encoder on the sample-bearing (or optical system-bearing) stage, such that a 90-degree rotation is achieved for every 100 microns of sample travel, and a camera acquisition triggered at this 90-degree point. Thus every 400 microns there will be a complete set of images corresponding to all four illumination angles.

Appropriate delays 13810 are imposed on these images in order to align them spatially as shown by images 13812. The vertical illuminations are then differenced (indicated by operator 13814) and integrated along the vertical axis (indicated by operator 13816). The horizontal images are also differenced (operator 13818) and integrated (operator 13820), and finally a composite is generated (indicated by operator 13822) that corresponds to the phase delays observed in the sample. In alternate implementations, the computing subsystem applying the computational operations (operators 13814, 13816, 13818, 13820, 13822) may utilize a transfer function from the illumination conditions 13806 to the output images 13812. In some implementations, the imaging subsystem 13800 may be combined with additional illumination, for example at a wavelength corresponding to the resonant extinction of a plasmonic film, to measure film conditions and track fiducial markings.

Terms and Definitions

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise, and encompass "at least one." Any reference to "or" herein is intended to encompass "and/or" unless otherwise stated.

As used herein, the term "about" in some cases refers to an amount that is approximately the stated amount.

As used herein, the term "about" refers to an amount that is near the stated amount by 10%, 5%, or 1%, including increments therein.

As used herein, the term "about" in reference to a percentage refers to an amount that is greater or less the stated percentage by 10%, 5%, or 1%, including increments therein.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "flexible" as used herein refers to an object or material that is able to be bent or compressed without cracking or breaking. The term "semi-flexible" as used herein refers to an object or material that has a portion thereof that is able to be bent or compressed without cracking or breaking.

As used in any implementation herein, a "circuit" or "circuitry" may include, for example, singly or in any combination, hardwired circuitry, programmable circuitry, state machine circuitry, and/or firmware that stores instructions executed by programmable circuitry. An "integrated circuit" may be a digital, analog or mixed-signal semiconductor device and/or microelectronic device, such as, for example, but not limited to, a semiconductor integrated circuit chip.

The term "coupled" as used herein refers to any connection, coupling, link or the like by which signals carried by one system element are imparted to the "coupled" element. Such "coupled" devices, or signals and devices, are not necessarily directly connected to one another and may be separated by intermediate components or devices that may manipulate or modify such signals. Likewise, the terms "connected" or "coupled" as used herein in regard to mechanical or physical connections or couplings is a relative term and does not require a direct physical connection.

Unless otherwise stated, use of the word "substantially" may be construed to include a precise relationship, condition, arrangement, orientation, and/or other characteristic, and deviations thereof as understood by one of ordinary skill in the art, to the extent that such deviations do not materially affect the disclosed methods and systems.

It will be appreciated by those skilled in the art that any block diagrams herein represent conceptual views of illustrative circuitry embodying the principles of the disclosure. Similarly, it will be appreciated that any flow charts, flow diagrams, state transition diagrams, pseudocode, and the like represent various processes which may be substantially represented in computer readable medium and so executed by a computer or processor, whether or not such computer or processor is explicitly shown. Software modules, or simply modules which are implied to be software, may be represented herein as any combination of flowchart elements or other elements indicating performance of process steps and/or textual description. Such modules may be executed by hardware that is expressly or implicitly shown.

Also, various inventive concepts may be embodied as one or more methods, of which an example has been provided. The acts performed as part of the method may be ordered in any suitable way. Accordingly, implementations may be constructed in which acts are performed in an order different than illustrated, which may include performing some acts simultaneously, even though shown as sequential acts in illustrative implementations.

While various implementations have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the implementations described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific inventive implementations described herein. It is, therefore, to be understood that the foregoing implementations are presented by way of example only and that, within the scope of the appended claims and equivalents thereto, implementations may be practiced otherwise than as specifically described and claimed. In addition, any combination of two or more such features, systems, aspects, articles, materials, kits, and/or methods, if such features, systems, aspects, articles, materials, kits, and/or methods are not mutually inconsistent, is included within the inventive scope of the present disclosure. Particularly, any element of the disclosure and any aspect thereof may be combined, in any order and any combination, with any other element of the disclosure and any aspect thereof.

The above-described implementations can be implemented in any of numerous ways. For example, the implementations may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device. Also, a computer may have one or more input and output devices. These devices can be used, among other things, to present a user interface. Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

Implementations of the methods described herein may be implemented using a processor and/or other programmable device. To that end, the methods described herein may be implemented on a tangible, non-transitory computer readable medium having instructions stored thereon that when executed by one or more processors perform the methods. The computer readable medium may include any type of tangible medium, for example, any type of disk including floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, magnetic or optical cards, or any type of media suitable for storing electronic instructions.

The terms "program" or "software" are used herein in a generic sense to refer to any type of computer code or set of computer-executable instructions that can be employed to program a computer or other processor to implement various aspects of implementations as discussed above. Additionally, it should be appreciated that according to one aspect, one or more computer programs that when executed perform methods of the present disclosure need not reside on a single computer or processor, but may be distributed in a modular fashion amongst a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various implementations. Also, data structures may be stored in computer-readable media in any suitable form.

Also, various inventive concepts may be embodied as one or more methods, of which an example has been provided. The acts performed as part of the method may be ordered in any suitable way. Accordingly, implementations may be constructed in which acts are performed in an order different than illustrated, which may include performing some acts simultaneously, even though shown as sequential acts in illustrative implementations.

Computing System

Referring to FIG. 139, a block diagram is shown depicting an exemplary machine that includes a computer system 13900 (e.g., a processing or computing system) within which a set of instructions can execute for causing a device to perform or execute any one or more of the aspects and/or methodologies for static code scheduling of the present disclosure. The components in FIG. 139 are examples only and do not limit the scope of use or functionality of any hardware, software, embedded logic component, or a combination of two or more such components implementing particular implementations.

Computer system 13900 may include one or more processors 13901, a memory 13903, and a storage 13908 that communicate with each other, and with other components, via a bus 13940. The bus 13940 may also link a display 13932, one or more input devices 13933 (which may, for example, include a keypad, a keyboard, a mouse, a stylus, etc.), one or more output devices 13934, one or more storage devices 13935, and various tangible storage media 13936. All of these elements may interface directly or via one or more interfaces or adaptors to the bus 13940. For instance, the various tangible storage media 13936 can interface with the bus 13940 via storage medium interface 13926. Computer system 13900 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Computer system 13900 includes one or more processor(s) 13901 (e.g., central processing units (CPUs) or general purpose graphics processing units (GPGPUs)) that carry out functions. Processor(s) 13901 optionally contains a cache memory unit 13902 for temporary local storage of instructions, data, or computer addresses. Processor(s) 13901 are configured to assist in execution of computer readable instructions. Computer system 13900 may provide functionality for the components depicted in FIG. 139 as a result of the processor(s) 13901 executing non-transitory, processor-executable instructions embodied in one or more tangible computer-readable storage media, such as memory 13903, storage 13908, storage devices 13935, and/or storage medium 13936. The computer-readable media may store software that implements particular implementations, and processor(s) 13901 may execute the software. Memory 13903 may read the software from one or more other computer-readable media (such as mass storage device(s) 13935, 13936) or from one or more other sources through a suitable interface, such as network interface 13920. The software may cause processor(s) 13901 to carry out one or more processes or one or more steps of one or more processes described or illustrated herein. Carrying out such processes or steps may include defining data structures stored in memory 13903 and modifying the data structures as directed by the software.

The memory 13903 may include various components (e.g., machine readable media) including, but not limited to, a random access memory component (e.g., RAM 13904) (e.g., static RAM (SRAM), dynamic RAM (DRAM), ferroelectric random access memory (FRAM), phase-change random access memory (PRAM), etc.), a read-only memory component (e.g., ROM 13905), and any combinations thereof. ROM 13905 may act to communicate data and instructions unidirectionally to processor(s) 13901, and RAM 13904 may act to communicate data and instructions bidirectionally with processor(s) 13901. ROM 13905 and RAM 13904 may include any suitable tangible computer-readable media described below. In one example, a basic input/output system 13906 (BIOS), including basic routines that help to transfer information between elements within computer system 13900, such as during start-up, may be stored in the memory 13903.

Fixed storage 13908 is connected bidirectionally to processor(s) 13901, optionally through storage control unit 13907. Fixed storage 13908 provides additional data storage capacity and may also include any suitable tangible computer-readable media described herein. Storage 13908 may be used to store operating system 13909, executable(s) 13910, data 13911, applications 13912 (application programs), and the like. Storage 13908 can also include an optical disk drive, a solid-state memory device (e.g., flash-based systems), or a combination of any of the above. Information in storage 13908 may, in appropriate cases, be incorporated as virtual memory in memory 13903.

In one example, storage device(s) 13935 may be removably interfaced with computer system 13900 (e.g., via an external port connector (not shown)) via a storage device interface 13925. Particularly, storage device(s) 13935 and an associated machine-readable medium may provide non-volatile and/or volatile storage of machine-readable instructions, data structures, program modules, and/or other data for the computer system 13900. In one example, software may reside, completely or partially, within a machine-readable medium on storage device(s) 13935. In another example, software may reside, completely or partially, within processor(s) 13901.

Bus 13940 connects a wide variety of subsystems. Herein, reference to a bus may encompass one or more digital signal lines serving a common function, where appropriate. Bus 13940 may be any of several types of bus structures including, but not limited to, a memory bus, a memory controller, a peripheral bus, a local bus, and any combinations thereof, using any of a variety of bus architectures. As an example and not by way of limitation, such architectures include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, and any combinations thereof.

Computer system 13900 may also include an input device 13933. In one example, a user of computer system 13900 may enter commands and/or other information into computer system 13900 via input device(s) 13933. Examples of an input device(s) 13933 include, but are not limited to, an alpha-numeric input device (e.g., a keyboard), a pointing device (e.g., a mouse or touchpad), a touchpad, a touch screen, a multi-touch screen, a joystick, a stylus, a gamepad, an audio input device (e.g., a microphone, a voice response system, etc.), an optical scanner, a video or still image capture device (e.g., a camera), and any combinations thereof. In some implementations, the input device is a Kinect, Leap Motion, or the like. Input device(s) 13933 may be interfaced to bus 13940 via any of a variety of input interfaces 13923 (e.g., input interface 13923) including, but not limited to, serial, parallel, game port, USB, FIREWIRE, THUNDERBOLT, or any combination of the above.

In particular implementations, when computer system 13900 is connected to network 13930, computer system 13900 may communicate with other devices, specifically mobile devices and enterprise systems, distributed computing systems, cloud storage systems, cloud computing systems, and the like, connected to network 13930. Communications to and from computer system 13900 may be sent through network interface 13920. For example, network interface 13920 may receive incoming communications (such as requests or responses from other devices) in the form of one or more packets (such as Internet Protocol (IP) packets) from network 13930, and computer system 13900 may store the incoming communications in memory 13903 for processing. Computer system 13900 may similarly store outgoing communications (such as requests or responses to other devices) in the form of one or more packets in memory 13903 and communicated to network 13930 from network interface 13920. Processor(s) 13901 may access these communication packets stored in memory 13903 for processing.

Examples of the network interface 13920 include, but are not limited to, a network interface card, a modem, and any combination thereof. Examples of a network 13930 or network segment 13930 include, but are not limited to, a distributed computing system, a cloud computing system, a wide area network (WAN) (e.g., the Internet, an enterprise network), a local area network (LAN) (e.g., a network associated with an office, a building, a campus or other relatively small geographic space), a telephone network, a direct connection between two computing devices, a peer-to-peer network, and any combinations thereof. A network, such as network 13930, may employ a wired and/or a wireless mode of communication. In general, any network topology may be used.

Information and data can be displayed through a display 13932. Examples of a display 13932 include, but are not limited to, a cathode ray tube (CRT), a liquid crystal display (LCD), a thin film transistor liquid crystal display (TFT-LCD), an organic liquid crystal display (OLED) such as a passive-matrix OLED (PMOLED) or active-matrix OLED (AMOLED) display, a plasma display, and any combinations thereof. The display 13932 can interface to the processor(s) 13901, memory 13903, and fixed storage 13908, as well as other devices, such as input device(s) 13933, via the bus 13940. The display 13932 is linked to the bus 13940 via a video interface 13922, and transport of data between the display 13932 and the bus 13940 can be controlled via the graphics control 13921. In some implementations, the display is a video projector. In some implementations, the display is a head-mounted display (HMD) such as a VR headset. In further implementations, suitable VR headsets include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, and the like. In still further implementations, the display is a combination of devices such as those disclosed herein.

In addition to a display 13932, computer system 13900 may include one or more other peripheral output devices 13934 including, but not limited to, an audio speaker, a printer, a storage device, and any combinations thereof. Such peripheral output devices may be connected to the bus 13940 via an output interface 13924. Examples of an output interface 13924 include, but are not limited to, a serial port, a parallel connection, a USB port, a FIREWIRE port, a THUNDERBOLT port, and any combinations thereof.

In addition or as an alternative, computer system 13900 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both.

Those of skill in the art will appreciate that the various illustrative logical blocks, modules, circuits, and algorithm steps described in connection with the implementations disclosed herein may be implemented as electronic hardware, computer software, or combinations of both. To clearly illustrate this interchangeability of hardware and software, various illustrative components, blocks, modules, circuits, and steps have been described above generally in terms of their functionality.

The various illustrative logical blocks, modules, and circuits described in connection with the implementations disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the implementations disclosed herein may be embodied directly in hardware, in a software module executed by one or more processor(s), or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In accordance with the description herein, suitable computing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will also recognize that select televisions, video players, and digital music players with optional computer network connectivity are suitable for use in the system described herein. Suitable tablet computers, in various implementations, include those with booklet, slate, and convertible configurations, known to those of skill in the art.

In some implementations, the computing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some implementations, the operating system is provided by cloud computing. Those of skill in the art will also recognize that suitable mobile smartphone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

Non-Transitory Computer Readable Storage Medium

In some implementations, the platforms, systems, media, and methods disclosed herein include one or more non-transitory computer readable storage media encoded with a program including instructions executable by the operating system of an optionally networked computing device. In further implementations, a computer readable storage medium is a tangible component of a computing device. In still further implementations, a computer readable storage medium is optionally removable from a computing device. In some implementations, a computer readable storage medium includes, by way of non-limiting examples, CD-ROMs, DVDs, flash memory devices, solid state memory, magnetic disk drives, magnetic tape drives, optical disk drives, distributed computing systems including cloud computing systems and services, and the like. In some cases, the program and instructions are permanently, substantially permanently, semi-permanently, or non-transitorily encoded on the media.

Computer Program

In some implementations, the platforms, systems, media, and methods disclosed herein include at least one computer program, or use of the same. A computer program includes a sequence of instructions, executable by one or more processor(s) of the computing device's CPU, written to perform a specified task. Computer readable instructions may be implemented as program modules, such as functions, objects, Application Programming Interfaces (APIs), computing data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some implementations, a computer program comprises one sequence of instructions. In some implementations, a computer program comprises a plurality of sequences of instructions. In some implementations, a computer program is provided from one location. In other implementations, a computer program is provided from a plurality of locations. In various implementations, a computer program includes one or more software modules. In various implementations, a computer program includes, in part or in whole, one or more web applications, one or more mobile applications, one or more standalone applications, one or more web browser plug-ins, extensions, add-ins, or add-ons, or combinations thereof.

Software Modules

In some implementations, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various implementations, a software module comprises a file, a section of code, a programming object, a programming structure, or combinations thereof. In further various implementations, a software module comprises a plurality of files, a plurality of sections of code, a plurality of programming objects, a plurality of programming structures, or combinations thereof. In various implementations, the one or more software modules comprise, by way of non-limiting examples, a web application, a mobile application, and a standalone application. In some implementations, software modules are in one computer program or application. In other implementations, software modules are in more than one computer program or application. In some implementations, software modules are hosted on one machine. In other implementations, software modules are hosted on more than one machine. In further implementations, software modules are hosted on a distributed computing platform such as a cloud computing platform. In some implementations, software modules are hosted on one or more machines in one location. In other implementations, software modules are hosted on one or more machines in more than one location.

Databases

In some implementations, the platforms, systems, media, and methods disclosed herein include one or more databases, or use of the same. In view of the disclosure provided herein, those of skill in the art will recognize that many databases are suitable for storage and retrieval of image data, cell types, attribute categories, labels, assay data, or any combination thereof. In various implementations, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some implementations, a database is internet-based. In further implementations, a database is web-based. In still further implementations, a database is cloud computing-based. In a particular implementation, a database is a distributed database. In other implementations, a database is based on one or more local computer storage devices.

Numbered Implementations

The following implementations recite nonlimiting permutations of combinations of features disclosed herein. Other permutations of combinations of features are also contemplated. In particular, each of these numbered implementations is contemplated as depending from or relating to every previous or subsequent numbered implementation, independent of their order as listed. 1. A cell culture system, comprising: a cell culture container comprising a cell culture, the cell culture receiving input cells; a cell imaging subsystem configured to acquire images of the cell culture; a computing subsystem configured to perform a cell culture process on the cell culture according to the images acquired by the cell imaging subsystem; and a cell editing subsystem configured to edit the cell culture to produce output cell products according to the cell culture process. 2. The cell culture system of implementation 1, further comprising at least one sensor configured to acquire sensor data, wherein the computing subsystem is further configured to perform the cell culture process according to the sensor data. 3. The cell culture system of implementation 1 or 2, further comprising at least one control component configured to affect environmental or physical aspects of the cell culture system, wherein the computing subsystem is further configured to control the at least one control component. 4. The cell culture system of any one of implementations 1-3, wherein the computing subsystem is further configured to perform input cell assays on the input cells. 5. The cell culture system of any one of implementations 1-4, wherein the computing subsystem is further configured to perform output cell product assays on the output cell products. 6. The cell culture system of any one of implementations 1-5, wherein the cell imaging subsystem comprises: a light source that illuminates the cell culture; a sensor configured to detect a plurality of light signals; and a multi-focus mechanism disposed between the cell culture surface and the sensor configured to generate the plurality of light signals from light reflected by the cell culture, wherein the plurality of light signals are representative of cell location and structure data in three dimensions; wherein the cell culture container and the imaging subsystem are configured to move relative to each other along a direction of movement. 7. The cell culture system of implementation 6, wherein the multi-focus mechanism comprises tilting the sensor along the direction of movement. 8. The cell culture system of implementation 6 or 7, wherein the multi-focus mechanism comprises a plurality of beam splitters that splits the reflected light into a plurality of paths; and the sensor comprises a plurality of detector arrays, each detector array located in a different one of the plurality of paths and located a different distance away from each beam splitter. 9. The cell culture system of any one of implementations 6-8, wherein the multi-focus mechanism comprises a diffractive element that diffracts the reflected light into the plurality of light signals, each light signal representing data at a different height relative to the cell culture. 10. The cell culture system of any one of implementations 6-9, wherein the cell imaging subsystem further comprises focus enhancing module configured to provide visual cues for adjusting a focus of the cell imaging subsystem system. 11. The cell culture system of any one of implementations 1-5, wherein the cell imaging subsystem comprises: a multi-wavelength light source illuminating the cell culture, wherein different wavelengths of light illuminate the cell culture at different angles; a wavelength separation unit that separates light exiting the cell culture into separate light signals, each associated with a different wavelength band; one or more detectors configured to detect the separate light signals and output detector signals; and a processing unit that receives the detector signals and is configured to form a representation of the cell culture from the detector signals. 12. The cell culture system of implementation 11, wherein the cell culture is divided into a plurality of linear regions and imaging subsystem images each linear region sequentially. 13. The cell culture system of implementation 11 or 12, wherein the cell imaging subsystem is continuously translated relative to the cell culture. 14. The cell culture system of any one of implementations 11-13, wherein the cell imaging subsystem further comprises an autofocus system. 15. The cell culture system of any one of implementations 11-14, wherein the cell imaging subsystem further comprises a registration system. 16. The cell culture system of any one of implementations 11-15, wherein the cell culture comprises induced pluripotent stem cells. 17. The cell culture system of any one of implementations 11-16, wherein the cell culture is located in a closed cassette having transparent cell chamber walls. 18. The cell culture system of any one of implementations 1-5, wherein said imaging subsystem is configured for imaging and scanning and comprises: at least one light source illuminating a cell culture sample having cells grown on a growth plane of the cell culture; an objective capturing light from the at least one light source passing through the cell culture sample, wherein the objective is tilted at an angle with respect to a perpendicular axis of the growth plane; and one or more sensors to measure the light from the objective; wherein the cell culture sample is moved relative to the imaging and scanning system such that the imaging system generates images at multiple heights along the perpendicular axis of the growth plane. 19. The cell culture system of implementation 18, wherein the cell imaging subsystem comprises a multi-focus mechanism disposed between a cell culture surface and the one or more sensors, wherein the one or more sensors are configured to generate a plurality of light signals from light reflected by the cell culture and captured by the objective, wherein the plurality of light signals are representative of cell location and structure data in three dimensions. 20. The cell culture system of implementation 18 or 19, wherein the at least one light source comprises a multi-wavelength light source illuminating the cell culture sample, wherein different wavelengths of light illuminate the cell culture sample at different angles. 21. The cell culture system of any one of implementations 18-20, wherein the cell imaging subsystem comprises a wavelength separation unit that separates light exiting the cell culture into separate light signals, each associated with a different wavelength band. 22. The cell culture system of implementation 21, wherein the cell imaging subsystem comprises one or more detectors configured to detect the separate light signals and output detector signals. 23. The cell culture system of implementation 22, wherein the cell imaging subsystem comprises a processing unit that receives the detector signals and is configured to form a representation of the cell culture from the detector signals. 24. The cell culture system of any one of implementations 18-23, wherein the cell imaging subsystem comprises: a laser pulse generated by a laser source and incident on the cell culture sample; and an acousto-optic deflector/modular to adjust an incident angle of the laser pulse relative to the perpendicular axis of the growth plane; wherein the cell culture sample is moved relative to the cell imaging subsystem such that the laser pulse is capable of focusing on any part of the growth plane. 25. The cell culture system of any one of implementations 1-24, wherein the cell culture container comprises: a cell culture chamber having a first surface, a second surface, and an interior between the first surface and the second surface; one or more cells in an interior of the cell culture chamber and adhered to the first surface; a magnetic tool in the interior of the cell culture chamber and resting on at least one of the first surface or the second surface; a magnetic component on the exterior of the cell culture chamber and resting on at least one of the first surface or the second surface, the magnetic component magnetically coupled to the magnetic tool; and an actuator removably coupled to the magnetic component and configured to move the magnetic component in one or more directions, wherein moving the magnetic component also moves the magnetic tool in the same manner. 26. The cell culture system of implementation 25, wherein the actuator is further configured to rotate the magnetic component. 27. The cell culture system of implementation 26, wherein the rotation mixes fluid media inside the cell culture chamber. 28. The cell culture system of any one of implementations 25-27, wherein the actuator is configured to translate the magnetic component around the first surface or the second surface. 29. The cell culture system of any one of implementations 25-28, wherein the magnetic tool is configured to push debris in the interior of the cell culture chamber and rest on the first surface or the second surface when the magnetic component is translated around the first surface or the second surface. 30. The cell culture system of any one of implementations 25-29, wherein the cell culture container further comprises an imaging objective configured to determine a position of the magnetic tool. 31. The cell culture system of implementation 30, wherein the computing subsystem is configured to control the actuator based on the position of the magnetic tool. 32. The cell culture system of any one of implementations 25-31, wherein the magnetic tool is configured to lyse or destroy one or more cells. 33. The cell culture system of any one of implementations 25-32, wherein the magnetic tool comprises: a permanent magnet; a blade comprising a tip, a high-angle edge, and a low-angle edge. 34. The cell culture system of implementation 33, wherein the tip and/or the high-angle edge is used to lyse or destroy the one or more cells. 35. The cell culture system of implementation 33, wherein the low-angle edge is used to lift the one or more cells from the first surface. 36. The cell culture system of any one of implementations 25-35, wherein the magnetic tool comprises a permanent magnet and a circular blade. 37. The cell culture system of any one of implementations 25-35, wherein the magnetic tool has a length and comprises: a permanent magnet; a sharp tip on a first end of the length; and a flexible scoop on a second end of the length. 38. The cell culture system of any one of implementations 1-37, wherein the cell editing subsystem is configured to manipulate the magnetic tool. 39. The cell culture system of any one of implementations 38, wherein the cell editing subsystem comprises the actuator that is configured to move the magnetic component in one or more directions. 40. The cell culture system of any one of implementations 1-39, wherein the cell editing subsystem comprises an ultrasound subsystem configured to selectively lyse cells using targeted ultrasound. 41. The cell culture system of any one of implementations 1-39, wherein: the cell culture container comprises a cell culture chamber having a first surface and one or more cells in an interior of the cell culture chamber and adhered to the first surface; the cell imaging subsystem is configured to capture one or more images of the one or more cells; the computing subsystem is configured to classify cells, cell regions, or cell colonies from the one or more images; the cell editing subsystem comprises an ultrasound subsystem that acts through the first surface to selectively lyse cells according to the classifications provided by the computing subsystem; and a mechanism to remove material generated from cell lysis. 42. The cell culture system of implementation 41, wherein the ultrasound subsystem comprises a focused ultrasound subsystem. 43. The cell culture system of implementation 41, wherein the ultrasound subsystem comprises a phased-array ultrasound subsystem. 44. The cell culture system of any one of implementations 40-43, wherein the ultrasound subsystem and the imaging subsystem are combined as a single head that translate across the first surface. 45. The cell culture system of any one of implementations 1-44, wherein the cell culture container comprises a cell culture chamber comprising: fluid media between a first wall and a second wall, wherein the second wall is flexible; a cell culture adherent or semi-adherent on the inside of the first wall; and a first actuator configured to push against the second wall to create a constricted region in the cell culture chamber; and a mechanism to create a high velocity flow through the constricted region, causing dislodging of cells or cell debris from the first wall. 46. The cell culture system of implementation 45, wherein the mechanism comprises a pump that pumps the fluid media through the constricted region. 47. The cell culture system of implementation 45 or 46, wherein the cell culture chamber is sealed and the mechanism comprises a second actuator that pushes against the second wall to force the fluid media through the constricted region. 48. The cell culture system of any one of implementations 1-44, wherein the cell culture container comprises a cell culture chamber comprising: fluid media between a first wall and a second wall, wherein the second wall is flexible; a cell culture adherent or semi-adherent on the inside of the first wall; and at least one acoustic transducer configured to apply acoustic waves to the cell culture chamber, causing dislodging of cells or cell debris from the first wall. 49. The cell culture system of implementation 48, wherein the at least one acoustic transducer is located on the outside of the cell culture chamber proximate to the first wall and applies the acoustic towards the first wall in a direction perpendicular to a plane of the first wall. 50. The cell culture system of implementation 49, wherein the at least one acoustic transducer comprises two acoustic transducers coupled to the outside of the first wall and configured to create local distortions perpendicular to the plane of the first wall using the acoustic waves. 51. A method of using the cell culture system of any one of implementations 1-50, comprising: providing the cell culture container comprising the cell culture, the cell culture receiving input cells; acquiring, with the cell imaging subsystem, images of the cell culture; performing, with the computing subsystem, the cell culture process on the cell culture according to the images acquired by the cell imaging subsystem; and editing, with the cell editing subsystem, the cell culture to produce output cell products according to the cell culture process. 52. A method of controlling a cell culture system such as that of any one of implementations 1-50, comprising: receiving, at a plurality of points of time, a plurality of images of a cell culture; identifying one or more cell colonies from the plurality of images; tracking the one or more cell colonies through the plurality of points of time; predicting an outcome of the one or more cell colonies; and editing the cell culture based on the predicted outcomes of the one or more cell colonies. 53. A method of controlling a cell culture system such as that of any one of implementations 1-50, comprising: receiving, at a plurality of points of time, a plurality of images of a cell culture; identifying a plurality of cells from the plurality of images; identifying one or more cell colonies from the plurality of cells; tracking the one or more cell colonies through the plurality of points of time; predicting an outcome of the one or more cell colonies; and editing the cell culture based on the predicted outcomes of the one or more cell colonies. 54. The method of implementation 52 or 53, the method further comprising preprocessing the plurality of images. 55. The method of implementation 54, wherein preprocessing the plurality of images comprises: normalizing the plurality of images; and stitching the plurality of images into a single stitched image of the cell culture. 56. The method of any one of implementations 52-55, wherein predicting the outcome of the one or more cell colonies comprises generating an outcome score for each of the one or more cell colonies, the outcome score representing a likelihood that the cell colony will generate an output cell product. 57. The method of any one of implementations 52-56, wherein editing the cell culture comprises removing one or more cells or one or more cell colonies from the cell culture. 58. The method of any one of implementations 52-57, 59. A method of classifying image data in a cell culture system such as that of any one of implementations 1-50, comprising: growing one or more cell cultures of a first cell type; obtaining image data of the one or more cell cultures; generating, by an unsupervised learning engine, a plurality of visual categories for the first cell type from the image data; associating, by the unsupervised learning engine, the plurality of visual categories with a plurality of attribute categories; and labeling, by an unsupervised inference engine, the image data with the plurality of attribute categories. 60. The method of implementation 59, wherein the image data is label-free. 61. The method of clam 59 or 60, further comprising: acquiring assay data from the one or more cell cultures; and utilizing the assay data to associate the plurality of visual categories with a plurality of attribute categories. 62. The method of any one of implementations 59-61, further comprising: obtaining labeled image data of the one or more cell cultures; and utilizing the labeled image data to associate the plurality of visual categories with a plurality of attribute categories. 63. A method producing cells in a cell culture system such as that of any one of implementations 1-50, comprising: growing one or more cell cultures of a first cell type; obtaining image data of the one or more cell cultures; generating, by an unsupervised inference engine, one or more attribute maps from the image data, wherein each attribute map comprises an image of a cell culture annotated with cell attributes; determining one or more actions based on the one or more attribute maps. 64. The method of implementation 63, wherein the cell attributes are associated with visual categories identifiable in the image data. 65. The method of implementation 63 or 64, wherein the one or more actions comprise lysing select cells in the one or more cell cultures, collecting assays on select cells in the one or more cell cultures, or changing parameters of cell growth of the one or more cell cultures. 66. A modular cell culture system comprising: a supporting structure; a plurality of process modules in the supporting structure, each process module comprising a plurality of connectors and configured to removably host a cell culture cassette; and a computing subsystem configured to monitor a status of each of the plurality of process modules and each cell culture cassette. 67. The modular cell culture system of implementation 66, wherein the supporting structure is a rack. 68. The modular cell culture system of implementation 66 or 67, wherein the supporting structure comprises at least one of the cell imaging subsystem, the cell editing subsystem, and a temperature control subsystem. 69. The modular cell culture system of any one of implementations 66-68, wherein the computing subsystem generates a digital file for each process module and cell culture cassette, the digital file comprising the current status of the associated component. 70. The modular cell culture system of any one of implementations 66-69, wherein when components are moved around the modular cell culture system, the associated digital file is also moved to ensure continuity of operations. 71. The modular cell culture system of any one of implementations 66-69, wherein when components are moved around the modular cell culture system, the associated digital file is also moved or modified to indicate the movement or location of the components in order to ensure continuity of operations. 72. The modular cell culture system of any one of implementations 66-71, wherein each of the plurality of process modules are configured to engage and disengage with a cell culture cassette quickly and without engaging and disengaging each of the plurality of connectors individually. 73. The modular cell culture system of any one of implementations 66-72, wherein the modular cell culture system comprises the cell culture system of any one of implementations 1-50. 74. The modular cell culture system of implementation 73, wherein the cell culture cassette comprises the cell culture container comprising the cell culture. 75. The modular cell culture system of implementation 73 or 74, wherein the cell imaging subsystem is configured to acquire images of one or more cells in each cell culture cassette. 76. The modular cell culture system of any one of implementations 73-75, wherein the computing subsystem is configured to monitor a status of each of the plurality of process modules and each cell culture cassette based at least on images of one or more cells in each cell culture cassette. 77. The modular cell culture system of any one of implementations 73-76, wherein the computing subsystem is configured to perform the cell culture process on each cell culture cassette based on the status of each of the plurality of process modules and each cell culture cassette. 78. The modular cell culture system of any one of implementations 73-77, wherein the cell editing subsystem is configured to edit the one or more cells in the cell culture cassette in order to produce output cell products according to the cell culture process. 79. A cell culture system such as that of any one of implementations 1-50 or 66-78, comprising: a cell culture container, the cell culture containing comprising a cell culture cavity with a first plurality of cells and a second plurality of cells, wherein: the first plurality of cells are of a first type/stage and at least semi-adherent to a top surface of the cell culture cavity; and the second plurality of cells are of a second type/stage and at least semi-adherent to the top surface of the cell culture cavity; a processor configured to: determine a location of each of the first plurality of cells and second plurality of cells; dislodge the second plurality of cells from the top surface, wherein the second plurality of cells re-adhere to a bottom surface of the cell culture cavity; invert the cell culture cavity; and remove the first plurality of cells from the cell culture cavity. 80. The cell culture system of implementation 79, wherein dislodging the second plurality of cells from the top surface comprises at least one of: using an agitation tool to create local forces acting on the second plurality of cells; generating a fluid flow that creates local forces acting on the second plurality of cells; and utilizing pulsed lasers to create local forces acting on the second plurality of cells. 81. The cell culture system of implementation 79 or 80, wherein removing the first plurality of cells from the cell culture cavity comprises at least one of: using a collection tool to push the first plurality of cells out of the cell culture cavity; generating a fluid flow to push the first plurality of cells out of the cell culture cavity; and utilizing pulsed lasers to lyse the first plurality of cells. 82. The cell culture system of any one of implementations 79-81, wherein inverting the cell culture cavity comprises turning the cell culture cavity such that the top surface and the bottom surface are reversed. 83. The cell culture system of any one of implementations 79-82, wherein the first and second plurality of cells are immune cells. 84. The cell culture system of implementation 83, wherein the immune cells include cells derived from myeloid or lymphoid lineages. 85. The cell culture system of any one of implementations 1-50 or 66-84, wherein the cell editing subsystem is configured for dislodging a subset of cells from a surface of a cell culture chamber of the cell culture container. 86. The cell culture system of implementation 85, further comprising a mechanism to remove the subset of cells from the cell culture chamber for analysis. 87. A cell culture system, comprising: a cell culture chamber having a first surface; one or more cells in an interior of the cell culture chamber and adhered to the first surface; an imaging subsystem configured to collect images of the one or more cells; a computing subsystem configured to select a subset of cells for analysis based on the images; a cell editing subsystem for dislodging the subset of cells from the first surface; a mechanism to remove the subset of cells from the cell culture chamber for analysis. 88. A method of cell extraction and analysis in a cell culture system such as that of any one of implementations 1-50 or 66-87, comprising: growing a cell culture in a cell culture container; obtaining one or more images of the cell culture; identifying one or more cells to extract from the cell culture based on the one or more images; extracting the identified cells from the cell culture chamber; and analyzing the extracted cells. 89. The method of implementation 88, further comprising adjusting a cell culture process for the cell culture based on the analysis. 90. The method of implementation 89, wherein the steps of growing, obtaining, extracting, and analyzing is performed by an automated cell culture system. 91. The method of any one of implementations 88-90, wherein the step of identifying is performed by a person. 92. A cell culture chamber, comprising: a cell bearing surface; a plurality of cells grown on the cell bearing surface; and a resonant optical film located on the cell bearing surface. 93. The cell culture chamber of implementation 92, wherein the resonant optical film absorbs more than 5% of incident light at a cell editing optical wavelength. 94. The cell culture chamber of implementation 92 or 93, wherein the resonant optical film absorbs less than 20% of incident light at a cell imaging optical wavelength. 95. The cell culture chamber of any one of implementations 92-94, wherein the resonant optical film has physical features smaller than 50% of the cell imaging optical wavelength. 96. The cell culture chamber of any one of implementations 92-95, wherein there is a foil between the resonant optical film and the cell bearing surface. 97. The cell culture chamber of implementation 96, wherein the foil is a membrane with pores. 98. The cell culture chamber of any one of implementations 92-97, wherein the resonant optical film has a resonant absorption peak at 532 nanometers (nm) and/or 1064 nm. 99. The cell culture chamber of any one of implementations 92-98, wherein the resonant optical film comprises gold nano-islands attached to an optically transparent material selected from the following: glass, cyclic olefin copolymer, polystyrene, polycarbonate, polyethylene terephthalate. 100. The cell culture chamber of implementation 99, wherein the gold nano-islands have a mean diameter less than 50 nm along at least one axis. 101. The cell culture system of any one of implementations 1-50 or 66-87, wherein the cell culture container comprises the cell culture chamber of any one of implementations 92-100. 102. A cassette system for cell culture processing, comprising: a) one or more cell culture chambers, each cell culture chamber configured to: i) provide a growth environment for adherent cell cultures; and ii) allow imaging of the adherent cell cultures grown in the cell culture chamber; and b) a liquid system coupled to the one or more cell culture chambers, wherein the liquid system is configured to: i) provide input fluid media to the one or more cell culture chambers; and ii) receive output fluid media from the one or more cell culture chambers; wherein the liquid system is configured to provide a closed, sterile liquid environment for the adherent cell cultures in each cell culture chamber. 103. The cassette system of implementation 102, wherein at least one of the input fluid media and the output fluid media comprises at least one of growth media, reagents, buffers, fluid waste, and cell collection media. 104. The cassette system of implementation 103, wherein the liquid system comprises one or more reservoirs for holding different types of fluid media. 105. The cassette system of implementation 102, wherein the cassette system further comprises at least one pump for directing the input fluid media, the output fluid media, or both through the liquid system. 106. The cassette system of implementation 105, wherein the at least one pump is bidirectional. 107. The cassette system of implementation 102, wherein each cell culture chamber comprises a first semi-transparent surface to allow for imaging of the adherent cell cultures. 108. The cassette system of implementation 107, wherein each cell culture chamber is further configured to allow removal of cells from the cell culture chamber using a cell editing mechanism. 109. The cassette system of implementation 108, wherein the cell editing mechanism is configured to direct laser energy, ultrasound, or mechanical forces upon the cell culture chamber to effectuate removal of cells. 110. The cassette system of implementation 109, wherein the laser energy comprises pulsed laser light. 111. The cassette system of implementation 109, wherein the first semi-transparent surface comprises a coating configured to absorb the laser energy at one or more wavelengths and convert the laser energy into thermal or mechanical energy to remove cells. 112. The cassette system of implementation 102, wherein at least one of the one or more cell culture chambers has a cell growth area of at least 50 $cm^2$. 113. The cassette system of implementation 102, wherein at least one of the one or more cell culture chambers is completely filled with fluid media. 114. The cassette system of implementation 102, wherein an internal height of at least one of the one or more cell culture chambers is less than 1 millimeter. 115. The cassette system of implementation 102, further comprising: a) one or more sensors; and b) a processor configured to communicate with the one or more sensors and a process module hosting the cassette system via a pluggable connector. 116. The cassette system of implementation 115, wherein the cassette system is removably coupled to the process module. 117. The cassette of implementation 116, wherein the cassette system is configured for insertion into the process module in a first orientation, a second, inverted orientation, or both. 118. The cassette system of implementation 115, wherein the one or more sensors comprise a temperature sensor, a humidity sensor, a gas-phase oxygen concentration sensor, a gas-phase carbon dioxide concentration sensor, a dissolved oxygen concentration sensor, a dissolved carbon dioxide concentration sensor, a gas flow rate sensor, a liquid flow rate sensor, a pH sensor, an optical absorption sensor, an optical scattering sensor, a mass spectroscopic sensor, a viscosity sensor, or any combination thereof. 119. The cassette system of implementation 102, wherein each cell culture chamber comprises a gas-permeable surface. 120. The cassette system of implementation 102, wherein the liquid system provides the input fluid media, receives the output fluid media, or both, via a one-time aseptic connector, a one-time aseptic disconnector, a reusable non-aseptic connector, or any combination thereof. 121. The cassette system of implementation 102, further comprising a mixing and exchange section configured to: a) mix a circulated fluid comprising the input fluid, the output fluid, or both; b) control a concentration of a dissolved gas in the circulated fluid; or c) control a temperature of the one or more cell culture chambers. 122. The cassette system of implementation 121, wherein the mixing and exchange section comprises a liquid feedback mechanism, a gas exchange mechanism, or both. 123. The cassette system of implementation 102, further comprising a sensing section configured to monitor a condition of the input fluid media, the output fluid media, or both. 124. The cassette system of implementation 102, wherein the liquid system is configured to provide the input media to each cell culture chamber at a velocity flow that applies a continuous or directional shear stress of less than about 10 dyne/$cm^2$ to the adherent cell culture. 125. The cassette system of implementation 102, wherein each adherent cell culture chamber comprises a registration mark, and wherein the imaging of the adherent cell cultures captures an image of the registration mark. 126. The cassette system of implementation 102, wherein the cassette system comprises a single-use portion and a permanent portion comprising a reusable housing enclosing the single-use portion, wherein the single-use portion comprises the one or more cell culture chambers and the liquid system. 127. The cassette system of implementation 126, wherein the single-use portion comprises one or more bags or chambers for holding media reagents, waste products, or cellular products. 128. The cassette system of implementation 102, wherein: a) the input fluid media is provided to the one or more cell culture chambers via a first valve; b) the output fluid media is received from the one or more cell culture chambers via a second valve; or c) both. 129. The cassette system of implementation 102, wherein imaging the cell cultures comprises transmission imaging, reflection imaging, brightfield imaging, darkfield imaging, phase imaging, differential interference contrast (DIC) imaging, quantitative phase imaging (QPI), transmission Fourier ptychographic imaging, reflection transmission Fourier ptychographic imaging, holographic imaging, or any combination thereof. 130. A cell culture system, comprising: a) a cell culture chamber having a first surface, a second surface, and an interior between the first surface and the second surface; b) a plurality of cells in the interior of the cell culture chamber and adhered to the first surface; c) a magnetic tool in the interior of the cell culture chamber; d) a magnetic component located exterior to the cell culture chamber, the magnetic component magnetically coupled to the magnetic tool; and e) an actuator removably coupled to the magnetic component and configured to move the magnetic component in one or more directions, wherein moving the magnetic component also moves the magnetic tool in the same manner. 131. The cassette system of implementation 130 wherein the actuator is configured to translate and/or rotate the magnetic component, thereby translating and/or rotating the magnetic tool. 132. The cell culture system of implementation 131, wherein the translation and/or rotation of the magnetic tool inside the cell culture chamber agitates fluid media inside the cell culture chamber. 133. The cell culture system of implementation 132, wherein the agitation dislodges cells, cell components, or cell products from the first surface and/or moves cells, cell components, or cell products floating in the fluid media around the cell culture chamber. 134. The cell culture system of implementation 131, wherein the magnetic tool makes physical contact with one or more cells in the plurality of cells to dislodge them from the first surface. 135. The cassette system of implementation 130 further comprising an imaging subsystem configured to capture images of the plurality of cells. 136. The cell culture system of implementation 135, further comprising a computing subsystem configured to: a) identify one or more cells in the plurality of cells for removal based on the images; and b) control the actuator to move the magnetic tool to remove the one or more cells. 137. The cell culture system of implementation 136, wherein the imaging system is further configured to capture images of the magnetic tool. 138. The cell culture system of implementation 136, wherein the computing subsystem identifies the one or more cells using a machine learning algorithm. 139. The cell culture system of implementation 136, wherein the computing subsystem is further configured to control a velocity, an orientation, a path, or any combination thereof of the actuator. 140. The cell culture system of implementation 136, wherein the computing subsystem is further configured to control a magnetic pole alignment of the actuator. 141. The cell culture system of implementation 136, wherein the computing subsystem is further configured to: a) engage the actuator with the first surface of the cell culture chamber; b) engage the actuator with the second surface of the cell culture chamber; c) disengage the actuator with the first surface of the cell culture chamber; d) disengage the actuator with the second surface of the cell culture chamber; or e) any combination thereof. 142. The cassette system of implementation 130 further comprising a cell culture container enclosing the cell culture chamber, wherein the cell culture container controls fluid media into and out of the cell culture chamber in a closed loop, sterile environment. 143. The cell culture system of implementation 142, wherein the cell culture container encloses a plurality of cell culture chambers. 144. The cassette system of implementation 130 wherein the magnetic tool contacts the first surface and the magnetic component rests on the exterior of the first surface. 145. The cassette system of implementation 130 wherein the magnetic tool contacts the second surface and the magnetic component rests on the exterior of the second surface. 146. The cassette system of implementation 130 wherein at least a portion of the magnetic tool and/or magnetic component is coated with a polymer. 147. The cell culture system of implementation 146, wherein the polymer is configured to make a surface of the magnetic tool and/or magnetic component that contacts the cell culture chamber inert, biocompatible, non-stick, non-scratching, or any combination thereof. 148. The cassette system of implementation 130 wherein the cell culture chamber has a growth area of at least about 50 $cm^2$. 149. The cassette system of implementation 130 wherein the cell culture chamber has a chamber height of less than about 3 mm. 150. The cassette system of implementation 130 wherein the magnetic tool further comprises a blade configured to lift one or more of the plurality of cells from the first surface, the second surface, or both. 151. The cell culture system of implementation 150, wherein the blade comprises a low angle edge configured for non-destructive incremental lifting of one or more of the plurality of cells. 152. The cell culture system of implementation 150, wherein the blade comprises a high angle edge configured to lyse and/or destroy one or more of the plurality of cells. 153. The cassette system of implementation 130 wherein at least a portion of the magnetic tool is flexible. 154. A modular bioprocessing system, comprising: a) one or more process modules, each process module configured to manage and monitor a cell culture process; b) a server rack, wherein the one or more process modules are removably located on the server rack; and c) one or more shared subsystems on the server rack and supporting the one or more process systems. 155. The modular bioprocessing system of implementation 154, wherein each process module is configured to removably couple to a cell culture cassette hosting the cell cultures via one or more pluggable connectors. 156. The modular bioprocessing system of implementation 154, wherein the cell culture process is carried out within a cell culture container comprising a closed cassette system, a micro plate, a flask, a cell culture vessel, a microfluidic chamber, or any combination thereof. 157. The modular bioprocessing system of implementation 156, further comprising a transport mechanism configured to transport the cell culture container between locations within the server rack. 158. The modular bioprocessing system of implementation 157, wherein the transport mechanism comprises a rail, a linear actuator, a motor, a bearing, a wheel, or any combination thereof. 159. The modular bioprocessing system of implementation 157, wherein the transport mechanism is configured to provide horizontal and/or vertical transportation of the cell culture container. 160. The modular bioprocessing system of implementation 156, wherein the closed cassette system comprises at least one transparent or semi-transparent surface that allows for light or laser-based imaging and editing. 161. The modular bioprocessing system of implementation 156, further comprising a front-facing instrument panel configured to receive and/or eject the closed cassette system, the micro plate, the flask, the cell culture vessel, the microfluidic chamber, or any combination thereof. 162. The modular bioprocessing system of implementation 154, wherein the one or more shared subsystems comprise at least one of a computing subsystem, a data storage subsystem, an environmental control subsystem, a laser source subsystem, and a gas distribution subsystem. 163. The modular bioprocessing system of implementation 154, wherein the one or more process modules comprises at least one of a cell imaging subsystem, a cell editing subsystem, and a temperature control subsystem. 164. The modular bioprocessing system of implementation 163, wherein the cell imaging subsystem comprises a brightfield imaging system, a phase imaging system, a quantitative phase imaging system, a transmissive darkfield imaging system, a reflective darkfield, imaging system, a fluorescent imaging system, or any combination thereof. 165. The modular bioprocessing system of implementation 163, wherein the cell imaging subsystem is configured to capture images of the cell culture process. 166. The modular bioprocessing system of implementation 165, wherein the one or more shared subsystems comprises a computing subsystem configured to perform a machine learning function to monitor the cell culture process based on the images. 167. The modular bioprocessing system of implementation 163, wherein the cell editing subsystem is configured to selectively remove one or more cells from the cell culture process. 168. The modular bioprocessing system of implementation 154, wherein the server rack has one or more standardized computer server rack sizes. 169. The modular bioprocessing system of implementation 154, further comprising a backup power module for providing uninterrupted power to the one or more process modules and the one or more shared subsystems. 170. The modular bioprocessing system of implementation 154, further comprising a temperature control subsystem configured to manage a temperature of at least one of the cell culture process and a reagent. 171. The modular bioprocessing system of implementation 154, further comprising a pH control subsystem configured to manage a pH of the cell culture process. 172. The modular bioprocessing system of implementation 154, further comprising a gas content control subsystem configured to manage a dissolved oxygen and/or carbon dioxide content of at least one of the cell culture process and a reagent. 173. The modular bioprocessing system of implementation 154, further comprising a media control subsystem configured to provide and/or extract a media from at least one of the one or more process modules. 174. The modular bioprocessing system of implementation 154, wherein the cell culture process comprises cell reprogramming, cell differentiation, cell gene editing, cell incubation, cell expansion, cell sorting or purification, cell-based bioproduction, or any combination thereof. 175. The modular bioprocessing system of implementation 154, wherein the modular bioprocessing system has a multi-rack configuration comprising a plurality of the server rack. 176. An imaging system, comprising: a) at least one light source illuminating a sample; b) an objective capturing light from the at least one light source passing through the sample; and c) one or more sensors to measure the light captured by the objective, wherein the sample moves continuously relative to the at least one light source and the objective during the measurement; and d) a computing subsystem configured to generate quantitative phase images of the sample based on the measurements from the one or more sensors. 177. The imaging system of implementation 176, wherein the movement of the sample relative to the at least one light source and the objective during the measurement generates image data at multiple focal planes along an axis perpendicular to a horizontal plane of the sample and the quantitative phase images are generated from the image data at multiple focal planes. 178. The imaging system of implementation 177, wherein the objective is tilted at an angle with respect to the axis. 179. The imaging system of implementation 176, wherein the movement of the sample relative to the at least one light source and the objective during the measurement generates image data at multiple illumination angles relative to the sample and the quantitative phase images are generated from the image data at multiple illumination angles. 180. The imaging system of implementation 179, wherein the at least one light source emits light at multiple wavelengths and different wavelengths illuminate the sample at different angles. 181. The imaging system of implementation 176, further comprising a laser source configured to manipulate the sample based on the quantitative phase images. 182. The imaging system of implementation 181, wherein the sample is moved continuously relative to the laser source. 183. The imaging system of implementation 181, wherein the laser source and the one or more light sources share the objective. 184. The imaging system of implementation 181, wherein the sample is a cell culture sample and the laser source is configured to edit the cell culture sample. 185. The imaging system of implementation 184, wherein the cell culture sample is enclosed in a cell culture chamber, the cell culture chamber comprising at least one transparent or semi-transparent surface. 186. The imaging system of implementation 185, wherein the cell culture chamber comprises a transparent upper window and a transparent lower window. 187. The imaging system of implementation 185, wherein the cell culture chamber comprises at least one semi-transparent coating on the at least one transparent surface configured to absorb laser radiation and direct absorbed energy to one or more cells in the cell culture chamber. 188. The imaging system of implementation 187, further comprising a film within the cell culture chamber, wherein the film comprises a fiducial marker and wherein the fiducial marker is patterned in the laser absorbing film. 189. The imaging system of implementation 181, wherein the laser source is configured to generate a laser having a wavelength of about 500 nm to about 600 nm or about 1000 nm to about 1100. 190. The imaging system of implementation 181, wherein the laser source is configured to generate a laser having a pulse rate of at least about 100 kHz. 191. The imaging system of implementation 181, further comprising a laser autofocus system configured to: a) project a laser from the laser source onto the cell culture; b) move the sample relative to the laser source; c) repeat steps a) and b); d) measure a sharpness of the laser based on the light captured by the objective lens during steps a)-c); and e) focus the laser based on the measured sharpness. 192. The imaging system of implementation 176, wherein the sensor comprises a CMOS sensor, a CCD sensor, or both. 193. The imaging system of implementation 176, wherein the sensor comprises an array of sensors in one or more directions. 194. The imaging system of implementation 176, wherein the computing subsystem is configured to compute structural information on individual cells, groups of cells, or regions or colonies using the quantitative phase images of the sample. 195. The imaging system of implementation 176, wherein the computing subsystem is configured to apply machine learning to analyze the measurements from the one or more samples. 196. The imaging system of implementation 195, wherein the computing subsystem is configured to use a convolutional neural network to reconstruct sample amplitude and phase. 197. The imaging system of implementation 195, wherein the computing subsystem is configured to use a convolutional neural network to reconstruct sample amplitude and phase or determine one or more cell quality features. 198. The imaging system of implementation 176, comprising a first light source and a second light source, wherein the first light source and the second light source emit light at different wavelengths. 199. A method for generating quantitative phase images of a sample, comprising: a) illuminating a sample using at least one light source; b) capturing, with an objective, light from the at least one light source passing through the sample; and c) measuring, with one or more sensors, the light captured by the objective, wherein the sample moves continuously relative to the at least one light source and the objective during the measurement; and d) generating, with a computing subsystem, quantitative phase images of the sample based on the measurements from the one or more sensors. 200. A monoclonal induced pluripotent stem cell (iPSC) product made by the process comprising: a) placing input cells in a cell culture chamber of a closed cell culture container; b) reprogramming at least a portion of the input cells into a plurality of clonal iPSC candidate cells; c) collecting imaging data on a plurality of clonal iPSC candidate cell colonies emerging from the plurality of clonal iPSC candidate cells; d) selecting one of the plurality of clonal iPSC candidates cell colonies for expansion based on the imaging data; e) removing non-selected clonal iPSC candidate cell colonies using a cell editing mechanism; and f) expanding the selected clonal iPSC candidate cell colony into the monoclonal iPSC product. 201. The monoclonal iPSC product of implementation 200, wherein the imaging data comprises a time-series images of the plurality of clonal iPSC candidate cell colonies. 202. The monoclonal iPSC product of implementation 200, wherein selecting one of the plurality of clonal iPSC candidates cell colonies for expansion comprises: a) applying a predictive model to the image data to predict clonal quality and functionality of each of the plurality of clonal iPSC candidate cell colonies; and b) selecting one of the plurality of clonal iPSC candidates cell colonies based on the predicted clonal quality and functionality of each of the plurality of clonal iPSC candidate cell colonies. 203. The monoclonal iPSC product of implementation 202, wherein the predictive model is trained on prior clonal cell colony data and clonal iPSC product quality and functionality assays. 204. The monoclonal iPSC product of implementation 202, wherein the clonal quality and functionality are determined by based on one or more phenotypic features. 205. The monoclonal iPSC product of implementation 204, wherein the one or more phenotypic features comprise a cell morphology, a cell proliferation rate, a chromatin condensation, a nucleus to cytosol ratio, a cell migration pattern, or any combination thereof. 206. The monoclonal iPSC product of implementation 200, the process further comprising: removing contaminant cells in proximity to the plurality of clonal iPSC candidate cell colonies using the cell editing mechanism. 207. The monoclonal iPSC product of implementation 200, wherein the closed cell culture container further comprises a sterile-sealed liquid system for providing fluid media to the cell culture chamber and receiving fluid media from the cell culture chamber. 208. The monoclonal iPSC product of implementation 200, wherein the cell editing mechanism comprises laser radiation. 209. The monoclonal iPSC product of implementation 200, wherein a surface of the cell culture chamber is laser-absorbant. 210. The monoclonal iPSC product of implementation 200, wherein the cell editing mechanism comprises a magnetic tool in the cell culture chamber and actuated from outside the cell culture chamber. 211. The iPSC product of implementation 210, wherein the magnetic tool comprises a rare-earth magnet. 212. The monoclonal iPSC product of implementation 200, wherein the cell editing mechanism comprises focused ultrasound waves. 213. The monoclonal iPSC product of implementation 200, wherein the cell editing mechanism comprises directed energy projected from outside the cell culture chamber. 214. The monoclonal iPSC product of implementation 200, wherein the closed cell culture container comprises a single closed cell culture container. 215. The monoclonal iPSC product of implementation 200, wherein the one or more of the input cells comprise a B lymphocytes cell, a blood-derived epithelial cell, a C lymphocytes cell, a cardiac muscle cell, a chondrocyte cell, an endothelial cell, an epidermal cell, an epithelial cell, an erythrocyte cell, a fibroblast cell, a granulosa epithelial cell, a hair follicle cell, a hematopoietic cell, a hepatocyte cell, a keratinocyte cell, a macrophage cell, a melanocyte cell, a monocyte cell, a mononuclear cell, a neuron cell, a pancreatic islet cell, a sertoli cell, a somatic cells, a urine-derived epithelial cell, or any combination thereof. 216. The monoclonal iPSC product of implementation 200, wherein the reprogramming is performed using genome integration, non-genome integration, minicircle vectors, the Sendai protocol, mRNA, self-replicating RNA, CRISPR activators, recombinant proteins, or any combination thereof. 217. The monoclonal iPSC product of implementation 216, wherein the monoclonal iPSC product is transgene-free. 218. The monoclonal iPSC product of implementation 200, wherein the monoclonal iPSC product is suitable for differentiation into a target cell type. 219. The monoclonal iPSC product of implementation 200, wherein the non-selected clonal iPSC candidate cell colonies are determined based on at least a cell division time, a cell high reprogramming cargo load, a cell migration characteristic, a cell speed, a cell trackability, or any combination thereof. 220. The monoclonal iPSC product of implementation 200, wherein the process is performed within a cassette system providing a closed, sterile environment for cell culture processing. 221. The monoclonal iPSC product of implementation 200, wherein the process is performed within a modular bioprocessing system configured to produce a plurality of monoclonal iPSC products corresponding to different subjects. 222. A method for producing a monoclonal induced pluripotent stem cell (iPSC) product, comprising: a) placing input cells in a cell culture chamber of a closed cell culture container; b) reprogramming at least a portion of the input cells into a plurality of clonal iPSC candidate cells; c) collecting imaging data on a plurality of clonal iPSC candidate cell colonies emerging from the plurality of clonal iPSC candidate cells; d) selecting one of the plurality of clonal iPSC candidates cell colonies for expansion based on the imaging data; e) removing non-selected clonal iPSC candidate cell colonies using a cell editing mechanism; and f) expanding the selected clonal iPSC candidate cell colony into the monoclonal iPSC product. 223. A cell culture system, comprising: a cell culture container containing one or more cells in a fluid media and a film; an imaging subsystem that utilizes the film to capture images of the one or more cells; and a measurement subsystem that utilizes the film to measure characteristics of the one or more cells or the fluid media using surface enhanced Raman spectroscopy (SERS). 224. The cell culture system of implementation 223, wherein the film is semi-transparent so that the imaging system may image contents of the cell culture container. 225. The cell culture system of implementation 223, wherein: the measurement system comprises a laser configured to emit an excitation beam at an excitation wavelength towards the film; the film is configured to scatter the excitation beam at wavelengths shifted from the excitation wavelength; and the measurement system is configured to capture light scattered by the film, wherein the scattered light is indicative of a chemical composition of contents of the cell culture container. 226. The cell culture system of implementation 225, wherein the laser is further configured to emit a poration beam to temporarily porate the one or more cells. 227. The cell culture system of implementation 226, wherein the poration beam has a wavelength that is approximately equal to a resonant absorption wavelength of the film to create transient microbubbles in the cell culture container, the transient microbubbles causing the one or more cells to temporarily porate. 228. The cell culture system of implementation 225, wherein the measurement system is configured to measure characteristics of cell contents from the temporarily porated cells. 229. The cell culture system of implementation 225, wherein the laser is further configured to remove biofouling from a surface of the film. 230. The cell culture system of implementation 225, wherein the laser is further configured to lyse a portion of the one or more cells. 231. The cell culture system of implementation 225, wherein the laser is shared by the measurement subsystem and the imaging subsystem. 232. A imaging subsystem comprising: a sample; an LED array on a first side of the sample, illuminating the sample, wherein each LED in the LED array is individually addressable; and an objective on a second side of the sample configured to capture light transmitted through the sample. 233. The imaging subsystem of implementation 232, wherein the objective is translated relative to the sample. 234. The imaging subsystem of implementation 233, wherein as the objective is translated, different LEDs in the LED array are turned on/off or their intensities adjusted. 235. A cell culture container comprising: a cell culture surface; and a film attached to the cell culture surface, the film comprising one or more fiducial markings, wherein the one or more fiducial markings are used to determine a position of the cell culture surface relative to one or more subsystems within a cell culture system. 236. The cell culture container of implementation 235, wherein: the cell culture surface is illuminated at one or more imaging wavelengths to capture images of cells on the cell culture surface without capturing images of the fiducial markings; and the cell culture surface is illuminated at one or more fiducial wavelengths to capture images of the fiducial markings. 237. A cell culture chamber, comprising: a membrane having a porous surface upon which cells are cultured; and a film attached to the membrane, the film configured to enable imaging of the cells and laser interaction with the cells. 238. The cell culture chamber of implementation 237, wherein the membrane separates the cell culture chamber into two or more sub-compartments. 239. A cell culture system, comprising: a plurality of cell process modules, each cell process module comprising a cell culture container supporting a cell culture; and one or more laser subsystems, wherein each laser subsystem is configured to act on the cell culture on one or more of the plurality of cell process modules and wherein the plurality of cell process modules shares the one or more laser subsystems. 240. A cell culture system, comprising: a cell culture container comprising a flexible foil; a cell culture adhered to the flexible foil; and one or more imaging subsystems and cell editing subsystems. 241. The cell culture system of implementation 240, wherein the cell culture container comprises a cylinder and the flexible foil is located on the interior of the cylinder. 242. The cell culture system of implementation 241, further comprising cell culture media located inside the cell culture container, wherein the cell culture container is rotated to expose the cell culture to the cell culture media. 243. The cell culture system of implementation 240, wherein the cell culture container comprises an interior cylinder an exterior cylinder and the interior cylinder is configured to rotate independently of the exterior cylinder. 244. The cell culture system of implementation 243, wherein the flexible foil is located on the interior of the interior cylinder. 245. The cell culture system of implementation 243, wherein the flexible foil is located between the interior cylinder and the exterior cylinder. 246. The cell culture system of implementation 240, further comprising at least two rolls, wherein the flexible foil is transported between the at least two rolls. 247. The cell culture system of implementation 240, further comprising a plurality of media bath stations and a plurality of imaging and/or laser processing subsystems, wherein the flexible foil is moved along the plurality of media bath stations and the plurality of imaging and/or laser processing subsystems. 248. A cell culture container, comprising: a first wall and a second wall enclosing cell culture media and a cell culture; a plasmonic film attached to the first wall, wherein the plasmonic film has a resonant peak when irradiated; and an optical subsystem that illuminates the plasmonic film and measures reflected or transmitted light, wherein the measurement is used to determine one or more parameters of the cell culture media and the cell culture. 249. The cell culture container of implementation 248, wherein the cell culture is adhered to the plasmonic film. 250. The cell culture container of implementation 248, further comprising a laser processing subsystem configured to remove and/or porate one or more cells in the cell culture using a pulsed laser, the pulsed laser passing through the plasmonic film. 251. A imaging subsystem, comprising: a first illumination source illuminating a sample, wherein the first illumination source provides a conical light beam; an objective configured to capture light transmitted from the sample, wherein the sample is in motion relative to the first illumination source; and an image sensor configured to capture images of the sample at high speeds. 252. A cell culture system, comprising: (a) a cell culture chamber having a first surface, a second surface, and an interior between the first surface and the second surface; (b) a plurality of cells in the interior of the cell culture chamber and adhered to the first surface; (c) a magnetic tool in the interior of the cell culture chamber; (d) a magnetic component located exterior to the cell culture chamber, the magnetic component magnetically coupled to the magnetic tool; (e) an actuator removably coupled to the magnetic component and configured to move the magnetic component in one or more directions, wherein moving the magnetic component also moves the magnetic tool in the same manner; (f) an image sensor configured to acquire image data of the plurality of cells; and (g) a computer processor programmed to (1) perform a machine learning analysis of the acquired image data of the plurality of cells, to determine visual features of the plurality of cells, (2) identify a subset of the plurality of cells for selective removal, based at least in part on the subset of the plurality of cells having undesired attributes associated with the visual features, and (3) control the actuator to move the magnetic component such that the identified subset of the plurality of cells is selectively removed by the magnetic tool. 253. The cell culture system of implementation 252, wherein the computer processor is further programmed to translate and/or rotate the magnetic component, thereby translating and/or rotating the magnetic tool. 254. The cell culture system of implementation 253, wherein the computer processor is further programmed to translate or rotate the magnetic component such that the magnetic tool agitates fluid media inside the cell culture chamber, wherein the agitating is sufficient to create turbulent flow. 255. The cell culture system of implementation 254, wherein the turbulent flow is sufficient to dislodge cells, cell components, or cell products from the first surface. 256. The cell culture system of implementation 253, wherein the magnetic tool makes physical contact with one or more cells of the plurality of cells to dislodge the one or more cells from the first surface. 257. The cell culture system of implementation 252, wherein the image sensor is further configured to acquire image data of the magnetic tool. 258. The cell culture system of implementation 252, wherein the computer processor is further programmed to control a position, a velocity, an orientation, a rotation, a path, or any combination thereof of the actuator. 259. The cell culture system of implementation 252, wherein the computer processor is further programmed to control a magnetic pole alignment of the actuator. 260. The cell culture system of implementation 252, wherein the computer processor is further programmed to control the actuator to: (1) engage the magnetic component with an exterior of the first surface of the cell culture chamber; (2) engage the magnetic component with the second surface of the cell culture chamber; (3) disengage the magnetic component from the exterior of the first surface of the cell culture chamber; or (4) disengage the magnetic component from the second surface of the cell culture chamber. 261. The cell culture system of implementation 252, further comprising a cell culture container enclosing the cell culture chamber, wherein the cell culture container controls transfer of fluid media into and out of the cell culture chamber in a closed loop, sterile environment. 262. The cell culture system of implementation 261, wherein the cell culture chamber comprises a plurality of cell culture chambers; wherein each of the plurality of cell culture chambers has a first surface, a second surface, and an interior between the first surface and the second surface; and wherein the cell culture container encloses the plurality of cell culture chambers. 263. The cell culture system of implementation 252, wherein the magnetic tool contacts an interior of the first surface, and wherein the magnetic component is located on an exterior of the first surface. 264. The cell culture system of implementation 252, wherein the magnetic tool contacts an interior of the second surface, and wherein the magnetic component is located on an exterior of the second surface. 265. The cell culture system of implementation 252, wherein the magnetic tool and/or the magnetic component is at least partially coated with a polymer. 266. The cell culture system of implementation 265, wherein the polymer is configured to make a surface of the magnetic tool and/or the magnetic component that contacts the cell culture chamber inert, biocompatible, non-stick, non-scratching, or any combination thereof. 267. The cell culture system of implementation 252, wherein the cell culture chamber has a growth area of at least about 50 square centimeters ($cm^2$). 268. The cell culture system of implementation 252, wherein the cell culture chamber has a chamber height of less than about 3 millimeters (mm). 269. The cell culture system of implementation 252, wherein the magnetic tool further comprises a blade configured to lift one or more of the plurality of cells from the first surface, the second surface, or both. 270. The cell culture system of implementation 269, wherein the blade comprises a low-angle edge configured to perform non-destructive incremental lifting of the one or more of the plurality of cells. 271. The cell culture system of implementation 269, wherein the blade comprises a high-angle edge configured to lyse and/or destroy one or more of the plurality of cells. 272. The cell culture system of implementation 252, wherein at least a portion of the magnetic tool is flexible. 273. The cell culture system of implementation 252, wherein the machine learning analysis of the acquired image data of the plurality of cells comprises determining a cell culture state, a cell quality, or a cell phenotype, of the plurality of cells; and wherein the computer processor is further programmed to identify the subset of the plurality of cells for selective removal, based at least in part on the subset of the plurality of cells having an undesired cell culture state, cell quality, or cell phenotype. 274. The cell culture system of implementation 273, wherein the cell culture state comprises an assessment of cell growth within a designated growth area or beyond the designated growth area; and wherein the computer processor is further programmed to identify the subset of the plurality of cells for selective removal, based at least in part on the subset of the plurality of cells having cell growth beyond the designated growth area. 275. The cell culture system of implementation 273, wherein the cell quality comprises an assessment of dense or sparse cell growth, cell morphology, cell division rate, cell motility, or any combination thereof. 276. The cell culture system of implementation 275, wherein the cell quality comprises the assessment of dense or sparse cell growth; and wherein the computer processor is further programmed to identify the subset of the plurality of cells for selective removal, based at least in part on the subset of the plurality of cells having excessively dense cell growth. 277. The cell culture system of implementation 273, wherein the cell phenotype comprises an induced pluripotent stem cell (iPSC) phenotype or a non-iPSC phenotype; and wherein the computer processor is further programmed to identify the subset of the plurality of cells for selective removal, based at least in part on the subset of the plurality of cells having the non-iPSC phenotype. 278. The cell culture system of implementation 273, wherein the cell phenotype comprises a spontaneously differentiated phenotype or a non-spontaneously differentiated phenotype; and wherein the computer processor is further programmed to identify the subset of the plurality of cells for selective removal, based at least in part on the subset of the plurality of cells having the spontaneously differentiated phenotype. 279. The cell culture system of implementation 252, wherein the magnetic tool further comprises a first magnetic tool located on an interior of the first surface and a second magnetic tool located on an interior of the second surface, wherein the magnetic component further comprises a first magnetic component located on an exterior of the first surface, and a second magnetic component located on an exterior of the second surface, and wherein the magnetic tool is configured to reversibly magnetically couple to the first magnetic component at a location on the exterior of the first surface or magnetically couple to the second magnetic component at a location on the exterior of the second surface, responsive to reversing a polarity of the first magnetic component and the second magnetic component. 280. A modular bioprocessing system, comprising: (a) one or more cell culture process modules, each of the one or more cell culture process modules configured to (i) receive one or more cell culture containers, each of the one or more cell culture containers configured for performing a cell culture process therein, and (ii) manage and monitor cell culture functions of the cell culture processes being performed within the one or more cell culture containers; (b) a server rack, wherein the one or more cell culture process modules are removably located on the server rack; and (c) one or more shared subsystems on the server rack and supporting the one or more cell culture process modules. 281. The modular bioprocessing system of implementation 280, wherein each of the one or more cell culture process modules is configured to removably couple to a cell culture cassette hosting the cell culture process via one or more pluggable connectors. 282. The modular bioprocessing system of implementation 280, wherein each of the one or more cell culture containers comprises a closed cassette system, a micro plate, a flask, a cell culture vessel, a microfluidic chamber, or any combination thereof. 283. The modular bioprocessing system of implementation 280, further comprising a transporter configured to transport the one or more cell culture containers between locations within the server rack. 284. The modular bioprocessing system of implementation 283, wherein the transporter further comprises a rail, a linear actuator, a motor, a bearing, a wheel, or a combination thereof. 285. The modular bioprocessing system of implementation 283, wherein the transporter is configured to provide horizontal and/or vertical transportation of each of the one or more cell culture containers. 286. The modular bioprocessing system of implementation 282, wherein the closed cassette system comprises at least one transparent or semi-transparent surface for performing light-based or laser-based cell imaging or cell editing. 287. The modular bioprocessing system of implementation 282, further comprising a front-facing instrument panel configured to receive and/or eject the closed cassette system, the micro plate, the flask, the cell culture vessel, the microfluidic chamber, or a combination thereof. 288. The modular bioprocessing system of implementation 280, wherein the one or more shared subsystems further comprise at least one of a computing subsystem, a data storage subsystem, an environmental control subsystem, a laser source subsystem, and a gas distribution subsystem. 289. The modular bioprocessing system of implementation 280, wherein the one or more cell culture process modules further comprise at least one of a cell imaging subsystem, a cell editing subsystem, and a temperature control subsystem. 290. The modular bioprocessing system of implementation 289, wherein the cell imaging subsystem further comprises a brightfield imaging system, a phase imaging system, a quantitative phase imaging system, a transmissive darkfield imaging system, a reflective darkfield imaging system, a fluorescent imaging system, or any combination thereof. 291. The modular bioprocessing system of implementation 289, wherein the cell imaging subsystem is configured to capture images of the cell culture processes. 292. The modular bioprocessing system of implementation 291, wherein the one or more shared subsystems further comprise a computing subsystem configured to monitor the cell culture processes based at least in part on performing machine learning analysis of the captured images of the cell culture processes. 293. The modular bioprocessing system of implementation 289, wherein the cell editing subsystem is configured to selectively remove one or more cells from at least one of the one or more cell culture containers. 294. The modular bioprocessing system of implementation 280, wherein the server rack comprises one or more server rack units with standardized computer server rack sizes. 295. The modular bioprocessing system of implementation 280, further comprising a backup energy storage configured to provide uninterrupted power to the one or more cell culture process modules and the one or more shared subsystems. 296. The modular bioprocessing system of implementation 280, further comprising a temperature control subsystem configured to manage a temperature of at least one of the cell culture processes or a reagent used in the cell culture processes. 297. The modular bioprocessing system of implementation 280, further comprising a pH control subsystem configured to manage a pH of at least one of the cell culture processes. 298. The modular bioprocessing system of implementation 280, further comprising a gas content control subsystem configured to manage a dissolved oxygen and/or carbon dioxide content of at least one of the cell culture processes or a reagent used in the cell culture processes. 299. The modular bioprocessing system of implementation 280, further comprising a media control subsystem configured to provide a media to, and/or extract a media from, at least one of the one or more cell culture containers. 300. The modular bioprocessing system of implementation 280, wherein the cell culture processes further comprise cell reprogramming, cell differentiation, cell gene editing, cell incubation, cell expansion, cell sorting, cell purification, cell-based bioproduction, or a combination thereof. 301. The modular bioprocessing system of implementation 280, wherein the server rack has a multi-rack configuration. 302. The modular bioprocessing system of implementation 280, wherein the one or more shared subsystems are configured to perform the cell culture functions of the cell culture processes. 303. The modular bioprocessing system of implementation 280, wherein the one or more cell culture process modules are located at a stationary location on the server rack while the cell culture processes are performed within the one or more cell culture containers. 304. The modular bioprocessing system of implementation 280, wherein the cell culture process comprises culturing induced pluripotent stem cells (iPSCs). 305. An imaging system, comprising: (a) a light source configured to illuminate a cell culture sample, wherein the cell culture sample comprises one or more cells that are adherent to a surface of the cell culture chamber; (b) an objective configured to capture light from the light source passing through the cell culture sample; and (c) a sensor configured to acquire image data from the captured light, wherein (i) the cell culture chamber undergoes continuous movement relative to the light source and the objective or (ii) the light source and the objective undergo continuous movement relative to the cell culture chamber, while the image data is acquired; and (d) a computer processor programmed to generate quantitative phase images of the cell culture sample based at least in part on the acquired image data. 306. The imaging system of implementation 305, wherein the continuous movement of the cell culture chamber relative to the light source and the objective or the continuous movement of the light source and the objective relative to the cell culture chamber allows image data to be acquired at each of a plurality of different focal planes along an axis perpendicular to a horizontal plane of the cell culture sample. 307. The imaging system of implementation 306, wherein the objective is tilted at an angle with respect to the axis. 308. The imaging system of implementation 305, wherein the continuous movement of the cell culture chamber relative to the light source and the objective or the continuous movement of the light source and the objective relative to the cell culture chamber allows image data to be acquired at each of a plurality of different illumination angles relative to the cell culture sample. 309. The imaging system of implementation 308, wherein the light source emits light at a plurality of different wavelengths, and wherein the plurality of different wavelengths illuminates the cell culture sample at a plurality of different angles. 310. The imaging system of implementation 305, further comprising a laser source configured to manipulate the cell culture sample based at least in part on the quantitative phase images. 311. The imaging system of implementation 310, wherein the cell culture chamber further undergoes continuous movement relative to the laser source, or the laser source further undergoes continuous movement relative to the cell culture chamber. 312. The imaging system of implementation 310, wherein the objective is shared by the laser source and the light source. 313. The imaging system of implementation 310, wherein the laser source is further configured to edit the cell culture sample. 314. The imaging system of implementation 313, wherein the cell culture sample is enclosed in the cell culture chamber, and wherein the cell culture chamber comprises a transparent or semi-transparent surface. 315. The imaging system of implementation 314, wherein the cell culture chamber further comprises a transparent upper window and a transparent lower window. 316. The imaging system of implementation 314, wherein the cell culture chamber further comprises a semi-transparent coating on the transparent surface configured to absorb laser radiation and direct absorbed energy to one or more cells in the cell culture chamber. 317. The imaging system of implementation 316, further comprising a film within the cell culture chamber, wherein the film comprises a fiducial marker patterned thereon. 318. The imaging system of implementation 310, wherein the laser source is further configured to generate a laser having a wavelength of about 500 nanometers (nm) to about 600 nm, or about 1000 nm to about 1100 nm. 319. The imaging system of implementation 310, wherein the laser source is further configured to generate a laser having a pulse rate of at least about 100 kilohertz (kHz). 320. The imaging system of implementation 305, further comprising a laser autofocus system configured to: (i) project a laser from the laser source onto the cell culture sample; (ii) move the cell culture sample relative to the laser source, or move the laser source relative to the cell culture sample; (iii) measure a sharpness of the laser based at least in part on light captured by the objective during operations (i) and (ii); and (iv) focus the laser based at least in part on the measured sharpness of the laser. 321. The imaging system of implementation 305, wherein the sensor comprises a complementary metal-oxide semiconductor (CMOS) sensor, a charge-coupled device (CCD) sensor, or a combination thereof. 322. The imaging system of implementation 305, wherein the sensor comprises an array of sensors oriented in one or more directions. 323. The imaging system of implementation 305, wherein the computer processor is further programmed to determine structural information of individual cells, groups of cells, regions of cells, or colonies of cells, based at least in part on the quantitative phase images of the cell culture sample. 324. The imaging system of implementation 323, wherein the structural information comprises a location, a density, a nuclear location, an intracellular structure, a 3-dimensional (3-D) profile, a refractive index, or a combination thereof. 325. The imaging system of implementation 305, wherein the cell culture sample comprises induced pluripotent stem cells (iPSCs). 326. The imaging system of implementation 305, wherein the computer processor is further programmed to perform a machine learning analysis of the acquired measurements or the quantitative phase images. 327. The imaging system of implementation 326, wherein the computer processor is further programmed to determine features indicative of a cell culture state, a cell quality, or a cell phenotype of one or more cells of the cell culture sample, based at least in part on the machine learning analysis. 328. The imaging system of implementation 327, wherein the cell culture state comprises an assessment of cell growth within a designated growth area or beyond the designated growth area. 329. The imaging system of implementation 327, wherein the cell quality comprises an assessment of dense or sparse cell growth, cell morphology, cell division rate, cell motility, or any combination thereof. 330. The imaging system of implementation 327, wherein the cell phenotype comprises an induced pluripotent stem cell (iPSC) phenotype, a non-iPSC phenotype, a spontaneously differentiated phenotype, or a non-spontaneously differentiated phenotype. 331. The imaging system of implementation 326, wherein the machine learning analysis further comprises using a convolutional neural network to reconstruct amplitude and phase information of the cell culture sample. 332. The imaging system of implementation 326, wherein the machine learning analysis further comprises using a convolutional neural network to determine one or more features indicative of a cell quality of the cell culture sample. 333. The imaging system of implementation 305, wherein the light source further comprises a first light source and a second light source, wherein the first light source and the second light source emit light at different wavelengths. 334. A method for generating quantitative phase images of a cell culture sample, comprising: (a) illuminating a cell culture sample using a light source, wherein the cell culture sample comprises one or more cells that are adherent to a surface of the cell culture chamber; (b) capturing, with an objective, light from the light source passing through the cell culture sample; (c) acquiring, with a sensor, image data from the captured light, while (i) continuously moving the cell culture chamber relative to the light source and the objective or (ii) continuously moving the light source and the objective relative to the cell culture chamber; and (d) generating, with a computer processor, quantitative phase images of the cell culture sample based at least in part on the acquired image data. 335. A method for producing a monoclonal induced pluripotent stem cell (iPSC) product, comprising: (a) placing input cells in a cell culture chamber of a closed cell culture container; (b) reprogramming at least a portion of the input cells into a plurality of clonal iPSC candidate cells; (c) acquiring, using an image sensor, image data of a plurality of clonal iPSC candidate cell colonies emerging from the plurality of clonal iPSC candidate cells; (d) processing, by a computer processor, the acquired image data using a trained machine learning model to predict clonal quality or clonal functionality of the plurality of clonal iPSC candidate cell colonies; (e) selecting, by the computer processor, at least one of the plurality of clonal iPSC candidate cell colonies for expansion based at least in part on the predicted clonal quality or clonal functionality of the plurality of clonal iPSC candidate cell colonies; (f) removing non-selected clonal iPSC candidate cell colonies of the plurality of clonal iPSC candidate cell colonies from the cell culture chamber using a cell editor; and (g) expanding the selected at least one of the clonal iPSC candidate cell colonies into the monoclonal iPSC product. 336. The method of implementation 335, wherein the image data comprises a plurality of time-series images of the plurality of clonal iPSC candidate cell colonies. 337. The method of implementation 335, wherein the trained machine learning model is trained with prior clonal cell colony data, clonal iPSC product quality assay data, and clonal iPSC functionality assay data. 338. The method of implementation 337, further comprising assaying the monoclonal iPSC product to produce quality assay data or functionality assay data, and further training the trained machine learning model using the quality assay data or functionality assay data. 339. The method of implementation 338, further comprising performing one or more additional iterations of (d) to (g), subsequent to further training the trained machine learning model. 340. The method of implementation 335, wherein (d) further comprises applying the trained machine learning model to one or more phenotypic features of the acquired image data. 341. The method of implementation 340, wherein the one or more phenotypic features comprise a cell morphology, a cell proliferation rate, a chromatin condensation, a nucleus-to-cytosol ratio, a cell migration pattern, or any combination thereof. 342. The method of implementation 335, wherein (f) further comprises controlling, by the computer processor, the cell editor to remove the non-selected clonal iPSC candidate cell colonies. 343. The method of implementation 335, further comprising controlling, by the computer processor, the cell editor to remove contaminant cells in proximity to the plurality of clonal iPSC candidate cell colonies. 344. The method of implementation 335, wherein the closed cell culture container further comprises a sterile-sealed liquid system, and wherein the method further comprises providing fluid media to the cell culture chamber and receiving fluid media from the cell culture chamber. 345. The method of implementation 335, wherein (f) further comprises directing laser radiation using the cell editor. 346. The method of implementation 345, wherein the cell culture chamber comprises a laser-absorbent surface. 347. The method of implementation 335, wherein the cell editor further comprises a magnetic tool in the cell culture chamber, and wherein the method further comprises actuating the magnetic tool from outside the cell culture chamber. 348. The method of implementation 347, wherein the magnetic tool further comprises a rare-earth magnet. 349. The method of implementation 335, wherein (f) further comprises directing focused ultrasound waves using the cell editor. 350. The method of implementation 335, wherein (f) further comprises directing energy projected from outside the cell culture chamber. 351. The method of implementation 335, wherein the closed cell culture container is a single closed cell culture container. 352. The method of implementation 335, wherein the input cells comprise a B lymphocyte cell, a blood-derived epithelial cell, a C lymphocyte cell, a cardiac muscle cell, a chondrocyte cell, an endothelial cell, an epidermal cell, an epithelial cell, an erythrocyte cell, a fibroblast cell, a granulosa epithelial cell, a hair follicle cell, a hematopoietic cell, a hepatocyte cell, a keratinocyte cell, a macrophage cell, a melanocyte cell, a monocyte cell, a mononuclear cell, a neuron cell, a pancreatic islet cell, a sertoli cell, a somatic cells, a urine-derived epithelial cell, or any combination thereof. 353. The method of implementation 335, wherein the reprogramming further comprises using genome integration, non-genome integration, minicircle vectors, a Sendai protocol, messenger ribonucleic acid (mRNA), self-replicating RNA, Clustered Regularly Interspaced Short Palindromic Repeats (CRISPR) activators, recombinant proteins, or a combination thereof. 354. The method of implementation 335, wherein the monoclonal iPSC product is transgene-free. 355. The method of implementation 335, wherein the monoclonal iPSC product is suitable for differentiation into a target cell type. 356. The method of implementation 335, wherein the non-selected clonal iPSC candidate cell colonies are determined based at least in part on a cell division time, a cell high reprogramming cargo load, a cell migration characteristic, a cell speed, a cell trackability, or any combination thereof. 357. The method of implementation 335, wherein the method is performed within a cassette system, and wherein the method further comprises using the cassette system to provide a closed, sterile environment for cell culture processing. 358. The method of implementation 335, wherein the method is performed within a modular bioprocessing system, and wherein the method further comprises using the modular bioprocessing system to produce a plurality of different monoclonal iPSC products corresponding to a plurality of different subjects. 359. A system for cell culture processing, comprising: (a) one or more cell culture chambers, each of the one or more cell culture chambers configured to: (i) provide a growth environment for adherent cell cultures to grow therein; and (ii) allow imaging of the adherent cell cultures grown in the cell culture chamber; (b) a liquid handler coupled to the one or more cell culture chambers, wherein the liquid handler is configured to: (i) provide input fluid media to the one or more cell culture chambers; (ii) receive output fluid media from the one or more cell culture chambers; and (iii) mix a circulated fluid within the one or more cell culture chambers, wherein the circulated fluid comprises the input fluid media, the output fluid media, or both; (c) a cassette enclosing the one or more cell culture chambers and the liquid handler, wherein the cassette is configured to provide a closed, sterile liquid environment for the adherent cell cultures grown in each cell culture chamber; and (d) a docking station configured to host the cassette via a pluggable connector. 360. The system of implementation 359, wherein at least one of the input fluid media and the output fluid media comprises growth media, reagents, buffers, fluid waste, or cell collection media. 361. The system of implementation 360, wherein the liquid handler further comprises one or more reservoirs for holding different types of fluid media. 362. The system of implementation 359, further comprising a pump configured to direct at least one of the input fluid media and the output fluid media through the liquid handler. 363. The system of implementation 362, wherein the pump is bidirectional. 364. The system of implementation 359, wherein each of the one or more cell culture chambers further comprises a first semi-transparent surface configured to allow for imaging of the adherent cell cultures. 365. The system of implementation 364, further comprising a cell editor enclosed in the cassette, wherein each of the one or more cell culture chambers is further configured to allow removal of cells from the cell culture chamber using the cell editor. 366. The system of implementation 365, wherein the cell editor is further configured to direct laser energy, ultrasound, or mechanical forces upon the cell culture chamber to effectuate the removal of the cells. 367. The system of implementation 366, wherein the laser energy further comprises pulsed laser light. 368. The system of implementation 366, wherein the first semi-transparent surface comprises a coating configured to absorb the laser energy at one or more wavelengths and convert the laser energy into thermal or mechanical energy to effectuate the removal of the cells. 369. The system of implementation 359, wherein at least one of the one or more cell culture chambers has a cell growth area of at least 50 square centimeters ($cm^2$). 370. The system of implementation 359, wherein at least one of the one or more cell culture chambers is configured to be completely filled with fluid media. 371. The system of implementation 359, wherein at least one of the one or more cell culture chambers has an internal height of less than 1 millimeter. 372. The system of implementation 359, further comprising: (1) one or more sensors configured to obtain sensor data of the growth environment; and (2) a processor communicatively coupled to the one or more sensors, wherein the processor is programmed to receive the sensor data of the growth environment. 373. The system of implementation 372, wherein the one or more sensors further comprise a monitoring sensor configured to monitor a condition of the input fluid media, the output fluid media, or both. 374. The system of implementation 372, wherein the one or more sensors comprise a temperature sensor, a humidity sensor, a gas-phase oxygen concentration sensor, a gas-phase carbon dioxide concentration sensor, a dissolved oxygen concentration sensor, a dissolved carbon dioxide concentration sensor, a gas flow rate sensor, a liquid flow rate sensor, a pH sensor, an optical absorption sensor, an optical scattering sensor, a mass spectroscopic sensor, a viscosity sensor, or a combination thereof. 375. The system of implementation 359, wherein the cassette is removably coupled to the docking station. 376. The system of implementation 375, wherein the cassette is further configured for insertion into the docking station in at least one of a first orientation and a second, inverted orientation. 377. The system of implementation 359, wherein each of the one or more cell culture chambers comprises a gas-permeable surface. 378. The system of implementation 359, wherein the liquid handler is configured to provide the input fluid media, receive the output fluid media, or both, via a one-time aseptic connector, a one-time aseptic disconnector, a reusable non-aseptic connector, or a combination thereof. 379. The system of implementation 359, further comprising a gas exchanger configured to control a concentration of a dissolved gas in the circulated fluid. 380. The system of implementation 359, wherein the liquid handler is further configured to provide the input fluid media to each of the one or more cell culture chambers at a velocity flow sufficient to apply a continuous or directional shear stress of less than about 10 dynes per square centimeter ($dyn/cm^2$) to the adherent cell cultures. 381. The system of implementation 359, wherein each of the one or more cell culture chambers comprises a registration mark, and wherein imaging the adherent cell cultures further comprises capturing an image of the registration mark. 382. The system of implementation 359, wherein the cassette further comprises a single-use portion and a permanent portion comprising a reusable housing enclosing the single-use portion, wherein the single-use portion encloses the one or more cell culture chambers and the liquid handler. 383. The system of implementation 382, wherein the single-use portion further comprises one or more bags or chambers for holding media reagents, waste products, or cellular products. 384. The system of implementation 359, wherein: (1) the input fluid media is provided to the one or more cell culture chambers via a first valve; (2) the output fluid media is received from the one or more cell culture chambers via a second valve; or (3) both. 385. The system of implementation 359, wherein imaging the adherent cell cultures further comprises transmission imaging, reflection imaging, brightfield imaging, darkfield imaging, phase imaging, differential interference contrast (DIC) imaging, quantitative phase imaging (QPI), transmission Fourier ptychographic imaging, reflection transmission Fourier ptychographic imaging, holographic imaging, or a combination thereof. 386. The system of implementation 359, wherein the liquid handler is further configured to control a mixing factor of the mixing of the circulated fluid. 387. The system of implementation 359, further comprising a temperature controller configured to control a temperature of the one or more cell culture chambers. 388. The system of implementation 359, wherein the adherent cell cultures comprise induced pluripotent stem cells (iPSCs). 389. A cell culture container, comprising: a cell culture chamber enclosing fluid media, wherein the cell culture chamber comprises a first surface interior to the cell culture chamber, wherein the first surface is at least partially transparent; a film attached to the first surface, wherein the film is configured to at least partially absorb a first incident light within a first wavelength range and at least partially transmit a second incident light within a second wavelength range; and a cell culture comprising cells adhered to the film. 390. The cell culture container of implementation 389, wherein the second incident light within the second wavelength range is used for performing optical imaging of the cell culture. 391. The cell culture chamber of implementation 389, wherein the film absorbs less than 20% of the second incident light within the second wavelength range. 392. The cell culture container of implementation 389, wherein the first incident light within the first wavelength range is used for performing laser editing operations on the cell culture. 393. The cell culture container of implementation 392, wherein the laser editing operations further comprise at least one of removal of one or more cells in the cell culture and poration of one or more cells in the cell culture. 394. The cell culture container of implementation 389, wherein responsive to providing a pulsed laser having a wavelength within the first wavelength range incident on the first surface, the film absorbs energy from the pulsed laser and forms microbubbles proximal to one or more cells in the cell culture. 395. The cell culture container of implementation 394, wherein the microbubbles dislodge the one or more cells from the film. 396. The cell culture container of implementation 394, wherein the microbubbles porate the one or more cells, thereby allowing transport of cargo into and out of the one or more cells. 397. The cell culture container of implementation 389, wherein the first incident light within the first wavelength range and the second incident light within the second wavelength range are generated by a pulsed laser that is incident on the first surface. 398. The cell culture container of implementation 389, wherein the film has a resonant absorption peak between 500 and 600 nanometers. 399. The cell culture container of implementation 389, wherein the film further comprises gold nano-islands attached to the first surface. 400. The cell culture container of implementation 399, wherein the first surface comprises a material selected from: glass, cyclic olefin copolymer, polystyrene, polycarbonate, and polyethylene terephthalate. 401. The cell culture container of implementation 389, wherein the film further comprises one or more fiducial markings thereon. 402. The cell culture container of implementation 401, wherein the one or more fiducial markers are used to determine a position of the first surface relative to at least one of an imaging subsystem and a cell editing subsystem. 403. The cell culture container of implementation 401, wherein: the first surface is configured to be illuminated with the second incident light within the second wavelength range to allow images of the cell culture to be captured without capturing images of the fiducial markings; and the first surface is configured to be illuminated with the first incident light within the first wavelength range to allow images of the fiducial markings to be captured. 404. The cell culture container of implementation 389, wherein: the film further comprises a plasmonic film having a resonant peak responsive to being irradiated with the first incident light within the first wavelength range. 405. The cell culture container of implementation 404, wherein, responsive to the plasmonic film being irradiated at the resonant peak at a first location, a spectral response of the plasmonic film contains information indicative of one or more of: cells in the cell culture proximal to the first location, the fluid media proximal to the first location, and adsorbed protein molecules proximal to the first location. 406. The cell culture container of implementation 404, wherein the resonant peak does not overlap with the first wavelength range and the second wavelength range. 407. The cell culture container of implementation 404, wherein the plasmonic film comprises gold nanoislands. 408. The cell culture container of implementation 389, wherein the first surface is transparent. 409. A cell culture system, comprising: a cell culture container, the cell culture container comprising a cell culture chamber containing a cell culture of a first cell type adhered to a first interior surface of the cell culture chamber, wherein the first interior surface is at least partially transparent; a cell imaging subsystem configured to capture images of the cell culture; a cell editing subsystem configured to perform cell editing operations on the cell culture; and a computer processor programmed to: analyze the images to determine a location and one or more characteristics of a set of cell colonies in the cell culture; identify at least one of the set of cell colonies to be destroyed based at least in part on the location and the one or more characteristics of the set of cell colonies; and control the cell editing subsystem to destroy the identified at least one of the set of cell colonies; and repeat a) to d) as the cell culture undergoes a cell culture process to transform from the first cell type to a second cell type. 410. The cell culture system of implementation 409, wherein the cell culture process is a reprogramming process, wherein the first cell type is a somatic cell, and wherein the second cell type is an induced pluripotent stem cell (iPSC). 411. The cell culture system of implementation 409, wherein the cell culture process is a differentiation process, wherein the first cell type is an induced pluripotent stem cell (iPSC). 412. The cell culture system of implementation 411, wherein the second cell type is a dopaminergic neuron cell or a retinal pigment epithelium cell. 413. The cell culture system of implementation 409, wherein the cell culture comprises cells that are adhered to the first interior surface throughout the cell culture process. 414. The cell culture system of implementation 409, wherein the cell editing subsystem further comprises a laser processing subsystem configured to generate laser illumination incident on the cell culture chamber. 415. The cell culture system of implementation 414, wherein the cell culture comprises cells that are adhered to a film attached to the first interior surface, wherein the film is configured to at least partially absorb a first incident light within a first wavelength range and at least partially transmit a second incident light within a second wavelength range. 416. The cell culture system of implementation 415, wherein the cell imaging subsystem is further configured to generate imaging illumination within the second wavelength range. 417. The cell culture system of implementation 415, wherein the laser processing subsystem is further configured to generate laser processing illumination within the first wavelength range. 418. The cell culture system of implementation 417, wherein responsive to providing a pulsed laser having a wavelength within the first wavelength range incident on the first surface, the film absorbs energy from the pulsed laser and forms microbubbles proximal to one or more cells in the cell culture. 419. The cell culture system of implementation 418, wherein the microbubbles dislodge the one or more cells from the film. 420. The cell culture system of implementation 418, wherein the microbubbles porate the one or more cells, thereby allowing transport of cargo into and out of the one or more cells. 421. The cell culture system of implementation 409, wherein the cell imaging subsystem is further configured to generate quantitative phase images of the cell culture. 422. The cell culture system of implementation 409, wherein the cell imaging subsystem is further configured to perform label-free capture of the images of the cell culture. 423. The cell culture system of implementation 409, wherein the computer processor is further programmed to use one a machine learning algorithm to determine the one or more characteristics of the set of cell colonies. 424. The cell culture system of implementation 409, wherein the computer processor is further programmed to use a machine learning algorithm to identify the at least one of the set of cell colonies to be destroyed. 425. The cell culture system of implementation 409, wherein the cell culture chamber is a sterile, sealed fluidic chamber. 426. The cell culture system of implementation 409, wherein the cell culture container is a closed cassette. 427. The cell culture system of implementation 409, further comprising a plurality of cell culture containers. 428. The cell culture system of implementation 427, wherein each individual cell culture container of the plurality of cell culture containers comprising an individual cell culture chamber containing an individual cell culture of a cell type adhered to an individual interior surface of the individual cell culture chamber, wherein the individual interior surface is at least partially transparent. 429. The cell culture system of implementation 427, wherein at least one of the cell imaging subsystem, the cell editing subsystem, and the computer processor are shared among the plurality of cell culture containers.

What is claimed is:

1. A cell culture system for culturing a plurality of cells from a plurality of subjects, comprising:

a plurality of cell samples from a plurality of subjects;

a plurality of closed cell culture containers, each of the plurality of closed cell culture containers comprising a cell culture of a cell sample of a subject of the plurality of subjects adhered to a first surface of the closed cell culture container, the cell culture comprising a plurality of cell colonies;

a transport mechanism configured to transport each of the plurality of closed cell culture containers between locations within the cell culture system;

a closed liquid loop comprising a liquid handler, a fresh media reservoir, and a waste reservoir, wherein the liquid handler is configured to perform fluid media exchanges for each of the plurality of closed cell culture containers, and wherein performing the fluid media exchanges comprises (i) supplying fresh fluid media from the fresh media reservoir to each of the plurality of closed cell culture containers and (ii) pumping spent fluid media from each of the plurality of closed cell culture containers to the waste reservoir, while maintaining a closed, sterile liquid environment for the cell culture in each of the plurality of closed cell culture containers;

a cell editing subsystem configured to selectively remove one or more cells from the first surface of each of the plurality of closed cell culture containers;

an imaging subsystem configured to generate time-series images of the cell culture in each of the plurality of closed cell culture containers; and a computing subsystem configured to control the cell editing subsystem and to manage, in parallel, a plurality of cell culture processes being performed in the plurality of closed cell culture containers to produce a clonal induced pluripotent stem cell (iPSC) output product for each subject of the plurality of subjects, wherein the managing is based at least in part on the time-series images, and wherein managing the cell culture processes of a first cell culture container of the plurality of closed cell culture containers comprises at least one of:

removing a first cell colony on the first surface of the first cell culture container that is predicted to collide with a second cell colony on the first surface of the first cell culture container;

fragmenting the first cell colony into a plurality of sub-colonies; and removing at least a portion of the first cell colony to reduce a confluence or density of the first cell colony.

2. The cell culture system of claim 1, wherein managing the cell culture processes of the first cell culture container further comprises at least one of:

removing cell colonies that grow outside of a designated region of the first surface of the first cell culture container;

removing cells that break off from the plurality of cell colonies; and removing cells neighboring the plurality of cell colonies that do not belong to the plurality of cell colonies.

3. The cell culture system of claim 1, wherein managing the cell culture processes of the first cell culture container further comprises harvesting the first cell colony from the first cell culture container, wherein one or more assays are performed on the first cell colony after the harvesting.

4. The cell culture system of claim 3, wherein the computing subsystem is configured to further manage the cell culture processes based at least in part on the one or more assays.

5. The cell culture system of claim 1, wherein managing the cell culture processes of the first cell culture container further comprises at least one of:

removing cell colonies that have not been successfully reprogrammed into iPSCs;

removing cell colonies that are not clonal iPSC cell colonies; and removing iPSC cell colonies that have spontaneously differentiated.

6. The cell culture system of claim 1, further comprising one or more cell culture process modules, wherein each of the one or more cell culture process modules is configured to removably receive a closed cell culture container of the plurality of closed cell culture containers.

7. The cell culture system of claim 6, wherein the one or more cell culture process modules, the cell editing subsystem, the imaging subsystem, and the computing subsystem have standardized sizes to fit on a vertical rack.

8. The cell culture system of claim 1, wherein the computing subsystem is configured to performing machine learning analysis on the time-series images.

9. The cell culture system of claim 1, wherein the first surface comprises a semi-transparent surface configured to enable light-based cell imaging when illuminated with light within a first wavelength range and enable light-based cell manipulation by the cell editing subsystem when illuminated with light within a second wavelength range.

10. The cell culture system of claim 9, wherein the cell editing subsystem comprises a laser configured to direct light within the second wavelength range toward the cell culture in the plurality of closed cell culture containers, such that the directed light within the second wavelength range is at least partially absorbed by the semi-transparent surface to selectively remove one or more cells from the semi-transparent surface.

11. The cell culture system of claim 1, wherein the cell culture processes comprise at least one of adherent cell proliferation, cell reprogramming, cell differentiation, cell gene editing, cell incubation, cell expansion, cell sorting, cell purification, cell-based bioproduction, and a combination thereof.

12. The cell culture system of claim 1, wherein the computing subsystem is configured to manage the cell culture processes of the first cell culture container for at least 30 days.

13. The cell culture system of claim 1, wherein the plurality of closed cell culture containers prevent cross-contamination between the plurality of cell samples of the plurality of subjects.

14. The cell culture system of claim 1, wherein the closed liquid loop further comprises a pump and a valve, wherein the pump and the valve are collectively configured to control the supplying of the fresh fluid media and the pumping of the spent fluid media.

15. A method of managing cell culture processes in a cell culture system for culturing a plurality of cells from a plurality of subjects, comprising:

obtaining a plurality of cell samples from a plurality of subjects;

establishing, for each of a plurality of closed cell culture containers, a cell culture of a cell sample of a subject of the plurality of subjects adhered to a first surface of the closed cell culture container, the cell culture comprising a plurality of cell colonies;

transporting each of the plurality of closed cell culture containers between locations within the cell culture system;

using a liquid handler to perform fluid media exchanges for each of the plurality of closed cell culture containers, wherein performing the fluid media exchanges comprises (i) supplying fresh fluid media from a fresh media reservoir to each of the plurality of closed cell culture containers and (ii) pumping spent fluid media from each of the plurality of closed cell culture containers to a waste reservoir, while maintaining a closed, sterile liquid environment for the cell culture in each of the plurality of closed cell culture containers, wherein the liquid handler, the fresh media reservoir, and the waste reservoir form a closed liquid loop;

generating, by an imaging subsystem, time-series images of the cell culture in each of the plurality of closed cell culture containers;

managing, in parallel by a computing subsystem, a plurality of cell culture processes being performed in the plurality of closed cell culture containers to produce a clonal induced pluripotent stem cell (iPSC) output product for each subject of the plurality of subjects, wherein the managing is based at least in part on the time-series images, and wherein managing the cell culture process of a first cell culture container of the plurality of closed cell culture containers comprises at least one of:

removing a first cell colony on the first surface of the first cell culture container that is predicted to collide with a second cell colony on the first surface of the first cell culture container;

fragmenting the first cell colony into a plurality of sub-colonies;

removing at least a portion of the first cell colony to reduce a confluence or density of the first cell colony; and controlling, by the computing subsystem, a cell editing subsystem to remove one or more cells from the first surface of the first cell culture container of the plurality of closed cell culture containers.

16. The method of claim 15, wherein managing the cell culture processes of the first cell culture container further comprises at least one of:

removing cell colonies that grow outside of a designated region of the first surface of the first cell culture container;

removing cells that break off from the plurality of cell colonies; and removing cells neighboring the plurality of cell colonies that do not belong to the plurality of cell colonies.

17. The method of claim 15, wherein managing the cell culture processes of the first cell culture container further comprises harvesting the first cell colony from the first cell culture container, and wherein the method further comprises performing one or more assays on the first cell colony after the harvesting.

18. The method of claim 17, further comprising managing, by the computing subsystem, the cell culture processes based at least in part on performing the one or more assays.

19. The method of claim 15, wherein managing the cell culture process of the first cell culture container further comprises at least one of:

removing cell colonies that have not been successfully reprogrammed into iPSCs;

removing cell colonies that are not clonal iPSC cell colonies; and removing iPSC cell colonies that have spontaneously differentiated.

20. The method of claim 15, further comprising performing, by the computing subsystem, machine learning analysis on the time-series images.

21. The method of claim 15, wherein the first surface comprises a semi-transparent surface configured to enable light-based cell imaging when illuminated with light within a first wavelength range and enable light-based cell manipulation by the cell editing subsystem when illuminated with light within a second wavelength range.

22. The method of claim 21, wherein the cell editing subsystem comprises a laser configured to direct light within the second wavelength range, and wherein the method further comprises directing the light within the second wavelength range toward the cell culture in the plurality of closed cell culture containers, such that the directed light within the second wavelength range is at least partially absorbed by the semi-transparent surface to selectively remove one or more cells from the semi-transparent surface.

23. The method of claim 15, wherein the cell culture processes comprise at least one of adherent cell proliferation, cell reprogramming, cell differentiation, cell gene editing, cell incubation, cell expansion, cell sorting, cell purification, cell-based bioproduction, and a combination thereof.

24. The method of claim 15, further comprising managing, by the computing subsystem, the cell culture processes of the first cell culture container for at least 30 days.

25. The method of claim 15, wherein, the plurality of closed cell culture containers prevent cross-contamination between the plurality of cell samples of the plurality of subjects.

26. The method of claim 15, wherein the closed liquid loop further comprises a pump and a valve, and wherein the method further comprises using the pump and the valve to control the supplying of the fresh fluid media and the pumping of the spent fluid media.

* * * * *